US010590086B2

(12) United States Patent
Cowley et al.

(10) Patent No.: US 10,590,086 B2
(45) Date of Patent: Mar. 17, 2020

(54) PHARMACEUTICAL COMPOUND

(71) Applicant: IOmet Pharma Ltd., Edinburgh, Midlothian (GB)

(72) Inventors: Phillip M. Cowley, Edinburgh (GB); Alan Wise, Edinburgh (GB); Susan Davis, Dundee (GB); Michael Kiczun, Dundee (GB)

( * ) Notice: Subject to any disclaimer, the term of this patent is extended or adjusted under 35 U.S.C. 154(b) by 0 days.

(21) Appl. No.: 15/524,142

(22) PCT Filed: Nov. 2, 2015

(86) PCT No.: PCT/EP2015/075486
§ 371 (c)(1),
(2) Date: May 3, 2017

(87) PCT Pub. No.: WO2016/071293
PCT Pub. Date: May 12, 2016

(65) Prior Publication Data
US 2018/0354908 A1 Dec. 13, 2018

(30) Foreign Application Priority Data

Nov. 3, 2014 (GB) .................................. 1419570.5
May 8, 2015 (GB) .................................. 1507883.5

(51) Int. Cl.
*A61K 31/416* (2006.01)
*A61K 31/454* (2006.01)
(Continued)

(52) U.S. Cl.
CPC .......... *C07D 231/56* (2013.01); *A61K 31/416* (2013.01); *A61K 31/435* (2013.01);
(Continued)

(58) Field of Classification Search
None
See application file for complete search history.

(56) References Cited

U.S. PATENT DOCUMENTS 7,759,339 B2  7/2010 Aertgeerts et al.
8,536,169 B2 * 9/2013 Baldwin .............. C07D 401/14
                                                  514/234.5
(Continued)

FOREIGN PATENT DOCUMENTS

CN  1248246 A  3/2003
CN  1484638 A  3/2004
(Continued)

OTHER PUBLICATIONS

Database Registry Chemical Abstracts Service, Columbus, Ohio, Accession No. RN 685109-08-4, Entered STN: May 24, 2004.*
(Continued)

Primary Examiner — Samantha L Shterengarts

(57) ABSTRACT

Provided is a tryptophan-2,3-dioxygenase (TDO) and/or indoleamine-2,3-dioxygenase (IDO) inhibitor compound for use in medicine, which compound comprises formula (I) wherein $X^1$, and $X^2$ may be the same or different and each is independently selected from C, N, O and S; $X^3$, $X^4$, $X^5$, and $X^6$ may be the same or different and each is independently selected from C and N; each bond represented by a dotted line may be present or absent, provided that at least one such bond is present; $R^1$, $R^2$, $R^3$, $R^4$, $R^5$ and $R^6$ may be present or absent and may be the same or different and each is independently selected from H and a substituted or unsubstituted organic group, provided that the number of $R^1$, $R^2$, $R^3$, $R^4$, $R^5$ and $R^6$ groups present is such that the respective valencies of $X^1$, $X^2$, $X^3$, $X^4$, $X^5$, and $X^6$ are maintained; and wherein at least one of $R^5$ and $R^6$ comprises a group Y, wherein Y is a group having a formula selected from (II), (III), (IV), (V), (VI), (VII) wherein L may be present or absent, and may be a substituted or unsubstituted organic linking group; $R^{31}$ and $R^{32}$ may be the same or different and are selected from H and a substituted or unsubstituted organic group; each $R^{34}$ may be the same or different and is selected from H and a substituted or unsubstituted organic group; $R^{35}$ is selected from a substituted or unsubstituted alcohol group or ether group; each $R^{36}$ may be the same or different and is selected from H and a substituted or unsubstituted organic group; $X^7$ may be selected from C and N; $X^8$, $X^9$, $X^{10}$, $X^{11}$, $X^{12}$, $X^{13}$, $X^{14}$, $X^{15}$ and $X^{16}$ may be the same or different and each is independently selected from C, N, O and S; each bond represented by a dotted line may be present or absent; and each $R^{313}$ may be the same or different and is selected from H and a substituted or unsubstituted organic group.

(I)

(II)

(III)

(Continued)

Figure 1:
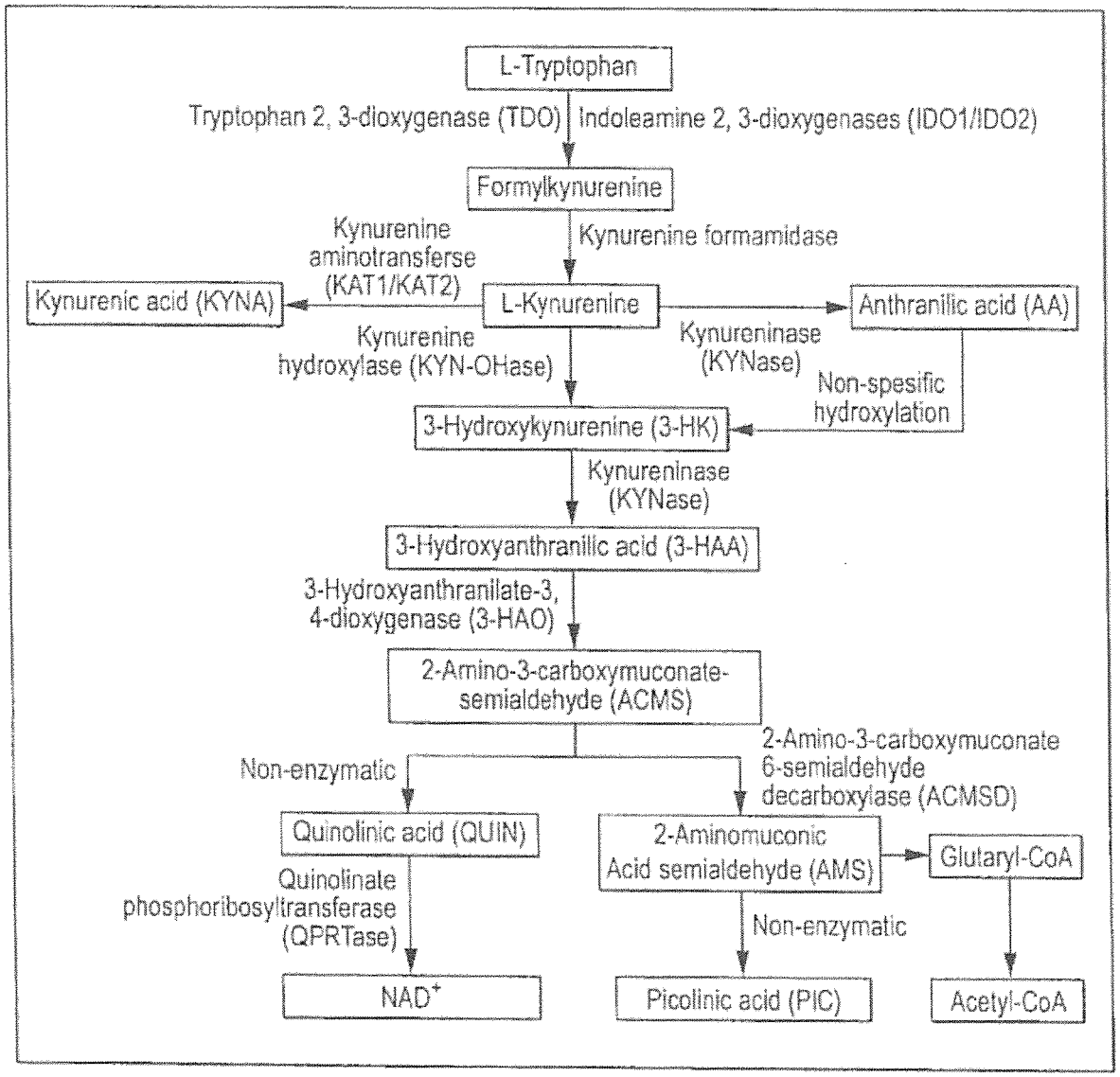

US 10,590,086 B2
Page 2

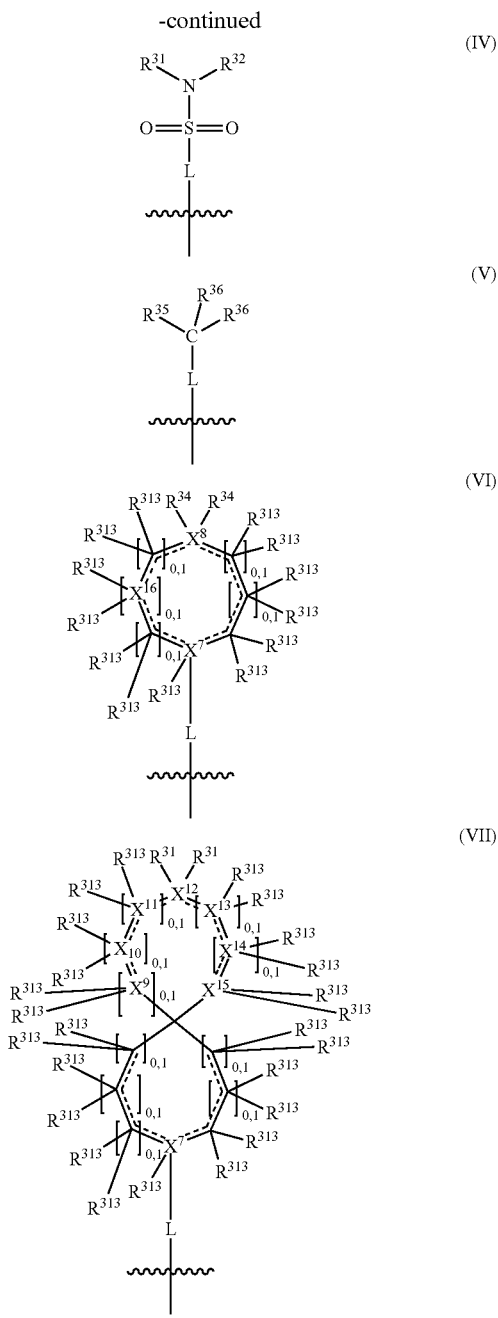

10 Claims, 2 Drawing Sheets

(51) Int. Cl.
| A61K 31/496 | (2006.01) |
| A61K 31/435 | (2006.01) |
| A61K 31/551 | (2006.01) |
| C07D 231/56 | (2006.01) |
| C07D 401/04 | (2006.01) |
| C07D 403/04 | (2006.01) |
| C07D 471/08 | (2006.01) |
| C07D 471/10 | (2006.01) |
| A61K 31/445 | (2006.01) |
| A61K 31/439 | (2006.01) |
| C07D 417/12 | (2006.01) |
| A61K 31/4523 | (2006.01) |
| A61K 31/4985 | (2006.01) |
| A61K 31/4995 | (2006.01) |
| C07D 498/08 | (2006.01) |
| C07D 498/04 | (2006.01) |
| C07D 487/04 | (2006.01) |
| A61K 31/438 | (2006.01) |
| A61K 31/499 | (2006.01) |
| C07D 471/04 | (2006.01) |
| C07D 498/10 | (2006.01) |
| C07D 405/06 | (2006.01) |
| C07D 401/14 | (2006.01) |
| C07D 261/20 | (2006.01) |
| C07D 403/14 | (2006.01) |
| C07D 403/12 | (2006.01) |
| C07D 417/14 | (2006.01) |
| A61K 45/06 | (2006.01) |

(52) U.S. Cl.
CPC .......... *A61K 31/438* (2013.01); *A61K 31/439* (2013.01); *A61K 31/445* (2013.01); *A61K 31/454* (2013.01); *A61K 31/4523* (2013.01); *A61K 31/496* (2013.01); *A61K 31/499* (2013.01); *A61K 31/4985* (2013.01); *A61K 31/4995* (2013.01); *A61K 31/551* (2013.01); *A61K 45/06* (2013.01); *C07D 261/20* (2013.01); *C07D 401/04* (2013.01); *C07D 401/14* (2013.01); *C07D 403/04* (2013.01); *C07D 403/12* (2013.01); *C07D 403/14* (2013.01); *C07D 405/06* (2013.01); *C07D 417/12* (2013.01); *C07D 417/14* (2013.01); *C07D 471/04* (2013.01); *C07D 471/08* (2013.01); *C07D 471/10* (2013.01); *C07D 487/04* (2013.01); *C07D 498/04* (2013.01); *C07D 498/08* (2013.01); *C07D 498/10* (2013.01)

(56) References Cited

U.S. PATENT DOCUMENTS

| 2002/0115670 A1 | 8/2002 | Kelly |
| 2003/0087908 A1 | 5/2003 | Geuns-Meyer |
| 2004/0087595 A1 | 5/2004 | Kelly |
| 2004/0106667 A1 | 6/2004 | Damour |
| 2004/0167122 A1 | 8/2004 | Bernotas |
| 2004/0192749 A1 | 9/2004 | Kelly et al. |
| 2005/0267096 A1 | 12/2005 | Allerton |
| 2007/0167431 A1 | 7/2007 | Comery |
| 2007/0249575 A1 | 10/2007 | Rathinavelu |
| 2008/0318941 A1 | 12/2008 | Dunn |

FOREIGN PATENT DOCUMENTS

| CN | 1771244 A | 5/2006 |
| CN | 101730680 A | 6/2010 |
| EA | 200601985 A1 | 4/2007 |
| EP | 0999208 | 5/2000 |
| EP | 1188747 | 3/2002 |
| EP | 1403255 | 3/2004 |
| JP | 2007145786 A | 6/2007 |
| RU | 2417997 C2 | 5/2011 |
| WO | 1998035942 A1 | 8/1998 |
| WO | WO9835943 | 8/1998 |
| WO | WO2005039564 | 5/2005 |
| WO | WO2007038284 | 4/2007 |
| WO | 2011067365 A1 | 6/2011 |
| WO | WO2011067366 | 6/2011 |
| WO | 2012044090 A2 | 5/2012 |

(56) References Cited

FOREIGN PATENT DOCUMENTS

| WO | WO2013130855 | 9/2013 |
|----|--------------|--------|
| WO | WO2013131609 | 9/2013 |
| WO | WO2014159248 | 10/2014 |

OTHER PUBLICATIONS

Database Registry Chemical Abstracts Service, Columbus, Ohio, Accession No. RN 1540442-69-0, Entered STN: Feb. 10, 2014.*
Ito, Nobuyuki. Cancer Science 94(1), (2003) 3-8.*
Dolus, Tryptophan 2,3-Dioxygenase (TDO) Inhibitors, 3-(2-(Pyridyl)ethyl)indoles as Potential Anticancer Immunomodulators, Journal of Medicinal Chemistry, 2011, 5320-5334, 54-15.
Feng, Yangbo, et al., Structure-activity relationships, and drug metabolism and pharmacokinetic properities for indazole piperazine and indazole piperidine inhibitors of ROCK-II, Bioorganic & Medicinal Chemistry Letters, 2007, p. 7355-2360, vol. 17.
Galiana-Rosello, In vitro and in vivo antileishmanial and trypanocidal studies of new N-benzene-and N-naphthalenesulfonamide derivatives, Journal of Medicinal Chemistry, 2013, 8984-8998, 56-22.
Mombelli, Identification of 1,3-Diiminoisoindoline Carbohydrazides as Potential Antimalarial Candidates, Chem Med Chem, 2012, 151-158, 7-1.
Perner, In vitro structure-activity relationship and in vivo characterization of 1-(Aryl)-3-(4-(amino)benzyl)urea transient receptor potential vanilloid 1 antagonists, Journal of Medicinal Chemistry, American Chemical Society, 2007, 2651-3660, 50-15.
STN Search Report.
PubChem CID 54866317, create Jan. 24, 2012, on-line data based May 22, 2019.
PubChem CID 83445889, create Oct. 20, 2014, on-line data based May 23, 2019.

* cited by examiner

PHARMACEUTICAL COMPOUND

CROSS-REFERENCE TO RELATED APPLICATIONS

The present application is a 371 national phase application of international application no. PCT/EP2015/075486, filed Nov. 2, 2015, which claims the benefit of GB Application No. 1419570.5, filed Nov. 3, 2014, and GB Application No. 1507883.5, filed May 8, 2015; hereby incorporated by reference in their entirety.

The present invention relates to tryptophan-2,3-dioxygenase (TDO) or indoleamine-2,3-dioxygenase (IDO [IDO1 or IDO2]) inhibitors, and in particular TDO and IDO inhibitors for use in medicine. The inhibitors of the invention may be used in pharmaceutical compositions, and in particular pharmaceutical compositions for treating a cancer, an inflammatory condition, an infectious disease, a central nervous system disease or disorder and other diseases, conditions and disorders. The invention also relates to methods of manufacture of such inhibitors, and methods of treatment using such inhibitors.

Tryptophan Metabolism

The kynurenine pathway (KP) is responsible for >95% of the degradation of the essential amino acid tryptophan. The kynurenine pathway for tryptophan metabolism leads to the production of the essential pyridine nucleotide NAD+ and a number of neuroactive metabolites, including kynurenine (KYN), kynurenic acid (KYNA), the neurotoxic free-radical generator 3-hydroxykynurenine (3-HK), anthranilic acid, 3-HAA, picolinic acid (PIC), and the excitatory N-methyl-D-aspartate (NMDA) receptor agonist and neurotoxin, quinolinic acid (QUIN) (see FIG. 1). The remaining 5% of tryptophan is metabolised by tryptophan hydroxylase to 5-hydroxytryptophan and then further to 5-hydroxytryptamine (serotonin) and melatonin.

Both the depletion of tryptophan and accumulation of immunosuppressive tryptophan catabolites act to supress antigen-specific T-cell and natural killer cell responses and induce the formation of regulatory T cells. Because tryptophan catabolism is induced by inflammatory mediators, notably IFN-γ, it is thought to represent an endogenous mechanism that restricts excessive immune responses, thereby preventing immunopathology. However, there is evidence that in disease states this feedback loop may not be beneficial (reviewed in (Munn and Mellor, 2013).

IDO/TDO

The first step of tryptophan catabolism is catalysed by either TDO or IDO. Both enzymes catalyze the oxidative cleavage of the 2,3 double bond in the indole ring, converting tryptophan to N-formylkynurenine. This is the rate-limiting step in tryptophan catabolism by the kynurenine pathway (Grohmann et al., 2003; Stone and Darlington, 2002). TDO is a homotetramer with each monomer having a molecular mass of 48 kDa, whereas IDO has a molecular mass of 45 kDa and a monomeric structure (Sugimoto et al., 2006; Thackray et al., 2008; Zhang et al., 2007). Despite mediating the same reaction, TDO and IDO are structurally distinct, sharing only 10% homology mainly within the active site (Thackray et al., 2008).

TDO is expressed at high levels in the liver and is responsible for regulating systemic tryptophan levels. TDO is not induced or regulated by signals from the immune system, however TDO expression can be induced by tryptophan or corticosteroids (Miller et al., 2004; Salter and Pogson, 1985). More recently, TDO has been found to be expressed in the brain, where it regulates the production of neuroactive tryptophan metabolites such as kynurenic acid and quinolinic acid (Kanai et al., 2009).

IDO is the predominant tryptophan catabolising enzyme extrahepatically and is found in numerous cells, including macrophages, microglia, neurons and astrocytes (Guillemin et al., 2007; Guillemin et al., 2001; Guillemin et al., 2003; Guillemin et al., 2005). IDO transcription is stringently controlled, responding to specific inflammatory mediators. The mouse and human IDO gene promoters contain multiple sequence elements that confer responsiveness to type I (IFN-α/β) and, more potently, type II (IFN-γ) interferons (Chang et al., 2011; Dai and Gupta, 1990; Hassanain et al., 1993; Mellor et al., 2003). Various cell types, including certain myeloid-lineage cells (monocyte-derived macrophages and DCs), fibroblasts, endothelial cells and some tumour-cell lines, express IDO after exposure to IFN-γ (Burke et al., 1995; Hwu et al., 2000; Mellor et al., 2003; Munn et al., 1999; Varga et al., 1996). However, the control of IDO transcription is complex and cell-type specific. IDO activity is found constitutively at the maternal-fetal interface, expressed by human extravillous trophoblast cells (Kudo and Boyd, 2000). Outside of the placenta, functional IDO expression was reported to be highest in the mouse epididymis, gut (distal ileum and colon), lymph nodes, spleen, thymus and lungs (Takikawa et al., 1986).

Another recent variant enzyme of IDO has been shown to catalyse the same enzymatic step: indoleamine-2,3-dioxygenase 2 (IDO2). However, its physiological relevance remains unclear due to its very low activity, the presence of common polymorphisms that inactivate its enzymatic activity in approximately half of all Caucasians and Asians, and the presence of multiple splice variants (Lob et al., 2008; Meininger et al., 2011; Metz et al., 2007).

IDO-deficient mice are at a gross level phenotypical normal (Mellor et al., 2003), however, they are slightly more prone to induction of autoimmunity and stimulation of the innate immune system. IDO −/− knockout mice also display enhanced inflammatory-mediated colon carcinogenesis and exhibit resistance to inflammation-driven lung and skin cancers (Chang et al., 2011; Yan et al., 2010).

The TDO −/− knockout mouse appears phenotypically normal. However, the TDO knockout mice have a 9-fold increase in the plasma concentration of L-Trp, while IDO −/− knockout mice had WT levels of L-Trp, this suggests that TDO and not IDO regulates systemic Trp. TDO ablation increases Trp in the brain as well as serotonin (5-HT) and is therefore a modulator of anxiety related behaviour (Kanai et al., 2009). TDO also plays a role in the maintenance of brain morphology in adult mice as TDO −/− mice show increased neurogenesis in the hippocampus and subventricular zone during adulthood (Funakoshi et al., 2011).

Immuno-Modulation: Tryptophan Depletion and Kynurenine Accumulation

Immunoregulation by tryptophan metabolism modulates the immune system by depletion of the TDO/IDO substrate (tryptophan) in the microenvironment and the accumulation of products such as kynurenine.

Effector T cells are particularly susceptible to low tryptophan concentrations, therefore, depletion of the essential amino acid tryptophan from the local microenvironment resulting in effector T-cell anergy and apoptosis. The depletion of tryptophan is detected by the general control non-derepressible-2 kinase (GCN2) (Munn et al., 2005). The activation of GCN2 triggers a stress-response program that results in cell-cycle arrest, differentiation, adaptation or apoptosis. T cells lacking GCN2 in mice are not susceptible to IDO-mediated anergy by myeloid cells, including dendritic cells in tumor-draining lymph nodes (Munn et al., 2005).

Tryptophan metabolites such as kynurenine, kynurenic acid, 3-hydroxy-kynurenine, and 3-hydroxy-anthranilic acid suppress T-cell function and are capable of inducing T-cell apoptosis. Recent studies have shown that the aryl hydrocarbon receptor (AHR) is a direct target of kynurenine (Mezrich et al., 2010; Nguyen et al., 2010; Opitz et al., 2011). The AHR is a basic helix-loop-helix Per-Arnt-Sim (PAS) family transcription factor. As kynurenine accumulates in a tumour, KYN binds the AHR, translocates to the nucleus and activates transcription of target genes regulated by dioxin-responsive elements (DREs). In T-helper-cells kynurenine results in the generation of regulatory T cells (Treg).

Pharmacological inhibitors of TDO and/or IDO have utility in a wide range of indications, including Infectious diseases, cancer, neurological conditions and many other diseases.

Infectious Diseases and Inflammation

Infection by bacteria, parasites, or viruses induces a strong IFN-γ-dependent inflammatory response. IDO can dampen protective host immunity, thus indirectly leading to increased pathogen burdens. For example, IDO activity attenuates *Toxoplasma gondii* replication in the lung, and the inflammatory damage is significantly decreased by the administration of the IDO inhibitor 1MT after infection (Murakami et al., 2012). Also, in mice infected with murine leukaemia virus (MuLV), IDO was found to be highly expressed, and ablation of IDO enhanced control of viral replication and increased survival (Hoshi et al., 2010). In a model of influenza infection, the immunosuppressive effects of IDO could predispose lungs to secondary bacterial infection (van der Sluijs., et al 2006). In Chagas Disease, which is caused by the *Trypanosoma cruzi* parasite, kynurenine is increased in patients and correlates with disease severity (Maranon et al., 2013). Therefore, IDO inhibitors could be used to improve the outcomes of patients with a wide variety of infectious diseases and inflammatory conditions. Given the role of TDO in controlling systemic Trp levels, TDO inhibitors could also be used to improve the outcomes of patients with a wide variety of infectious diseases and inflammatory conditions.

IDO and Immunity to Gut Bacteria

IDO plays a role in regulating mucosal immunity to the intestinal microbiota. IDO has been shown to regulate commensal induced antibody production in the gut; IDO-deficient mice had elevated baseline levels of immunoglobulin A (IgA) and immunoglobulin G (IgG) in the serum and increased IgA in intestinal secretions. Due to elevated antibody production, IDO deficient mice were more resistant to intestinal colonization by the gram-negative enteric bacterial pathogen *Citrobacter rodentium* than WT mice. IDO-deficient mice also displayed enhanced resistance to the colitis caused by infection with *C. rodentium* (Harrington et al., 2008).

Therefore, pharmacological targeting of IDO activity may represent a new approach to manipulating intestinal immunity and controlling the pathology caused by enteric pathogens including colitis (Harrington et al., 2008).

HIV Infection

Patients infected with HIV have chronically reduced levels of plasma tryptophan and increased levels of kynurenine, and increased IDO expression (Fuchs et al., 1990 and Zangerle et al., 2002).

In HIV patients the upregulation of IDO acts to suppress immune responses to HIV antigens contributing to the immune evasion of the virus. HIV triggers high levels of IDO expression when it infects human macrophages in vitro (Grant et al., 2000), and simian immunodeficiency virus (SIV) infection of the brain in vivo induces IDO expression by cells of the macrophage lineage (Burudi et al., 2002).

The pathogenesis of HIV is characterized by CD4+ T cell depletion and chronic T cell activation, leading ultimately to AIDS (Douek et al., 2009). CD4+T helper (TH) cells provide protective immunity and immune regulation through different immune cell functional subsets, including TH1, TH2, T regulatory (Treg), and TH17 cells. Progressive HIV is associated with the loss of TH17 cells and a reciprocal increase in the fraction of the immunosuppressive Treg cells. The loss of TH17/Treg balance is associated with induction of IDO by myeloid antigen-presenting dendritic cells (Favre et al., 2010). In vitro, the loss of TH17/Treg balance is mediated directly by the proximal tryptophan catabolite from IDO metabolism, 3-hydroxyanthranilic acid. Therefore in progressive HIV, induction of IDO contributes to the inversion of the TH17/Treg balance and maintenance of a chronic inflammatory state (Favre et al., 2010). Therefore, IDO inhibitors could have utility in addressing the TH17/Treg balance in HIV.

Sepsis-Induced Hypotension

Systemic inflammation such as sepsis is characterized by arterial hypotension and systemic inflammatory response syndrome (Riedemann et al., 2003). The associated increase in circulating pro-inflammatory cytokines, including interferon-γ (IFN-γ), leads to the unchecked production of effector molecules such as reactive oxygen and nitrogen species that themselves can contribute to pathology (Riedemann et al., 2003).

The metabolism of tryptophan to kynurenine by IDO expressed in endothelial cells contributes to arterial vessel relaxation and the control of blood pressure (Wang et al., 2010). Infection of mice with malarial parasites (*Plasmodium berghei*), and experimental induction of endotoxemia, caused endothelial expression of IDO, resulting in decreased plasma tryptophan, increased kynurenine, and hypotension. Pharmacological inhibition of IDO increased blood pressure in systemically inflamed mice, but not in mice deficient for IDO or interferon-γ, which is required for IDO induction. Arterial relaxation by kynurenine was mediated by activation of the adenylate and soluble guanylate cyclase pathways. (Wang et al., 2010). Therefore, inhibitors of IDO (and TDO, given its role in controlling systemic Trp levels) could have utility in treating sepsis-induced hypotension.

CNS Disorders

In the central nervous system both fates of TRP which act as a precursor to kynurenine and serotonin are pathways of interest and importance. Metabolites produced by the kynurenine pathway have been implicated to play a role in the pathomechanism of neuroinflammatory and neurodegenerative disorder (summarised in FIG. 2). The first stable intermediate from the kynurenine pathway is KYN. Subsequently, several neuroactive intermediates are generated. They include kynurenic acid (KYNA), 3-hydroxykynurenine (3-HK), and quinolinic acid (QUIN). 3-HK and QUIN are neurotoxic by distinct mechanisms; 3-HK is a potent free-radical generator (Hiraku et al., 1995; Ishii et al., 1992; Thevandavakkam et al., 2010), whereas QUIN is an excitotoxic N-methyl-D-aspartate (NMDA) receptor agonist (Schwarcz et al., 1983; Stone and Perkins, 1981). KYNA, on the other hand, has neuroprotective properties as an antagonist of excitatory amino acid receptors and a free-radical scavenger (Carpenedo et al., 2001; Foster et al., 1984; Goda et al., 1999; Vecsei and Beal, 1990). Changes in the concentration levels of kynurenines can shift the balance to pathological conditions. The ability to influence the metabolism towards the neuroprotective branch of the kynurenine pathway, i.e. towards kynurenic acid (KYNA) synthesis, may be one option in preventing neurodegenerative diseases.

In the CNS, the kynurenine pathway is present to varying extents in most cell types, Infiltrating macrophages, activated microglia and neurons have the complete repertoire of kynurenine pathway enzymes. On the other hand, neuroprotective astrocytes and oligodendrocytes lack the enzyme, kynurenine 3-monooxygenase (KMO) and IDO respectively, and are incapable of synthesizing the excitotoxin, quinolinic acid (QUIN) (Guillemin et al., 2000; Lim et al., 2007). TDO is expressed in low quantities in the brain, and is induced by TRP or corticosteroids (Salter and Pogson 1985; Miller et al., 2004).

Given the role of TDO and IDO in the pathogenesis of several CNS disorders as well as the role of TDO in controlling systemic Trp levels, IDO and/or TDO inhibitors could be used to improve the outcomes of patients with a wide variety of CNS diseases and neurodegeneration.

Amyotrophic Lateral Sclerosis

Amyotrophic lateral sclerosis (ALS), or Lou Gehrig's disease, is a progressive and fatal neurodegenerative disease targeting the motor system. ALS results in the selective attacking and destruction of motor neurons in the motor cortex, brainstem and spinal cord.

Although multiple mechanisms are likely to contribute to ALS, the kynurenine pathway activated during neuroinflammation is emerging as a contributing factor. Initial inflammation may inflict a nonlethal injury to motor neurons of individuals with a susceptible genetic constitution, in turn triggering a progressive inflammatory process which activates microglia to produce neurotoxic kynurenine metabolites that further destroy motor neurons.

In the brain and spinal cord of ALS patients large numbers of activated microglia, reactive astrocytes, T cells and infiltrating macrophages have been observed (Graves et al., 2004; Henkel et al., 2004). These cells release inflammatory and neurotoxic mediators, among others IFN-γ, the most potent inducer of IDO (McGeer and McGeer 2002). The neuronal and microglial expression of IDO is increased in ALS motor cortex and spinal cord (Chen et al., 2010). It has been proposed that the release of immune activating agents activates the rate-limiting enzyme of the KP, IDO, which generates metabolites such as the neurotoxin QUIN. Therefore, inhibition of IDO would reduce the synthesis of neurotoxic QUIN, which has been clearly implicated in the pathogenesis of ALS.

Huntington's Disease

Huntington's disease (HD) is a genetic autosomal dominant neurodegenerative disorder caused by expansion of the CAG repeats in the huntingtin (htt) gene. Patients affected by HD display progressive motor dysfunctions characterized by abnormality of voluntary and involuntary movements (choreoathetosis) and psychiatric and cognitive disturbances. In-life monitoring of metabolites within the KYN pathway provides one of the few biomarkers that correlates with the number of CAG repeats and hence the severity of the disorder (Forrest et al., 2010). Post mortem very high levels of QUIN are found located in areas of neurodegeneration, while striatal glutamatergic neurones, on which QUIN acts as an excitotoxin, are a principal class lost in the disease. Importantly, TDO ablation in a *Drosophila* model of Huntington's disease ameliorated neurodegeneration (Campesan et al., 2011).

Alzheimer's Disease

Alzheimer's disease (AD) is an age-related neurodegenerative disorder characterised by neuronal loss and dementia. The histopathology of the disease is manifested by the accumulation of intracellular β-amyloid (Aβ) and subsequent formation of neuritic plaques as well as the presence of neurofibrillary tangles in specific brain regions associated with learning and memory. The pathological mechanisms underlying this disease are still controversial, however, there is growing evidence implicating KP metabolites in the development and progression of AD.

It has been shown that Aβ (1-42) can activate primary cultured microglia and induce IDO expression (Guillemin et al., 2003; Walker et al., 2006). Furthermore, IDO overexpression and increased production of QUIN have been observed in microglia associated with the amyloid plaques in the brain of AD patients (Guillemin et al., 2005). QUIN has been shown to lead to tau hyperphosphorylation in human cortical neurons (Rahman et al., 2009). Thus, overexpression of IDO and over-activation of the KP in microglia are implicated in the pathogenesis of AD.

There is also evidence for TDO involvement in Alzheimer's disease. TDO is upregulated in the brain of patients and AD mice models. Furthermore, TDO co-localizes with quinolinic acid, neurofibrillary tangles-tau and amyloid deposits in the hippocampus of AD patients (Wu et al., 2013). Therefore, the kynurenine pathway is over-activated in AD by both TDO and IDO and may be involved in neurofibrillary tangle formation and associated with senile plaque formation.

Psychiatric Disorders and Pain

Most tryptophan is processed through the kynurenine pathway. A small proportion of tryptophan is processed to 5-HT and hence to melatonin, both of which are also substrates for IDO. It has long been known that amongst other effects acute tryptophan depletion can trigger a depressive episode and produces a profound change in mood even in healthy individuals. These observations link well with the clinical benefits of serotonergic drugs both to enhance mood and stimulate neurogenesis.

The co-morbidity of depressive symptoms, implication of the kynurenine pathway in inflammation and an emerging link between TDO and the glucocorticoid mediated stress response also implicate a role in the treatment of chronic pain (Stone and Darlington 2013).

Schizophrenic patients exhibit elevated KYN levels both in CSF and brain tissue, particularly the frontal cortex. This has been associated with the "hypofrontality" observed in schizophrenia. Indeed rodents treated with neuroleptics show a marked reduction in frontal KYN levels. These changes have been associated with reduced KMO and 3HAO. Evidence includes an association between a KMO polymorphism, elevated CSF KYN and schizophrenia (Holtze etr al., 2012). Taken together there is potential for manipulations in this pathway to be both pro-cognate and neuroleptic.

Pain and depression are frequently comorbid disorders. It has been shown that IDO plays a key role in this comorbidity. Recent studies have shown that IDO activity is linked to (a) decreased serotonin content and depression (Dantzer et al., 2008; Sullivan et al., 1992) and (b) increased kynurenine content and neuroplastic changes through the effect of its derivatives such as quinolinic acid on glutamate receptors (Heyes et al., 1992).

In rats chronic pain induced depressive behaviour and IDO upregulation in the bilateral hippocampus. Upregulation of IDO resulted in the increased kynurenine/tryptophan ratio and decreased serotonin/tryptophan ratio in the bilateral hippocampus. Furthermore, IDO gene knockout or pharmacological inhibition of hippocampal IDO activity attenuated both nociceptive and depressive behaviour (Kim et al., 2012).

Since proinflammatory cytokines have been implicated in the pathophysiology of both pain and depression, the regulation of brain IDO by proinflammatory cytokines serves as a critical mechanistic link in the comorbid relationship between pain and depression through the regulation of tryptophan metabolism.

Multiple Sclerosis

Multiple sclerosis (MS) is an autoimmune disease characterized by inflammatory lesions in the white matter of the nervous system, consisting of a specific immune response to the myelin sheet resulting in inflammation and axonal loss (Trapp et al., 1999; Owens, 2003).

Accumulation of neurotoxic kynurenine metabolites caused by the activation of the immune system is implicated in the pathogenesis of MS. QUIN was found to be selectively elevated in the spinal cords of rats with EAE, an autoimmune animal model of MS (Flanagan et al., 1995). The origin of the increased QUIN in EAE was suggested to be the macrophages. QUIN is an initiator of lipid peroxidation and high local levels of QUIN near myelin may contribute to the demyelination in EAE and possibly MS.

Interferon beta 1b (IFN-β1b) induces KP metabolism in macrophages at concentrations comparable to those found in the sera of IFN-b treated patients, this which may be a limiting factor in its efficacy in the treatment of MS (Guillemin et al., 2001). After IFN-β administration, increased kynurenine levels and kynurenine/tryptophan ratio were found in the plasma of MS patients receiving IFN-b injection compared to healthy subjects indicating an induction of IDO by IFN-β (Amirkhani et al., 2005). IFN-β1b, leads to production of QUIN at concentrations sufficient to disturb the ability of neuronal dendrites to integrate incoming signals and kill oligodendrocytes (Cammer 2001). In IFN-β1b-treated patients concomitant blockade of the KP with an IDO/TDO inhibitor may improve its efficacy of IFN-β1b.

Parkinson's Disease

Parkinson's disease (PD) is a common neurodegenerative disorder characterised by loss of dopaminergic neurons and localized neuroinflammation.

Parkinson's disease is associated with chronic activation of microglia (Gao and Hong, 2008). Microglia activation release neurotoxic substances including reactive oxygen species (ROS) and proinflammatory cytokines such as INF-γ (Block et al., 2007), a potent activator of KP via induction of IDO expression. KP in activated microglia leads to upregulation of 3HK and QUIN. 3HK is toxic primarily as a result of conversion to ROS (Okuda et al., 1998). The combined effects of ROS and NMDA receptor-mediated excitotoxicity by QUIN contribute to the dysfunction of neurons and their death (Braidy et al., 2009; Stone and Perkins, 1981). However, picolinic acid (PIC) produced through KP activation in neurons, has the ability to protect neurons against QUIN-induced neurotoxicity, being NMDA agonist (Jhamandas et al., 1990). Microglia can become overactivated, by proinflammatory mediators and stimuli from dying neurons and cause perpetuating cycle of further microglia activation microgliosis. Excessive microgliosis will cause neurotoxicity to neighbouring neurons and resulting in neuronal death, contributing to progression of Parkinson's disease. (Zinger et al 2011): Therefore, PD is associated with an imbalance between the two main branches of the KP within the brain. KYNA synthesis by astrocytes is decreased and concomitantly, QUIN production by microglia is increased.

HIV

HIV patients, particularly those with HIV-linked dementia (Kandanearatchi & Brew 2012), often have significantly elevated KYN levels in CSF. These levels are directly related to the development of neurocognitive decline and often the presence of sever psychotic symptoms (Stone & Darlington 2013).

Cancer

It is clear that tumours can induce tolerance to their own antigens. Tryptophan catabolism in cancer is increasingly being recognized as an important micro-environmental factor that suppresses antitumor immune responses. Depletion of tryptophan and accumulation of immunosuppressive tryptophan catabolites such as kynurenine create an immunosuppressive milieu in tumours and in tumour-draining lymph nodes by inducing T-cell anergy and apoptosis. Such immunosuppression in the tumour microenvirom-nent may help cancers evade the immune response and enhance tumorigenicity (reviewed in Adam et al., 2012).

Recently, both TDO and IDO have been implicated in tumour progression. Individually TDO or IDO have been found to be overexpressed in various cancers, furthermore, several cancers overexpress both TDO and IDO. TDO and IDO mediate immunosuppressive effects through the metabolization of Trp to kynurenine, triggering downstream signalling through GCN2, mTOR and AHR that can affect differentiation and proliferation of T cells. Also, expression of IDO by activated dendritic cells can serve to activate regulatory T cells (Tregs) and inhibit tumor-specific effector CD8+ T cells, thereby constituting a mechanism by which the immune system can restrict excessive lymphocyte reactivity (reviewed in Platten et al., 2012).

IDO

Increased expression of IDO has been shown to be an independent prognostic variable for reduced survival in patients with acute myeloid leukemia (AML), small-cell lung, melanoma, ovarian, colorectal, pancreatic, and endometrial cancers (Okamoto et al., 2005; Ino et al., 2006). Indeed, sera from cancer patients have higher kynurenine/tryptophan ratios than sera from normal volunteers (Liu et al., 2010; Weinlich et al., 2007; Huang et al., 2002). The level of IDO expression was also shown to correlate with the number of tumour infiltrating lymphocytes in colorectal carcinoma patients (Brandacher et al., 2006).

In preclinical models, transfection of immunogenic tumour cells with recombinant IDO prevented their rejection in mice (Uyttenhove et al., 2003). While, ablation of IDO expression led to a decrease in the incidence and growth of 7,12-dimethylbenz(a)anthracene-induced premalignant skin papillomas (Muller et al., 2008). Moreover, IDO inhibition slows tumour growth and restores anti-tumour immunity (Koblish et al., 2010) and IDO inhibition synergises with cytotoxic agents, vaccines and cytokines to induce potent anti-tumour activity (Uyttenhove et al., 2003; Muller et al., 2005; Zeng et al., 2009).

TDO

TDO is predominantly expressed in the liver and is believed to regulate systemic Trp concentrations, however, TDO was found to be frequently activated and constitutively expressed in glioma cells. TDO derived KYN was shown to suppress antitumor immune responses and promote tumor-cell survival and motility through the AhR in an autocrine manner (Opitz et al., 2011). It was also shown that TDO is elevated in human hepatocellular carcinomas and detected sporadically in other cancers. In a preclinical model, TDO expression prevented rejection of tumor grafts by preimmunized mice. Systemic administration of the TDO inhibitor, LM10, restored the ability of mice to reject TDO-expressing tumors (Pilotte et al., 2012).

Therefore inhibitors of TDO or IDO could have wide ranging therapeutic efficacy in the treatment of cancer. Also dual inhibitors blocking both TDO and IDO may demonstrate improved clinical efficacy by targeting both of these key Trp-metabolising enzymes and would also treat a wider patient population: in a series of 104 human tumor lines of various histological types, 20 tumors expressed only TDO, 17 expressing only IDO and 16 expressed both. Therefore, targeting both IDO and TDO would allow reaching 51% of tumors instead of 32% with IDO or 35% with TDO alone (Pilotte et al., 2012). Moreover, given the role of TDO in controlling systemic Trp levels, TDO inhibitors could also be used to improve the outcomes of patients with a wide variety of cancers and neoplastic diseases that do not express TDO.

Inhibition of IDO and/or TDO will dramatically lower kynurenine levels, relieving the brake on the immune system allowing it to attack and eliminate tumours. While there is evidence that a TDO/IDO inhibitor would be useful as a stand-alone agent, inhibitors of this type would be particularly effective when used in combination with other cancer immunotherapies. In fact, upregulation of IDO expression has been identified as a mechanism by which tumours gain resistance to the CTLA-4 blocking antibody ipilimumab. Ipilimumab blocks the co-stimulatory molecule CTLA-4, causing tumour-specific T cells to remain in an activated state. IDO knockout mice treated with anti-CTLA-4 antibody demonstrate a striking delay in B16 melanoma tumor growth and increased overall survival when compared with wild-type mice. Also, CTLA-4 blockade strongly synergizes with IDO inhibitors to mediate tumour rejection. Similar data was also reported for IDO inhibitors in combination with anti-PD1 and anti-PDL-1 antibodies (Holmgaard et al., 2013).

Agents that will influence an immunosuppressive environment may also be relevant to chimeric antigen receptor T cell therapy (CAR-T) therapies to enhance efficacy and patient responses.

Other Diseases

Although these effects are defensive strategies to cope with infection and inflammation, they may have unintended consequences because kynurenines formed during IDO and TDO-mediated degradation of tryptophan can chemically modify proteins and have been shown to be cytotoxic (Morita et al., 2001; Okuda et al., 1998). In coronary heart disease, inflammation and immune activation are associated with increased blood levels of kynurenine (Wirleitner et al., 2003) possibly via interferon-γ-mediated activation of IDO. In experimental chronic renal failure, activation of IDO leads to increased blood levels of kynurenines (Tankiewicz et al., 2003), and in uremic patients kynurenine-modified proteins are present in urine (Sala et al., 2004). Further, renal IDO expression may be deleterious during inflammation, because it enhances tubular cell injury.

General anaesthesia unfortunately mimics many of these effects inducing stress and inflammatory processes. Post anaesthesia cognitive dysfunction has often been correlated with these sequelae. Recently these deficits have been shown to be correlated with changes in kynurenine pathway markers, but not cytokines, following cardiac surgery and in recovering stroke patients (Stone and Darlington 2013).

Cataracts

A cataract is a clouding of the lens inside the eye that leads to a decrease in vision. Recent studies suggest that kynurenines might chemically alter protein structure in the human lens leading to cataract formation. In the human lens IDO activity is present mainly in the anterior epithelium (Takikawa et al., 1999). Several kynurenines, such as kynurenine (KYN), 3-hydroxykynurenine (3OHKYN), and 3-hydroxykynurenine glucoside (3OHKG) have been detected in the lens; where they were thought to protect the retina by absorbing UV light and therefore are commonly referred to as UV filters. However, several recent studies show that kynurenines are prone to deamination and oxidation to form α,β-unsaturated ketones that chemically react and modify lens proteins (Taylor et al., 2002). Kynurenine mediated modification could contribute to the lens protein modifications during aging and cataractogenesis. They may also reduce the chaperone function of α-crystallin, which is necessary for maintaining lens transparency.

Transgenic mouse lines that overexpress human IDO in the lens developed bilateral cataracts within 3 months of birth. It was demonstrated that IDO-mediated production of kynurenines results in defects in fibre cell differentiation and their apoptosis (Mailankot et al., 2009). Therefore inhibition of IDO may slow the progression of cataract formation.

Female Reproductive Health

Endometriosis

Endometriosis, the presence of endometrium outside the uterine cavity, is a common gynaecological disorder, causing abdominal pain, dyspareunia and infertility. IDO expression was found to be higher in eutopic endometrium from women with endometriosis by microarray analysis (Burney et al., 2007 and Aghajanova et al., 2011). Furthermore, IDO was shown to enhance the survival and invasiveness of endometrial stromal cells (Mei et al., 2013). Therefore, an IDO/TDO inhibitor could be used as a treatment for endometriosis.

Contraception and Abortion

The process of implantation of an embryo requires mechanisms that prevent allograft rejection; and tolerance to the fetal allograft represents an important mechanism for maintaining a pregnancy. Cells expressing IDO in the foeto-maternal interface protect the allogeneic foetus from lethal rejection by maternal immune responses. Inhibition of IDO by exposure of pregnant mice to 1-methyl-tryptophan induced a T cell-mediated rejection of allogeneic concepti, whereas syngeneic concepti were not affected; this suggests that IDO expression at the foetal-maternal interface is necessary to prevent rejection of the foetal allograft (Munn et al., 1998). Accumulating evidence indicates that IDO production and normal function at the foetal-maternal interface may play a prominent role in pregnancy tolerance (Durr and Kindler., 2013). Therefore, an IDO/TDO inhibitor could be used as a contraceptive or abortive agent.

On the above basis, the inventors have determined that a strong rationale exists for the therapeutic utility of drugs which block the activity of TDO and or IDO, in treating the above-mentioned diseases, conditions and disorders.

WO 2004/113304 discloses protein tyrosine kinase inhibitors for treating cancer, which comprise inter alia indazole, benzisoxazole and benzisothiazole compounds similar to those envisaged by the present inventors. In these compounds the 3-position of the indazole must be substituted with —$NH_2$. However, these compounds are not disclosed as having an IDO or a TDO inhibitory activity.

WO 2013/130855 describes MetAP2 inhibitors for treating MetAP2 related diseases, primarily obesity. These also comprise inter alia indazole compounds similar to those envisaged by the present inventors. In these compounds the 6-position of the indazole must be substituted with a $C_1$-$C_3$ haloalkyl, such as —$CF_3$. However, these compounds are not disclosed as having an IDO or a TDO inhibitory activity.

In published patent application WO 2014/033167 (Janssen R&D) compounds for the treatment of hepatitis B are disclosed. These compounds are in some cases similar to the present compounds, but the document does not disclose TDO and IDO inhibitory activity.

In the Journal of Medicinal Chemistry, Vol. 56 (22), 2013, pp 8984-8998, Galiana-Rosello et al., disclose antileishmanial and trypanocidal compounds. Some compounds are similar to those of the present invention, but TDO and IDO inhibitory activity is not disclosed.

In published patent application WO 2014/066491 (Merck Sharp & Dohme) sodium ion channel blocking compounds for the treatment of neuropathic pain disorders are disclosed. These compounds are in some cases similar to the present compounds, but the document does not disclose TDO and IDO inhibitory activity.

In published patent application US 2009/318470 (Liu) compounds for the treatment of CNS disorders are disclosed. These compounds are in some cases similar to the present compounds, but the document does not disclose TDO and IDO inhibitory activity.

In published patent application WO 2011/067366 (Glaxo) PI3-kinase inhibitor compounds are disclosed for treating in particular respiratory diseases, allergic diseases and autoimmune diseases. Amongst a long list of other possible diseases, cancer is included A wide general formula is disclosed, but none of the specific compounds disclosed are similar to the specific compounds of the present invention and TDO and IDO inhibitory activity is not disclosed.

In published patent application WO 2006/135383 (Myriad Genetics Inc.) compounds for treating and/or delaying the onset of viral infection are disclosed. These compounds are in some cases similar to the present compounds, but the document does not disclose TDO and IDO inhibitory activity.

Having regard to the above, it is an aim of the present invention to provide TDO or IDO inhibitors, and in particular TDO and IDO inhibitors for use in medicine. It is thus an aim to provide a compound for use in medicine for inhibiting tryptophan-2,3-dioxygenase (TDO) and/or indoleamine-2,3-dioxygenase (IDO). It is a further aim to provide pharmaceutical compositions comprising such inhibitors, and in particular to provide compounds and pharmaceutical compositions for treating a cancer, an inflammatory condition, an infectious disease, a central nervous system disease or disorder and other diseases, conditions and disorders. It is also an aim to provide methods of synthesis of the compounds.

Accordingly, the present invention provides a tryptophan-2,3-dioxygenase (TDO) and/or indoleamine-2,3-dioxygenase (IDO) inhibitor compound for use in medicine, which compound comprises the following formula:

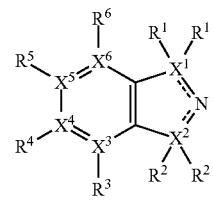

wherein $X^1$, and $X^2$ may be the same or different and each is independently selected from C, N, O and S; $X^3$, $X^4$, $X^5$, and $X^6$ may be the same or different and each is independently selected from C and N; each bond represented by a dotted line may be present or absent, provided that at least one such bond is present; $R^1$, $R^2$, $R^3$, $R^4$, $R^5$ and $R^6$ may be present or absent and may be the same or different and each is independently selected from H and a substituted or unsubstituted organic group, provided that the number of $R^1$, $R^2$, $R^3$, $R^4$, $R^5$ and $R^6$ groups present is such that the respective valencies of $X^1$, $X^2$, $X^3$, $X^4$, $X^5$, and $X^6$ are maintained; and wherein at least one of $R^5$ and $R^6$ comprises a group Y, wherein Y is a group having a formula selected from the following:

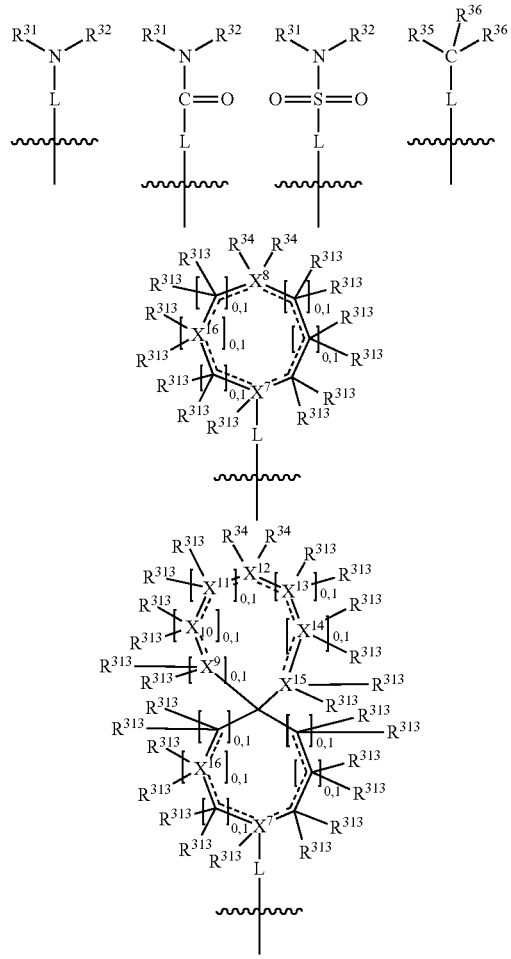

wherein L may be present or absent, and may be a substituted or unsubstituted organic linking group; $R^{31}$ and $R^{32}$ may be the same or different and are selected from H and a substituted or unsubstituted organic group; each $R^{34}$ may be the same or different and is selected from H and a substituted or unsubstituted organic group; $R^{35}$ is selected from a substituted or unsubstituted alcohol group or ether group; each $R^{36}$ may be the same or different and is selected from H and a substituted or unsubstituted organic group; $X^7$ may be selected from C and N; $X^8$, $X^9$, $X^{10}$, $X^{11}$, $X^{12}$, $X^{13}$, $X^{14}$, $X^{15}$, and $X^{16}$ may be the same or different and each is independently selected from C, N, O and S; each bond represented by a dotted line may be present or absent; and each $R^{313}$ may be the same or different and is selected from H and a substituted or unsubstituted organic group.

Throughout this disclosure, any of the compounds disclosed may typically be suitable for use in medicine in a treatment comprising tryptophan-2,3-dioxygenase (TDO) and/or indoleamine-2,3-dioxygenase (IDO) inhibition.

In the context of the present invention, maintaining the valency means ensuring that an atom has its normal (typically most common) valency in organic compounds (i.e. 2 for oxygen and sulphur, 3 for nitrogen and 4 for carbon). Nitrogen atoms may, in some instances, have 4 bonds, but in such cases they are typically positively charged such that the compound may have a counter-ion. Such compounds are also considered to be part of the invention, and in these cases, due to the positive charge, it will be clear that the nitrogen atom still maintains its normal valency of 3. For the avoidance of doubt, where the number of R groups may vary according to the choice of X group, it may vary as follows.

$R^1$ is absent when $X^1$ is N and has a double bond, and when $X^1$ is O or S, and one $R^1$ is present when $X^1$ is N without a double bond, and when $X^1$ is C with a double bond, and two $R^1$ are present when $X^1$ is C without a double bond. $R^2$ is absent when $X^2$ is N and has a double bond, and when $X^2$ is O or S, and one $R^2$ is present when $X^2$ is N without a double bond, and when $X^2$ is C with a double bond, and two $R^2$ are present when $X^2$ is C without a double bond. $R^3$ is absent when $X^3$ is N and one $R^3$ is present when $X^3$ is C. $R^4$ is absent when $X^4$ is N and one $R^4$ is present when $X^4$ is C. $R^5$ is absent when $X^5$ is N and one $R^5$ is present when $X^5$ is C. $R^6$ is absent when $X^6$ is N and one $R^6$ is present when $X^6$ is C. $R^{313}$ is absent when $X^7$ is N, or when $X^7$ is C and has a double bond, and one $R^{313}$ is present when $X^7$ is C that does not have a double bond. $R^{34}$ is absent when $X^8$ is N and has a double bond and when $X^8$ is O or S, one $R^{34}$ is present when $X^8$ is N without a double bond and when $X^8$ is C with a double bond, and two $R^{34}$ are present when $X^8$ is C without a double bond. $R^{34}$ is absent when $X^{12}$ is N and has a double bond and when $X^{12}$ is O or S, one $R^{34}$ is present when $X^{12}$ is N without a double bond and when $X^{12}$ is C with a double bond, and two $R^{34}$ are present when $X^{12}$ is C without a double bond. $R^{313}$ is absent when $X^9$ is N and has a double bond and when $X^9$ is O or S, one $R^{313}$ is present when $X^9$ is N without a double bond and when $X^9$ is C with a double bond, and two $R^{313}$ are present when $X^9$ is C without a double bond. $R^{313}$ is absent when $X^{10}$ is N and has a double bond and when $X^{10}$ is O or S, one $R^{313}$ is present when $X^{12}$ is N without a double bond and when $X^{10}$ is C with a double bond, and two $R^{313}$ are present when $X^{10}$ is C without a double bond. $R^{313}$ is absent when $X^{11}$ is N and has a double bond and when $X^{11}$ is O or S, one $R^{313}$ is present when $X^{11}$ is N without a double bond and when $X^{11}$ is C with a double bond, and two $R^{313}$ are present when $X^{11}$ is C without a double bond. $R^{313}$ is absent when $X^{13}$ is N and has a double bond and when $X^3$ is O or S, one $R^{313}$ is present when $X^{13}$ is N without a double bond and when $X^{13}$ is C with a double bond, and two $R^{313}$ are present when $X^{13}$ is C without a double bond. $R^{313}$ is absent when $X^{14}$ is N and has a double bond and when $X^{14}$ is O or S, one $R^{313}$ is present when $X^{14}$ is N without a double bond and when $X^{14}$ is C with a double bond, and two $R^{33}$ are present when $X^{14}$ is C without a double bond. $R^{313}$ is absent when $X^{15}$ is N and has a double bond and when $X^{15}$ is O or S, one $R^{313}$ is present when $X^{15}$ is N without a double bond and when $X^{15}$ is C with a double bond, and two $R^{313}$ are present when $X^{15}$ is C without a double bond. $R^{313}$ is absent when $X^{16}$ is N and has a double bond and when $X^{16}$ is O or S, one $R^{313}$ is present when $X^{16}$ is N without a double bond and when $X^{16}$ is C with a double bond, and two $R^{313}$ are present when $X^{16}$ is C without a double bond.

In the present context the invention includes compounds in which a single $R^{313}$ group on an atom, or two $R^{313}$ groups on the same atom, may form a group which is double bonded to that atom. Accordingly, an $R^{313}$ group, or two $R^{313}$ groups attached to the same atom, may together form a =O group, or a =C(R')$_2$ group (wherein each R' group is the same or different and is H or an organic group, preferably H or a straight or branched substituted or unsubstituted $C_1$-$C_6$ alkyl group). Typically, all $R^{313}$ groups are H, or one or more of the $R^{313}$ groups adjacent to the $X^8$, (or adjacent to $X^{12}$) and/or adjacent to the $X^7$, are not H. In some instances two $R^{313}$ groups on the same atom adjacent to the $X^8$, (or adjacent to the $X^{12}$) and/or adjacent to the $X^7$, are not H, and in other instances one $R^{313}$ group on each of the two different atoms adjacent to the $X^8$, (or adjacent to the $X^{12}$) and/or adjacent to the $X^7$, is not H. Typically, one or more of the $R^{313}$ groups adjacent to the $X^8$, (or adjacent to the $X^{12}$) and/or adjacent to the $X^7$, are selected from a $C_1$-$C_6$ alkyl group. In some instances two $R^{313}$ groups on the same atom adjacent to the $X^8$, (or adjacent to the $X^{12}$) and/or adjacent to the $X^7$, may form a ring, preferably a substituted or unsubstituted $C_3$-$C_6$ saturated carbocyclic ring together with the atom to which they are attached (such as a substituted or unsubstituted cyclopropyl ring or a substituted or unsubstituted cyclobutyl ring).

In some instances (more typical, although not most preferred), two $R^{313}$ groups on adjacent atoms may together form a ring, or an $R^{34}$ and an $R^{313}$ on adjacent atoms may form a ring. This may be a saturated or unsaturated and/or a substituted or unsubstituted ring. In typical embodiments, such rings may be 5 or 6 membered rings, and may be heterocyclic or carbocyclic, and are typically aromatic. Such rings may be selected from:

a substituted or unsubstituted cyclic $C_3$-$C_8$ alkyl group (such as cyclopropyl, cyclobutyl, cyclopentyl, cyclohexyl, cycloheptyl and cyclooctyl);

a substituted or unsubstituted aromatic group (such as Ph-, F-Ph-, Cl-Ph-, Br-Ph-, I-Ph-, $F_2$-Ph-, $Cl_2$-Ph-, $Br_2$-Ph-, $I_2$-Ph-, $Me_2$-Ph-, $Et_2$-Ph-, $Pr_2$-Ph-, $Bu_2$-Ph-, $(CN)_2$-Ph-, $(NO_2)_2$-Ph-, $(NH_2)_2$-Ph-, $(MeO)_2$-Ph-, $(CF_3)_2$-Ph-, Me-Ph-, Et-Ph-, Pr-Ph-, Bu-Ph-, (CN)-Ph-, $(NO_2)$-Ph-, $(NH_2)$-Ph-, MeO-Ph-, $(NH_2$—CO)-Ph-, $CF_3$-Ph-, $CF_3$O-Ph-, and a saturated or unsaturated, substituted or unsubstituted, heterocyclic group including an aromatic heterocyclic group and/or a non-aromatic heterocyclic group (such as pyrrole, pyrazole, imidazole, 1,2,3-triazole, 1,2,4-triazole, pyridine, pyridazine, pyrimidine, pyrazine, pyrrolidine, piperidine, 2-azapiperidine, 3-azapiperidine, piperazine, furan, pyran, 2-azapyran, 3-azapyran, 4-azapyran, tetrahydrofuran, 2-aza-tetrahydrofuran, 3-aza-tetrahydrofuran, tetrahydropyran, 2-aza-tetrahydropyran, 3-aza-tetrahydropyran, morpholine, thiophene, isothiazole, thiazole, thiopyran, 2-azathiopyran, 3-azathiopyran, 4-azathiopyran, thiolane, thiane, oxazole, isoxazole, furazan, 1,3,4-oxadiazole, 1,2,4-oxadiazole; and tetrazole).

More typically, such rings may be selected from a substituted or unsubstituted phenyl ring, a substituted or unsubstituted pyridine ring, a substituted or unsubstituted 1,2 diazole ring, a substituted or unsubstituted 1,3 diazole ring, a substituted or unsubstituted 1,3 oxazole ring, and a substituted or unsubstituted 1,3 thiazole ring.

More generally, in some instances (especially where the compound does not comprise another aminocarbonyl group, carbonylamino group, aminosulphonyl group, or sulphonylamino group) one or more of the $R^{313}$ groups adjacent to the $X^8$, (or adjacent to the $X^{12}$) and/or adjacent to the $X^7$, are selected from a group comprising an aminocarbonyl group, a carbonylamino group, an aminosulphonyl group, a sulphonylamino group, a substituted or unsubstituted piperidinyl group (which may itself be substituted with a carbonyl group or a sulphonyl group), a substituted or unsubstituted piperazinyl group (which may itself be substituted with a carbonyl group or a sulphonyl group), a substituted or unsubstituted alcohol group (which may itself be substituted with a carbonyl group or a sulphonyl group), a substituted or unsubstituted ether group (which may itself be substituted with a carbonyl group or a sulphonyl group), and/or a saturated or unsaturated, substituted or unsubstituted, carbocyclic group (which may itself be substituted with a carbonyl group or a sulphonyl group) such as a substituted or unsubstituted cyclohexyl group or a substituted or unsubstituted phenyl group. In such instances, the following $R^{313}$ groups are especially preferred:

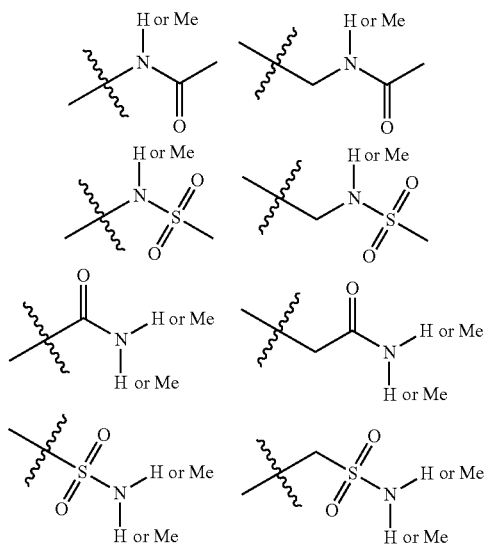

In some cases an R group in the core bicyclic ring system may form a ring with another R group on an adjacent and/or proximal atom, although this is not typical. Thus, the following substituents may together form a ring: $R^1$ and $R^6$, $R^2$ and $R^3$, $R^3$ and $R^4$, $R^4$ and $R^5$, and $R^5$ and $R^6$. In the context of the present invention, an adjacent and/or proximal atom may mean another atom directly bonded to an atom (adjacent), or may be two atoms with only a single atom in between (proximal), or may mean two atoms close enough sterically to be capable of forming a ring (proximal). Preferably R groups attached to the same atom do not together form a ring, although this is not excluded (for example, in the case of $R^{313}$ above).

In some cases, any R group or L in the Y group may form a ring with any other group on an adjacent and/or proximal atom, although this is not typical (except in the case of two $R^{313}$ groups on adjacent atoms, or an $R^{34}$ and an $R^{313}$ on a adjacent atom as already described above in which case this is more typical, although not most preferred); the other group may be a group either in the ring system or in the Y group. Thus, in certain embodiments the following substituents may each together form a ring: $R^{31}$ and $R^{32}$, L and $R^{31}$ and/or L and $R^{32}$, $R^{31}$ with $R^{313}$, $R^{32}$ with $R^{313}$, $R^{313}$ with another $R^{313}$ (either another $R^{313}$ on the same atom or an $R^{313}$ on a different atom), $R^{34}$ with another $R^{34}$, $R^{35}$ with an $R^{36}$, $R^{35}$ with L, $R^{36}$ with another $R^{36}$, one or both of $R^{36}$ with one or more $R^{313}$ and one or both of $R^{36}$ with L. In addition, the following substituents may each together form a ring: $R^1$ and L, $R^1$ and $R^{31}$, $R^1$ and $R^{32}$, $R^1$ and $R^{35}$, $R^1$ and $R^{36}$, $R^2$ and L, $R^2$ and $R^{31}$, and $R^2$ and $R^{32}$, $R^2$ and $R^{35}$, $R^2$ and $R^{36}$, $R^3$ and L, $R^3$ and $R^{31}$, $R^3$ and $R^{32}$, $R^3$ and $R^{35}$, $R^3$ and $R^{36}$, $R^4$ and L, $R^4$ and $R^{31}$, $R^4$ and $R^{32}$, $R^4$ and $R^{35}$, $R^4$ and $R^{36}$, $R^5$ and L, $R^5$ and $R^{31}$, $R^5$ and $R^{32}$, $R^5$ and $R^{35}$, $R^5$ and $R^{36}$, and $R^6$ and L, $R^6$ and $R^{31}$, $R^6$ and $R^{32}$, $R^6$ and $R^{35}$, $R^6$ and $R^{36}$.

In the present invention, $X^7$ may be C or N, and both C and N are equally preferred at $X^7$. $X^8$ may be C, N, O or S, but C and N are more preferred. Where present, $X^9$, $X^{10}$, $X^{11}$, $X^{13}$, $X^{14}$, $X^{15}$ and $X^{16}$ may be C, N, O or S, but C and N are more preferred for each of these. $X^{12}$ may be C, N, O or S, but C and N are more preferred.

In the present context the dotted line between two atoms indicates the possible presence of a further bond. In a case where two atoms are already joined by a solid line, but also have a dotted line, then those atoms have at least a single bond, but possibly a double bond in some cases. Thus, in such cases, each atom having a dotted line may independently have a double bond or a single bond, provided that valencies at each atom are maintained.

In the present context the part of the structure present in brackets may be repeated the number of times given by the numbers next to the brackets (whether regular brackets or square brackets). For example, in the case of $(C(R))_{0,1,2}$ or $[C(R)]_{0,1,2}$ the C—R group may be absent, present once i.e. —C(R)—; or present twice i.e. —C(R)—C(R)—.

In the context of the present invention, a compound is considered to be a TDO inhibitor if its presence is capable of preventing, reducing or slowing the conversion of tryptophan into N-formylkynurenine by TDO as compared to the same conversion in its absence. Similarly, in the context of the present invention, a compound is considered to be an IDO inhibitor if its presence is capable of preventing, reducing or slowing the conversion of tryptophan into N-formylkynurenine by IDO as compared to the same conversion in its absence. The compounds of the invention may be selective TDO inhibitors, or selective IDO inhibitors, or may be inhibitors of both IDO and TDO.

Throughout this disclosure, any of the compounds disclosed may typically be suitable for use in medicine for inhibiting tryptophan-2,3-dioxygenase (TDO) and/or indoleamine-2,3-dioxygenase (IDO). Thus, typically the compounds are suitable for use in medicine in a treatment of a disease (such as a cancer) which treatment may be effected by tryptophan-2,3-dioxygenase (TDO) and/or indoleamine-2,3-dioxygenase (IDO) inhibition.

In typical embodiments, the invention provides a compound as defined above comprising one or other of the following formulae:

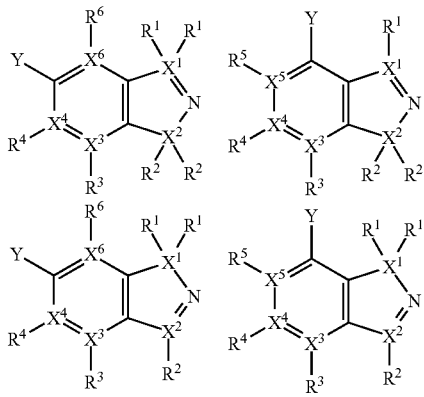

where each of the variables Y, R and X has the same meaning as above and below herein. Thus, in typical embodiments the compound takes the form of a substituted fused heterocyclic compound wherein the ring system comprises an aromatic 6-membered carbocyclic or heterocyclic ring fused to an aromatic heterocyclic 5-membered ring.

In all of the embodiments of this invention (both above and below herein), the Y group is not especially limited, provided that it does not prevent the TDO or IDO inhibitory function from occurring. In certain typical embodiments, both above and in the following, the Y group comprises an aminocarbonyl group, a carbonylamino group, an aminosulphonyl group, a sulphonylamino group, a substituted or unsubstituted piperidinyl group, a substituted or unsubstituted piperazinyl group, a substituted or unsubstituted alcohol group, a substituted or unsubstituted ether group, and/or a saturated or unsaturated, substituted or unsubstituted, carbocyclic group such as a substituted or unsubstituted cyclohexyl group or a substituted or unsubstituted phenyl group.

In all of the embodiments of this invention (both above and below herein), unless otherwise specified, the substituent (such as any R group, any X group, or any other substituent) is not especially limited, provided that it does not prevent the TDO or IDO inhibitory function from occurring. In all of the embodiments mentioned in connection with this invention, both above and in the following, the substituents are selected from H and an organic group. Thus, both above and in the following, the terms 'substituent' and 'organic group' are not especially limited and may be any functional group or any atom, especially any functional group or atom common in organic chemistry. Thus, 'substituent' and 'organic group' may have any of the following meanings.

The substituent or organic group may comprise any organic group and/or one or more atoms from any of groups IIIA, IVA, VA, VIA or VIIA of the Periodic Table, such as a B, Si, N, P, O, or S atom (e.g. OH, OR, $NH_2$, NHR, $NR_2$, SH, SR, $SO_2R$, $SO_3H$, $PO_4H_2$) or a halogen atom (e.g. F, Cl, Br or I) where R is a substituted or unsubstituted linear or branched lower hydrocarbon (1-6 C atoms) or a substituted or unsubstituted linear or branched higher hydrocarbon (7 C atoms or more, e.g. 7-40 C atoms).

When the substituent comprises an organic group, the organic group preferably comprises a hydrocarbon group.

The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups.

When the hydrocarbon comprises a cyclic group it may comprise an aromatic ring, a non-aromatic ring, an aliphatic ring, a heterocyclic group, and/or fused ring derivatives of these groups. The ring may be fully saturated, partially saturated, or fully unsaturated. The cyclic group may thus comprise a benzene, naphthalene, anthracene, phenanthrene, phenalene, biphenylene, pentalene, indene, as-indacene, s-indacene, acenaphthylene, fluorene, fluoranthene, acephenanthrylene, azulene, heptalene, pyrrole, pyrazole, imidazole, 1,2,3-triazole, 1,2,4-triazole, tetrazole, pyrrolidine, furan, tetrahydrofuran, 2-aza-tetrahydrofuran, 3-aza-tetrahydrofuran, oxazole, isoxazole, furazan, 1,2,4-oxadiazol, 1,3,4-oxadiazole, thiophene, isothiazole, thiazole, thiolane, pyridine, pyridazine, pyrimidine, pyrazine, piperidine, 2-azapiperidine, 3-azapiperidine, piperazine, pyran, tetrahydropyran, 2-azapyran, 3-azapyran, 4-azapyran, 2-aza-tetrahydropyran, 3-aza-tetrahydropyran, morpholine, thiopyran, 2-azathiopyran, 3-azathiopyran, 4-azathiopyran, thiane, indole, indazole, benzimidazole, 4-azaindole, 5-azaindole, 6-azaindole, 7-azaindole, isoindole, 4-azaisoindole, 5-azaisoindole, 6-azaisoindole, 7-azaisoindole, indolizine, 1-azaindolizine, 2-azaindolizine, 3-azaindolizine, 5-azaindolizine, 6-azaindolizine, 7-azaindolizine, 8-azaindolizine, 9-azaindolizine, purine, carbazole, carboline, benzofuran, isobenzofuran, benzothiophene, isobenzothiophene, quinoline, cinnoline, quinazoline, quinoxaline, 5-azaquinoline, 6-azaquinoline, 7-azaquinoline, isoquinoline, phthalazine, 6-azaisoquinoline, 7-azaisoquinoline, pteridine, chromene, isochromene, acridine, phenanthridine, perimidine, phenanthroline, phenoxazine, xanthene, phenoxanthiin, and/or thianthrene, as well as regioisomers of the above groups. These groups may generally be attached at any point in the group, and also may be attached at a hetero-atom or at a carbon atom. In some instances particular attachment points are preferred, such as at 1-yl, 2-yl and the like, and these are specified explicitly where appropriate. All tautomeric ring forms are included in these definitions. For example pyrrole is intended to include 1H-pyrrole, 2H-pyrrole and 3H-pyrrole.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The lower hydrocarbon group may be a methyl, ethyl, propyl, butyl, pentyl or hexyl group or regioisomers of these, such as isopropyl, isobutyl, tert-butyl, etc. The number of atoms in the ring of the cyclic group is not especially limited, but preferably the ring of the cyclic group comprises from 3-10 atoms, such as 3, 4, 5, 6, 7, 8, 9 or 10 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, sulphonyl groups, and phosphate groups etc. The substituent may also comprise derivatives of these groups, such as carboxylic acid anhydrides and carboxylic acid halides.

In addition, any substituent may comprise a combination of two or more of the substituents and/or functional groups defined above.

The invention will now be explained in more detail, by way of example only, with reference to the following Figures.

FIG. 1 shows a schematic diagram of tryptophan catabolism along the KP (from "The Kynurenine Pathway in Brain Tumour Pathogenesis", Adam et al., 2012, Cancer Res 72:5649-57).

Figure 2:
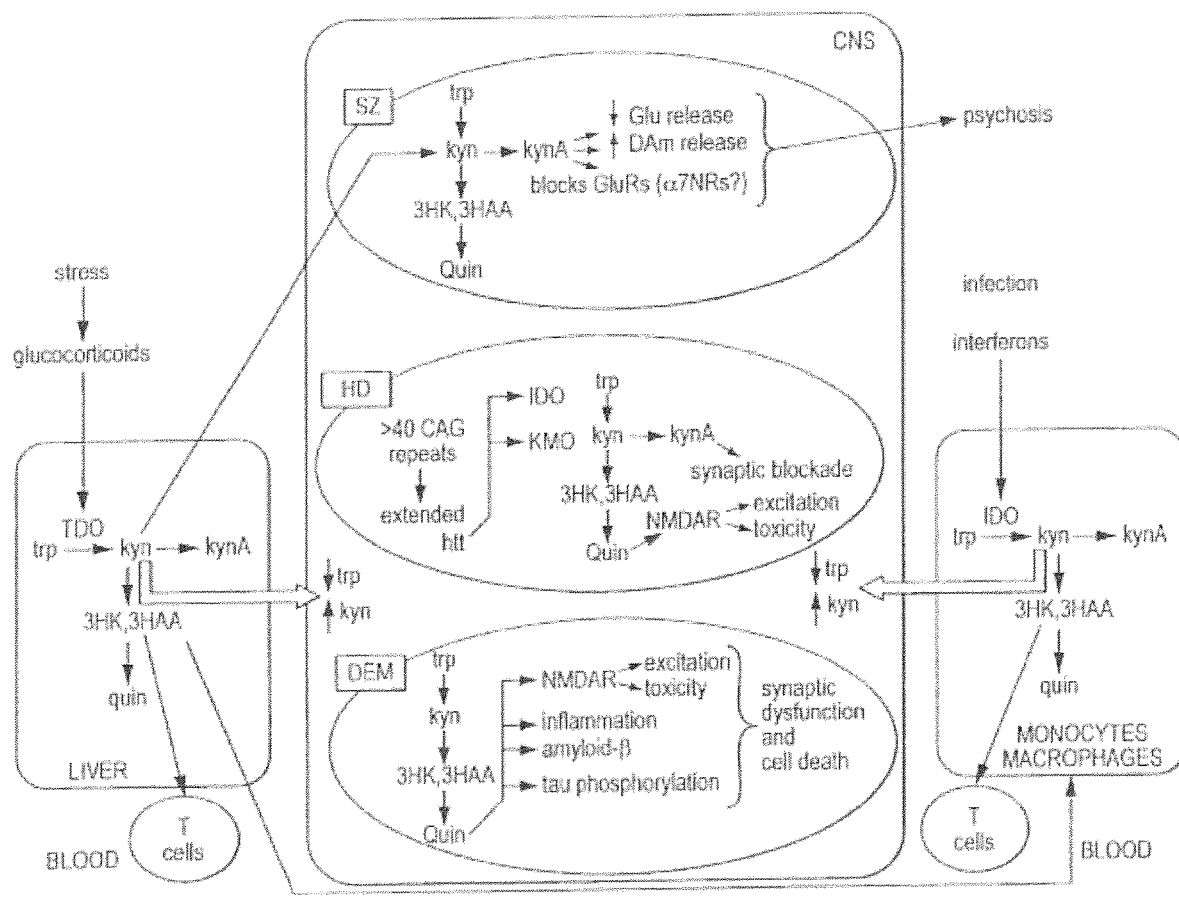

FIG. 2 shows a schematic summary of the involvement of kynurenine in CNS disorders (from "The kynurenine pathway as a therapeutic target in cognitive and neurodegenerative disorders", Stone and Darlington. Br. J. Pharmacol. 2013 169(6):1211-27).

The invention will now be described in more detail. Firstly a number of typical general structures of the compounds of the invention will be described.

As has been described, the invention relates to a tryptophan-2,3-dioxygenase (TDO) and/or indoleamine-2,3-dioxygenase (IDO) inhibitor compound for use in medicine, which compound comprises the following formula:

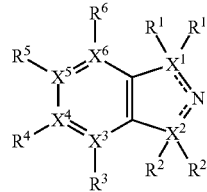

wherein $X^1$, and $X^2$ may be the same or different and each is independently selected from C, N, O and S; $X^3$, $X^4$, $X^5$, and $X^6$ may be the same or different and each is independently selected from C and N; each bond represented by a dotted line may be present or absent, provided that at least one such bond is present; $R^1$, $R^2$, $R^3$, $R^4$, $R^5$ and $R^6$ may be present or absent and may be the same or different and each is independently selected from H and a substituted or unsubstituted organic group, provided that the number of $R^1$, $R^2$, $R^3$, $R^4$, $R^5$ and $R^6$ groups present is such that the respective valencies of $X^1$, $X^2$, $X^3$, $X^4$, $X^5$, and $X^6$ are maintained; and wherein at least one of $R^5$ and $R^6$ comprises a group Y, wherein Y is a group having a formula selected from the following:

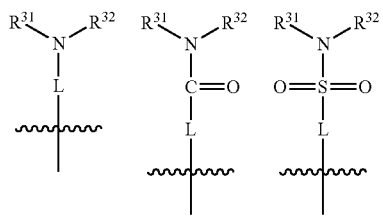

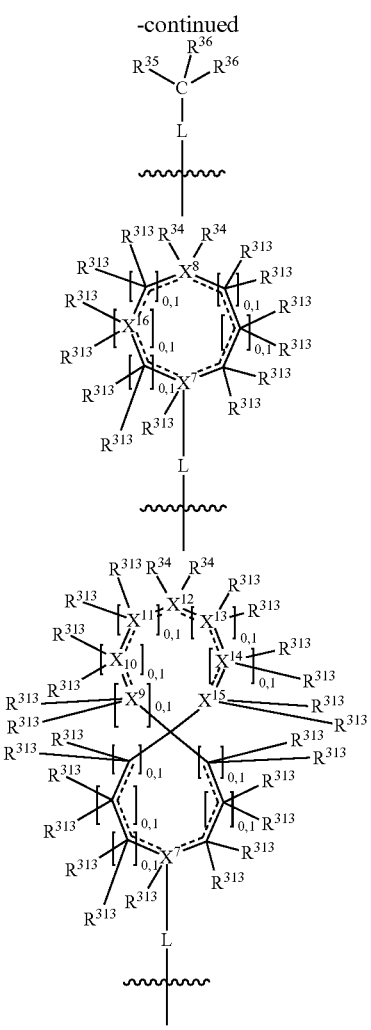

wherein L may be present or absent, and may be a substituted or unsubstituted organic linking group; $R^{31}$ and $R^{32}$ may be the same or different and are selected from H and a substituted or unsubstituted organic group; each $R^{34}$ may be the same or different and is selected from H and a substituted or unsubstituted organic group; $R^{35}$ is selected from a substituted or unsubstituted alcohol group or ether group; each $R^{36}$ may be the same or different and is selected from H and a substituted or unsubstituted organic group; $X^7$ may be selected from C and N; $X^8$, $X^9$, $X^{10}$, $X^{11}$, $X^{11}$, $X^{13}$, $X^{14}$, $X^{15}$ and $X^{16}$ may be the same or different and each is independently selected from C, N, O and S; each bond represented by a dotted line may be present or absent; and each $R^{313}$ may be the same or different and is selected from H and a substituted or unsubstituted organic group.

The fused bicyclic ring system is preferably aromatic. All tautomeric forms of the ring system (including the tautomeric forms of the 6-membered ring and the tautomeric forms of the 5-membered ring) are included.

The group L is a linking group and is not especially limited provided that it does not impair the IDO or TDO inhibitory activity of the compounds. It may be present or absent. When absent, the N atom (or the $X^7$, or the $C(R^{35})$, or the C=O, or the O=S=O) of group Y is directly attached to the ring system. When present, L may be divalent, such that it may simply link the N atom of group Y (or the $X^7$, or the $C(R^{35})$, or the C=O, or the O=S=O of group Y) to the bicyclic fused ring system. Alternatively L may be trivalent if in addition it forms a ring with $R^{31}$ or $R^{32}$ (or with $R^{35}$ or $R^{36}$), and further alternatively L may be quadravalent if it forms a ring with both $R^{31}$ and $R^{32}$ (or with $R^{35}$ and $R^{36}$).

In typical embodiments, $X^3$, $X^4$, $X^5$ and $X^6$ are all C atoms. In other typical embodiments, one of $X^3$, $X^4$, $X^5$ and $X^6$ is N.

In typical embodiments both above and below herein, $X^1$ is a C atom. In other typical embodiments, $X^1$ and $X^2$ are both C atoms. In other typical embodiments, one of $X^1$ and $X^2$ is N. In other typical embodiments, one of $X^1$ and $X^2$ is O.

In typical embodiments both above and below herein, Y comprises an aminocarbonyl group, a carbonylamino group, an aminosulphonyl group, a sulphonylamino group, a substituted or unsubstituted piperidinyl group, a substituted or unsubstituted piperazinyl group, a substituted or unsubstituted alcohol group, a substituted or unsubstituted ether group, and/or a saturated or unsaturated, substituted or unsubstituted, carbocyclic group such as a substituted or unsubstituted cyclohexyl group or a substituted or unsubstituted phenyl group.

In typical embodiments both above and below herein, L is absent. In alternative typical embodiments L may comprise a substituted or unsubstituted $C_1$-$C_7$ alkylene group (such as —$CH_2$—, —$CH_2CH_2$—, —$CH_2CH_2CH_2$—, —CH($CH_3$)$CH_2$—, —C($CH_3$)$_2$—, —$CH_2CH_2CH_2CH_2$—, —CH($CH_3$)$CH_2CH_2$—, —CH($CH_3$)CH($CH_3$)—, —CH($CH_2CH_3$)$CH_2$—, —C($CH_3$)$_2CH_2$—, —$CH_2CH_2CH_2CH_2CH_2$—, and —$CH_2CH_2CH_2CH_2CH_2CH_2$—), or a $C_1$-$C_7$ divalent alkoxy group (such as —$OCH_2$—, —$OCH_2CH_2$—, —$OCH_2CH_2CH_2$—, —O—CH($CH_3$)$CH_2$—, —OC($CH_3$)$_2$—, —$OCH_2CH_2CH_2CH_2$—, —OCH($CH_3$)$CH_2CH_2$—, —OCH($CH_3$)CH($CH_3$)—, —OCH($CH_2C_3$)$CH_2$, —OC($CH_3$)$_2CH_2$—, —$OCH_2CH_2CH_2CH_2CH_2$—, —$OCH_2CH_2CH_2CH_2CH_2CH_2$—, —OCHF—, —$OCF_2$—, —O-phenylene-, —O—$CH_2$-phenylene-, —O—$CH_2$-(2,3 or 4)-F-phenylene-, —O—$CH_2$-(2,3 or 4)-Cl-phenylene-, —$CH_2OCH_2$—, —$CH_2OCH_2CH_2$—, —$CH_2OCH_2CH_2CH_2$—, —$CH_2OCH_2CH_2CH_2CH_2$—, —$CH_2CH_2OCH_2$—, —$CH_2CH_2CH_2OCH_2$—, —$CH_2CH_2CH_2CH_2OCH_2$—, —$CH_2CH_2CH_2CH_2CH_2OCH_2$—, —$CH_2CH_2CH_2CH_2CH_2CH_2OCH_2$—, —$CH_2CH_2OCH_2CH_2$—, —$CH_2CH_2OCH_2CH_2CH_2$—, —$CH_2CH_2OCH_2CH_2CH_2CH_2$—, —$CH_2CH_2OCH_2CH_2CH_2CH_2CH_2$—, —$CH_2CH_2CH_2OCH_2CH_2$—, —$CH_2CH_2CH_2OCH_2CH_2CH_2$—, and —$CH_2CH_2CH_2OCH_2CH_2CH_2CH_2$—. Alternatively, L may be an —O— atom, or an —N($R^{32}$)— group (such as an —NH— group).

Thus, in view of the typical compounds already described, in more typical embodiments the invention relates to a compound comprising one of the following formulae:

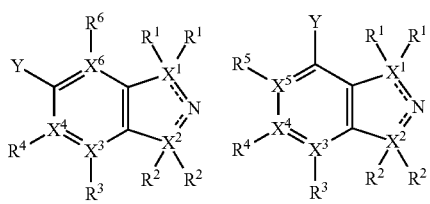

wherein, in each case, the substituents Y, R and X are as defined in any of the above and below embodiments described herein.

In all embodiments above and below herein, the 6-membered ring of the bicyclic fused ring system is aromatic and the 5-membered ring of the bicyclic fused ring system is aromatic, and the bicyclic fused ring system as a whole is aromatic.

Furthermore, in view of the typical compounds already described, in more typical embodiments the invention relates to a compound comprising one of the following formulae:

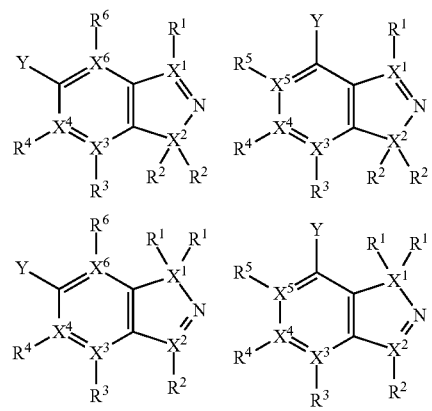

wherein, in each case, the substituents Y, X and R are as defined in any of the above or below embodiments described herein.

Furthermore, in view of the typical compounds already described, in more typical embodiments the invention relates to a compound comprising one of the following formulae:

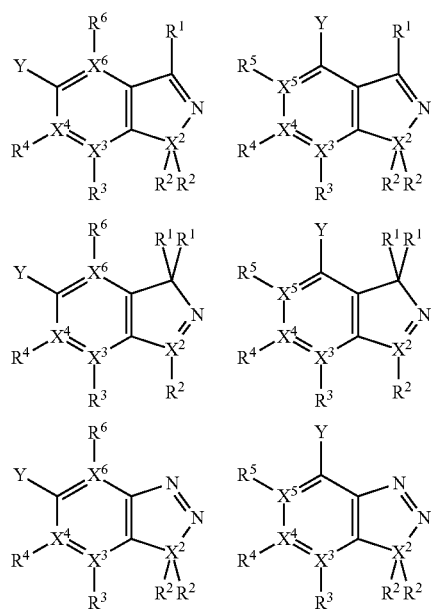

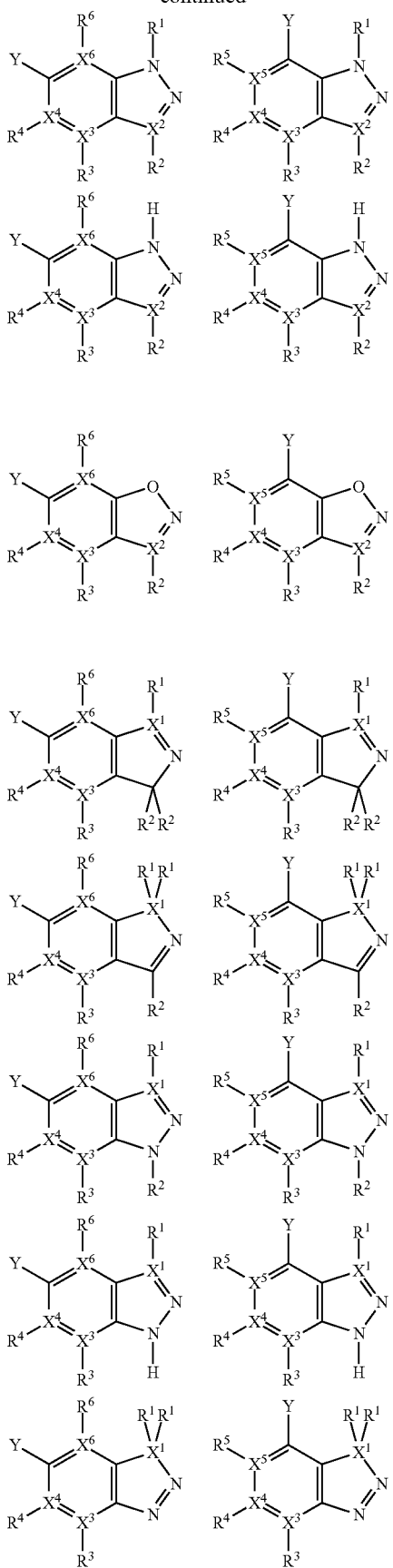
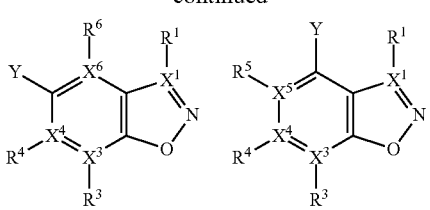
preferably wherein the compound comprises the following formula:
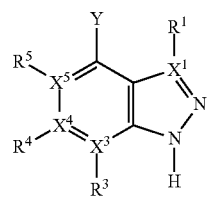
wherein, in each case, the substituents Y, X and R are as defined in any of the above or below embodiments described herein.
Furthermore, in view of the typical compounds already described, in more typical embodiments the invention relates to a compound comprising one of the following formulae:
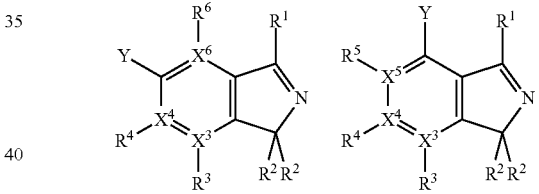
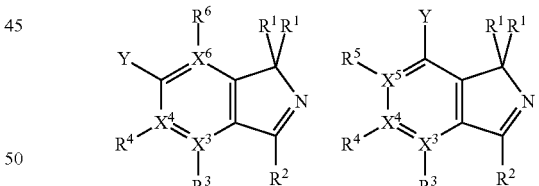
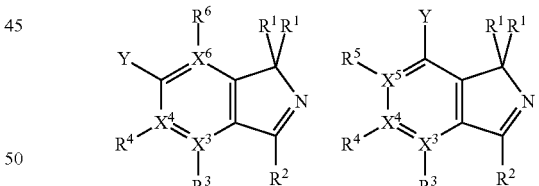
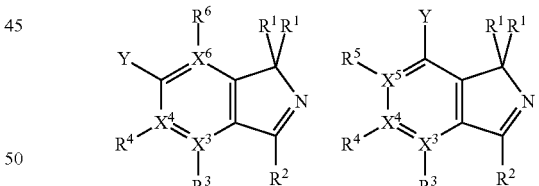

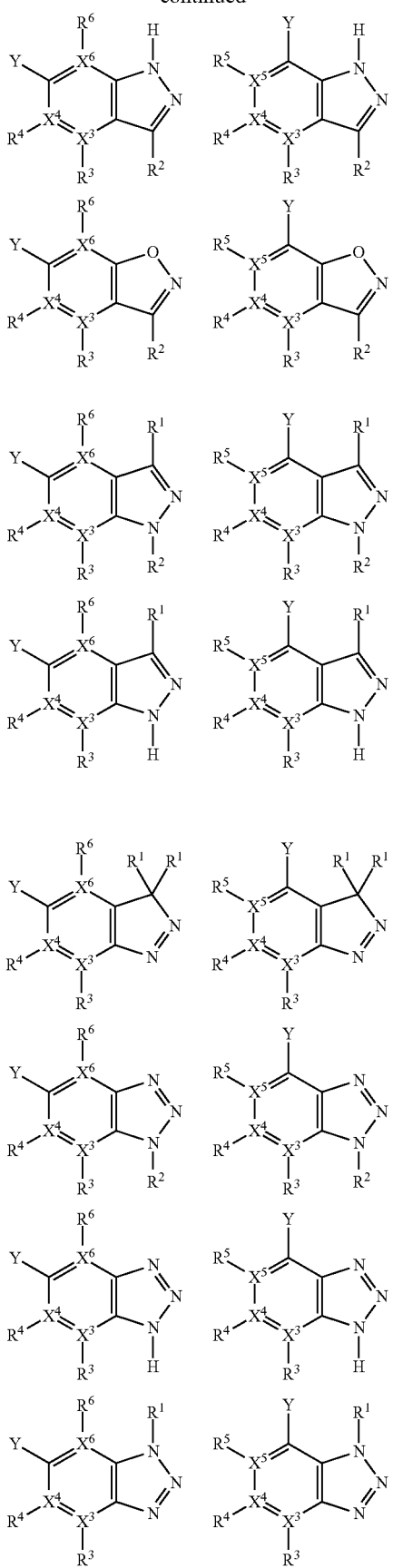
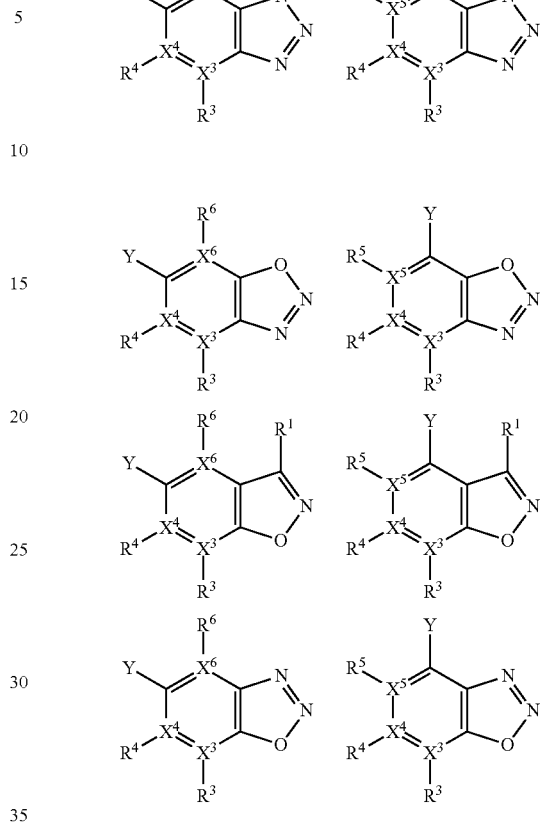
preferably wherein the compound comprises the following formula:
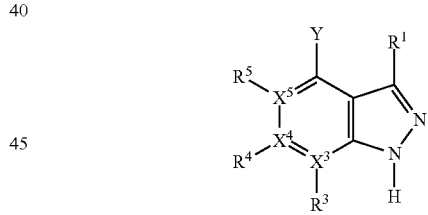
wherein, in each case, the substituents Y, X and R are as defined in any of the above or below embodiments described herein.
Furthermore, in view of the typical compounds already described, in more typical embodiments the invention relates to a compound comprising one of the following formulae:
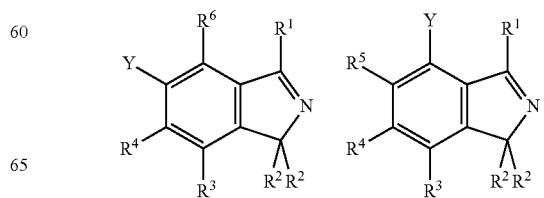

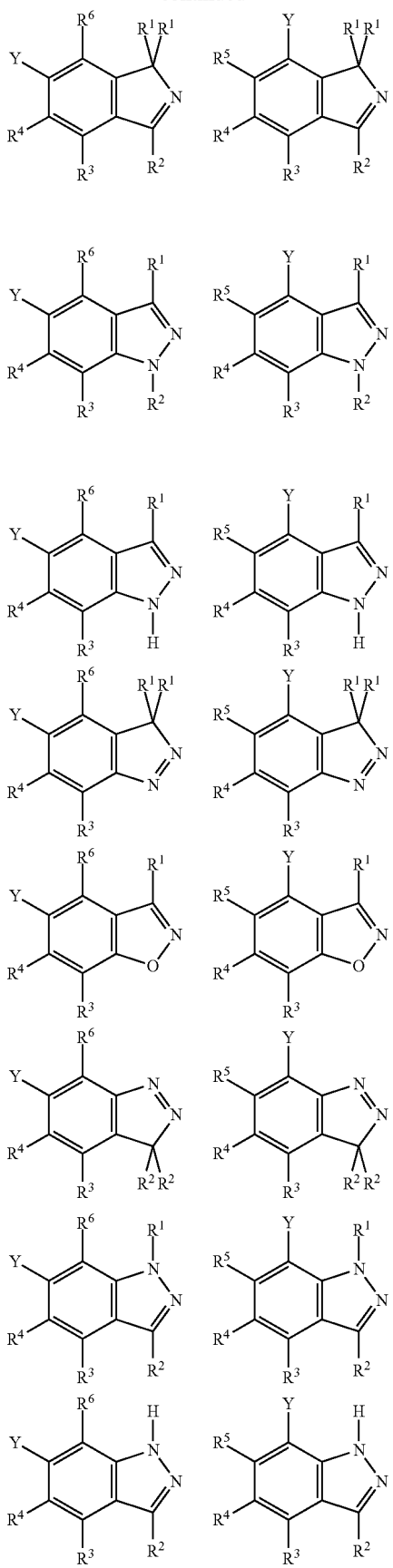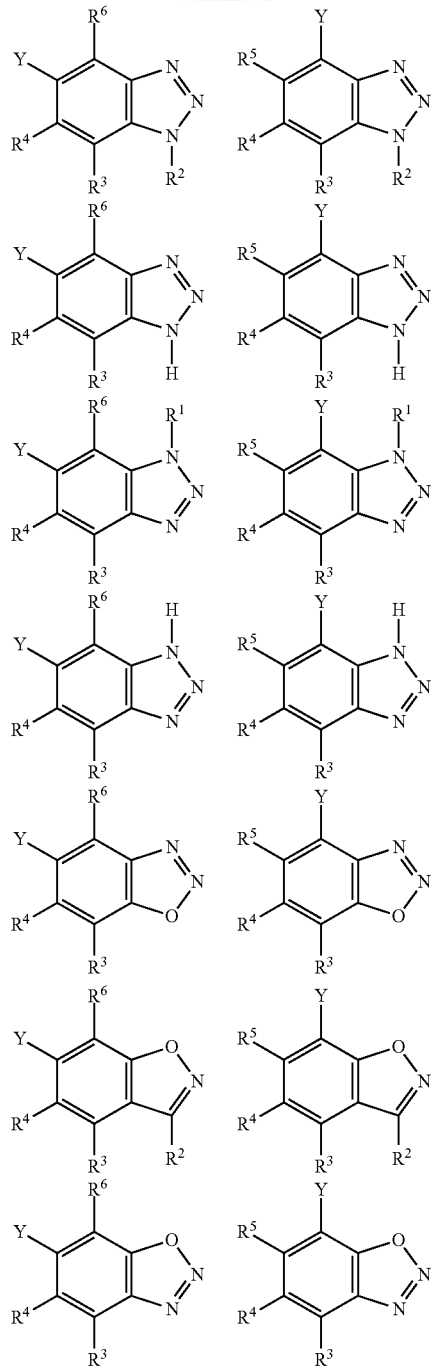
preferably wherein the compound comprises the following formula:
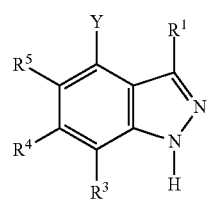

wherein, in each case, the substituents Y and R are as defined in any of the above or below embodiments described herein.

Furthermore, in view of the typical compounds already described, in more typical embodiments the invention relates to a compound comprising one of the following formulae:

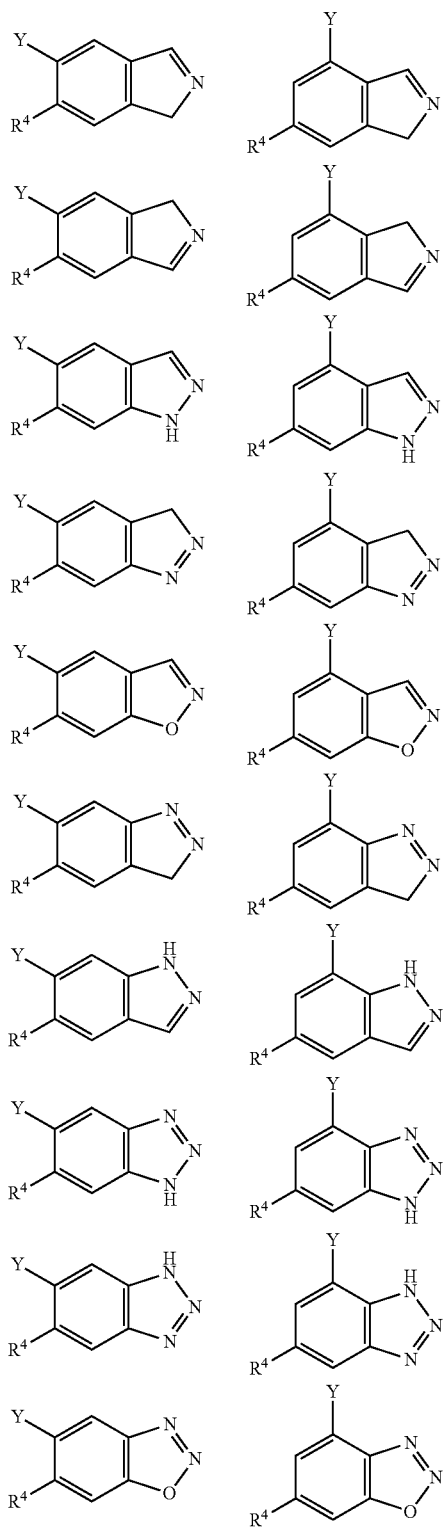

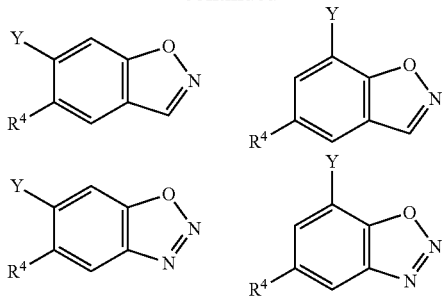

wherein, in each case, the substituents Y and $R^4$ are as defined in any of the above or below embodiments described herein, preferably wherein $R^4$ is selected from H, a halogen (such as —F, —Cl and Br), a substituted or unsubstituted $C_1$-$C_6$ alkyl group (such as a —$CF_3$ group), a substituted or unsubstituted $C_3$-$C_6$ cycloalkyl group (such as a cyclopropyl group), a substituted or unsubstituted $C_1$-$C_6$ alkoxy group, and a nitrile group, and more typically wherein $R^4$ is not H; preferably wherein the compound has the following formula:

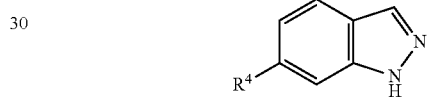

wherein, in each case, the substituents Y and $R^4$ are as defined in any of the above or below embodiments described herein, preferably wherein $R^4$ is selected from H, a halogen (such as —F, —Cl and Br), a substituted or unsubstituted $C_1$-$C_6$ alkyl group (such as a —$CF_3$ group), a substituted or unsubstituted $C_3$-$C_6$ cycloalkyl group (such as a cyclopropyl group), a substituted or unsubstituted $C_1$-$C_6$ alkoxy group, and a nitrile group, and more typically wherein $R^4$ is not H.

Furthermore, in view of the typical compounds already described, in more typical embodiments the invention relates to a compound comprising one of the following formulae:

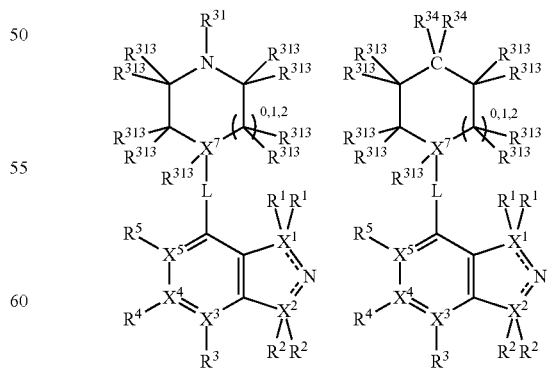

wherein, in each case, the substituents X, L and R are as defined in any of the above or below embodiments described herein, and L may be present or absent.

Furthermore, in view of the typical compounds already described, in more typical embodiments the invention relates to a compound comprising one of the following formulae:

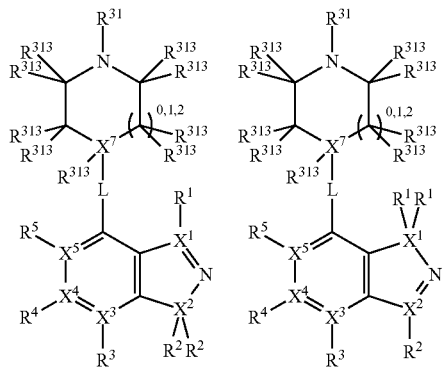

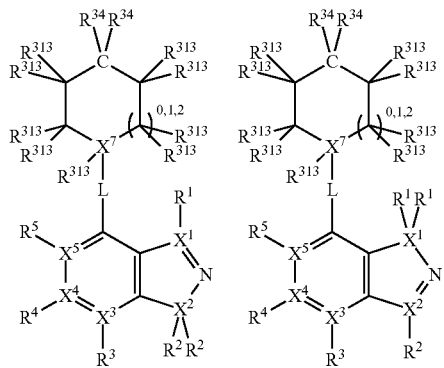

wherein, in each case, the substituents X, L and R are as defined in any of the above or below embodiments described herein, and L may be present or absent.

Furthermore, in view of the typical compounds already described, in more typical embodiments the invention relates to a compound comprising one of the following formulae:

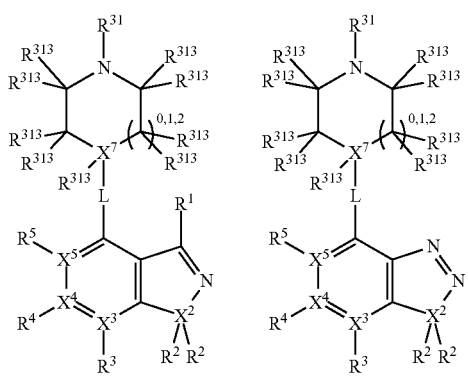

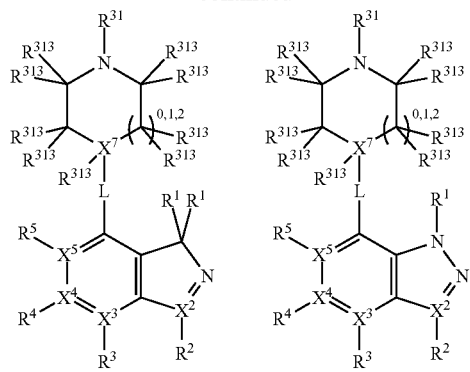

-continued

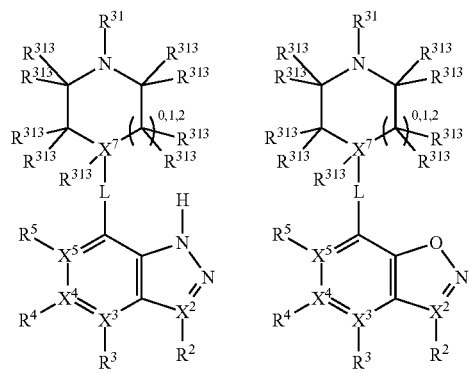

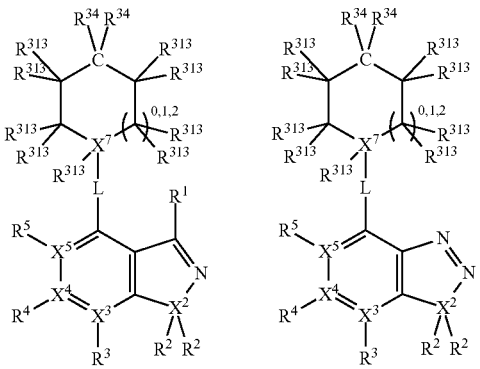

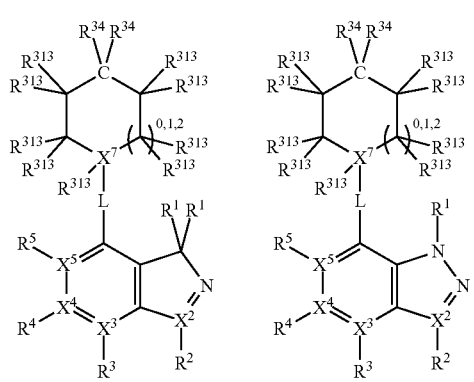

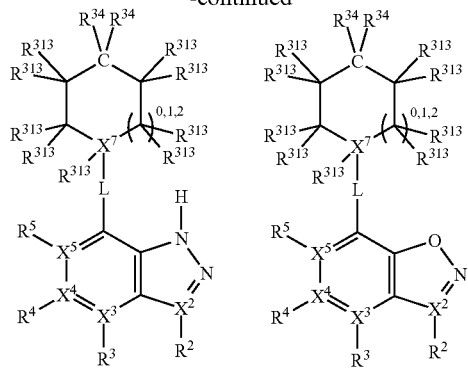

wherein, in each case, the substituents X, L and R are as defined in any of the above or below embodiments described herein, and L may be present or absent.

Furthermore, in view of the typical compounds already described, in more typical embodiments the invention relates to a compound comprising one of the following formulae:

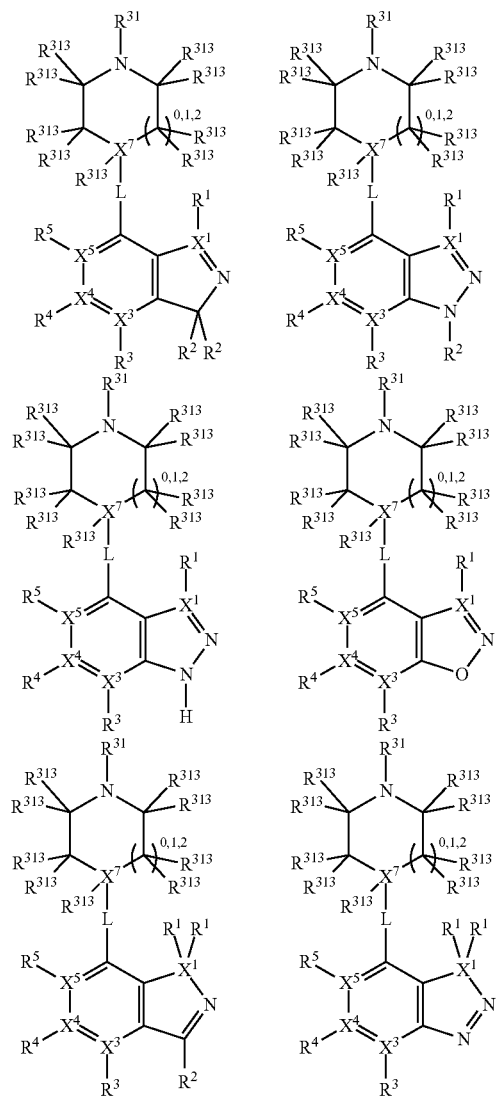

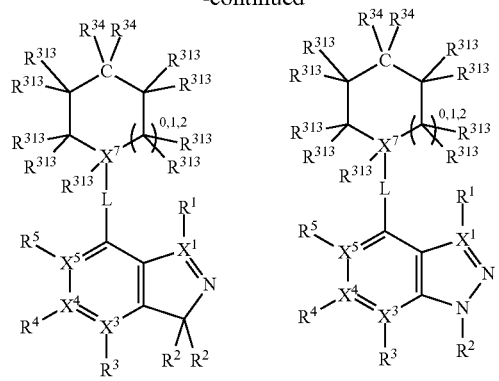

preferably wherein the compound has one of the following formulae:

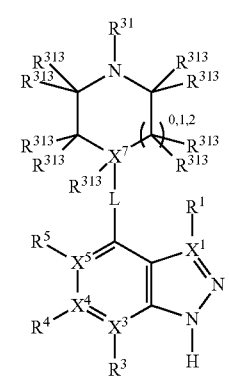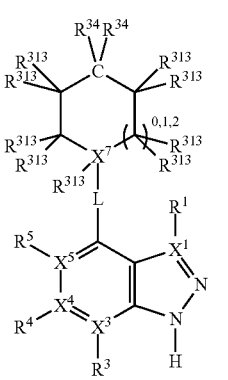

wherein, in each case, the substituents X, L and R are as defined in any of the above or below embodiments described herein, and L may be present or absent.

In such embodiments in particular, but also in other embodiments herein, $R^{31}$ (and $R^{32}$ in other embodiments) are each independently selected from H and the following groups:

- a substituted or unsubstituted linear or branched $C_1$-$C_6$ alkyl group (such as Me, Et, Pr, i-Pr, n-Bu, i-Bu, t-Bu, pentyl and hexyl);
- a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);
- a substituted or unsubstituted linear or branched $C_1$-$C_6$ halogenated alkyl group (such as —CH$_2$F, —CF$_3$, and —CH$_2$CF$_3$);
- a substituted or unsubstituted cyclic amine or amido group (such as pyrrolidin-3-yl, piperidin-3-yl, piperidin-4-yl, 2-keto-pyrrolidinyl, 3-keto-pyrrolidinyl, 2-keto-piperidinyl, 3-keto-piperidinyl, and 4-keto-piperidinyl);
- a substituted or unsubstituted cyclic $C_3$-$C_8$ alkyl group (such as cyclopropyl, cyclobutyl, cyclopentyl, cyclohexyl, cycloheptyl and cyclooctyl);
- a substituted or unsubstituted linear or branched $C_2$-$C_6$ alcohol group (such as —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$OH, and —CH$_2$CH$_2$CH$_2$CH$_2$CH$_2$OH);
- a substituted or unsubstituted linear or branched $C_1$-$C_7$ alkoxy or aryloxy group linked through —O via at least two further C atoms (such as —CH$_2$CH$_2$OPh-CH$_2$CH$_2$OMe, —CH$_2$CH$_2$OEt, —CH$_2$CH$_2$OPr, —CH$_2$CH$_2$OBu, —CH$_2$CH$_2$CH$_2$OPh, —CH$_2$CH$_2$CH$_2$OMe, —CH$_2$CH$_2$CH$_2$CH$_2$OMe, and —CH$_2$CH$_2$CH$_2$CH$_2$CH$_2$OMe);
- a substituted or unsubstituted linear or branched $C_2$-$C_6$ carboxylic acid group (such as —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);
- a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;
- a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);
- a substituted or unsubstituted linear or branched $C_1$-$C_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);
- a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO$_2$-pyrrolidine-N-yl, —SO$_2$-morpholine-N-yl, —SO$_2$NHCH$_2$OMe, and —SO$_2$NHCH$_2$CH$_2$OMe;
- a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F$_2$-Ph-, 2, (3,4,5 or 6)-Cl$_2$-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-Cl$_2$-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and
- a saturated or unsaturated, substituted or unsubstituted, heterocyclic group including an aromatic heterocyclic group and/or a non-aromatic heterocyclic group (such as pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl).

In such embodiments in particular, but also in other embodiments herein, at least one of the $R^{34}$ groups may comprise a saturated or unsaturated, substituted or unsubstituted, heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, 2-oxoimidazole-1-yl, 2-oxoimidazole-3-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl)

Furthermore, in view of the typical compounds already described, in more typical embodiments the invention relates to a compound comprising one of the following formulae:

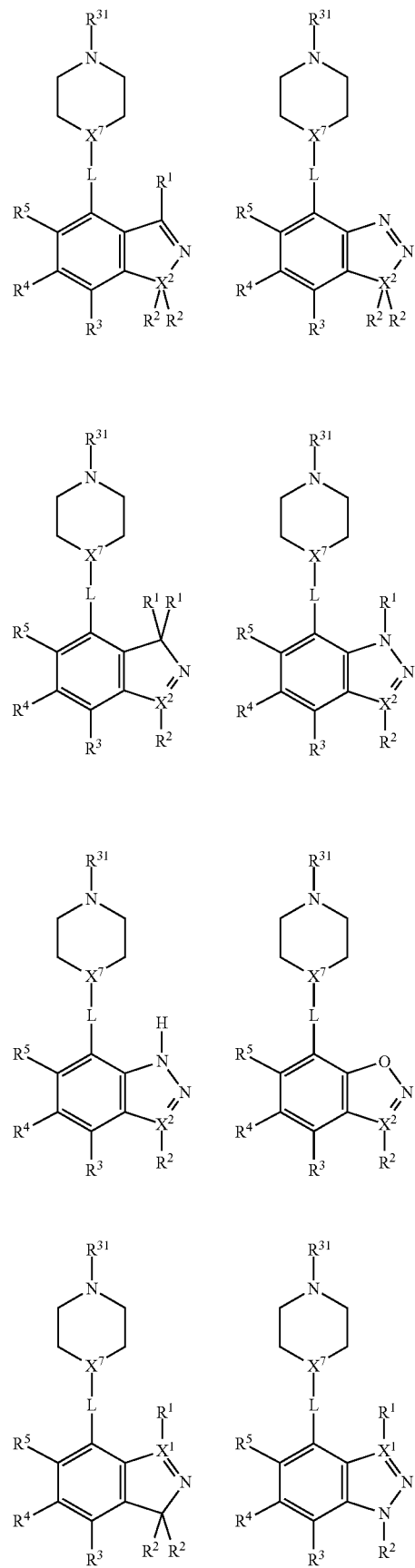

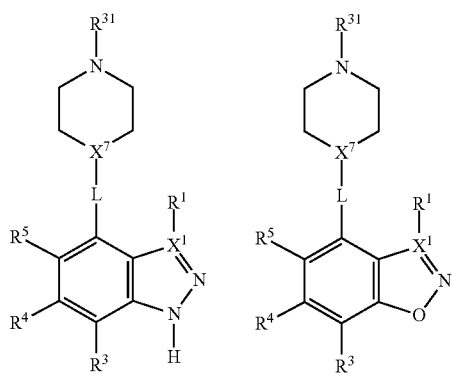
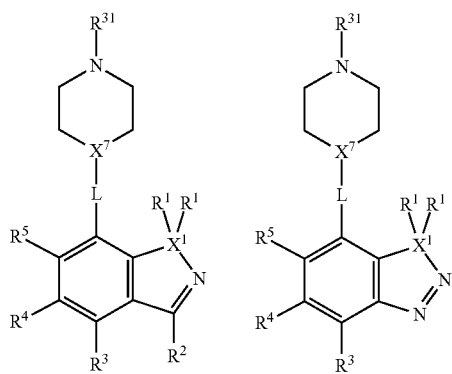
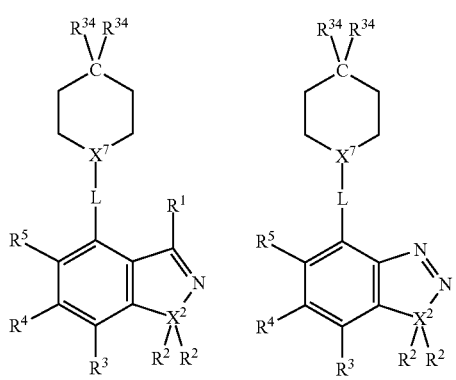
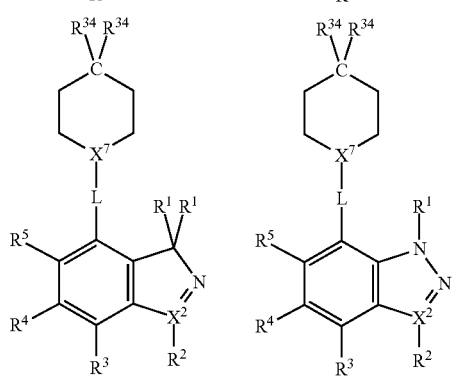
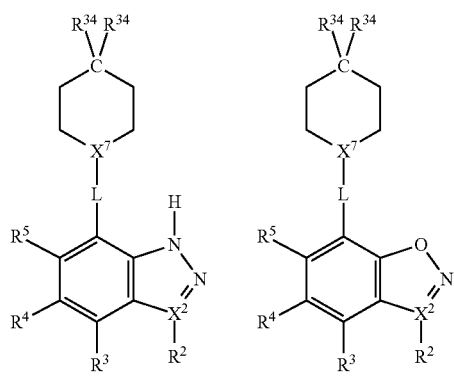
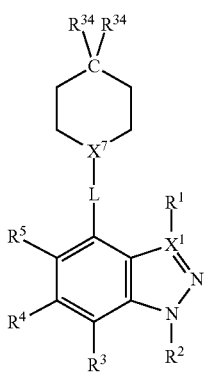
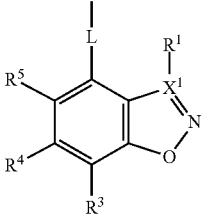
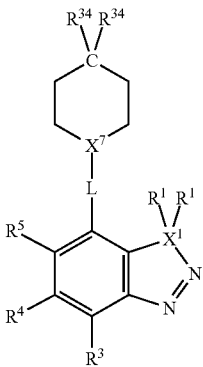

preferably wherein the compound has one of the following formulae:

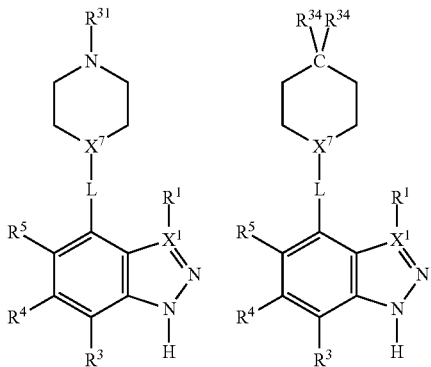

wherein, in each case, the substituents X, L and R are as defined in any of the above or below embodiments described herein, and L may be present or absent.

In such embodiments in particular, but also in other embodiments herein, $R^{31}$ and $R^{32}$ are each independently selected from H and the following groups:

- a substituted or unsubstituted linear or branched $C_1$-$C_6$ alkyl group (such as Me, Et, Pr, i-Pr, n-Bu, i-Bu, t-Bu, pentyl and hexyl);
- a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);
- a substituted or unsubstituted linear or branched $C_1$-$C_6$ halogenated alkyl group (such as —CH$_2$F, —CF$_3$, and —CH$_2$CF$_3$);
- a substituted or unsubstituted cyclic amine or amido group (such as pyrrolidin-3-yl, piperidin-3-yl, piperidin-4-yl, 2-keto-pyrrolidinyl, 3-keto-pyrrolidinyl, 2-keto-piperidinyl, 3-keto-piperidinyl, and 4-keto-piperidinyl);
- a substituted or unsubstituted cyclic $C_3$-$C_8$ alkyl group (such as cyclopropyl, cyclobutyl, cyclopentyl, cyclohexyl, cycloheptyl and cyclooctyl);
- a substituted or unsubstituted linear or branched $C_2$-$C_6$ alcohol group (such as —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);
- a substituted or unsubstituted linear or branched $C_2$-$C_6$ carboxylic acid group (such as —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);
- a substituted or unsubstituted linear or branched $C_1$-$C_7$ alkoxy or aryloxy group linked through —O via at least two further C atoms (such as —CH$_2$CH$_2$OPh-CH$_2$CH$_2$OMe, —CH$_2$CH$_2$OEt, —CH$_2$CH$_2$OPr, —CH$_2$CH$_2$OBu, —CH$_2$CH$_2$CH$_2$OPh, —CH$_2$CH$_2$CH$_2$OMe, —CH$_2$CH$_2$CH$_2$CH$_2$OMe, and —CH$_2$CH$_2$CH$_2$CH$_2$CH$_2$OMe);
- a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;
- a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);
- a substituted or unsubstituted linear or branched $C_1$-$C_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);
- a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO2-pyrrolidine-N-yl, —SO$_2$-morpholine-N-yl, —SO$_2$NHCH$_2$OMe, and —SO$_2$NHCH$_2$CH$_2$OMe;
- a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F$_2$-Ph-, 2, (3,4,5 or 6)-Cl$_2$-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-Cl$_2$-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and
- a saturated or unsaturated, substituted or unsubstituted, heterocyclic group including an aromatic heterocyclic group and/or a non-aromatic heterocyclic group (such as pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl).

In such embodiments in particular, but also in other embodiments herein, at least one of the $R^{34}$ groups may comprise a saturated or unsaturated, substituted or unsubstituted, heterocyclic group including an aromatic heterocyclic group and/or a non-aromatic heterocyclic group (such as pyrrole-1-yl, pyrrole-2-yl, pole-3-yl, pyrazole-1-yl, pyrazole-3-yl, pyrazole-4-yl, pyrazole-5-yl, 2-oxoimidazole-1-yl, 2-oxoimidazole-3-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-2-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl).

The Y, R and X groups in all of the compounds and structures both above and below herein will now be described in more detail.

As has been mentioned, the number of R substituents on an X or a ring atom will depend on its valency. Thus, it will be apparent in all of the embodiments of the invention, both above and below, that an X will have no substituents if it is O or S or N with a double bond, and 1 substituent (H or an organic group as defined herein) if it is N with a single bond or C with a double bond, and two substituents if it is C without a double bond.

As has been mentioned, in all of the embodiments of this invention (both above and below herein), the substituent is not especially limited, provided that it does not prevent the TDO or IDO inhibitory function from occurring. However, in typical embodiments, the substituents may be selected independently as follows.

$R^1$ and $R^2$ are typically each independently selected from H and a group selected from the following groups:

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted linear or branched $C_1$-$C_6$ halogenated alkyl group (such as —CH$_2$F, —CF$_3$, and —CH$_2$CF$_3$);

an —NH$_2$ group, or a substituted or unsubstituted linear or branched primary secondary or tertiary $C_1$-$C_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2, (3,4,5 or 6)F$_2$-Ph, —NH-2, (3,4,5 or 6)Cl$_2$-Ph, —NH-2, (3,4,5 or 6)Br$_2$-Ph, —NH-2, (3,4,5 or 6)I$_2$-Ph, —NH-2, (3,4,5 or 6)Me$_2$-Ph, —NH-2, (3,4,5 or 6)Et$_2$-Ph, —NH-2, (3,4,5, or 6)Pr$_2$-Ph, —NH-2, (3,4,5 or 6)Bu$_2$-Ph, a substituted or unsubstituted cyclic $C_3$-$C_8$ alkyl group (such as cyclopropyl, cyclobutyl, cyclopentyl, cyclohexyl, cycloheptyl and cyclooctyl);

an —OH or a substituted or unsubstituted linear or branched $C_1$-$C_6$ alcohol group (such as —CH$_2$OH, —CH₂CH₂OH, —CH₂CH₂CH₂OH, —CH(CH₃)CH₂OH, —C(CH₃)₂OH, —CH₂CH₂CH₂CH₂OH, —CH(CH₃)CH₂CH₂OH, —CH(CH₃)CH(CH₃)OH, —CH(CH₂CH₃)CH₂OH, —C(CH₃)₂CH₂OH, —CH₂CH₂CH₂CH₂CH₂OH, and —CH₂CH₂CH₂CH₂CH₂CH₂);

a substituted or unsubstituted linear or branched $C_1$-$C_6$ carboxylic acid group (such as —COOH, —CH₂COOH, —CH₂CH₂COOH, —CH₂CH₂CH₂COOH, —CH₂CH₂CH₂CH₂COOH, and —CH₂CH₂CH₂CH₂CH₂COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH₂Ph, —(CO)CH₂OH, —(CO)CH₂OCH₃, —(CO)CH₂NH₂, —(CO)CH₂NHMe, —(CO)CH₂NMe₂, —(CO)-cyclopropyl, —(CO)-1,3-epoxypropan-2-yl; —(CO)NH₂, —(CO)NHMe, —(CO)NMe₂, —(CO)NHEt, —(CO)NEt₂, —(CO)-pyrollidine-N-yl, —(CO)-morpholine-N-yl, —(CO)-piperazine-N-yl, —(CO)—N-methyl-piperazine-N-yl, —(CO)NHCH₂CH₂OH, —(CO)NHCH₂CH₂OMe, —(CO)NHCH₂CH₂NH₂, —(CO)NHCH₂CH₂NHMe, and —(CO)NHCH₂CH₂NMe₂;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH₂COOMe, —CH₂CH₂COOMe, —CH₂CH₂CH₂COOMe, and —CH₂CH₂CH₂CH₂COOMe);

a substituted or unsubstituted linear or branched $C_1$-$C_6$ amide group (such as —CO—NH₂, —CO—NMeH, —CO—NMe₂, —CO—NEtH, —CO—NEtMe, —CO—NEt₂, —CO—NPrH, —CO—NPrMe, and —CO—NPrEt);

a substituted or unsubstituted linear or branched $C_1$-$C_7$ amino carbonyl group (such as —NH—CO-Me, —NH—CO-Et, —NH—CO—Pr, —NH—CO-Bu, —NH—CO-pentyl, —NH—CO-hexyl, —NH—CO-Ph, —NMe-CO-Me, —NMe-CO-Et, —NMe-CO—Pr, —NMe-CO-Bu, —NMe-CO-pentyl, —NMe-CO-hexyl, —NMe-CO-Ph;

a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH₂F, —OCHF₂, —OCF₃, —O-Ph, —O—CH₂-Ph, —O—CH₂-(2,3 or 4)-F-Ph, —O—CH₂-(2,3 or 4)-Cl-Ph, —CH₂OMe, —CH₂OEt, —CH₂OPr, —CH₂OBu, —CH₂CH₂OMe, —CH₂CH₂CH₂OMe, —CH₂CH₂CH₂CH₂OMe, and —CH₂CH₂CH₂CH₂CH₂OMe);

a substituted or unsubstituted linear or branched aminoalkoxy group (such as —OCH₂CH₂NH₂, —OCH₂CH₂NHMe, —OCH₂CH₂NMe₂, —OCH₂CH₂NHEt, and —OCH₂CH₂NEt₂;

a substituted or unsubstituted sulphonyl group (such as —SO₂Me, —SO₂Et, —SO₂Pr, —SO₂iPr, —SO₂Ph, —SO₂-(2,3 or 4)-F-Ph, —SO₂-cyclopropyl, —SO₂CH₂CH₂OCH₃), —SO₂NH₂, —SO₂NHMe, —SO₂NMe₂, —SO₂NHEt, —SO₂NEt₂, —SO₂-pyrolidine-N-yl, —SO₂-morpholine-N-yl, —SO₂NHCH₂OMe, and —SO₂NHCH₂CH₂OMe;

an substituted or unsubstituted aminosulphonyl group (such as —NHSO₂Me, —NHSO₂Et, —NHSO₂Pr, —NHSO₂iPr, —NHSO₂Ph, —NHSO₂-(2,3 or 4)-F-Ph, —NHSO₂-cyclopropyl, —NHSO₂CH₂CH₂OCH₃);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F₂-Ph-, 2, (3,4,5 or 6)-Cl₂-Ph-, 2, (3,4,5 or 6)-Br₂-Ph-, 2, (3,4,5 or 6)-I₂-Ph-, 2, (3,4,5 or 6)-Me₂-Ph-, 2, (3,4,5 or 6)-Et₂-Ph-, 2, (3,4,5 or 6)-Pr₂-Ph-, 2, (3,4,5 or 6)-Bu₂-Ph-, 2, (3,4,5 or 6)-(CN)₂-Ph-, 2, (3,4,5 or 6)-(NO₂)₂-Ph-, 2, (3,4,5 or 6)-(NH₂)₂-Ph-, 2, (3,4,5 or 6)-(MeO)₂-Ph-, 2, (3,4,5 or 6)-(CF₃)₂-Ph-, 3, (4 or 5)-F₂-Ph-, 3, (4 or 5)-Cl₂-Ph-, 3, (4 or 5)-Br₂-Ph-, 3, (4 or 5)-I₂-Ph-, 3, (4 or 5)-Me₂-Ph-, 3, (4 or 5)-Et₂-Ph-, 3, (4 or 5)-Pr₂-Ph-, 3, (4 or 5)-Bu₂-Ph-, 3, (4 or 5)-(CN)₂-Ph-, 3, (4 or 5)-(NO₂)₂-Ph-, 3, (4 or 5)-(NH₂)₂-Ph-, 3, (4 or 5)-(MeO)₂-Ph-, 3, (4 or 5)-(CF₃)₂-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO₂)-Ph-, 3-(NO₂)-Ph-4-(NO₂)-Ph-, 2-(NH₂)-Ph-, 3-(NH₂)-Ph-, 4-(NH₂)-Ph-, 2-MeO-Ph-, 3-MeO-Ph-, 4-MeO-Ph-, 2-H₂—CO)Ph-, 3-(NH₂—CO)-Ph-, 4-(NH₂—CO)-Ph-, 2-CF₃-Ph-, 3-CF₃-Ph-, 4-CF₃-Ph, 2-CF₃O-Ph-, 3-CF₃O-Ph-, and 4-CF₃O-Ph-); and a saturated or unsaturated, substituted or unsubstituted, heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrazine-2-yl, pyrrolidine-1-yl, pyrolidine-2-yl, pyrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydrofuran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thine-3-yl, thine-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl).

$R^3$, $R^4$, $R^5$, $R^6$ and $R^{313}$ are typically each independently selected from H and a group selected from the following groups:

- a halogen (such as —F, —Cl, —Br and —I);
- a nitrile group;
- a substituted or unsubstituted linear or branched $C_1$-$C_6$ alkyl group (such as Me, Et, Pr, i-Pr, n-Bu, i-Bu, t-Bu, pentyl and hexyl);
- a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —C$_2$H$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);
- a substituted or unsubstituted linear or branched $C_1$-$C_6$ halogenated alkyl group (such as —CH$_2$F, —CH$_2$Cl, —CF$_3$, —CCl$_3$—CBr$_3$, —CI$_3$, —CH$_2$CF$_3$, —CH$_2$CCl$_3$, —CH$_2$CBr$_3$, and —CH$_2$CI$_3$);
- an —NH$_2$ group, or a substituted or unsubstituted linear or branched primary secondary or tertiary $C_1$-$C_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);
- a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2, (3,4,5 or 6)F$_2$-Ph, —NH-2, (3,4,5 or 6)Cl$_2$-Ph, —NH-2, (3,4,5 or 6)Br$_2$-Ph, —NH-2, (3,4,5 or 6)I$_2$-Ph, —NH-2, (3,4,5 or 6)Me$_2$-Ph, —NH-2, (3,4,5 or 6)Et$_2$-Ph, —NH-2, (3,4,5, or 6)Pr$_2$-Ph, —NH-2, (3,4,5 or 6)Bu$_2$-Ph,
- a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);
- a substituted or unsubstituted cyclic $C_3$-$C_8$ alkyl group (such as cyclopropyl, cyclobutyl, cyclopentyl, cyclohexyl, cycloheptyl and cyclooctyl);
- an —OH or a substituted or unsubstituted linear or branched $C_1$-$C_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);
- a substituted or unsubstituted linear or branched $C_1$-$C_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);
- a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;
- a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);
- a substituted or unsubstituted linear or branched $C_1$-$C_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);
- a substituted or unsubstituted linear or branched $C_1$-$C_7$ amino carbonyl group (such as —NH—CO-Me, —NH—CO-Et, —NH—CO—Pr, —NH—CO-Bu, —NH—CO-pentyl, —NH—CO-hexyl, —NH—CO-Ph, —NMe-CO-Me, —NMe-CO-Et, —NMe-CO—Pr, —NMe-CO-Bu, —NMe-CO-pentyl, —NMe-CO-hexyl, —NMe-CO-Ph;
- a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);
- a substituted or unsubstituted linear or branched amino-alkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;
- a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO$_2$-pyrrolidine-N-yl, —SO$_2$-morpholine-N-yl, —SO$_2$NHCH$_2$OMe, and —SO$_2$NHCH$_2$CH$_2$OMe;
- an substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);
- a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F$_2$-Ph-, 2, (3,4,5 or 6)-Cl$_2$-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-Cl$_2$-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-);

a saturated or unsaturated, substituted or unsubstituted, heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl);

and where there are two R$^{313}$ groups attached to the same atom, they may together form a group which is double bonded to that atom, (such as a carbonyl group (═O) or an alkene group (═C(R')$_2$) wherein each R' group is the same or different and is H or an organic group, preferably H or a straight or branched C$_1$-C$_6$ alkyl group), or the two R$^{313}$ groups on the same atom may form a ring, preferably a substituted or unsubstituted C$_3$-C$_6$ saturated carbocyclic ring together with the atom to which they are attached (such as a substituted or unsubstituted cyclopropyl ring or a substituted or unsubstituted cyclobutyl ring), this being more preferable when the two R$^{313}$ groups are on an atom adjacent to the X$^8$, or adjacent to the X$^{12}$ and/or adjacent to the X$^7$.

More typically, where present, R$^1$ and R$^2$ are independently selected from H, a substituted or unsubstituted C$_1$-C$_6$ alkyl group, an —NH$_2$ group and a substituted or unsubstituted C$_1$-C$_6$ amino group, and a substituted or unsubstituted C$_1$-C$_6$ alkoxy group. Most typically, R$^1$ and R$^2$ are both H. More typically, where present R$^3$, R$^5$ and R$^6$ are independently selected from H, a halogen (such as —F, —Cl and —Br) a substituted or unsubstituted C$_1$-C$_6$ alkyl group (such as a —CF$_3$ group), an —NH$_2$ group and a substituted or unsubstituted C$_1$-C$_6$ amino group, a substituted or unsubstituted C$_1$-C$_6$ alkoxy group, and a nitrile group. More typically, R$^4$ is selected from H, a halogen (such as —F, —Cl and Br), a substituted or unsubstituted C$_1$-C$_6$ alkyl group (such as a —CF$_3$ group), a substituted or unsubstituted C$_3$-C$_6$ cycloalkyl group (such as a cyclopropyl group), a substituted or unsubstituted C$_1$-C$_6$ alkoxy group, and a nitrile group, and further typically R$^4$ is not H. More typically each R$^{313}$ is selected from H, a halogen (such as —F and —Cl) a substituted or unsubstituted C$_1$-C$_6$ alkyl group, an —NH$_2$ group and a substituted or unsubstituted C$_1$-C$_6$ amino group, a substituted or unsubstituted C$_1$-C$_6$ alkoxy group, a nitrile group, a substituted or unsubstituted aromatic or aliphatic cyclic group (such as a carbocyclic group or a heterocyclic group, such as a substituted or unsubstituted phenyl group). Typically when two R$^{33}$ groups on the same atom form a ring, it is a ring as described already above, and may typically be a C$_3$-C$_6$ saturated carbocyclic ring such as a cyclopropyl ring or a cyclobutyl ring. In certain embodiments, where present (and not a group Y) all of R$^1$, R$^2$, R$^3$, R$^4$, R, R$^6$ and R$^{313}$ are H, or one of R$^1$, R$^2$, R$^3$, R$^4$, R$^5$ and R$^6$ that is not Y is not H and all of R$^{313}$ are H.

As has been mentioned the group Y has the following formula:

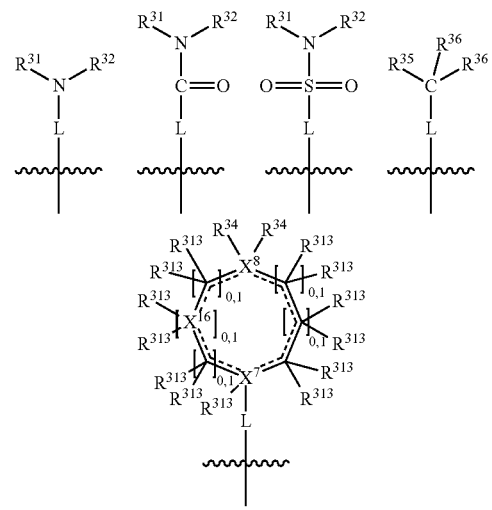

-continued

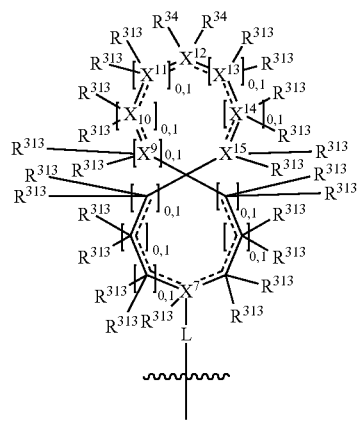

wherein L may be present or absent, and may be any substituted or unsubstituted organic linking group; $R^{31}$ and $R^{32}$ may be the same or different and are selected from H and a substituted or unsubstituted organic group; each $R^{34}$ may be the same or different and is selected from H and a substituted or unsubstituted organic group; $R^{35}$ is selected from a substituted or unsubstituted alcohol group or ether group; each $R^{36}$ may be the same or different and is selected from H and a substituted or unsubstituted organic group; $X^7$ is selected from C and N; each bond represented by a dotted line may be present or absent; and each $R^{313}$ may be the same or different and is selected from H and a substituted or unsubstituted organic group.

The following Y group:

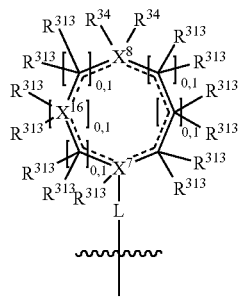

is typically a group having one of the following formulae:

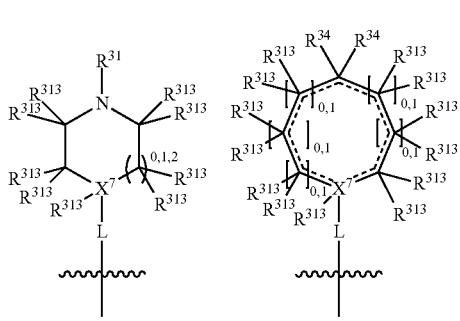

-continued

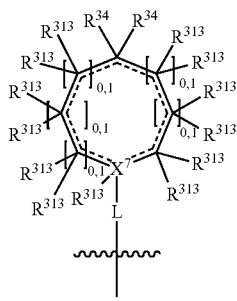

In turn, the following Y group:

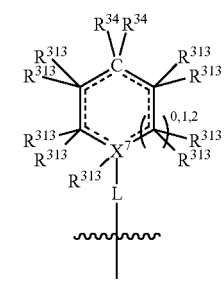

is more typically a group having one of the following formula:

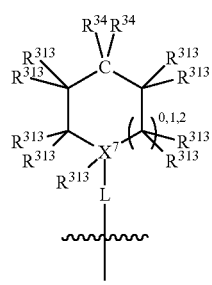

and more typically a group having one of the following formulae:
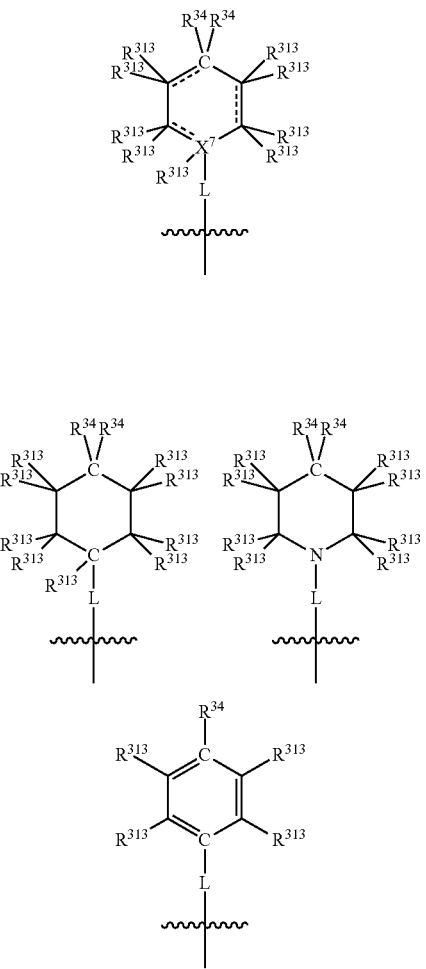
such as.
The following Y group:
is typically a group having the following formula:
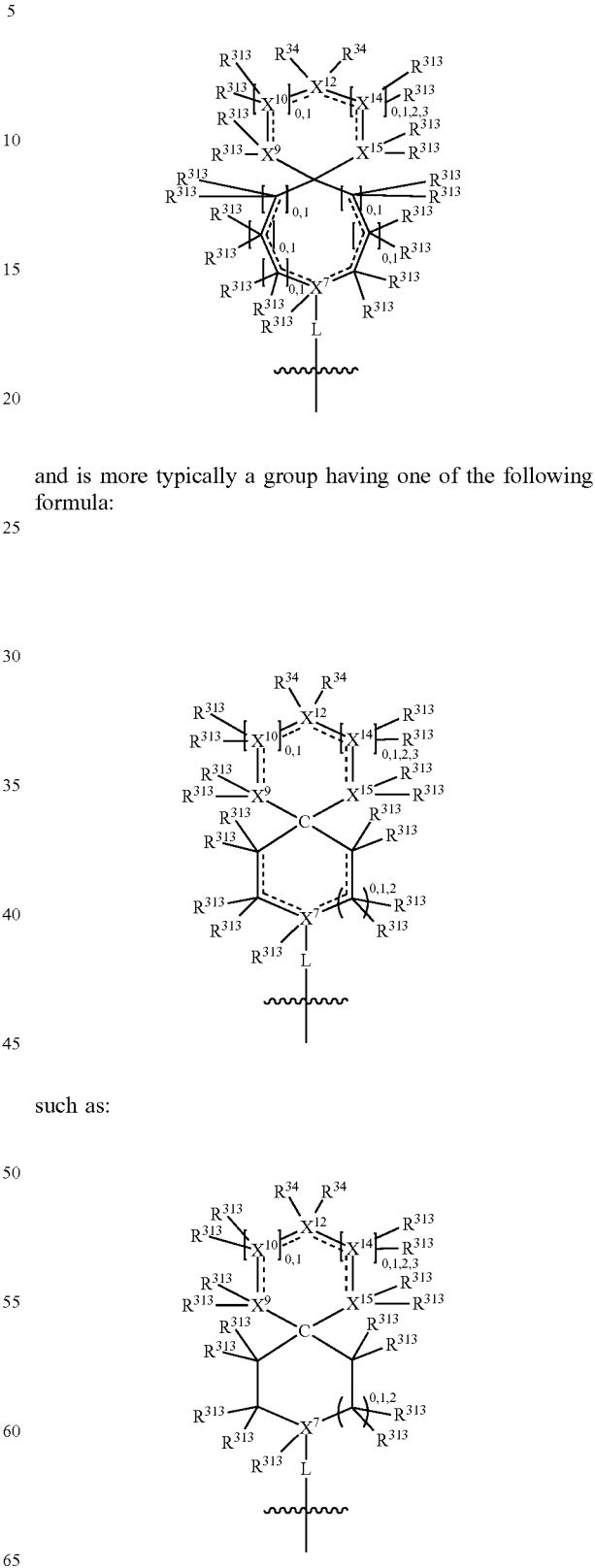
and is more typically a group having one of the following formula:
such as:

and more typically still a group having one of the following formulae:

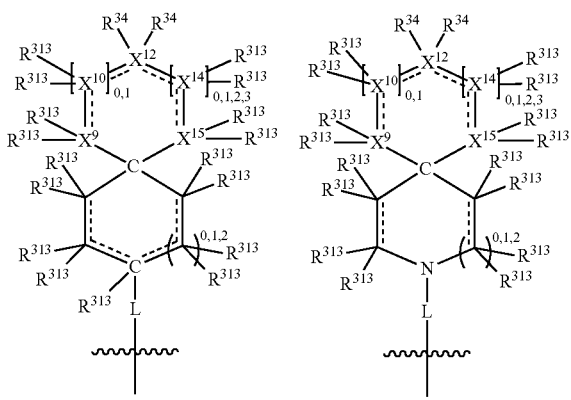

In the present context, any group may be a linking group provided that it is capable of joining the ring system to the rest of the Y group. Typically the linking group is divalent, but may be trivalent or tetravalent in some embodiments. In some typical embodiments, $R^{32}$ is H:

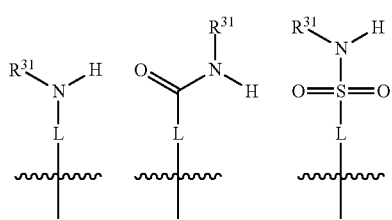

or $R^3$ is H:

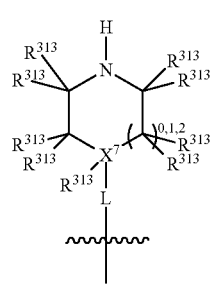

or at least one $R^{34}$ is H:

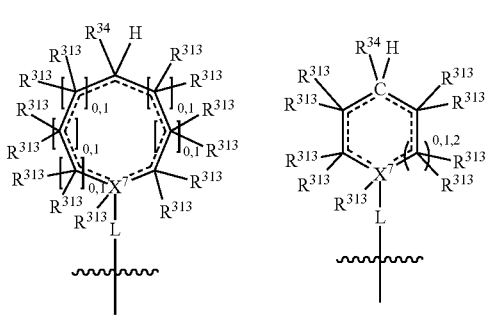

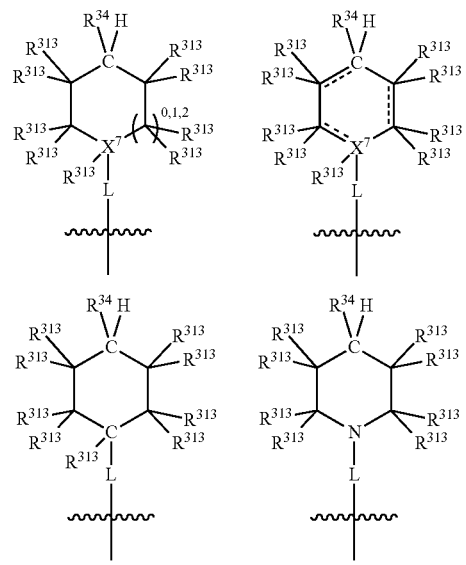

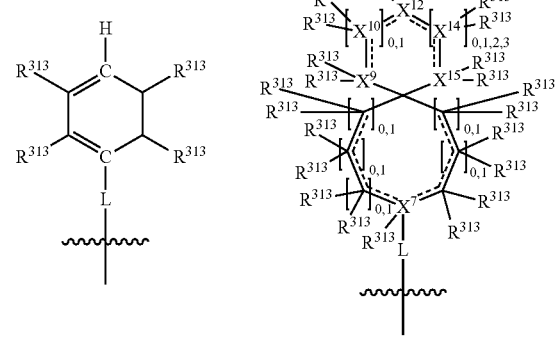

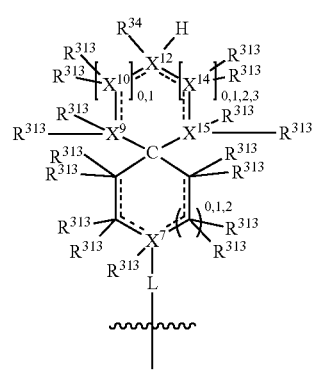

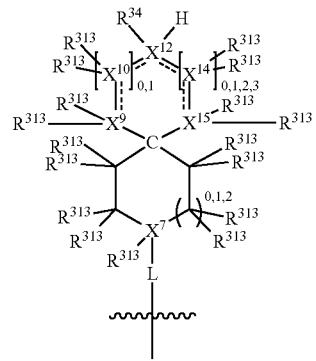

-continued

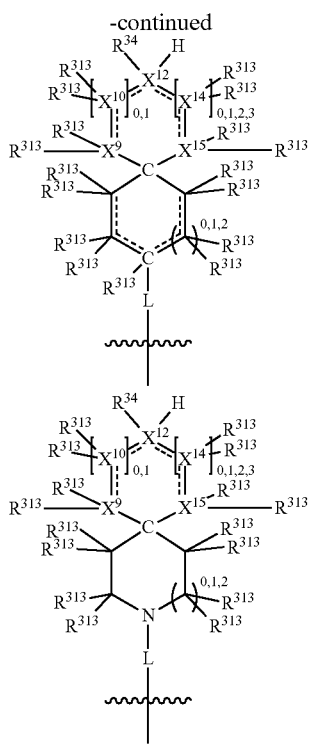

or one or both of $R^{36}$ is H:

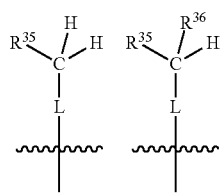

In typical embodiments there is one Y group present, but it is not excluded that a plurality of Y groups may be present in some cases, such as 2 or more Y groups, or 3 or more Y groups, or 4 or more Y groups. Provided that at lease one of $R^5$ and $R^6$ is Y, any one or more of $R^3$, $R^4$, $R^5$ and $R^6$ may comprise the further group Y. Thus, $R^3$ may comprise a Y group. $R^4$ may comprise a Y group. $R^5$ may comprise a Y group. $R^6$ may comprise a Y group.

As has been mentioned, in typical embodiments, the group L may be present or absent. When present L is a linker group attaching Y to the ring system. L is not especially limited, provided that the function of the molecule is not impaired. Accordingly, any known linking groups in organic chemistry may be employed. Typically L is a divalent group, suitable for linking the ring system to the group Y. In such embodiments L may, for example, comprise a substituted or unsubstituted $C_1$-$C_7$ alkylene group (such as —$CH_2$—, —$CH_2CH_2$—, —$CH_2CH_2CH_2$—, —$CH(CH_3)CH_2$—, —$C(CH_3)_2$—, —$CH_2CH_2CH_2CH_2$—, —$CH(CH_3)CH_2CH_2$—, —$CH(CH_3)CH(CH_3)$—, —$CH(CH_2CH_3)CH_2$—, —$C(CH_3)_2CH_2$—, —$CH_2CH_2CH_2CH_2CH_2$—, and —$CH_2CH_2CH_2CH_2CH_2CH_2$—), or a $C_1$-$C_7$ divalent alkoxy group (such as —$OCH_2$—, —$OCH_2CH_2$—, —$OCH_2CH_2CH_2$—, —$O$—$CH(CH_3)CH_2$—, —$OC(CH_3)_2$—, —$OCH_2CH_2CH_2CH_2$—, —$OCH(CH_3)CH_2CH_2$—, —$OCH(CH_3)CH(CH_3)$—, —$OCH(CH_2CH_3)CH_2$—, —$OC(CH_3)_2CH_2$—, —$OCH_2CH_2CH_2CH_2$—, —$OCH_2CH_2CH_2CH_2CH_2CH_2$—, —$OCHF$—, —$OCF_2$—, —$O$-phenylene-, —$O$—$CH_2$-phenylene-, —$O$—$CH_2$-(2,3 or 4)-F-phenylene-, —$O$—$CH_2$-(2,3 or 4)-Cl-phenylene-, —$CH_2OCH_2$—, —$CH_2OCH_2CH_2$—, —$CH_2OCH_2CH_2CH_2$—, —$CH_2OCH_2CH_2CH_2CH_2$—, —$CH_2CH_2OCH_2$—, —$CH_2CH_2CH_2OCH_2$—, —$CH_2CH_2CH_2CH_2CH_2$—, —$CH_2CH_2CH_2CH_2CH_2OCH_2$—, —$CH_2CH_2CH_2CH_2CH_2CH_2OCH_2$—, —$CH_2CH_2OCH_2CH_2$—, —$CH_2CH_2OCH_2CH_2CH_2$—, —$CH_2CH_2OCH_2CH_2CH_2CH_2$—, —$CH_2CH_2OCH_2CH_2CH_2CH_2CH_2$—, —$CH_2CH_2CH_2OCH_2CH_2$—, —$CH_2CH_2CH_2OCH_2CH_2CH_2$—, and —$CH_2CH_2OCH_2CH_2CH_2CH_2CH_2$—. Alternatively, L may be an —O— atom, or an —$N(R^{32})$— group (such as an —NH— group).

The group Y typically comprises an aminocarbonyl group, a carbonylamino group, an aminosulphonyl group, a sulphonylamino group, a substituted or unsubstituted piperidinyl group a substituted or unsubstituted piperazinyl group, a substituted or unsubstituted alcohol group, a substituted or unsubstituted ether group, and/or a saturated or unsaturated, substituted or unsubstituted, carbocyclic group such as a substituted or unsubstituted cyclohexyl group or a substituted or unsubstituted phenyl group. Typically the N atom in the above formula for Y forms the amino part of these groups, although it is not excluded that the N atom is not the amino part of these groups.

In some typical such embodiments L is absent, and Y may be selected from the following groups:

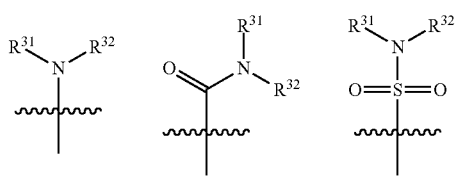

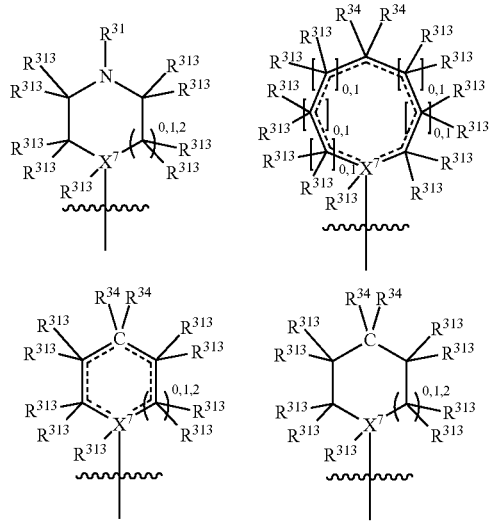

-continued
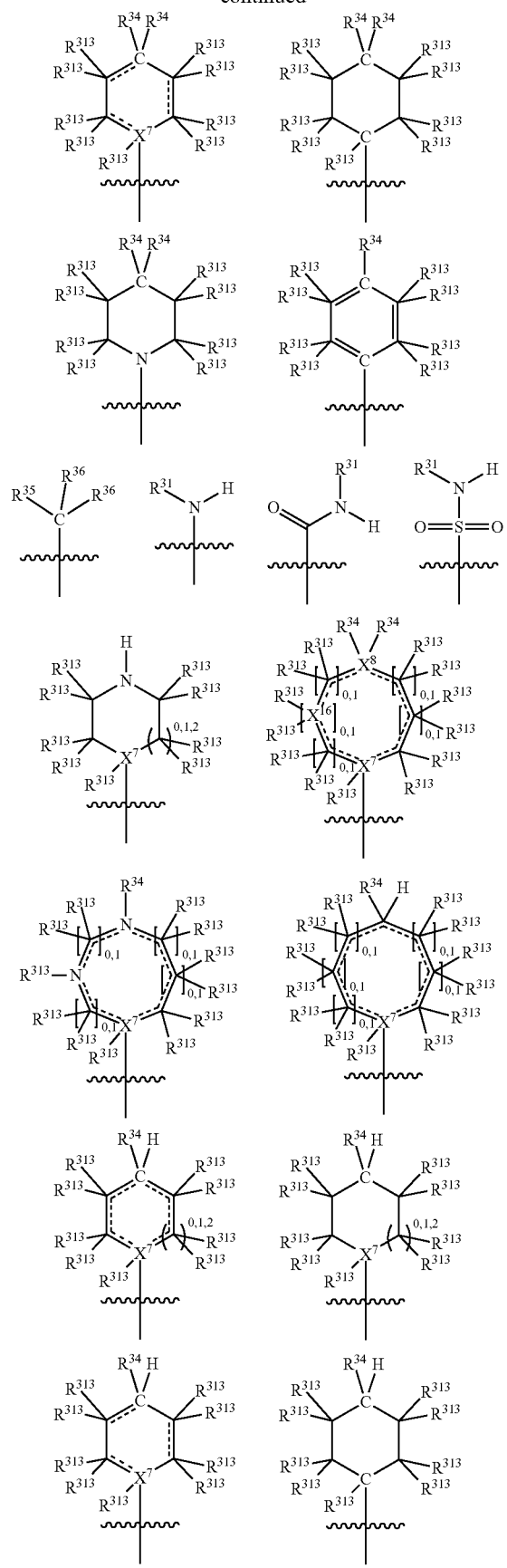
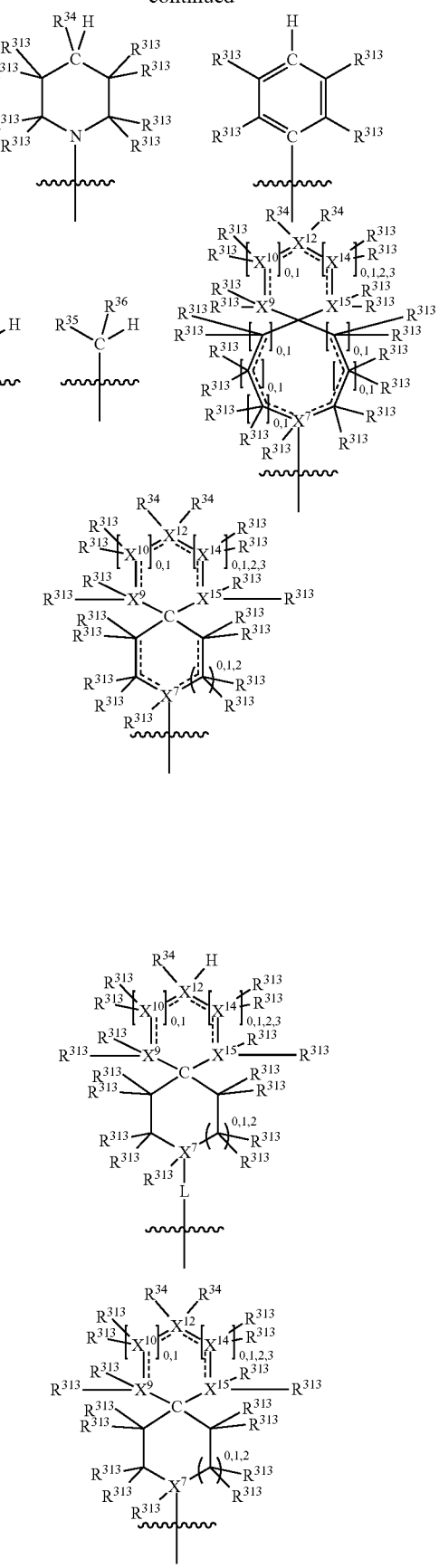

-continued

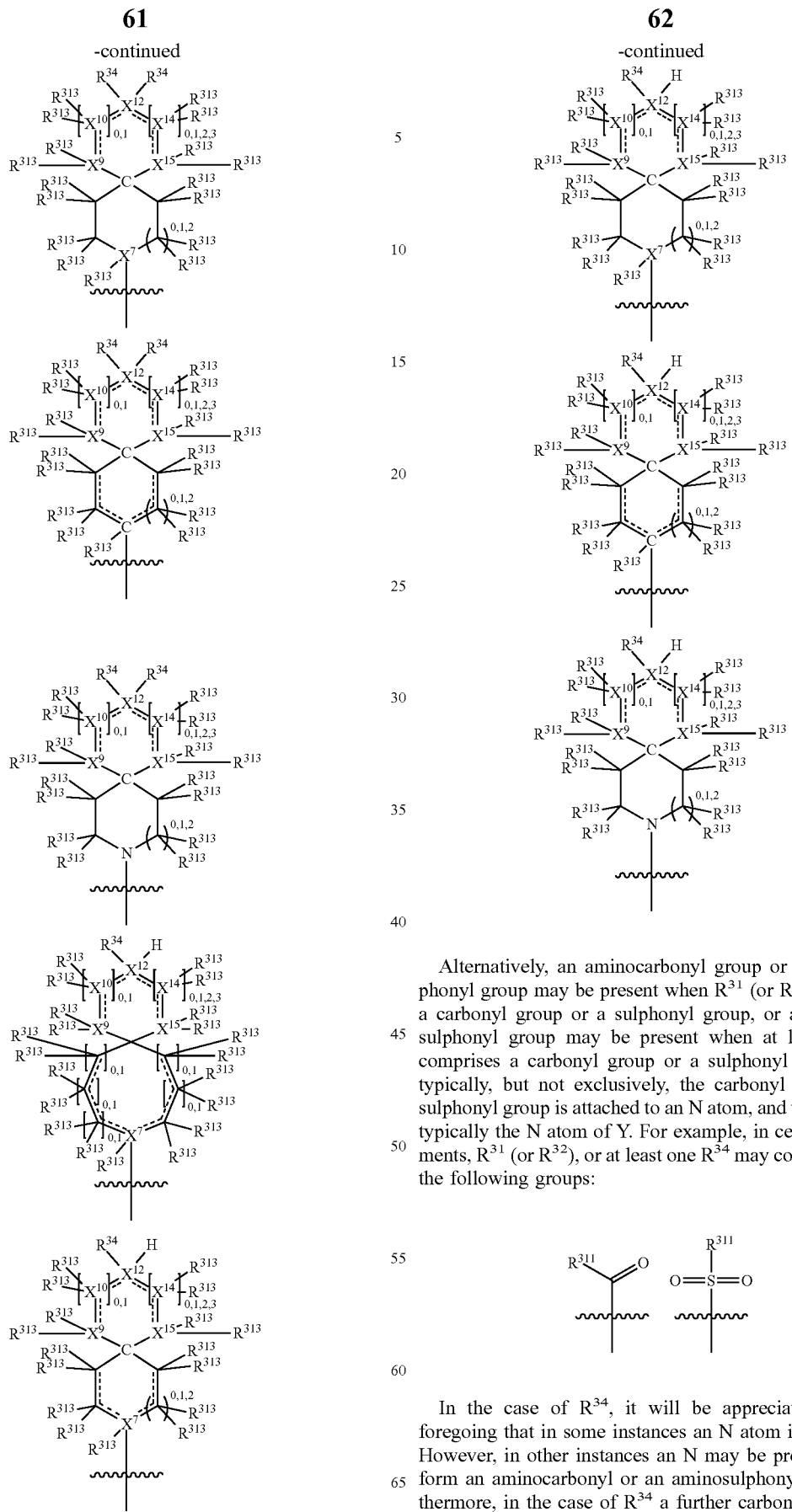

Alternatively, an aminocarbonyl group or an aminosulphonyl group may be present when $R^{31}$ (or $R^{32}$) comprises a carbonyl group or a sulphonyl group, or a carbonyl or sulphonyl group may be present when at least one $R^{34}$ comprises a carbonyl group or a sulphonyl group. Thus, typically, but not exclusively, the carbonyl group or the sulphonyl group is attached to an N atom, and where present typically the N atom of Y. For example, in certain embodiments, $R^{31}$ (or $R^{32}$), or at least one $R^{34}$ may comprise one of the following groups:

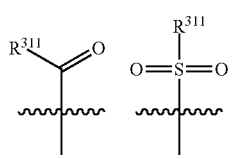

In the case of $R^{34}$, it will be appreciated from the foregoing that in some instances an N atom is not present. However, in other instances an N may be present so as to form an aminocarbonyl or an aminosulphonyl group. Furthermore, in the case of $R^{34}$ a further carbon atom (which may be substituted or unsubstituted) may be present between the aminocarbonyl (or aminosulphonyl) group and the ring. Thus, $R^{34}$ may in some cases comprise a group having one of the following formulae:

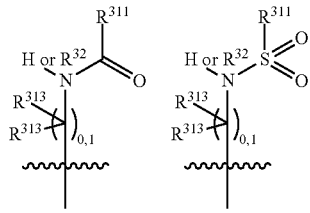

In the above formulae, $R^{311}$ is selected from H and a substituted or unsubstituted organic group. In some instances, the N(H or $R^{32}$) group in these groups may be absent such that $R^{34}$ may in some cases comprise a group having one of the following formulae:

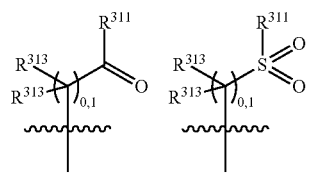

Accordingly, the Y group is typically selected from the following:

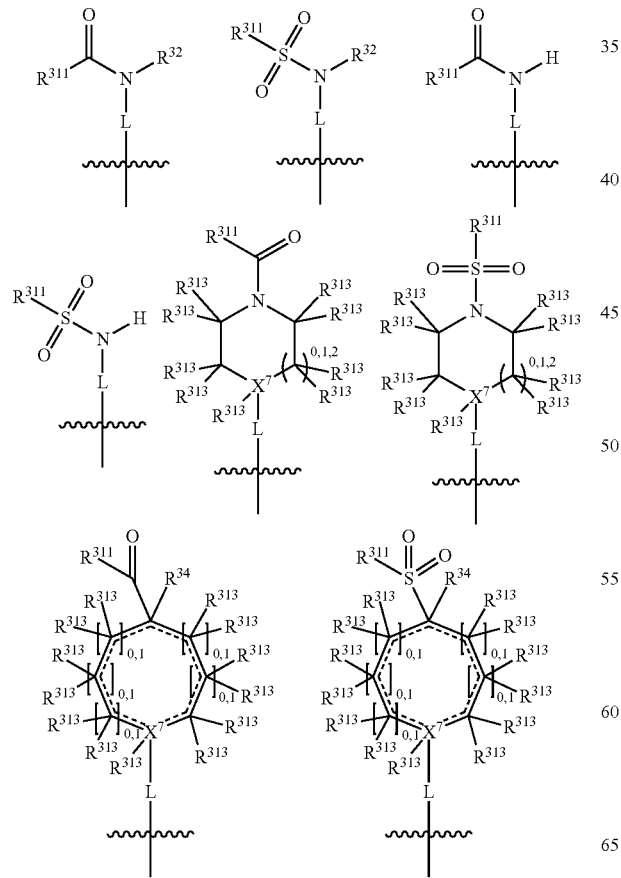

-continued

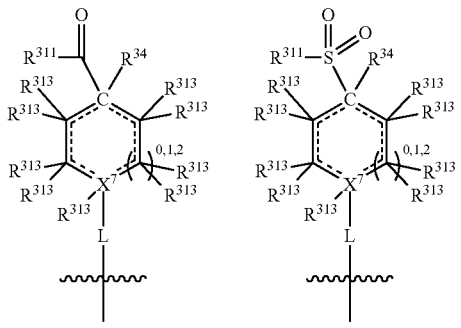

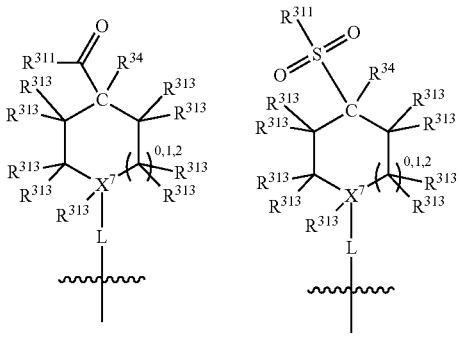

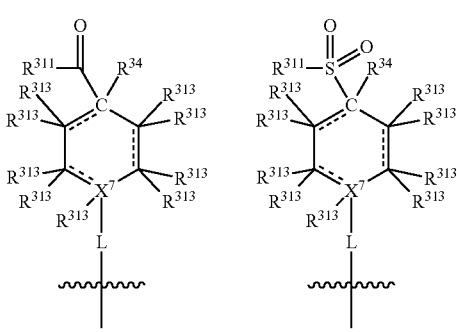



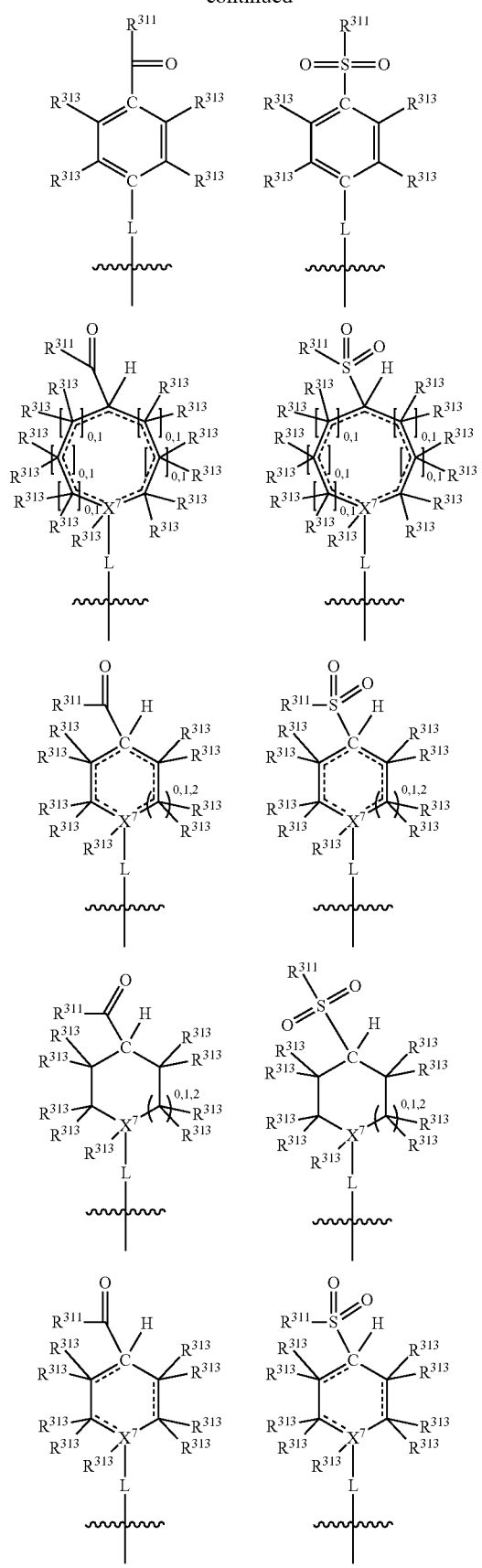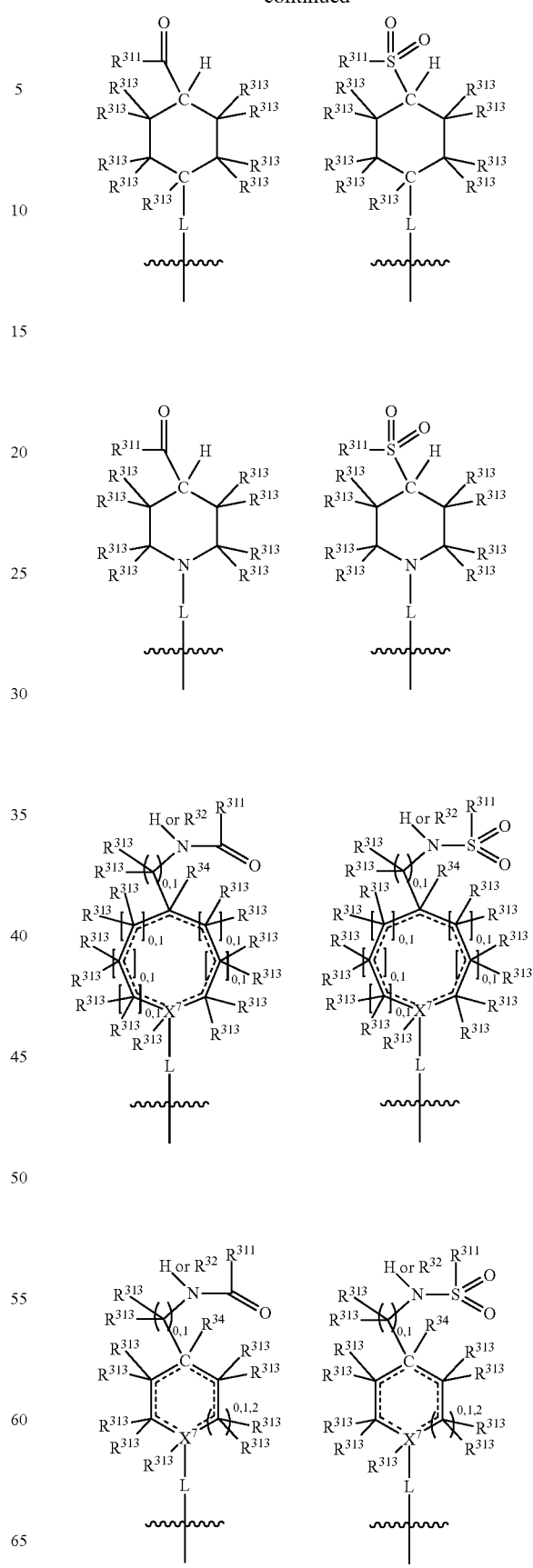

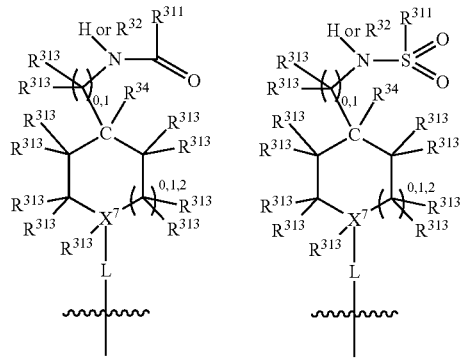
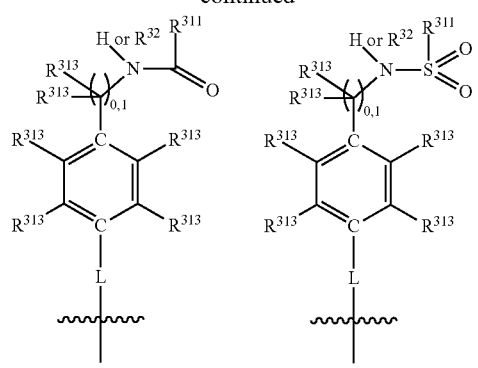
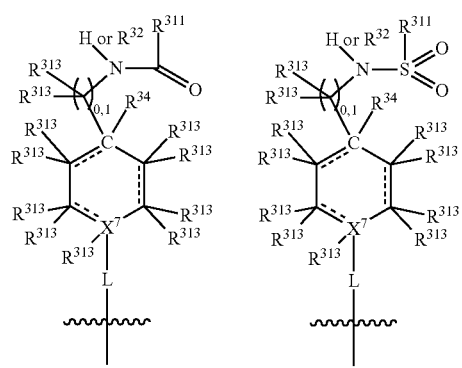
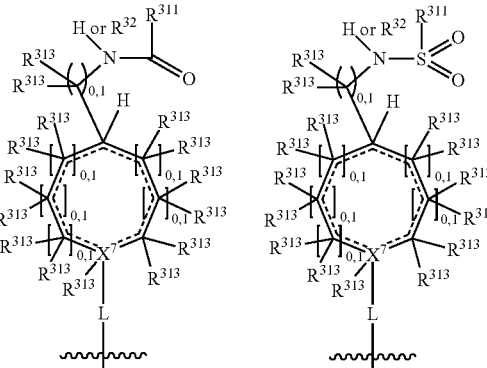
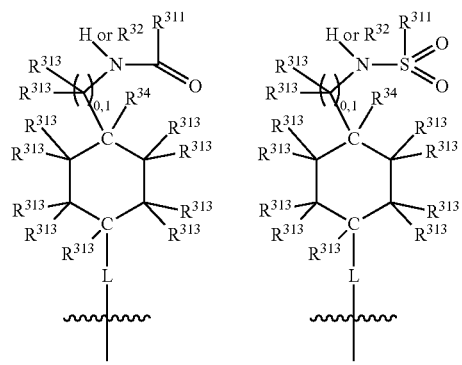
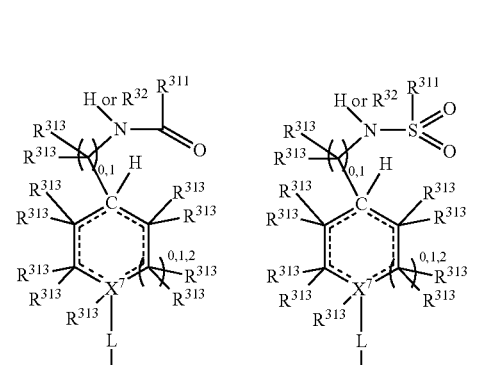
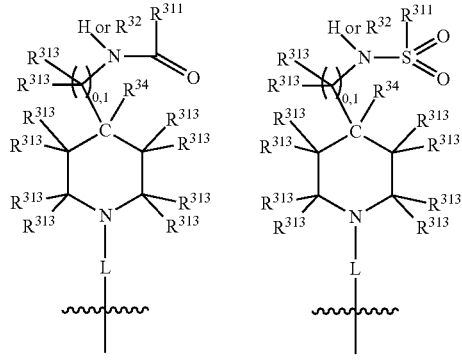
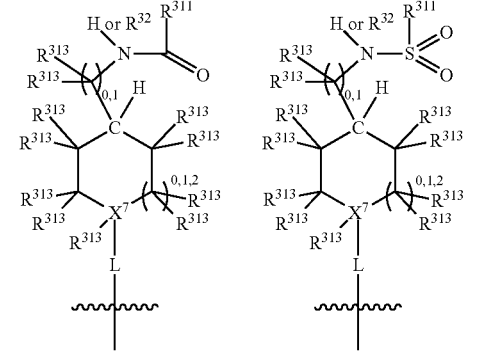

-continued

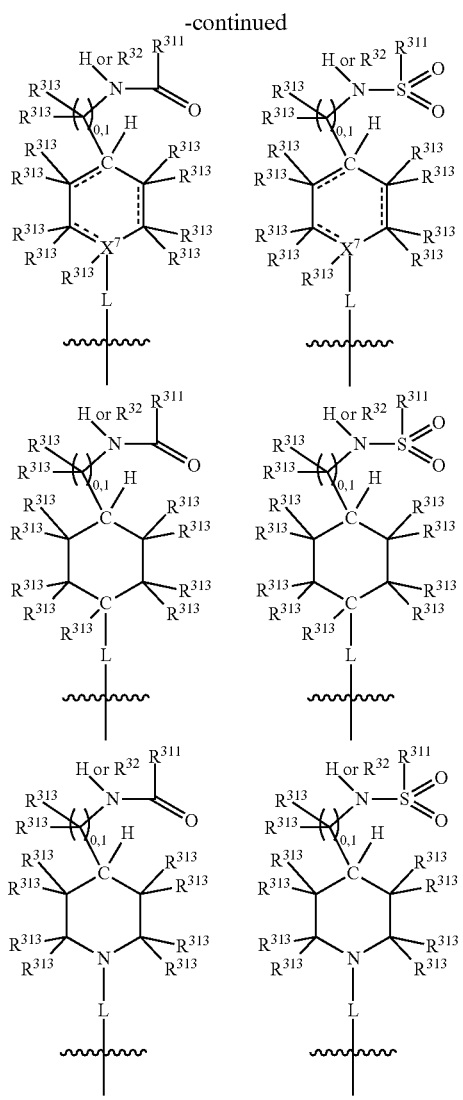

where L is present and L, $R^{32}$, $R^{34}$, $R^{311}$ and $R^{313}$ have the same meaning as anywhere above or below herein, except that in these cases $R^{32}$ is not H and $R^{34}$ is not H. In some instances the N(H or $R^{32}$) group may be absent in these compounds.

In typical embodiments, $R^{311}$ is selected from the following:
- a substituted or unsubstituted linear or branched $C_1$-$C_6$ alkyl group (such as Me, Et, Pr, i-Pr, n-Bu, i-Bu, t-Bu, pentyl and hexyl);
- a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);
- a substituted or unsubstituted linear or branched $C_1$-$C_6$ halogenated alkyl group (such as —CH$_2$F, —CF$_3$, —CH$_2$CF$_3$);
- an —NH$_2$ group, or a substituted or unsubstituted linear or branched primary secondary or tertiary $C_1$-$C_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);
- a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2, (3,4,5 or 6)F$_2$-Ph, —NH-2, (3,4,5 or 6)Cl$_2$-Ph, —NH-2, (3,4,5 or 6)Br$_2$-Ph, —NH-2, (3,4,5 or 6)I$_2$-Ph, —NH-2, (3,4,5 or 6)Me$_2$-Ph, —NH-2, (3,4,5 or 6)Et$_2$-Ph, —NH-2, (3,4,5, or 6)Pr$_2$-Ph, —NH-2, (3,4,5 or 6)Bu$_2$-Ph,
- a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);
- a substituted or unsubstituted cyclic $C_3$-$C_8$ alkyl group (such as cyclopropyl, cyclobutyl, cyclopentyl, cyclohexyl, cycloheptyl and cyclooctyl);
- a substituted or unsubstituted linear or branched $C_1$-$C_6$ alcohol group (such as —CH$_2$OH, —CH$_2$CH$_2$OH, —CH$_2$CH$_2$CH$_2$, —CH$_2$CH$_2$CH$_2$O, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);
- a substituted or unsubstituted linear or branched $C_1$-$C_7$ amino carbonyl group (such as —NH—CO-Me, —NH—CO-Et, —NH—CO—Pr, —NH—CO-Bu, —NH—CO-pentyl, —NH—CO-hexyl, —NH—CO-Ph, —NMe-CO-Me, —NMe-CO-Et, —NMe-CO—Pr, —NMe-CO-Bu, —NMe-CO-pentyl, —NMe-CO-hexyl, —NMe-CO-Ph;
- a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);
- a substituted or unsubstituted linear or branched aminoalkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;
- a substituted or unsubstituted aminosulphonyl group (such as —NHSO$_2$Me, —NHSO$_2$Et, —NHSO$_2$Pr, Pr, —NHSO$_2$Ph, —NHSO$_2$-(2,3 or 4)-F-Ph, —NHSO$_2$-cyclopropyl, —NHSO$_2$CH$_2$CH$_2$OCH$_3$);
- a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F$_2$-Ph-, 2, (3,4,5 or 6)-Cl$_2$-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-C$_2$-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(Me)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-);

a saturated or unsaturated, substituted or unsubstituted, heterocyclic group including an aromatic heterocyclic group and/or a non-aromatic heterocyclic group (such as pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl).

In more preferred embodiments, R$^{311}$ is selected from the following:

a substituted or unsubstituted linear or branched C$_1$-C$_6$ alkyl group (such as Me, Et, Pr, i-Pr, n-Bu, i-Bu, t-Bu, pentyl and hexyl);

a substituted or unsubstituted linear or branched C$_1$-C$_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)$_1$-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted cyclic C$_3$-C$_8$ alkyl group (such as cyclopropyl, cyclobutyl, cyclopentyl, cyclohexyl, cycloheptyl and cyclooctyl);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F$_2$-Ph-, 2, (3,4,5 or 6)-Cl$_2$-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-Cl$_2$-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-);

a saturated or unsaturated, substituted or unsubstituted, heterocyclic group including an aromatic heterocyclic group and/or a non-aromatic heterocyclic group (such as pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridine-4-yl, pyrazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl).
In these cases, typically L does not comprise a carbonyl or a sulphonyl, although this is not excluded.
In typical embodiments, the linker L is absent. In such cases, Y may be selected from any of the following:
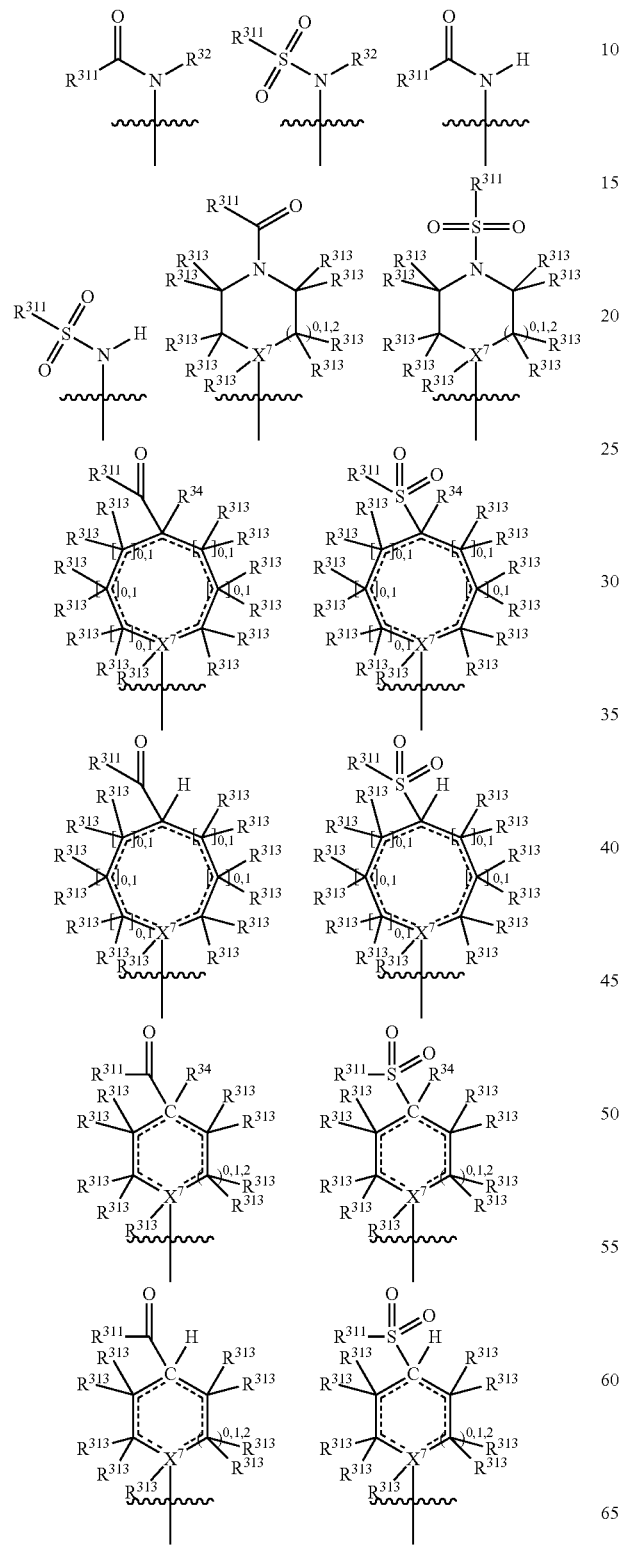
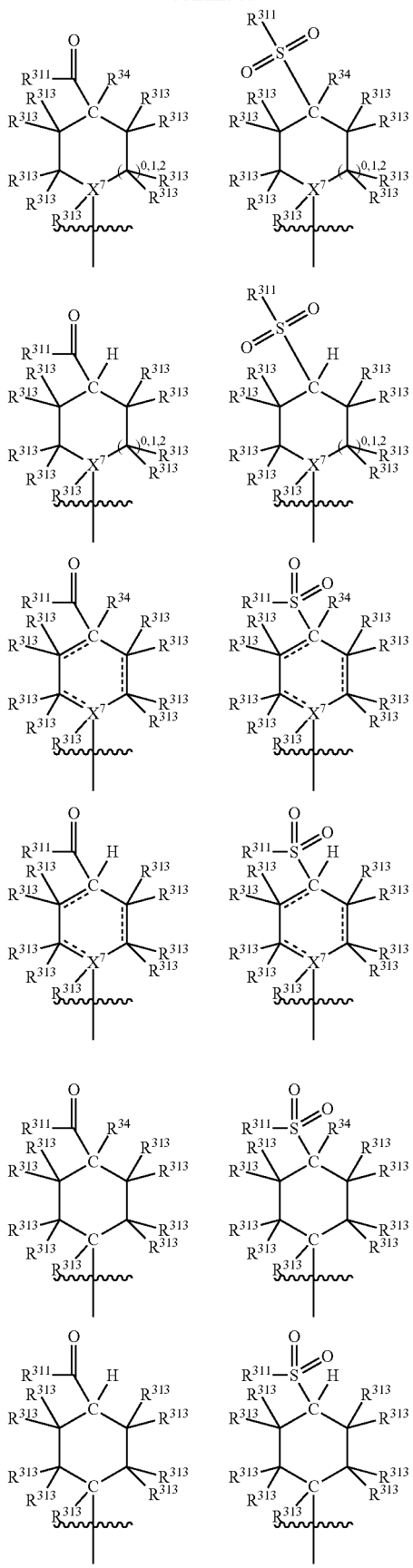
-continued -continued
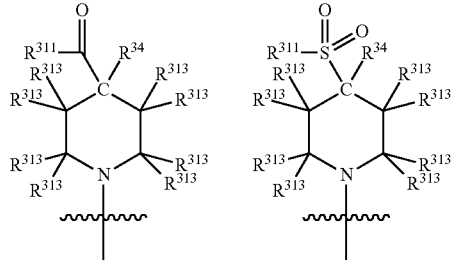
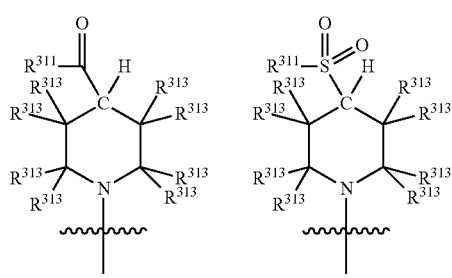
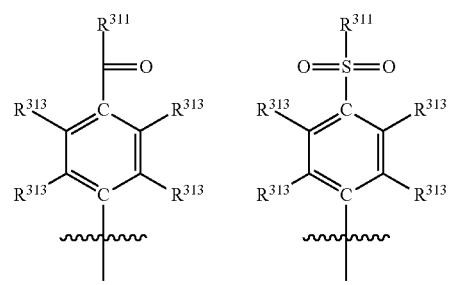
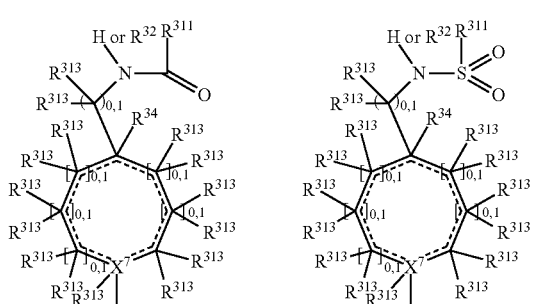
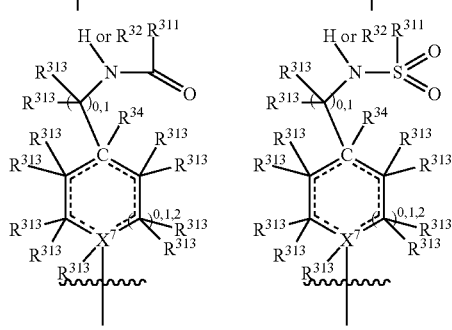
-continued
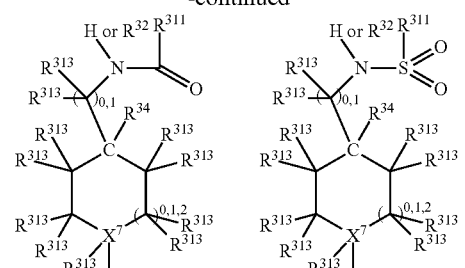
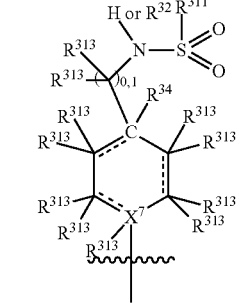
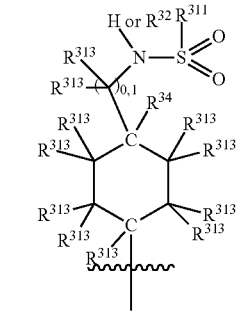
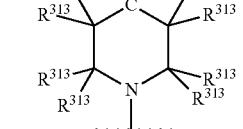
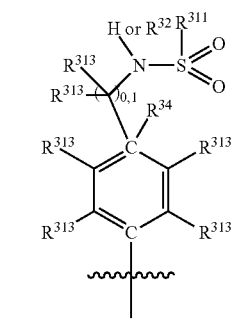

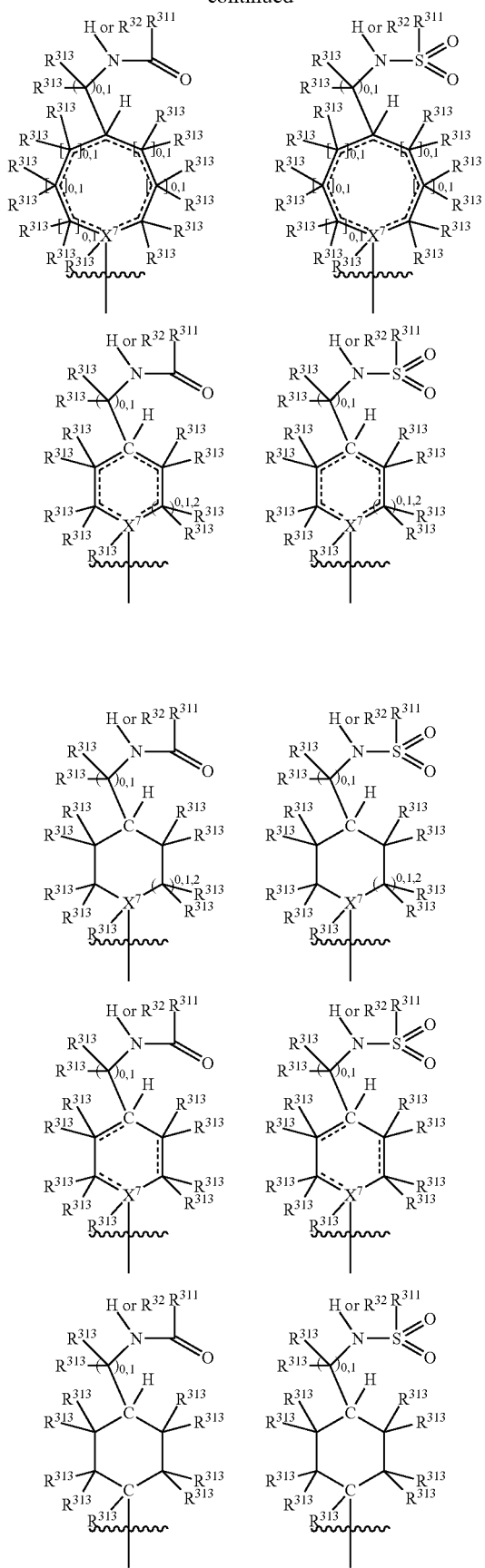

wherein $R^{32}$, $R^{34}$, $R^{311}$ and $R^{313}$ have the same meaning as anywhere above or below herein, except that in these cases $R^{32}$ is not H and $R^{34}$ is not H. In some instances the N(H or $R^{32}$) group may be absent in these compounds.

In the present context $R^{312}$ is selected from the following:

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph), a substituted or unsubstituted linear or branched $C_1$-$C_6$ halogenated alkyl group (such as —CH$_2$F, —CF$_3$, —CH$_2$CF$_3$);

an —NH$_2$ or a substituted or unsubstituted linear or branched primary secondary or tertiary $C_1$-$C_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2, (3,4,5 or 6)F$_2$-Ph, —NH-2, (3,4,5 or 6)Cl$_2$-Ph, —NH-2, (3,4,5 or 6)Br$_2$-Ph, —NH-2, (3,4,5 or 6)I$_2$-Ph, —NH-2, (3,4,5 or 6)Me$_2$-Ph, —NH-2, (3,4,5 or 6)Et$_2$-Ph, —NH-2, (3,4,5, or 6)Pr$_2$-Ph, —NH-2, (3,4,5 or 6)Bu$_2$-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic $C_3$-$C_8$ alkyl group (such as cyclopropyl, cyclobutyl, cyclopentyl, cyclohexyl, cycloheptyl and cyclooctyl);

a substituted or unsubstituted linear or branched $C_1$-$C_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched C$_1$-C$_7$ amino carbonyl group (such as —NH—CO-Me, —NH—CO-Et, —NH—CO—Pr, —NH—CO-Bu, —NH—CO-pentyl, —NH—CO-hexyl, —NH—CO-Ph, —NMe-CO-Me, —NMe-CO-Et, —NMe-CO—Pr, —NMe-CO-Bu, —NMe-CO-pentyl, —NMe-CO-hexyl, —NMe-CO-Ph;

a substituted or unsubstituted linear or branched C$_1$-C$_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$H$_2$CH$_2$CH$_2$CH$_2$OMe);

a substituted or unsubstituted linear or branched aminoalkoxy group (such as, —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$CH$_3$);

a substituted or unsubstituted 6 membered carbocyclic or heterocyclic aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F$_2$-Ph-, 2, (3,4,5 or 6)-Cl$_2$-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-Cl$_2$-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-, pyridin-2-yl, pyridine-3-yl, pyridin-4-yl, pyrimidin-2-yl, pyrimidin-5-yl, pyrimidin-4-yl, pyridazin-3-yl, pyridazine-4-yl);

a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl).

In more typical embodiments R$^{312}$ is selected from:

a substituted or unsubstituted linear or branched C$_1$-C$_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)$_1$-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted cyclic C$_3$-C$_8$ alkyl group (such as cyclopropyl, cyclobutyl, cyclopentyl, cyclohexyl, cycloheptyl and cyclooctyl);

a substituted or unsubstituted 6 membered carbocyclic or heterocyclic aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F$_2$-Ph-, 2, (3,4,5 or 6)-Cl$_2$-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-Cl$_2$-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-, pyridin-2-yl, pyridine-3-yl, pyridin-4-yl, pyrimidin-2-yl, pyrimidin-5-yl, pyrimidin-4-yl, pyridazin-3-yl, pyridazine-4-yl);

a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl).

In other typical embodiments, the piperidine piperazine and cyclohexyl substituents that comprise Y may be selected from any of the following:

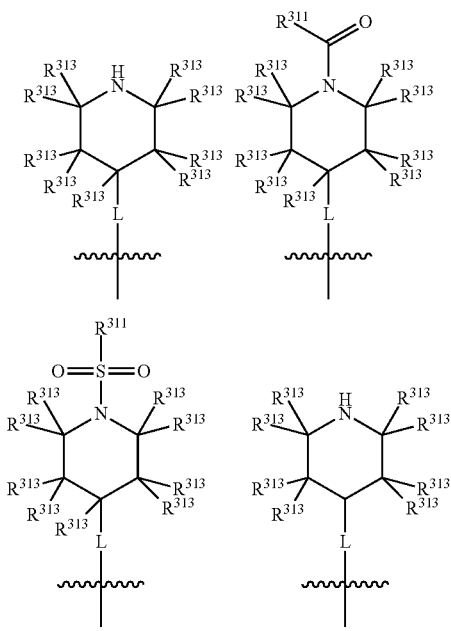

-continued
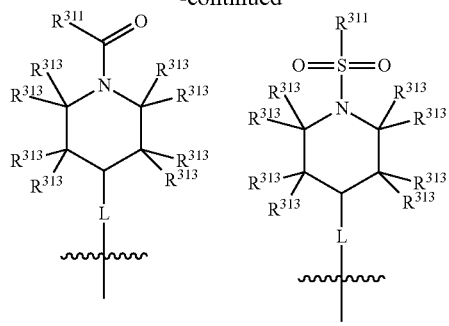
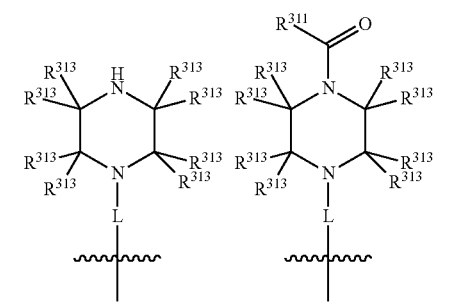
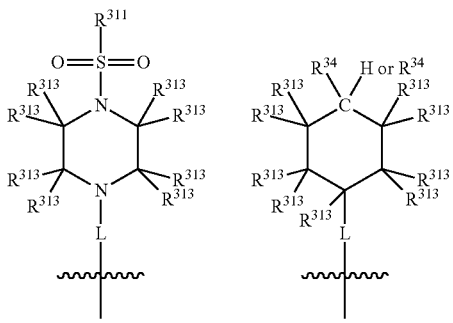
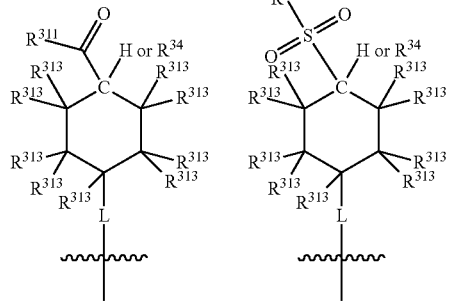
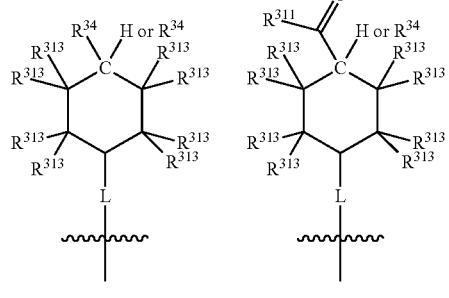
-continued
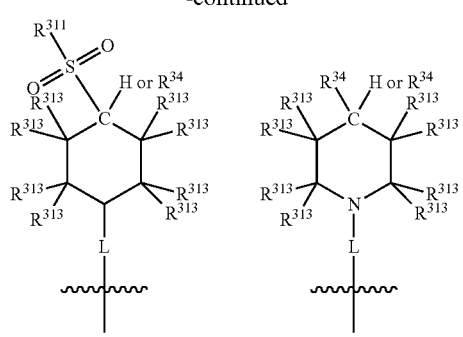
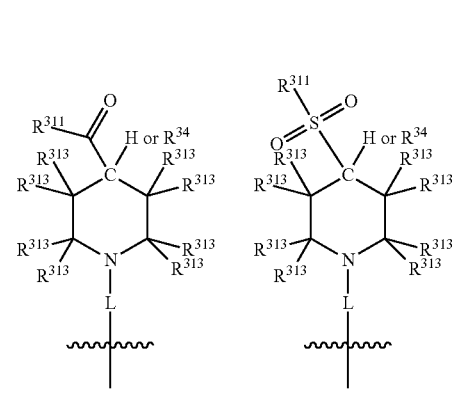
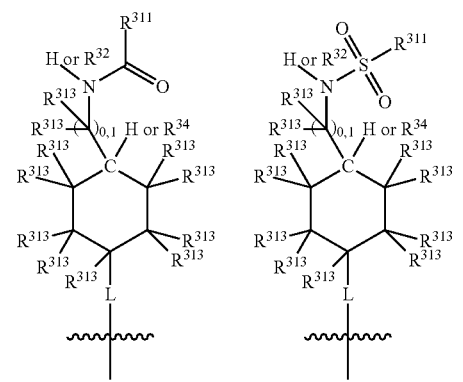
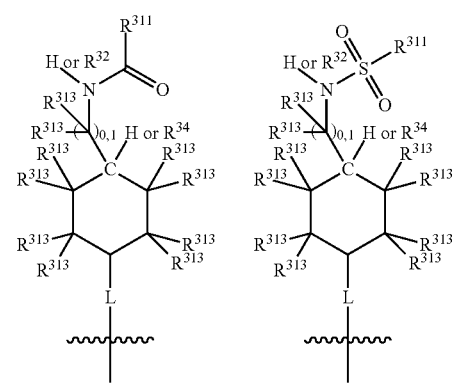

-continued

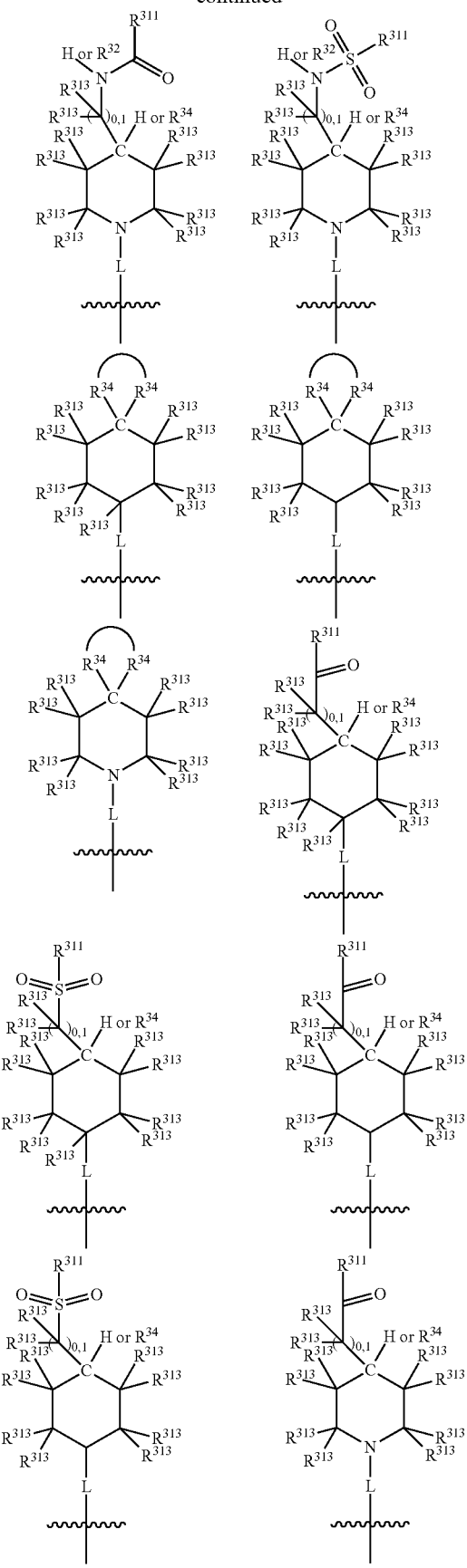

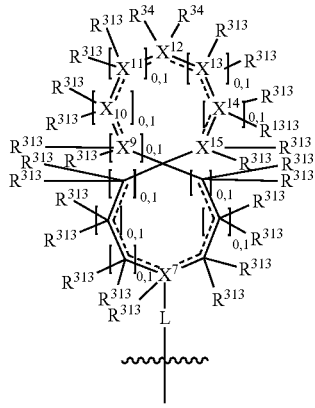

wherein in each case L may be present or absent. Typically, but not exclusively the curved line forming the ring between the $R^{34}$ groups may be a substituted or unsubstituted alkylene group having from 1 to 6 C atoms, such as $-CH_2-$, $-CH_2CH_2-$, $-CH_2CH_2CH_2-$, $-CH(CH_3)CH_2-$, $-C(CH_3)_2-$, $-CH_2CH_2CH_2CH_2-$, $-CH(CH_3)CH_2CH_2-$, $-CH(CH_3)CH(CH_3)-$, $-CH(CH_2CH_3)CH_2-$, $-C(CH_3)_2CH_2-$, $-CH_2CH_2CH_2CH_2CH_2-$, and $-CH_2CH_2CH_2CH_2CH_2CH_2-$. In cases where the $R^{34}$ groups form a ring with each other, the $R^{34}$ groups are typically both methylene ($-CH_2-$) groups.

In more specific embodiments, the curved line joining the $R^{34}$ groups forms spiro compounds, in which the Y group is a group of formula:

more preferably a group of formula:

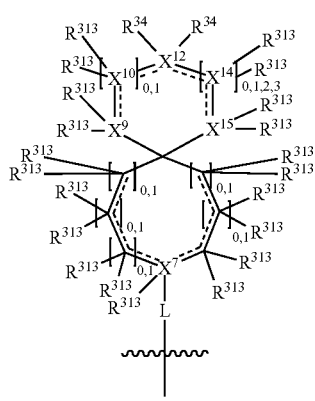

such as:
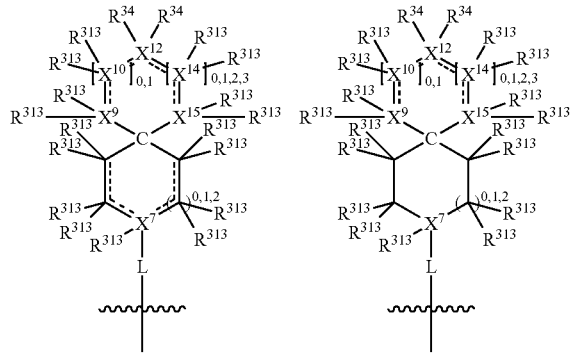
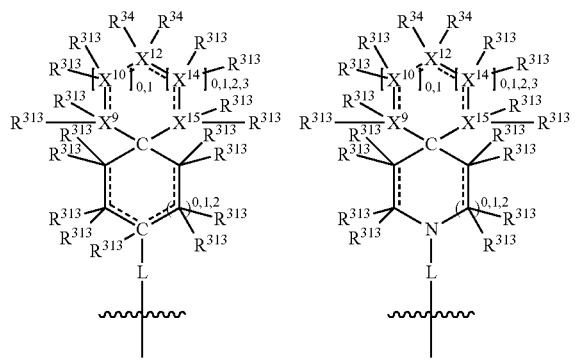
where L may be present or absent (but is typically absent).
In more preferred embodiments of this type, the compounds of the invention may have one of the following formulae:
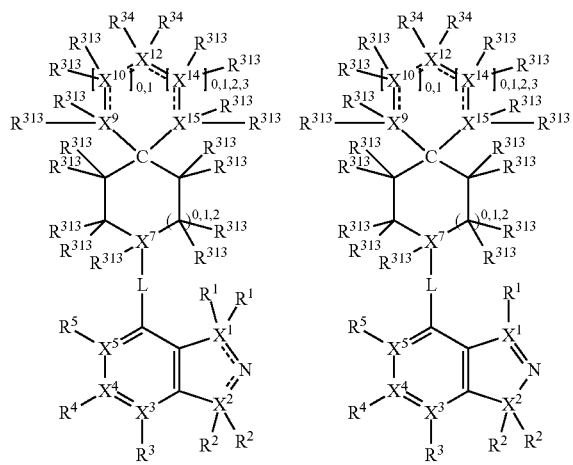
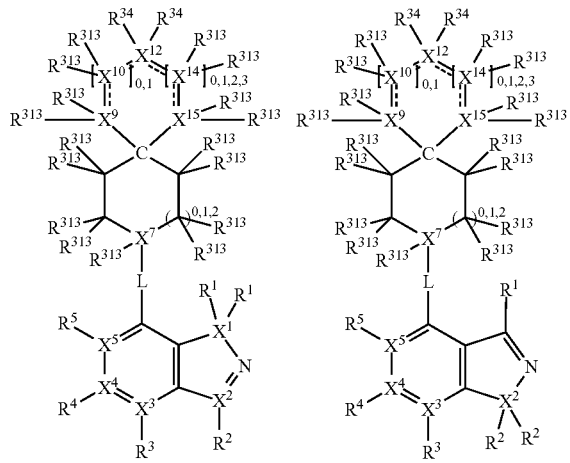
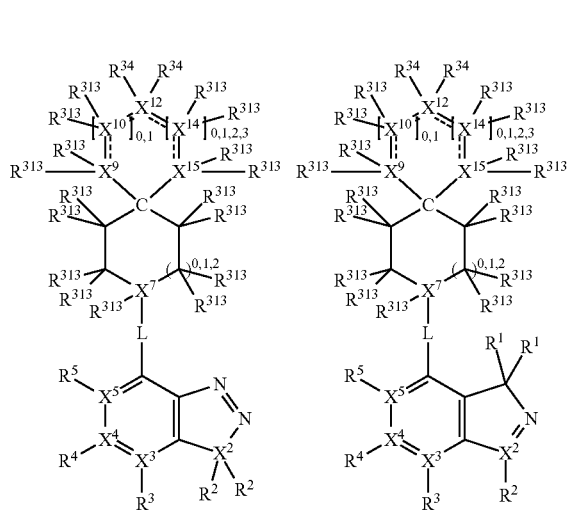
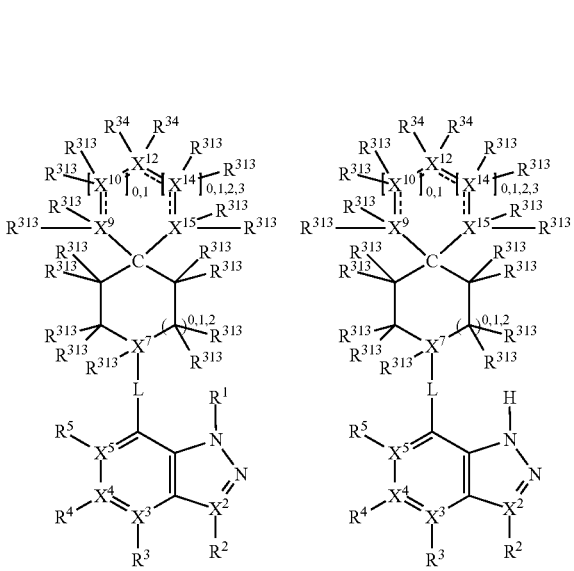

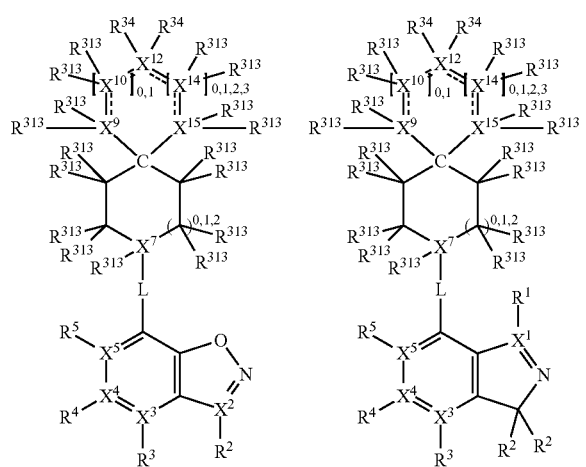
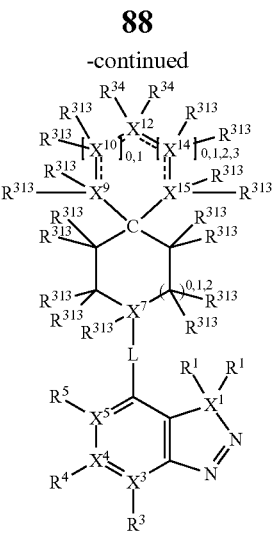
where L may be present or absent (but is typically absent).
In more preferred embodiments throughout this disclosure, as has been mentioned, the Y group has the following formula:
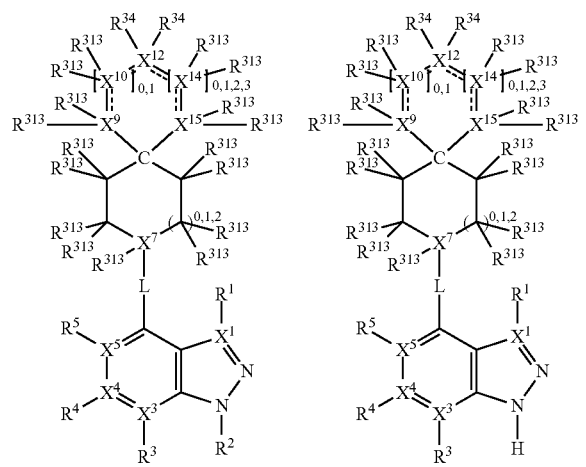
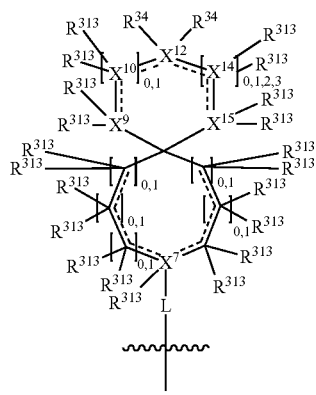
where L is present or absent (and is preferably absent). Y may therefore have one of the following preferred formulae:
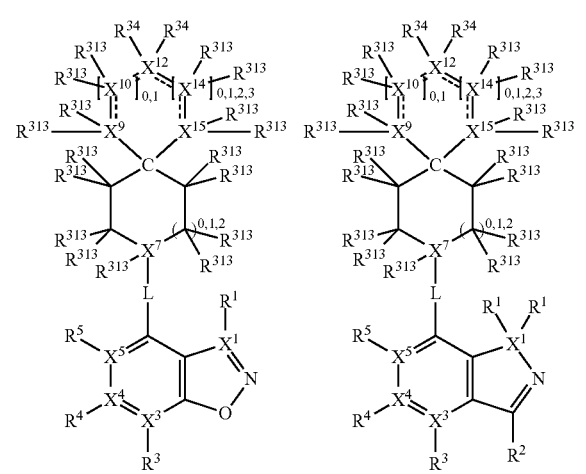
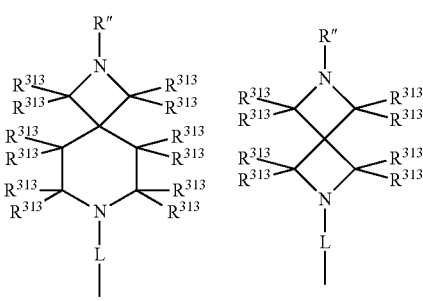

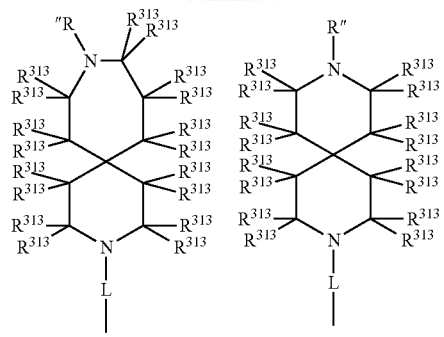
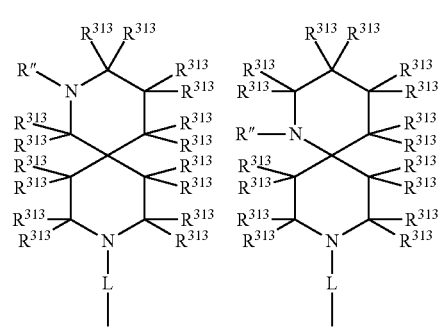
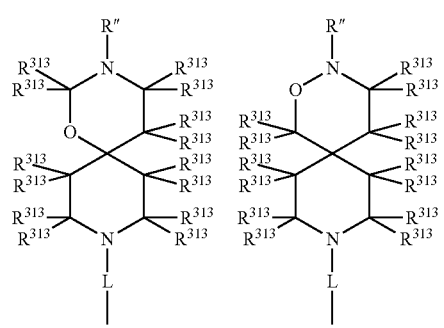
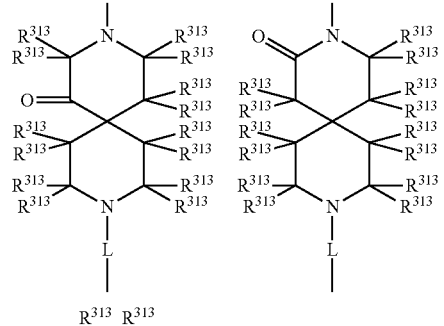
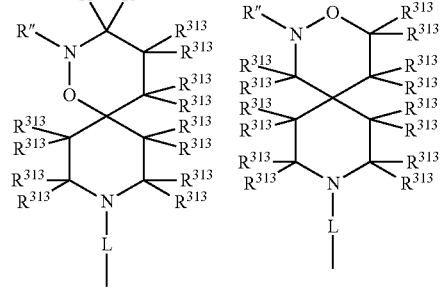
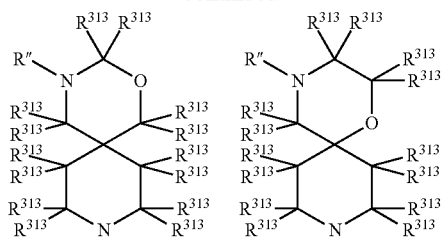
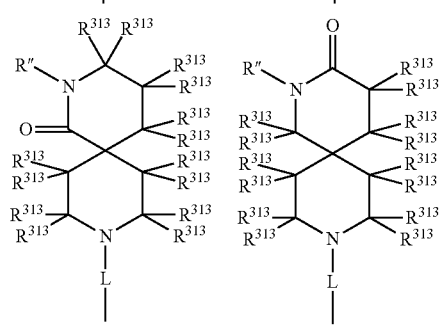
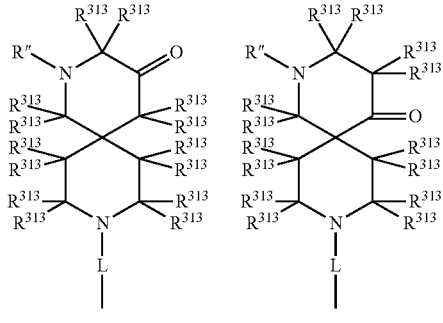
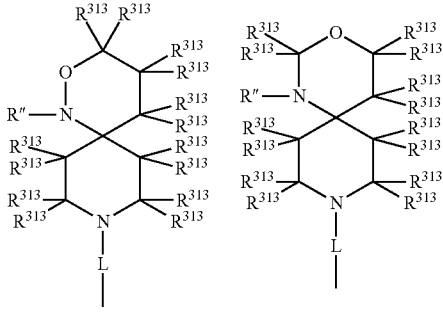
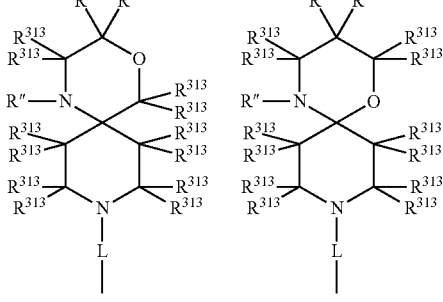

-continued

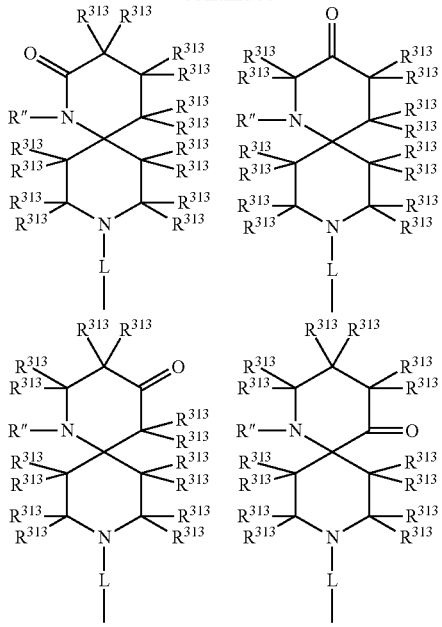

wherein L may be present or absent (and is preferably absent) and wherein $R^{313}$ is as defined anywhere herein (although in these embodiments, unless otherwise specified, it is preferred that all $R^{313}$ are H) and wherein R" is selected from H and any if the following groups:

- a substituted or unsubstituted linear or branched $C_1$-$C_6$ alkyl group (such as Me, Et, Pr, i-Pr, n-Bu, i-Bu, t-Bu, pentyl and hexyl);
- a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);
- a substituted or unsubstituted linear or branched $C_1$-$C_6$ halogenated alkyl group (such as —CH$_2$F, —CF$_3$, and —CH$_2$CF$_3$);
- a substituted or unsubstituted cyclic amine or amido group (such as pyrrolidin-3-yl, piperidin-3-yl, piperidin-4-yl, 2-keto-pyrrolidinyl, 3-keto-pyrrolidinyl, 2-keto-piperidinyl, 3-keto-piperidinyl, and 4-keto-piperidinyl) which group may be attached via a —CH$_2$— or a —CH$_2$CH$_2$— group;
- a substituted or unsubstituted cyclic $C_3$-$C_8$ alkyl group (such as cyclopropyl, cyclobutyl, cyclopentyl, cyclohexyl, cycloheptyl and cyclooctyl) which group may be attached via a —CH$_2$— or a —CH$_2$CH$_2$— group;
- a substituted or unsubstituted linear or branched $C_2$-$C_6$ alcohol group (such as —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);
- a substituted or unsubstituted linear or branched $C_1$-$C_7$ alkoxy or aryloxy group linked through —O— via at least two further C atoms (such as —CH$_2$CH$_2$OPh, CH$_2$CH$_2$OMe, —CH$_2$CH$_2$OEt, —CH$_2$CH$_2$OPr, —CH$_2$CH$_2$OBu, —CH$_2$CH$_2$CH$_2$OPh, —CH$_2$CH$_2$CH$_2$Me, —CH$_2$CH$_2$CH$_2$CH$_2$OMe, and —CH$_2$CH$_2$CH$_2$CH$_2$CH$_2$OMe);
- a substituted or unsubstituted linear or branched $C_2$-$C_6$ carboxylic acid group (such as —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);
- a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$CH$_2$NMe$_2$;
- a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);
- a substituted or unsubstituted linear or branched $C_1$-$C_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);
- a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO$_2$-pyrolidine-N-yl, —SO$_2$-morpholine-N-yl, —SO$_2$NHCH$_2$OMe, and —SO$_2$NHCH$_2$CH$_2$OMe;
- a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph-, 4-I-Ph-, 2, (3,4,5 or 6)-F$_2$-Ph-, 2, (3,4,5 or 6)-Cl$_2$-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-Cl$_2$-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2—CF$_3$O-Ph-, 3-CF$_3$O-Ph-, and 4-CF$_3$O-Ph-) which group may be attached via a —CH$_2$— or a —CH$_2$CH$_2$— group; and
- a saturated or unsaturated, substituted or unsubstituted, heterocyclic group including an aromatic heterocyclic group and/or a non-aromatic heterocyclic group (such as pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl) which group may be attached via a —$CH_2$— or a —$CH_2CH_2$— group.

Preferably, R" is selected from one of the following groups:
- a substituted or unsubstituted linear or branched $C_1$-$C_6$ alkyl group (such as Me, Et, Pr, i-Pr, n-Bu, i-Bu, t-Bu, pentyl and hexyl);
- a substituted or unsubstituted linear or branched $C_2$-$C_6$ alcohol group (such as —$CH_2CH_2OH$, —$CH_2CH_2CH_2OH$, —$CH(CH_3)CH_2OH$, —$C(CH_3)_2OH$, —$CH_2CH_2CH_2CH_2OH$, —$CH(CH_3)CH_2CH_2OH$, —$CH(CH_3)CH(CH_3)OH$, —$CH(CH_2CH_3)CH_2OH$, —$C(CH_3)_2CH_2OH$, —$CH_2CH_2CH_2CH_2CH_2OH$, and —$CH_2CH_2CH_2CH_2CH_2CH_2OH$);
- a substituted or unsubstituted linear or branched $C_1$-$C_7$ alkoxy or aryloxy group linked through —O via at least two further C atoms (such as —$CH_2CH_2OPh$-$CH_2CH_2OMe$, —$CH_2CH_2OEt$, —$CH_2CH_2OPr$, —$CH_2CH_2OBu$, —$CH_2CH_2CH_2OPh$, —$CH_2CH_2CH_2OMe$, —$CH_2CH_2CH_2CH_2OMe$, and —$CH_2CH_2CH_2CH_2CH_2OMe$);
- a substituted or unsubstituted linear or branched $C_1$-$C_6$ halogenated alkyl group (such as —$CH_2F$, —$CF_3$, and —$CH_2CF_3$);
- a substituted or unsubstituted cyclic amine or amido group (such as pyrrolidin-3-yl, piperidin-3-yl, piperidin-4-yl, 2-keto-pyrrolidinyl, 3-keto-pyrrolidinyl, 2-keto-piperidinyl, 3-keto-piperidinyl, and 4-keto-piperidinyl) which group may be attached via a —$CH_2$— or a —$CH_2CH_2$— group;
- a substituted or unsubstituted cyclic $C_3$-$C_8$ alkyl group (such as cyclopropyl, cyclobutyl, cyclopentyl, cyclohexyl, cycloheptyl and cyclooctyl) which group may be attached via a —$CH_2$— or a —$CH_2CH_2$— group;
- a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-$F_2$-Ph-, 2, (3,4,5 or 6)-$Cl_2$-Ph-, 2, (3,4,5 or 6)-$Br_2$-Ph-, 2, (3,4,5 or 6)-$I_2$-Ph-, 2, (3,4,5 or 6)-$Me_2$-Ph-, 2, (3,4,5 or 6)-$Et_2$-Ph-, 2, (3,4,5 or 6)-$Pr_2$-Ph-, 2, (3,4,5 or 6)-$Bu_2$-Ph-, 2, (3,4,5 or 6)-$(CN)_2$-Ph-, 2, (3,4,5 or 6)-$(NO_2)_2$-Ph-, 2, (3,4,5 or 6)-$(NH_2)_2$-Ph-, 2, (3,4,5 or 6)-$(MeO)_2$-Ph-, 2, (3,4,5 or 6)-$(CF_3)_2$-Ph-, 3, (4 or 5)-$F_2$-Ph-, 3, (4 or 5)-$Cl_2$-Ph-, 3, (4 or 5)-$Br_2$-Ph-, 3, (4 or 5)-$I_2$-Ph-, 3, (4 or 5)-$Me_2$-Ph-, 3, (4 or 5)-$Et_2$-Ph-, 3, (4 or 5)-$Pr_2$-Ph-, 3, (4 or 5)-$Bu_2$-Ph-, 3, (4 or 5)-$(CN)_2$-Ph-, 3, (4 or 5)-$(NO_2)_2$-Ph-, 3, (4 or 5)-$(NH_2)_2$-Ph-, 3, (4 or 5)-$(MeO)_2$-Ph-, 3, (4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-($NO_2$)-Ph-, 3-($NO_2$)-Ph-, 4-($NO_2$)-Ph-, 2-($NH_2$)-Ph-, 3-($NH_2$)-Ph-, 4-($NH_2$)-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3$O-Ph-, 3-$CF_3$O-Ph-, and 4-$CF_3$O-Ph-) which group may be attached via a —$CH_2$— or a —$CH_2CH_2$— group; and
- a saturated or unsaturated, substituted or unsubstituted, heterocyclic group including an aromatic heterocyclic group and/or a non-aromatic heterocyclic group (such as pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl) which group may be attached via a —CH$_2$— or a —CH$_2$CH$_2$— group.

In some embodiments, R" may be selected from a carbonyl group or a sulphonyl group such as:

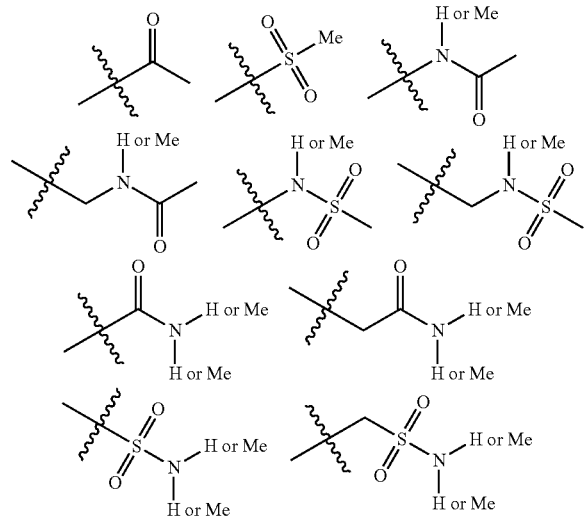

Having regard to the above, it will be apparent that particularly preferred compounds of the present invention may also comprise one of the following formulae:

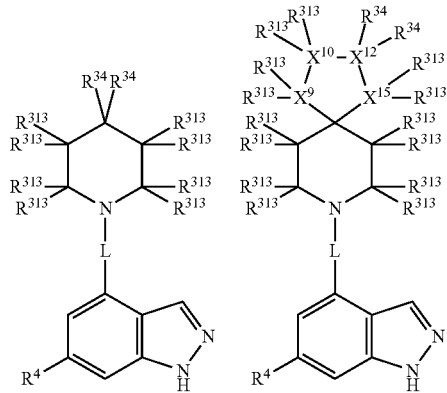

wherein L is present or absent (and is preferably absent) and wherein $R^4$, $R^{34}$, $R^{313}$, $X^9$, $X^{10}$, $X^{12}$ and $X^{15}$ may have any of the meanings described above and below herein. In these embodiments $R^{34}$ may further have any of the meanings described herein for $R^{313}$. In more preferred embodiments, $X^9$, $X^{10}$, $X^{12}$ and $X^{15}$ are selected from C, N and O, more preferably from C and N. It is further preferred that at least one of $X^9$, $X^{10}$, $X^{12}$ and $X^{15}$ comprises an N, and more preferably at least two of $X^9$, $X^{10}$, $X^{12}$ and $X^{15}$ comprise N.

Where at least one of $X^9$, $X^{10}$, $X^{12}$ and $X^{15}$ comprises N, at least one of these N groups is substituted by —R", where R" is any of the groups as defined above or below herein.

In some embodiments, two $R^{34}$ groups, and/or two $R^{313}$ groups, may together form a =O group to the C to which they are attached. Where the =O group is attached to an X, that X is a C atom. There may be one, two or more such =O groups present in a compound.

In some instances (more typical, although not most preferred), two $R^{313}$ groups on adjacent atoms may together form a ring, or an $R^{34}$ and an $R^{313}$ on adjacent atoms may form a ring. This may be a saturated or unsaturated and/or a substituted or unsubstituted ring. In typical embodiments, such rings may be 5 or 6 membered rings, and may be heterocyclic or carbocyclic, and are typically aromatic. Such rings may be selected from:

a substituted or unsubstituted cyclic $C_3$-$C_8$ alkyl group (such as cyclopropyl, cyclobutyl, cyclopentyl, cyclohexyl, cycloheptyl and cyclooctyl);

a substituted or unsubstituted aromatic group (such as Ph-, F-Ph-, Cl-Ph-, Br-Ph-, I-Ph-, F$_2$-Ph-, Cl$_2$-Ph-, Br$_2$-Ph-, I$_2$-Ph-, Me$_2$-Ph-, Et$_2$-Ph-, Pr$_2$-Ph-, Bu$_2$-Ph-, (CN)$_2$-Ph-, (NO$_2$)$_2$-Ph-, (NH$_2$)$_2$-Ph-, (MeO)$_2$-Ph-, (CF$_3$)$_2$-Ph-, Me-Ph-, Et-Ph-, Pr-Ph-, Bu-Ph-, (CN)-Ph-, (NO$_2$)-Ph-, (NH$_2$)-Ph-, MeO-Ph-, (NH$_2$—CO)-Ph-, CF$_3$-Ph-, CF$_3$O-Ph-, and a saturated or unsaturated, substituted or unsubstituted, heterocyclic group including an aromatic heterocyclic group and/or a non-aromatic heterocyclic group (such as pyrrole, pyrazole, imidazole, 1,2,3-triazole, 1,2,4-triazole, pyridine, pyridazine, pyrimidine, pyrazine, pyrrolidine, piperidine, 2-azapiperidine, 3-azapiperidine, piperazine, furan, pyran, 2-azapyran, 3-azapyran, 4-azapyran, tetrahydrofuran, 2-aza-tetrahydrofuran, 3-aza-tetrahydrofuran, tetrahydropyran, 2-aza-tetrahydropyran, 3-aza-tetrahydropyran, morpholine, thiophene, isothiazole, thiazole, thiopyran, 2-azathiopyran, 3-azathiopyran, 4-azathiopyran, thiolane, thiane, oxazole, isoxazole, furazan, 1,3,4-oxadiazole, 1,2,4-oxadiazole; and tetrazole).

More typically, such rings may be substituted or unsubstituted phenyl rings, substituted or unsubstituted pyridine rings, substituted or unsubstituted 1,2 diazole rings, substituted or unsubstituted 1,3 diazole rings, substituted or unsubstituted 1,3 oxazole rings, and substituted or unsubstituted 1,3 thiazole rings.

In some instances (especially where the compound does not comprise another aminocarbonyl group, carbonylamino group, aminosulphonyl group, or sulphonylamino group) one or more of the $R^{313}$ groups may be selected from a group comprising an aminocarbonyl group, a carbonylamino group, an aminosulphonyl group, a sulphonylamino group, a substituted or unsubstituted piperidinyl group, a substituted or unsubstituted piperazinyl group, a substituted or unsubstituted alcohol group, a substituted or unsubstituted ether group, and/or a saturated or unsaturated, substituted or unsubstituted, carbocyclic group such as a substituted or unsubstituted cyclohexyl group or a substituted or unsubstituted phenyl group. In such instances, the following $R^{313}$ groups are especially preferred:

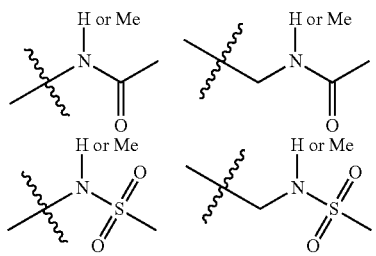

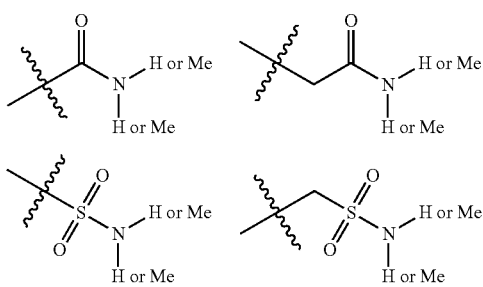
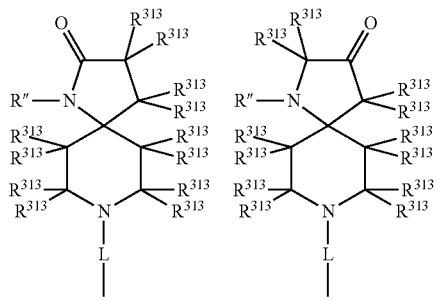
Thus, particularly preferred compounds of this type may have a Y group having one of the following formulae:
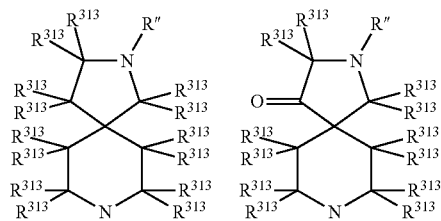
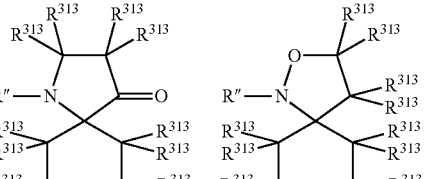
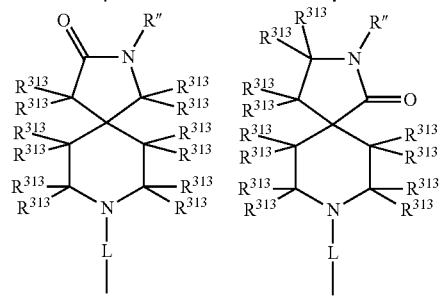
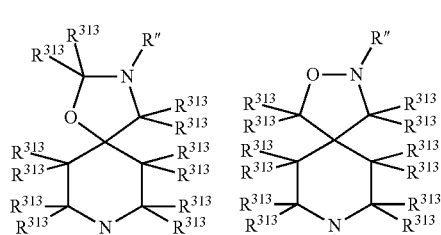
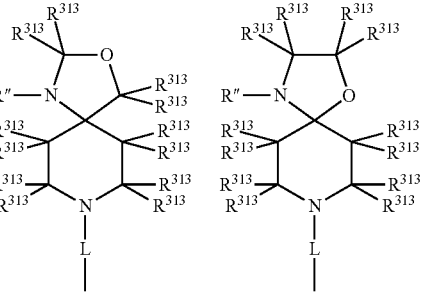
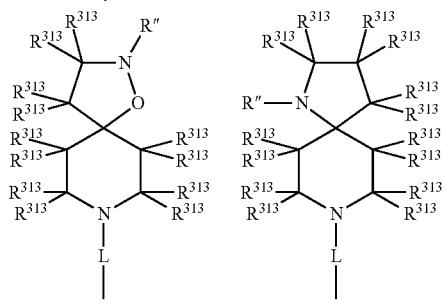
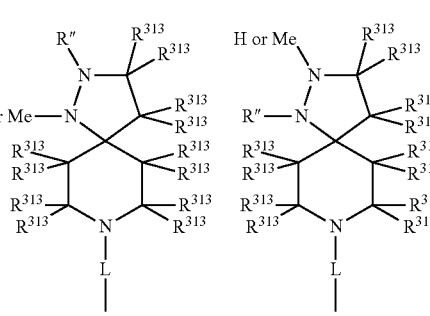

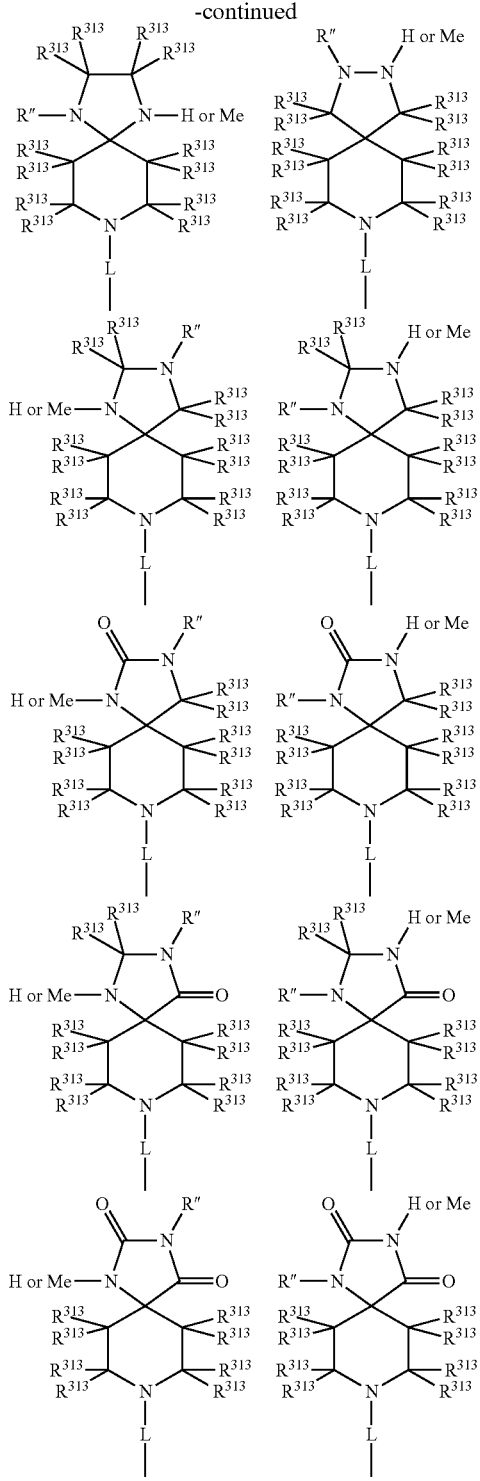

wherein L is present or absent (and is preferably absent) and wherein $R^{313}$ is as defined anywhere herein (although in these embodiments, unless otherwise specified, it is preferred that all $R^{313}$ are H) and wherein R" is selected from H and any if the following groups:

- a substituted or unsubstituted linear or branched $C_1$-$C_6$ alkyl group (such as Me, Et, Pr, i-Pr, n-Bu, i-Bu, t-Bu, pentyl and hexyl);
- a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);
- a substituted or unsubstituted linear or branched $C_1$-$C_6$ halogenated alkyl group (such as —CH$_2$F, —CF$_3$, and —CH$_2$CF$_3$);
- a substituted or unsubstituted cyclic amine or amido group (such as pyrrolidin-3-yl, piperidin-3-yl, piperidin-4-yl, 2-keto-pyrrolidinyl, 3-keto-pyrrolidinyl, 2-keto-piperidinyl, 3-keto-piperidinyl, and 4-keto-piperidinyl) which group may be attached via a —CH$_2$— or a —CH$_2$CH$_2$— group;
- a substituted or unsubstituted cyclic $C_3$-$C_8$ alkyl group (such as cyclopropyl, cyclobutyl, cyclopentyl, cyclohexyl, cycloheptyl and cyclooctyl) which group may be attached via a —CH$_2$— or a —CH$_2$CH$_2$— group;
- a substituted or unsubstituted linear or branched $C_2$-$C_6$ alcohol group (such as —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_2$CH$_3$)CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);
- a substituted or unsubstituted linear or branched $C_1$-$C_7$ alkoxy or aryloxy group linked through —O via at least two further C atoms (such as —CH$_2$CH$_2$OPh-CH$_2$CH$_2$OMe, —CH$_2$CH$_2$OEt, —CH$_2$CH$_2$OPr, —CH$_2$CH$_2$OBu, —CH$_2$CH$_2$CH$_2$OPh, —CH$_2$CH$_2$CH$_2$OMe, —CH$_2$CH$_2$CH$_2$CH$_2$OMe, and —CH$_2$CH$_2$CH$_2$CH$_2$CH$_2$OMe);
- a substituted or unsubstituted linear or branched $C_2$-$C_6$ carboxylic acid group (such as —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);
- a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;
- a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);
- a substituted or unsubstituted linear or branched $C_1$-$C_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);
- a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO$_2$-pyrrolidine-N-yl, —SO$_2$-morpholine-N-yl, —SO$_2$NHCH$_2$OMe, and —SO$_2$NHCH$_2$CH$_2$OMe;

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F$_2$-Ph-, 2, (3,4,5 or 6)-Cl$_2$-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-Cl$_2$-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-) which group may be attached via a —CH$_2$— or a —CH$_2$CH$_2$— group; and a saturated or unsaturated, substituted or unsubstituted, heterocyclic group including an aromatic heterocyclic group and/or a non-aromatic heterocyclic group (such as pyrrole-2-yl, pyrrole-3-yl, pyrazole-3-yl, pyrazole-4-yl, pyrazole-5-yl, imidazole-2-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, oxazol-2-yl, oxazol-3-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl) which group may be attached via a —CH$_2$— or a —CH$_2$CH$_2$— group.

Preferably, R" is selected from one of the following groups:

a substituted or unsubstituted linear or branched C$_1$-C$_6$ alkyl group (such as Me, Et, Pr, i-Pr, n-Bu, i-Bu, t-Bu, pentyl and hexyl);

a substituted or unsubstituted linear or branched C$_2$-C$_6$ alcohol group (such as —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$H$_2$CH$_2$CH$_2$CH$_2$OH);

a substituted or unsubstituted linear or branched C$_1$-C$_7$ alkoxy or aryloxy group linked through —O via at least two further C atoms (such as —CH$_2$CH$_2$OPh-CH$_2$CH$_2$OMe, —CH$_2$CH$_2$OEt, —CH$_2$CH$_2$OPr, —CH$_2$CH$_2$OBu, —CH$_2$CH$_2$CH$_2$OPh, —CH$_2$CH$_2$CH$_2$OMe, —CH$_2$CH$_2$CH$_2$CH$_2$OMe, and —CH$_2$CH$_2$CH$_2$CH$_2$CH$_2$OMe);

a substituted or unsubstituted linear or branched C$_1$-C$_6$ halogenated alkyl group (such as —CH$_2$F, —CF$_3$, and —CH$_2$CF$_3$);

a substituted or unsubstituted cyclic amine or amido group (such as pyrrolidin-3-yl, piperidin-3-yl, piperidin-4-yl, 2-keto-pyrrolidinyl, 3-keto-pyrrolidinyl, 2-keto-piperidinyl, 3-keto-piperidinyl, and 4-keto-piperidinyl) which group may be attached via a —CH$_2$— or a —CH$_2$CH$_2$— group;

a substituted or unsubstituted cyclic C$_3$-C$_8$ alkyl group (such as cyclopropyl, cyclobutyl, cyclopentyl, cyclohexyl, cycloheptyl and cyclooctyl) which group may be attached via a —CH$_2$— or a —CH$_2$CH$_2$— group;

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F$_2$-Ph-, 2, (3,4,5 or 6)-Cl$_2$-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-Cl$_2$-Ph-, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-) which group may be attached via a —CH$_2$— or a —CH$_2$CH$_2$— group; and a saturated or unsaturated, substituted or unsubstituted, heterocyclic group including an aromatic heterocyclic group and/or a non-aromatic heterocyclic group (such as pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl) which group may be attached via a —$CH_2$— or a —$CH_2CH_2$— group.

In some embodiments, R" may be selected from a carbonyl group or a sulphonyl group such as:

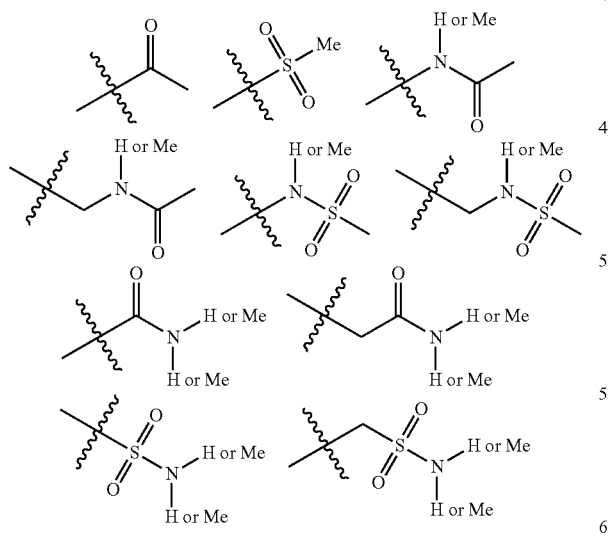

As has been mentioned, in some cases L may form a ring with $R^{31}$ or $R^{32}$, and/or $R^{31}$ and $R^{32}$ may form a ring with each other. The ring may be substituted or unsubstituted and may be carbocyclic or heterocyclic and may be saturated or unsaturated. In some such embodiments, the Y group may be selected from the following structures:

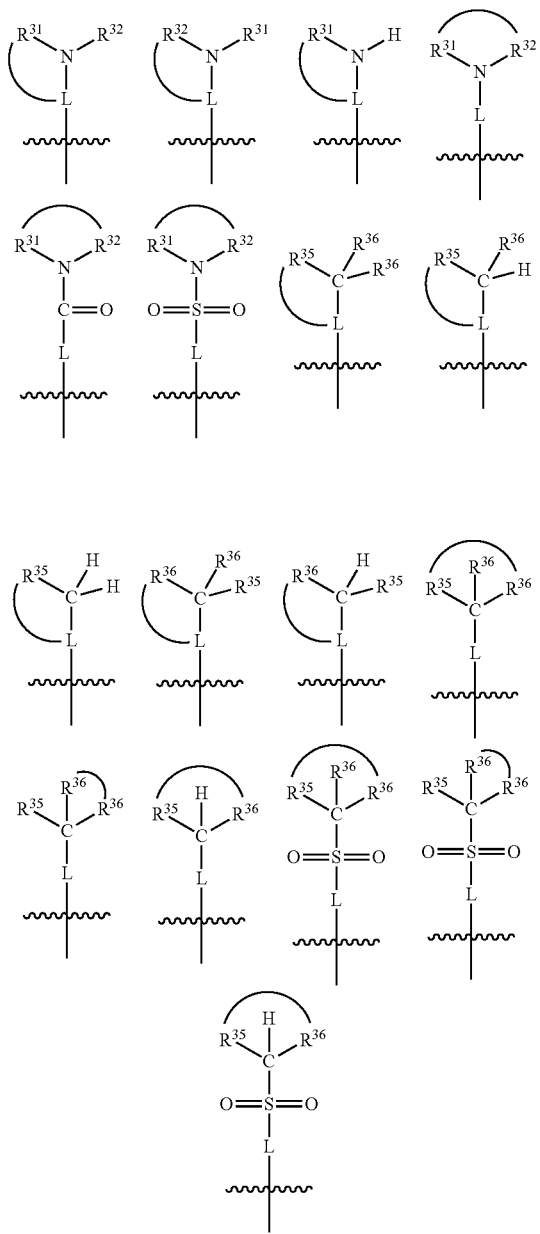

In these groups, L, $R^{31}$, $R^{32}$, $R^{35}$ and $R^{36}$ may have the meaning as defined anywhere herein. In each case L may be present or absent. The curved line represents any organic group joining $R^{31}$ and L, or $R^{31}$ and $R^{32}$, or $R^{35}$ and L, or $R^{36}$ and L, or $R^{35}$ and $R^{36}$ to form a ring. Typically, but not exclusively the curved line may be a substituted or unsubstituted alkylene group having from 1 to 6 C atoms, such as —$CH_2$—, —$CH_2CH_2$—, —$CH_2CH_2CH_2$—, —$CH(CH_3)CH_2$—, —$C(CH_3)_2$—, —$CH_2CH_2CH_2CH_2$, —$CH(CH_3)CH_2CH_2$—, —$CH(CH_3)CH(CH_3)$—, —$CH(CH_2CH_3)CH_2$—, —$C(CH_3)_2CH_2$—, —$CH_2CH_2CH_2CH_2CH_2$—, and —$CH_2CH_2CH_2CH_2CH_2CH_2$—. In cases where the R groups form a ring with each other or with L, the R groups are typically methylene (—$CH_2$—) groups.

In typical embodiments, the atom of L which forms the ring with $R^{31}$ or $R^{32}$ or $R^{35}$ or $R^{36}$ is an atom directly bonded to the N or C of Y.

Further typically, the atom of L which forms the ring with $R^{31}$ or $R^{32}$ or $R^{35}$ or $R^{36}$ is a C atom, which may be doubly bonded to the rest of L, or singly bonded to the rest of L. Thus, in such cases, Y may be selected from the following groups:

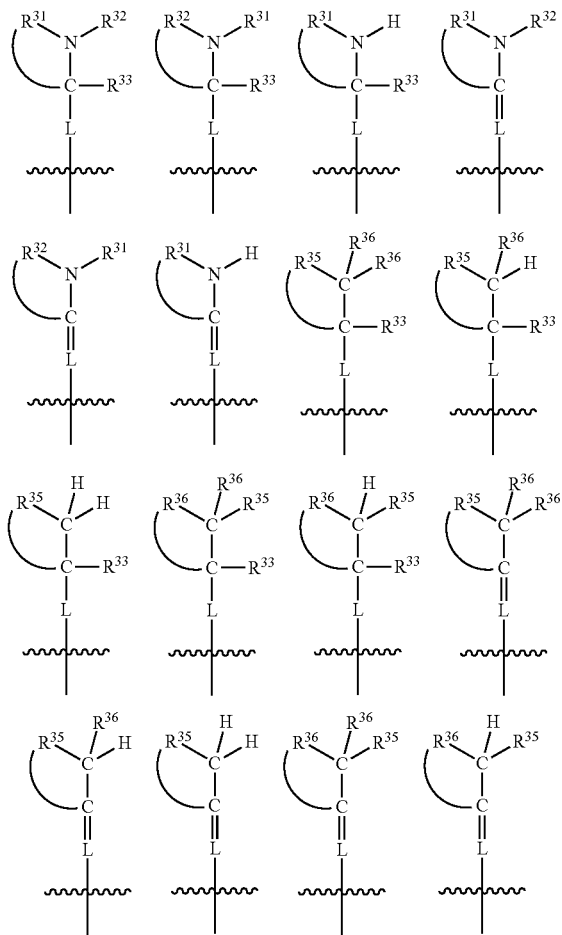

where $R^{33}$ may be selected from H and a substituted or unsubstituted organic group. In the case where L is double bonded at one end, such as to C in the above, then the valency of L is maintained. In such cases, L is trivalent rather than divalent, and may comprise a substituted or unsubstituted $C_1$-$C_6$ alkenyl group (such as =CH—, =CHCH$_2$—, =CHCH$_2$CH$_2$—, =CHCH$_2$CH$_2$CH$_2$—, =CHCH$_2$CH$_2$CH$_2$CH$_2$—, and =CHCH$_2$CH$_2$CH$_2$CH$_2$CH$_2$—).

In some cases, the rest of the linker, L, is absent (in these cases the linker comprises only the C atom which forms the ring with $R^{31}$, or comprises only —$CR^{33}$— when $R^{33}$ is present)

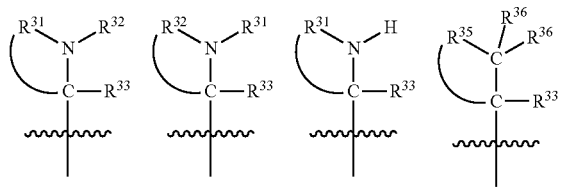

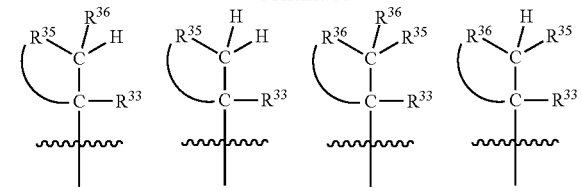

In typical embodiments of the invention, $R^{31}$ and $R^{32}$ are each independently selected from H and the following groups:
- a substituted or unsubstituted linear or branched $C_1$-$C_6$ alkyl group (such as Me, Et, Pr, i-Pr, n-Bu, i-Bu, t-Bu, pentyl and hexyl);
- a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);
- a substituted or unsubstituted linear or branched $C_1$-$C_6$ halogenated alkyl group (such as —CH$_2$F, —CF$_3$, and —CH$_2$CF$_3$);
- a substituted or unsubstituted cyclic amine or amido group (such as pyrrolidin-3-yl, piperidin-3-yl, piperidin-4-yl, 2-keto-pyrrolidinyl, 3-keto-pyrrolidinyl, 2-keto-piperidinyl, 3-keto-piperidinyl, and 4-keto-piperidinyl);
- a substituted or unsubstituted cyclic $C_3$-$C_8$ alkyl group (such as cyclopropyl, cyclobutyl, cyclopentyl, cyclohexyl, cycloheptyl and cyclooctyl);
- a substituted or unsubstituted linear or branched $C_2$-$C_6$ alcohol group (such as —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$OCH$_2$OH, and —CH$_2$CH$_2$CH$_2$CH$_2$CH$_2$CH$_2$OH),
- a substituted or unsubstituted linear or branched $C_1$-$C_7$ alkoxy or aryloxy group linked through —O via at least two further C atoms (such as —CH$_2$CH$_2$OPh-CH$_2$CH$_2$OMe, —CH$_2$CH$_2$OEt, —CH$_2$CH$_2$OPr, —CH$_2$CH$_2$OBu, —CH$_2$CH$_2$CH$_2$Ph, —CH$_2$CH$_2$CH$_2$OMe, —CH$_2$CH$_2$CH$_2$CH$_2$OMe, and —CH$_2$CH$_2$CH$_2$CH$_2$CH$_2$OMe);
- a substituted or unsubstituted linear or branched $C_2$-$C_6$ carboxylic acid group (such as —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);
- a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —$CH_2$COOMe, —$CH_2CH_2$COOMe, —$CH_2CH_2CH_2$COOMe, and —$CH_2CH_2CH_2CH_2$COOMe);

a substituted or unsubstituted linear or branched $C_1$-$C_6$ amide group (such as —CO—$NH_2$, —CO—NMeH, —CO—$NMe_2$, —CO—NEtH, —CO—NEtMe, —CO—$NEt_2$, —CO—NPrH, —CO—NPrMe, and —CO—NPrEt);

a substituted or unsubstituted sulphonyl group (such as —$SO_2$Me, —$SO_2$Et, —$SO_2$Pr, —$SO_2$iPr, —$SO_2$Ph, —$SO_2$-(2,3 or 4)-F-Ph, —$SO_2$-cyclopropyl, —$SO_2CH_2CH_2OCH_3$), —$SO_2NH_2$, —$SO_2$NHMe, —$SO_2NMe_2$, —$SO_2$NHEt, —$SO_2NEt_2$, —$SO_2$-pyrrolidine-N-yl, —$SO_2$-morpholine-N-yl, —$SO_2NHCH_2$OMe, and —$SO_2NHCH_2CH_2$OMe;

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-$F_2$-Ph-, 2, (3,4,5 or 6)-$Cl_2$-Ph-, 2, (3,4,5 or 6)-$Br_2$-Ph-, 2, (3,4,5 or 6)-$I_2$-Ph-, 2, (3,4,5 or 6)-$Me_2$-Ph-, 2, (3,4,5 or 6)-$Et_2$-Ph-, 2, (3,4,5 or 6)-$Pr_2$-Ph-, 2, (3,4,5 or 6)-$Bu_2$-Ph-, 2, (3,4,5 or 6)-$(CN)_2$-Ph-, 2, (3,4,5 or 6)-$(NO_2)_2$-Ph-, 2, (3,4,5 or 6)-$(NH_2)_2$-Ph-, 2, (3,4,5 or 6)-$(MeO)_2$-Ph-, 2, (3,4,5 or 6)-$(CF_3)_2$-Ph-, 3, (4 or 5)-$F_2$-Ph-, 3, (4 or 5)-$Cl_2$-Ph-, 3, (4 or 5)-$Br_2$-Ph-, 3, (4 or 5)-$I_2$-Ph-, 3, (4 or 5)-$Me_2$-Ph-, 3, (4 or 5)-$Et_2$-Ph-, 3, (4 or 5)-$Pr_2$-Ph-, 3, (4 or 5)-$Bu_2$-Ph-, 3, (4 or 5)-$(CN)_2$-Ph-, 3, (4 or 5)-$(NO_2)_2$-Ph-, 3, (4 or 5)-$(NH_2)_2$-Ph-, 3, (4 or 5)-$(MeO)_2$-Ph-, 3, (4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-($NO_2$)-Ph-, 3-($NO_2$)-Ph-4-($NO_2$)-Ph-, 2-($NH_2$)-Ph-, 3-($NH_2$)-Ph-, 4-($NH_2$)-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3$O-Ph-, 3° $CF_3$O-Ph-, and 4-$CF_3$O-Ph-); and a saturated or unsaturated, substituted or unsubstituted, heterocyclic group including an aromatic heterocyclic group and/or a non-aromatic heterocyclic group (such as pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyridine-4-yl, pyrimidine-5-yl, pyrazine-2-yl, pyrrolidine-2-yl, pyrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl).

Independently, in typical embodiments of the invention, $R^{33}$ is selected from H and the following groups:

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —$CH_2$Ph, —$CH_2$(2,3 or 4)F-Ph, —$CH_2$(2,3 or 4)Cl-Ph, —$CH_2$(2,3 or 4)Br-Ph, —$CH_2$(2,3 or 4)I-Ph, —$CH_2CH_2$Ph, —$CH_2CH_2CH_2$Ph, —$CH_2CH_2CH_2CH_2$Ph, —$CH_2CH_2CH_2CH_2CH_2$Ph, and —$CH_2CH_2CH_2CH_2CH_2CH_2$Ph);

a substituted or unsubstituted linear or branched $C_1$-$C_6$ halogenated alkyl group (such as —$CH_2$F, —$CH_2$Cl, —$CF_3$, —$CCl_3$—$CBr_3$, —$CI_3$, —$CH_2CF_3$, —$CH_2CCl_3$, —$CH_2CBr_3$, and —$CH_2CI_3$);

an —$NH_2$ group, or a substituted or unsubstituted linear or branched primary secondary or tertiary $C_1$-$C_6$ amine group (such as —NMeH, —$NMe_2$, —NEtH, —NEtMe, —$NEt_2$, —NPrH, —NPrMe, —NPrEt, —$NPr_2$, —NBuH, —NBuMe, —NBuEt, —$CH_2$—$NH_2$, —$CH_2$—NMeH, —$CH_2$—$NMe_2$, —$CH_2$—NEtH, —$CH_2$—NEtMe, —$CH_2$—$NEt_2$, —$CH_2$—NPrH, —$CH_2$—NPrMe, and —$CH_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)$_1$-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2, (3,4,5 or 6)$F_2$-Ph, —NH-2, (3,4,5 or 6)$Cl_2$-Ph, —NH-2, (3,4,5 or 6)$Br_2$-Ph, —NH-2, (3,4,5 or 6)$I_2$-Ph, —NH-2, (3,4,5 or 6)$Me_2$-Ph, —NH-2, (3,4,5 or 6)$Et_2$-Ph, —NH-2, (3,4,5, or 6)$Pr_2$-Ph, —NH-2, (3,4,5 or 6)$Bu_2$-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic $C_3$-$C_8$ alkyl group (such as cyclopropyl, cyclobutyl, cyclopentyl, cyclohexyl, cycloheptyl and cyclooctyl);

an —OH, or a substituted or unsubstituted linear or branched $C_1$-$C_6$ alcohol group (such as —$CH_2$OH, —$CH_2CH_2$OH, —$CH_2CH_2$OH, —CH($CH_3$)$CH_2$OH, —C($CH_3$)$_2$OH, —$CH_2CH_2CH_2$OH, —CH($CH_3$)$CH_2CH_2$OH, —CH($CH_3$)CH($CH_3$)OH, —CH($CH_2CH_3$)$CH_2$OH, —C($CH_3$)$_2CH_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched C$_1$-C$_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NH$_2$CH$_2$CH$_2$NH$_2$, —(CO)NHCH$_2$CH$_2$NHMe, and —(CO)NHCH$_2$CH$_2$NMe$_2$;

a substituted or unsubstituted linear or branched C$_1$-C$_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);

a substituted or unsubstituted linear or branched C$_1$-C$_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);

a substituted or unsubstituted linear or branched C$_1$-C$_7$ amino carbonyl group (such as —NH—CO-Me, —NH—CO-Et, —NH—CO—Pr, —NH—CO-Bu, —NH—CO-pentyl, —NH—CO-hexyl, —NH—CO-Ph, —NMe-CO-Me, —NMe-CO-Et, —NMe-CO—Pr, —NMe-CO-Bu, —NMe-CO-pentyl, —NMe-CO-hexyl, —NMe-CO-Ph;

a substituted or unsubstituted linear or branched C$_1$-C$_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$Me, —CH$_2$CH$_2$CH$_2$OMe, and —CH$_2$CH$_2$CH$_2$CH$_2$OMe);

a substituted or unsubstituted linear or branched aminoalkoxy group (such as, —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO$_2$-pyrolidine-N-yl, —SO$_2$-morpholine-N-yl, —SO$_2$NHCH$_2$OMe, and —SO$_2$NHCH$_2$CH$_2$OMe;

a substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6) F$_2$-Ph-, 2, (3,4,5 or 6)-Cl$_2$-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Br$_2$-Ph-, 2, (3,4,5 or 6)-(CN)$_2$-Ph, 2, (3,4,5 or 6)-NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-C$_2$-Ph, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)Ph-, 3-(NO$_2$)-Ph-4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and a saturated or unsaturated, substituted or unsubstituted, heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyrazine-3-yl, pyridazine-4-yl, pyridine-2-yl, pyrimidin-4-yl, pyrimidin-5-yl, pyrazine-2-yl, pyrolidine-1-yl, pyrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2, 4-oxadiazol)-3-yl, (1,2,4-oxadiazol)-5-yl; and tetrazole-1-yl, tetrazole-2-yl, tetrazole-5-yl).

In more typical embodiments, $R^{31}$ is selected from a carbocyclic or heterocyclic group, which may be saturated or unsaturated, or aromatic or aliphatic, such as a substituted or unsubstituted phenyl group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F$_2$-Ph-, 2, (3,4,5 or 6)-Cl$_2$-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-Cl$_2$-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-).

In more typical embodiments, $R^{32}$ is selected from H or a $C_1$-$C_6$ alkyl group (such as Me, Et, Pr, i-Pr, n-Bu, i-Bu, t-Bu, pentyl and hexyl).

In more typical embodiments, $R^{33}$ is selected from H, a substituted or unsubstituted $C_1$-$C_6$ alkyl group, an —NH$_2$ group or a substituted or unsubstituted $C_1$-$C_6$ amino group, a substituted or unsubstituted $C_1$-$C_6$ alkoxy group, and a nitrile group.

Each $R^{34}$ is typically independently selected from H and a group selected from the following groups:

a halogen (such as —F, —Cl, —Br and —I);

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted linear or branched $C_1$-$C_6$ halogenated alkyl group (such as —CH$_2$F, —CH$_2$Cl, —CF$_3$, —CCl$_3$—CBr$_3$, —CI$_3$, —CH$_2$CF$_3$, —CH$_2$CCl$_3$, —CH$_2$CBr$_3$, and —CH$_2$CI$_3$);

an —NH$_2$ group, or a substituted or unsubstituted linear or branched primary secondary or tertiary $C_1$-$C_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)$_1$-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2, (3,4,5 or 6)F$_2$-Ph, —NH-2, (3,4,5 or 6)Cl$_2$-Ph, —NH-2, (3,4,5 or 6)Br$_2$-Ph, —NH-2, (3,4,5 or 6)I$_2$-Ph, —NH-2, (3,4,5 or 6)Me$_2$-Ph, —NH-2, (3,4,5 or 6)Et$_2$-Ph, —NH-2, (3,4,5, or 6)Pr$_2$-Ph, —NH-2, (3,4,5 or 6)Bu$_2$-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic $C_3$-$C_8$ alkyl group (such as cyclopropyl, cyclobutyl, cyclopentyl, cyclohexyl, cycloheptyl and cyclooctyl);

an —OH or a substituted or unsubstituted linear or branched $C_1$-$C_6$ alcohol group (such as —CH$_2$OH, —CH$_2$CH$_2$OH, —CH$_2$CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched $C_1$-$C_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);

a substituted or unsubstituted linear or branched $C_1$-$C_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);

a substituted or unsubstituted linear or branched $C_1$-$C_7$ amino carbonyl group (such as —NH—CO-Me, —NH—CO-Et, —NH—CO—Pr, —NH—CO-Bu, —NH—CO-pentyl, —NH—CO-hexyl, —NH—CO-Ph, —NMe-CO-Me, —NMe-CO-Et, —NMe-CO—Pr, —NMe-CO-Bu, —NMe-CO-pentyl, —NMe-CO-hexyl, —NMe-CO-Ph;

a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$OMe, —CH$_2$CH$_2$OMe, —CH$_2$CH$_2$CH$_2$OMe, and —CH$_2$CH$_2$CH$_2$CH$_2$OMe);

a substituted or unsubstituted linear or branched aminoalkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO$_2$-pyrrolidine-N-yl, —SO$_2$-morpholine-N-yl, —SO$_2$NHCH$_2$OMe, and —SO$_2$NHCH$_2$CH$_2$OMe;

an substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);

a substituted or unsubstituted aromatic group (such as Ph-, 2-F-Ph-, 3-F-Ph-, 4-F-Ph-, 2-Cl-Ph-, 3-Cl-Ph-, 4-C-Ph-, 2-Br-Ph-, 3-Br-Ph-, 4-Br-Ph-, 2-I-Ph-, 3-I-Ph, 4-I-Ph-, 2, (3,4,5 or 6)-F$_2$-Ph-, 2, (3,4,5 or 6)-Cl$_2$-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-Cl$_2$-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and a saturated or unsaturated, substituted or unsubstituted, heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl).

In some embodiments the $R^{34}$ groups form a ring with each other. In such cases the ring is typically a 3, 4, 5, 6 or 7 membered substituted or unsubstituted carbocyclic ring or heterocyclic ring, which may be saturated or unsaturated.

In some embodiments, one $R^{34}$ group is —H and one is not —H. In other embodiments, both $R^{34}$ groups are —H. In yet further embodiments neither $R^{34}$ group is —H.

As has been mentioned, $R^{35}$ is selected from an alcohol group or an ether group. Typically $R^{35}$ is selected from a group of formula —(C$_0$-C$_7$)—O—(C$_0$-C$_7$) where the C$_0$-C$_7$ groups may be linear or branched alkyl groups, or may be phenyl groups, or may be absent (C$_0$). More typically, $R^{35}$ may be a —(C$_1$-C$_7$)—OH alcohol group, a —O—(C$_1$-C$_7$) ether group, or a —(C$_1$-C$_4$)—O—(C$_1$-C$_4$) ether group, or a —(C$_1$-C$_3$)—O—(C$_1$-C$_3$) ether group.

$R^{35}$ is typically selected from the following oxygen-containing groups:

an —OH or a substituted or unsubstituted linear or branched C$_1$-C$_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched C$_1$-C$_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, —CH$_2$CH$_2$CH$_2$CH$_2$CH$_2$OMe, —CH$_2$CH$_2$CH$_2$CH$_2$CH$_2$CH$_2$OMe, —CH$_2$CH$_2$OEt, —CH$_2$CH$_2$Pr, —CH$_2$CH$_2$OBu, —CH$_2$CH$_2$Opentyl, —CH$_2$CH$_2$CH$_2$OEt, —CH$_2$CH$_2$CH$_2$OPr, and —CH$_2$CH$_2$CH$_2$OBu).

In preferred embodiments $R^{35}$ is selected from an —OH group and an —OR" group where R" is a C$_1$-C$_6$ alkyl group (such as Me, Et, Pr, i-Pr, n-Bu, i-Bu, t-Bu, pentyl and hexyl).

Each $R^{36}$ is typically each independently selected from H and a group selected from the following groups:

a halogen (such as —F, —Cl, —Br and —I, preferably —F);

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —$CH_2$Ph, —$CH_2$(2,3 or 4)F-Ph, —$CH_2$(2,3 or 4)Cl-Ph, —$CH_2$(2,3 or 4)Br-Ph, —$CH_2$(2,3 or 4)$_1$-Ph, —$CH_2CH_2$Ph, —$CH_2CH_2CH_2$Ph, —$CH_2CH_2CH_2CH_2$Ph, —$CH_2CH_2CH_2CH_2CH_2$Ph, and —$CH_2CH_2CH_2CH_2CH_2CH_2$Ph);

a substituted or unsubstituted linear or branched $C_1$-$C_6$ halogenated alkyl group (such as —$CH_2$F, —$CH_2$Cl, —$CF_3$, —$CCl_3$—$CBr_3$, —$CI_3$, —$CH_2CF_3$, —$CH_2CCl_3$, —$CH_2CBr_3$, and —$CH_2CI_3$);

an —$NH_2$ group, or a substituted or unsubstituted linear or branched primary secondary or tertiary $C_1$-$C_6$ amine group (such as —NMeH, —$NMe_2$, —NEtH, —NEtMe, —$NEt_2$, —NPrH, —NPrMe, —NPrEt, —$NPr_2$, —NBuH, —NBuMe, —NBuEt, —$CH_2$—$NH_2$, —$CH_2$—NMeH, —$CH_2$—$NMe_2$, —$CH_2$—NEtH, —$CH_2$—NEtMe, —$CH_2$—$NEt_2$, —$CH_2$—NPrH, —$CH_2$—NPrMe, and —$CH_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2, (3,4,5 or 6)$F_2$-Ph, —NH-2, (3,4,5 or 6)$Cl_2$-Ph, —NH-2, (3,4,5 or 6)$Br_2$-Ph, —NH-2, (3,4,5 or 6)$I_2$-Ph, —NH-2, (3,4,5 or 6)$Me_2$-Ph, —NH-2, (3,4,5 or 6)$Et_2$-Ph, —NH-2, (3,4,5, or 6)$Pr_2$-Ph, —NH-2, (3,4,5 or 6)$Bu_2$-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-ketopiperidinyl, and 4-keto-piperidinyl);

a substituted or unsubstituted cyclic $C_3$-$C_8$ alkyl group (such as cyclopropyl, cyclobutyl, cyclopentyl, cyclohexyl, cycloheptyl and cyclooctyl);

an —OH or a substituted or unsubstituted linear or branched $C_1$-$C_6$ alcohol group (such as —$CH_2$OH, —$CH_2CH_2$OH, —$CH_2CH_2CH_2$OH, —$CH(CH_3)CH_2$OH, —$C(CH_3)_2$OH, —$CH_2CH_2CH_2CH_2$OH, —$CH(CH_3)CH_2CH_2$OH, —$C(CH_3)CH(CH_3)$OH, —$CH(CH_2CH_3)CH_2$OH, —$C(CH_3)_2CH_2$OH, —$CH_2CH_2CH_2CH_2CH_2$OH, and —$CH_2CH_2CH_2CH_2CH_2CH_2$OH);

a substituted or unsubstituted linear or branched $C_1$-$C_6$ carboxylic acid group (such as —COOH, —$CH_2$COOH, —$CH_2CH_2$COOH, —$CH_2CH_2CH_2$COOH, —$CH_2CH_2CH_2CH_2$COOH, and —$CH_2CH_2CH_2CH_2CH_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)$CH_2$Ph, —(CO)$CH_2$OH, —(CO)$CH_2OCH_3$, —(CO)$CH_2NH_2$, —(CO)$CH_2$NHMe, —(CO)$CH_2NMe_2$, —(CO)-cyclopropyl, —(CO)-1,3-epoxypropan-2-yl; —(CO)$NH_2$, —(CO)NHMe, —(CO)$NMe_2$, —(CO)NHEt, —(CO)$NEt_2$, —(CO)-pyrollidine-N-yl, —(CO)-morpholine-N-yl, —(CO)-piperazine-N-yl, —(CO)—N-methyl-piperazine-N-yl, —(CO)NH$CH_2CH_2$OH, —(CO)NH$CH_2CH_2$OMe, —(CO)NH$CH_2CH_2NH_2$, —(CO)NH$CH_2CH_2$NHMe, and —(CO)NH$CH_2CH_2NMe_2$;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —$CH_2$COOMe, —$CH_2CH_2$COOMe, —$CH_2CH_2CH_2$COOMe, and —$CH_2CH_2CH_2CH_2$COOMe);

a substituted or unsubstituted linear or branched $C_1$-$C_6$ amide group (such as —CO—$NH_2$, —CO—NMeH, —CO—$NMe_2$, —CO—NEtH, —CO—NEtMe, —CO—$NEt_2$, —CO—NPrH, —CO—NPrMe, and —CO—NPrEt);

a substituted or unsubstituted linear or branched $C_1$-$C_7$ amino carbonyl group (such as —NH—CO-Me, —NH—CO-Et, —NH—CO—Pr, —NH—CO-Bu, —NH—CO-pentyl, —NH—CO-hexyl, —NH—CO-Ph, —NMe-CO-Me, —NMe-CO-Et, —NMe-CO—Pr, —NMe-CO-Bu, —NMe-CO-pentyl, —NMe-CO-hexyl, —NMe-CO-Ph;

a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —$OCH_2$F, —$OCHF_2$, —$OCF_3$, —O-Ph, —O—$CH_2$-Ph, —O—$CH_2$-(2,3 or 4)-F-Ph, —O—$CH_2$-(2,3 or 4)-Cl-Ph, —$CH_2$OMe, —$CH_2$OEt, —$CH_2$OPr, —$CH_2$OBu, —$CH_2CH_2$OMe, —$CH_2CH_2CH_2$OMe, —$CH_2CH_2CH_2CH_2$OMe, and —$CH_2CH_2CH_2CH_2CH_2$OMe);

a substituted or unsubstituted linear or branched aminoalkoxy group (such as —$OCH_2CH_2NH_2$, —$OCH_2CH_2$NHMe, —$OCH_2CH_2NMe_2$, —$OCH_2CH_2$NHEt, and —$OCH_2CH_2NEt_2$;

a substituted or unsubstituted sulphonyl group (such as —$SO_2$Me, —$SO_2$Et, —$SO_2$Pr, —$SO_2$iPr, —$SO_2$Ph, —$SO_2$-(2,3 or 4)-F-Ph, —$SO_2$-cyclopropyl, —$SO_2CH_2CH_2OCH_3$), —$SO_2NH_2$, —$SO_2$NHMe, —$SO_2NMe_2$, —$SO_2$NHEt, —$SO_2NEt_2$, —$SO_2$-pyrrolidine-N-yl, —$SO_2$-morpholine-N-yl, —$SO_2$NH$CH_2$OMe, and —$SO_2$NH$CH_2CH_2$OMe;

an substituted or unsubstituted aminosulphonyl group (such as —$NHSO_2$Me, —$NHSO_2$Et, —$NHSO_2$Pr, —$NHSO_2$iPr, —$NHSO_2$Ph, —$NHSO_2$-(2,3 or 4)-F-Ph, —$NHSO_2$-cyclopropyl, —$NHSO_2CH_2CH_2OCH_3$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-$F_2$-Ph-, 2, (3,4,5 or 6)-$Cl_2$-Ph-, 2, (3,4,5 or 6)-$Br_2$-Ph-, 2, (3,4,5 or 6)-$I_2$-Ph-, 2, (3,4,5 or 6)-$Me_2$-Ph-, 2, (3,4,5 or 6)-$Et_2$-Ph-, 2, (3,4,5 or 6)-$Pr_2$-Ph-, 2, (3,4,5 or 6)-$Bu_2$-Ph-, 2, (3,4,5 or 6)-$(CN)_2$-Ph-, 2, (3,4,5 or 6)-$(NO_2)_2$-Ph-, 2, (3,4,5 or 6)-$(NH_2)_2$-Ph-, 2, (3,4,5 or 6)-$(MeO)_2$-Ph-, 2, (3,4,5 or 6)-$(CF_3)_2$-Ph-, 3, (4 or 5)-$F_2$-Ph-, 3, (4 or 5)-$Cl_2$-Ph-, 3, (4 or 5)-$Br_2$-Ph-, 3, (4 or 5)-$I_2$-Ph-, 3, (4 or 5)-$Me_2$-Ph-, 3, (4 or 5)-$Et_2$-Ph-, 3, (4 or 5)-$Pr_2$-Ph-, 3, (4 or 5)-$Bu_2$-Ph-, 3, (4 or 5)-$(CN)_2$-Ph-, 3, (4 or 5)-$(NO_2)_2$-Ph-, 3, (4 or 5)-$(NH_2)_2$-Ph-, 3, (4 or 5)-$(MeO)_2$-Ph-, 3, (4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-($NO_2$)-Ph-, 3-($NO_2$)-Ph-, 4-($NO_2$)-Ph-, 2-($NH_2$)-Ph-, 3-($NH_2$)-Ph-, 4-($NH_2$)-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3$O-Ph-, 3-$CF_3$O-Ph-, and 4-$CF_3$O-Ph-); and a saturated or unsaturated, substituted or unsubstituted, heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl).

In some embodiments the $R^{36}$ groups form a ring with each other. In such cases the ring is typically a 3, 4, 5, 6 or 7 membered substituted or unsubstituted carbocyclic ring or heterocyclic ring, which may be saturated or unsaturated.

In some embodiments, one $R^{36}$ group is —H and one is not —H. In other embodiments, both $R^{36}$ groups are —H. In yet further embodiments neither $R^{36}$ group is —H.

In preferred embodiments, at least one $R^{36}$ group comprises an alkyl group (such as a lower alkyl group or a $C_1$-$C_6$ alkyl group such as Me, Et, Pr, i-Pr, n-Bu, i-Bu, t-Bu, pentyl and hexyl) or at least one $R^{36}$ group comprises a cycloalkyl group (such as a 3, 4, 5, 6 or 7 membered carbocyclic ring), which alkyl group cycloalkyl group or may be saturated or unsaturated, or at least one $R^{36}$ group is a halogen (preferably —F).

In some typical embodiments, the invention therefore provides a tryptophan-2,3-dioxygenase (TDO) and/or indoleamine-2,3-dioxygenase (IDO) inhibitor compound for use in medicine, which compound comprises the following formula:

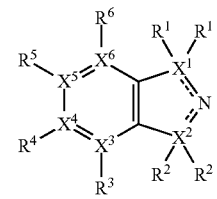

wherein $X^1$, and $X^2$ may be the same or different and each is independently selected from C, N, O and S; $X^3$, $X^4$, $X^5$, and $X^6$ may be the same or different and each is independently selected from C and N; each bond represented by a dotted line may be present or absent, provided that at least one such bond is present; $R^1$, $R^2$, $R^3$, $R^4$, $R^5$ and $R^6$ may be present or absent and may be the same or different and each is independently selected from H and a substituted or unsubstituted organic group, provided that the number of $R^1$, $R^2$, $R^3$, $R^4$, R and $R^6$ groups present is such that the respective valencies of $X^1$, $X^2$, $X^3$, $X^4$, $X^5$, and $X^6$ are maintained; and wherein at least one of $R^5$ and $R^6$ comprises a group Y, wherein Y is a group having a formula selected from the following:

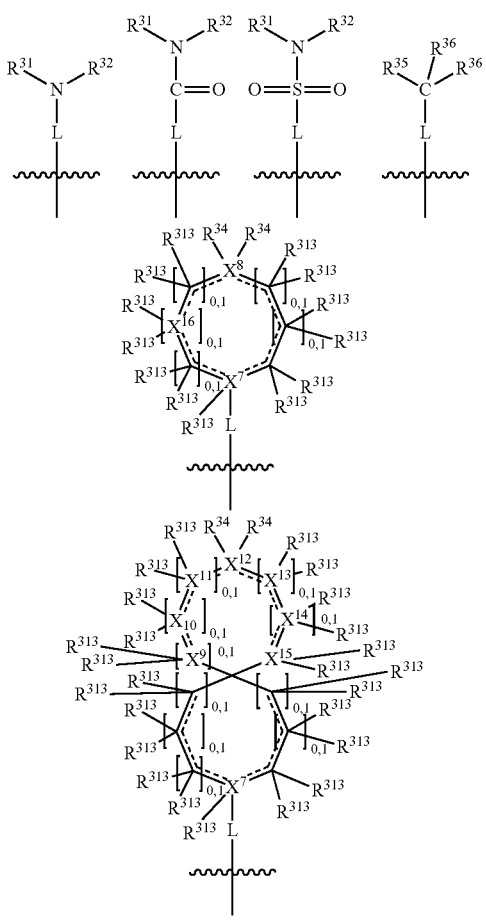

wherein L may be present or absent, and may be a substituted or unsubstituted organic linking group; $R^{31}$ and $R^{32}$ may be the same or different and are selected from H and a substituted or unsubstituted organic group; each $R^{34}$ may be the same or different and is selected from H and a substituted or unsubstituted organic group; $R^{35}$ is selected from a substituted or unsubstituted alcohol group or ether group; each $R^{36}$ may be the same or different and is selected from H and a substituted or unsubstituted organic group; $X^7$ may be selected from C and N; $X^8, X^9, X^{10}, X^{11}, X^{12}, X^{13}, X^{14}, X^{15}$ and $X^{16}$ may be the same or different and each is independently selected from C, N, O and S; each bond represented by a dotted line may be present or absent; and each $R^{313}$ may be the same or different and is selected from H and a substituted or unsubstituted organic group;

and wherein if Y is a group of the following formula:

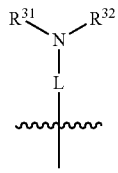

in which L is absent, $R^{32}$ is H, and $R^{31}$ comprises a carbonyl group directly bonded to the N, (or $R^{31}$ is H, and $R^{32}$ comprises a carbonyl group directly bonded to the N) then Y is a group having the following formula:

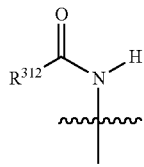

wherein $R^{312}$ is selected from any of the following:
- a substituted or unsubstituted linear or branched $C_1$-$C_6$ alkyl group (such as Me, Et, Pr, i-Pr, n-Bu, i-Bu, t-Bu, pentyl and hexyl);
- a substituted or unsubstituted linear or branched $C_1$-$C_6$ alkyl-aryl group (such as —$CH_2$Ph, —$CH_2$(2,3 or 4)F-Ph, —$CH_2$(2,3 or 4)Cl-Ph, —$CH_2$(2,3 or 4)Br-Ph, —$CH_2$(2,3 or 4)I-Ph, —$CH_2CH_2$Ph, —$CH_2CH_2CH_2$Ph, —$CH_2CH_2CH_2CH_2$Ph, —$CH_2CH_2CH_2CH_2CH_2$Ph, and —$CH_2CH_2CH_2CH_2CH_2CH_2$Ph);
- a substituted or unsubstituted linear or branched $C_1$-$C_6$ halogenated alkyl group (such as —$CH_2$F, —$CF_3$, —$CH_2CF_3$);
- an —$NH_2$ or a substituted or unsubstituted linear or branched primary secondary or tertiary $C_1$-$C_6$ amine group (such as —NMeH, —$NMe_2$, —NEtH, —NEtMe, —$NEt_2$, —NPrH, —NPrMe, —NPrEt, —$NPr_2$, —NBuH, —NBuMe, —NBuEt, —$CH_2$—$NH_2$, —$CH_2$—NMeH, —$CH_2$—$NMe_2$, —$CH_2$—NEtH, —$CH_2$—NEtMe, —$CH_2$—$NEt_2$, —$CH_2$—NPrH, —$CH_2$—NPrMe, and —$CH_2$—NPrEt);
- a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2, (3,4,5 or 6)$F_2$-Ph, —NH-2, (3,4,5 or 6)$Cl_2$-Ph, —NH-2, (3,4,5 or 6)$Br_2$-Ph, —NH-2, (3,4,5 or 6)$I_2$-Ph, —NH-2, (3,4,5 or 6)$Me_2$-Ph, —NH-2, (3,4,5 or 6)$Et_2$-Ph, —NH-2, (3,4,5, or 6)$Pr_2$-Ph, —NH-2, (3,4,5 or 6)$Bu_2$-Ph,
- a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);
- a substituted or unsubstituted cyclic $C_3$-$C_8$ alkyl group (such as cyclopropyl, cyclobutyl, cyclopentyl, cyclohexyl, cycloheptyl and cyclooctyl);
- a substituted or unsubstituted linear or branched $C_1$-$C_6$ alcohol group (such as —$CH_2$OH, —$CH_2CH_2$OH, —$CH_2CH_2CH_2$OH, —$CH(CH_3)CH_2$OH, —$C(CH_3)_2$OH, —$CH_2CH_2CH_2CH_2$OH, —$CH(CH_3)CH_2CH_2$OH, —$CH(CH_3)CH(CH_3)$OH, —$CH(CH_2CH_3)CH_2$OH, —$C(CH_3)_2CH_2$OH, —$CH_2CH_2CH_2CH_2CH_2$OH, and —$CH_2CH_2CH_2CH_2CH_2CH_2$OH);
- a substituted or unsubstituted linear or branched $C_1$-$C_7$ amino carbonyl group (such as —NH—CO-Me, —NH—CO-Et, —NH—CO—Pr, —NH—CO-Bu, —NH—CO-pentyl, —NH—CO-hexyl, —NH—CO-Ph, —NMe-CO-Me, —NMe-CO-Et, —NMe-CO—Pr, —NMe-CO-Bu, —NMe-CO-pentyl, —NMe-CO-hexyl, —NMe-CO-Ph;
- a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —$OCH_2$F, —$OCHF_2$, —$OCF_3$, —O-Ph, —O—$CH_2$-Ph, —O—$CH_2$-(2,3 or 4)-F-Ph, —O—$CH_2$-(2,3 or 4)-Cl-Ph, —$CH_2$OMe, —$CH_2$OEt, —$CH_2$OPr, —$CH_2$OBu, —$CH_2CH_2$OMe, —$CH_2CH_2CH_2$OMe, —$CH_2CH_2CH_2CH_2$OMe, and —$CH_2CH_2CH_2CH_2CH_2$OMe);
- a substituted or unsubstituted linear or branched aminoalkoxy group (such as —$OCH_2CH_2NH_2$, —$OCH_2CH_2$NHMe, —$OCH_2CH_2NMe_2$, —$OCH_2CH_2$NHEt, and —$OCH_2CH_2NEt_2$;
- a substituted or unsubstituted aminosulphonyl group (such as —$NHSO_2$Me, —$NHSO_2$Et, —$NHSO_2$Pr, —$NHSO_2$iPr, —$NHSO_2$Ph, —$NHSO_2$-(2,3 or 4)-F-Ph, —$NHSO_2$-cyclopropyl, —$NHSO_2CH_2CH_2OCH_3$);
- a substituted or unsubstituted 6 membered carbocyclic or heterocyclic aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-$F_2$-Ph-, 2, (3,4,5 or 6)-$Cl_2$-Ph-, 2, (3,4,5 or 6)-$Br_2$-Ph-, 2, (3,4,5 or 6)-$I_2$-Ph-, 2, (3,4,5 or 6)-$Me_2$-Ph-, 2, (3,4,5 or 6)-$Et_2$-Ph-, 2, (3,4,5 or 6)-$Pr_2$-Ph-, 2, (3,4,5 or 6)-$Bu_2$-Ph-, 2, (3,4,5 or 6)-$(CN)_2$-Ph-, 2, (3,4,5 or 6)-$(NO_2)_2$-Ph-, 2, (3,4,5 or 6)-$(NH_2)_2$-Ph-, 2, (3,4,5 or 6)-$(MeO)_2$-Ph-, 2, (3,4,5 or 6)-$(CF_3)_2$-Ph-, 3, (4 or 5)-$F_2$-Ph-, 3, (4 or 5)-$Cl_2$-Ph-, 3, (4 or 5)-$Br_2$-Ph-, 3, (4 or 5)-$I_2$-Ph-, 3, (4 or 5)-$Me_2$-Ph-, 3, (4 or 5)-$Et_2$-Ph-, 3, (4 or 5)-$Pr_2$-Ph-, 3, (4 or 5)-$Bu_2$-Ph-, 3, (4 or 5)-$(CN)_2$-Ph-, 3, (4 or 5)-$(NO_2)_2$-Ph-, 3, (4 or 5)-$(NH_2)_2$-Ph-, 3, (4 or 5)-$(MeO)_2$-Ph-, 3, (4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-($NO_2$)-Ph-, 3-($NO_2$)-Ph-, 4-($NO_2$)-Ph-, 2-($NH_2$)-Ph-, 3-($NH_2$)-Ph-, 4-($NH_2$)-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3$O-Ph-, 3-$CF_3$O-Ph-, and 4-$CF_3$O-Ph-, pyridin-2-yl, pyridine-3-yl, pyridin-4-yl, pyrimidin-2-yl, pyrimidin-5-yl, pyrimidin-4-yl, pyridazin-3-yl, pyridazine-4-yl);

a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl);

preferably wherein $R^{312}$ is selected from the following:

a substituted or unsubstituted linear or branched $C_1$-$C_6$ alkyl-aryl group (such as —$CH_2$Ph, —$CH_2$(2,3 or 4)F-Ph, —$CH_2$(2,3 or 4)Cl-Ph, —$CH_2$(2,3 or 4)Br-Ph, —$CH_2$(2,3 or 4)I-Ph, —$CH_2CH_2$Ph, —$CH_2CH_2CH_2$Ph, —$CH_2CH_2CH_2CH_2$Ph, —$CH_2CH_2CH_2CH_2CH_2$Ph, and —$CH_2CH_2CH_2CH_2CH_2CH_2$Ph);

a substituted or unsubstituted cyclic $C_3$-$C_8$ alkyl group (such as cyclopropyl, cyclobutyl, cyclopentyl, cyclohexyl, cycloheptyl and cyclooctyl);

a substituted or unsubstituted 6 membered carbocyclic or heterocyclic aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-$F_2$-Ph-, 2, (3,4,5 or 6)-$Cl_2$-Ph-, 2, (3,4,5 or 6)-$Br_2$-Ph-, 2, (3,4,5 or 6)-$I_2$-Ph-, 2, (3,4,5 or 6)-$Me_2$-Ph-, 2, (3,4,5 or 6)-$Et_2$-Ph-, 2, (3,4,5 or 6)-$Pr_2$-Ph-, 2, (3,4,5 or 6)-$Bu_2$-Ph-, 2, (3,4,5 or 6)-$(CN)_2$-Ph-, 2, (3,4,5 or 6)-$(NO_2)_2$-Ph-, 2, (3,4,5 or 6)-$(NH_2)_2$-Ph-, 2, (3,4,5 or 6)-$(MeO)_2$-Ph-, 2, (3,4,5 or 6)-$(CF_3)_2$-Ph-, 3, (4 or 5)-$F_2$-Ph-, 3, (4 or 5)-$Cl_2$-Ph-, 3, (4 or 5)-$Br_2$-Ph-, 3, (4 or 5)-$I_2$-Ph-, 3, (4 or 5)-$Me_2$-Ph-, 3, (4 or 5)-$Et_2$-Ph-, 3, (4 or 5)-$Pr_2$-Ph-, 3, (4 or 5)-$Bu_2$-Ph-, 3, (4 or 5)-$(CN)_2$-Ph-, 3, (4 or 5)-$(NO_2)_2$-Ph-, 3, (4 or 5)-$(NH_2)_2$-Ph-, 3, (4 or 5)-$(MeO)_2$-Ph-, 3, (4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-($NO_2$)-Ph-, 3-($NO_2$)-Ph-, 4-($NO_2$)-Ph-, 2-($NH_2$)-Ph-, 3-($NH_2$)-Ph-, 4-($NH_2$)-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3$O-Ph-, 3-$CF_3$O-Ph-, and 4-$CF_3$O-Ph-, pyridin-2-yl, pyridine-3-yl, pyridine-4-yl, pyrimidin-5-yl, pyrimidin-2-yl, pyrimidin-5-pyrimidin-4-yl, pyridazin-3-yl, pyridazine-4-yl);

a substituted or unsubstituted saturated heterocyclic group (such as piperidin-2-yl, piperidin-3-yl, piperidin-4-yl, tetrahydrofuran-2-yl, and tetrahydrofuran-3-yl, tetrahydropyran-2-yl, tetrahydropyran-3-yl, tetrahydropyran-4-yl).

In some further typical embodiments, the invention therefore provides a tryptophan-2,3-dioxygenase (TDO) and/or indoleamine-2,3-dioxygenase (IDO) inhibitor compound for use in medicine, which compound comprises the following formula:

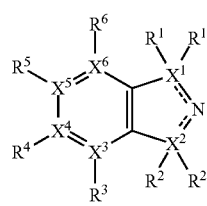

wherein $X^1$, and $X^2$ may be the same or different and each is independently selected from C, N, O and S; $X^3$, $X^4$, $X^1$, and $X^6$ may be the same or different and each is independently selected from C and N; each bond represented by a dotted line may be present or absent, provided that at least one such bond is present; $R^1$, $R^2$, $R^3$, $R^4$, $R^5$ and $R^6$ may be present or absent and may be the same or different, provided that the number of $R^1$, $R^2$, $R^3$, $R^4$, $R^5$ and $R^6$ groups present is such that the respective valencies of $X^1$, $X^2$, $X^3$, $X^4$, $X^5$, and $X^6$ are maintained; and wherein at least one of $R^5$ and $R^6$ comprises a group Y, wherein Y is a group having a formula selected from the following:

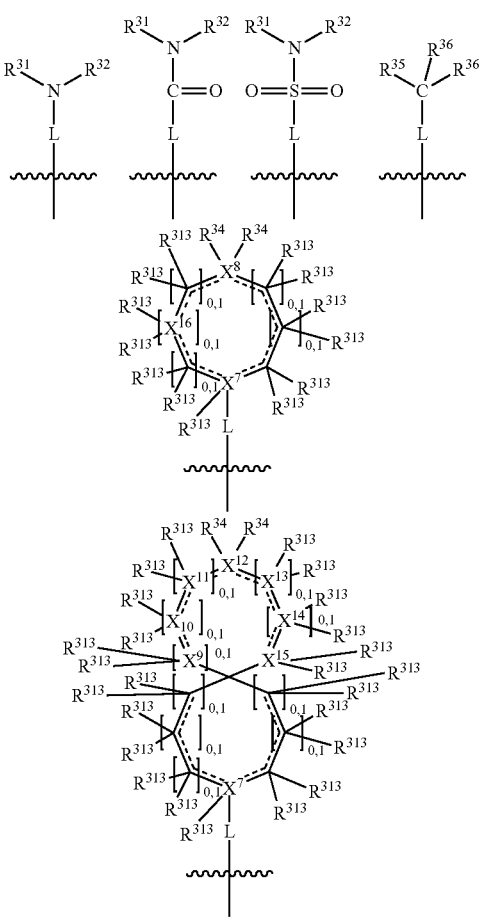

wherein L may be present or absent, and is a substituted or unsubstituted organic linking group selected from a substituted or unsubstituted $C_1$-$C_7$ alkylene group (such as —$CH_2$—, —$CH_2CH_2$—, —$CH_2CH_2CH_2$—, —$CH(CH_3)CH_2$—, —$C(CH_3)_2$—, —$CH_2CH_2CH_2CH_2$—, —$CH(CH_3)CH_2CH_2$—, —$CH(CH_3)CH(CH_3)$—, —$CH(CH_2CH_3)CH_2$—, —$C(CH_3)_2CH_2$—, —$CH_2CH_2CH_2CH_2CH_2$—, and —$CH_2CH_2CH_2CH_2CH_2CH_2$—), a $C_1$-$C_7$ divalent alkoxy group (such as —$OCH_2$—, —$OCH_2CH_2$—, —$OCH_2CH_2CH_2$—, —O—$CH(CH_3)CH_2$—, —$OC(CH_3)_2$—, —$OCH_2CH_2CH_2CH_2$—, —$OCH(CH_3)CH_2CH_2$—, —$OCH(CH_3)CH(CH_3)$—, —$OCH(CH_2CH_3)CH_2$—, —$OC(CH_3)_2CH_2$—, —$OCH_2CH_2CH_2CH_2CH_2$—, —$OCH_2CH_2CH_2CH_2CH_2CH_2$—, —OCHF—, —$OCF_2$—, —O-phenylene-, —O—$CH_2$-phenylene-, —O—$CH_2$-(2,3 or 4)-F-phenylene-, —O—$CH_2$-(2,3 or 4)-Cl-phenylene-, —$CH_2OCH_2$—, —$CH_2OCH_2CH_2$—, —CH$_2$OCH$_2$CH$_2$—, —CH$_2$OCH$_2$CH$_2$CH$_2$—,
—CH$_2$CH$_2$OCH$_2$—, —CH$_2$CH$_2$CH$_2$OCH$_2$—,
—CH$_2$CH$_2$CH$_2$CH$_2$OCH$_2$—,
—CH$_2$CH$_2$CH$_2$CH$_2$CH$_2$OCH$_2$—,
—CH$_2$CH$_2$CH$_2$CH$_2$CH$_2$CH$_2$OCH$_2$—,
—CH$_2$CH$_2$OCH$_2$CH$_2$—, —CH$_2$CH$_2$OCH$_2$CH$_2$CH$_2$—,
—CH$_2$CH$_2$OCH$_2$CH$_2$CH$_2$CH$_2$—,
—CH$_2$CH$_2$OCH$_2$CH$_2$CH$_2$CH$_2$CH$_2$—,
—CH$_2$CH$_2$CH$_2$OCH$_2$CH$_2$—,
—CH$_2$CH$_2$CH$_2$OCH$_2$CH$_2$CH$_2$—, and
—CH$_2$CH$_2$CH$_2$OCH$_2$CH$_2$CH$_2$CH$_2$—, an —O— atom, and
a —N(R$^{32}$)— group (such as a —NH— group); R$^{31}$ and R$^{32}$
may be the same or different; each R$^{34}$ may be the same or
different; R$^{35}$ is selected from a substituted or unsubstituted
alcohol group or ether group; each R$^{36}$ may be the same or
different; X$^7$ may be selected from C and N; X$^8$, X$^9$, X$^{10}$,
X$^{11}$, X$^{12}$, X$^{13}$, X$^{14}$, X$^{15}$ and X$^{16}$ may be the same or different
and each is independently selected from C, N, O and S; each
bond represented by a dotted line may be present or absent;
and each R$^{313}$ may be the same or different;
and wherein R$^1$, R$^2$, R$^3$ and R$^4$ do not comprise a group
having a cyclic group, and if one of R$^5$ and R$^6$ is not Y it also
does not comprise a group having a cyclic group;
and wherein R$^1$, R$^2$, R$^3$, R$^4$, R$^5$ and R$^6$ do not form rings with
each other;
and wherein, where present, R$^1$ and R$^2$ are each independently selected from H and a group selected from the
following groups:
  a substituted or unsubstituted linear or branched C$_1$-C$_6$
    alkyl group (such as Me, Et, Pr, r, n-Bu, i-Bu, t-Bu,
    pentyl and hexyl);
  a substituted or unsubstituted linear or branched C$_1$-C$_6$
    alkyl-aryl group (such as —CH$_2$Ph, —CH$_2$(2,3 or
    4)F-Ph, —CH$_2$(2,3 or 4)Cl-Ph, —CH$_2$(2,3 or 4)Br-Ph,
    —CH$_2$(2,3 or 4)I-Ph, —CH$_2$CH$_2$Ph,
    —CH$_2$CH$_2$CH$_2$Ph, —CH$_2$CH$_2$CH$_2$CH$_2$Ph,
    —CH$_2$CH$_2$CH$_2$CH$_2$CH$_2$Ph, and
    —CH$_2$CH$_2$CH$_2$CH$_2$CH$_2$CH$_2$Ph);
  a substituted or unsubstituted linear or branched C$_1$-C$_6$
    halogenated alkyl group (such as —CH$_2$F, —CF$_3$, and
    —CH$_2$CF$_3$);
  an —NH$_2$ group, or a substituted or unsubstituted linear or
    branched primary secondary or tertiary C$_1$-C$_6$ amine
    group (such as —NMeH, —NMe$_2$, —NEtH,
    —NEtMe, —NEt$_2$, —NPrH, —NPrMe, —NPrEt,
    —NPr$_2$, —NBuH, —NBuMe, —NBuEt, —CH$_2$—
    NH$_2$, —CH$_2$—NMeH, —CH$_2$—NMe$_2$, —CH$_2$—
    NEtH, —CH$_2$—NEtMe, —CH$_2$—NEt$_2$, —CH$_2$—
    NPrH, —CH$_2$—NPrMe, and —CH$_2$—NPrEt);
  a substituted or unsubstituted amino-aryl group (such as
    —NH-Ph, —NH-(2,3 or 4)F-Ph, —NH-(2,3 or 4)Cl-
    Ph, —NH-(2,3 or 4)Br-Ph, —NH-(2,3 or 4)I-Ph,
    —NH-(2,3 or 4)Me-Ph, —NH-(2,3 or 4)Et-Ph, —NH-
    (2,3 or 4)Pr-Ph, —NH-(2,3 or 4)Bu-Ph, NH-(2,3 or
    4)OMe-Ph, —NH-(2,3 or 4)OEt-Ph, —NH-(2,3 or
    4)OPr-Ph, —NH-(2,3 or 4)OBu-Ph, —NH-2, (3,4,5 or
    6)F$_2$-Ph, —NH-2, (3,4,5 or 6)Cl$_2$-Ph, —NH-2, (3,4,5
    or 6)Br$_2$-Ph, —NH-2, (3,4,5 or 6)I$_2$-Ph, —NH-2, (3,4,5
    or 6)Me$_2$-Ph, —NH-2, (3,4,5 or 6)Et$_2$-Ph, —NH-2,
    (3,4,5, or 6)Pr$_2$-Ph, —NH-2, (3,4,5 or 6)Bu$_2$-Ph,
  a substituted or unsubstituted cyclic C$_3$-C$_8$ alkyl group
    (such as cyclopropyl, cyclobutyl, cyclopentyl, cyclohexyl, cycloheptyl and cyclooctyl);
  an —OH, or a substituted or unsubstituted linear or
    branched C$_1$-C$_6$ alcohol group (such as —CH$_2$OH,
    —CH$_2$CH$_2$OH, —CH$_2$CH$_2$CH$_2$OH, —CH(CH$_3$)
    CH$_2$OH, —C(CH$_3$)$_2$OH, —CH$_2$CH$_2$CH$_2$CH$_2$OH,
    —CH(CH$_3$)CH$_2$CH$_2$OH, —CH(CH$_3$)CH(CH$_3$)OH,
    —CH(CH$_2$CH$_3$)CH$_2$OH, —C(CH$_3$)$_2$CH$_2$OH,
    —CH$_2$CH$_2$CH$_2$CH$_2$CH$_2$OH, and
    —CH$_2$CH$_2$CH$_2$CH$_2$CH$_2$OH);
  a substituted or unsubstituted linear or branched C$_1$-C$_6$
    carboxylic acid group (such as —COOH,
    —CH$_2$COOH, —CH$_2$CH$_2$COOH,
    —CH$_2$CH$_2$CH$_2$COOH, —CH$_2$CH$_2$CH$_2$CH$_2$COOH,
    and —CH$_2$CH$_2$CH$_2$CH$_2$CH$_2$COOH);
  a substituted or unsubstituted linear or branched carbonyl
    group (such as —(CO)Me, —(CO)Et, —(CO)Pr,
    —(CO)iPr, —(CO)nBu, —(CO)iBu, —(CO)tBu,
    —(CO)Ph, —(CO)CH$_2$Ph, —(CO)CH$_2$OH, —(CO)
    CH$_2$OCH$_3$, —(CO)CH$_2$NH$_2$, —(CO)CH$_2$NHMe,
    —(CO)CH$_2$NMe$_2$, —(CO)-cyclopropyl, —(CO)-1,3-
    epoxypropan-2-yl; —(CO)NH$_2$, —(CO)NHMe,
    —(CO)NMe$_2$, —(CO)NHEt, —(CO)NEt$_2$, —(CO)-
    pyrollidine-N-yl, —(CO)-morpholine-N-yl, —(CO)-
    piperazine-N-yl, —(CO)—N-methyl-piperazine-N-yl,
    —(CO)NHCH$_2$CH$_2$OH, —(CO)NHCH$_2$CH$_2$OMe,
    —(CO)NHCH$_2$CH$_2$NH$_2$, —(CO)NHCH$_2$CH$_2$NHMe,
    and —(CO)NHCH$_2$CH$_2$NMe$_2$;
  a substituted or unsubstituted linear or branched C$_1$-C$_6$
    carboxylic acid ester group (such as —COOMe,
    —COOEt, —COOPr, —COO-i-Pr, —COO-n-Bu,
    —COO-i-Bu, —COO-t-Bu, —CH$_2$COOMe,
    —CH$_2$CH$_2$COOMe, —CH$_2$CH$_2$CH$_2$COOMe, and
    —CH$_2$CH$_2$CH$_2$CH$_2$COOMe);
  a substituted or unsubstituted linear or branched C$_1$-C$_6$
    amide group (such as —CO—NH$_2$, —CO—NMeH,
    —CO—NMe$_2$, —CO—NEtH, —CO—NEtMe,
    —CO—NEt$_2$, —CO—NPrH, —CO—NPrMe, and
    —CO—NPrEt);
  a substituted or unsubstituted linear or branched C$_1$-C$_7$
    amino carbonyl group (such as —NH—CO-Me,
    —NH—CO-Et, —NH—CO—Pr, —NH—CO-Bu,
    —NH—CO-pentyl, —NH—CO-hexyl, —NH—CO-
    Ph, —NMe-CO-Me, —NMe-CO-Et, —NMe-CO—Pr,
    —NMe-CO-Bu, —NMe-CO-pentyl, —NMe-CO-
    hexyl, —NMe-CO-Ph;
  a substituted or unsubstituted linear or branched C$_1$-C$_7$
    alkoxy or aryloxy group (such as —OMe, —OEt,
    —OPr, —O-i-Pr, —O-n-Bu, —O-i-Bu, —O-t-Bu,
    —O-pentyl, —O-hexyl, —OCH$_2$F, —OCHF$_2$,
    —OCF$_3$, —O-Ph, —O—CH$_2$-Ph, —O—CH$_2$-(2,3 or
    4)-F-Ph, —O—CH$_2$-(2,3 or 4)-Cl-Ph, —CH$_2$OMe,
    —CH$_2$OEt, —CH$_2$OPr, —CH$_2$OBu, —CH$_2$CH$_2$OMe,
    —CH$_2$CH$_2$CH$_2$OMe, —CH$_2$CH$_2$CH$_2$CH$_2$OMe, and
    —CH$_2$CH$_2$CH$_2$CH$_2$CH$_2$OMe);
  a substituted or unsubstituted linear or branched amino-
    alkoxy group (such as —OCH$_2$CH$_2$NH$_2$,
    —OCH$_2$CH$_2$NHMe, —OCH$_2$CH$_2$NMe$_2$,
    —OCH$_2$CH$_2$NHEt, and —OCH$_2$CH$_2$NEt$_2$;
  a substituted or unsubstituted sulphonyl group (such as
    —SO$_2$Me, —SO$_2$Et, —SO$_2$Pr, —SO$_2$iPr, —SO$_2$Ph,
    —SO$_2$-(2,3 or 4)-F-Ph, —SO$_2$-cyclopropyl,
    —SO$_2$CH$_2$CH$_2$OCH$_3$), —SO$_2$NH$_2$, —SO$_2$NHMe,
    —SO$_2$NMe$_2$, —SO$_2$NHEt, —SO$_2$NEt$_2$, —SO$_2$-pyrrolidine-N-yl, —SO$_2$-morpholine-N-yl,
    —SO$_2$NHCH$_2$OMe, and —SO$_2$NHCH$_2$CH$_2$OMe;
  a substituted or unsubstituted aminosulphonyl group
    (such as —NHSO$_2$Me, —NHSO$_2$Et, —NHSO$_2$Pr,
    —NHSO$_2$iPr, —NHSO$_2$Ph, —NHSO$_2$-(2,3 or 4)-F-Ph,
    —NHSO$_2$-cyclopropyl, —NHSO$_2$CH$_2$CH$_2$OCH$_3$);
  a substituted or unsubstituted aromatic group (such as
    Ph-, 2-F-Ph-, 3-F-Ph-, 4-F-Ph-, 2-Cl-Ph-, 3-Cl-Ph-,
    4-Cl-Ph-, 2-Br-Ph-, 3-Br-Ph-, 4-Br-Ph-, 2-I-Ph-, 3-I-

Ph, 4-I-Ph-, 2, (3,4,5 or 6)-F$_2$-Ph-, 2, (3,4,5 or 6)-Cl$_2$-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-Cl$_2$-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and a saturated or unsaturated, substituted or unsubstituted, heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl);

and wherein, where present, $R^3$, $R^4$, $R^5$, $R^6$ and $R^{313}$ are each independently selected from H and a group selected from the following groups:

a halogen (such as —F, —Cl, —Br and —I);

a nitrile group;

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted linear or branched $C_1$-$C_6$ halogenated alkyl group (such as —CH$_2$F, —CH$_2$Cl, —CF$_3$, —CCl$_3$—CBr$_3$, —Cl$_3$, —CH$_2$CF$_3$, —CH$_2$CCl$_3$, —CH$_2$CBr$_3$, and —CH$_2$Cl$_3$);

an —NH$_2$ group, or a substituted or unsubstituted linear or branched primary secondary or tertiary $C_1$-$C_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2, (3,4,5 or 6)F$_2$-Ph, —NH-2, (3,4,5 or 6)Cl$_2$-Ph, —NH-2, (3,4,5 or 6)Br$_2$-Ph, —NH-2, (3,4,5 or 6)I$_2$-Ph, —NH-2, (3,4,5 or 6)Me$_2$-Ph, —NH-2, (3,4,5 or 6)Et$_2$-Ph, —NH-2, (3,4,5, or 6)Pr$_2$-Ph, —NH-2, (3,4,5 or 6)Bu$_2$-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic $C_3$-$C_8$ alkyl group (such as cyclopropyl, cyclobutyl, cyclopentyl, cyclohexyl, cycloheptyl and cyclooctyl);

an —OH, or a substituted or unsubstituted linear or branched $C_1$-$C_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched $C_1$-$C_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH₂Ph, —(CO)CH₂OH, —(CO)CH₂OCH₃, —(CO)CH₂NH₂, —(CO)CH₂NHMe, —(CO)CH₂NMe₂, —(CO)-cyclopropyl, —(CO)-1,3-epoxypropan-2-yl; —(CO)NH₂, —(CO)NHMe, —(CO)NMe₂, —(CO)NHEt, —(CO)NEt₂, —(CO)-pyrollidine-N-yl, —(CO)-morpholine-N-yl, —(CO)-piperazine-N-yl, —(CO)—N-methyl-piperazine-N-yl, —(CO)NHCH₂CH₂OH, —(CO)NHCH₂CH₂OMe, —(CO)NHCH₂CH₂NH₂, —(CO)NHCH₂CH₂NHMe, and —(CO)NHCH₂CH₂NMe₂;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH₂COOMe, —CH₂CH₂COOMe, —CH₂CH₂CH₂COOMe, and —CH₂CH₂CH₂CH₂COOMe);

a substituted or unsubstituted linear or branched $C_1$-$C_6$ amide group (such as —CO—NH₂, —CO—NMeH, —CO—NMe₂, —CO—NEtH, —CO—NEtMe, —CO—NEt₂, —CO—NPrH, —CO—NPrMe, and —CO—NPrEt);

a substituted or unsubstituted linear or branched $C_1$-$C_7$ amino carbonyl group (such as —NH—CO-Me, —NH—CO-Et, —NH—CO—Pr, —NH—CO-Bu, —NH—CO-pentyl, —NH—CO-hexyl, —NH—CO-Ph, —NMe-CO-Me, —NMe-CO-Et, —NMe-CO—Pr, —NMe-CO-Bu, —NMe-CO-pentyl, —NMe-CO-hexyl, —NMe-CO-Ph;

a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH₂F, —OCHF₂, —OCF₃, —O-Ph, —O—CH₂-Ph, —O—CH₂-(2,3 or 4)-F-Ph, —O—CH₂-(2,3 or 4)-Cl-Ph, —CH₂OMe, —CH₂OEt, —CH₂OPr, —CH₂OBu, —CH₂CH₂OMe, —CH₂CH₂CH₂OMe, —CH₂CH₂CH₂CH₂OMe, and —CH₂CH₂CH₂CH₂CH₂OMe);

a substituted or unsubstituted linear or branched amino-alkoxy group (such as —OCH₂CH₂NH₂, —OCH₂CH₂NHMe, —OCH₂CH₂NMe₂, —OCH₂CH₂NHEt, and —OCH₂CH₂NEt₂;

a substituted or unsubstituted sulphonyl group (such as —SO₂Me, —SO₂Et, —SO₂Pr, —SO₂iPr, —SO₂Ph, —SO₂-(2,3 or 4)-F-Ph, —SO₂-cyclopropyl, —SO₂CH₂CH₂OCH₃), —SO₂NH₂, —SO₂NHMe, —SO₂NMe₂, —SO₂NHEt, —SO₂NEt₂, —SO₂-pyrrolidine-N-yl, —SO₂-morpholine-N-yl, —SO₂NHCH₂OMe, and —SO₂NHCH₂CH₂OMe;

a substituted or unsubstituted aminosulphonyl group (such as —NHSO₂Me, —NHSO₂Et, —NHSO₂Pr, —NHSO₂iPr, —NHSO₂Ph, —NHSO₂-(2,3 or 4)-F-Ph, —NHSO₂-cyclopropyl, —NHSO₂CH₂CH₂OCH₃);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F₂-Ph-, 2, (3,4,5 or 6)-Cl₂-Ph-, 2, (3,4,5 or 6)-Br₂-Ph-, 2, (3,4,5 or 6)-I₂-Ph-, 2, (3,4,5 or 6)-Me₂-Ph-, 2, (3,4,5 or 6)-Et₂-Ph-, 2, (3,4,5 or 6)-Pr₂-Ph-, 2, (3,4,5 or 6)-Bu₂-Ph-, 2, (3,4,5 or 6)-(CN)₂-Ph-, 2, (3,4,5 or 6)-(NO₂)₂-Ph-, 2, (3,4,5 or 6)-(NH₂)₂-Ph-, 2, (3,4,5 or 6)-(MeO)₂-Ph-, 2, (3,4,5 or 6)-(CF₃)₂-Ph-, 3, (4 or 5)-F₂-Ph-, 3, (4 or 5)-Cl₂-Ph-, 3, (4 or 5)-Br₂-Ph-, 3, (4 or 5)-I₂-Ph-, 3, (4 or 5)-Me₂-Ph-, 3, (4 or 5)-Et₂-Ph-, 3, (4 or 5)-Pr₂-Ph-, 3, (4 or 5)-Bu₂-Ph-, 3, (4 or 5)-(CN)₂-Ph-, 3, (4 or 5)-(NO₂)₂-Ph-, 3, (4 or 5)-(NH₂)₂-Ph-, 3, (4 or 5)-(MeO)₂-Ph-, 3, (4 or 5)-(CF₃)₂-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO₂)-Ph-, 3-(NO₂)-Ph-, 4-(NO₂)-Ph-, 2-(NH₂)-Ph-, 3-(NH₂)-Ph-, 4-(NH₂)-Ph-, 2-MeO-Ph-, 3-MeO-Ph-, 4-MeO-Ph-, 2-(NH₂—CO)-Ph-, 3-(NH₂—CO)-Ph-, 4-(NH₂—CO)-Ph-, 2-CF₃-Ph-, 3-CF₃-Ph-, 4-CF₃-Ph-, 2-CF₃O-Ph-, 3-CF₃O-Ph-, and 4-CF₃O-Ph-);

a saturated or unsaturated, substituted or unsubstituted, heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl); and where there are two $R^{313}$ groups attached to the same atom, they may together form a group which is double bonded to that atom, (such as a carbonyl group (=O) or an alkene group (=C(R')₂) wherein each R' group is the same or different and is H or an organic group, preferably H or a straight or branched $C_1$-$C_6$ alkyl group), or the two $R^{313}$ groups on the same atom may form a ring, preferably a substituted or unsubstituted $C_3$-$C_6$ saturated carbocyclic ring together with the atom to which they are attached (such as a substituted or unsubstituted cyclopropyl ring or a substituted or unsubstituted cyclobutyl ring), this being more preferable when the two $R^{313}$ groups are on an atom adjacent to the $X^8$, or adjacent to the $X^{12}$ and/or adjacent to the $X^7$;

and wherein where present $R^{31}$ and $R^{32}$ are each independently selected from H and the following groups:

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted linear or branched $C_1$-$C_6$ halogenated alkyl group (such as —CH$_2$F, —CF$_3$, and —CH$_2$CF$_3$);

a substituted or unsubstituted monocyclic amine or amido group (such as pyrrolidin-3-yl, piperidin-3-yl, piperidin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted monocyclic $C_3$-$C_8$ alkyl group (such as cyclopropyl, cyclobutyl, cyclopentyl, cyclohexyl, cycloheptyl and cyclooctyl);

a substituted or unsubstituted linear or branched $C_2$-$C_6$ alcohol group (such as —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$OH, and —CH$_2$CH$_2$CH$_2$CH$_2$CH$_2$OH);

a substituted or unsubstituted linear or branched $C_1$-$C_7$ alkoxy or aryloxy group linked through —O via at least two further C atoms (such as —CH$_2$CH$_2$OPh-CH$_2$CH$_2$OMe, —CH$_2$CH$_2$OEt, —CH$_2$CH$_2$OPr, —CH$_2$CH$_2$OBu, —CH$_2$CH$_2$CH$_2$OPh, —CH$_2$CH$_2$CH$_2$OMe, —CH$_2$CH$_2$CH$_2$CH$_2$OMe, and —CH$_2$CH$_2$CH$_2$CH$_2$CH$_2$OMe);

a substituted or unsubstituted linear or branched $C_2$-$C_6$ carboxylic acid group (such as —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);

a substituted or unsubstituted linear or branched $C_1$-$C_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);

a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO$_2$-pyrrolidine-N-yl, —SO$_2$-morpholine-N-yl, —SO$_2$NHCH$_2$OMe, and —SO$_2$NHCH$_2$CH$_2$OMe;

a substituted or unsubstituted monocyclic aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F$_2$-Ph-, 2, (3,4,5 or 6)-Cl$_2$-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-Cl$_2$-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and a saturated or unsaturated, substituted or unsubstituted, heterocyclic group including an aromatic heterocyclic group and/or a non-aromatic heterocyclic group (such as pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl);
and wherein where present each $R^{34}$ is independently selected from H and a group selected from the following groups:

- a halogen (such as —F, —Cl, —Br and —I);
- a substituted or unsubstituted linear or branched $C_1$-$C_6$ alkyl group (such as Me, Et, Pr, i-Pr, n-Bu, i-Bu, t-Bu, pentyl and hexyl);
- a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);
- a substituted or unsubstituted linear or branched $C_1$-$C_6$ halogenated alkyl group (such as —CH$_2$F, —CH$_2$Cl, —CF$_3$, —CCl$_3$—CBr$_3$, —Cl$_3$, —CH$_2$CF$_3$, —CH$_2$CCl$_3$, —CH$_2$CBr$_3$, and —CH$_2$Cl$_3$);
- an —NH$_2$ group, or a substituted or unsubstituted linear or branched primary secondary or tertiary $C_1$-$C_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);
- a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2, (3,4,5 or 6)F$_2$-Ph, —NH-2, (3,4,5 or 6)Cl$_2$-Ph, —NH-2, (3,4,5 or 6)Br$_2$-Ph, —NH-2, (3,4,5 or 6)I$_2$-Ph, —NH-2, (3,4,5 or 6)Me$_2$-Ph, —NH-2, (3,4,5 or 6)Et$_2$-Ph, —NH-2, (3,4,5, or 6)Pr$_2$-Ph, —NH-2, (3,4,5 or 6)Bu$_2$-Ph,
- a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);
- a substituted or unsubstituted cyclic $C_3$-$C_8$ alkyl group (such as cyclopropyl, cyclobutyl, cyclopentyl, cyclohexyl, cycloheptyl and cyclooctyl);
- an —OH or a substituted or unsubstituted linear or branched $C_1$-$C_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);
- a substituted or unsubstituted linear or branched $C_1$-$C_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);
- a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;
- a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);
- a substituted or unsubstituted linear or branched $C_1$-$C_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);
- a substituted or unsubstituted linear or branched $C_1$-$C_7$ amino carbonyl group (such as —NH—CO-Me, —NH—CO-Et, —NH—CO—Pr, —NH—CO-Bu, —NH—CO-pentyl, —NH—CO-hexyl, —NH—CO-Ph, —NMe-CO-Me, —NMe-CO-Et, —NMe-CO—Pr, —NMe-CO-Bu, —NMe-CO-pentyl, —NMe-CO-hexyl, —NMe-CO-Ph;
- a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);
- a substituted or unsubstituted linear or branched aminoalkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;
- a substituted or unsubstituted sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO$_2$-pyrrolidine-N-yl, —SO$_2$-morpholine-N-yl, —SO$_2$NHCH$_2$OMe, and —SO$_2$NHCH$_2$CH$_2$OMe;
- an substituted or unsubstituted aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);
- a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F$_2$-Ph-, 2, (3,4,5 or 6)-Cl$_2$-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-Cl$_2$-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and a saturated or unsaturated, substituted or unsubstituted, heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl);

and wherein, where present, R$^{35}$ is selected from alcohol and ether groups of formula —(C$_0$-C$_7$)—O—(C$_0$-C$_7$) where the C$_0$-C$_7$ groups may be linear or branched alkyl groups, or may be phenyl groups, or may be absent (CO);

more preferably wherein R$^{35}$ is selected from a —(C$_1$-C$_7$)—OH alcohol group, a —O—(C$_1$-C$_7$) ether group, and a —(C$_1$-C$_4$)—O—(C$_1$-C$_4$) ether group;

or more preferably still R$^{35}$ is selected from:

an —OH or a substituted or unsubstituted linear or branched C$_1$-C$_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH); or a substituted or unsubstituted linear or branched C$_1$-C$_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, —CH$_2$CH$_2$CH$_2$CH$_2$CH$_2$OMe, —CH$_2$CH$_2$CH$_2$CH$_2$CH$_2$OMe, —CH$_2$CH$_2$OEt, —CH$_2$CH$_2$OPr, —CH$_2$CH$_2$OBu, —CH$_2$CH$_2$Opentyl, —CH$_2$CH$_2$CH$_2$OEt, —CH$_2$CH$_2$CH$_2$OPr, and —CH$_2$CH$_2$CH$_2$OBu);

and wherein, where present, each R$^{36}$ is typically each independently selected from H and a group selected from the following groups:

a halogen (such as —F, —Cl, —Br and —I, preferably —F);

a substituted or unsubstituted linear or branched C$_1$-C$_6$ alkyl group (such as Me, Et, Pr, i-Pr, n-Bu, i-Bu, t-Bu, pentyl and hexyl);

a substituted or unsubstituted linear or branched C$_1$-C$_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted linear or branched C$_1$-C$_6$ halogenated alkyl group (such as —CH$_2$F, —CH$_2$Cl, —CF$_3$, —CCl$_3$, —CBr$_3$, —Cl$_3$, —CH$_2$CF$_3$, —CH$_2$CCl$_3$, —CH$_2$CBr$_3$, and —CH$_2$Cl$_3$);

an —NH$_2$ group, or a substituted or unsubstituted linear or branched primary secondary or tertiary C$_1$-C$_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2, (3,4,5 or 6)F$_2$-Ph, —NH-2, (3,4,5 or 6)Cl$_2$-Ph, —NH-2, (3,4,5 or 6)Br$_2$-Ph, —NH-2, (3,4,5 or 6)I$_2$-Ph, —NH-2, (3,4,5 or 6)Me$_2$-Ph, —NH-2, (3,4,5 or 6)Et$_2$-Ph, —NH-2, (3,4,5 or 6)Pr$_2$-Ph, —NH-2, (3,4,5 or 6)Bu$_2$-Ph, a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl);

a substituted or unsubstituted cyclic $C_3$-$C_8$ alkyl group (such as cyclopropyl, cyclobutyl, cyclopentyl, cyclohexyl, cycloheptyl and cyclooctyl);

an —OH or a substituted or unsubstituted linear or branched $C_1$-$C_6$ alcohol group (such as —$CH_2OH$, —$CH_2CH_2OH$, —$CH_2CH_2CH_2OH$, —$CH(CH_3)CH_2OH$, —$C(CH_3)_2OH$, —$CH_2CH_2CH_2CH_2OH$, —$CH(CH_3)CH_2CH_2OH$, —$CH(CH_3)CH(CH_3)OH$, —$CH(CH_2CH_3)CH_2OH$, —$C(CH_3)_2CH_2OH$, —$CH_2CH_2CH_2CH_2CH_2OH$, and —$CH_2CH_2CH_2CH_2CH_2CH_2OH$);

a substituted or unsubstituted linear or branched $C_1$-$C_6$ carboxylic acid group (such as —COOH, —$CH_2COOH$, —$CH_2CH_2COOH$, —$CH_2CH_2CH_2COOH$, —$CH_2CH_2CH_2CH_2COOH$, and —$CH_2CH_2CH_2CH_2CH_2COOH$);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)$CH_2$Ph, —(CO)$CH_2$OH, —(CO)$CH_2OCH_3$, —(CO)$CH_2NH_2$, —(CO)$CH_2$NHMe, —(CO)$CH_2NMe_2$, —(CO)-cyclopropyl, —(CO)-1,3-epoxypropan-2-yl; —(CO)$NH_2$, —(CO)NHMe, —(CO)$NMe_2$, —(CO)NHEt, —(CO)$NEt_2$, —(CO)-pyrollidine-N-yl, —(CO)-morpholine-N-yl, —(CO)-piperazine-N-yl, —(CO)—N-methyl-piperazine-N-yl, —(CO)NH$CH_2CH_2$OH, —(CO)NH$CH_2CH_2$OMe, —(CO)NH$CH_2CH_2NH_2$, —(CO)NH$CH_2CH_2$NHMe, and —(CO)NH$CH_2CH_2NMe_2$;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —$CH_2$COOMe, —$CH_2CH_2$COOMe, —$CH_2CH_2CH_2$COOMe, and —$CH_2CH_2CH_2CH_2$COOMe);

a substituted or unsubstituted linear or branched $C_1$-$C_6$ amide group (such as —CO—$NH_2$, —CO—NMeH, —CO—$NMe_2$, —CO—NEtH, —CO—NEtMe, —CO—$NEt_2$, —CO—NPrH, —CO—NPrMe, and —CO—NPrEt);

a substituted or unsubstituted linear or branched $C_1$-$C_7$ amino carbonyl group (such as —NH—CO-Me, —NH—CO-Et, —NH—CO—Pr, —NH—CO-Bu, —NH—CO-pentyl, —NH—CO-hexyl, —NH—CO-Ph, —NMe-CO-Me, —NMe-CO-Et, —NMe-CO—Pr, —NMe-CO-Bu, —NMe-CO-pentyl, —NMe-CO-hexyl, —NMe-CO-Ph;

a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —$OCH_2F$, —$OCHF_2$, —$OCF_3$, —O-Ph, —O—$CH_2$-Ph, —O—$CH_2$-(2,3 or 4)-F-Ph, —O—$CH_2$-(2,3 or 4)-Cl-Ph, —$CH_2$OMe, —$CH_2$OEt, —$CH_2$OPr, —$CH_2$OBu, —$CH_2CH_2$OMe, —$CH_2CH_2CH_2$OMe, —$CH_2CH_2CH_2CH_2$OMe, and —$CH_2CH_2CH_2CH_2CH_2$OMe);

a substituted or unsubstituted linear or branched aminoalkoxy group (such as —$OCH_2CH_2NH_2$, —$OCH_2CH_2$NHMe, —$OCH_2CH_2NMe_2$, —$OCH_2CH_2$NHEt, and —$OCH_2CH_2NEt_2$;

a substituted or unsubstituted sulphonyl group (such as —$SO_2$Me, —$SO_2$Et, —$SO_2$Pr, —$SO_2$iPr, —$SO_2$Ph, —$SO_2$-(2,3 or 4)-F-Ph, —$SO_2$-cyclopropyl, —$SO_2CH_2CH_2OCH_3$), —$SO_2NH_2$, —$SO_2$NHMe, —$SO_2NMe_2$, —$SO_2$NHEt, —$SO_2NEt_2$, —$SO_2$-pyrrolidine-N-yl, —$SO_2$-morpholine-N-yl, —$SO_2$NH$CH_2$OMe, and —$SO_2$NH$CH_2CH_2$OMe;

an substituted or unsubstituted aminosulphonyl group (such as —$NHSO_2$Me, —$NHSO_2$Et, —$NHSO_2$Pr, —$NHSO_2$iPr, —$NHSO_2$Ph, —$NHSO_2$-(2,3 or 4)-F-Ph, —$NHSO_2$-cyclopropyl, —$NHSO_2CH_2CH_2OCH_3$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-$F_2$-Ph-, 2, (3,4,5 or 6)-$Cl_2$-Ph-, 2, (3,4,5 or 6)-$Br_2$-Ph-, 2, (3,4,5 or 6)-$I_2$-Ph-, 2, (3,4,5 or 6)-$Me_2$-Ph-, 2, (3,4,5 or 6)-$Et_2$-Ph-, 2, (3,4,5 or 6)-$Pr_2$-Ph-, 2, (3,4,5 or 6)-$Bu_2$-Ph-, 2, (3,4,5 or 6)-$(CN)_2$-Ph-, 2, (3,4,5 or 6)-$(NO_2)_2$-Ph-, 2, (3,4,5 or 6)-$(NH_2)_2$-Ph-, 2, (3,4,5 or 6)-$(MeO)_2$-Ph-, 2, (3,4,5 or 6)-$(CF_3)_2$-Ph-, 3, (4 or 5)-$F_2$-Ph-, 3, (4 or 5)-$Cl_2$-Ph-, 3, (4 or 5)-$Br_2$-Ph-, 3, (4 or 5)-$I_2$-Ph-, 3, (4 or 5)-$Me_2$-Ph-, 3, (4 or 5)-$Et_2$-Ph-, 3, (4 or 5)-$Pr_2$-Ph-, 3, (4 or 5)-$Bu_2$-Ph-, 3, (4 or 5)-$(CN)_2$-Ph-, 3, (4 or 5)-$(NO_2)_2$-Ph-, 3, (4 or 5)-$(NH_2)_2$-Ph-, 3, (4 or 5)-$(MeO)_2$-Ph-, 3, (4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-($NO_2$)-Ph-, 3-($NO_2$)-Ph-, 4-($NO_2$)-Ph-, 2-($NH_2$)-Ph-, 3-($NH_2$)-Ph-, 4-($NH_2$)-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3$O-Ph-, 3-$CF_3$O-Ph-, and 4-$CF_3$O-Ph-); and a saturated or unsaturated, substituted or unsubstituted, heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4- yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl);

preferably wherein $R^{35}$ is selected from an —OH group and an —OR" group where R" is a $C_1$-$C_6$ alkyl group (such as Me, Et, Pr, i-Pr, n-Bu, i-Bu, t-Bu, pentyl and hexyl);

and/or preferably wherein at least one $R^{36}$ group comprises an alkyl group (such as a lower alkyl group or a $C_1$-$C_6$ alkyl group such as Me, Et, Pr, i-Pr, n-Bu, i-Bu, t-Bu, pentyl and hexyl) or at least one $R^{36}$ group comprises a cycloalkyl group (such as a 3, 4, 5, 6 or 7 membered carbocyclic ring), which alkyl group cycloalkyl group or may be saturated or unsaturated, or at least one $R^{36}$ group is a halogen (preferably —F).

Thus, the present invention provides a TDO or IDO inhibitor compound for use in medicine, which compound comprises a formula selected from one of the following:

1
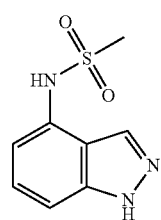

2
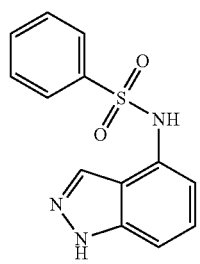

3
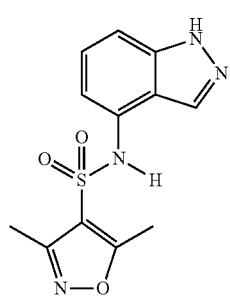

4
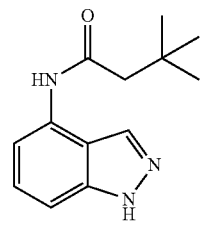

5
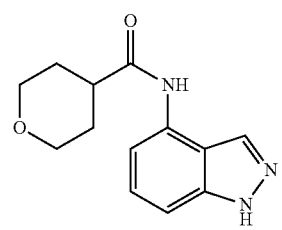

6
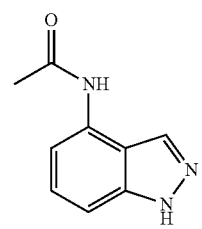

7
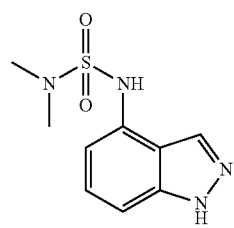

8
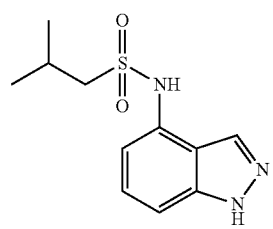

9
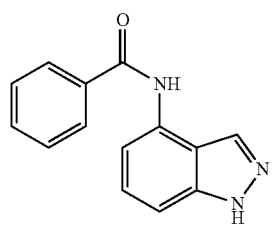

-continued
10 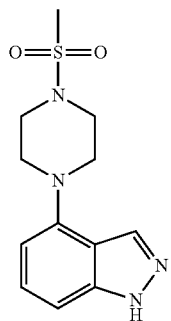
11 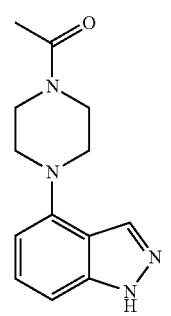
12 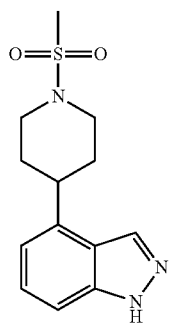
13 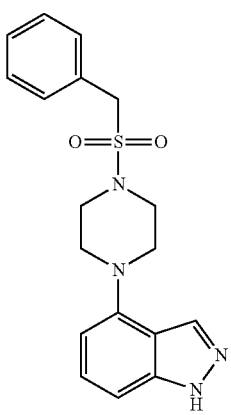
-continued
14 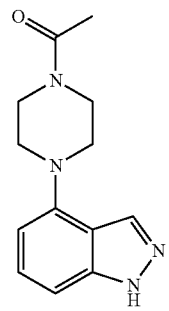
15 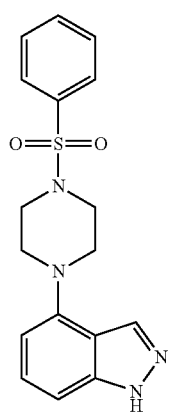
16 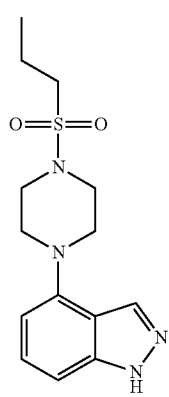
17 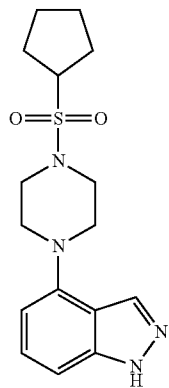

| | | | |
|---|---|---|---|
| 18 | 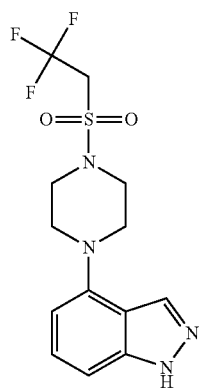 | 22 | 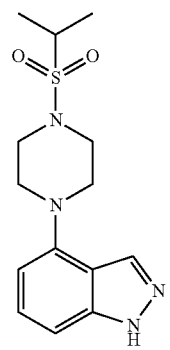 |
| 19 | 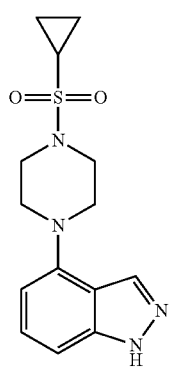 | 23 | 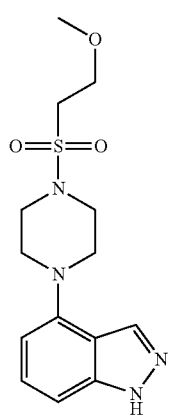 |
| 20 | 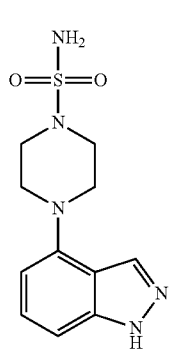 | 24 | 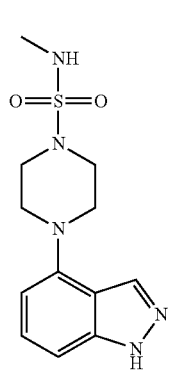 |
| 21 | 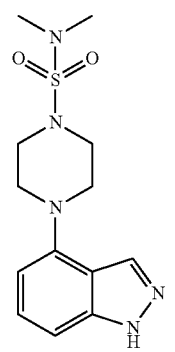 | 25 | |

| 143 -continued | | 144 -continued | |
|---|---|---|---|
| 26 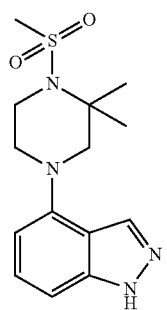 | | 30 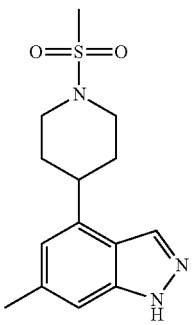 | |
| 27 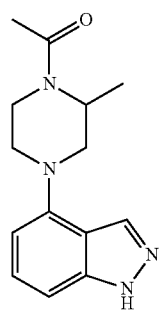 | | 31 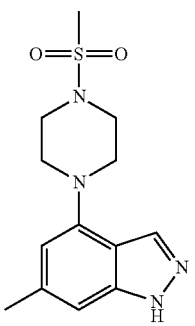 | |
| 28 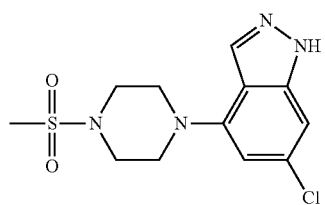 | | 32 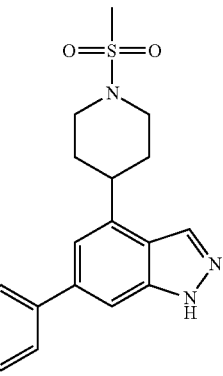 | |
| 29 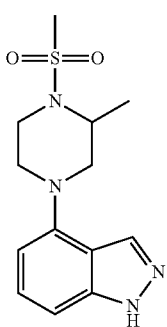 | | 33 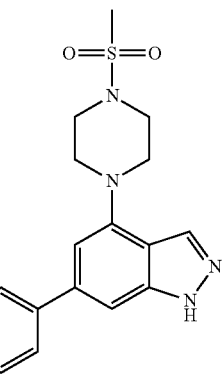 | |

-continued
34
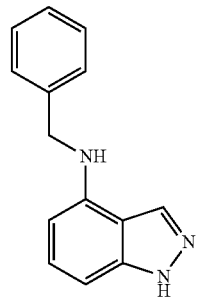
35
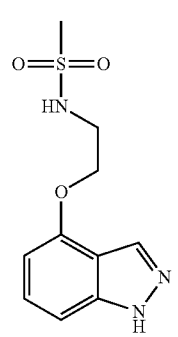
36
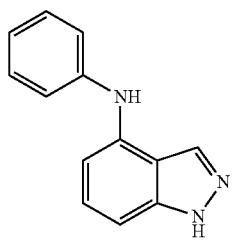
37
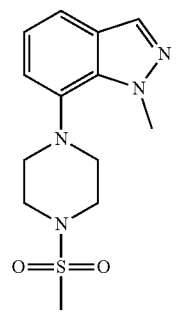
38
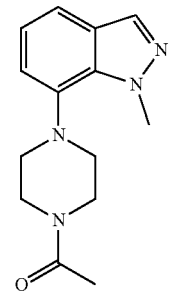
-continued
39
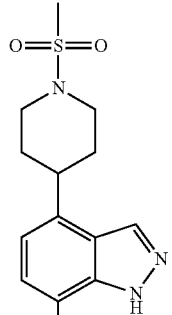
40
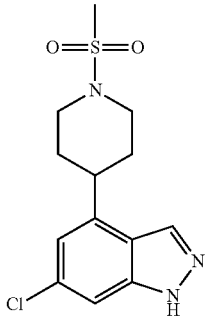
41
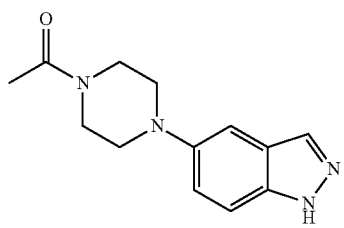
42
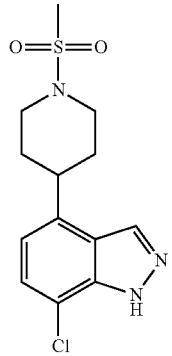
43
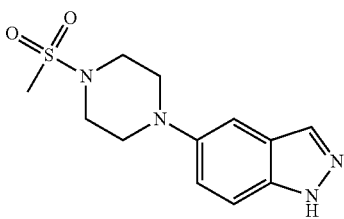

| 44 | 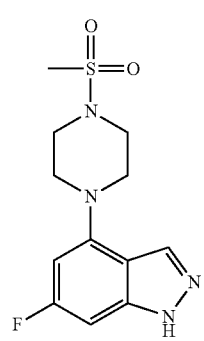 |
|---|---|
| 45 | 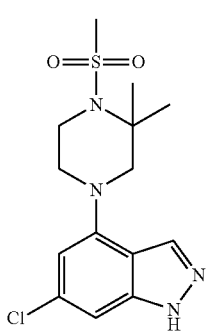 |
| 46 | 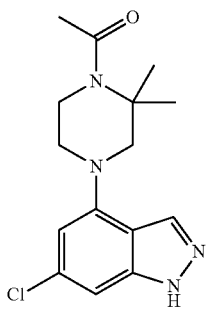 |
| 47 | 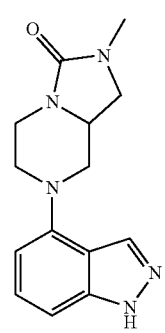 |
| 48 | 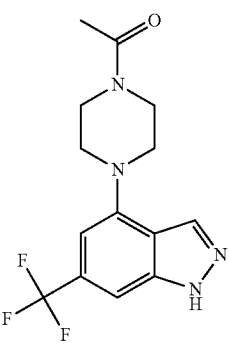 |
|---|---|
| 49 | 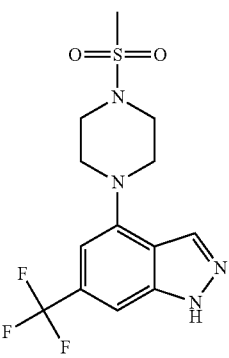 |
| 50 | 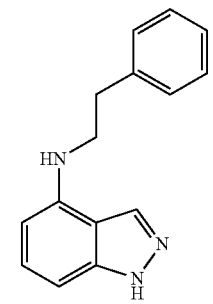 |
| 51 | 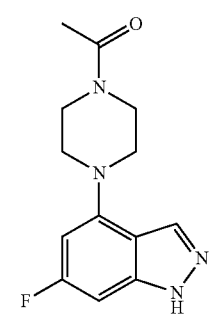 |

52
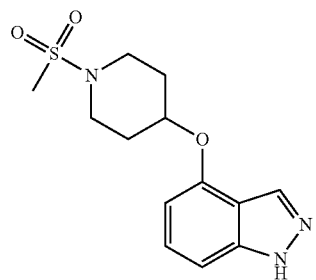
53
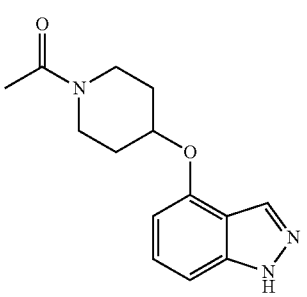
54
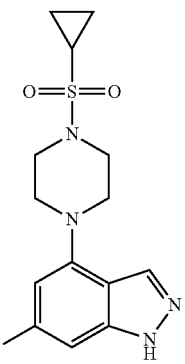
55
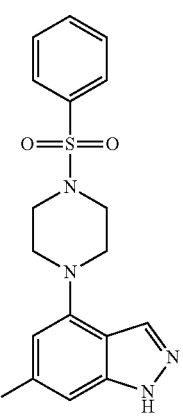
56
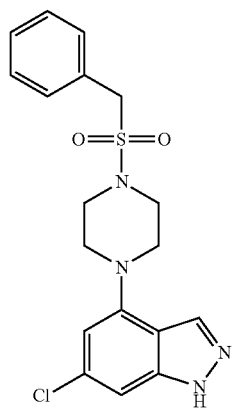
57
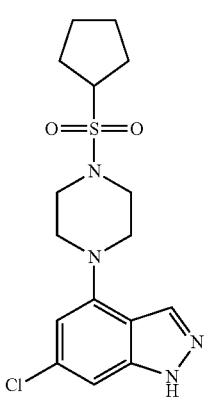
58
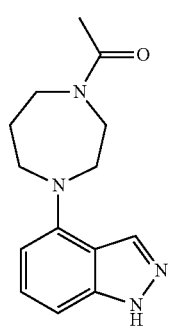
59
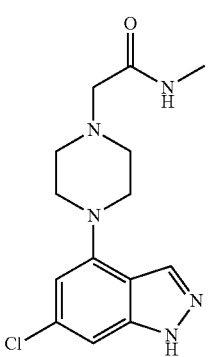

| 151 -continued | 152 -continued |
|---|---|
| 60 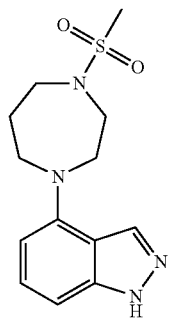 | 63 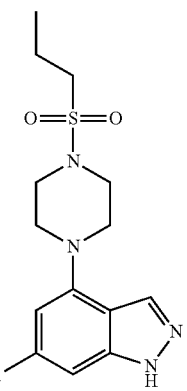 |
| 61 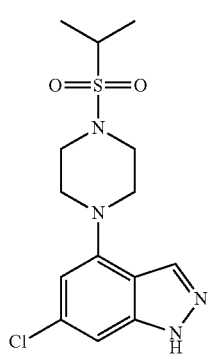 | 64 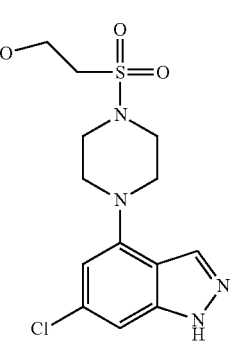 |
|  | 65 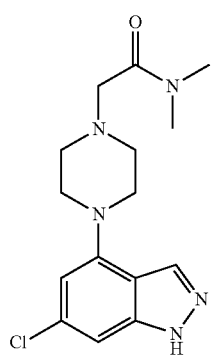 |
| 62 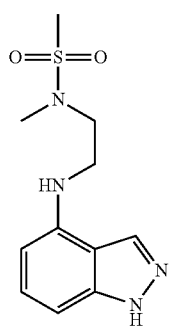 | 66 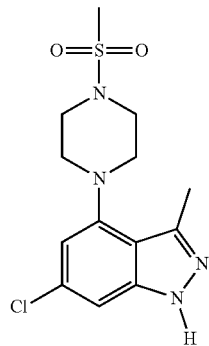 |

| 67 | 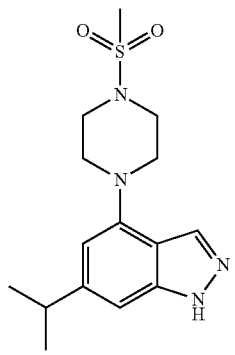 |
|---|---|
| 68 | 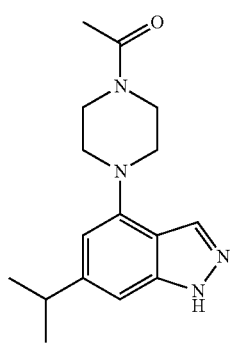 |
| 69 | 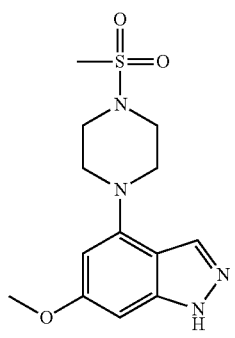 |
| 70 | 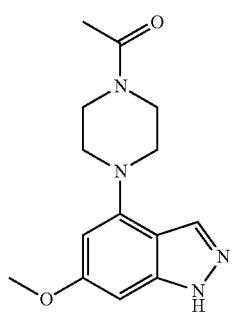 |
| 71 | 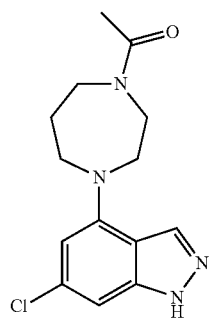 |
|---|---|
| 72 | 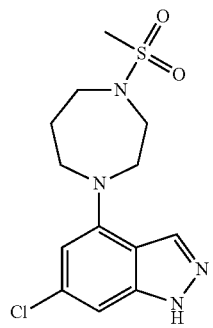 |
| 73 | 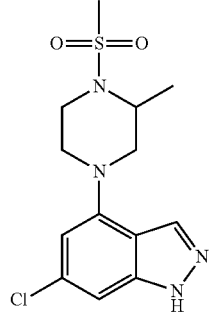 |
| 74 | 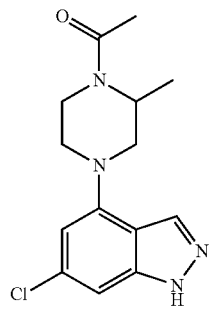 |
| 75 | 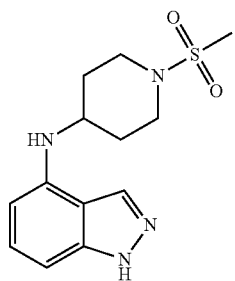 |

| 155 -continued | 156 -continued |
|---|---|
| 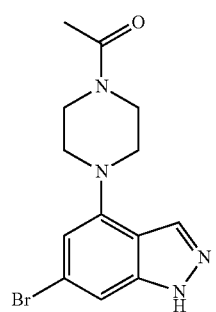 76 | 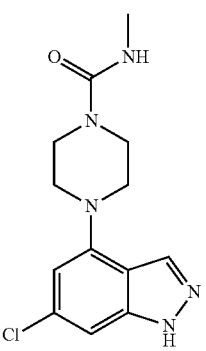 80 |
| 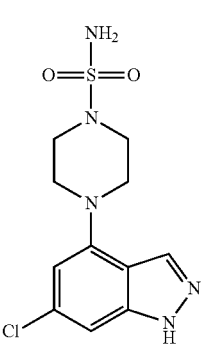 77 | 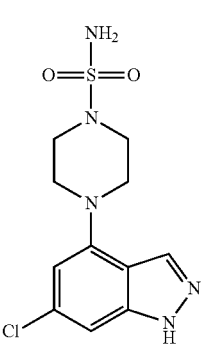 81 |
| 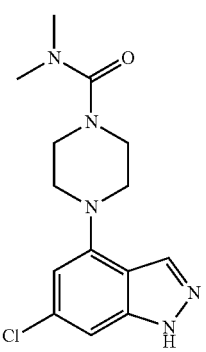 78 | 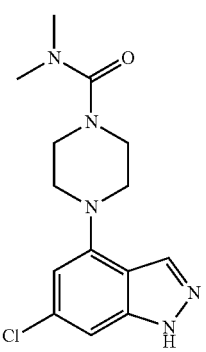 82 |
| 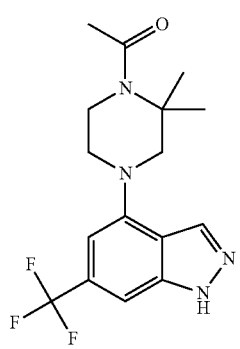 79 | 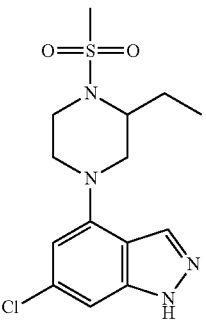 83 |

-continued
84 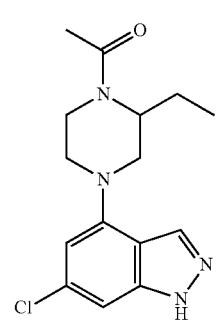
85 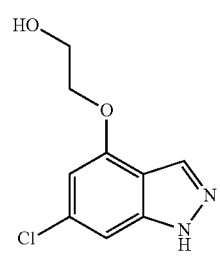
86 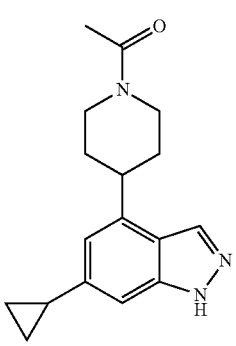
87 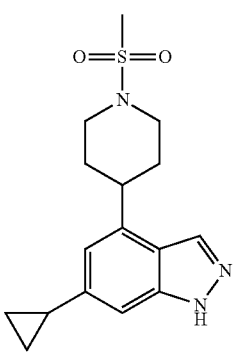
88 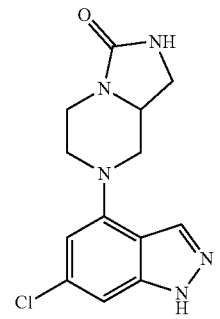
-continued
89 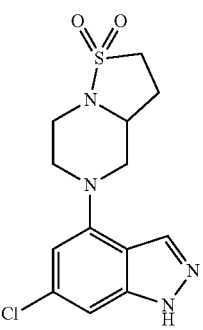
90 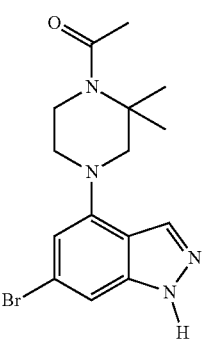
91 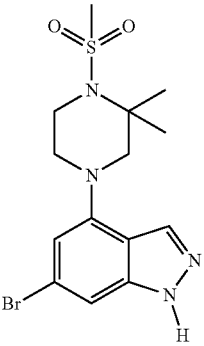
92 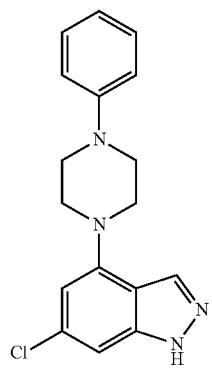

| 93 | 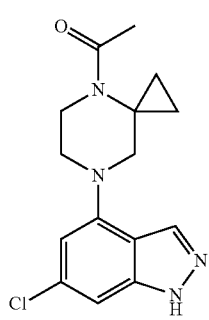 | 97 | 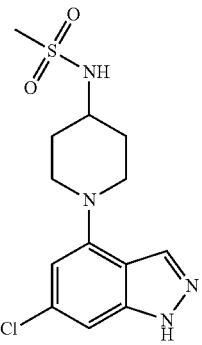 |
| 94 | 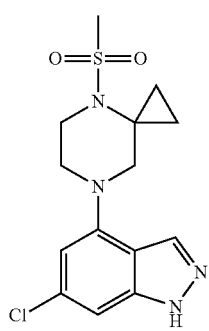 | 98 | 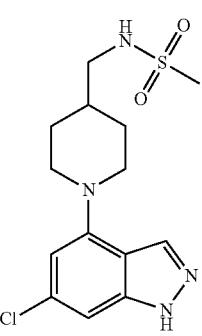 |
| 95 | 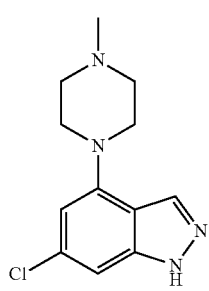 | 99 | 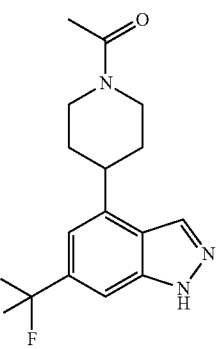 |
| 96 | 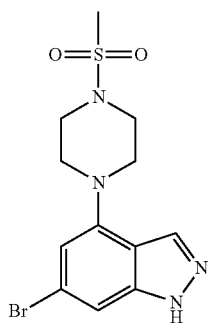 | 100 | 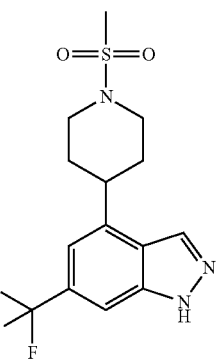 |

161
-continued
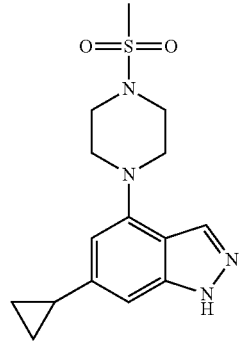
101
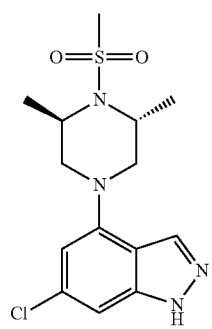
102
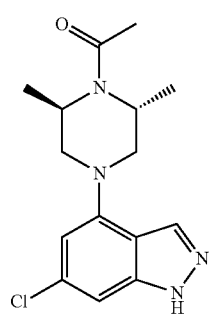
103
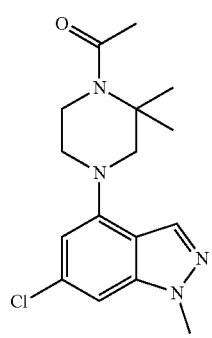
104
162
-continued
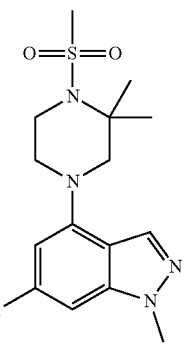
105
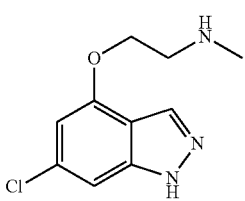
106
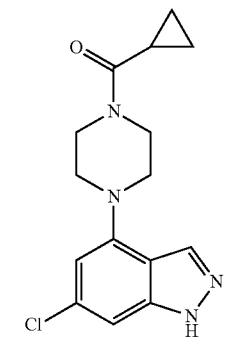
107
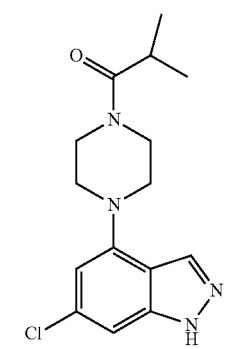
108
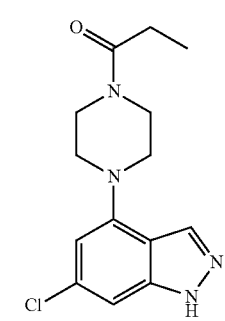
109

110 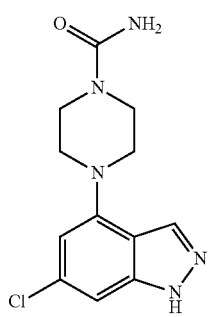
111 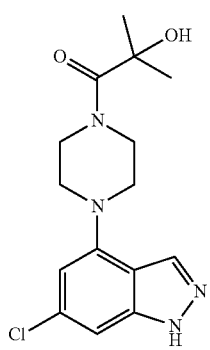
112 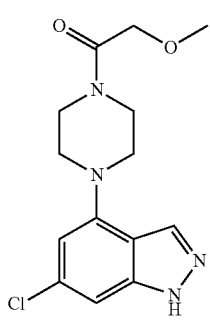
113 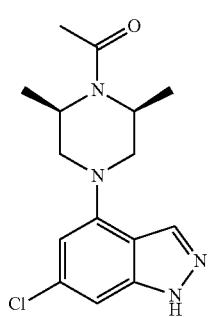
114 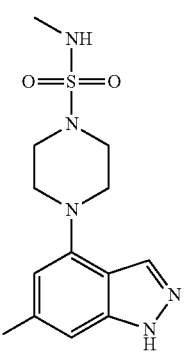
115 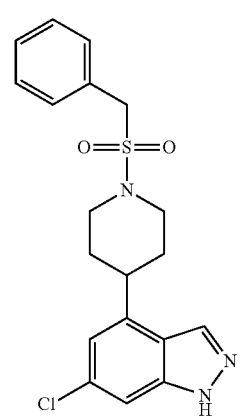
116 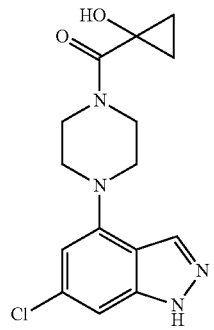

| 117 | 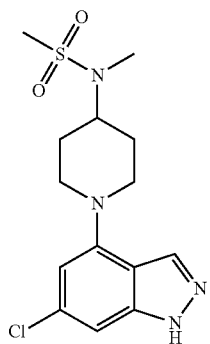 | 121 | 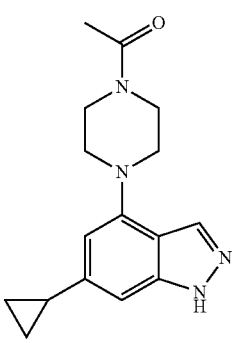 |
| 118 | 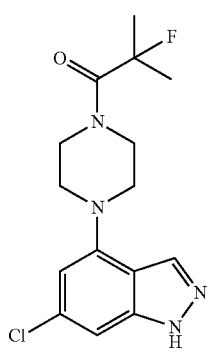 | 122 | 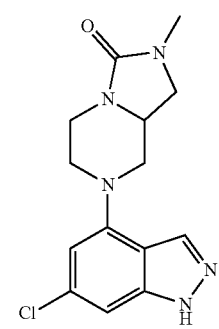 |
| 119 | 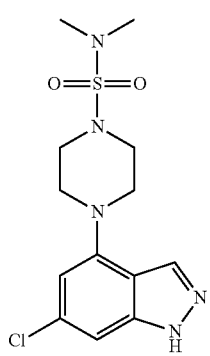 | 123 | 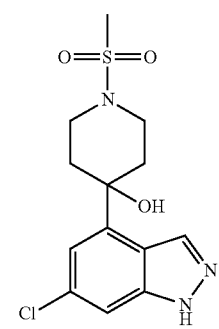 |
| 120 | 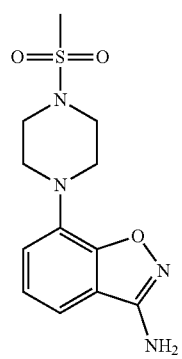 | 124 | 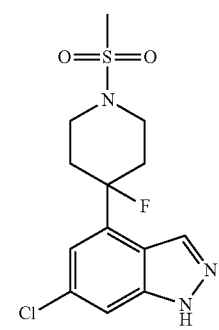 |

| 125 | 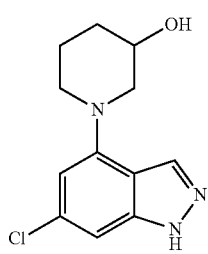 | 129 | 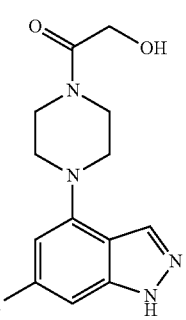 |
| 126 | 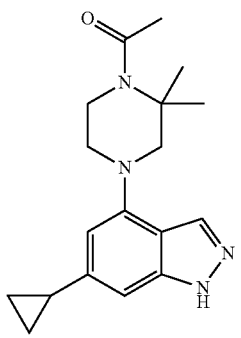 | 130 | 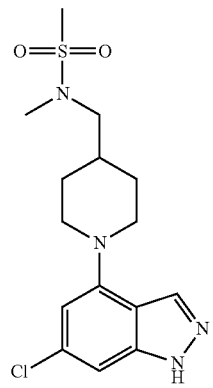 |
| 127 | 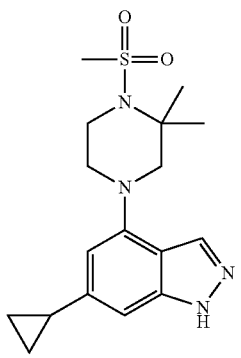 | 131 | 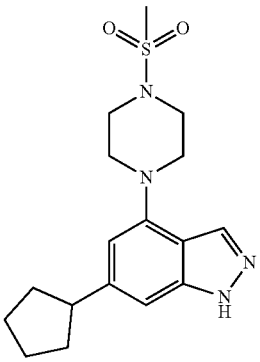 |
| 128 | 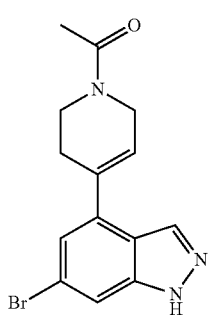 | 132 | 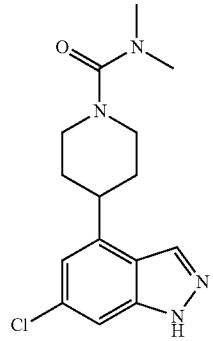 |

169
-continued
133
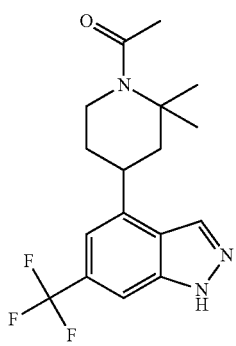
134
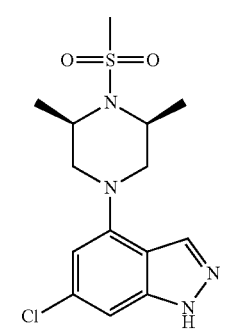
135
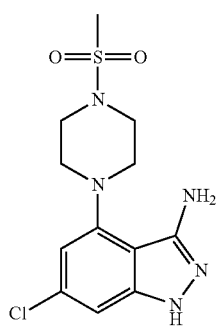
136
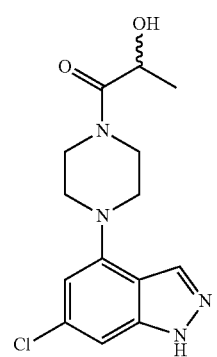
170
-continued
137
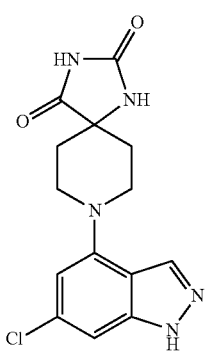
138
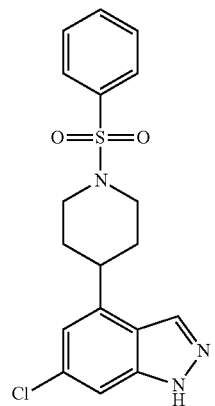
139
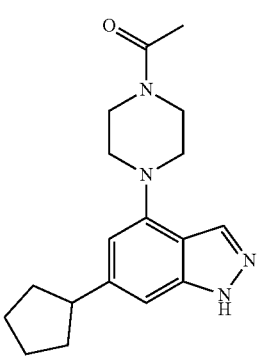
140
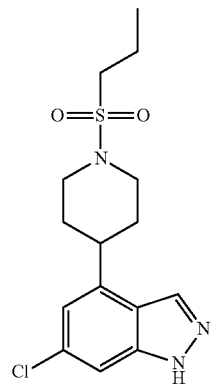

| | |
|---|---|
| 141 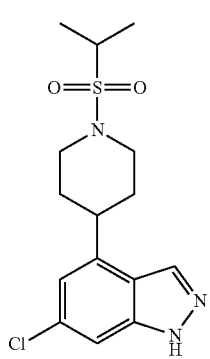 | 145 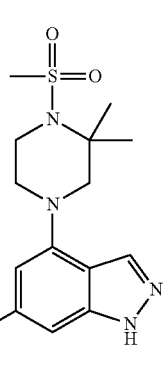 |
| 142 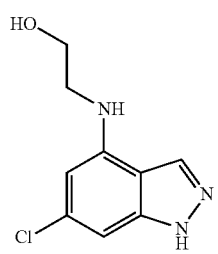 | 146 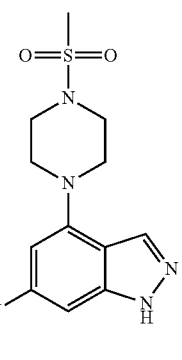 |
| 143 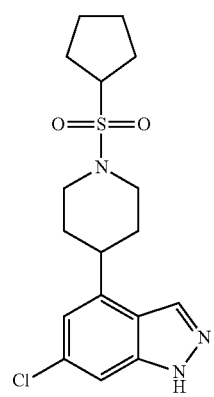 | 147 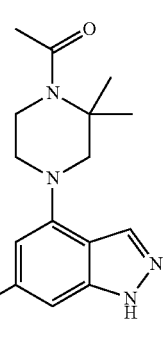 |
| 144 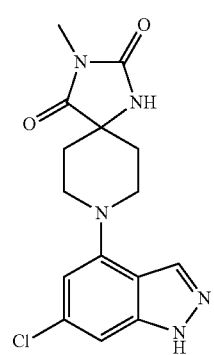 | 148 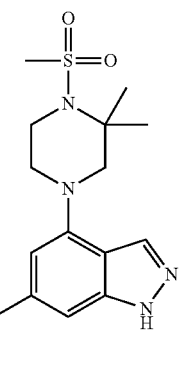 |

173
-continued
149
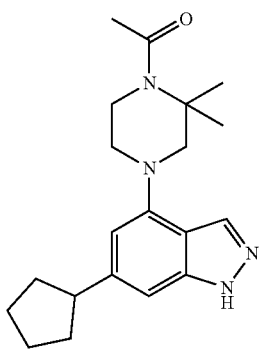
150
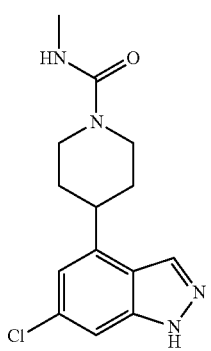
151
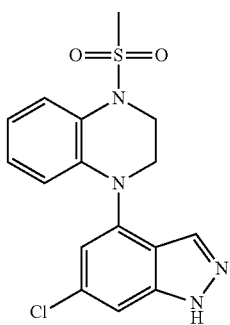
152
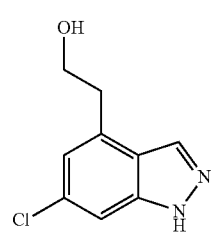
153
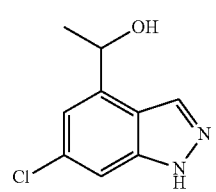
174
-continued
154
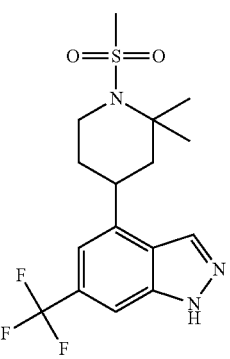
155
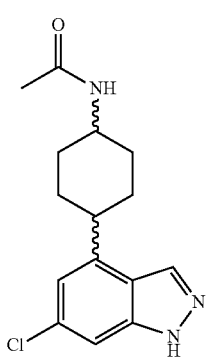
156
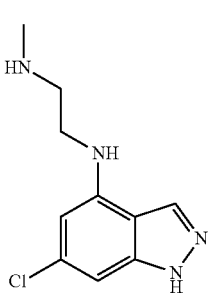
157
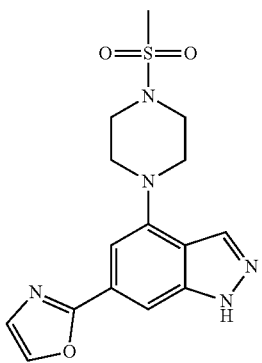

| | |
|---|---|
| 158 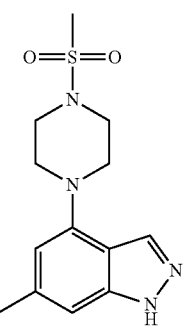 | 163 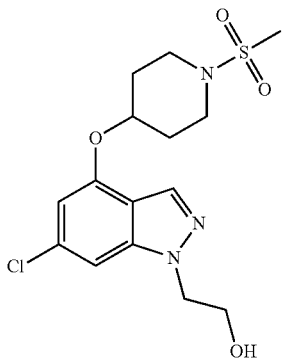 |
| 159 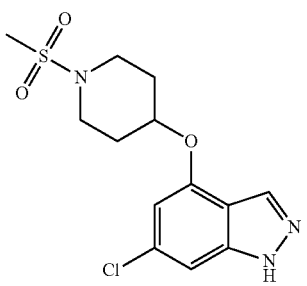 | 164 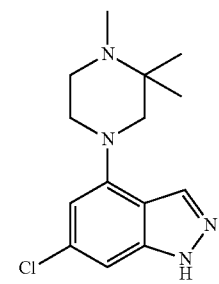 |
| 160 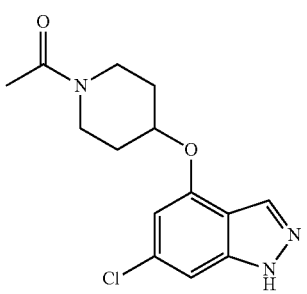 | 165 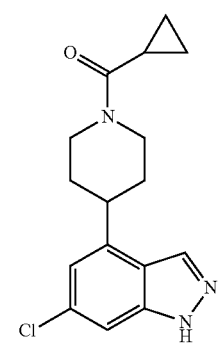 |
| 161 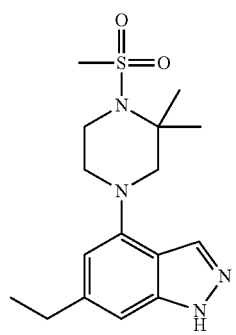 | 166 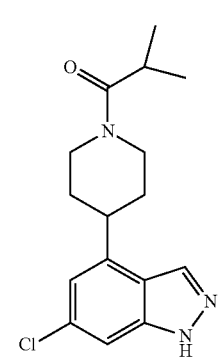 |
| 162 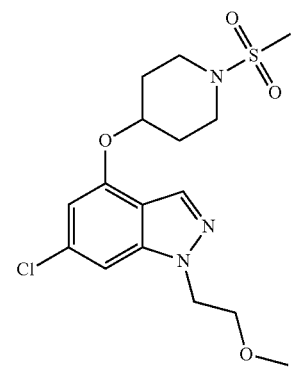 | 167 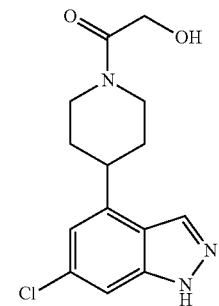 |

| | | |
|---|---|---|
| 168 | 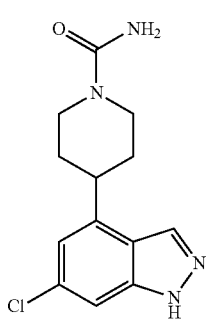 | 172 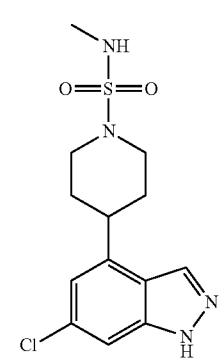 |
| 169 | 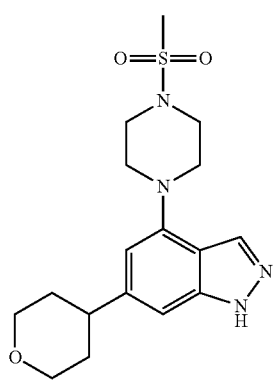 | 173 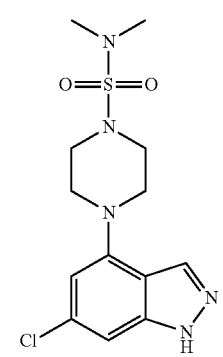 |
| 170 | 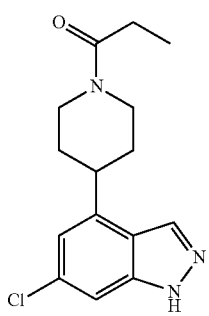 | 174 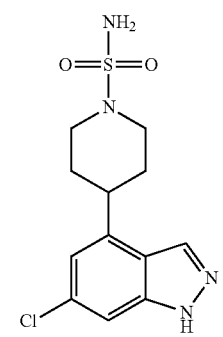 |
| 171 | 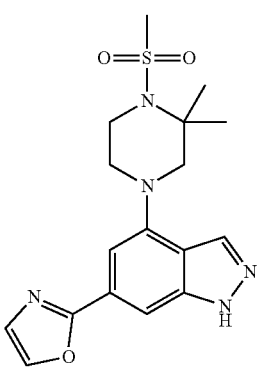 | 175 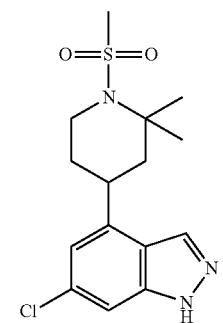 |

| | |
|---|---|
| 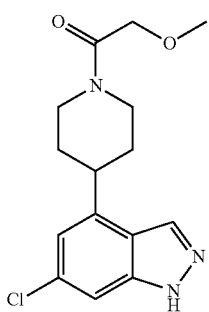 176 | 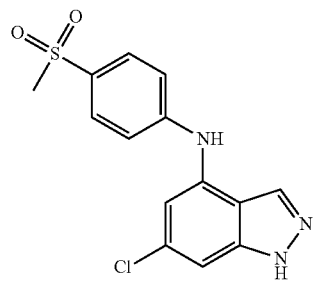 180 |
| 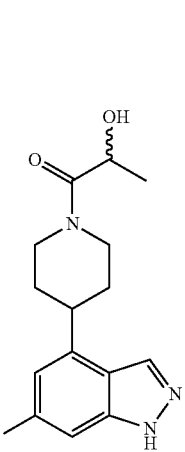 177 | 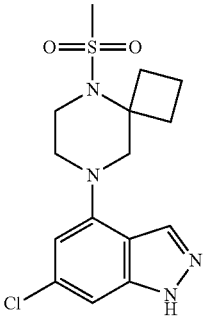 181 |
| | 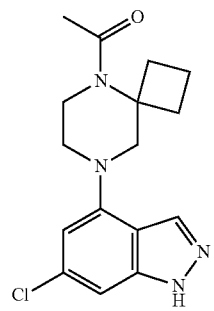 182 |
| 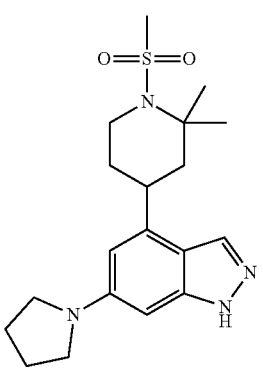 178 | 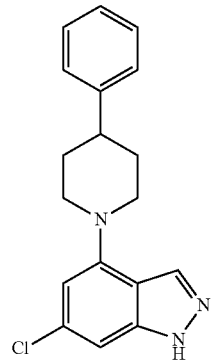 183 |
| 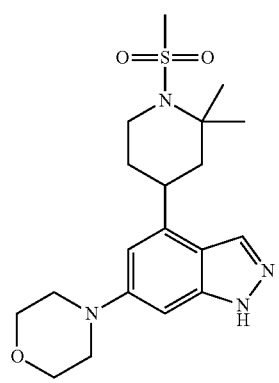 179 | 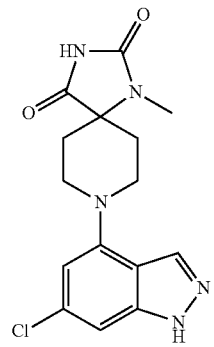 184 |

| 181 -continued | | 182 -continued | |
|---|---|---|---|
| | 185 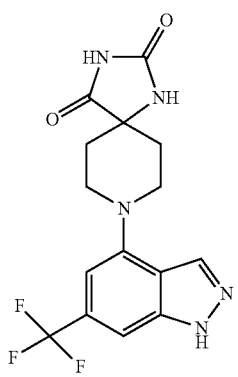 | 189 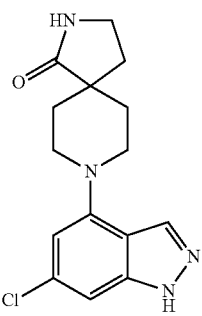 | |
| | 186 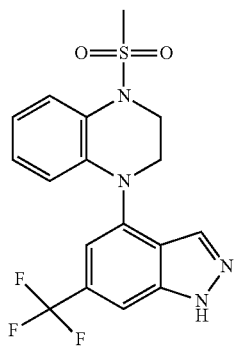 | 190 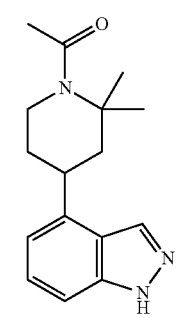 | |
| | 187 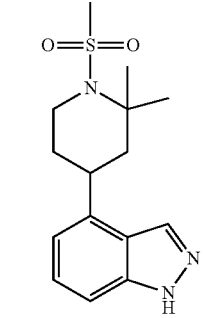 | 191 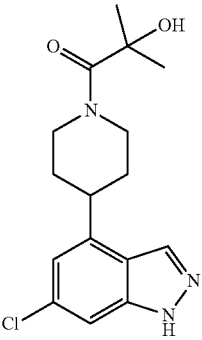 | |
| | 188 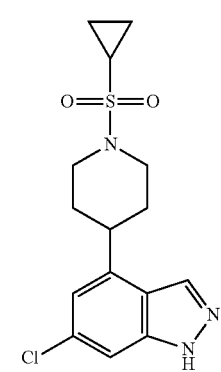 | 192 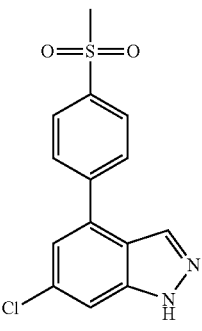 | |
| | | 193 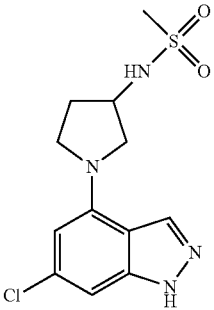 | |

194 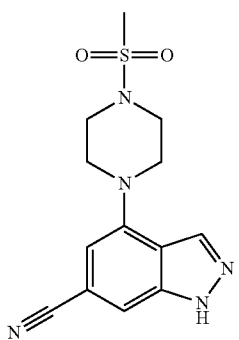
195 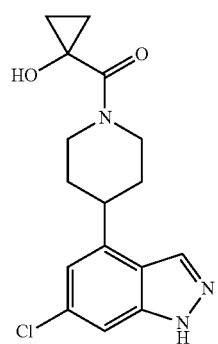
196 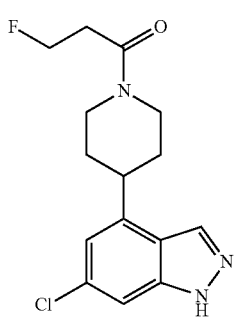
197 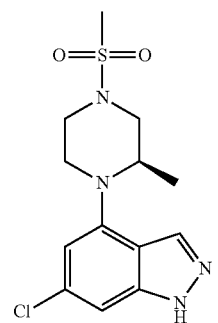
198 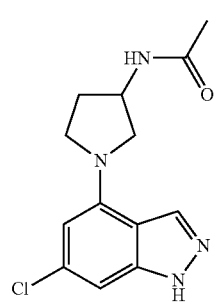
199 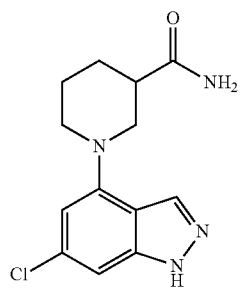
200 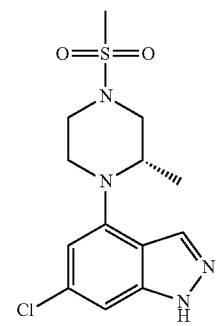
201 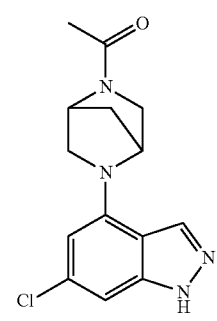
202 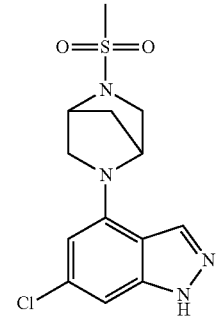
203 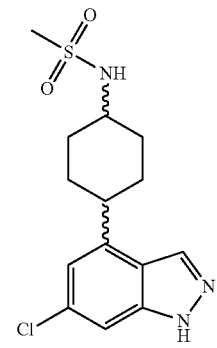

204 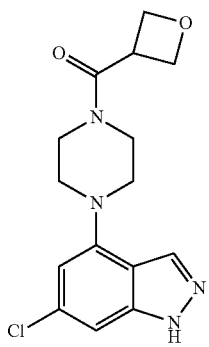
205 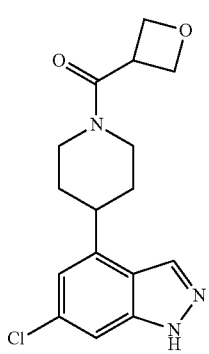
206 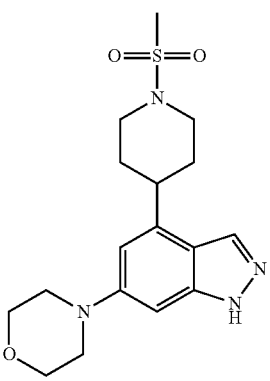
207 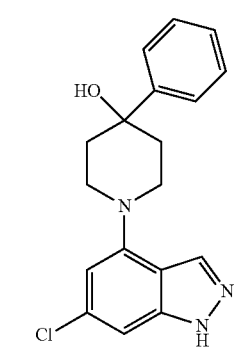
208 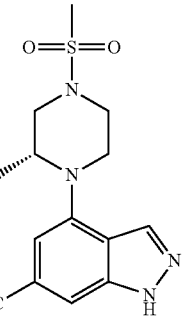
209 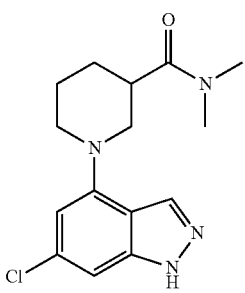
210 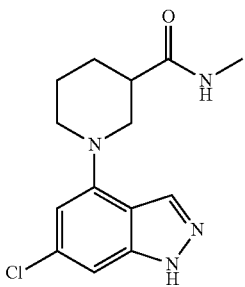
211 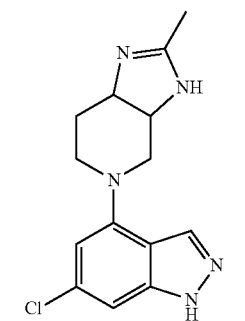
212 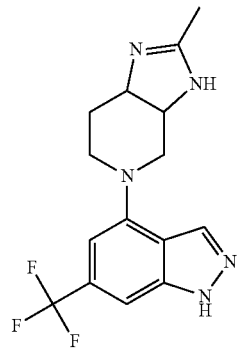

213 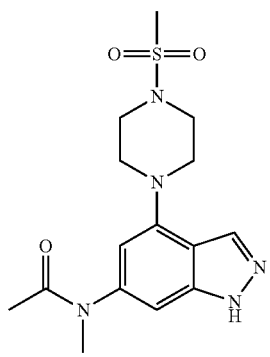
214 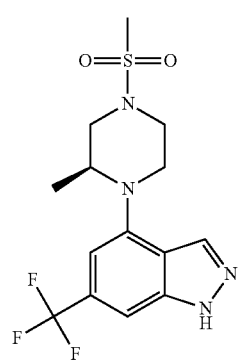
215 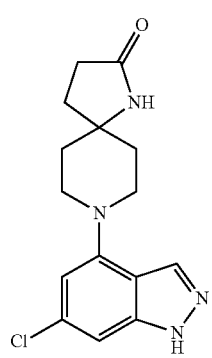
216 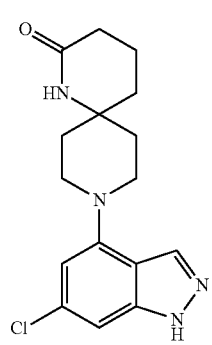
217 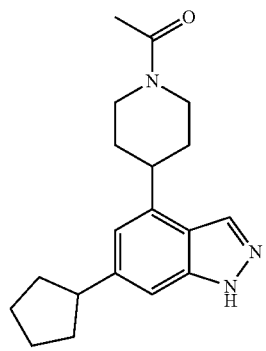
218 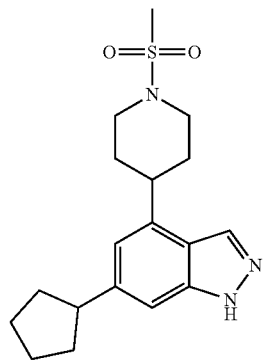
219 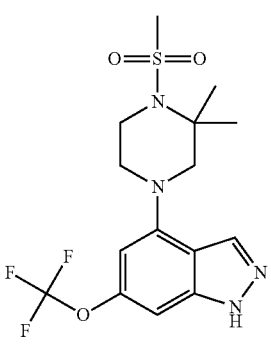
220 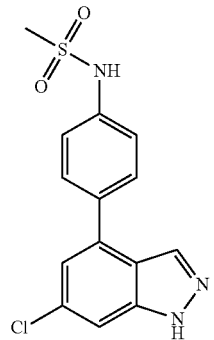

| 189 -continued | | 190 -continued | |
|---|---|---|---|
| 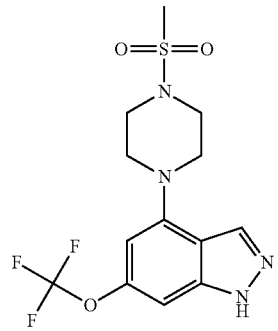 | 221 | 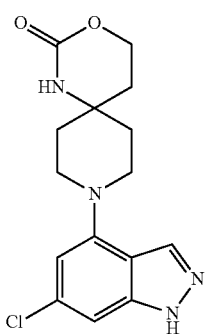 | 224 |
| 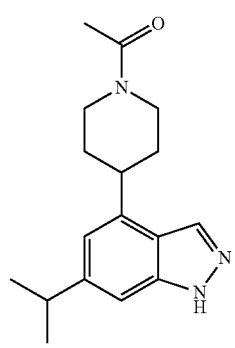 | 222 | 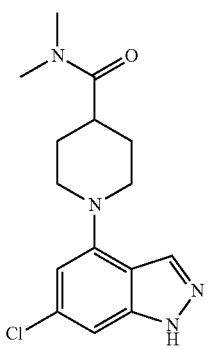 | 225 |
| 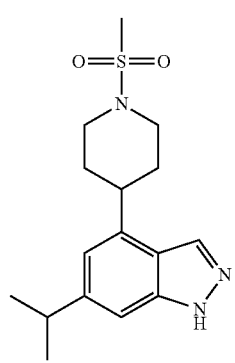 | 223 | 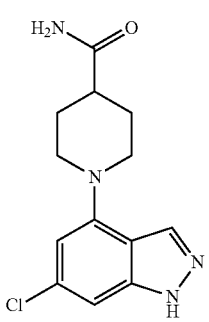 | 226 |

| 227 | 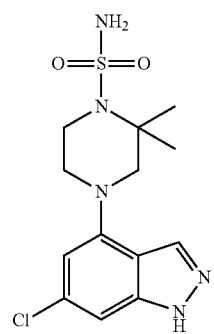 |
|---|---|
| 228 | 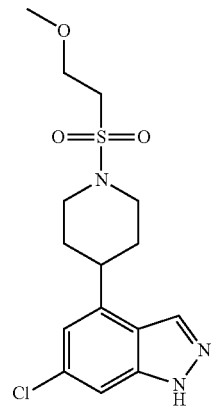 |
| 229 | 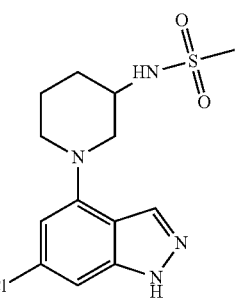 |
| 230 | 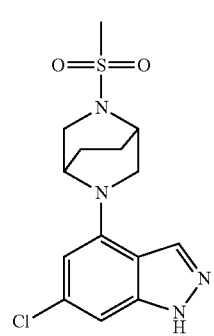 |
| 231 | 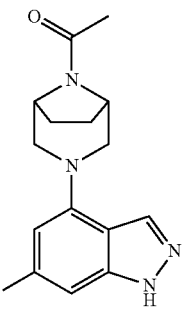 |
|---|---|
| 232 | 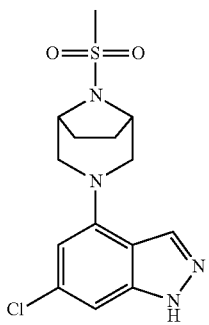 |
| 233 | 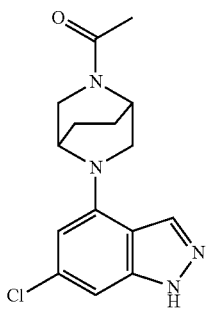 |
| 234 | 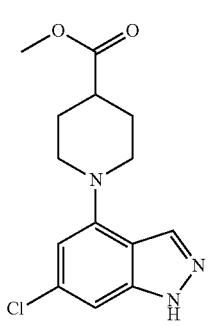 |
| 235 | 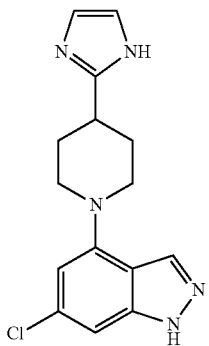 |

| | | |
|---|---|---|
| 236 | 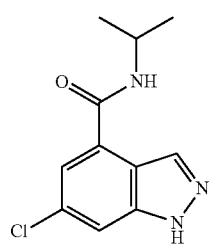 | 241 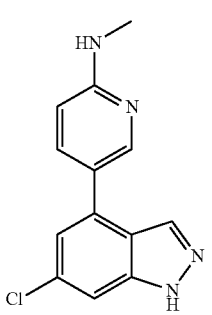 |
| 237 | 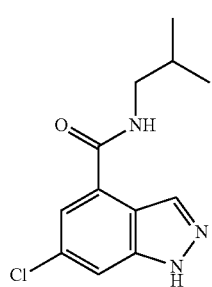 | |
| 238 | 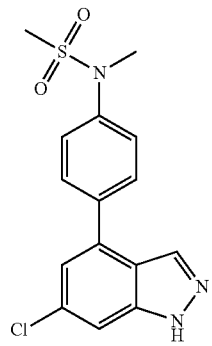 | 242 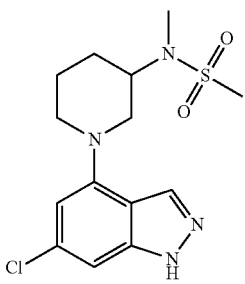 |
| 239 | 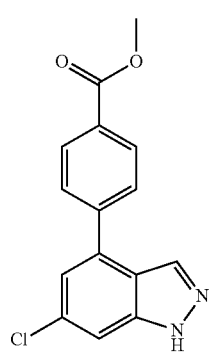 | 243 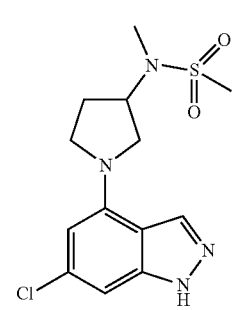 |
| 240 | | 244 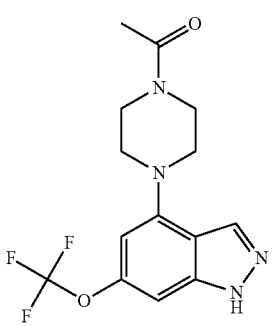 |

-continued
245 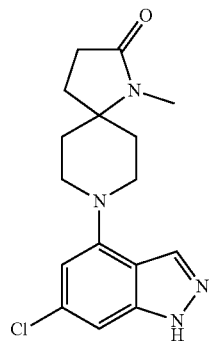
246 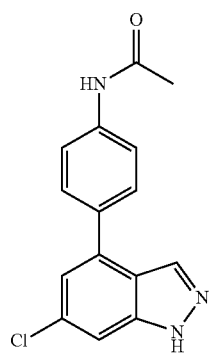
247 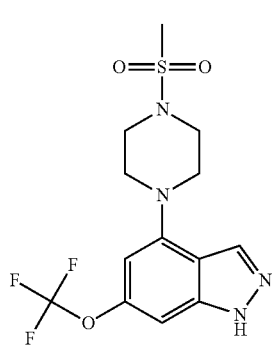
248 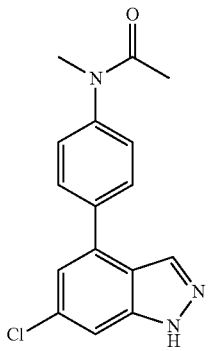
249 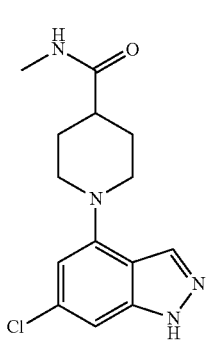
250 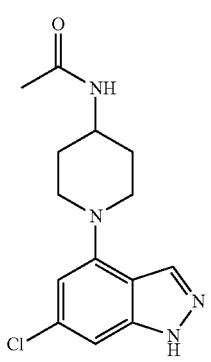
251 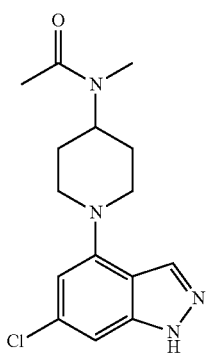

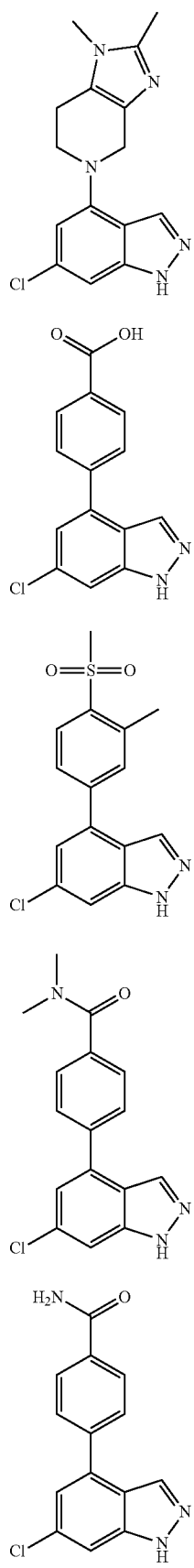
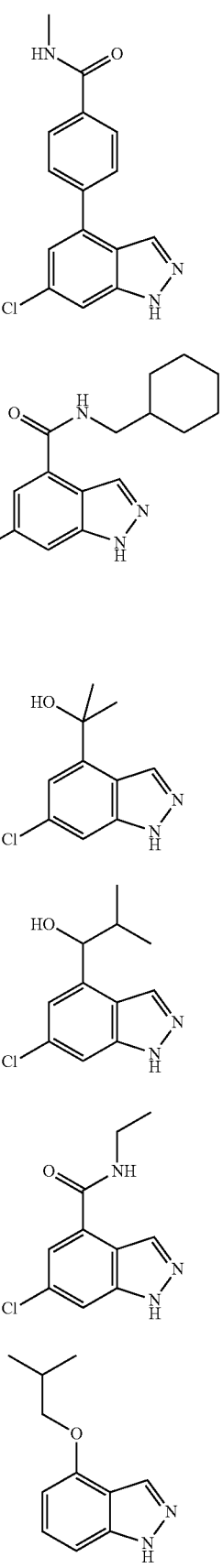

| 263 | 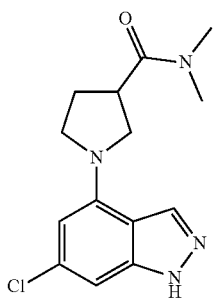 | 268 | 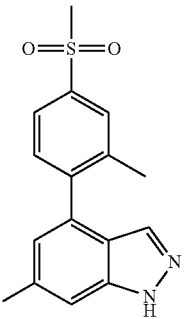 |
| 264 | 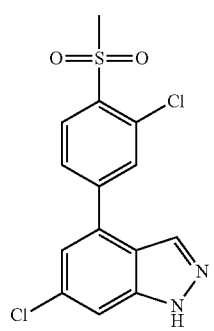 | 269 | 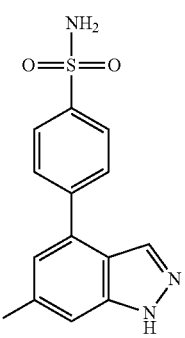 |
| 265 | 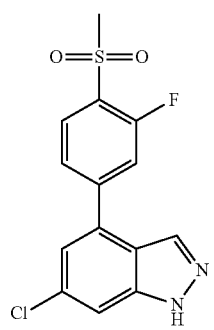 | 270 | 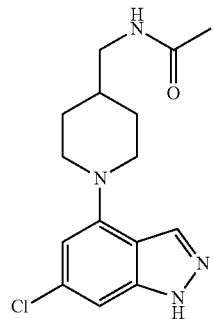 |
| 266 | 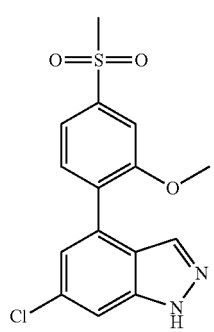 | 271 | 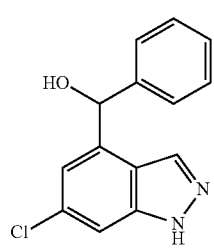 |
| 267 | 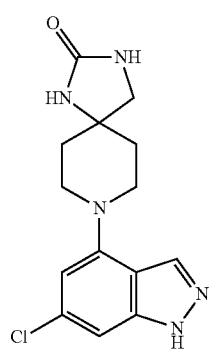 | 272 | 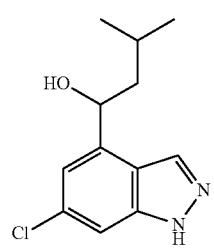 |

| | |
|---|---|
| 273 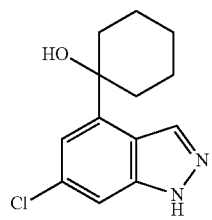 | 278 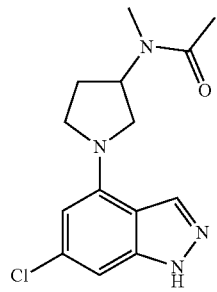 |
| 274 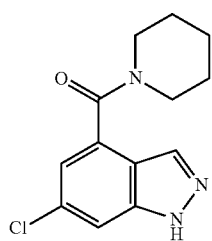 | 279 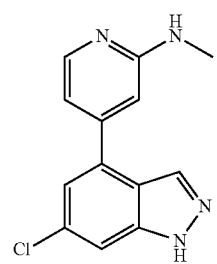 |
| 275 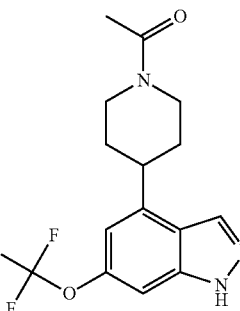 | 280 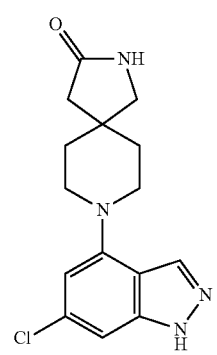 |
| 276 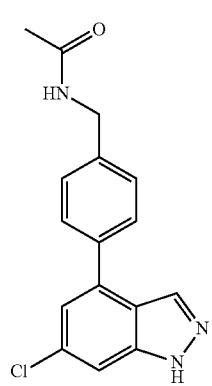 | 281 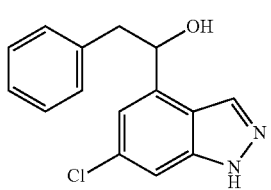 |
| 277 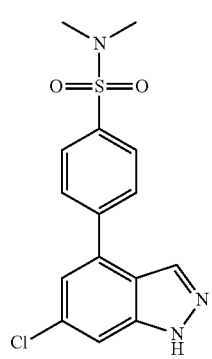 | 282 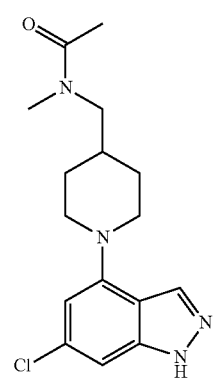 |

283 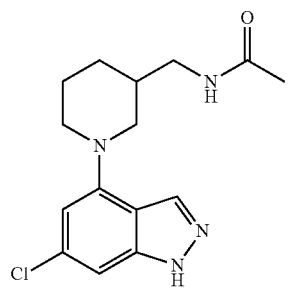
284 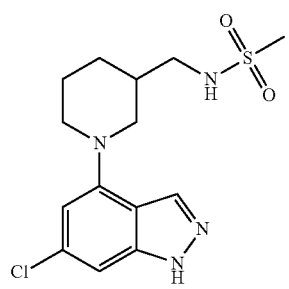
285 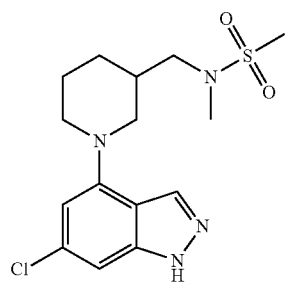
286 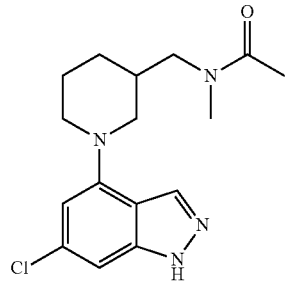
287 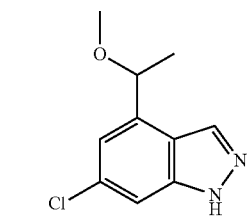
288 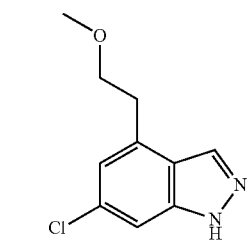
289 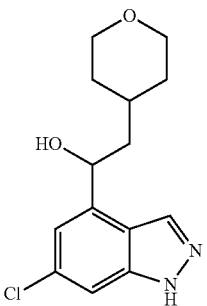
290 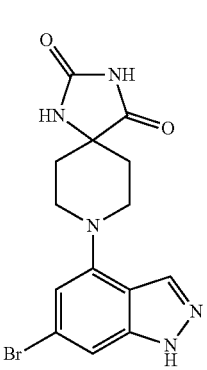
291 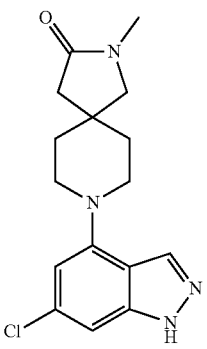
292 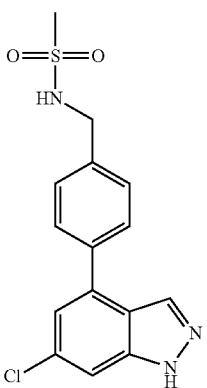
293 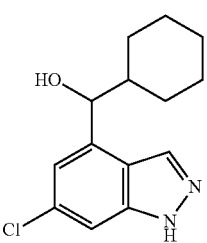

| 205 -continued | | 206 -continued | |
|---|---|---|---|
| 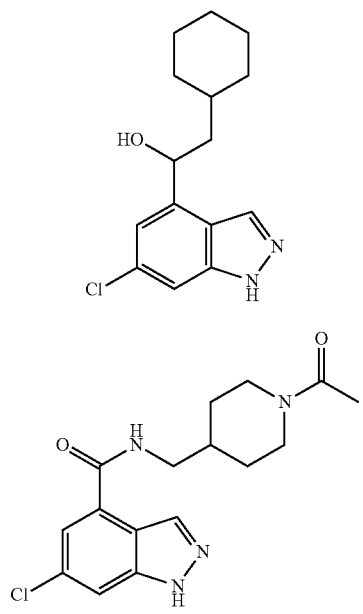 | 294 | 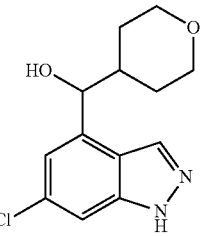 | 299 |
| 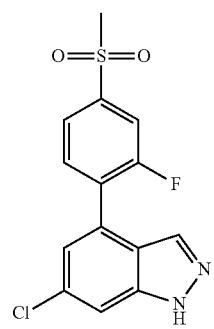 | 295 | 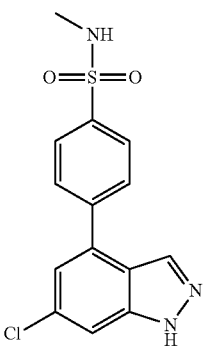 | 300 |
| | 296 | 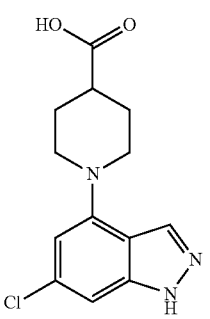 | 301 |
| | 297 | 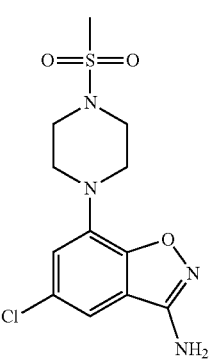 | 302 |
| 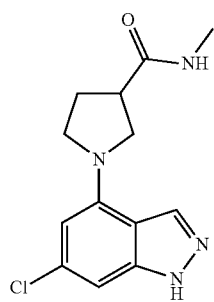 | 298 | 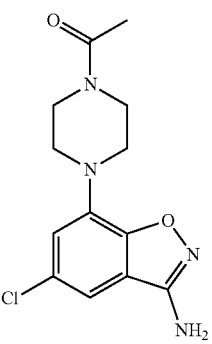 | 303 |

| | | | |
|---|---|---|---|
| 304 | 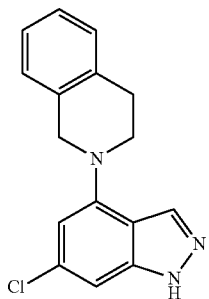 | 308 | 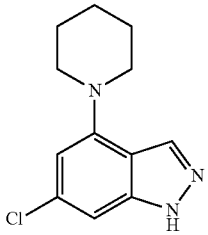 |
| 305 | 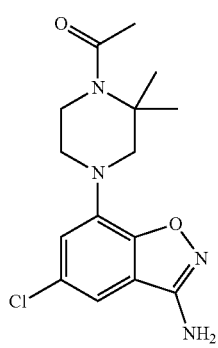 | 309 | 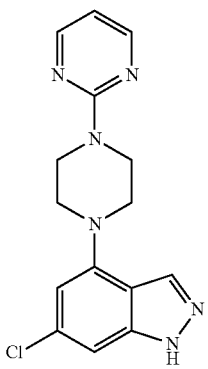 |
| 306 | 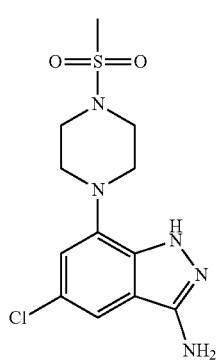 | 310 | 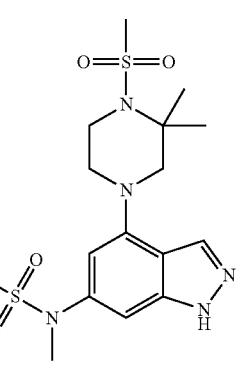 |
| 307 | 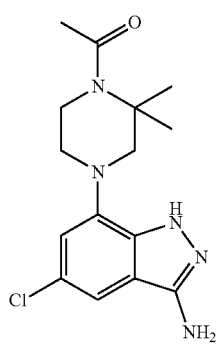 | 311 | 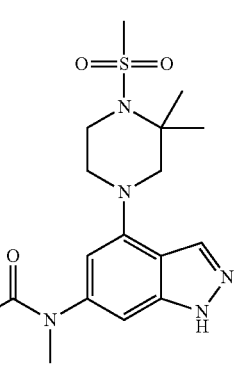 |

-continued
312
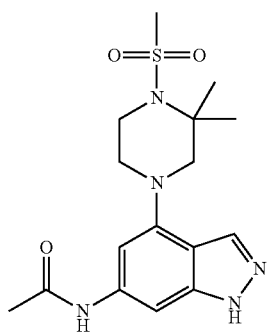
313
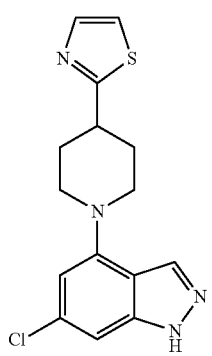
314
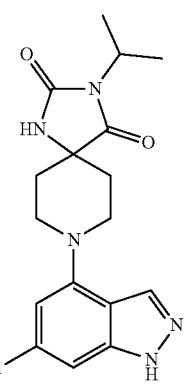
315
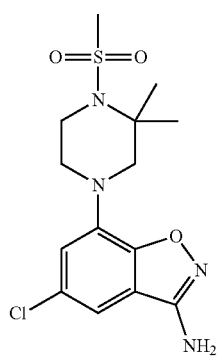
-continued
316
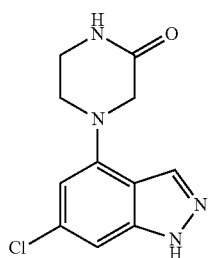
317
318
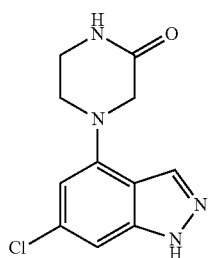
319
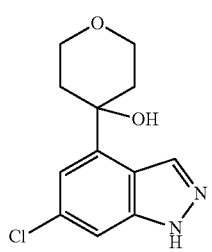

| 320 | 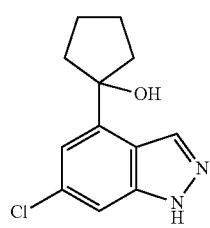 |
| 321 | 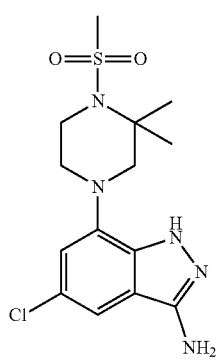 |
| 322 | 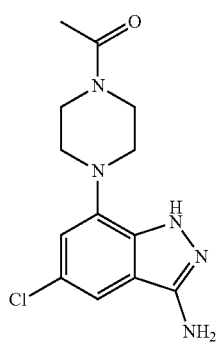 |
| 323 | 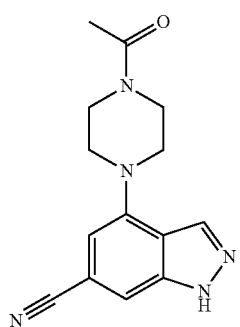 |
| 324 | 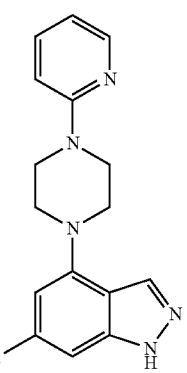 |
| 325 | 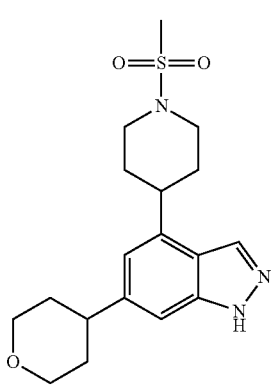 |
| 326 | 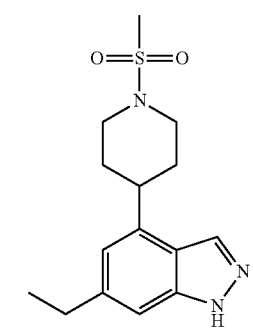 |
| 327 | 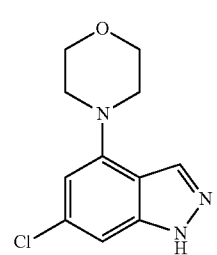 |

| 328 | 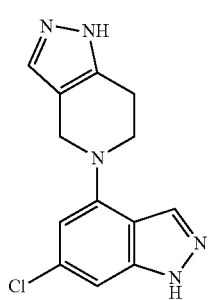 |
|---|---|
| 329 | 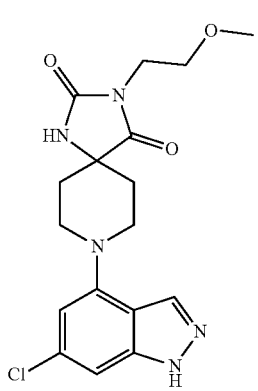 |
| 330 | 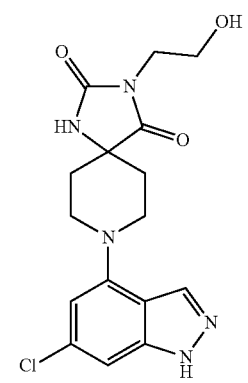 |
| 331 | 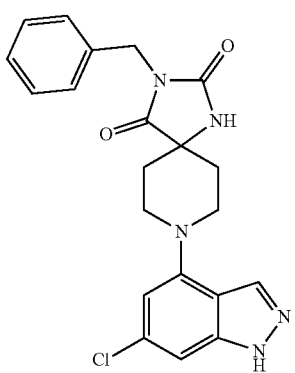 |
| 332 | 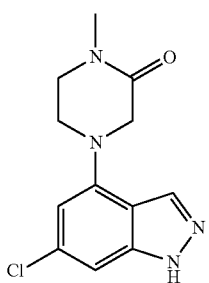 |
|---|---|
| 333 | 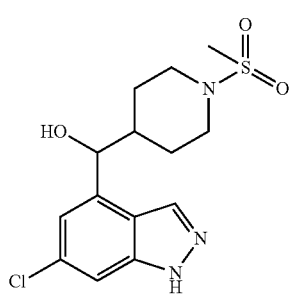 |
| 334 | 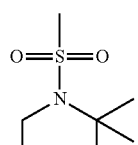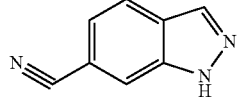 |
| 335 | 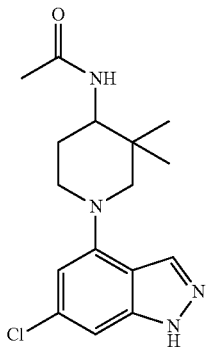 |
| 336 | 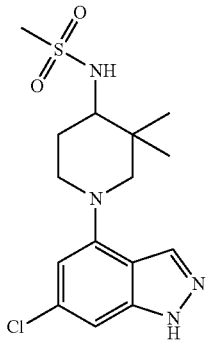 |

337
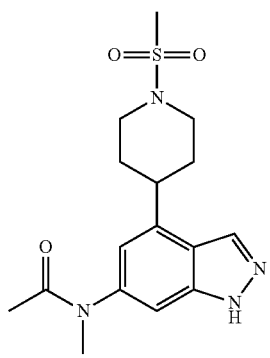
338
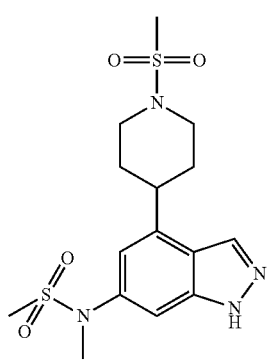
339
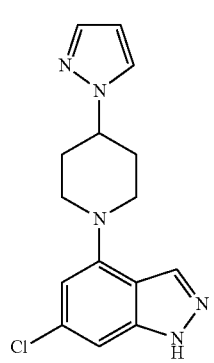
340
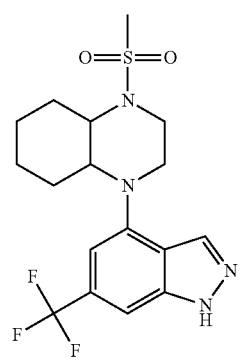
341
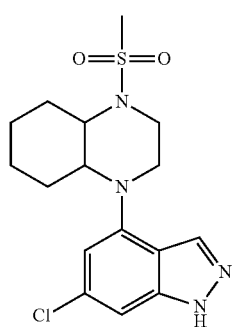
342
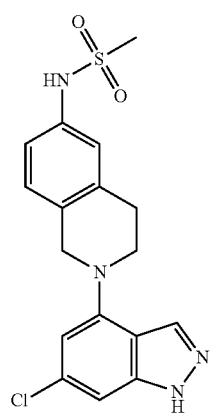
343
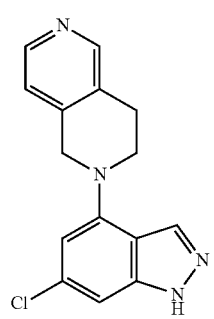
344
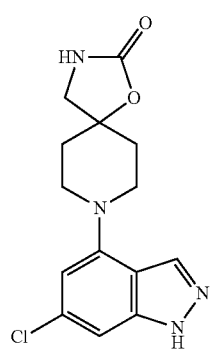

| 217 -continued | | 218 -continued | |
|---|---|---|---|
| | 345 | 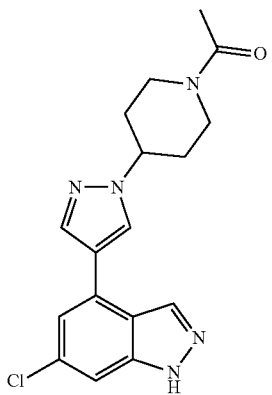 | 348 |
| 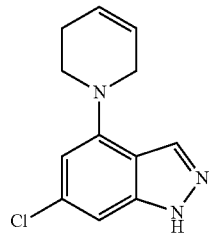 | 346 | 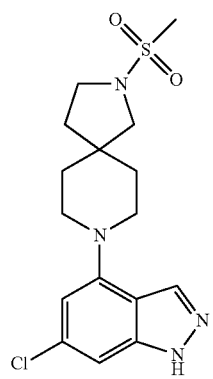 | 349 |
| 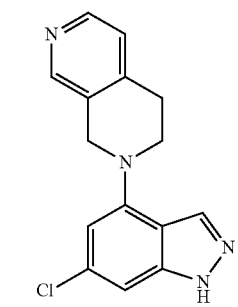 | 347 | 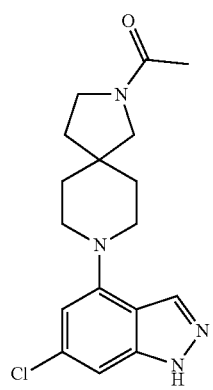 | 350 |
| 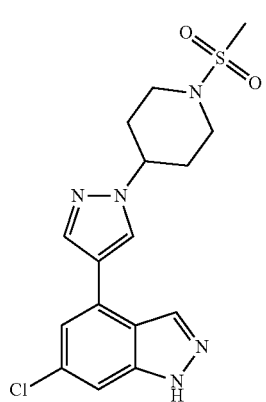 | | 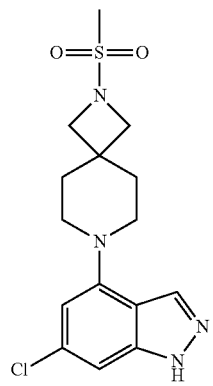 | 351 |

| | |
|---|---|
| 352 | 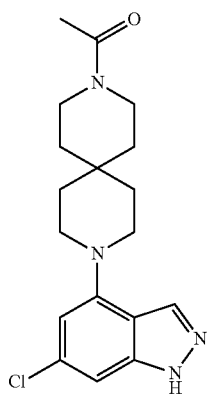 |
| 353 | 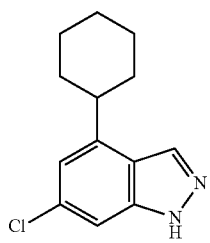 |
| 354 | 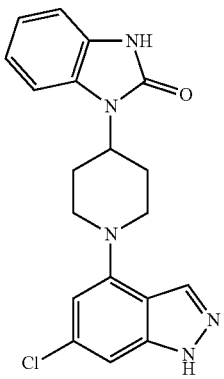 |
| 355 | 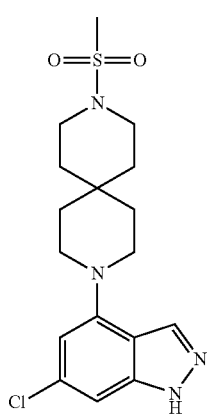 |
| | |
|---|---|
| 356 | 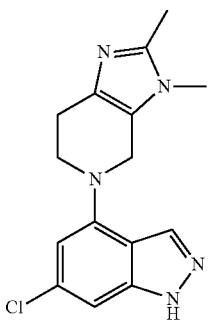 |
| 357 | 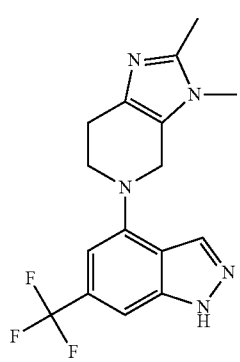 |
| 358 | 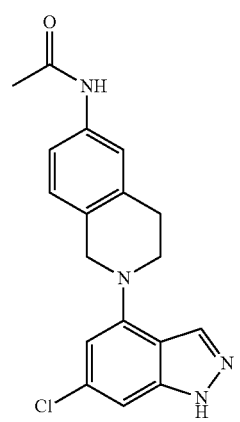 |
| 359 | 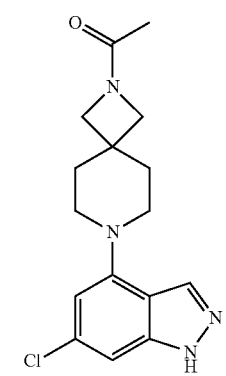 |

| | | |
|---|---|---|
| 360 | | 364 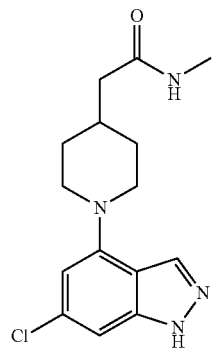 |
| 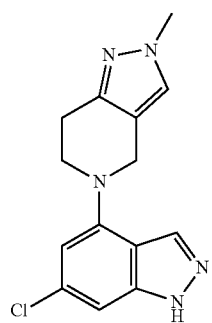 | | |
| 361 | | 365 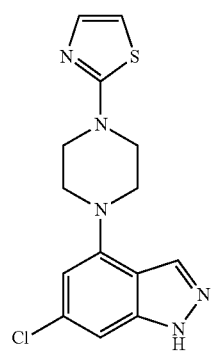 |
| 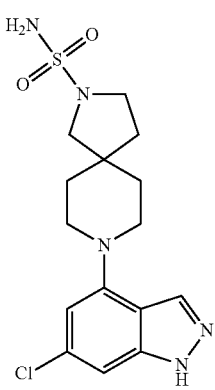 | | |
| | | 366 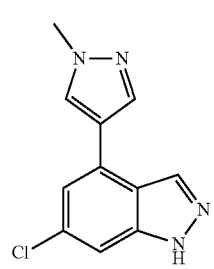 |
| 362 | | |
| 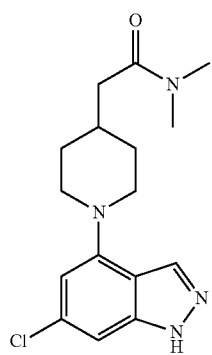 | | 367 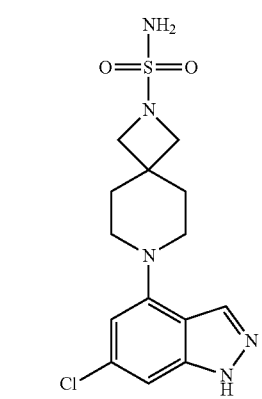 |
| 363 | | |
| 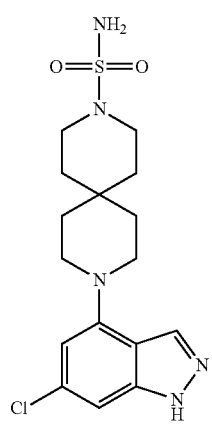 | | 368 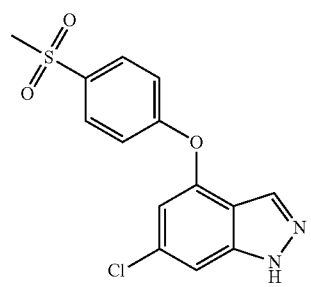 |

| 369 | 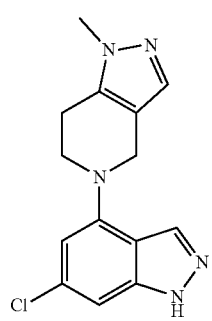 | 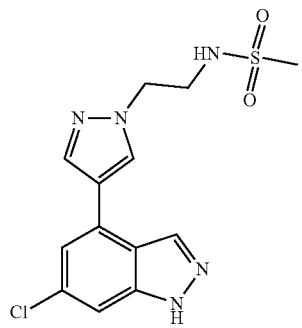 | 373 |
| 370 | 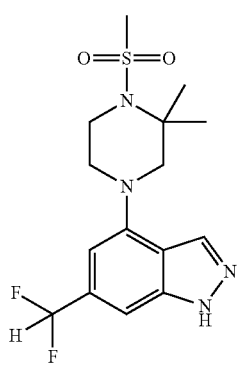 | 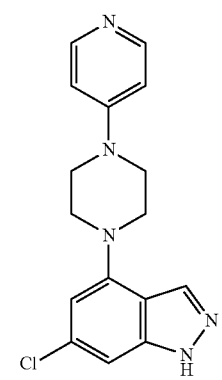 | 374 |
| 371 | 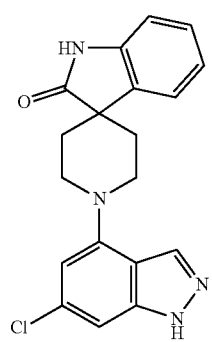 | 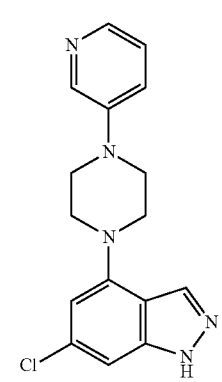 | 375 |
| 372 | 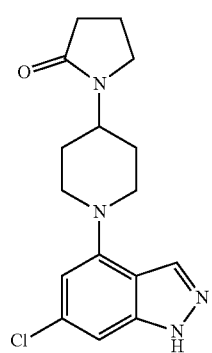 | 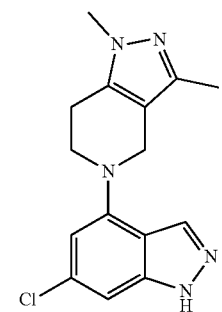 | 376 |

| | |
|---|---|
| 377 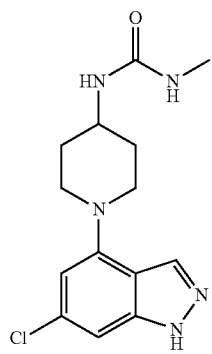 | 381 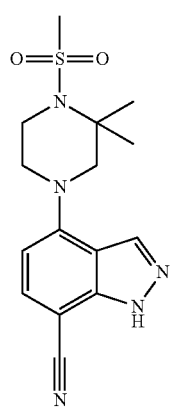 |
| 378 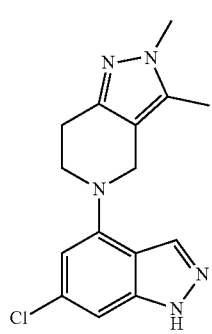 | 382 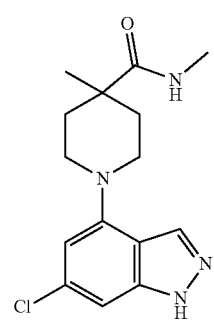 |
| 379 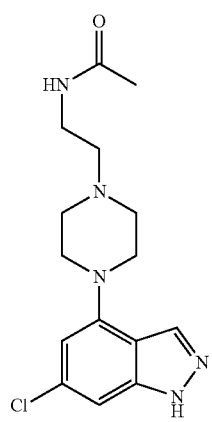 | 383 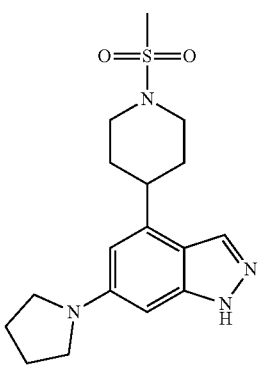 |
| 380 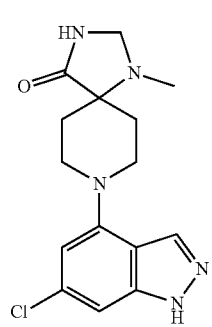 | 384 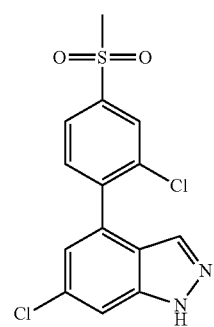 |

385 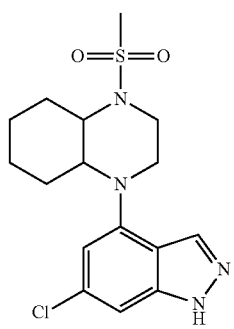
386 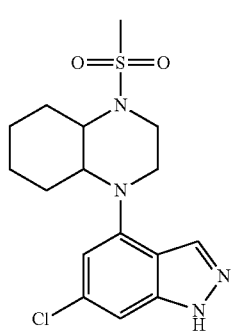
387 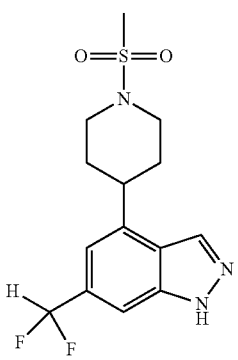
388 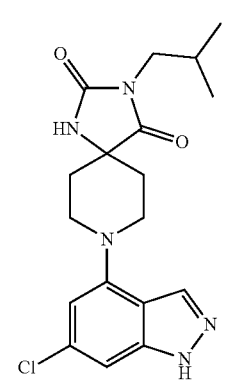
389 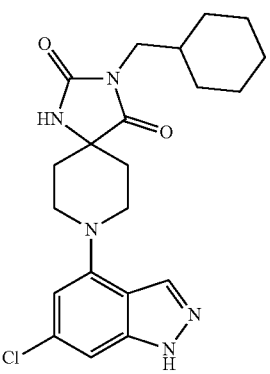
390 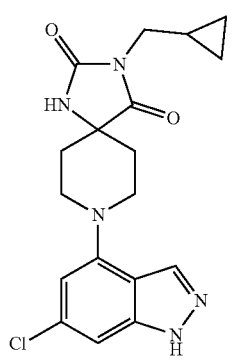
391 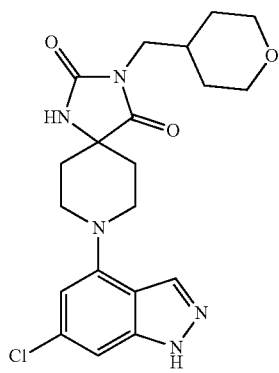
392 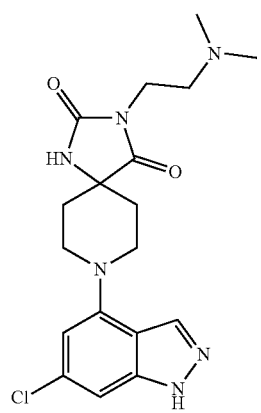

229
-continued
393
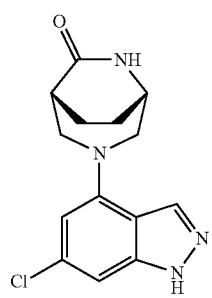
394
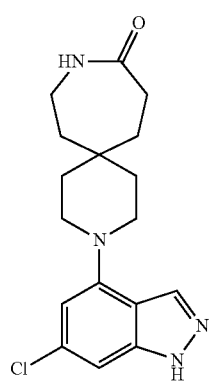
395
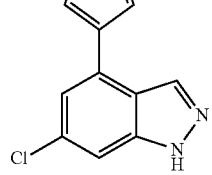
396
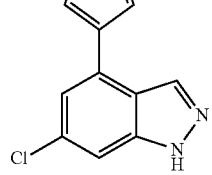
230
-continued
397
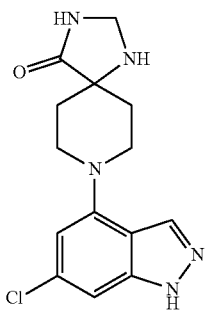
398
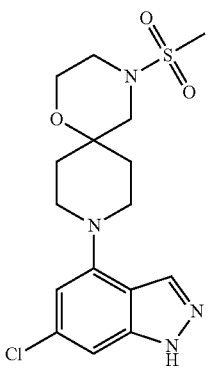
399
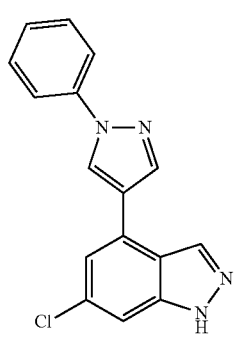
400
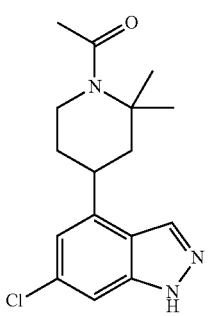

401 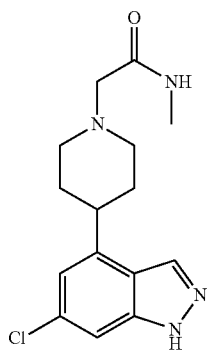
402 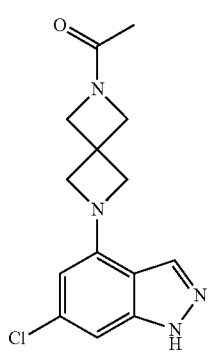
403 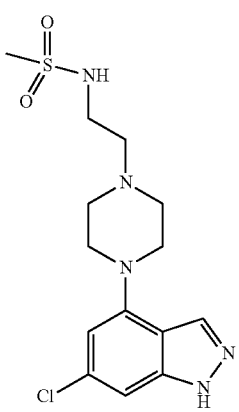
404 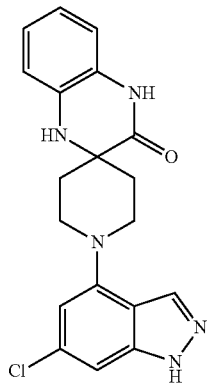
405 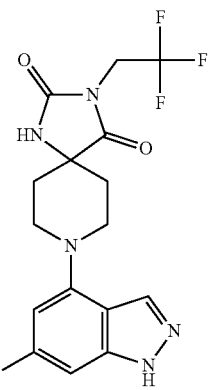
406 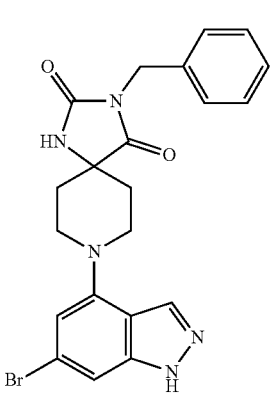
407 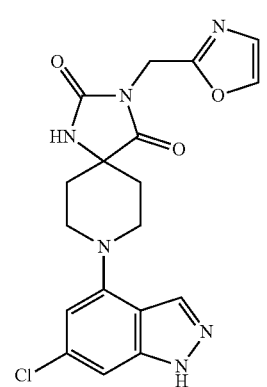
408 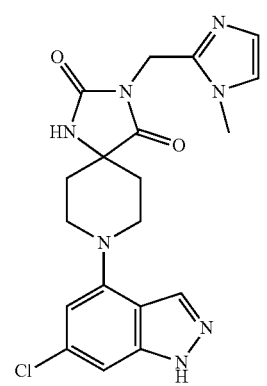

| 409 | 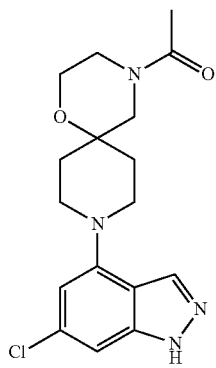 | 413 | 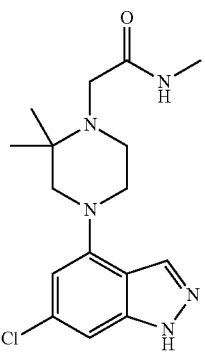 |
| 410 | 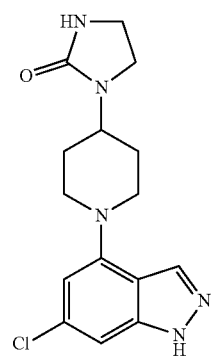 | 414 | 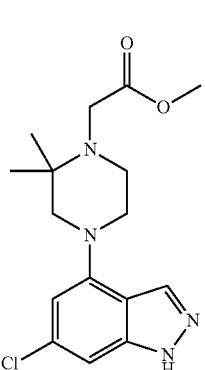 |
| 411 | 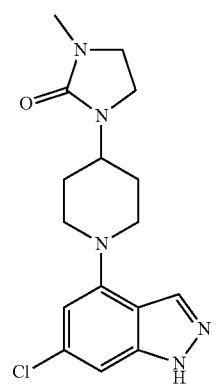 | 415 | 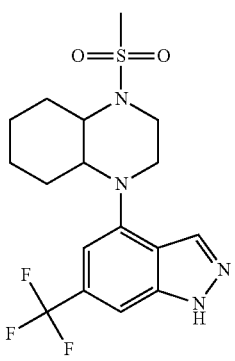 |
| 412 | 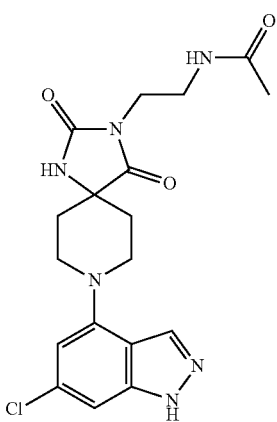 | 416 | 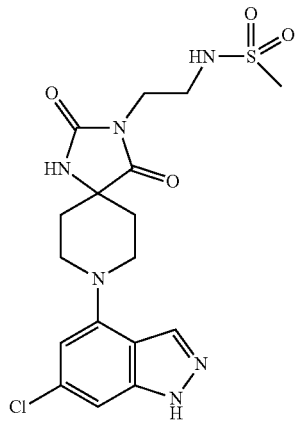 |

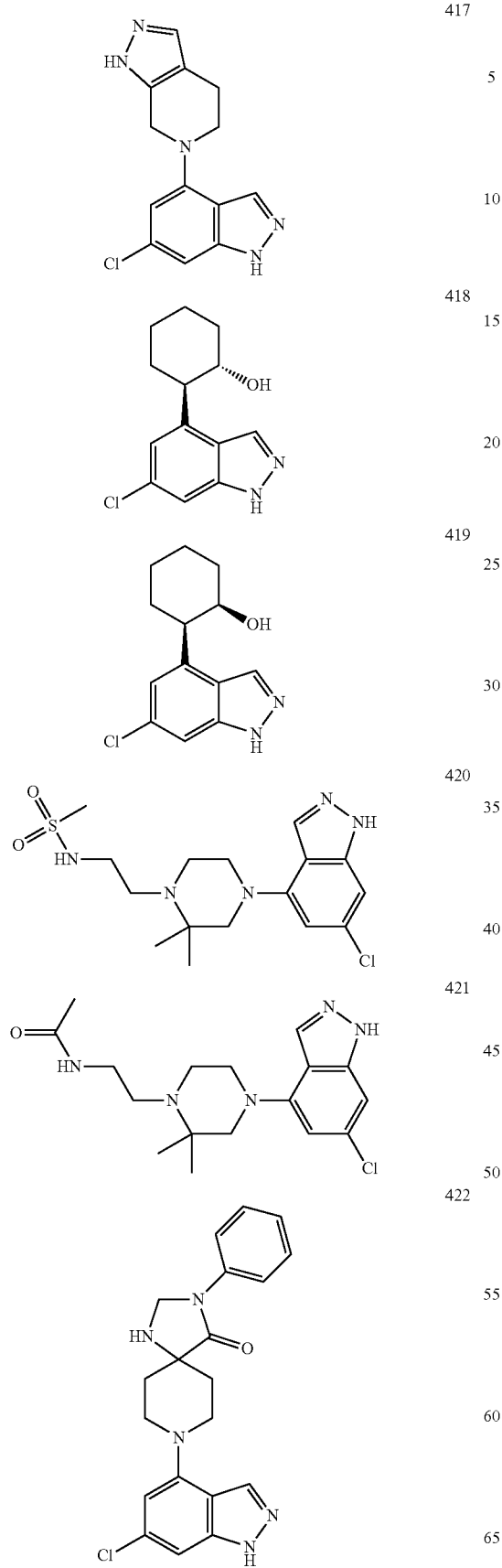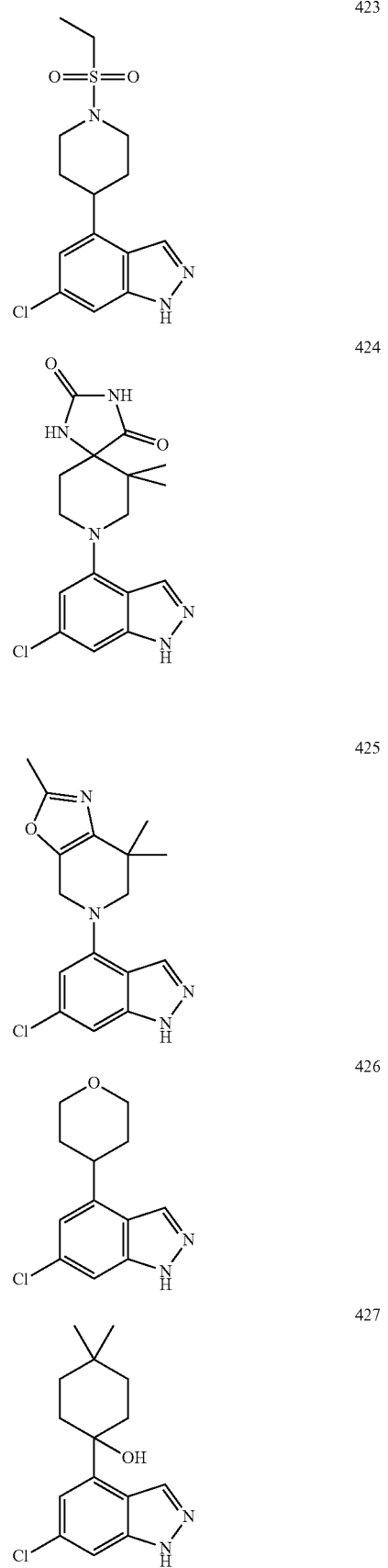

| | |
|---|---|
| 428 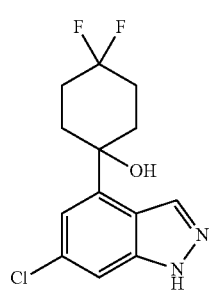 | 433 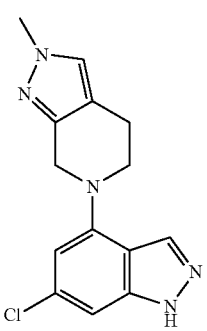 |
| 429 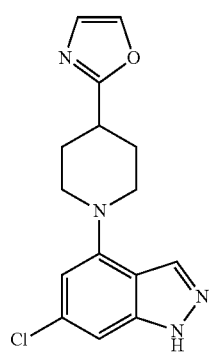 | 434 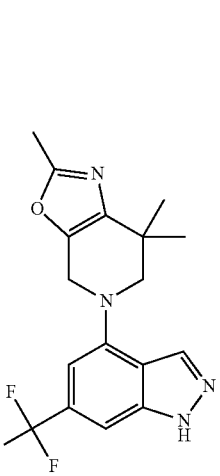 |
| 430 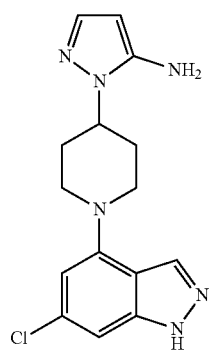 | 435 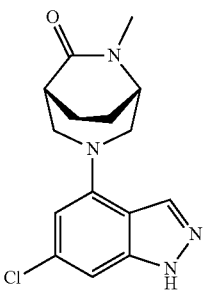 |
| 431 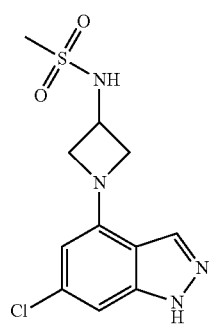 | 436 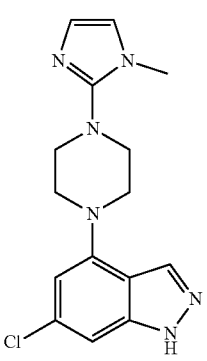 |
| 432 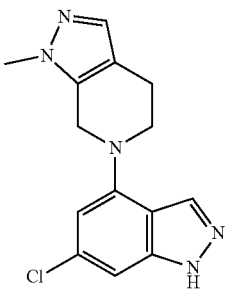 | |

437 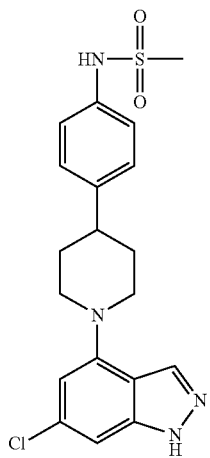
438 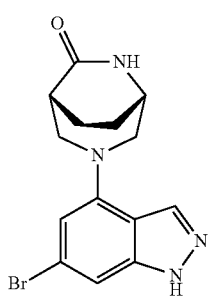
439 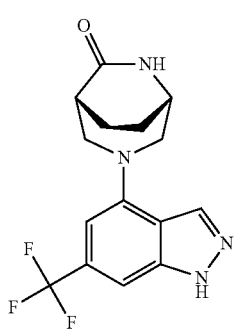
440 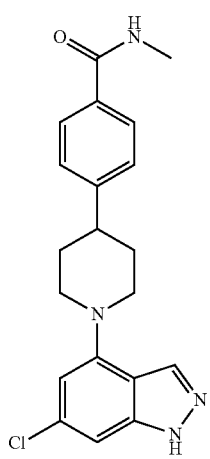
441 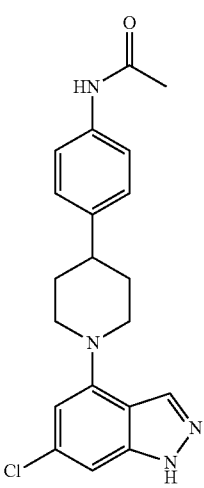
442 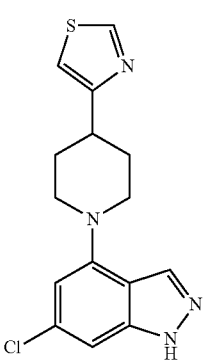
443 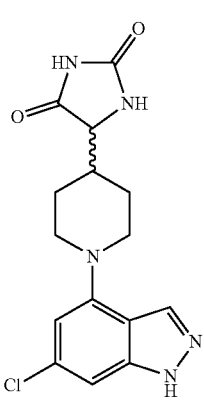
444 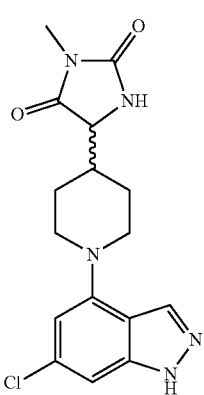

241
-continued
445
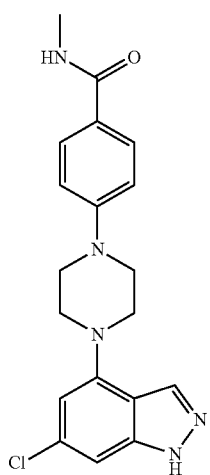
446
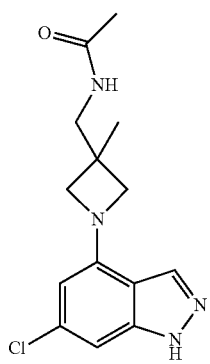
447
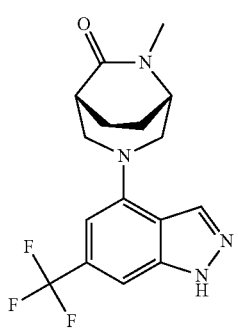
448
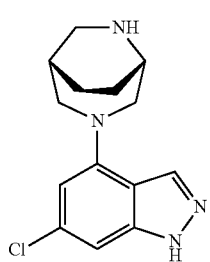
242
-continued
449
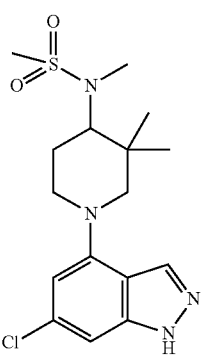
450
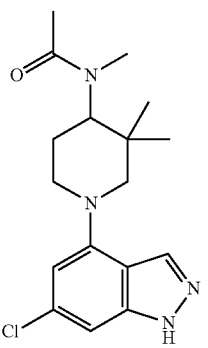
451
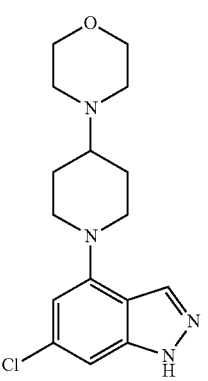
452
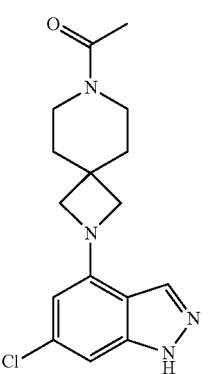

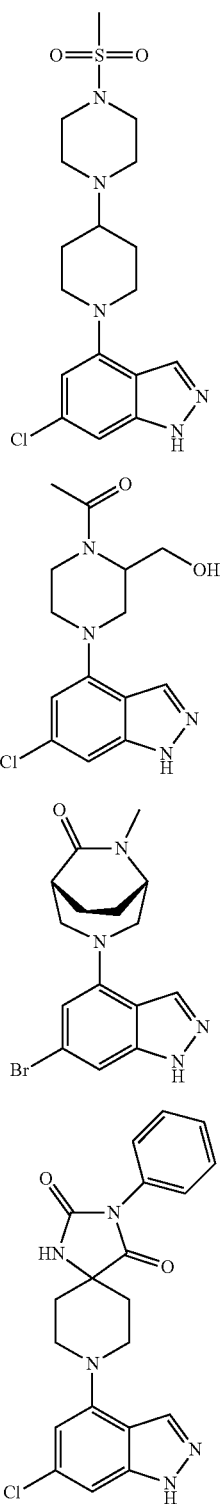

possible isolated diastereomers corresponding to the formula, all possible mixtures of diastereomers corresponding to the formula, all possible isolated epimers corresponding to the formula, all possible mixtures of epimers corresponding to the formula, all possible racemic mixtures corresponding to the formula, all possible isolated cis and trans isomers corresponding to the formula, and all possible mixtures of cis and trans isomers corresponding to the formula. In addition to this, the above formulae (and all formulae herein) are intended to represent all tautomeric forms equivalent to the corresponding formula. In the context of the present invention, the medicinal use is not especially limited, provided that it is a use which is facilitated by the TDO and/or the IDO inhibitory effect of the compound. Thus, the compounds of the invention may be for use in any disease, condition or disorder that may be prevented, ameliorated or treated using a TDO and/or IDO inhibitor. Typically this comprises a disease condition and/or a disorder selected from: a cancer, an inflammatory condition, an infectious disease, a central nervous system disease or disorder, coronary heart disease, chronic renal failure, post anaesthesia cognitive dysfunction, a disease condition and/or a disorder relating to female reproductive health including contraception or abortion, and cataracts.

When the disease, condition or disorder is an inflammatory disease, condition or disorder, it is not especially limited, provided that the disease, condition or disorder is one which may be treated, prevented or ameliorated by using a TDO and/or IDO inhibitor. However, typically the inflammatory condition is a condition relating to immune B cell T cell, dendritic cell, natural killer cell, macrophage, and/or neutrophil dysregulation.

When the disease, condition or disorder is a cancer, it is not especially limited, provided that the cancer is one which may be treated, prevented or ameliorated by using a TDO and/or IDO inhibitor. Thus the cancer may be a cancer selected from: a solid or liquid tumour including cancer of the eye, brain (such as gliomas, glioblastomas, medullablastomas, craniopharyngioma, ependymoma, and astrocytoma), spinal cord, kidney, mouth, lip, throat, oral cavity, nasal cavity, small intestine, colon, parathyroid gland, gall bladder, head and neck, breast, bone, bile duct, cervix, heart, hypopharyngeal gland, lung, bronchus, liver, skin, ureter, urethra, testicles, vagina, anus, laryngeal gland, ovary, thyroid, oesophagus, nasopharyngeal gland, pituitary gland, salivary gland, prostate, pancreas, adrenal glands; an endometrial cancer, oral cancer, melanoma, neuroblastoma, gastric cancer, an angiomatosis, a hemangioblastoma, a pheochromocytoma, a pancreatic cyst, a renal cell carcinoma, Wilms' tumour, squamous cell carcinoma, sarcoma, osteosarcoma, Kaposi sarcoma, rhabdomyosarcoma, hepatocellular carcinoma, PTEN Hamartoma-Tumor Syndromes (PHTS) (such as Lhermitte-Duclos disease, Cowden syndrome, Proteus syndrome, and Proteus-like syndrome), leukaemias and lymphomas (such as acute lymphoblastic leukaemia, chronic lymphocytic leukaemia, acute myelogenous leukaemia, chronic myelogenous leukaemia, hairy cell leukaemia, T-cell prolymphocytic leukemia (T-PLL), large granular lymphocytic leukemia, adult T-cell leukemia, juvenile myelornonocytic leukaemia, Hodgkin lymphoma, non-Hodgkin lymphoma, mantle lymphoma, follicular lymphoma, primary effusion lymphoma, AIDS-related lymphoma, Hodgkin lymphoma, diffuse B cell lymphoma, Burkitt lymphoma, and cutaneous T-cell lymphoma). However, when the compound is an IDO inhibitor, typically (but not exclusively) the cancer is a cancer selected from acute myeloid leukemia (AML), a small-cell lung cancer, a mela- Typically, but not exclusively, the above formulae (and all formulae herein) are shown in non-stereoisomeric form. For the avoidance of doubt, throughout the present disclosure a single formula is intended to represent all possible stereoisomers of a particular structure, including all possible isolated enantiomers corresponding to the formula, all possible mixtures of enantiomers corresponding to the formula, all noma, an ovarian cancer, a colorectal cancer, a pancreatic cancer, an endometrial cancer, and a skin papilloma. When the compound is a TDO inhibitor, typically (but not exclusively) the cancer is a cancer selected from a glioma, and a hepatocellular carcinoma.

When the disease is an infectious disease, it is not especially limited, provided that the disease is one which may be treated, prevented or ameliorated by using a TDO and/or IDO inhibitor. However, typically the infectious disease is selected from a bacterial infection and a viral infection, preferably a gut infection, sepsis, and sepsis induced hypotension.

When the disease, condition or disorder is a central nervous system disease, condition or disorder, it is not especially limited, provided that the disease, condition or disorder is one which may be treated, prevented or ameliorated by using a TDO and/or IDO inhibitor. However, the central nervous system disease, condition or disorder is typically selected from amyotrophic lateral sclerosis (AML), Huntington's disease, Alzheimer's disease, pain, a psychiatric disorder, multiple sclerosis, Parkinson's disease, and HIV related neurocognitive decline.

When the disease, condition or disorder is one relating to female reproductive health, it is not especially limited provided that the disease, condition or disorder is one which may be treated, prevented or ameliorated by using a TDO and/or IDO inhibitor. In typical embodiments the disease, condition or disorder is selected from gynaecological disorders such as endometriosis. Conditions relating to female reproductive health that are included in the invention include contraception and abortion such that the compounds of the invention may be used as a contraceptive and/or abortive agent.

The present invention also provides a pharmaceutical composition comprising a compound as defined above. Whilst the pharmaceutical composition is not especially limited, typically the composition further comprises a pharmaceutically acceptable additive and/or excipient. In the pharmaceutical composition, the compound as defined above may be present in the form described above, but may alternatively be in a form suitable for improving bioavailability, solubility, and/or activity, and/or may be in a form suitable for improving formulation. Thus, the compound may be in the form of a pharmaceutically acceptable salt, hydrate, acid, ester, or other alternative suitable form. Typically, the composition is for treating a disease, condition or disorder as defined above. In some instances, the compound may be present in the composition as a pharmaceutically acceptable salt, or other alternative form of the compound, in order to ameliorate pharmaceutical formulation.

In some embodiments the pharmaceutical composition is a composition for treating a cancer, further comprising a further agent for treating cancer. The further agent for treating cancer is not especially limited, provided that it affords some utility for cancer treatment. However, typically the further agent for treating cancer is selected from anti-microtubule agents, platinum coordination complexes, alkylating agents, antibiotic agents, topoisomerase II inhibitors, antimetabolites, topoisomerase I inhibitors, hormones and hormone analogues, signal transduction pathway inhibitors, non-receptor tyrosine kinase angiogenesis inhibitors, immunotherapeutic agents, proapoptotic agents and cell cycle signalling inhibitors. An immunotherapeutic agent may consist of but is not limited to an anti-tumour vaccine, an oncolytic virus, an immune stimulatory antibody such as anti-CTLA4, anti-PD1, anti-PDL-1, anti-OX40, anti-41BB, anti-CD27, anti-CD40, anti-LAG3, anti-TIM3, and anti-GITR, a novel adjuvant, a peptide, a cytokine, a chimeric antigen receptor T cell therapy (CAR-T), a small molecule immune modulator, tumour microenvironment modulators, and anti-angiogenic agents.

In still further embodiments the invention provides a pharmaceutical kit for treating a cancer, which pharmaceutical kit comprises:
(a) a compound as defined above; and
(b) a further agent for treating cancer; preferably wherein the further agent for treating cancer is selected from anti-microtubule agents, platinum coordination complexes, alkylating agents, antibiotic agents, topoisomerase II inhibitors, antimetabolites, topoisomerase I inhibitors, hormones and hormone analogues, signal transduction pathway inhibitors, non-receptor tyrosine kinase angiogenesis inhibitors, immunotherapeutic agents, proapoptotic agents and cell cycle signalling inhibitors;
wherein the compound and the further agent are suitable for administration simultaneously, sequentially or separately.

Further provided by the invention is a method of treating a disease and/or a condition and/or a disorder, which method comprises administering to a patient (or subject) a compound, or a composition, or a kit as defined above. The method is typically a method for treating any disease condition or disorder mentioned herein. In typical embodiments, the method is a method for treating a cancer. Preferably such a method comprises administering to a patient (or subject) a compound or a composition as defined above and a further agent for treating cancer as defined above. The compound or composition and the further agent may administered simultaneously, sequentially or separately, depending upon the agents and patients involved, and the type of cancer indicated.

Typically, in all embodiments of the invention, both above and below, the patient (or subject) is an animal, typically a mammal, and more typically a human.

In addition to compounds for use in medicine, the present invention, and in particular the synthetic method, provides compounds that were not previously known, such compounds comprising a formula selected from one of the following:

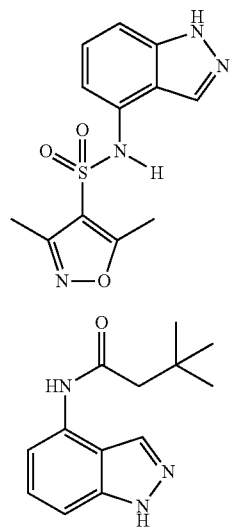

| 247 -continued | | 248 -continued | |
|---|---|---|---|
| 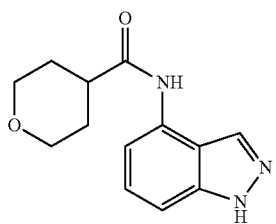 | 5 | 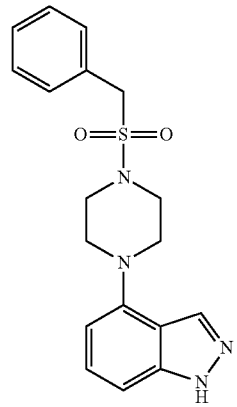 | 13 |
| 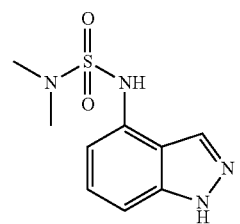 | 7 | | |
| 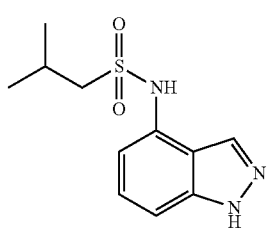 | 8 | 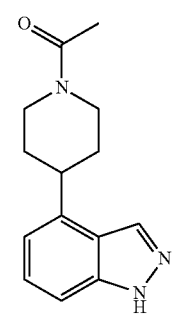 | 14 |
| 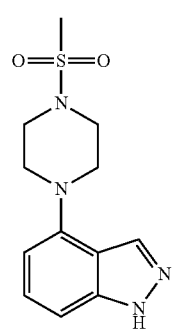 | 10 | 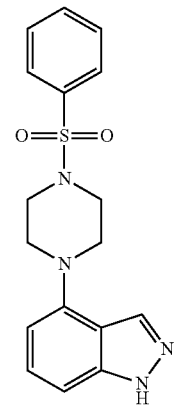 | 15 |
| | 11 | 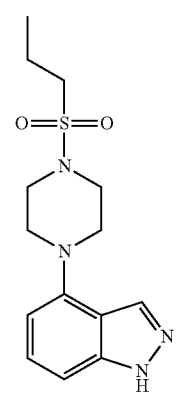 | 16 |

17
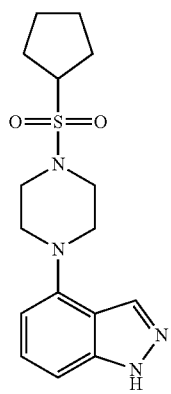
18
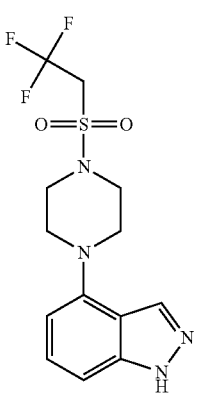
19
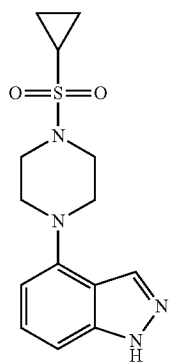
20
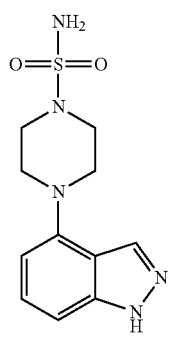
21
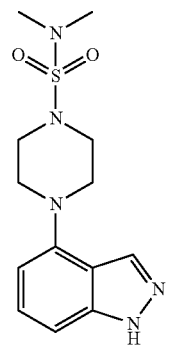
22
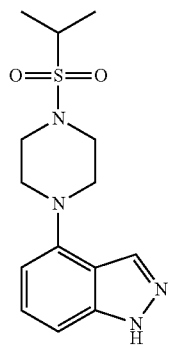
23
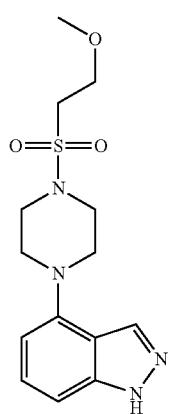

| 251 -continued | 252 -continued |
|---|---|
| 24 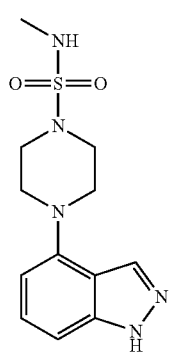 | 29 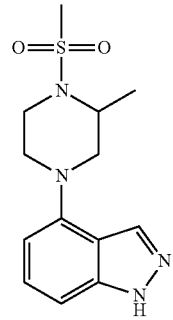 |
| 25 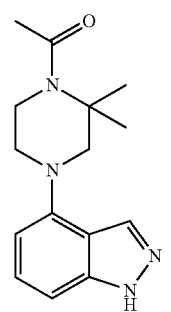 | 30 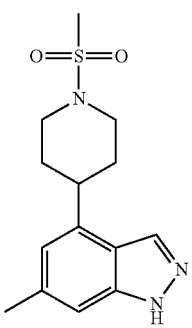 |
| 26 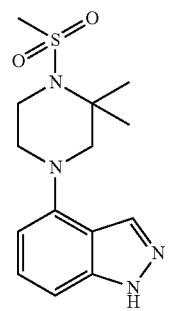 | 31 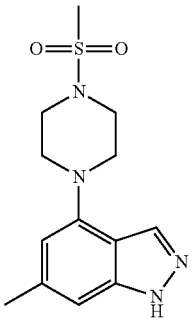 |
| 27 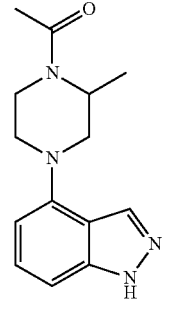 | 32 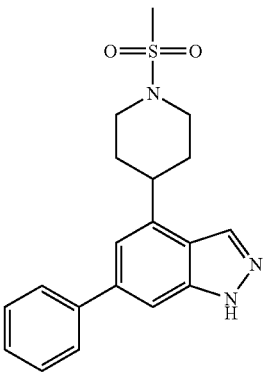 |
| 28 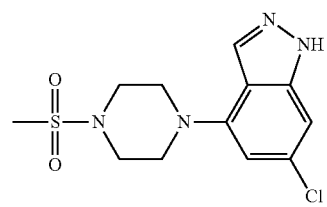 | |

33
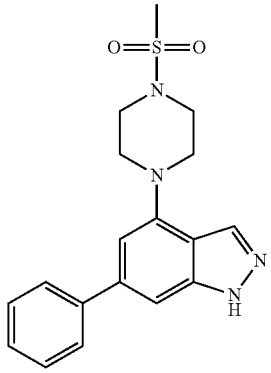
35
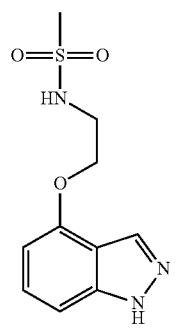
36
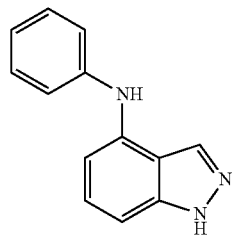
37
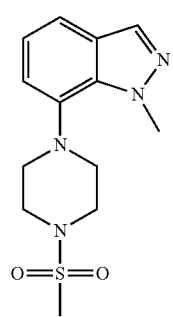
38
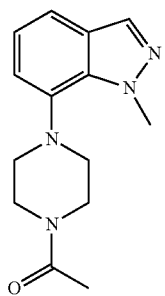
39
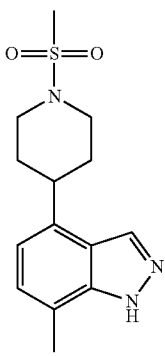
40
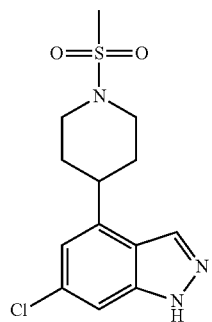
41
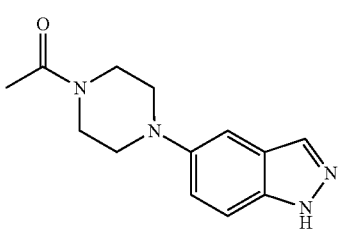

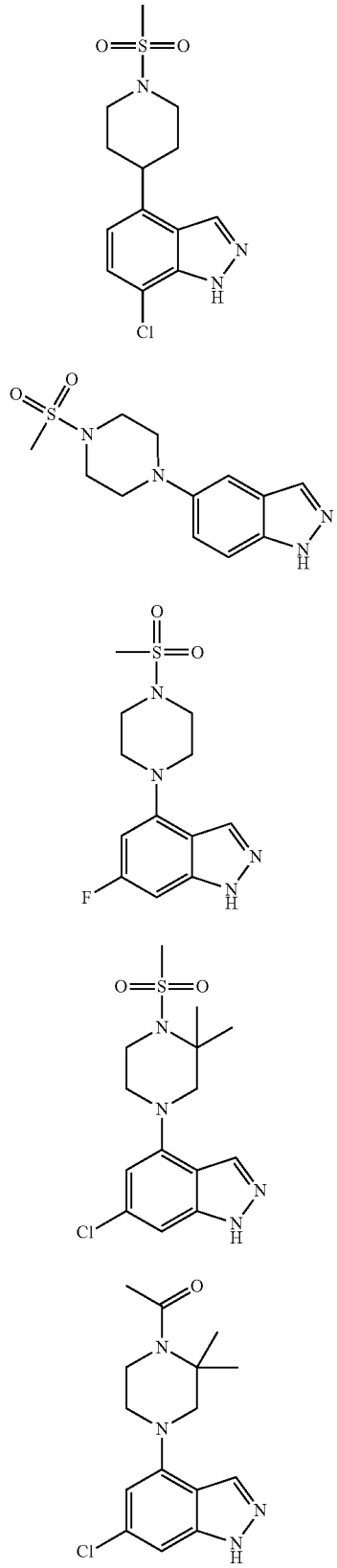
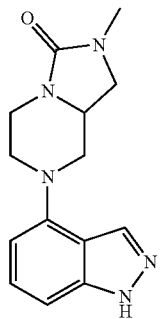
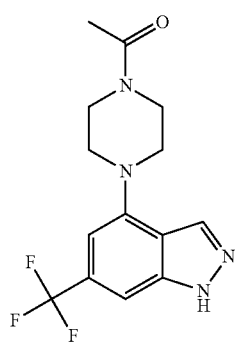
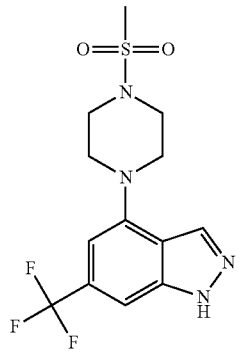
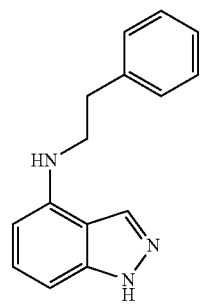
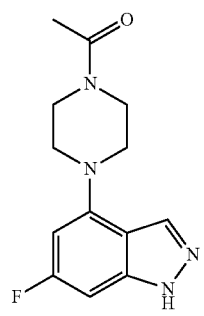

257
-continued
| | |
|---|---|
| 52 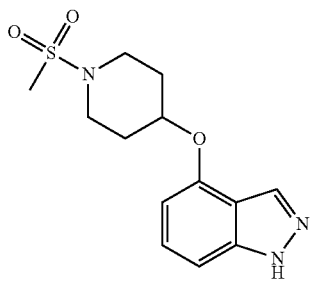 | 57 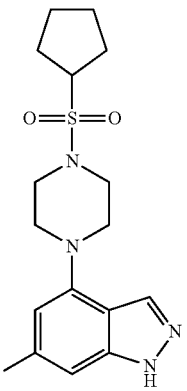 |
| 54 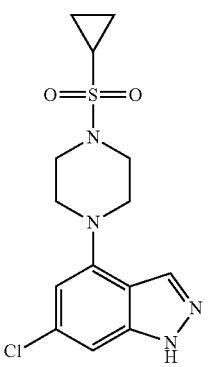 | 58 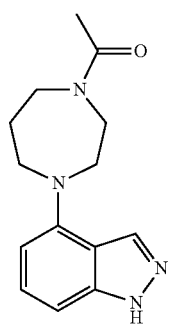 |
| 55 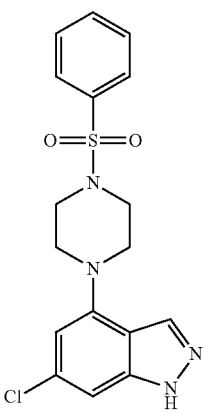 | 59 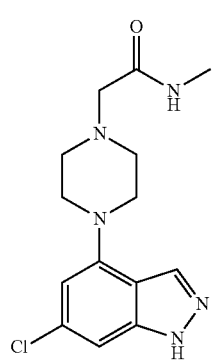 |
| 56 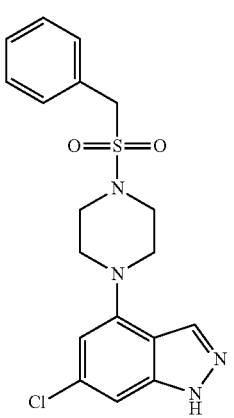 | 60 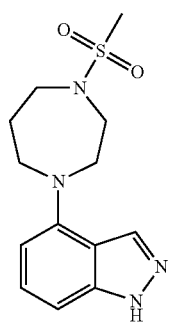 |
258
-continued 61
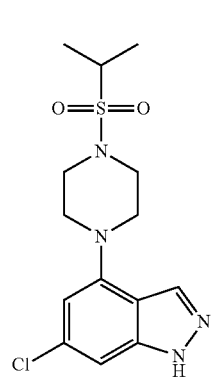
62
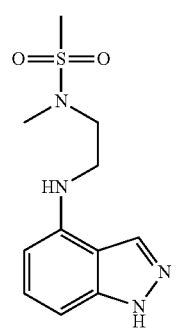
63
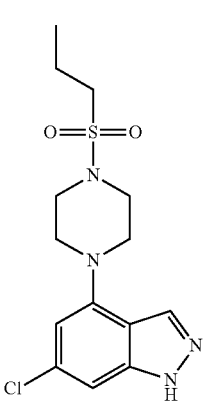
64
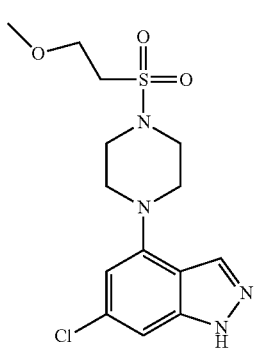
65
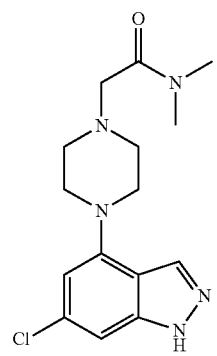
66
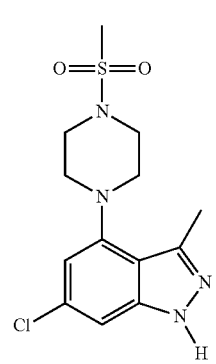
67
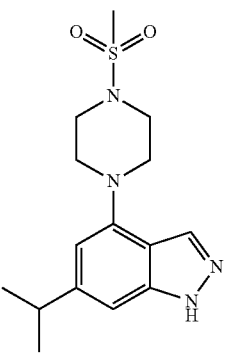
68
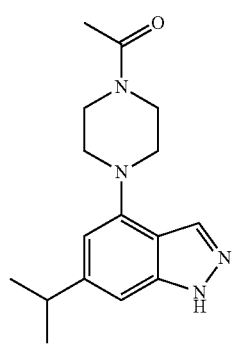

| 69 | 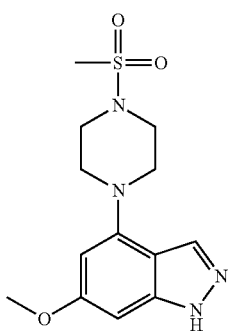 | | 74 | 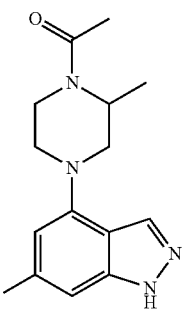 |
| 70 | 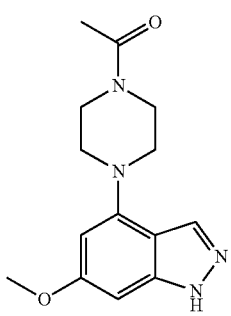 | | 75 | 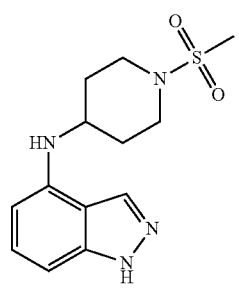 |
| 71 | 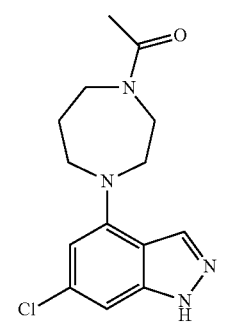 | | 76 | 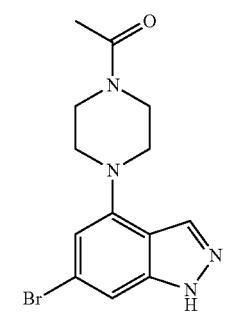 |
| 72 | 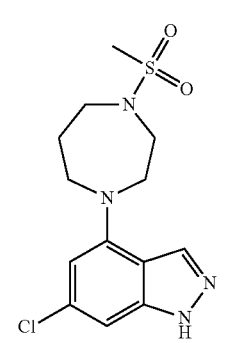 | | 77 | 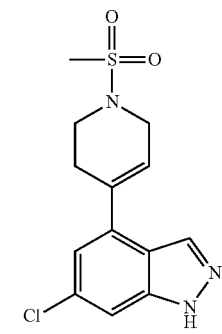 |
| 73 | 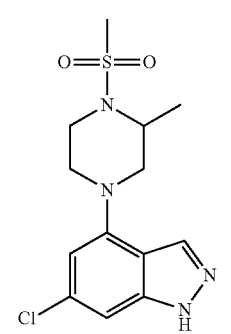 | | | |

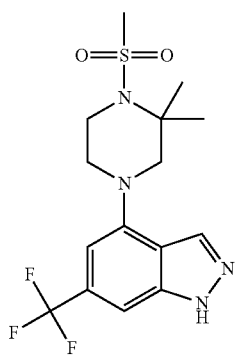
78
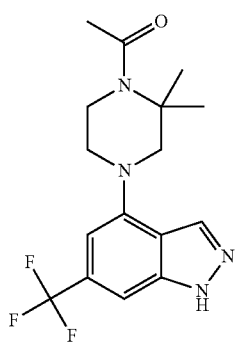
79
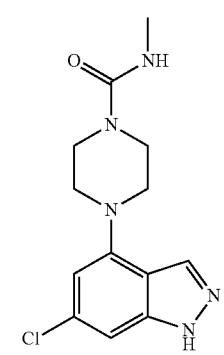
80
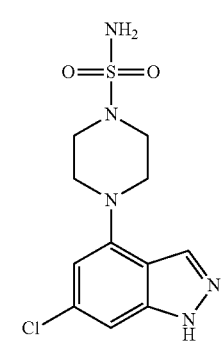
81
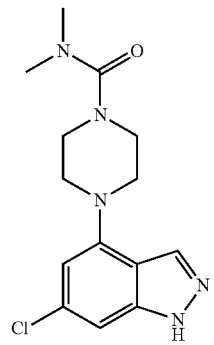
82
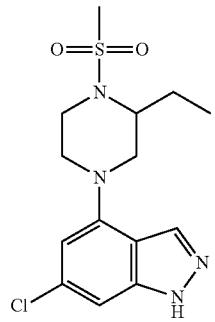
83
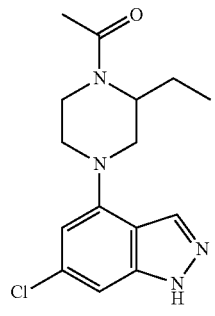
84
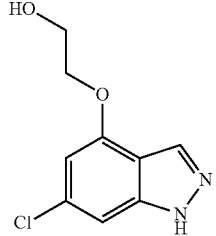
85
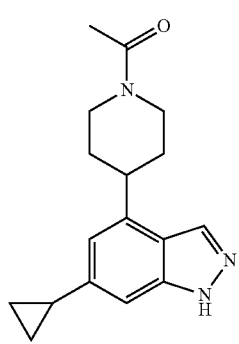
86

| 87 | 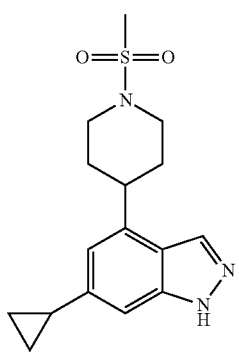 | 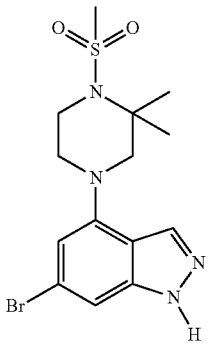 | 91 |
| 88 | 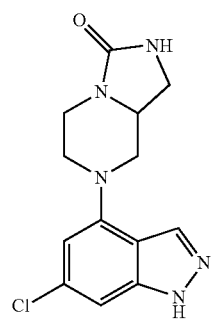 | 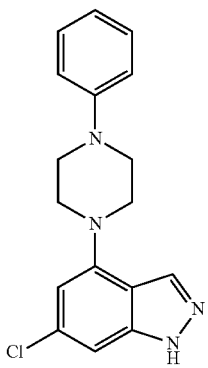 | 92 |
| | | | 93 |
| 89 | 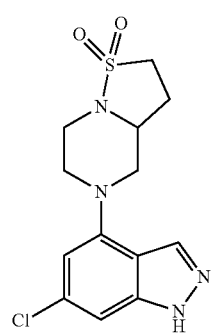 | 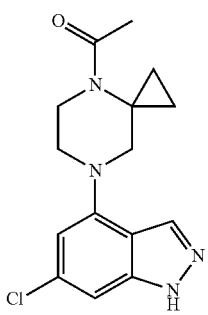 | 94 |
| 90 | 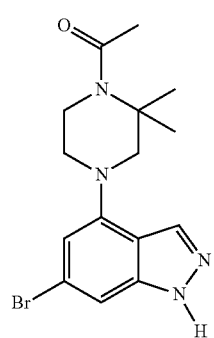 | 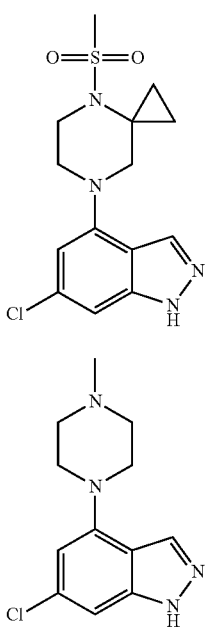 | 95 |

| | |
|---|---|
| 96 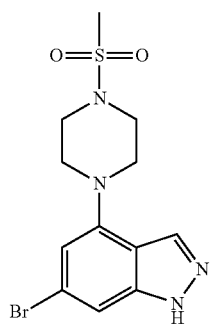 | 100 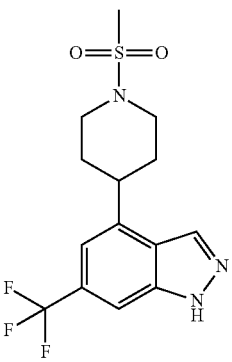 |
| 97 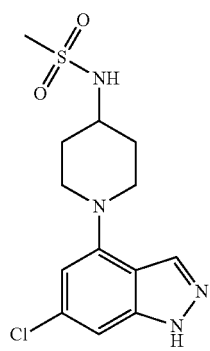 | 101 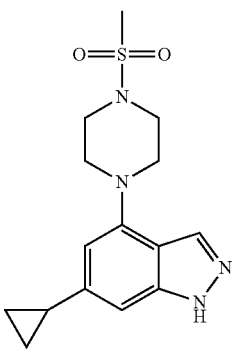 |
| 98 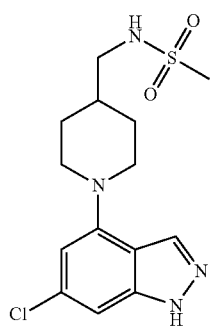 | 102 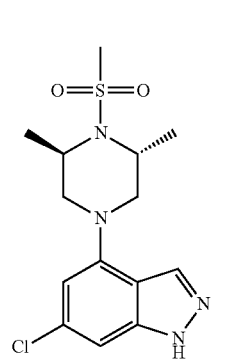 |
| 99 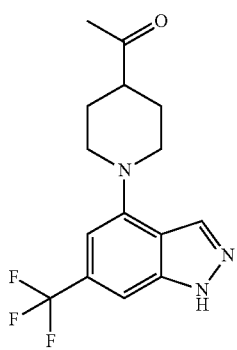 | 103 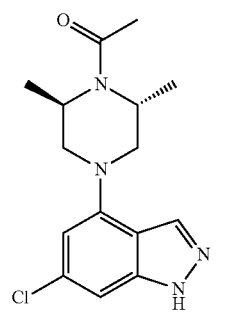 |

| | | |
|---|---|---|
| 104 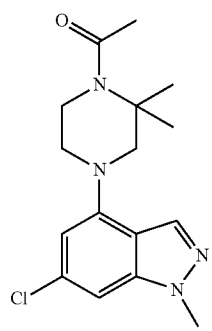 | 109 | 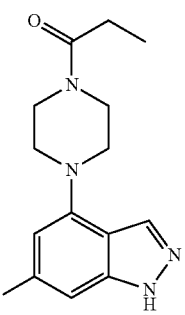 |
| 105 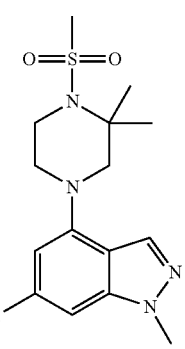 | 110 | 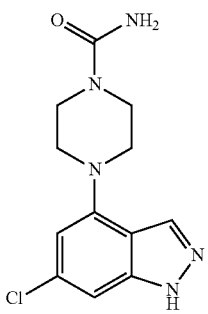 |
| 106 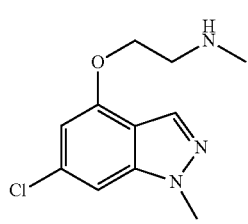 | 111 | 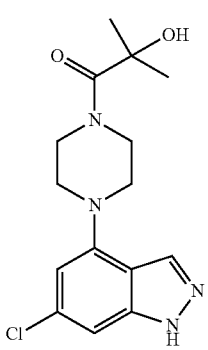 |
| 107 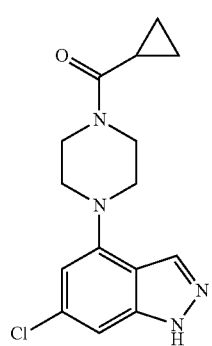 | 112 | 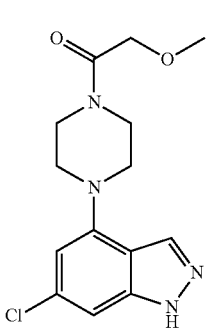 |
| 108 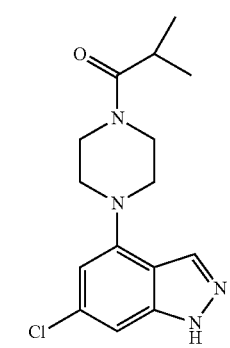 | 113 | 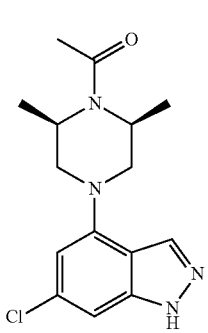 |

| 114 | 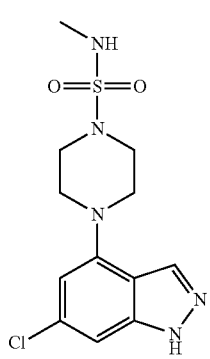 | 118 | 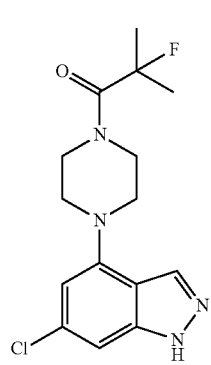 |
| 115 | 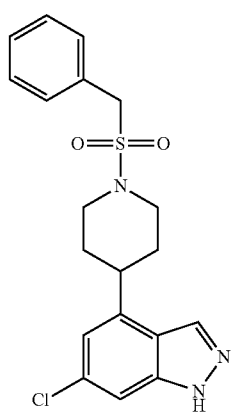 | 119 | 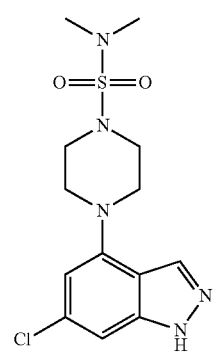 |
| 116 | 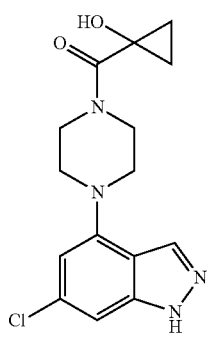 | 120 | 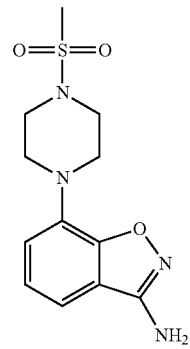 |
| 117 | 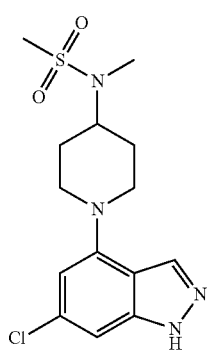 | 121 | 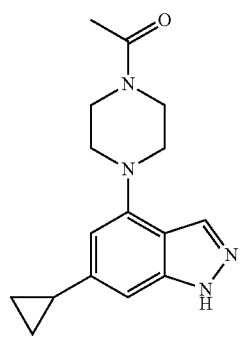 |

US 10,590,086 B2
273
-continued
122
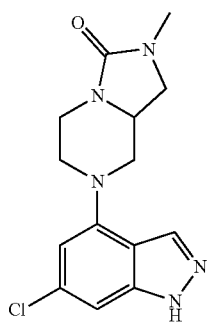
123
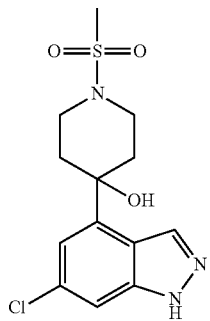
124
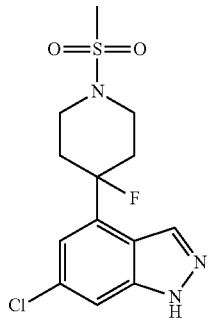
125
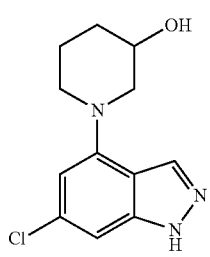
126
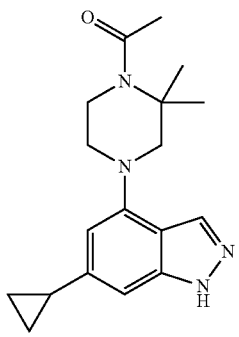
274
-continued
127
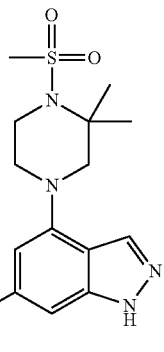
128
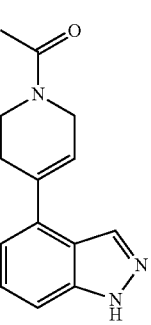
129
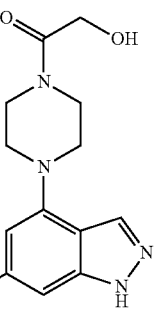
130
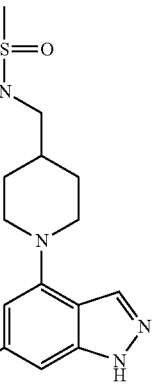

| 131 | 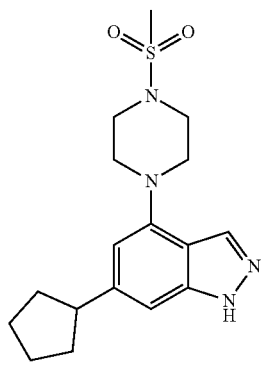 | 135 | 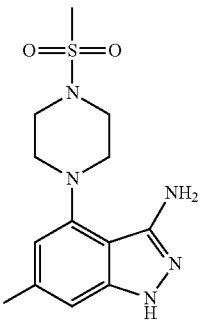 |
| 132 | 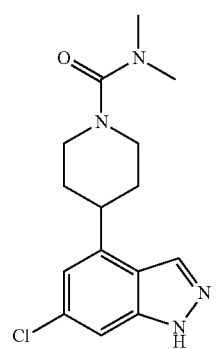 | 136 | 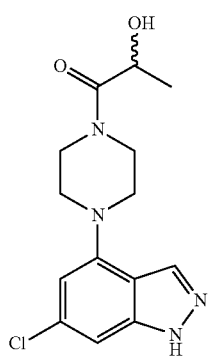 |
| 133 | 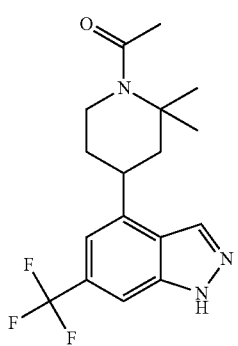 | 137 | 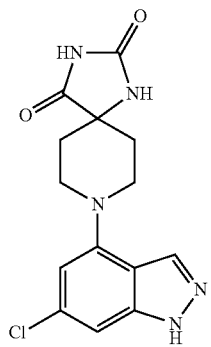 |
| 134 | 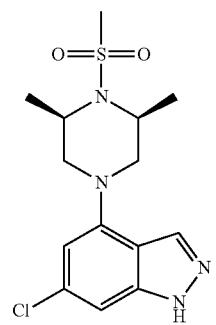 | 138 | 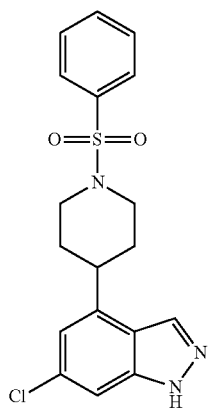 |

| | |
|---|---|
| 139 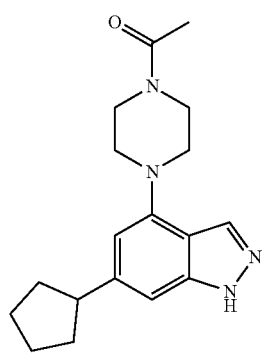 | 143 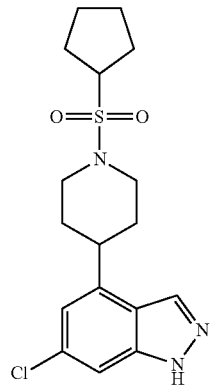 |
| 140 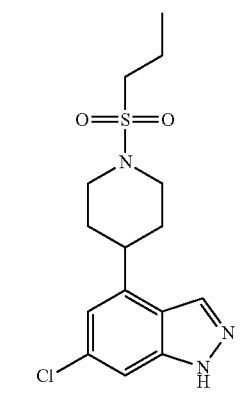 | 144 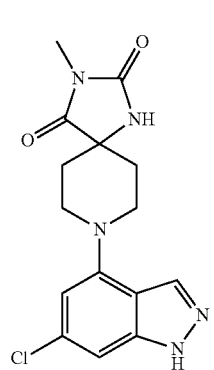 |
| 141 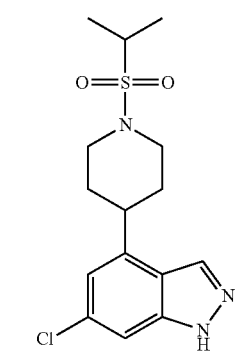 | 145 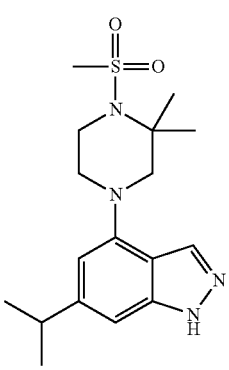 |
| 142 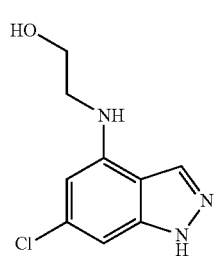 | 146 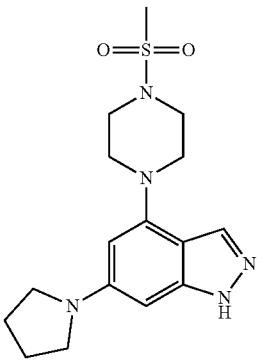 |

| 147 | 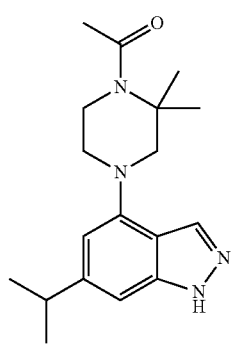 | 151 | 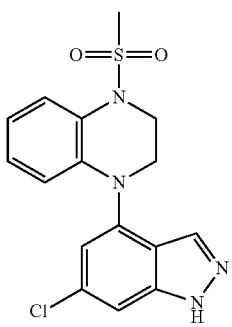 |
| 148 | 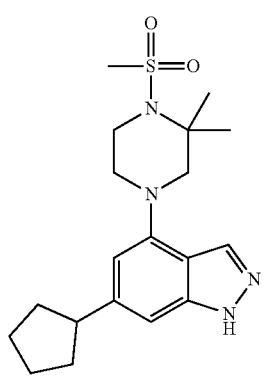 | 152 | 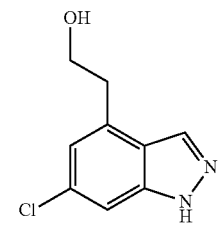 |
| | | 153 | 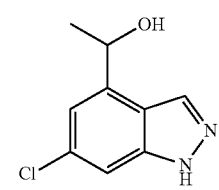 |
| 149 | 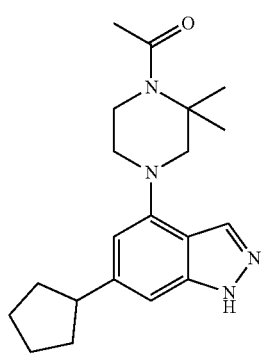 | 154 | 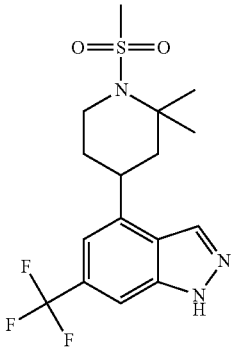 |
| 150 | 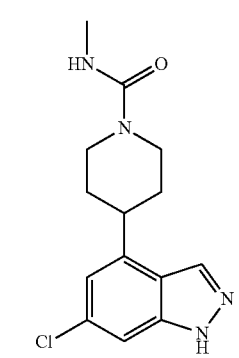 | 155 | 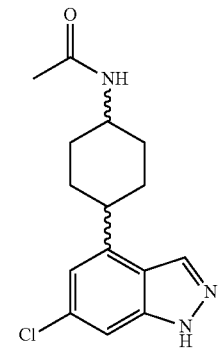 |

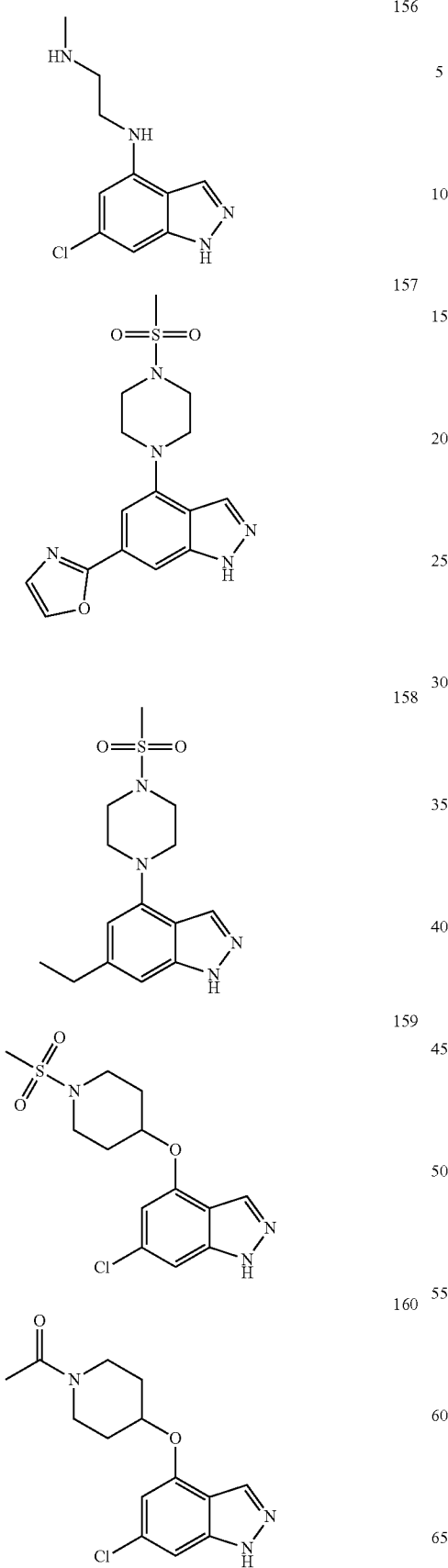
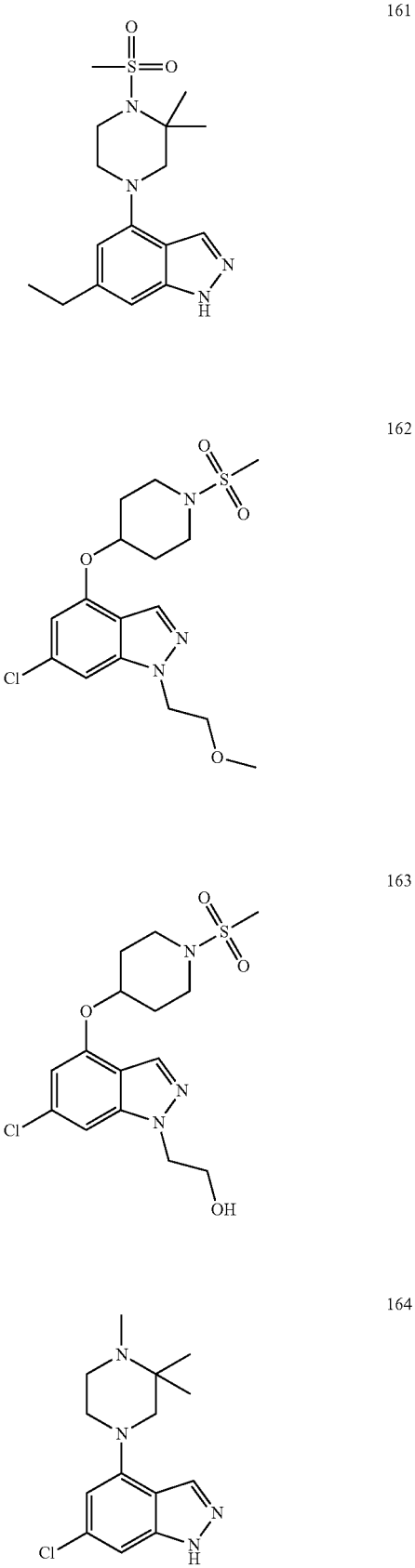

-continued
165
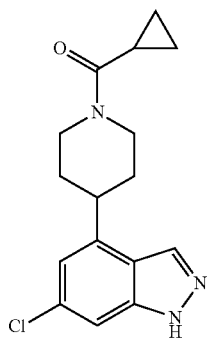
166
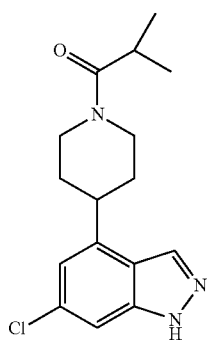
167
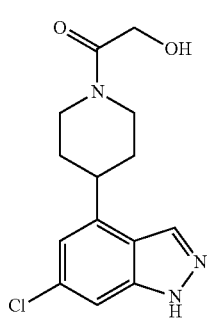
168
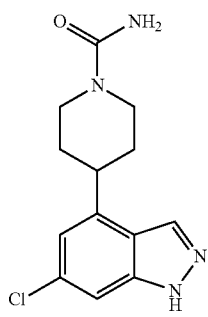
-continued
169
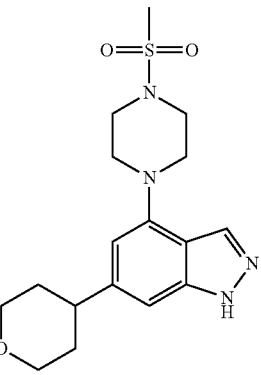
170
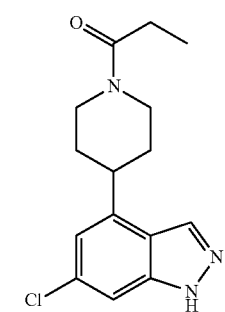
171
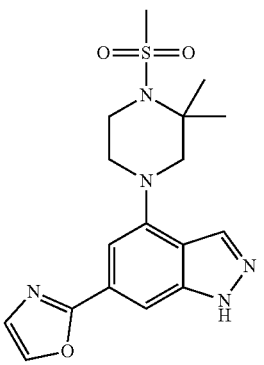
172
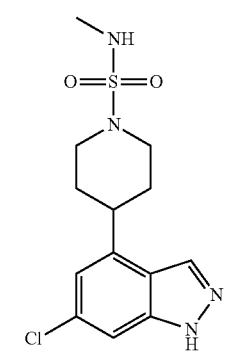

| 173 | 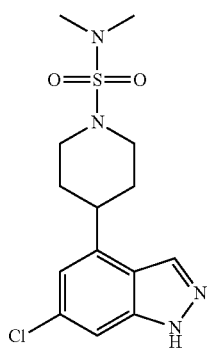 | 177 | 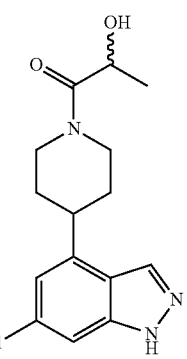 |
| 174 | 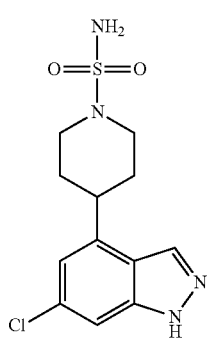 | 178 | 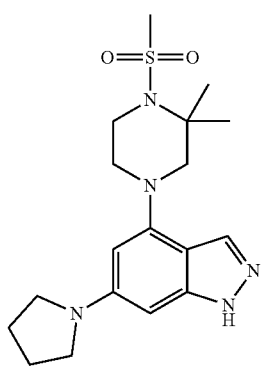 |
| 175 | 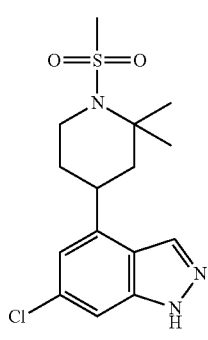 | 179 | 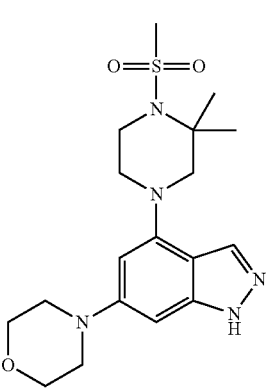 |
| 176 | 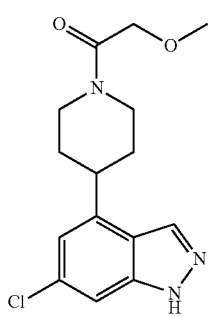 | 180 | 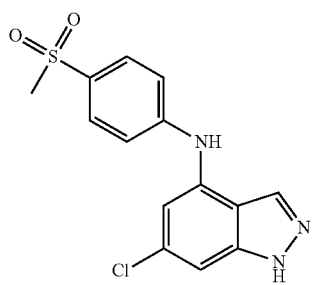 |

| 181 | 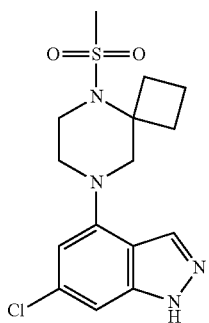 | 185 | 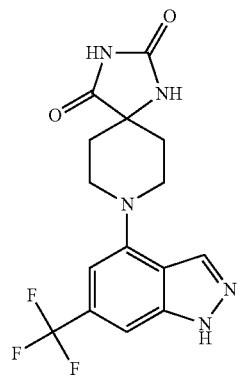 |
| 182 | 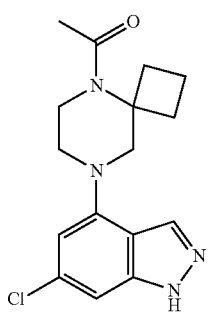 | 186 | 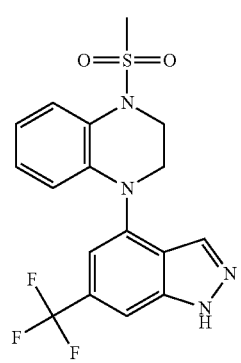 |
| 183 | 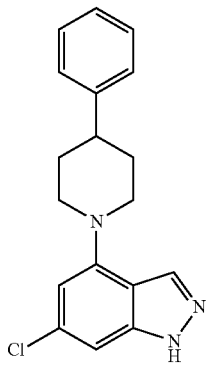 | 187 | 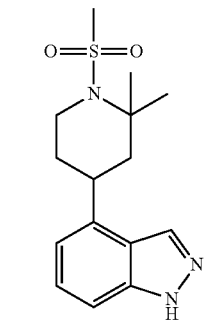 |
| 184 | 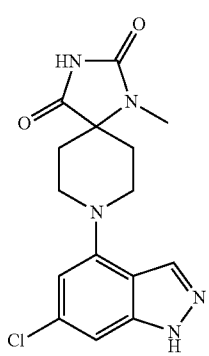 | 188 | 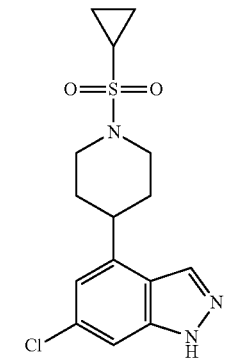 |

289
-continued
189
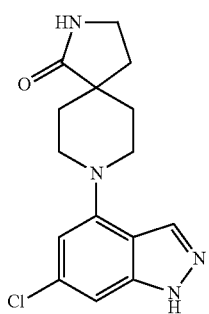
190
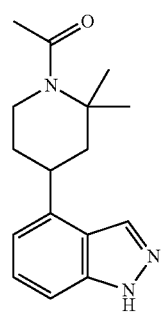
191
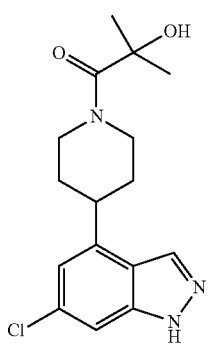
192
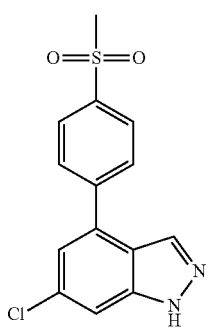
193
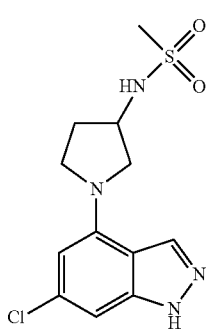
290
-continued
194
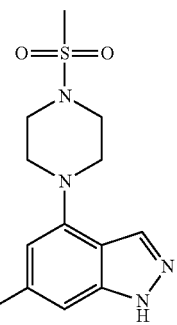
195
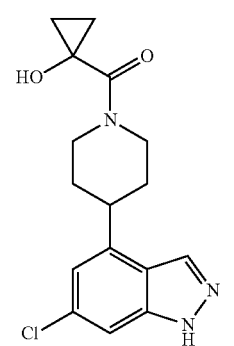
196
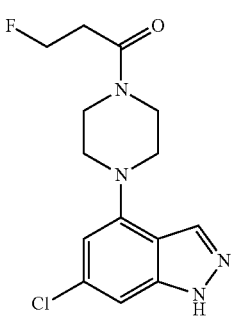
197
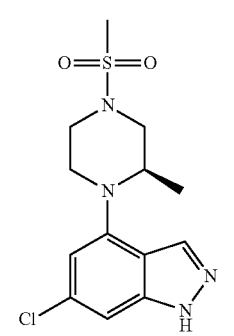
198
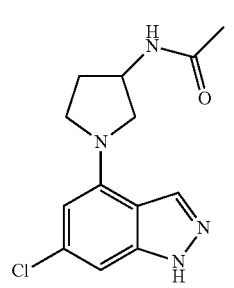

| | |
|---|---|
| 199 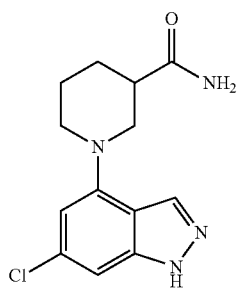 | 204 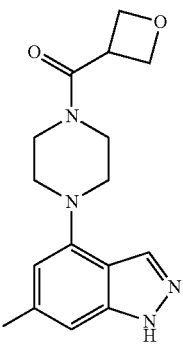 |
| 200 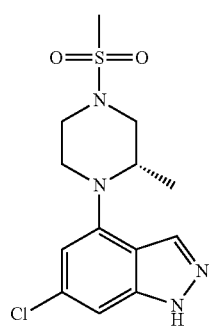 | 205 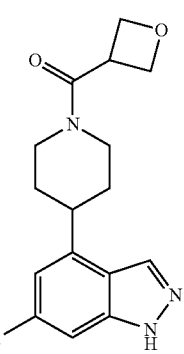 |
| 201 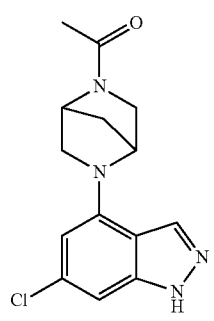 | 206 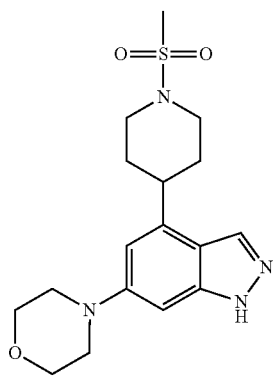 |
| 202 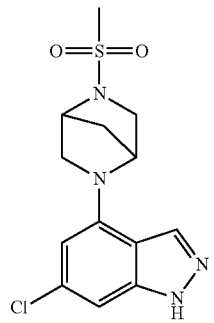 | 207 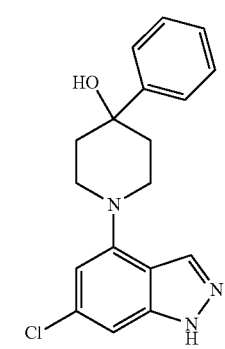 |
| 203 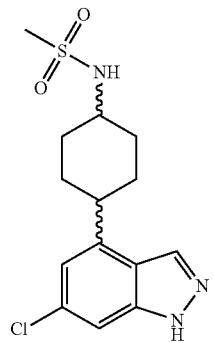 | |

| | |
|---|---|
| 208 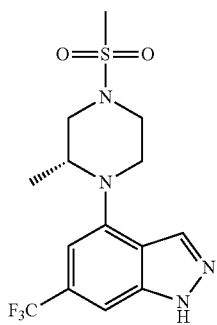 | 213 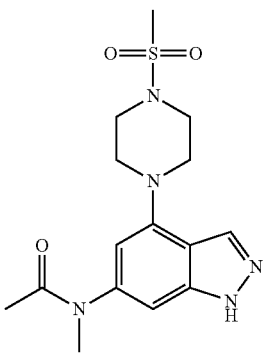 |
| 209 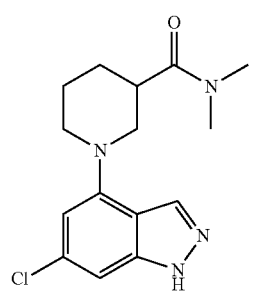 | 214 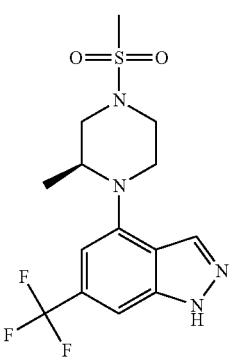 |
| 210 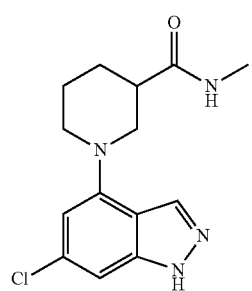 | 215 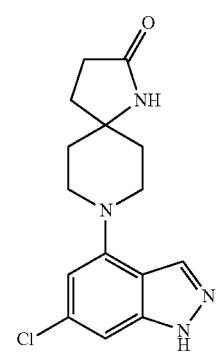 |
| 211 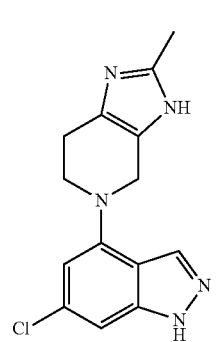 | 216 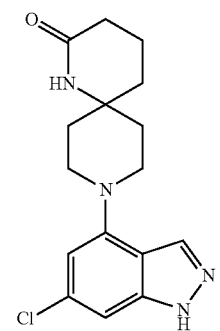 |
| 212 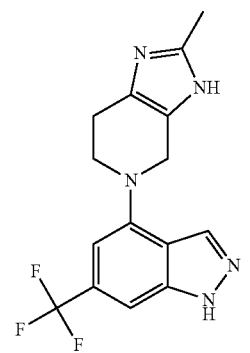 | |

| 217 | 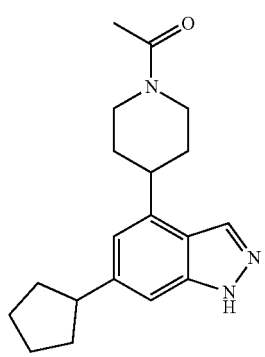 | 221 | 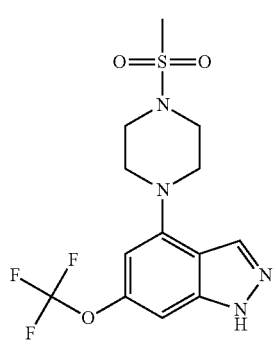 |
| 218 | 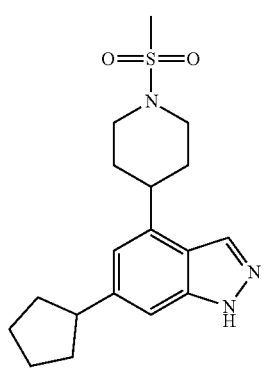 | 222 | 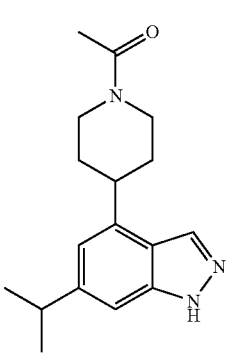 |
| 219 | 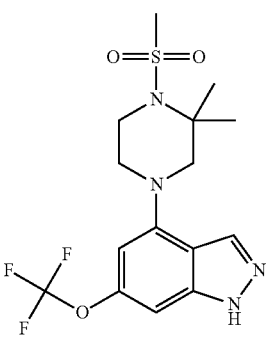 | 223 | 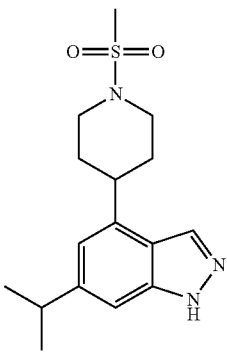 |
| 220 | 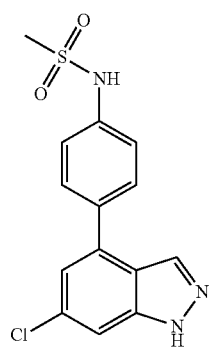 | 224 | 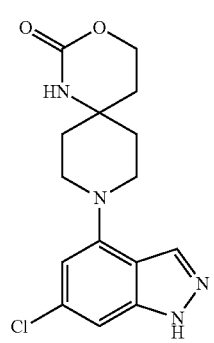 |

| 225 | 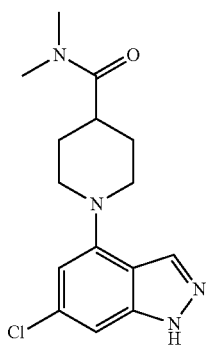 | 229 | 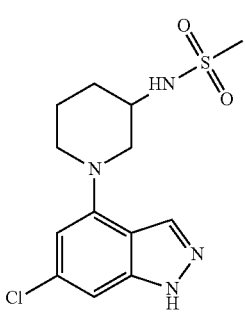 |
| 226 | 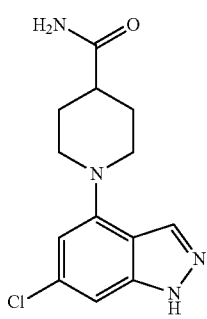 | 230 | 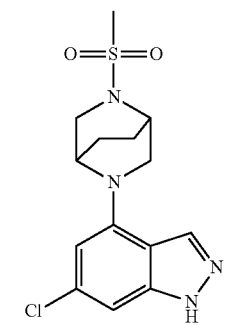 |
| | | 231 | 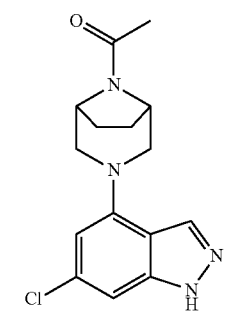 |
| 227 | 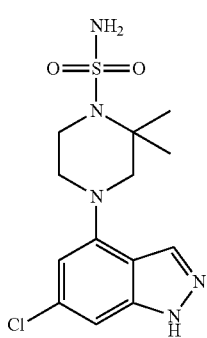 | 232 | 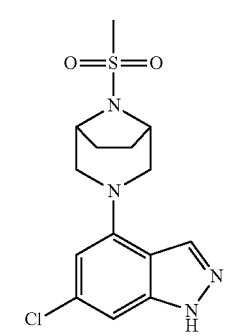 |
| 228 | 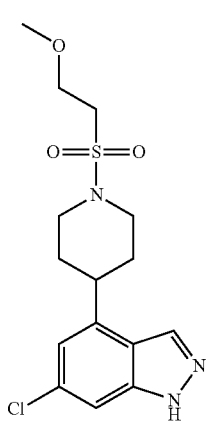 | 233 | 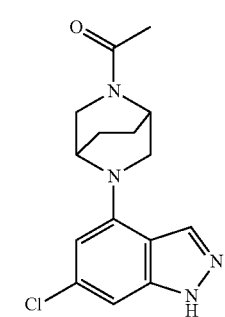 |

| 234 | 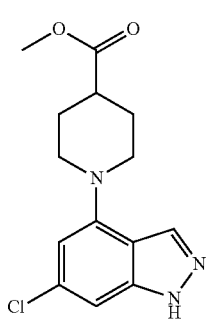 | 239 | 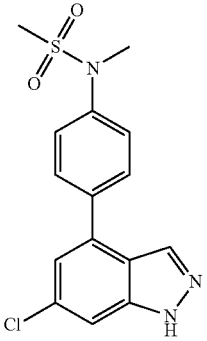 |
| 235 | 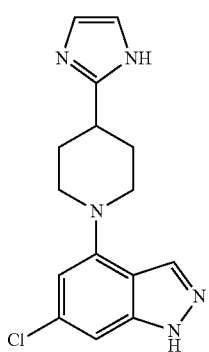 | 240 | 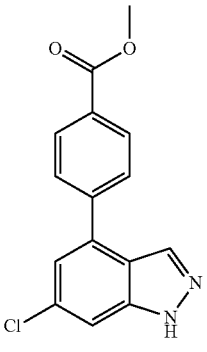 |
| 236 | 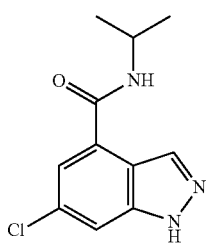 | 241 | 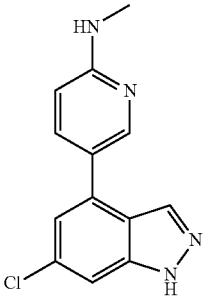 |
| 237 | 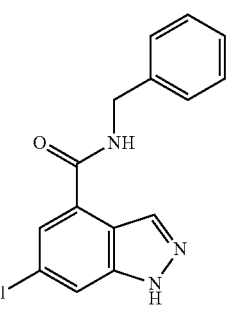 | 242 | 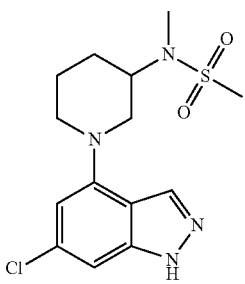 |
| 238 | 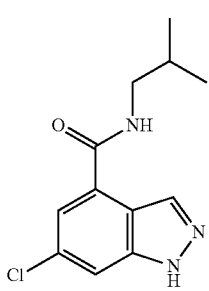 | 243 | 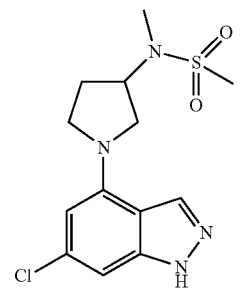 |

| | | |
|---|---|---|
| 244 | 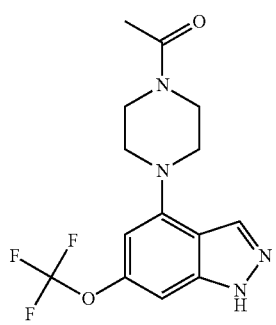 | 248 | 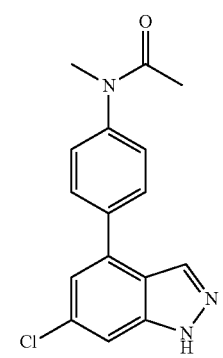 |
| 245 | 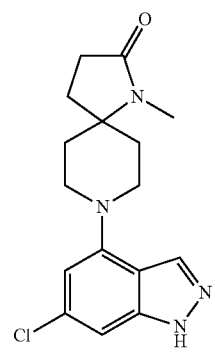 | 249 | 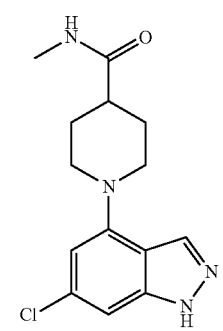 |
| 246 | 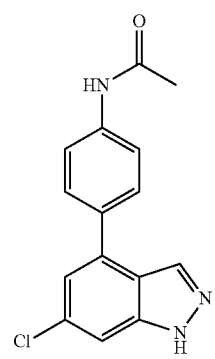 | 250 | 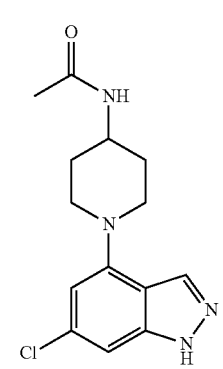 |
| 247 | 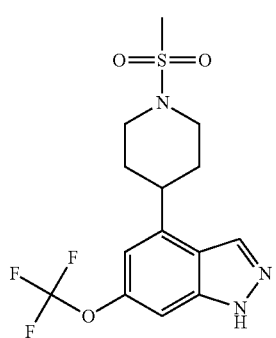 | 251 | 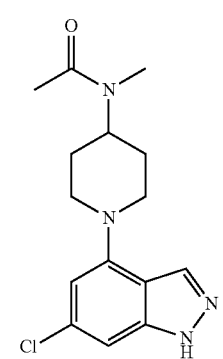 |

-continued
252 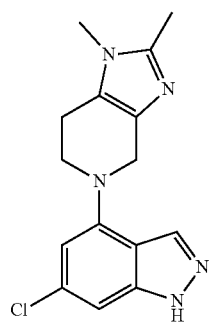
253 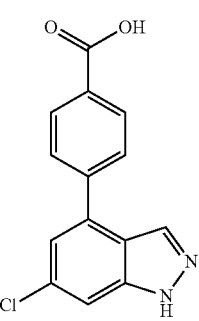
254 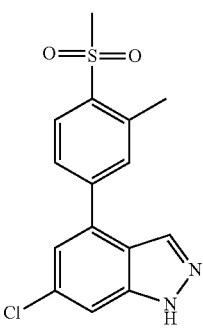
255 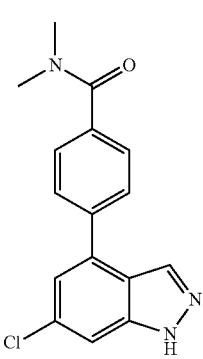
256 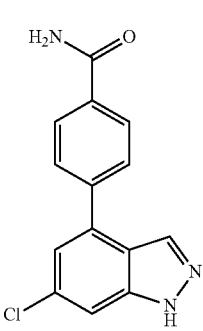
-continued
257 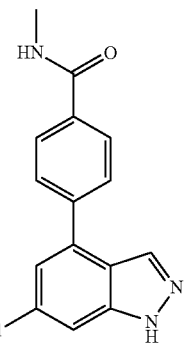
258 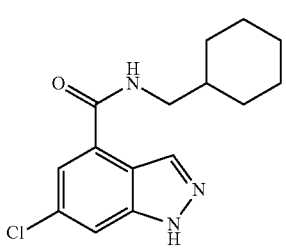
259 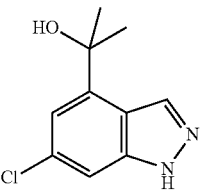
260 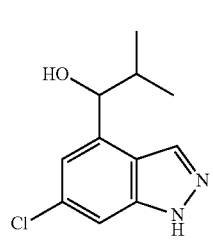
261 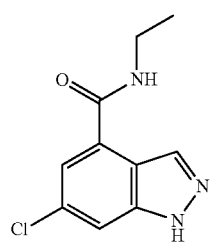

262 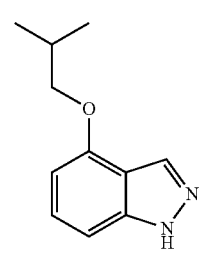
263 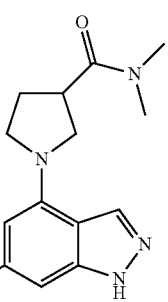
264 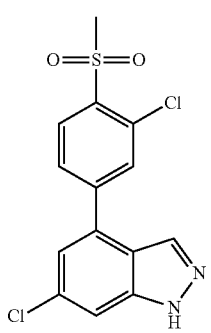
265 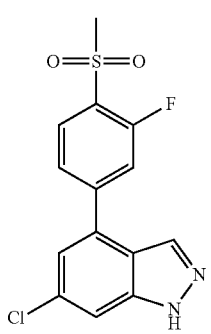
266 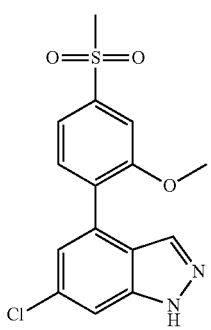
267 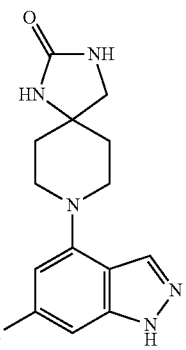
268 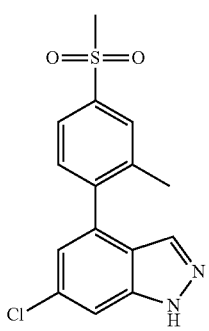
269 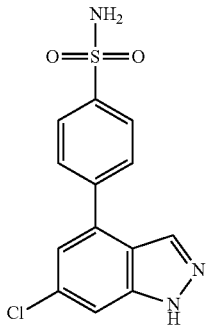
270 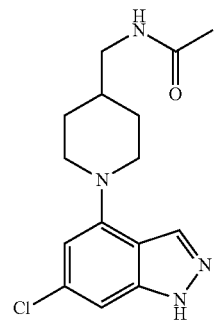

| 271 | 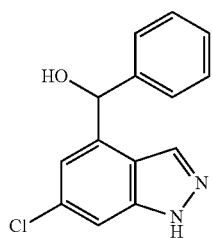 |
| 272 | 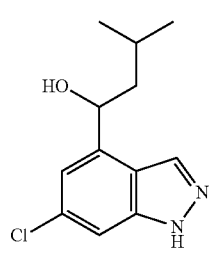 |
| 273 | 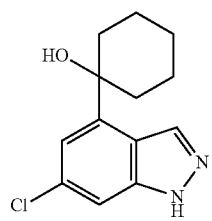 |
| 274 | 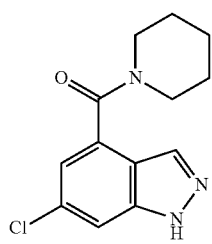 |
| 275 | 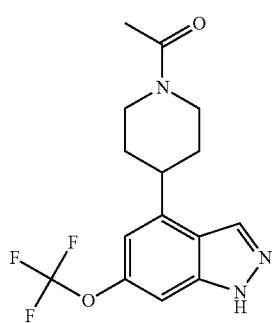 |
| 276 | 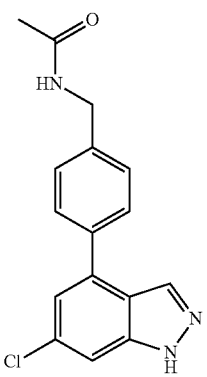 |
| 277 | 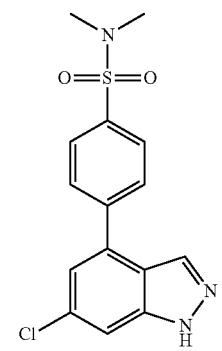 |
| 278 | 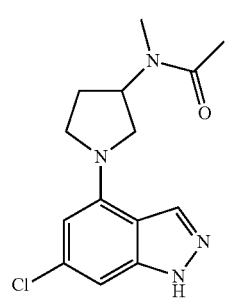 |
| 279 | 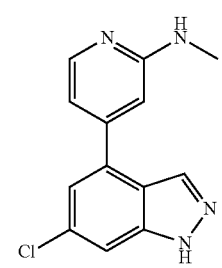 |

| 309 | 310 |
|---|---|
| 280 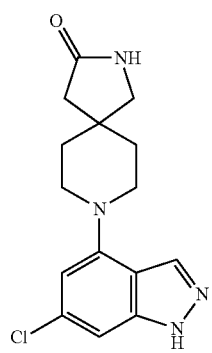 | 285 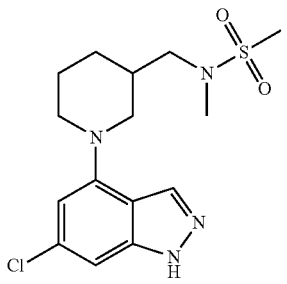 |
| 281 | 286 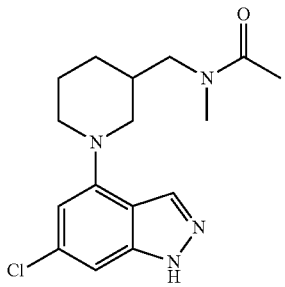 |
| 282 | 287 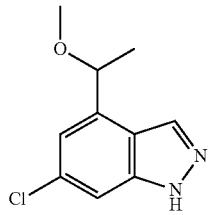 |
| 283 | 288 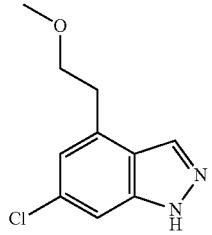 |
| 284 | 289 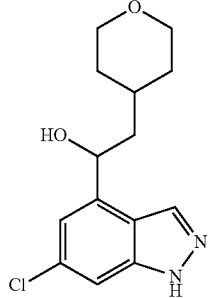 |

311
-continued
290
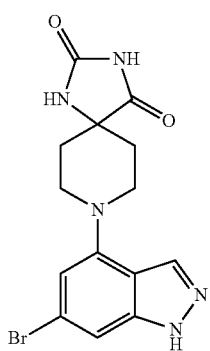
291
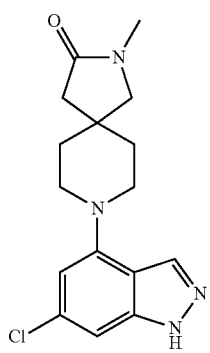
292
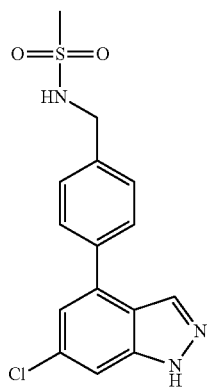
293
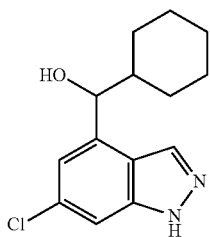
294
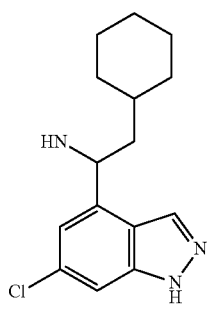
312
-continued
295
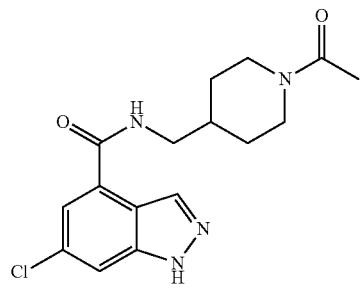
296
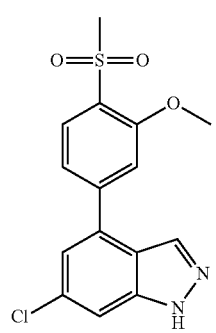
297
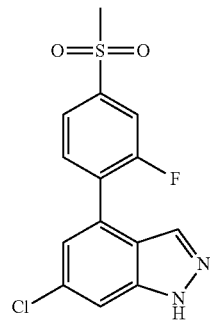
298
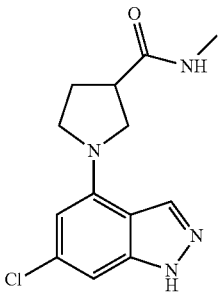
299
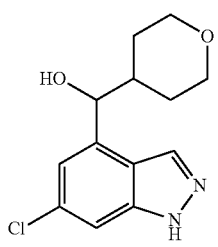

-continued
300 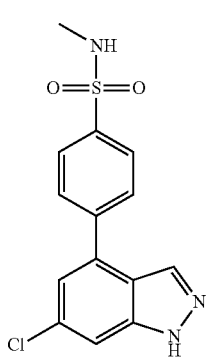
301 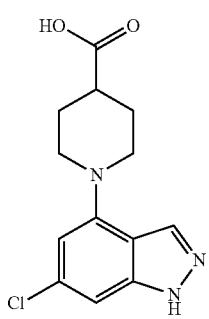
302 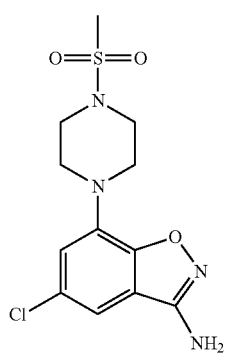
303 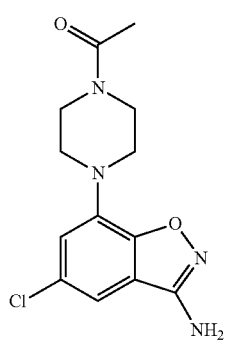
-continued
304 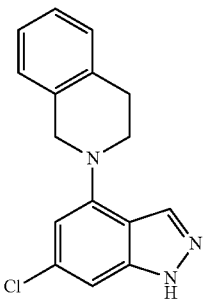
305 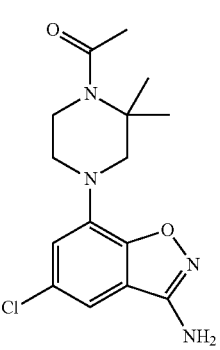
306 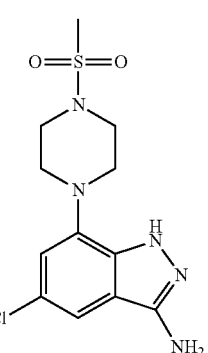
307 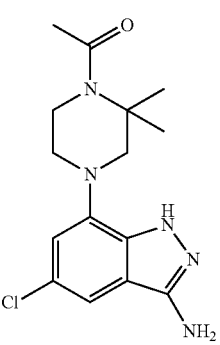
308 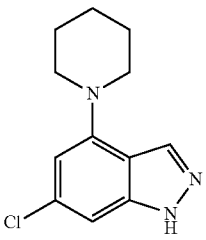

| 309 | 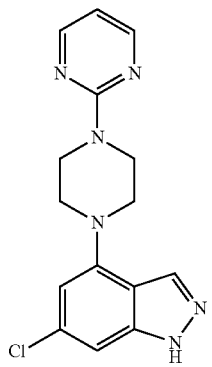 |
| --- | --- |
| 310 | 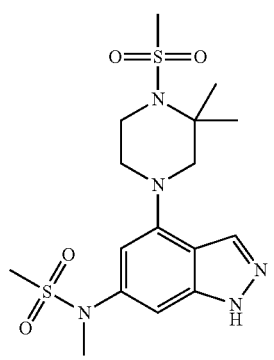 |
| 311 | 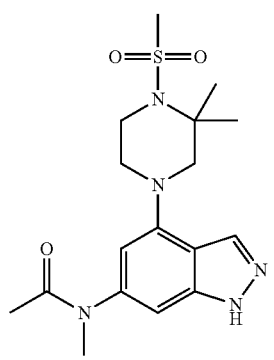 |
| 312 | 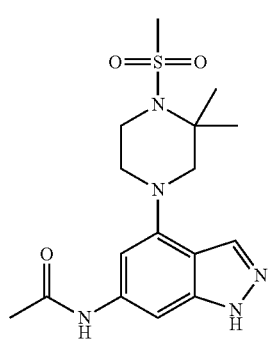 |
| 313 | 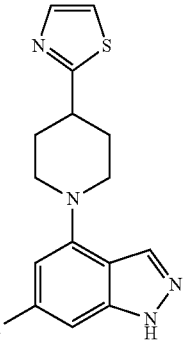 |
| --- | --- |
| 314 | 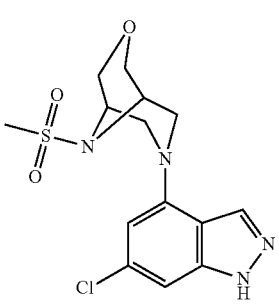 |
| 315 | 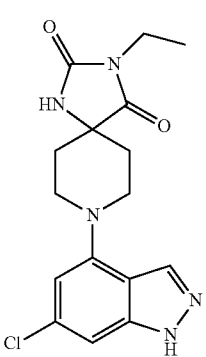 |
| 316 | 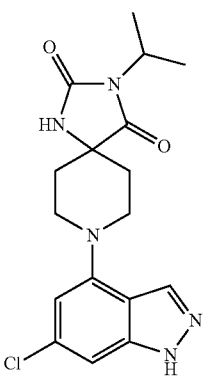 |

317
-continued
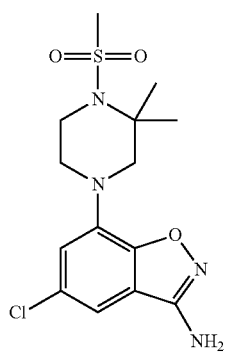
317
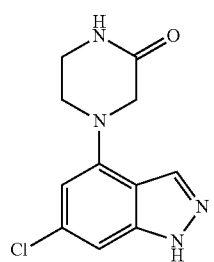
318
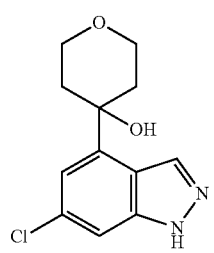
319
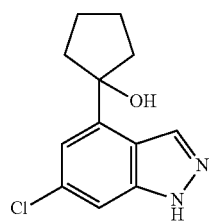
320
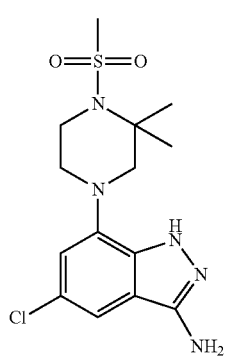
321
318
-continued
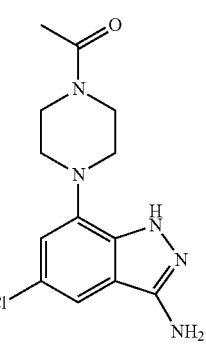
322
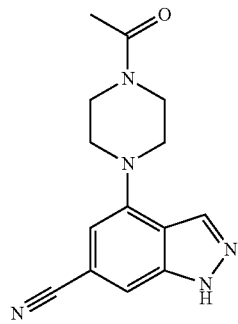
323
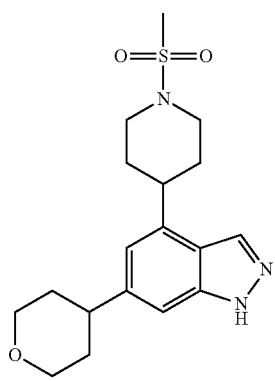
324
325

| 319 -continued | | 320 -continued | |
|---|---|---|---|
| 326 | 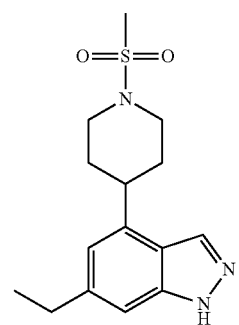 | 331 | 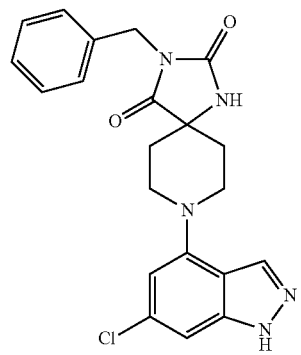 |
| 327 | 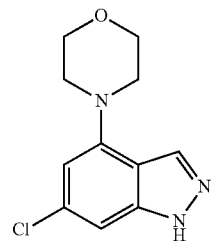 | 332 | 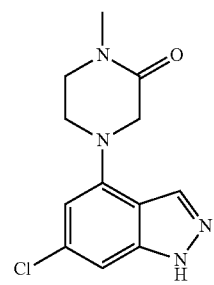 |
| 328 | 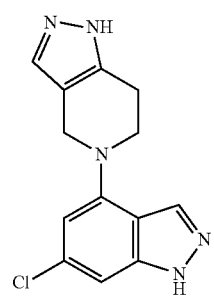 | 333 | 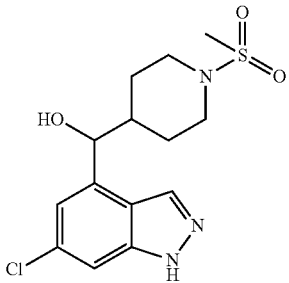 |
| 329 | 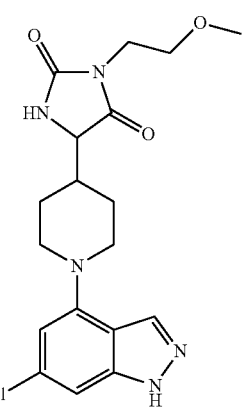 | 334 | 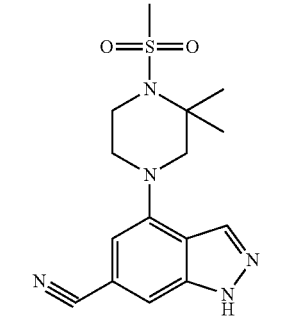 |
| 330 | 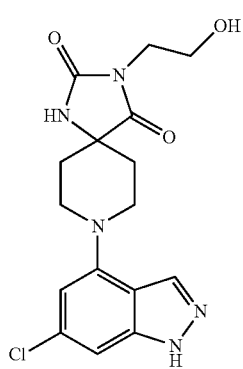 | 335 | 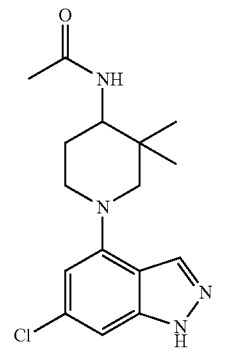 |

| 336 | 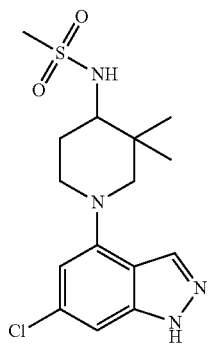 | 340 | 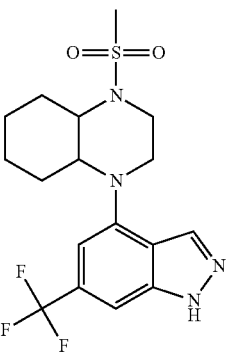 |
| 337 | 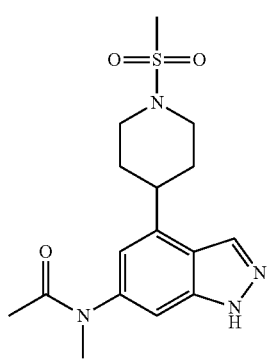 | 341 | 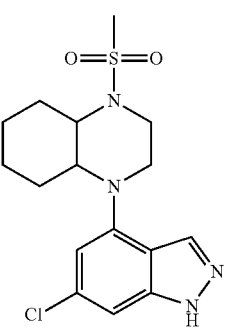 |
| 338 | 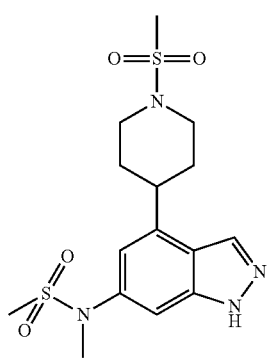 | 342 | 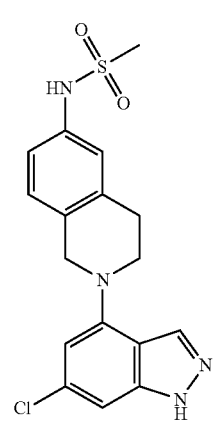 |
| 339 | 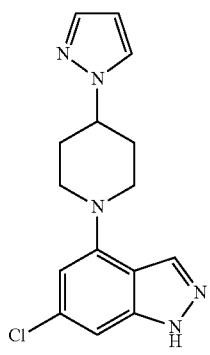 | 343 | 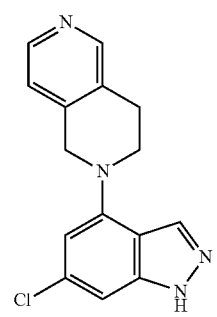 |

| 344 | 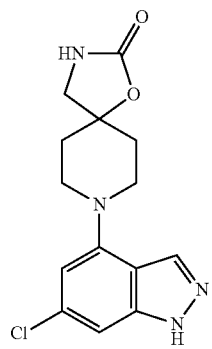 | 348 | 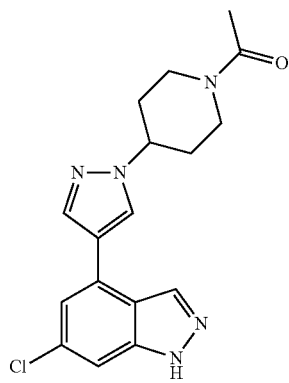 |
| 345 | 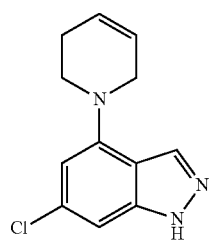 | 349 | 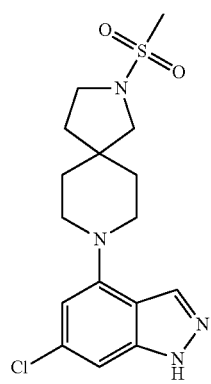 |
| 346 | 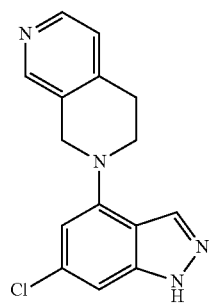 | 350 | 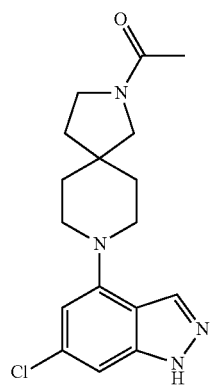 |
| 347 | 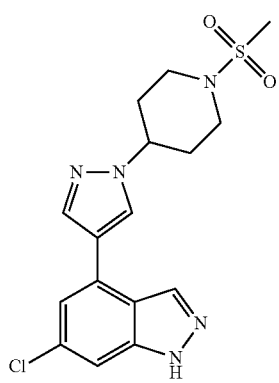 | 351 | 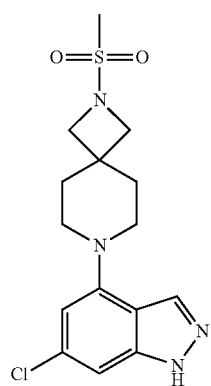 |

325
-continued
352
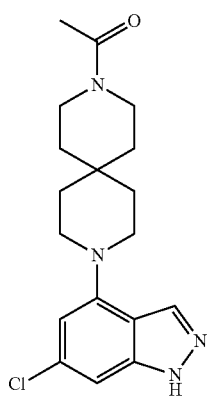
353
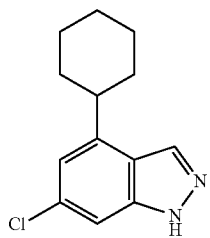
354
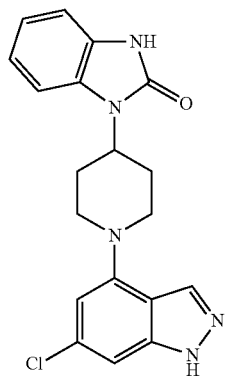
355
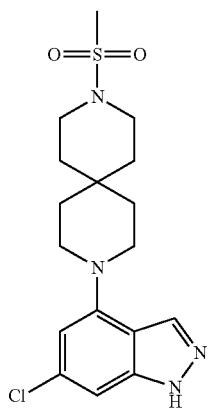
326
-continued
356
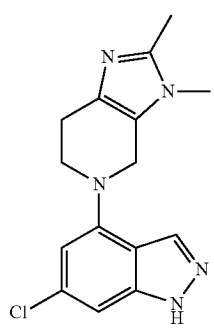
357
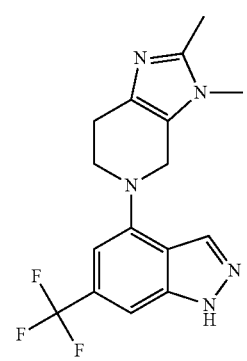
358
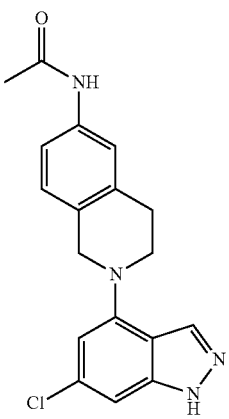
359
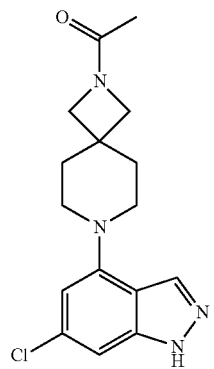

| 360 | 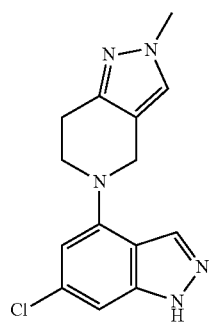 | 364 | 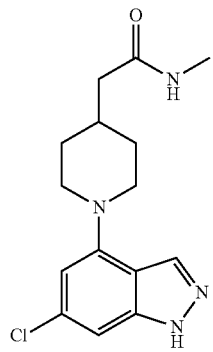 |
| 361 | 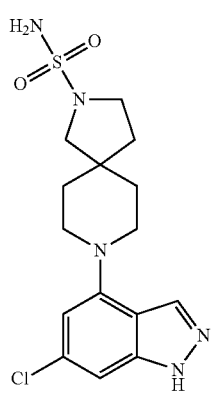 | 365 | 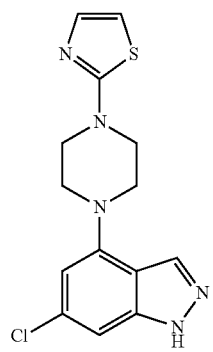 |
| | | 366 | 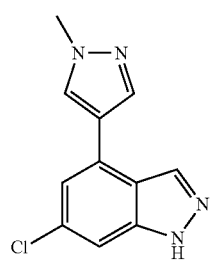 |
| 362 | 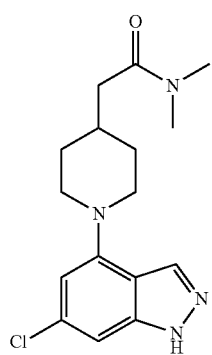 | 367 | 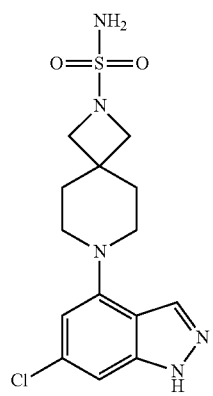 |
| 363 | 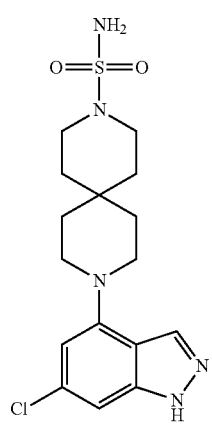 | 368 | 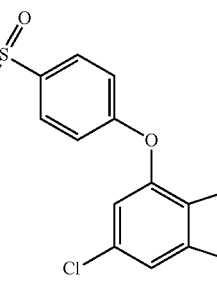 |

| 369 | 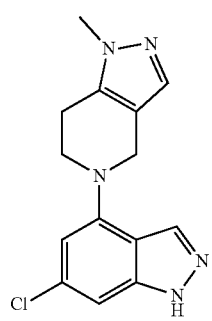 | 373 | 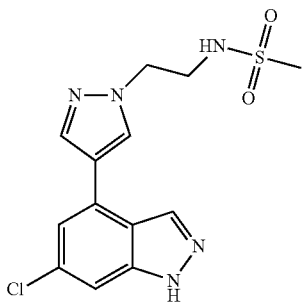 |
| 370 | 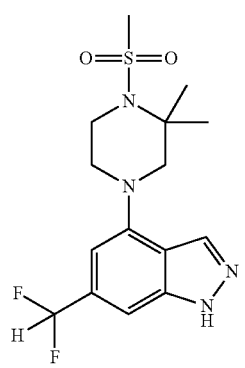 | 374 | 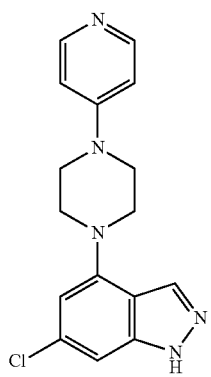 |
| 371 | 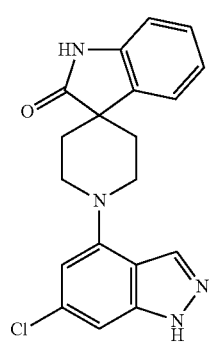 | 375 | 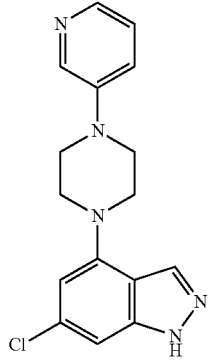 |
| 372 | 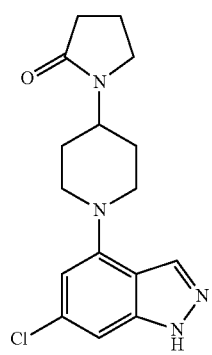 | 376 | 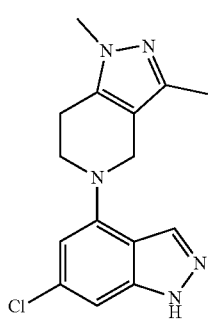 |

377 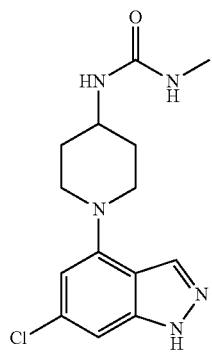
378 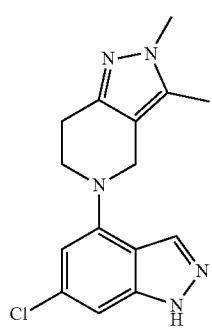
379 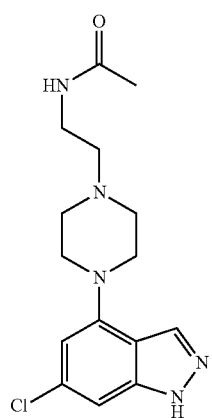
380 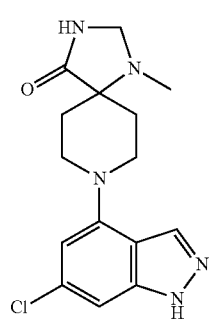
381 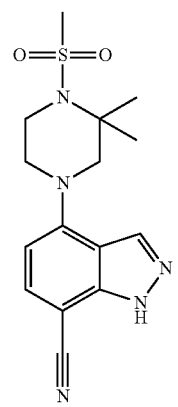
382 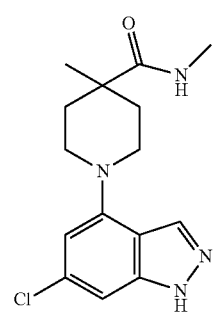
383 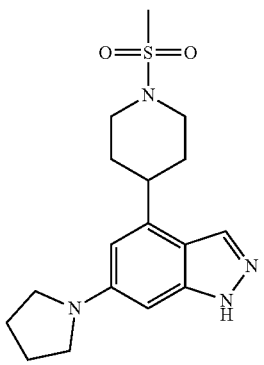
384 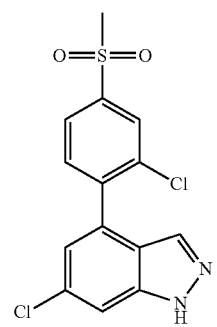

| 385 | 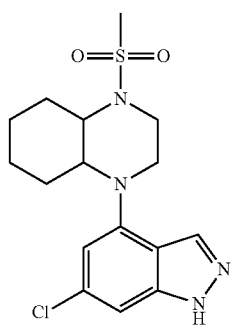 | 389 | 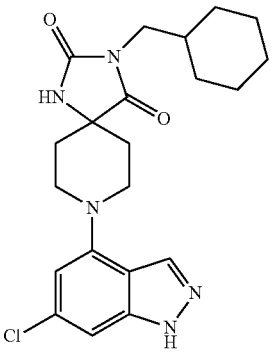 |
| 386 | 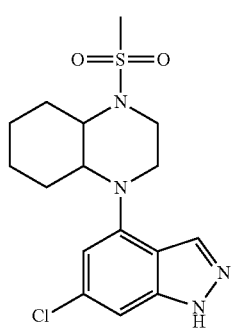 | 390 | 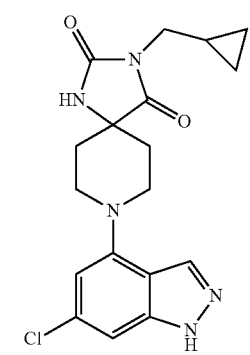 |
| 387 | 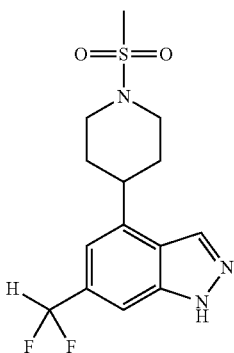 | 391 | 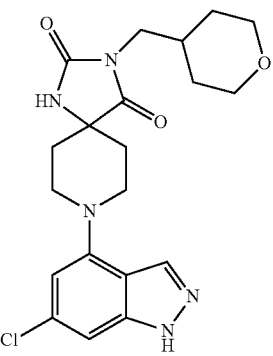 |
| 388 | 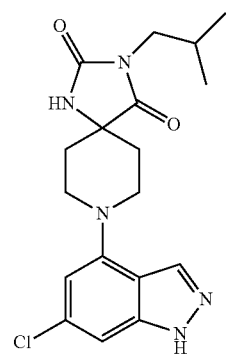 | 392 | 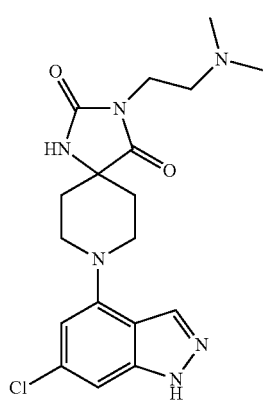 |

| 393 | 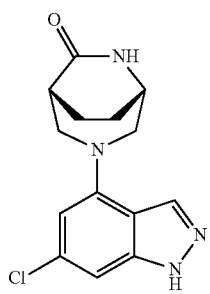 | 397 | 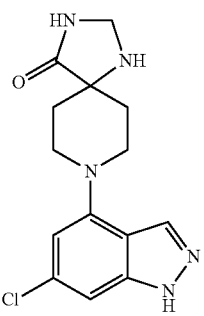 |
| 394 | 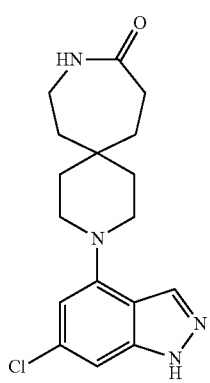 | 398 | 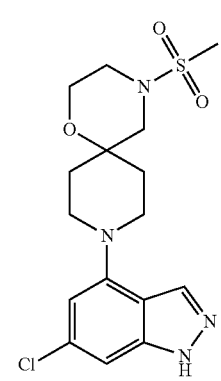 |
| 395 | 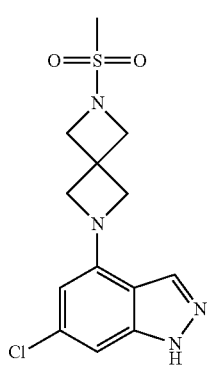 | 399 | 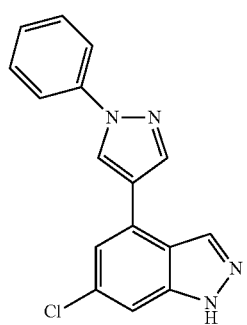 |
| 396 | 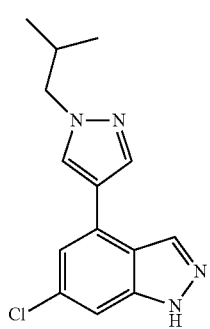 | 400 | 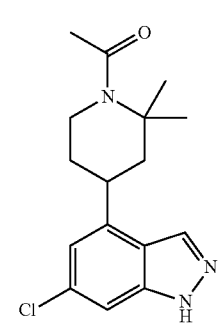 |

337
-continued
401
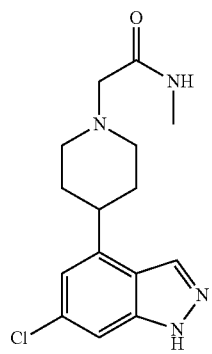
402
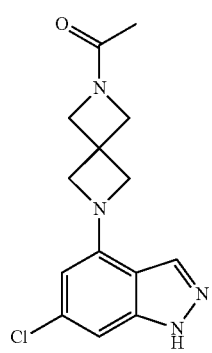
403
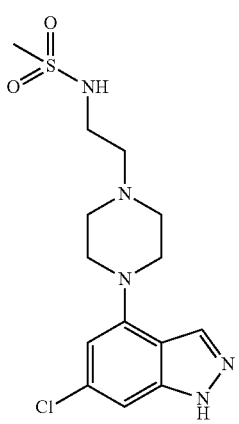
404
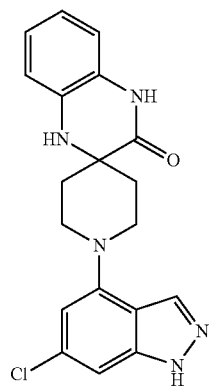
338
-continued
405
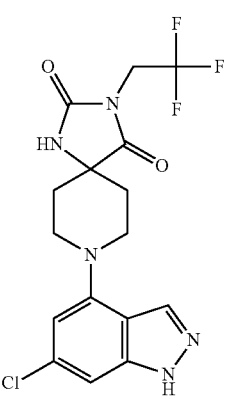
406
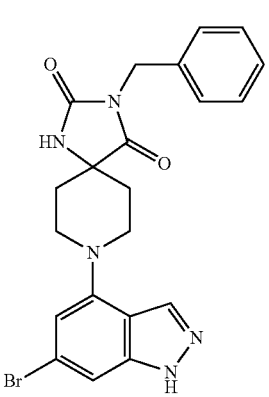
407
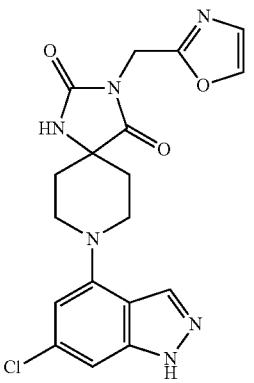
408
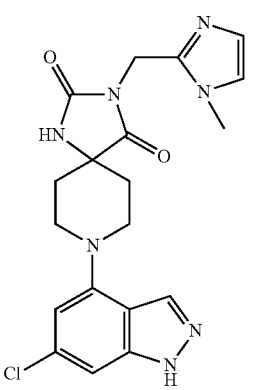

| 339 -continued | | 340 -continued | |
|---|---|---|---|
| 409 | 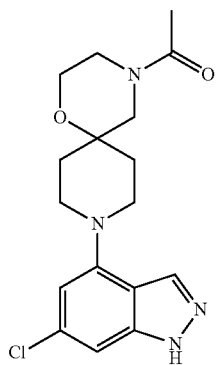 | 413 | 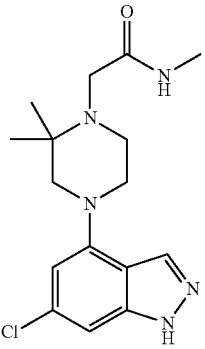 |
| 410 | 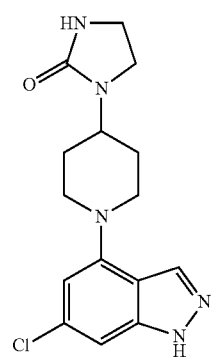 | 414 | 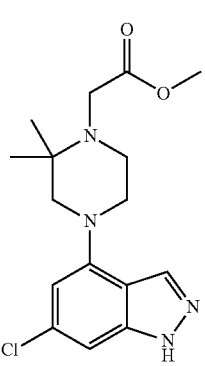 |
| 411 | 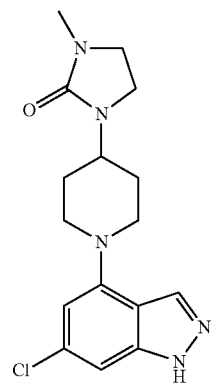 | 415 | 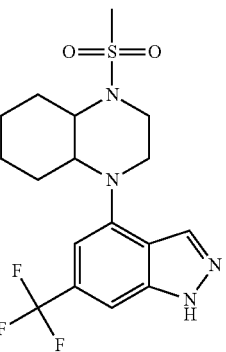 |
| 412 | 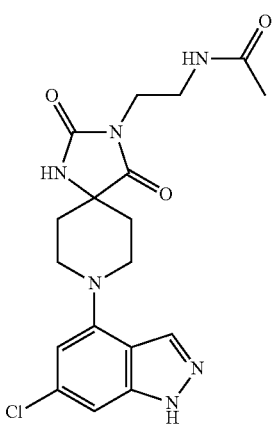 | 416 | 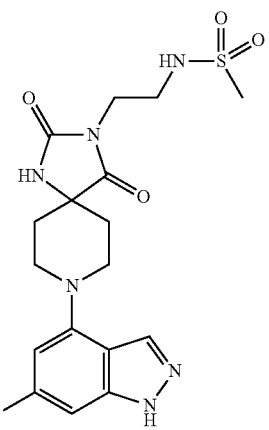 |

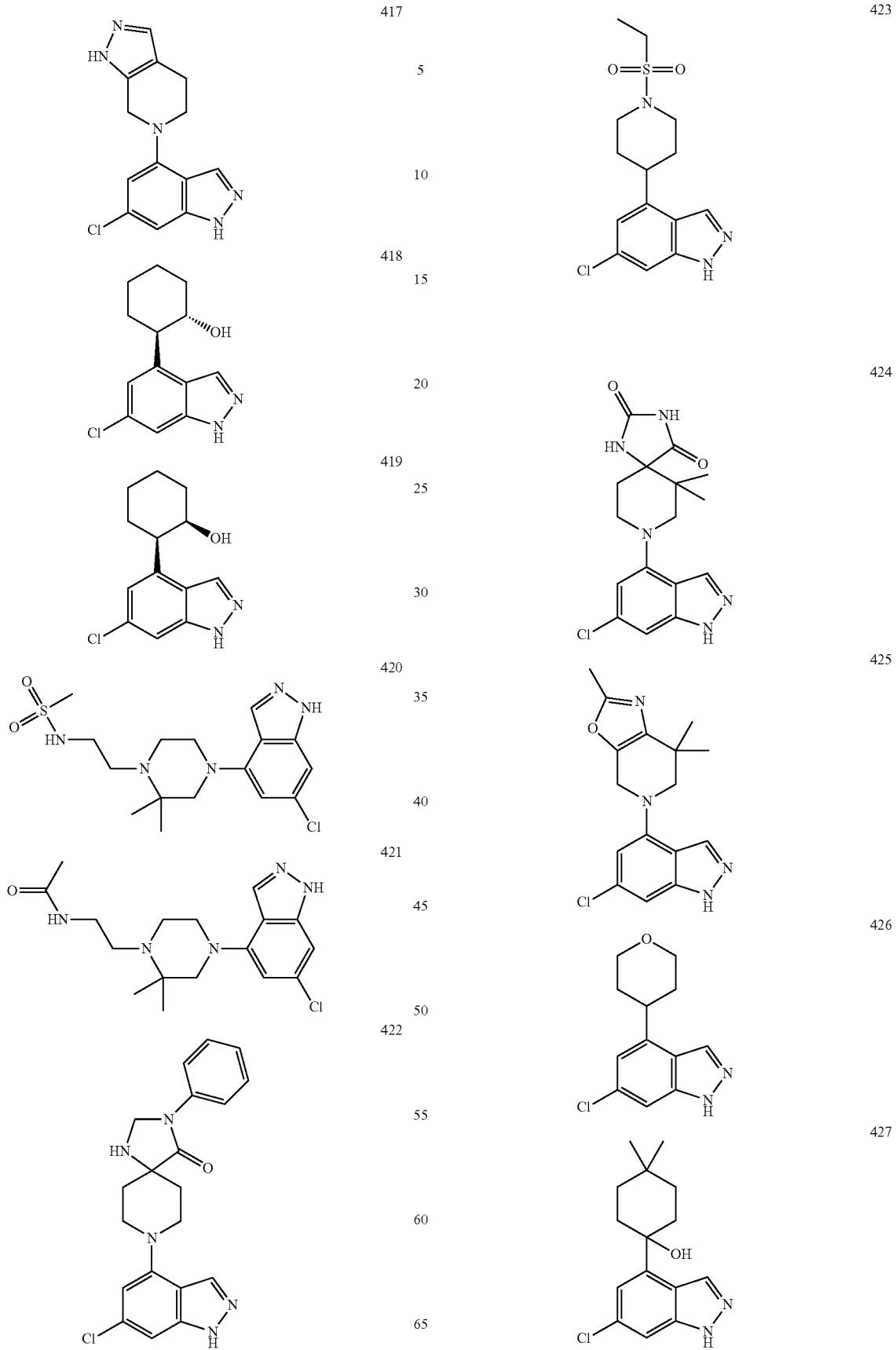

| | |
|---|---|
| 428 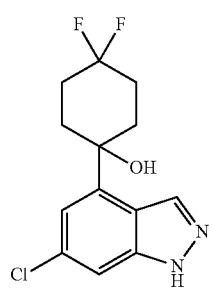 | 433 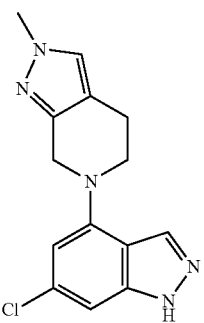 |
| 429 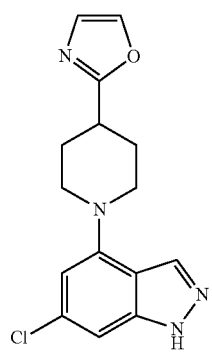 | 434 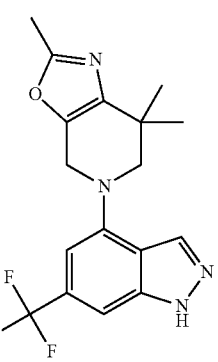 |
| 430 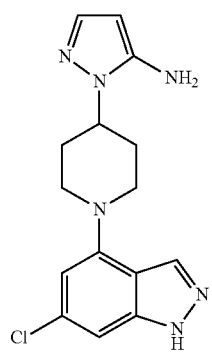 | 435 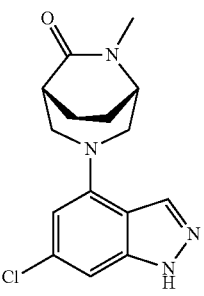 |
| 431 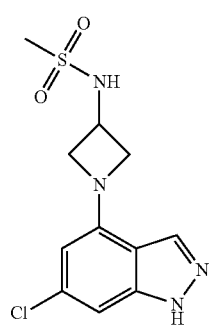 | 436 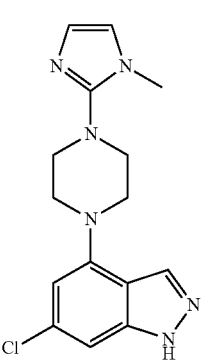 |
| 432 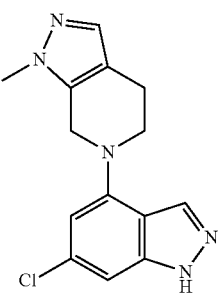 | |

| 437 | 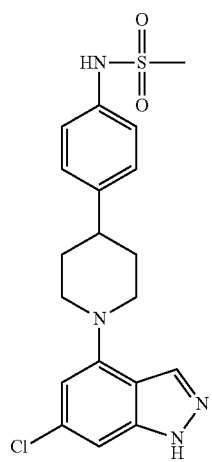 | 441 | 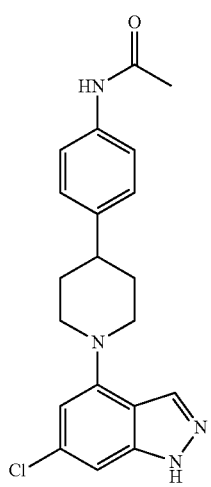 |
| --- | --- | --- | --- |
| 438 | 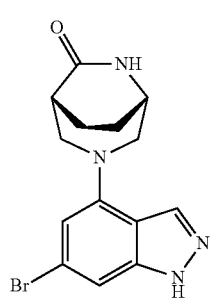 | 442 | 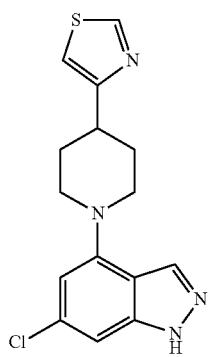 |
| 439 | 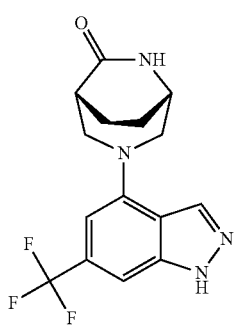 | 443 | 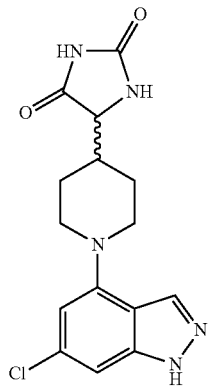 |
| 440 | 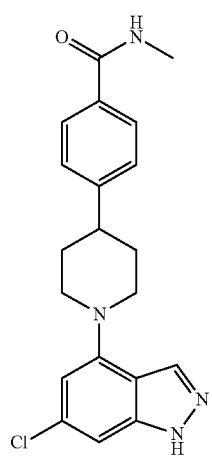 | 444 | 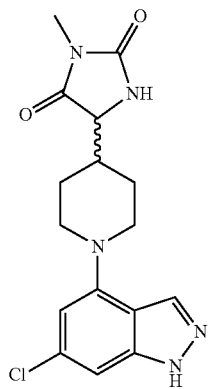 |

445 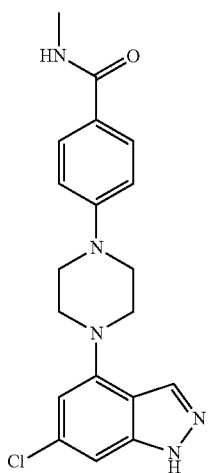
446 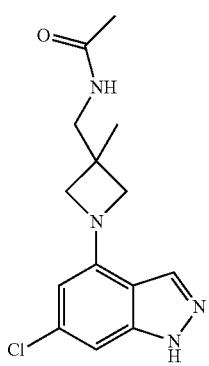
447 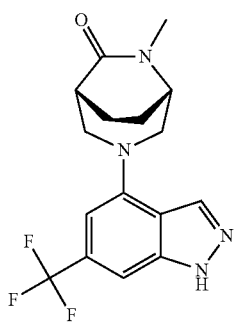
448 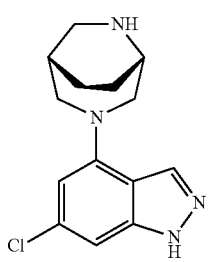
449 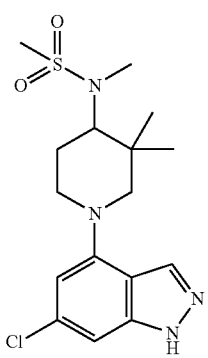
450 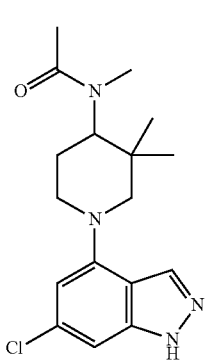
451 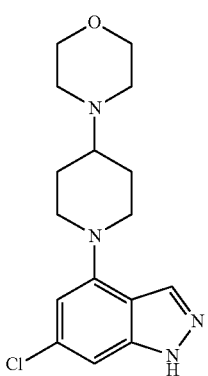
452 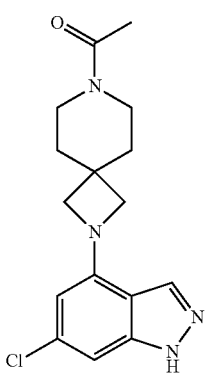

453 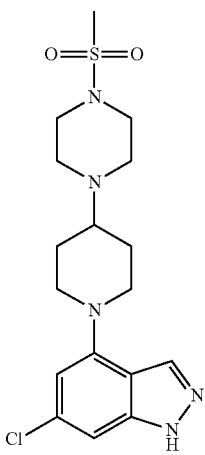

454 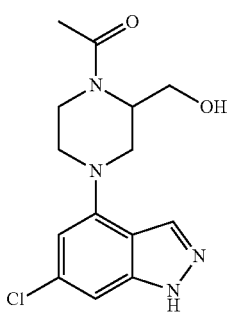

455 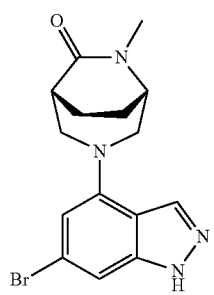

456 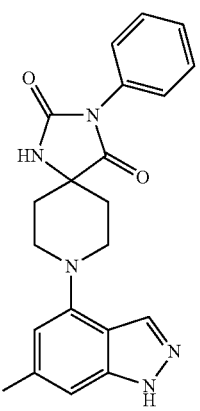

Typically, but not exclusively, the above formulae (and all formulae herein) are shown in non-stereoisomeric form. For the avoidance of doubt, throughout the present disclosure a single formula is intended to represent all possible stereoisomers of a particular structure, including all possible isolated enantiomers corresponding to the formula, all possible mixtures of enantiomers corresponding to the formula, all possible isolated diastereomers corresponding to the formula, all possible mixtures of diastereomers corresponding to the formula, all possible isolated epimers corresponding to the formula, all possible mixtures of epimers corresponding to the formula, all possible racemic mixtures corresponding to the formula, all possible isolated cis and trans isomers corresponding to the formula, and all possible mixtures of cis and trans isomers corresponding to the formula. In addition to this, the above formulae (and all formulae herein) are intended to represent all tautomeric forms equivalent to the corresponding formulae herein) are intended to represent: all tautomeric forms equivalent to the corresponding formula.

Further provided by the invention is a method of synthesis of novel compounds, as defined above, which method comprises a step of reacting a compound having one of the following formulae:

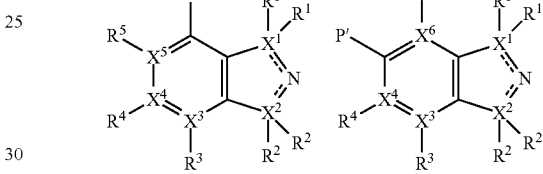

wherein the groups R and X are as in any one of the novel compounds defined herein, and wherein P' is a precursor group to group Y, in order to form the group Y from P' and produce a compound having one of the following formulae:

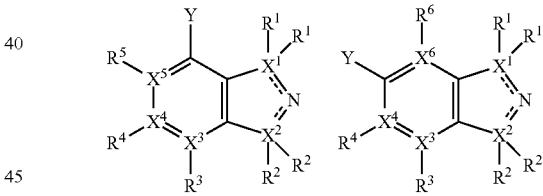

wherein the groups R, Y and X are as in any one of the novel compounds defined herein.

The skilled person may select the type of reagents, and the reaction conditions, with reference to known synthesis techniques. In some embodiments, the method comprises one or more additional substitution steps. Exemplary syntheses are shown in the Examples.

The invention will now be described in more detail, by way of example only, with reference to the following specific embodiments.

EXAMPLES

Example 1—Methods of Synthesis

The following syntheses are representative exemplary methods by which the compounds of the present invention may be synthesised:

A)
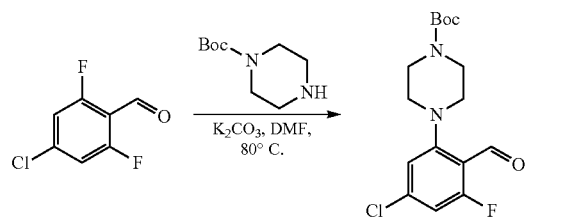
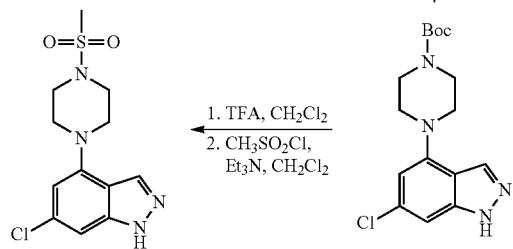
B)
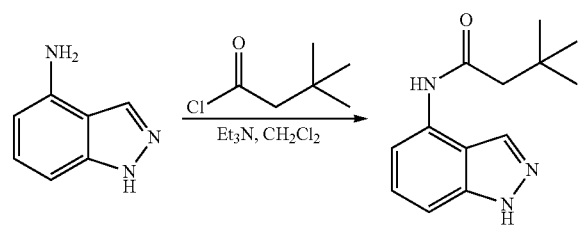
C)
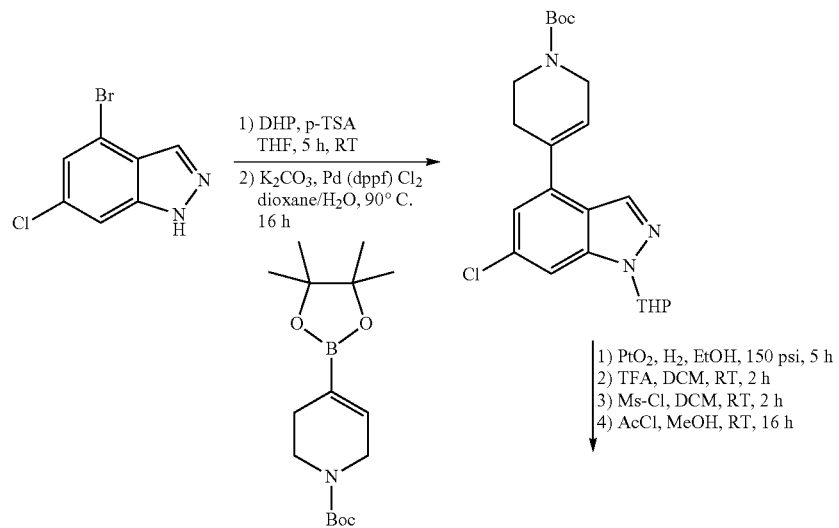
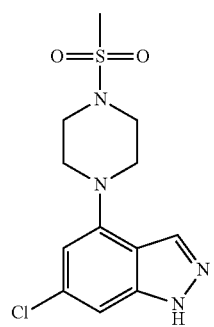

-continued
D)
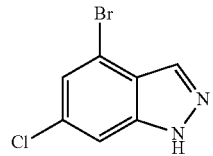 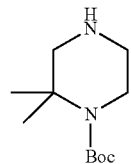 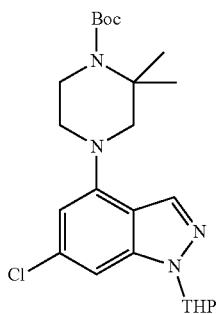
1) DHP, p-TSA THF, 5 h, RT
2) Pd$_2$(dba)$_3$, BINAP, NaOtBu, 1,4-dioxane 100° C., 4 h
1) AcCl, MeOH
2) MeSO$_2$Cl, DCM
3) NaOH, MeOH
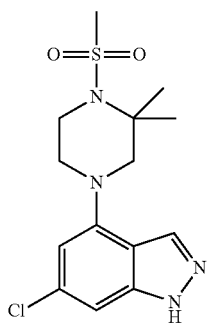
E)
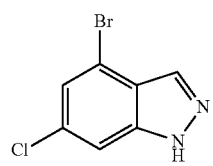 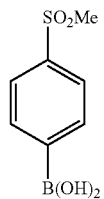 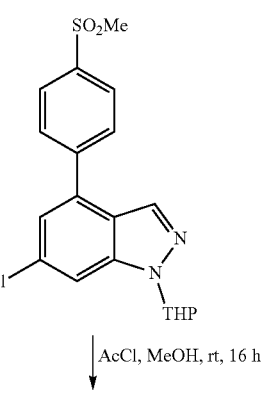
1) DHP, p-TSA THF, 5 h, RT
2) Pd(PPh$_3$)$_4$, Na$_2$CO$_3$, dioxane/H$_2$O, 100° C., 16 h
AcCl, MeOH, rt, 16 h
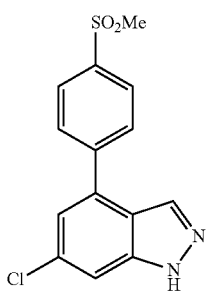

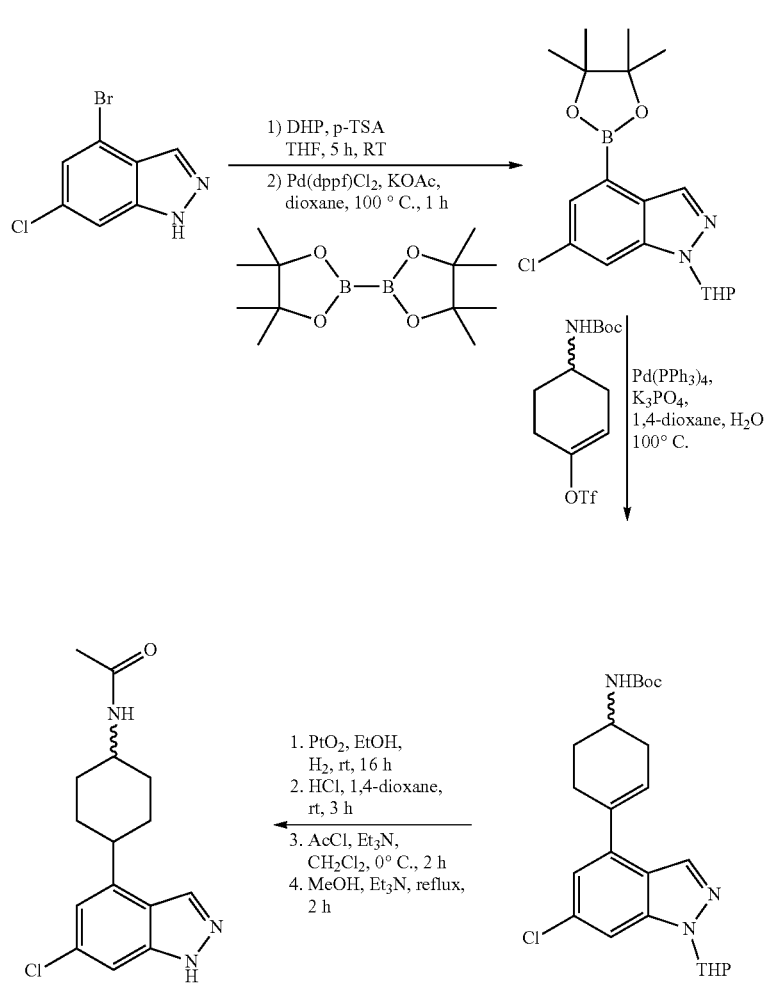

All syntheses may be performed using reagents and reaction conditions suitable for similar reactions known in the field. All the compounds of the present invention may be produced by employing analogous syntheses.

Some specific syntheses of compounds of the present invention are set out in the following. Reagents were purchased from commercial sources and were used as received. $^1$H NMR spectra were obtained on a Bruker AVANCE 300 spectrometer at 300 MHz and a Bruker AVANCE 400 spectrometer at 400 MHz with tetramethylsilane used as an internal reference. Thin-layer chromatography (TLC) was performed using Whatman No. 4500-101 (Diamond No. MK6F silica-gel 60 Å) plates. Visualization of TLC plates was performed using UV light (254 nm). The mass spectra were obtained on a Finnigan LCQ-DUO spectrometer and Shimadzu LCMS-2020 spectrometer using electrospray ionization. HPLC analyses were performed on an Agilent 1100 Series instrument and on a Shimadzu SIL-20A instrument. Impurities are expressed as % AUC by HPLC and are non-validated.

Synthesis of Compound 45

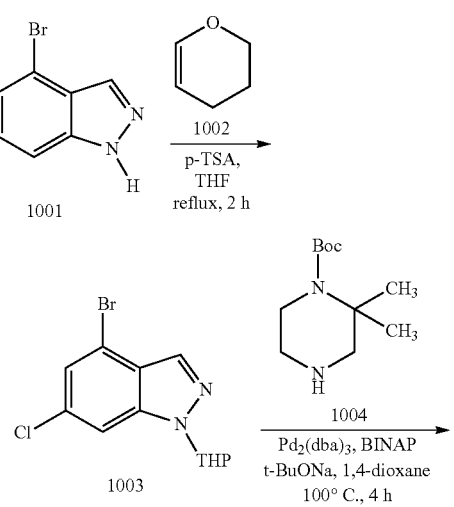

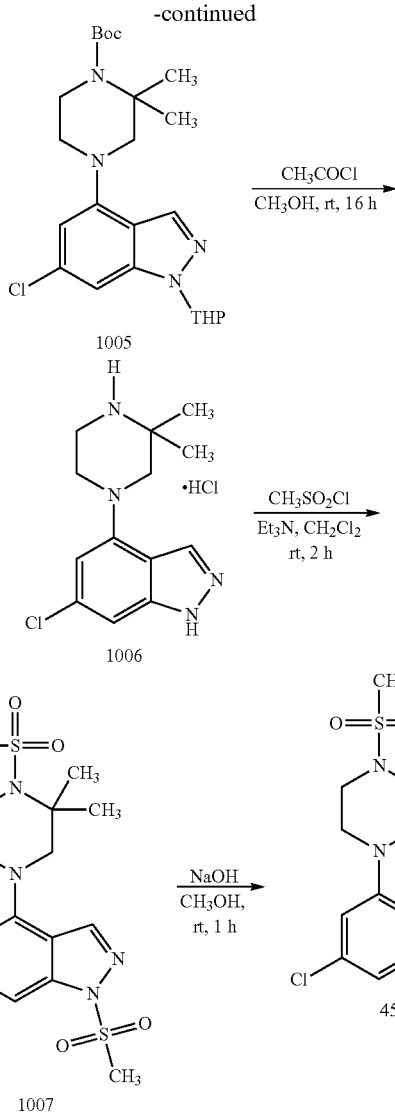

Preparation of 4-bromo-6-chloro-1-(tetrahydro-2H-pyran-2-yl)-1H-indazole, 1003

A solution of 1001 (5.0 g, 21.7 mmol) in THF (50 mL) was treated with dihydropyran 1002 (9.13 g, 108.6 mmol), p-toulenesulphonic acid (412 mg, 2.17 mmol) was added. After being stirred at reflux for 2 h, the reaction mixture was concentrated under reduced pressure. The reaction mixture was poured into water (100 mL) and extracted with $CH_2Cl_2$ (3×150 mL). The organic extracts were washed with water (1×200 mL) and brine (200 mL). The organic phase was separated, dried over anhydrous $Na_2SO_4$, filtered and concentrated in vacuo to afford 1003 (6.5 g crude) as an oil. The crude product was purified by Combiflash using 24 g Redisep® column (hexanes/EtOAc, 4:1) to afford 1003 (4.2 g, 62%) as an oil;

Preparation of tert-butyl tert-butyl 4-(6-chloro-1-(tetrahydro-2H-pyran-2-yl)-1H-indazol-4-yl)-2,2-dimethylpiperazine-1-carboxylate, 1005

A stirred solution of 1003 (3.1 g, 9.8 mmol) in 1,4-dioxane (800 mL) was charged with 1004 (2.1 g, 9.8 mmol) followed by t-BuONa (1.9 g, 19.6 mmol) and the mixture was purged with argon for 10 min. $Pd_2(dba)_3$ (56 mg, 0.098 mmol) and BINAP (122 mg, 0.196 mmol) were added and the mixture was heated at 100° C. for 4 h. Reaction mixture was cooled to room temperature (rt) and poured into water (100 mL), extracted with EtOAc (2×150 mL). The combined organic phase was washed with water (2×150 mL) and brine (150 mL). The organic phase was separated, dried over anhydrous $Na_2SO_4$, filtered and concentrated in vacuo to give a brown residue. This residue was further purified by Combiflash using 24 g Redisep® column (hexane/EtOAc, 1:1) to afford 1005 (2.4 g, 54%) as an oil.

MS (MM) m/z 449.1 $[M+H]^+$;

Preparation of chloro-chloro-4-(3,3-dimethylpiperazin-1-yl)-1H-indazole, .HCl, 1006

A solution of 1005 (2.4 g, 5.1 mmol) in $CH_3OH$ (15 mL) was treated with $CH_3COCl$ (3.2 g, 41 mmol) over 5 min. at 0° C. After being stirred at room temperature for 16 h, the solvent was concentrated under reduced pressure and washed with MTBE (2×25 mL) to remove excess of HCl. The resultant residue was dried in vacuo to afford 1006 (1.6 g, crude) as an off white solid.

MS (MM) m/z 265.1 $[M+H]^+$.

Preparation of 6-chloro-4-(3,3-dimethyl-4-(methylsulfonyl)piperazin-1-yl)-1-(methylsulfonyl)-1H-indazole, 1007

A solution of 1006 (700 mg, 1.40 mmol) in $CH_2Cl_2$ (8 mL) was treated with $Et_3N$ (0.37 mL, 2.8 mmol) followed by MsCl (0.163 mL, 2.10 mmol) over 5 min. at 0° C. After being stirred at room temperature for 1 h, the reaction mixture was poured into water (50 mL) and extracted with EtOAc (2×80 mL). The organic extracts were washed with water (2×50 mL) and brine (50 mL). The organic phase was separated, dried over anhydrous $Na_2SO_4$, filtered and concentrated in vacuo to afford 1007 (700 mg crude) as an off white solid.

MS (MM) m/z 421.1 $[M+H]^+$.

Preparation of 6-chloro-4-(3,3-dimethyl-4-(methylsulfonyl)piperazin-1-yl)-1H-indazole, 45

A solution of 1007 (700 mg, 1.66 mmol) in $CH_3OH$ (15 mL) was treated with NaOH (266 mg, 6.66 mmol) at room temperature. After being stirred at room temperature for 1 h, the solvent was concentrated under reduced pressure. Reaction mixture was poured into water (30 mL) and extracted with EtOAc (2×50 mL). The combined organic phase was washed with water (1×30 mL) and brine (30 mL). The organic phase was separated, dried over anhydrous $Na_2SO_4$, filtered and concentrated in vacuo to give an off white residue. The crude product was purified by Combiflash using 12 g Redisep® column ($CH_2Cl_2/CH_3OH$, 9:1) to afford 45 (72 mg) as an off-white solid.

MS (MM) m/z 343.0$[M]^+$.

HPLC: 99%, Symmetry C-18 column, 220 nm.

$^1$H NMR (400 MHz, DMSO-$d_6$): δ 13.05 (s, 1H), 8.13 (s, 1H), 7.01 (s, 1H), 6.34 (s, 1H), 3.60 (t, J=5.6 Hz, 2H), 3.45 (t, J=5.6 Hz, 2H), 3.29 (s, 2H), 3.02 (s, 3H), 1.51 (s, 6H).

Synthesis of Compound 393

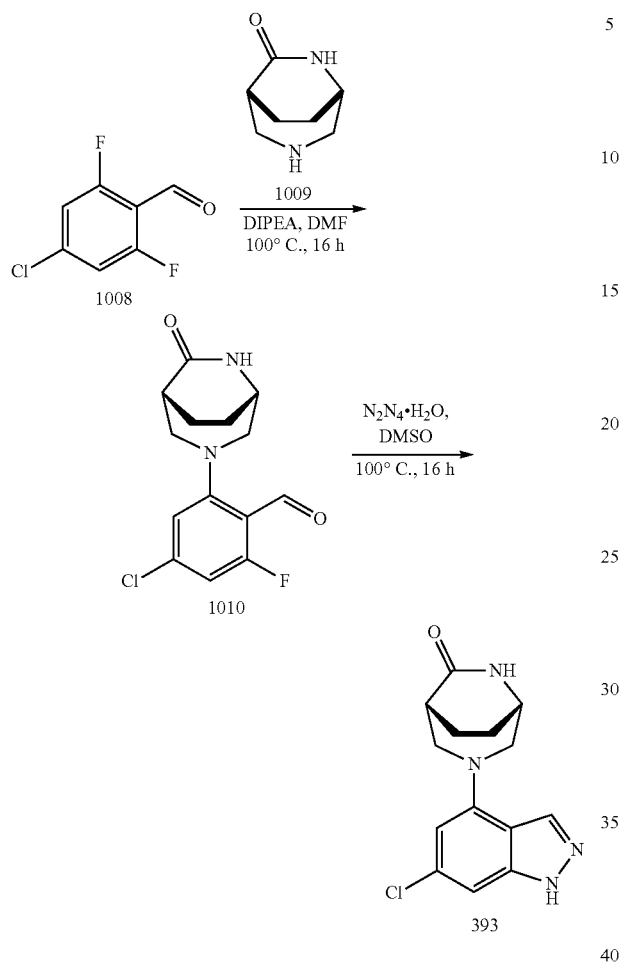

Preparation of 4-chloro-2-fluoro-6-((1R,5S)-7-oxo-3,6-diazabicyclo[3.2.2]nonan-3-yl)benzaldehyde, 1010

A solution of 4-chloro-2,6-difluorobenzaldehyde 1008 (300 mg, 1.69 mmol), (1R,5S)-3,6-diazabicyclo[3.2.2]nonan-7-one 1009 (214 mg, 1.52 mmol) and DIPEA (1.32 g, 10.19 mmol) in DMF (10 mL) was heated at 100° C. overnight. The mixture was cooled to rt, poured into ice water (25 ml) and extracted with ethyl acetate (100 ml). The organic layer washed with brine (25 ml), dried over anhydrous $Na_2SO_4$, and evaporated. The crude material was purified by Combiflash using 24 g Redisep® column (hexane/ethyl acetate, 1:9) to get desired product 1010 (335 mg, 74%) as a yellow solid.

MS (MM) m/z 297.1 [M+H]$^+$.

Preparation of (1R,5S)-3-(6-chloro-1H-indazol-4-yl)-3,6-diazabicyclo[3.2.2]nonan-7-one, 393

A solution of 4-chloro-2-fluoro-6-((1R,5S)-7-oxo-3,6-diazabicyclo[3.2.2]nonan-3-yl)benzaldehyde 1010 (330 mg, 1.11 mmol) and hydrazine monohydrate (3 ml) in DMSO (10 mL) was stirred at 100° C. for 16 h. The mixture was cooled to rt and poured into ice water (25 ml), extracted with ethyl acetate (100 ml). The organic layer was washed with brine (25 ml), dried over anhydrous $Na_2SO_4$ and evaporated. The crude material was purified by Combiflash using 12 g Redisep® column ($CH_2Cl_2/CH_3OH$, 1:24) to get 393 (275 mg, 85%) as an off-white solid.

MS (MM) m/z 291.0 [M+H]$^+$.

400 MHz, $^1$H NMR (DMSO); 13.06 (s, 1H), 8.13 (s, 1H), 8.05-8.06 (d, J=5.6 Hz, 1H), 7.05 (s, 1H), 6.39 (s, 1H), 3.74-3.82 (m, 2H), 3.68-3.70 (m, 1H), 3.17-3.20 (d, J=12.8 Hz, 1H), 3.05-3.09 (d, J=12.8 Hz, 1H), 2.62-2.68 (1H, m), 2.07-2.15 (m, 1H), 1.95-2.02 (m, 1H), 1.82-1.89 (m, 2H).

Synthesis of Compound 4

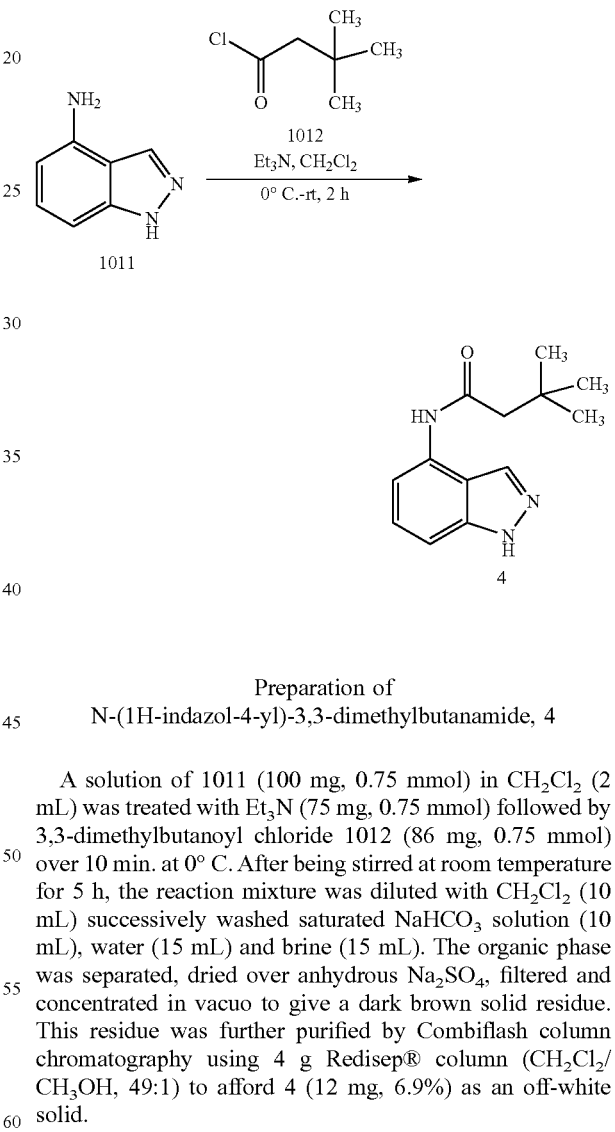

Preparation of N-(1H-indazol-4-yl)-3,3-dimethylbutanamide, 4

A solution of 1011 (100 mg, 0.75 mmol) in $CH_2Cl_2$ (2 mL) was treated with $Et_3N$ (75 mg, 0.75 mmol) followed by 3,3-dimethylbutanoyl chloride 1012 (86 mg, 0.75 mmol) over 10 min. at 0° C. After being stirred at room temperature for 5 h, the reaction mixture was diluted with $CH_2Cl_2$ (10 mL) successively washed saturated $NaHCO_3$ solution (10 mL), water (15 mL) and brine (15 mL). The organic phase was separated, dried over anhydrous $Na_2SO_4$, filtered and concentrated in vacuo to give a dark brown solid residue. This residue was further purified by Combiflash column chromatography using 4 g Redisep® column ($CH_2Cl_2/CH_3OH$, 49:1) to afford 4 (12 mg, 6.9%) as an off-white solid.

MS (MM) m/z 232[M+H]$^+$.

HPLC: 99%, Poroshell EC-18 column, 220 nm.

$^1$H NMR (300 MHz, DMSO-d$_6$): δ 13.02 (s, 1H), 9.79 (s, 1H), 8.23 (s, 1H), 7.59 (dd, J=6.9, 1.5 Hz, 1H), 7.26 (d, J=8.4 Hz, 1H), 7.21 (d, J=8.4 Hz, 1H), 2.33 (s, 2H), 1.06 (s, 9H).

Synthesis of Compound 28

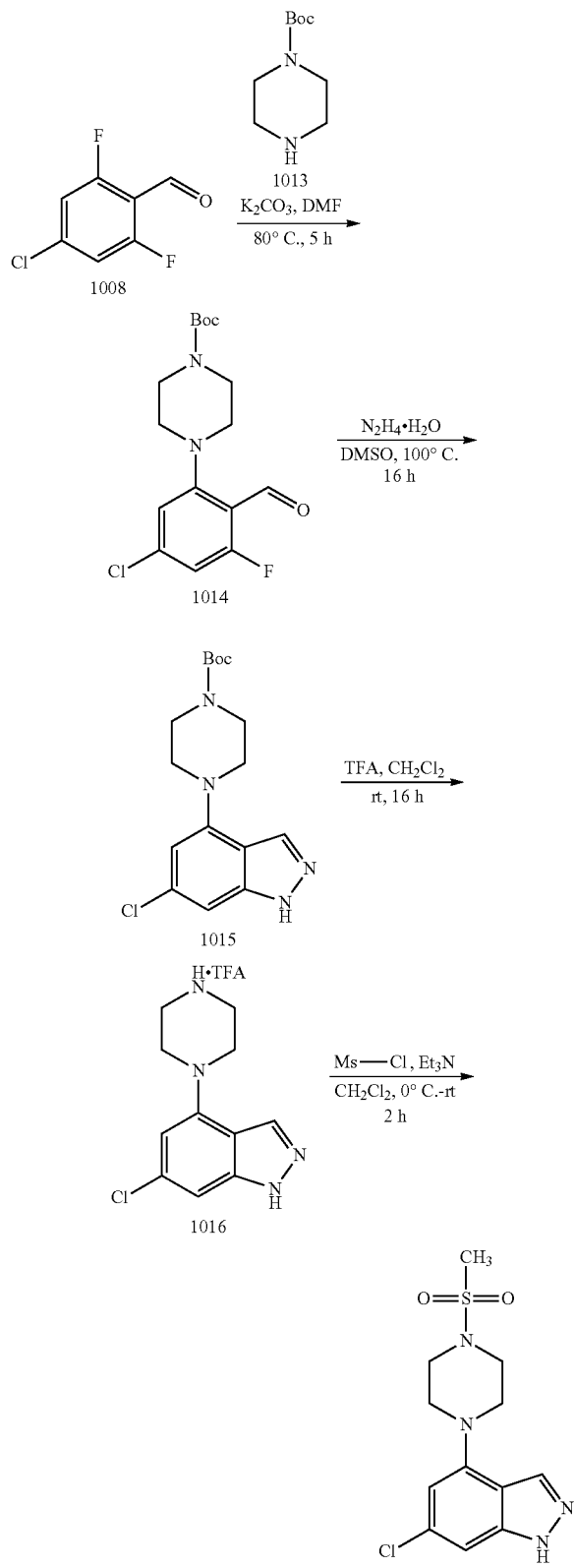

Preparation of tert-butyl 4-(5-chloro-3-fluoro-2-formylphenyl)piperazine-1-carboxylate, 1014

A stirred solution of 1008 (2.00 g, 11.36 mmol) and 1013 (2,10 g, 11.36 mmol) in DMF (50 mL) was treated K$_2$CO$_3$ (3.1 g, 22.72 mmol). The reaction mixture was allowed to stir at 80° C. for 5 h. The reaction mixture was poured into water and extracted with EtOAc (2×50 mL), washed with water (2×50 mL) and brine (50 mL). The organic phase was separated, dried over anhydrous Na$_2$SO$_4$, filtered and concentrated in vacuo to afford the crude product. This residue was purified by Combiflash column chromatography using 12 g Redisep® column (hexanes/EtOAc, 7:3) to afford 1014 (2.3 g, 58%) as a yellow solid.

MS (MM) m/z 343[M+H]$^+$.

Preparation of tert-butyl 4-(6-chloro-1H-indazol-4-yl)piperazine-1-carboxylate, 1015

A stirred solution of 1014 (2.30 g, 6.725 mmol) in DMSO (25 mL) was treated with hydrazine monohydrate (1.68 g, 33.62 mmol) at rt and stirred at 100° C. for 4 h. The reaction mixture was cooled to rt, poured into water and extracted with EtOAc (2×50 mL). The organic layer was washed with water (2×50 mL) and brine (50 mL). The organic phase was separated, dried over anhydrous Na$_2$SO$_4$, filtered and concentrated in vacuo to afford the crude product. This residue was purified by Combiflash column chromatography using 12 g Redisep® column (hexanes/EtOAc, 6:4) to afford 1015 (1.50 g, 66%) as an off white solid.

MS (MM) m/z 337 [M+H]$^+$.

Preparation of 6-chloro-4-(piperazin-1-yl)-1H-indazole.TFA, 1016

A stirred solution of 1015 (1.50 g, 4.5 mmol) in CH$_2$C$_2$(30 mL) was treated with TFA (2.06 g, 18 mmol) over 10 min. at 0° C. The reaction mixture was stirred at room temperature for 16 h and then concentrated under the reduced pressure to afford 1016 (200 mg, 79%) as TFA salt.

MS (MM) m/z 237 [M+H]$^+$.

Preparation of 6-chloro-4-(4-(methylsulfonyl)piperazin-1-yl)-1H-indazole, 28

A solution 1016 (300 mg, 0.85 mmol) in CH$_2$Cl$_2$ (6 mL) was treated with Et$_3$N (259 mg, 2.57 mmol) followed by MsCl (98 mg, 0.85 mmol) over 10 min. at 0° C. After being stirred at room temperature for 16 h, the reaction mixture was diluted with EtOAc (30 mL) washed with water (2×15 mL) and brine (15 mL). The organic phase was separated, dried over anhydrous Na$_2$SO$_4$, filtered and concentrated in vacuo to give a dark brown solid residue. This residue was further purified by Combiflash column chromatography using 4 g Redisep® column (hexanes/EtOAc, 1:1) to afford 28 (62 mg, 22%) as a pale yellow solid.

MS (MM) m/z 315 [M+H]$^+$.

HPLC: 97.1%, Eclipse XDB C-18, 220 nm.

$^1$H NMR (400 MHz, DMSO-d$_6$): δ 13.11 (s, 1H), 8.14 (s, 1H), 7.11 (s, 1H), 6.44 (s, 1H), 3.39-3.37 (m, 4H), 3.34-3.33 (m, 4H), 2.94 (s, 3H).

Synthesis of Compound 40

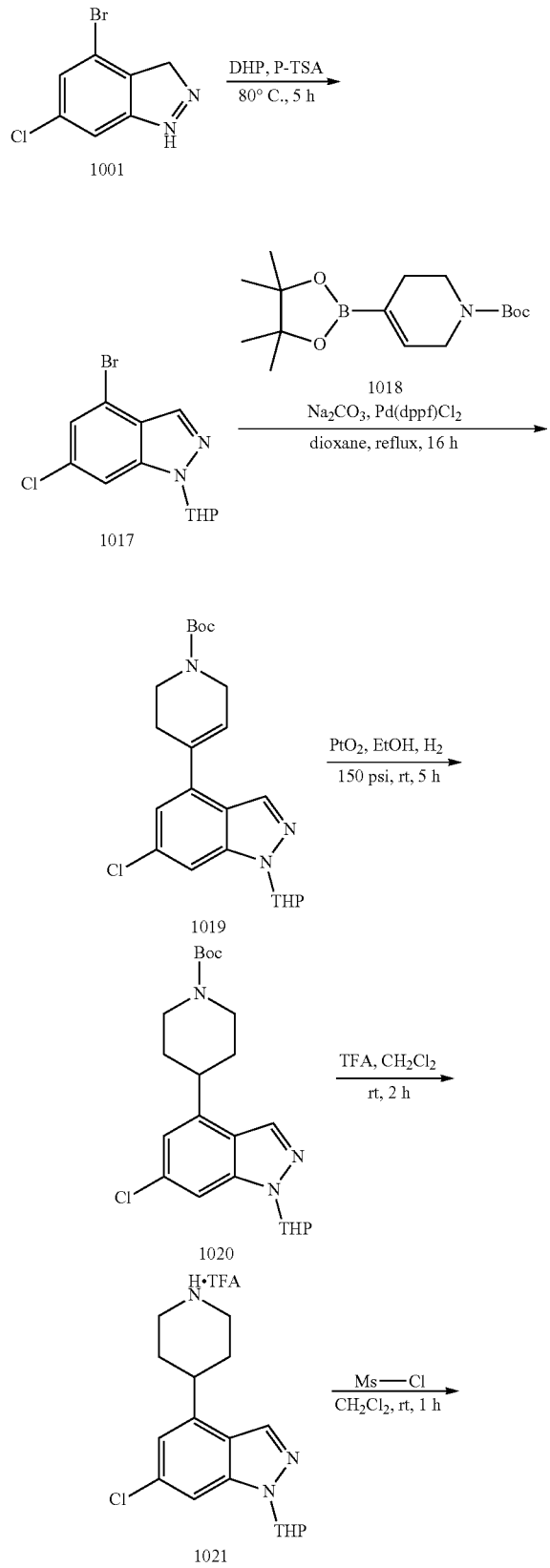

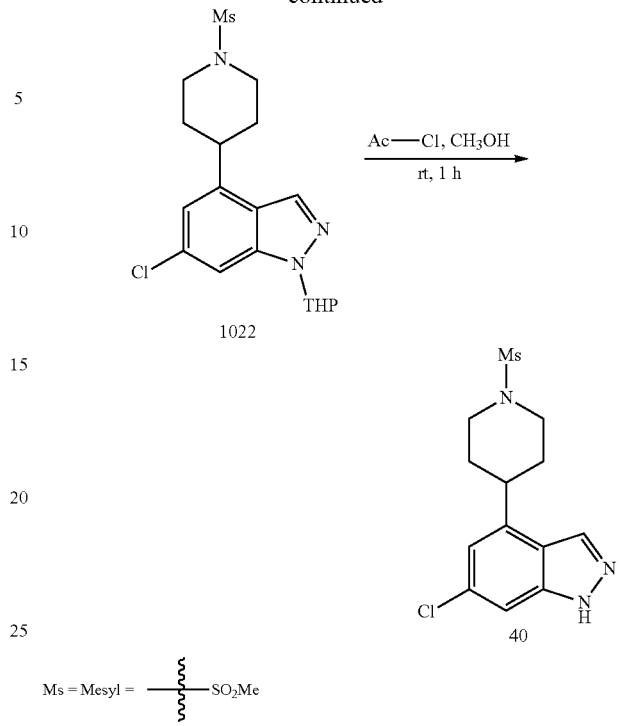

Ms = Mesyl = —SO₂Me

Preparation of 4-bromo-6-chloro-(tetrahydro-2H-pyran-2-yl)-1H-indazole, 1017

A solution of 1001 (500 mg, 2.17 mmol) in THF (10 mL) was treated with dihydropyran (913 mg, 10.86 mol), p-toulenesulphonic acid (41 mg, 0.21 mmol) was added. After being stirred at 80° C. for 5 h, the reaction mixture was cooled to rt, poured into water (10 mL) and extracted with EtOAc (2×10 mL). The combined organic phase was washed with water (2×10 mL) and brine (10 mL). The organic phase was separated, dried over anhydrous Na₂SO₄, filtered and concentrated in vacuo to give a dark brown residue. This residue was further purified by combiflash using 12 g Redisep® column (hexanes/EtOAc, 9:1) to afford 1017 (320 mg, 46%) as an orange solid.

Preparation of tert-butyl 4-(6-chloro-1-(tetrahydro-2H-pyran-2-yl)-1H-indazol-4-yl)-5,6-dihydropyridine-1 (2H)-carboxylate, 1019

A stirred solution of 1017 (320 g, 1.01 mmol) in a mixture of 1,4-dioxane (8 mL) and H₂O (2 mL) was charged with 1018 (254 mg, 1.11 mmol) followed by powdered Na₂CO₃ (408 mg, 2.031 mmol) and the mixture was purged with argon for 20 min. Pd(dppf)Cl₂ (41.4 g, 0.05 mmol) was added and the mixture was refluxed for 16 h. Reaction mixture was cooled to rt, poured into water (10 mL) and extracted with EtOAc (2×15 mL). The combined organic phases were washed with water (2×10 mL) and brine (10 mL). The organic phase was separated, dried over anhydrous Na₂SO₄, filtered and concentrated in vacuo to give a dark brown residue. This residue was further purified by combiflash using Redisep® column (hexanes/EtOAc, 8:2) to afford 1019 (350 mg, 82%) as off-white gummy solid.

Preparation of tert-butyl 4-(6-chloro-1-(tetrahydro-2H-pyran-2-yl)-1H-indazol-4-yl)piperidine-1-carboxylate, 1020

A stirred solution of 1019 (350 mg, 0.83 mmol) in EtOH (10 mL) was charged with $PtO_2$ (35 mg, 10 wt. %) under argon atmosphere at room temperature and subjected to hydrogenation at 150 psi for 5 h. The reaction mixture was filtered through a Celite® bed, washed well with $CH_3OH$ (50 mL) and concentrated under the reduced pressure to afford the crude product 1020 (320 mg, 91%) as colourless gum.

MS (MM) m/z 420.1 [M+H]$^+$.

Preparation of 6-chloro-4-(piperidin-4-yl)-1-(tetrahydro-2H-pyran-2-yl)-1H-indazole-TFA, 1021

A solution of 1020 (320 mg, 0.76 mmol) in $CH_2Cl_2$ (6 mL) was treated with TFA (349 mg, 3.054 mmol) over 5 min. at 0° C. After being stirred at room temperature for 2 h, the solvent was concentrated under reduced pressure, co-distilled with MTBE (3×10 mL) to remove excess of TFA and dried in vacuo to afford 1021 (300 g, crude) as a gummy orange solid.

Preparation of 6-chloro-4-(1-(methylsulfonyl)piperidin-4-yl)-1-(tetrahydro-2H-pyran-2-yl)-1H-indazole, 1022

A solution of 1021 (300 mg, 0.72 mmol) in $CH_2Cl_2$ (6 mL) was treated with $Et_3N$ (145 mg, 1.44 mmol) followed by MsCl (82.5 mg, 0.72 mmol) at 0° C. After being stirred at room temperature for 1 h, the reaction mixture was poured into water (15 mL) and extracted with $CH_2Cl_2$(2×15 mL). The organic extracts were washed with water (2×15 L) and brine (15 mL). The organic phase was separated, dried over anhydrous $Na_2SO_4$, filtered and concentrated in vacuo to afford 1022 (200 mg crude) as a reddish brown solid.

Preparation of 6-chloro-4-(1-(methylsulfonyl)piperidin-4-yl)-1H-indazole, 40

A solution of 1022 (200 mg, 0.503 mmol) in methanol (4 mL) was treated with AcCl (39.5 mg, 0.503 mmol) at room temperature. After being stirred at room temperature for 1 h, the reaction mixture was poured into water (10 mL), and extracted with EtOAc (2×20 mL). The organic extracts were washed with water (2×20 mL) and brine (20 mL). The organic phase was separated, dried over anhydrous $Na_2SO_4$, filtered and concentrated in vacuo to afford crude product. The crude product was purified by combiflash (4 g Redisep® column; hexanes: EtOAc 4:6) to afford 40 (55 mg) as an off white solid.

MS (MM) m/z 314.1[M+H]$^+$.

HPLC: 97.6%, Eclipse XDB-C-18 column, 220 nm.

$^1$H NMR (400 MHz, DMSO-d$_6$): δ 13.17 (s, 1H), 8.23 (s, 1H), 7.46 (s, 1H), 6.98 (s, 1H), 3.72 (d, J=11.6 Hz, 2H), 3.18-3.16 (m, 1H), 2.95-2.89 (m, 2H), 2.92 (s, 3H), 2.03-1.96 (m, 2H), 1.87-1.77 (qd, J=8.4, 4.0 Hz, 2H).

Synthesis of Compound 424

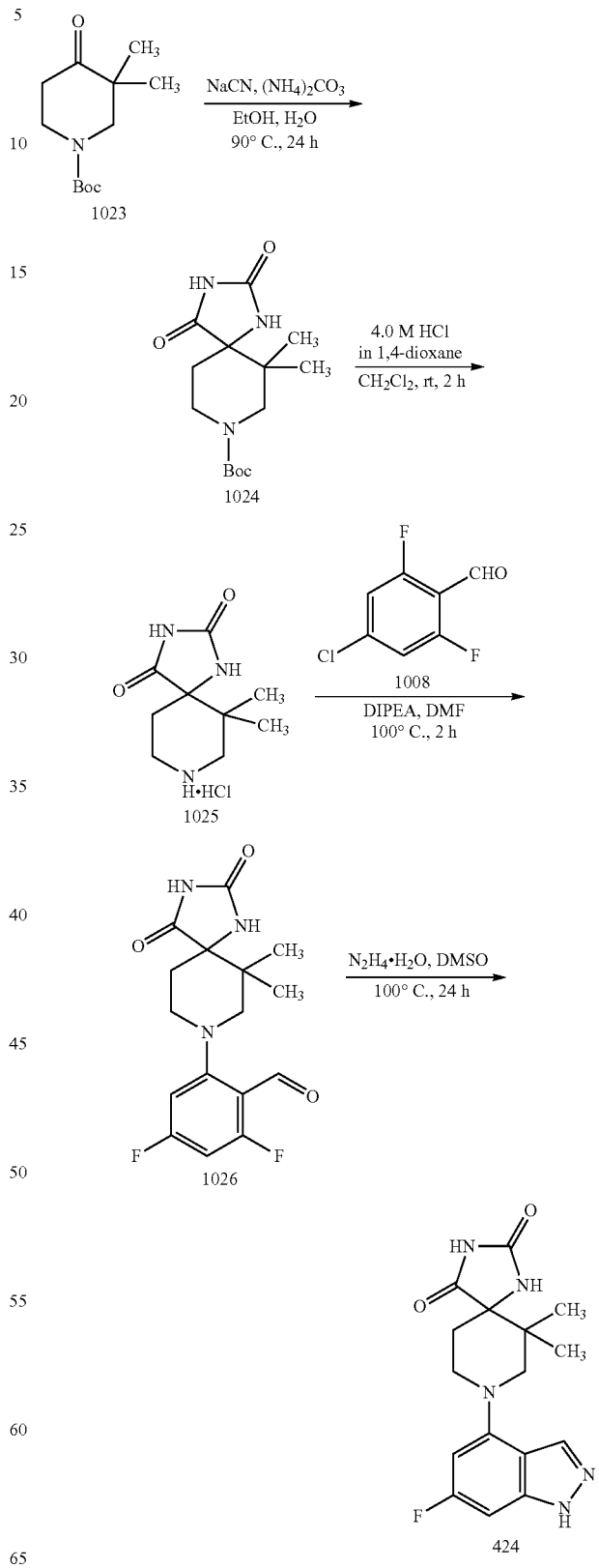

Preparation of tert-butyl 6,6-dimethyl-2,4-dioxo-1,3,8-triazaspiro[4.5]decane-8-carboxylate, 1024

A solution of 1023 (1 g, 44 mmol) in EtOH (18 mL) and water (5 mL) was placed in a sealed tube and treated with NaCN (875 mg, 144 mmol), ammonium carbonate (8.17 g, 8503 mmol). After being stirred at 85° C. for 16 h, the reaction mixture was poured into water (50 mL) and extracted with EtOAc (2×100 mL). The organic extracts were washed with water (2×50 mL) and brine (50 mL). The organic phase was separated, dried over anhydrous $Na_2SO_4$, filtered and concentrated in vacuo to afford 1024 (1.25 g, 94%) as an off white solid.

MS (MM) m/z 298.1 [M+H]$^+$.

Preparation of 6,6-dimethyl-1,3,8-triazaspiro[4.5]decane-2,4-dione hydrochloride, 25

A solution of 1024 (1.25 g, 42 mmol) in $CH_2Cl_2$ (10 mL) was treated with HCl in 1,4-dioxan (4.0 M solution, 20 mL) over 15 min. at 0° C. After being stirred at room temperature for 16 h, the solvent was concentrated under reduced pressure, co-distilled with MTBE (3×200 mL) to remove excess of HCl and dried in vacuo to afford 1025 (900 mg, crude) as an off white HCl salt.

MS (MM) m/z 198.1 [M+H]$^+$.

Preparation of 4-chloro-2-(6,6-dimethyl-2,4-dioxo-1,3,8-triazaspiro[4.5]decan-8-yl)-6-fluorobenzaldehyde, 1026

A stirred solution of 1025 (400 mg, 2.2 mmol) in DMF (10 mL) was charged with 1008 (447 mg, 2.2 mmol) and DIPEA (879 mg, 6.8 mmol) under argon atmosphere at 100° C. for 16 h. The reaction mixture was poured into water (50 mL) and extracted with EtOAc (2×100 mL). The organic extracts were washed with water (2×50 mL) and brine (50 mL). The organic phase was separated, dried over anhydrous $Na_2SO_4$, filtered and concentrated in vacuo to afford crude residue. The crude product was purified by Combiflash chromatography using 12 g Redisep® column (hexanes/EtOAc, 1:1) to afford 1026 (600 mg) as a yellow solid.

MS (MM) m/z 354.1 [M+H]$^+$.

Preparation of 8-(6-chloro-1H-indazol-4-yl)-6,6-dimethyl-1,3,8-triazaspiro[4.5]decane-2,4-dione, 424

A solution of 1026 (600 mg, 1.7 mmol) in DMSO (5 mL) was treated with hydrazine monohydrate (170 mg, 3.4 mol) and heated to 100° C. for 24 h. The reaction mixture was poured into water (50 mL) and extracted with EtOAc (2×25 mL). The organic extracts were washed with water (2×50 mL) and brine (50 mL). The organic phase was separated, dried over anhydrous $Na_2SO_4$, filtered and concentrated in vacuo to afford crude residue. The crude residue was purified by Combiflash chromatography using 12 g Redisep® column (hexanes/EtOAc, 1:9) to afford 424 (35 mg) as a yellow-brown solid.

MS (MM) m/z 348.1[M+H]$^+$.

HPLC: 96.6%, Eclipse XDB-C-18 column, 230 nm.

$^1$H NMR (400 MHz, DMSO-d$_6$): δ 10.69 (s, 1H), 8.20 (s, 1H), 8.10 (s, 1H), 7.04 (s, 1H), 6.39 (s, 1H), 3.45-3.36 (m, 2H), 3.32 (d, J=12.8 Hz, 1H), 3.16 (d, J=12.8 Hz, 1H), 2.08-1.93 (m, 2H), 1.04 (d, J=6.4 Hz, 6H).

Synthesis of Compound 273

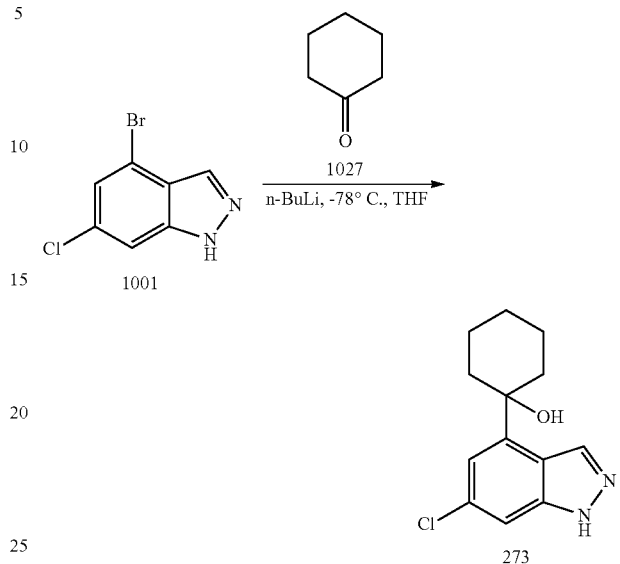

Preparation of 1-(6-chloro-1H-indazol-4-yl)cyclohexanol, 273

To a solution of 1001 (200 mg, 869 mmol) in THF (30 ml) was added n-butyl lithium (2.5 M soln. in hexane, 0.87 ml, 2.17 mmol) at −78° C. After being stirred for 15 min., cyclohexanone 1027 (426 mg, 4.34 mmol) was added and stirred at the same temperature for 3 h. The reaction was quenched with saturated ammonium chloride solution and extracted with EtOAc (2×50 ml). The organic phase was separated, washed with brine, dried over anhydrous $Na_2SO_4$, filtered and concentrated in vacuo to afford crude residue. The crude residue purified by Combiflash chromatography using 4 g Redisep® column (hexanes/EtOAc, 7:3) to afford 273 (35 mg, 16%) as a white solid.

MS (MM) m/z 251.1[M+H]$^+$.

HPLC: 97.02%, Eclipse XDB-C-18 column, 220 nm.

$^1$H NMR (400 MHz, DMSO-d$_6$): δ 13.20 (s, 1H), 8.33 (s, 1H), 7.45 (s, 1H), 7.14 (s, 1H), 5.06 (s, 1H), 1.99-1.90 (m, 2H), 1.85-1.67 (m, 5H), 1.56-1.37 (m, 3H).

Synthesis of Compound 155

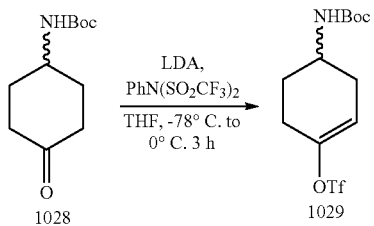

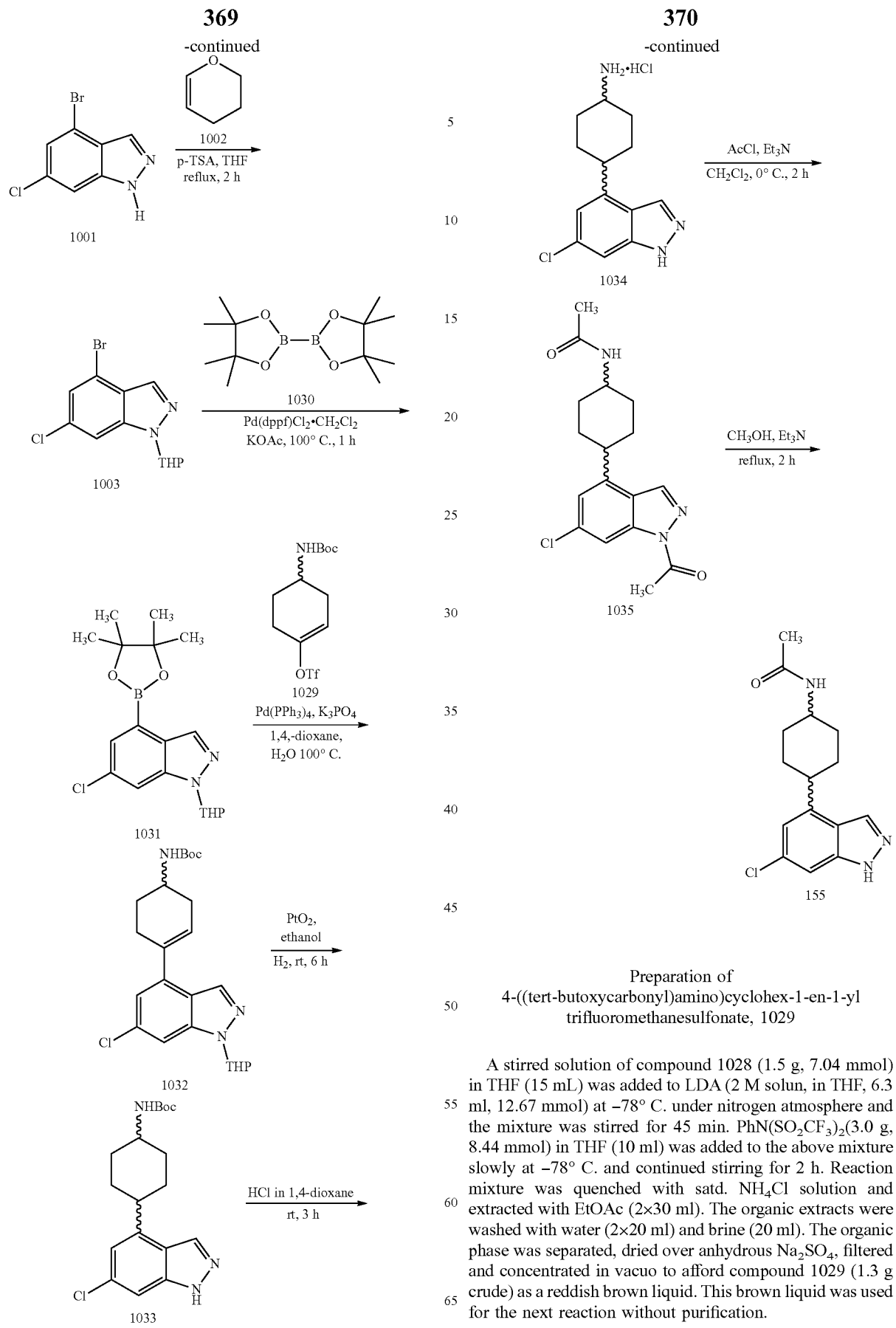

Preparation of
4-((tert-butoxycarbonyl)amino)cyclohex-1-en-1-yl
trifluoromethanesulfonate, 1029

A stirred solution of compound 1028 (1.5 g, 7.04 mmol) in THF (15 mL) was added to LDA (2 M solun, in THF, 6.3 ml, 12.67 mmol) at −78° C. under nitrogen atmosphere and the mixture was stirred for 45 min. PhN(SO$_2$CF$_3$)$_2$ (3.0 g, 8.44 mmol) in THF (10 ml) was added to the above mixture slowly at −78° C. and continued stirring for 2 h. Reaction mixture was quenched with satd. NH$_4$Cl solution and extracted with EtOAc (2×30 ml). The organic extracts were washed with water (2×20 ml) and brine (20 ml). The organic phase was separated, dried over anhydrous Na$_2$SO$_4$, filtered and concentrated in vacuo to afford compound 1029 (1.3 g crude) as a reddish brown liquid. This brown liquid was used for the next reaction without purification.

MS (MM) m/z 345.3 [M+H]$^+$.

Preparation of 4-bromo-6-chloro-1-(tetrahydro-2H-pyran-2-yl)-1H-indazole, 1003

A solution of compound 1001 (4 g, 17.28 mmol) in THF (40 ml) was treated with dihydropyran 1002 (2.18 g, 25.92 mmol) and p-toulenesulphonic acid (657 mg, 3.45 mmol) was added and the mixture was refluxed for 3 h. The reaction mixture was cooled to rt and concentrated under reduced pressure. This crude residue was purified by Combiflash using 24 g Redisep® column (hexanes/EtOAc, 0.5:9.5) to afford compound 1003 (1.5 g, 27%) as an off white solid;
MS (MM) m/z 315.6 [M+H]+.

Preparation of 6-chloro-1-(tetrahydro-2H-pyran-2-yl)-4-(4,5,5-tetramethyl-1,3,2-dioxaborolan-2-yl)-1H-indazole, 1031

A stirred solution of compound 1003 (1 g, 3.16 mmol) in 1,4-dioxane (10 mL) was added KOAc (930 mg, 9.48 mmol) and Bis(pinacolato)diboron (802 mg, 3.16 mmol). The mixture was purged with argon for 20 min. and Pd(dppf)Cl$_2$ (258 mg, 0.316 mmol) was added and refluxed for 3 h. Reaction mixture was filtered through Celite® bed and the filtrate was concentrated in vacuo to give a compound 1031 (1 g, crude) as a dark brown oil. This residue was used for the next reaction without purification.
MS (MM) m/z 362.7 [M+H]+.

6-chloro-1-(tetrahydro-2H-pyran-2-yl)-4-(4,5,5-tetramethyl-1,3,2-dioxaborolan-2-yl)-1H-indazole, 1032

A stirred solution of compound 1031 (1 g, 2.75 mmol) in a mixture of 1,4-dioxane (10 mL) and H$_2$O (2 mL) was charged with 1029 (952 mg, 2.75 mmol) followed by powdered K$_3$PO$_4$ (875 mg, 4.12 mmol) and the mixture was purged with argon for 20 min. Pd(PPh)$_4$ (317 mg, 0.27 mmol) was added into this mixture and refluxed for 3 h. Reaction mixture was filtered through Celite® bed and the filtrate was concentrated in vacuo to give a compound 1032 (600 mg, crude) as a dark brown residue. This residue was used for the next reaction without purification.
MS (MM) m/z 432.0 [M+H]+.

Preparation of tert-butyl (4-(6-chloro-1H-indazol-4-yl)cyclohexyl)carbamate, 1033

A stirred solution of compound 1032 (600 mg, 1.38 mmol) in ethanol (10 mL) was charged with PtO$_2$ (60 mg, 10 wt. %) under argon atmosphere at room temperature. Hydrogen atmosphere was introduced using a balloon and the reaction mixture was stirred for 16 h. The reaction mixtures was filtered through a Celite® bed, washed well with CH$_3$OH (20 mL) and concentrated under reduced pressure to afford compound 1033 (600 mg, crude) as a pale yellow oil. Along with the desired product, formation of des-chloro compound of 1033 was also observed by MS analysis.
MS (MM) m/z 349.9 [M+H]+.

Preparation of 4-(6-chloro-1H-indazol-4-yl)cyclohexanamine.HCl, 1034

A solution of compound 1033 (600 mg, 1.71 mmol) in CH$_2$Cl$_2$ (5 ml) was treated with HCl solution (4M soln. in dioxane, 6 ml) over 15 min. at 0° C. After being stirred at room temperature for 3 h, the solvent was concentrated under reduced pressure, co-distilled with MTBE (3×250 mL) to remove excess of HCl. The residue was further dried in vacuo to afford compound 1034 (600 mg, crude) as an off white solid;
MS (MM) m/z 249.1 [M+H]+.

Preparation of N-(4-(1-acetyl-6-chloro-1H-indazol-4-yl)cyclohexyl)acetamide, 1035

A solution of compound 1034 (200 mg, 0.802 mmol) in CH$_2$Cl$_2$ (5 mL) was treated with Et$_3$N (0.337 ml, 2.40 mmol) followed by AcCl (125 mg, 1.60 mmol) over 10 min. at 0° C. After being stirred at room temperature for 3 h, the reaction mixture was poured into water (10 ml) and extracted with CH$_2$Cl$_2$ (2×30 ml). The organic extracts were washed with water (2×20 ml) and brine (20 ml). The organic phase was separated, dried over anhydrous Na$_2$SO$_4$, filtered and concentrated in vacuo to afford compound 1035 (150 mg crude) as a yellow liquid.
MS (MM) m/z 333.8 [M+H]+.

Preparation of N-(4-(6-chloro-1H-indazol-4-yl)cyclohexyl) acetamide, 155

A solution of compound 1035 (150 mg, 0.449 mmol) in CH$_3$OH (5 mL) was treated with Et$_3$N (0.25 ml, 1.79 mmol) at rt and then the mixture was refluxed for 3 h. The reaction mixture was cooled to rt and concentrated under reduced pressure. This crude residue was purified by preparative HPLC to afford compound 155 as a mixture of cis/trans isomers (1:1) (8 mg, 6%) as an off white solid.
MS (MM) m/z 292 [M+H]+.
HPLC: >99%, Eclipse XDB-C-18 column, 220 nm.
$^1$H NMR (300 MHz, DMSO-d$_6$): δ 13.13 (s, 1H), 8.27 (s, 1H), 7.93 and 7.81 (d, J=7.5 Hz, 1H, isomer A and B), 7.41 (s, 1H), 7.02 and 6.95 (s, 1H, isomer A and B), 4.08-4.01 and 3.68-3.68 (m, 1H, isomer A and B), 3.06-2.86 (m, 1H), 1.89-1.80 (m, 6H), 1.71-1.63 (m, 4H), 1.47-1.23 (m, 2H).

Synthesis of Compound 396

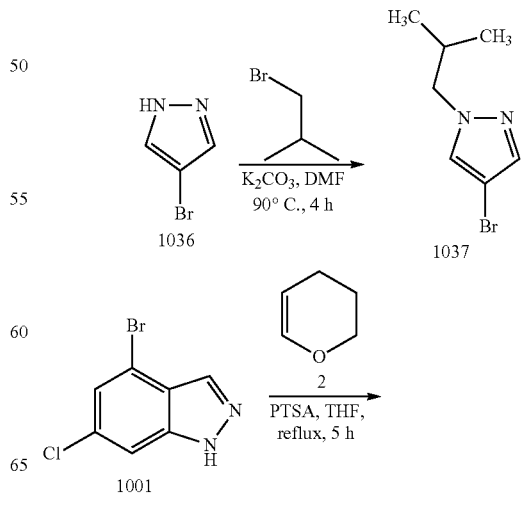

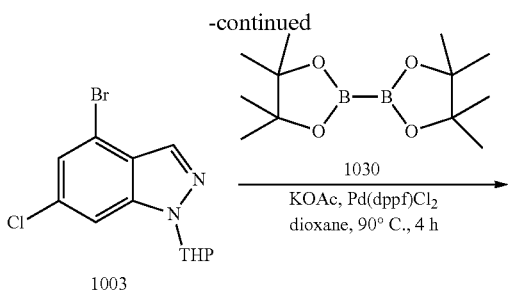

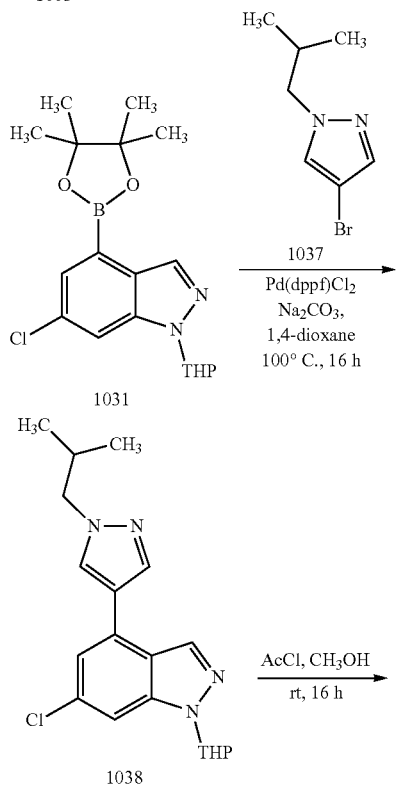

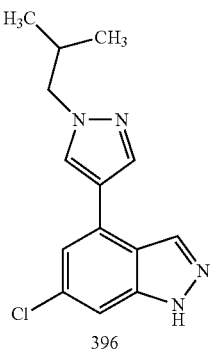 [SMILES: CC(C)Cn1cc(-c2cc(Cl)cc3[nH]ncc23)cn1]

by column chromatography (silica; hexanes/EtOAc, 6:4) to afford 1037 (350 mg, 84%) as a colourless liquid.

MS (ESI) m/z 204 [M+H]$^+$.

$^1$H NMR (400 MHz, CDCl$_3$): δ 7.47 (s, 1H), 7.36 (s, 1H), 3.88 (d, J=7.2 Hz, 2H), 2.22-2.11 (m, 1H), 0.90 (d, J=6.9 Hz, 6H).

Preparation of 6-chloro-1-(tetrahydro-2H-pyran-2-yl)-4-(4,4,5,5-tetramethyl-1,3,2-dioxaborolan-2-yl)-1H-indazole, 1031

The reaction flask was charged with bis(pinacolato)diboron 1030 (1.76 g, 6.96 mmol), KOAc (1.86 g, 18.9 mmol), and Pd(dppf)Cl$_2$ (462 mg, 0.63 mmol) and it was flushed with argon. Then, compound 1003 (2.0 g, 6.32 mmol, prepared as described above) dissolved in 1,4-dioxane (15 mL) was added. The reaction mixture was heated at 90° C. for 4 h, cooled to rt and then extracted with CH$_2$Cl$_2$ (2×100 mL). The combined organic layers were washed with brine, dried over anhydrous Na$_2$SO$_4$, concentrated in vacuo. The residue was purified by column chromatography (silica; hexanes/EtOAc, 9:1) to afford 1031 (1.1 g, 54%) as gummy solid.

MS (ESI) m/z 363 [M+H]$^+$.

$^1$H NMR (400 MHz, CDCl$_3$): δ 8.34 (d, J=1.0 Hz, 1H), 7.68-7.71 (m, 1H), 7.61 (d, J=1.7 Hz, 1H), 5.67 (dd, J=9.2, 3.0 Hz, 1H), 4.03-3.97 (m, 1H), 3.77-3.69 (m, 1H), 2.57-2.45 (m, 1H), 2.18-2.09 (m, 1H), 2.08-2.01 (m, 1H), 1.79-1.71 (m, 2H), 1.70-1.63 (m, 1H), 1.38 (s, 12H).

Preparation of 6-chloro-4-(I-isobutyl-1H-pyrazol-4-yl)-1-(tetrahydro-2H-pyran-2-yl)-1H-indazole, 1038

The reaction flask was charged with 1031 (100 mg, 0.31 mmol), 2M Na$_2$CO$_3$ (0.5 mL, 0.93 mmol) and Pd(dppf)Cl$_2$ (23 mg, 0.03 mmol) and it was flushed with argon. Then, compound 1037 (95 mg, 0.46 mmol) dissolved in 1,4-dioxane (3 mL) was added. The reaction mixture was heated at 100° C. for 16 h. The reaction mixture was cooled to rt, poured into water (50 mL) and extracted with EtOAc (2×60 mL). The combined organic phase was washed with water (2×25 mL) and brine (50 mL). The organic phase was separated, dried over Na$_2$SO$_4$, filtered and concentrated in vacuo. The residue was purified by column chromatography (silica; hexanes/EtOAc, 7:3) to afford 1038 (85 mg, 75%) as colourless liquid.

MS (ESI) m/z 359 [M+H]$^+$.

$^1$H NMR (400 MHz, CDCl$_3$): δ 8.13 (d, J=0.7 Hz, 1H), 7.90 (s, 1H), 7.74 (s, 1H), 7.48 (appt t, J=1.1, J=0.7 Hz, 1H), 7.21 (d, J=1.6 Hz, 1H) 5.67 (dd, J=9.2, 2.7 Hz, 1H), 4.06-4.01 (m, 1H), 3.99 (d, J=7.2 Hz, 2H), 3.79-3.71 (m, 1H), 2.60-2.48 (m, 1H), 2.33-2.23 (m, 1H), 2.20-2.11 (m, 1H), 2.10-2.04 (m, 1H), 1.80-1.70 (m, 2H), 1.69-1.63 (m, 1H), 0.96 (d, J=6.7 Hz, 6H).

Preparation of 6-chloro-4-(1-isobutyl-1H-pyrazol-4-yl)-1H-indazole, 396

A solution of 1038 (85 mg, 0.24 mmol) in CH$_3$OH (6 mL) was treated with AcCl (50 uL, 0.71 mmol) at room temperature. After stirring at room temperature for 16 h, the reaction mixture was basified with aq. NaHCO$_3$ solution and then concentrated in vacuo. The crude product was dissolved in water and purified by reverse phase column chromatography (C$_{18}$; H$_2$O/CH$_3$CN, 1:1) to afford 396 (28 mg, 43%) as an off-white solid.

MS (ESI) m/z 316 [M+H+CH$_3$CN]$^+$.

HPLC: >99%, Luna C18(2) Column, 254 rm.

Preparation of 4-bromo-1-isobutyl-1-pyrazole, 1037

Compound 1036 (300 mg, 2.0 mmol), 1-bromo-2-methylpropane (0.26 mL, 2.4 mmol) and K$_2$CO$_3$ (845 mg, 6.12 mmol) were dissolved in DMF (3 mL) and the mixture was heated at 90° C. in a sealed reaction vessel for 16 h. The reaction mixture was poured into water (60 mL) and extracted with EtOAc (2×60 mL). The combined organic phase was washed with brine (40 mL), dried over Na$_2$SO$_4$, filtered and concentrated in vacuo. This residue was purified $^1$H NMR (400 MHz, DMSO-d$_6$): δ 13.25 (br s, 1H), 8.49 (d, J=0.6 Hz, 1H), 8.43 (d, J=0.8 Hz, 1H), 8.13 (d, J=0.7 Hz, 1H), 7.43 (dd, J=1.5, J=1.0 Hz, 1H), 7.35 (d, J=1.6 Hz, 1H), 3.99 (d, J=7.2 Hz, 2H), 2.25-2.14 (m, 1H), 0.88 (d, J=6.6 Hz, 6H).

Synthesis of Compound 192

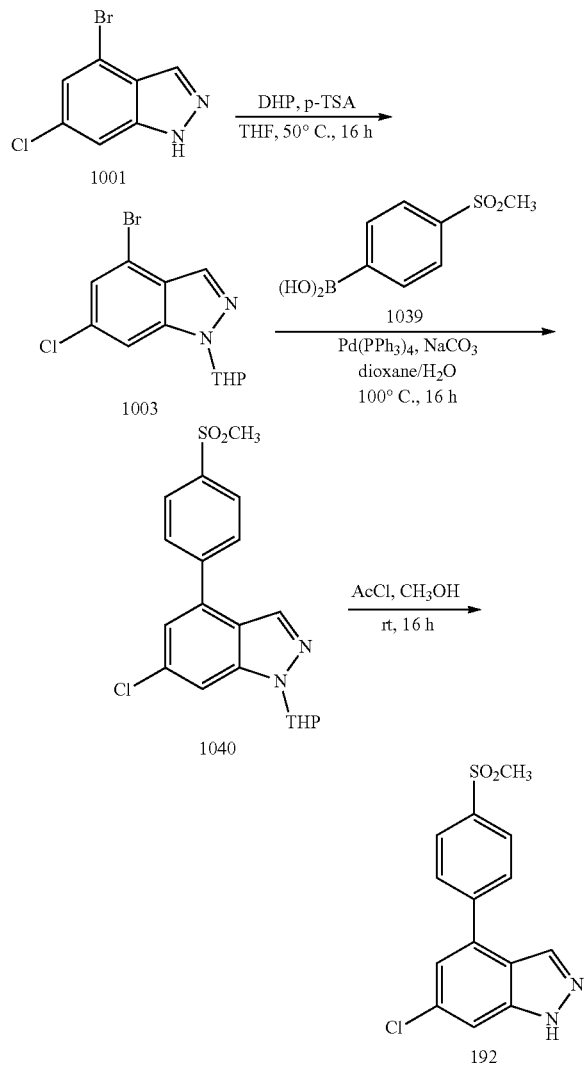

Preparation of 4-bromo-6-chloro-1-(tetrahydro-2H-pyran-2-yl)-1H-indazole, 1003

A solution of 1001 (5.0 g, 20.5 mmol) in THF (50 mL) was treated with dihydropyran (2.5 g, 30.8 mmol), p-toluenesulphonic acid (0.03 g, 0.18 mmol). After stirring at 50° C. for 16 h, the reaction mixture was concentrated in vacuo. This crude residue was purified by chromatography (silica; hexanes/EtOAc, 8.5:1.5) to afford 1003 (5.5 g, 81%) as an off-white solid.

MS (MM) m/z 316 [M+H]$^+$.

$^1$H NMR (400 MHz, CDCl$_3$): δ 7.97 (d, J=1.2 Hz, 1H), 7.57 (dd, J=1.6, 1.2 Hz, 1H), 7.32 (d, J=1.6 Hz, 1H), 5.64 (dd, J=9.2, 2.8 Hz, 1H), 4.01-3.97 (m, 1H), 3.76-3.73 (m, 1H), 2.53-2.43 (m, 1H), 2.14-2.06 (m, 2H), 1.78-1.67 (m, 3H).

Preparation of 6-chloro-4-(4-(methylsulfonyl)phenyl)-1-(tetrahydro-2H-pyran-2-yl)-1H-indazole, 1040

A solution of 1003 (2.0 g, 6.34 mmol) in a mixture of 1,4-dioxane (54 mL) and H$_2$O (6 mL) was charged with 1039 (1.9 g, 9.52 mmol) followed by Na$_2$CO$_3$ (2.0 g, 19.0 mmol) and the mixture was purged with argon for 20 min. Pd(PPh$_3$)$_4$(0.73 g, 0.63 mmol) was added and the mixture was stirred at 100° C. for 16 h. The reaction mixture were poured into water (100 mL) and extracted with EtOAc (2×60 mL). The combined organic phase was washed with water (2×25 mL) and brine (50 mL). The organic phase was separated, dried over anhydrous Na$_2$SO$_4$, filtered and concentrated in vacuo to give a dark brown residue. This residue was purified by chromatography (silica; hexanes/EtOAc, 4:6) to afford 1040 (1.2 g, 54%) as an off-white solid.

MS (MM) m/z 391 [M+H]$^+$.

$^1$H NMR (400 MHz, CDCl$_3$): δ 8.10-8.07 (m, 2H), 8.04 (d, J=0.8 Hz, 1H), 7.85-7.82 (m, 2H), 7.68 (t, J=1.2 Hz, 1H), 7.25 (d, J=1.6 Hz, 1H), 5.72 (dd, J=9.2, 2.8 Hz, 1H), 4.07-4.03 (m, 1H), 3.81-3.74 (m, 1H), 3.13 (s, 3H), 2.59-2.50 (m, 1H), 2.19-2.08 (m, 2H), 1.84-1.80 (m, 3H).

Preparation of 6-chloro-4-(4-(methylsulfonyl)phenyl)-1H-indazole, 192

A solution of 1040 (1.2 g, 3.06 mmol) in CH$_3$OH (40 mL) was treated with AcCl (7.7 g, 98.2 mmol) at room temperature over 5 min. After stirring at room temperature for 16 h, the reaction mixture was basified with solid NaHCO$_3$, filtered and concentrated in vacuo. This residue was purified by chromatography (silica; CH$_2$Cl$_2$/MeOH, 8.5:1.5) to afford 192 (0.61 g, 65%, as an off-white solid.

MS (MM) m/z 307 [M+H]$^+$.

HPLC: 97.7%, Luna C18(2) Column, UV 254 nm Detection;

$^1$H NMR (400 MHz, DMSO-d$_6$): δ 13.49 (br s, 1H), 8.25 (d, J=0.8 Hz, 1H), 8.09-8.03 (m, 4H), 7.72 (dd, J=1.6, 1.2 Hz, 1H), 7.37 (d, J=2.0 Hz, 1H), 3.30 (s, 3H).

Example 2—Assays

Exemplary compounds of the invention were prepared, and tested to determine their effect as TDO and/or IDO inhibitors. Two different assays were employed: 1. a cell-based assay for detecting the effect of test compounds on kynurenine production in two different cancer cell types. This assay utilised cancer cells which expressed either TDO or IDO and as such was used as a means of testing compound activity at these two enzymes in a cell-based context. 2. a TDO and IDO biochemical coupled assay which utilised recombinantly produced and purified TDO and IDO enzymes in combination with the enzyme formamidase. This coupled enzyme system allowed conversion of N-formylkynurenine produced by TDO or IDO activity to kynurenine which was then quantified by fluorescence following addition of Erhlich's Reagent The protocols for these are set out below.

Cell Based Assay for Detection of Kynurenine Produced by TDO and/or IDO

A172 (human glioblastoma) and SKOV3 (human ovarian adenocarcinoma) cells were seeded in a 96 well plate at 30,000 or 40,000 cells per well respectively in phenol red-free RPMI supplemented with 10% FCS, 2 mM L-glutamine and 500 µM L-tryptophan. IDO expression was induced in the SKOV3 cells by the addition of 500 ng/ml IFN-γ. Cells were incubated at 37° C. with or without the addition of test compound. After 48 hours, the cells were removed by centrifugation and Erhlich's reagent was added to the supernatant. The Erhlich's reagent was incubated for 5 minutes before the absorbance was read at 490 nM.

TDO and IDO Biochemical Coupled Assay

Recombinant human IDO or TDO was incubated in 50 mM KPO4 (pH 7.0), 0.5 mM EGTA, 0.5 mM EDTA, 0.05% Triton™ X100, 20 mM ascorbate, 10 µM methylene blue, 500 U/ml catalase, 50 µg/ml KynB (kynurenine formamidase). TDO assays were carried out in the presence of 330 µM L-tryptophan, while IDO assays had the addition of 45 µM L-tryptophan. After incubation for 17 minutes at room temperature the reactions were stopped by the addition of Erhlich's reagent and incubated at room temperature for 5 minutes before the fluorescence was read (Ex475, Em530).

The pIC50 values for a variety of test compounds are shown in Table 1 and Table 2. In these assays, compounds 340 and 341 were mixtures of cis and trans isomers and compounds 385, 386 and 415 were isolated cis or trans isomers (it has not yet been determined which).

TABLE 1 pIC50 values for Kynurenine cell-based assays determined for test compound

| Compound | A172 Kynurenine cell based assay pIC50 | SKOV3 Kynurenine cell based assay pIC50 |
|---|---|---|
| 4 | + | +/− |
| 6 | + | +/− |
| 10 | ++ | + |
| 11 | ++ | + |
| 12 | ++ | +/− |
| 13 | ++ | + |
| 14 | ++ | + |
| 15 | ++ | + |
| 16 | ++ | + |
| 17 | ++ | + |
| 18 | + | +/− |
| 19 | ++ | + |
| 20 | ++ | ++ |
| 21 | ++ | + |
| 22 | ++ | + |
| 23 | +/− | + |
| 24 | ++ | + |
| 25 | +++ | ++ |
| 26 | +++ | ++ |
| 27 | ++ | + |
| 28 | +++ | ++ |
| 29 | ++ | + |
| 30 | +++ | ++ |
| 31 | +++ | + |
| 32 | ++ | + |
| 33 | ++ | + |
| 34 | + | + |
| 36 | ++ | +/− |
| 39 | +/− | + |
| 40 | +++ | ++ |
| 41 | ++ | +/− |
| 42 | + | ++ |
| 43 | ++ | + |
| 45 | +++ | +++ |
| 46 | +++ | +++ |
| 47 | ++ | +/− |
| 48 | +++ | ++ |
| 49 | +++ | ++ |
| 50 | + | + |
| 51 | ++ | +/− |
| 52 | ++ | + |
| 53 | ++ | +++ |
| 54 | +++ | ++ |
| 55 | +++ | ++ |
| 56 | +++ | ++ |
| 57 | +++ | ++ |
| 58 | ++ | +/− |
| 59 | +++ | ++ |
| 60 | ++ | +/− |
| 61 | +++ | ++ |
| 62 | + | +/− |
| 63 | +++ | ++ |
| 64 | +++ | ++ |
| 65 | ++ | + |
| 66 | ++ | ++ |
| 67 | ++ | + |
| 68 | ++ | +/− |
| 69 | ++ | +/− |
| 70 | ++ | +/− |
| 71 | +++ | ++ |
| 72 | +++ | ++ |
| 73 | +++ | +++ |
| 74 | +++ | ++ |
| 75 | + | +/− |
| 76 | +++ | ++ |
| 77 | +++ | ++ |
| 78 | +++ | +++ |
| 79 | +++ | +++ |
| 80 | +++ | ++ |
| 81 | +++ | ++ |
| 82 | +++ | ++ |
| 83 | +++ | ++ |
| 84 | +++ | ++ |
| 85 | ++ | + |
| 86 | ++ | ++ |
| 87 | +++ | ++ |
| 88 | +++ | ++ |
| 89 | +++ | ++ |
| 90 | +++ | +++ |
| 91 | +++ | +++ |
| 92 | +++ | ++ |
| 93 | +++ | ++ |
| 94 | +++ | ++ |
| 95 | ++ | +/− |
| 96 | +++ | ++ |
| 97 | +++ | + |
| 98 | +++ | ++ |
| 99 | +++ | ++ |
| 100 | +++ | ++ |
| 101 | ++ | +/− |
| 102 | +++ | ++ |
| 103 | +++ | +/− |
| 104 | ++ | + |
| 105 | +/− | + |
| 106 | ++ | +/− |
| 107 | +++ | ++ |
| 108 | +++ | ++ |
| 109 | +++ | ++ |
| 110 | +++ | ++ |
| 111 | +++ | ++ |
| 112 | +++ | ++ |
| 113 | +++ | ++ |
| 114 | +++ | ++ |
| 115 | +++ | ++ |
| 116 | +++ | ++ |
| 117 | +++ | ++ |

TABLE 1-continued pIC50 values for Kynurenine cell-based assays determined for test compound

| Compound | A172 Kynurenine cell based assay pIC50 | SKOV3 Kynurenine cell based assay pIC50 |
|---|---|---|
| 118 | +++ | ++ |
| 119 | +++ | ++ |
| 120 | +/− | ++ |
| 121 | ++ | +/− |
| 122 | +++ | ++ |
| 123 | +++ | ++ |
| 124 | +++ | ++ |
| 125 | +++ | + |
| 126 | +++ | ++ |
| 127 | +++ | ++ |
| 128 | +++ | ++ |
| 129 | +++ | ++ |
| 130 | +++ | ++ |
| 131 | +/− | + |
| 132 | +++ | ++ |
| 133 | +++ | +++ |
| 134 | +++ | +++ |
| 135 | + | ++ |
| 136 | +++ | ++ |
| 137 | +++ | +++ |
| 138 | +++ | ++ |
| 139 | + | +/− |
| 140 | +++ | ++ |
| 141 | +++ | ++ |
| 142 | ++ | +/− |
| 143 | +++ | ++ |
| 144 | +++ | +++ |
| 145 | +++ | ++ |
| 146 | + | +/− |
| 147 | ++ | ++ |
| 148 | ++ | + |
| 149 | ++ | ++ |
| 150 | +++ | ++ |
| 151 | +/− | ++ |
| 152 | ++ | +/− |
| 153 | +++ | + |
| 154 | +++ | ++ |
| 155 | +++ | ++ |
| 156 | ++ | + |
| 157 | +/− | + |
| 158 | ++ | ++ |
| 159 | ++ | ++ |
| 160 | +++ | ++ |
| 161 | +++ | +++ |
| 162 | +/− | + |
| 163 | +/− | + |
| 164 | +++ | + |
| 165 | +++ | + |
| 166 | +++ | + |
| 167 | +++ | ++ |
| 168 | +++ | ++ |
| 169 | ++ | +/− |
| 170 | +++ | ++ |
| 171 | ++ | +/− |
| 172 | +++ | ++ |
| 173 | +++ | ++ |
| 174 | +++ | ++ |
| 175 | +++ | ++ |
| 176 | +++ | ++ |
| 177 | +++ | ++ |
| 178 | ++ | +/− |
| 179 | + | + |
| 180 | ++ | + |
| 181 | +++ | +++ |
| 182 | +++ | ++ |
| 183 | +++ | ++ |
| 184 | +++ | ++ |
| 185 | +++ | +++ |
| 186 | +/− | ++ |
| 187 | ++ | + |
| 188 | +++ | ++ |
| 189 | ++ | ++ |
| 190 | +++ | ++ |
| 191 | +++ | +/− |
| 192 | +++ | ++ |
| 193 | +++ | ++ |
| 194 | ++ | ++ |
| 195 | +++ | ++ |
| 196 | +++ | ++ |
| 197 | +++ | ++ |
| 198 | +++ | ++ |
| 199 | +++ | + |
| 200 | +++ | ++ |
| 201 | ++ | + |
| 202 | +++ | + |
| 203 | +++ | ++ |
| 204 | +++ | +/− |
| 205 | +++ | +/− |
| 206 | ++ | +/− |
| 207 | +++ | ++ |
| 208 | +++ | ++ |
| 209 | + | + |
| 210 | ++ | + |
| 211 | ++ | + |
| 212 | +++ | + |
| 213 | + | + |
| 214 | +++ | ++ |
| 215 | +++ | ++ |
| 216 | +++ | ++ |
| 217 | +/− | + |
| 218 | +/− | + |
| 219 | +++ | ++ |
| 220 | +++ | ++ |
| 221 | ++ | + |
| 222 | ++ | + |
| 223 | ++ | + |
| 224 | +++ | + |
| 225 | ++ | ++ |
| 226 | +++ | ++ |
| 227 | +++ | +++ |
| 228 | +++ | ++ |
| 229 | ++ | + |
| 230 | +++ | + |
| 231 | +++ | ++ |
| 232 | +++ | ++ |
| 233 | +++ | ++ |
| 234 | +++ | + |
| 235 | +++ | ++ |
| 236 | + | + |
| 237 | + | + |
| 238 | ++ | + |
| 239 | +++ | ++ |
| 240 | +++ | ++ |
| 241 | ++ | ++ |
| 242 | ++ | + |
| 243 | +++ | ++ |
| 244 | + | + |
| 245 | +++ | ++ |
| 246 | +++ | ++ |
| 247 | ++ | + |
| 248 | +++ | ++ |
| 249 | +++ | ++ |
| 250 | +++ | ++ |
| 251 | +++ | ++ |
| 252 | +++ | + |
| 253 | +++ | +/− |
| 254 | +++ | ++ |
| 255 | +++ | ++ |
| 256 | +++ | ++ |
| 257 | +++ | ++ |
| 258 | +/− | ++ |
| 259 | +++ | + |
| 260 | +++ | ++ |
| 261 | + | +/− |

TABLE 1-continued pIC50 values for Kynurenine cell-based assays determined for test compound

| Compound | A172 Kynurenine cell based assay pIC50 | SKOV3 Kynurenine cell based assay pIC50 |
| --- | --- | --- |
| 262 | +/− | ++ |
| 263 | ++ | ++ |
| 264 | +++ | +++ |
| 265 | +++ | ++ |
| 266 | +++ | ++ |
| 267 | +++ | ++ |
| 268 | +++ | ++ |
| 269 | +++ | ++ |
| 270 | +++ | ++ |
| 271 | +++ | + |
| 272 | +++ | ++ |
| 273 | +++ | ++ |
| 274 | ++ | + |
| 275 | + | + |
| 276 | +++ | ++ |
| 277 | +++ | ++ |
| 278 | +++ | ++ |
| 279 | +++ | +++ |
| 280 | +++ | ++ |
| 281 | +++ | ++ |
| 282 | +++ | ++ |
| 283 | ++ | ++ |
| 284 | ++ | + |
| 285 | ++ | + |
| 286 | ++ | ++ |
| 287 | ++ | +/− |
| 288 | +++ | +/− |
| 289 | +++ | + |
| 290 | +++ | +++ |
| 291 | +++ | ++ |
| 292 | +++ | ++ |
| 293 | +++ | + |
| 294 | +++ | + |
| 295 | +/− | + |
| 296 | ++ | ++ |
| 297 | +++ | +++ |
| 298 | ++ | ++ |
| 299 | +++ | +/− |
| 300 | +++ | ++ |
| 301 | ++ | +/− |
| 302 | ++ | ++ |
| 303 | ++ | +/− |
| 304 | +++ | + |
| 305 | ++ | + |
| 306 | ++ | ++ |
| 307 | +/− | ++ |
| 308 | +++ | +/− |
| 309 | +++ | +/− |
| 310 | + | +/− |
| 311 | ++ | ++ |
| 312 | ++ | +/− |
| 313 | +++ | ++ |
| 314 | +++ | + |
| 315 | +++ | +++ |
| 316 | +++ | ++ |
| 317 | +/− | + |
| 318 | ++ | +/− |
| 319 | +++ | + |
| 320 | +++ | ++ |
| 321 | ++ | ++ |
| 322 | ++ | ++ |
| 323 | + | + |
| 324 | +++ | ++ |
| 325 | + | + |
| 326 | ++ | ++ |
| 327 | ++ | ++ |
| 328 | +++ | ++ |
| 329 | +++ | +++ |
| 330 | +++ | +++ |
| 331 | +++ | +++ |
| 332 | +++ | +/− |
| 333 | ++ | + |
| 334 | +++ | ++ |
| 335 | +++ | ++ |
| 336 | +++ | ++ |
| 337 | +/− | ++ |
| 338 | ++ | +/− |
| 339 | +++ | ++ |
| 340 | ++ | + |
| 341 | ++ | + |
| 342 | +++ | ++ |
| 343 | +++ | + |
| 344 | +++ | ++ |
| 345 | +++ | ++ |
| 346 | +++ | ++ |
| 347 | +++ | ++ |
| 348 | +++ | ++ |
| 349 | +++ | + |
| 350 | +++ | ++ |
| 351 | +++ | ++ |
| 352 | +++ | +++ |
| 353 | +++ | + |
| 354 | +++ | ++ |
| 355 | +++ | ++ |
| 356 | ++ | ++ |
| 357 | +++ | +++ |
| 358 | +++ | ++ |
| 359 | +++ | ++ |
| 360 | +++ | ++ |
| 361 | +++ | ++ |
| 362 | ++ | ++ |
| 363 | +++ | ++ |
| 364 | +++ | ++ |
| 365 | +++ | ++ |
| 366 | +++ | ++ |
| 367 | +++ | ++ |
| 368 | ++ | ++ |
| 369 | +++ | ++ |
| 370 | +++ | +++ |
| 371 | ++ | ++ |
| 372 | +++ | ++ |
| 373 | +++ | + |
| 374 | +++ | + |
| 375 | +++ | ++ |
| 376 | +++ | ++ |
| 377 | +++ | ++ |
| 378 | +++ | ++ |
| 379 | +++ | +/− |
| 380 | ++ | ++ |
| 382 | +++ | ++ |
| 383 | + | +/− |
| 384 | +++ | ++ |
| 385 | + | + |
| 386 | ++ | ++ |
| 387 | +++ | ++ |
| 388 | +++ | +++ |
| 389 | +++ | +++ |
| 390 | +++ | +++ |
| 391 | +++ | +++ |
| 392 | +++ | +++ |
| 393 | +++ | + |
| 394 | +++ | +++ |
| 395 | +++ | +++ |
| 396 | +++ | +/− |
| 397 | +++ | +/− |
| 398 | +++ | +/− |
| 399 | +++ | +/− |
| 400 | +++ | +++ |
| 401 | +++ | +/− |
| 402 | +++ | +++ |
| 403 | +++ | +/− |
| 404 | ++ | +++ |
| 405 | +++ | +++ |
| 406 | +++ | +++ |

TABLE 1-continued pIC50 values for Kynurenine cell-based assays determined for test compound

| Compound | A172 Kynurenine cell based assay pIC50 | SKOV3 Kynurenine cell based assay pIC50 |
|---|---|---|
| 407 | +++ | +++ |
| 408 | +++ | +++ |
| 409 | ++ | +/− |
| 410 | +++ | ++ |
| 411 | +++ | +++ |
| 412 | +++ | +/− |
| 413 | +++ | ++ |
| 414 | +++ | +/− |
| 415 | ++ | +/− |
| 416 | +++ | ++ |
| 417 | +++ | +/− |
| 418 | +++ | +/− |
| 419 | +++ | +/− |
| 420 | +++ | +/− |
| 421 | +++ | +/− |
| 422 | +++ | +++ |
| 423 | +++ | ++ |
| 424 | +++ | +++ |
| 425 | +++ | +/− |
| 426 | +++ | +/− |
| 427 | +++ | +/− |
| 428 | +++ | ++ |
| 429 | +++ | ++ |
| 430 | ++ | +/− |
| 431 | +++ | +/− |
| 432 | +++ | +/− |
| 433 | ++ | +/− |
| 434 | +++ | +/− |
| 435 | +++ | +/− |
| 436 | +++ | +/− |
| 437 | +++ | +++ |
| 438 | +++ | +/− |
| 439 | +++ | +/− |
| 440 | +++ | ++ |
| 441 | +++ | +++ |
| 442 | +++ | +/− |
| 443 | +++ | +/− |
| 444 | +++ | +/− |
| 445 | +++ | +++ |
| 446 | +++ | +++ |
| 447 | +++ | +/− |
| 448 | +++ | +/− |
| 449 | +++ | ++ |
| 450 | +++ | +++ |
| 451 | +++ | +/− |
| 452 | +++ | +++ |
| 453 | +++ | +/− |
| 454 | +++ | +/− |
| 455 | +++ | +/− |
| 456 | +++ | NT |

Key:
+++ = pIC$_{50}$ ≥ 5.50
++ = pIC$_{50}$ 4.50-5.49
+ = pIC$_{50}$ 4.00-4.49
+/− = pIC$_{50}$ < 4.00

TABLE 2 pIC50 values for IDO and TDO inhibition determined for test compounds

| Compound | hTDO biochemical assay pIC50 | hIDO biochemical assay pIC50 |
|---|---|---|
| 1 | ++ | +/− |
| 2 | + | +/− |
| 3 | ++ | +/− |
| 4 | +++ | +/− |
| 5 | + | +/− |
| 7 | + | +/− |
| 8 | ++ | +/− |
| 9 | + | +/− |
| 10 | ++ | +/− |
| 11 | + | +/− |
| 12 | ++ | +/− |
| 14 | + | +/− |
| 15 | + | +/− |
| 17 | ++ | +/− |
| 19 | ++ | +/− |
| 21 | ++ | +/− |
| 22 | ++ | +/− |
| 25 | +++ | + |
| 26 | +++ | ++ |
| 28 | +++ | ++ |
| 30 | +++ | +++ |
| 34 | ++ | +/− |
| 35 | ++ | +/− |
| 36 | +++ | +/− |
| 37 | + | + |
| 38 | + | + |
| 40 | +++ | +++ |
| 41 | + | +/− |
| 44 | +++ | +/− |
| 45 | +++ | +++ |
| 78 | +++ | ++ |
| 91 | +++ | +++ |
| 97 | +++ | ++ |
| 137 | +++ | +++ |
| 183 | +++ | ++ |
| 192 | +++ | ++ |
| 198 | +++ | ++ |
| 199 | +++ | +/− |
| 207 | +++ | ++ |
| 209 | + | +/− |
| 210 | ++ | +/− |
| 211 | +++ | + |
| 212 | +++ | +/− |
| 213 | +/− | +/− |
| 214 | +++ | + |
| 215 | +++ | ++ |
| 216 | +++ | +/− |
| 217 | +/− | +/− |
| 218 | +/− | + |
| 219 | +++ | ++ |
| 220 | NT | +/− |
| 221 | NT | +/− |
| 222 | NT | ++ |
| 223 | NT | ++ |
| 224 | NT | + |
| 225 | NT | ++ |
| 226 | +++ | +++ |
| 227 | +++ | +++ |
| 228 | +++ | ++ |
| 229 | NT | +/− |
| 230 | NT | +/− |
| 231 | +++ | ++ |
| 232 | +++ | ++ |
| 233 | NT | + |
| 234 | NT | ++ |
| 235 | NT | +/− |
| 236 | NT | +/− |
| 237 | NT | +/− |
| 238 | NT | +/− |
| 239 | NT | + |
| 240 | NT | +/− |
| 241 | NT | +/− |
| 242 | NT | +/− |
| 243 | NT | + |
| 244 | NT | +/− |
| 245 | NT | ++ |
| 246 | +++ | +/− |
| 247 | NT | +/− |
| 248 | NT | ++ |

TABLE 2-continued pIC50 values for IDO and TDO inhibition determined for test compounds

| Compound | hTDO biochemical assay pIC50 | hIDO biochemical assay pIC50 |
|---|---|---|
| 249 | +++ | ++ |
| 250 | +++ | + |
| 251 | +++ | +++ |
| 252 | +++ | +/− |
| 253 | NT | +/− |
| 254 | NT | + |
| 255 | ++ | +/− |
| 256 | +++ | +/− |
| 257 | +++ | +/− |
| 258 | NT | +/− |
| 259 | +++ | +/− |
| 260 | +++ | ++ |
| 261 | NT | +/− |
| 262 | NT | +/− |
| 263 | NT | ++ |
| 264 | +++ | ++ |
| 265 | +++ | ++ |
| 266 | +++ | +/− |
| 267 | +++ | ++ |
| 268 | +++ | + |
| 269 | +++ | +/− |
| 270 | NT | ++ |
| 271 | +++ | +/− |
| 272 | +++ | + |
| 273 | +++ | ++ |
| 274 | NT | +/− |
| 275 | NT | +/− |
| 276 | NT | +/− |
| 277 | +++ | +/− |
| 278 | +++ | + |
| 279 | +++ | +/− |
| 280 | +++ | ++ |
| 281 | +++ | ++ |
| 282 | +++ | + |
| 283 | +++ | +/− |
| 284 | +++ | +/− |
| 285 | ++ | +/− |
| 286 | +++ | +/− |
| 287 | ++ | +/− |
| 288 | +++ | +/− |
| 289 | +++ | + |
| 290 | +++ | +++ |
| 291 | +++ | +/− |
| 292 | NT | +/− |
| 293 | NT | +/− |
| 294 | NT | +/− |
| 295 | +/− | +/− |
| 296 | NT | +/− |
| 297 | +++ | ++ |
| 298 | +++ | ++ |
| 299 | +++ | +/− |
| 300 | +++ | + |
| 301 | +++ | + |
| 302 | +/− | +/− |
| 303 | +/− | +/− |
| 304 | +++ | +/− |
| 305 | + | +/− |
| 306 | +/− | +/− |
| 307 | +++ | +++ |
| 308 | ++ | + |
| 309 | ++ | +/− |
| 310 | +/− | +/− |
| 311 | + | +/− |
| 312 | +/− | +/− |
| 313 | +++ | ++ |
| 314 | +++ | + |
| 315 | +++ | +++ |
| 316 | +++ | ++ |
| 317 | ++ | +/− |
| 318 | ++ | +/− |
| 319 | +++ | ++ |
| 320 | +++ | ++ |
| 321 | +/− | +/− |
| 322 | +/− | +/− |
| 323 | +/− | +/− |
| 324 | +++ | +/− |
| 325 | +/− | +/− |
| 326 | +++ | ++ |
| 327 | ++ | +/− |
| 328 | +++ | +/− |
| 329 | +++ | +++ |
| 330 | +++ | +++ |
| 331 | +++ | +++ |
| 332 | +++ | +/− |
| 333 | +++ | +/− |
| 334 | +++ | +++ |
| 335 | +++ | ++ |
| 336 | +++ | ++ |
| 337 | +/− | +/− |
| 338 | +/− | +/− |
| 339 | +++ | +++ |
| 340 | +/− | +/− |
| 341 | +/− | +/− |
| 342 | +++ | +/− |
| 343 | +++ | +/− |
| 344 | +++ | ++ |
| 345 | +++ | ++ |
| 346 | +++ | +/− |
| 347 | +++ | +/− |
| 348 | +++ | +/− |
| 349 | +++ | + |
| 350 | +++ | + |
| 351 | +++ | + |
| 352 | +++ | ++ |
| 353 | +++ | +/− |
| 354 | +++ | +/− |
| 355 | +++ | + |
| 356 | ++ | +/− |
| 357 | ++ | +/− |
| 358 | +++ | +/− |
| 359 | +++ | ++ |
| 360 | +++ | + |
| 361 | +++ | ++ |
| 362 | +++ | +/− |
| 363 | +++ | + |
| 364 | +++ | +/− |
| 365 | +++ | +/− |
| 366 | ++ | +/− |
| 367 | +++ | ++ |
| 368 | ++ | +/− |
| 369 | +++ | ++ |
| 370 | +++ | +++ |
| 371 | +++ | +/− |
| 372 | +++ | +/− |
| 373 | ++ | +/− |
| 374 | ++ | +/− |
| 375 | +++ | +/− |
| 376 | +++ | +/− |
| 377 | +++ | + |
| 378 | +++ | +/− |
| 379 | +++ | +/− |
| 380 | ++ | +/− |
| 382 | +++ | +/− |
| 383 | +/− | +/− |
| 384 | +++ | ++ |
| 385 | +/− | +/− |
| 386 | ++ | +/− |
| 387 | +++ | ++ |
| 388 | +++ | +++ |
| 389 | +++ | +++ |
| 390 | +++ | +++ |
| 391 | +++ | +++ |
| 392 | +++ | +++ |
| 393 | +++ | + |
| 394 | +++ | ++ |
| 395 | +++ | +/− |
| 396 | ++ | +/− |
| 397 | +++ | +/− |

TABLE 2-continued pIC50 values for IDO and TDO inhibition determined for test compounds

| Compound | hTDO biochemical assay pIC50 | hIDO biochemical assay pIC50 |
|---|---|---|
| 398 | +++ | +/− |
| 399 | +/− | +/− |
| 400 | +++ | +++ |
| 401 | +++ | +/− |
| 402 | +++ | + |
| 403 | +++ | +/− |
| 404 | +++ | + |
| 405 | +++ | +++ |
| 406 | +++ | +++ |
| 407 | +++ | +++ |
| 408 | +++ | +++ |
| 409 | +++ | + |
| 410 | +++ | +/− |
| 411 | +++ | +/− |
| 412 | +++ | +++ |
| 413 | +++ | +++ |
| 414 | +++ | + |
| 415 | ++ | +/− |
| 416 | +++ | +++ |
| 417 | +++ | +/− |
| 418 | +++ | +/− |
| 419 | +++ | +/− |
| 420 | +++ | ++ |
| 421 | +++ | ++ |
| 422 | +++ | ++ |
| 423 | +++ | +++ |
| 424 | +++ | +++ |
| 425 | +++ | +/− |
| 426 | +++ | ++ |
| 427 | ++ | +/− |
| 428 | +++ | ++ |
| 429 | +++ | ++ |
| 430 | +++ | +++ |
| 431 | +++ | +++ |
| 432 | +++ | ++ |
| 433 | +++ | +/− |
| 434 | +++ | +/− |
| 435 | +++ | ++ |
| 436 | +++ | +/− |
| 437 | +++ | ++ |
| 438 | +++ | ++ |
| 439 | +++ | ++ |
| 440 | +++ | ++ |
| 441 | +++ | +/− |
| 442 | +++ | ++ |
| 443 | +++ | +/− |
| 444 | +++ | +/− |
| 445 | +++ | +/− |
| 446 | +++ | +/− |
| 447 | +++ | ++ |
| 448 | +++ | ++ |
| 449 | +++ | ++ |
| 450 | +++ | +++ |
| 451 | +++ | + |
| 452 | +++ | +/− |
| 453 | +++ | ++ |
| 454 | +++ | + |
| 455 | +++ | ++ |
| 456 | +++ | +++ |

Key:
+++ = $pIC_{50} \geq 5.50$
++ = $pIC_{50}$ 4.50-5.49
+ = $pIC_{50}$ 4.00-4.49
+/− = $pIC_{50}$ < 4.00
NT = Not tested Table 3 shows more detailed pIC50 values for selected compounds which were synthesised in Example 1.

TABLE 3

| Compound | A172 Kynurenine cell based assay pIC50 | SKOV3 Kynurenine cell based assay pIC50 | hTDO biochemical assay pIC50 | hIDO biochemical assay pIC50 |
|---|---|---|---|---|
| 45 | 8.00 | 6.43 | 6.58 | 6.35 |
| 393 | 7.26 | 4.42 | 6.61 | 4.29 |
| 28 | 6.47 | 4.98 | 634 | 4.65 |
| 40 | 7.08 | 5.08 | 6.52 | 5.63 |
| 424 | 7.12 | 6.84 | 6.62 | 6.46 |
| 273 | 7.87 | 5.02 | 7.07 | 4.93 |
| 155 | 6.62 | 4.91 | NT | 3.72 |
| 396 | 6.08 | <5 | 5.44 | <3.59 |
| 192 | 7.61 | 5.25 | 6.89 | 4.81 |

The Tables show that a large number of the test compounds show strong TDO and IDO inhibitory function.

The invention claimed is:

1. A compound having a formula selected from one of the following, or a pharmaceutically acceptable salt thereof:

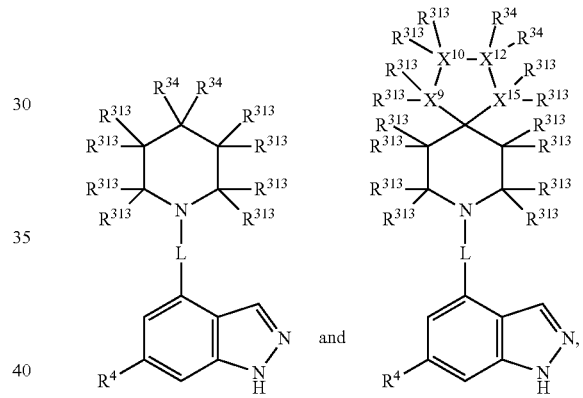

wherein L is absent;
R[4] is selected from hydrogen, halogen, $C_1$-$C_6$ alkyl, —$CF_3$, —$OCF_3$, $C_3$-$C_6$ cycloalkyl, $C_1$-$C_6$ alkoxy, nitrile, —N(CH$_3$)—C(O)CH$_3$, —N(CH$_3$)—SO$_2$CH$_3$, an aromatic group, and a heterocyclic group,
each R[34] is independently selected from H and a group selected from the following groups:
   a halogen selected from —F, —Cl, —Br and —I,
   a substituted or unsubstituted linear or branched $C_1$-$C_6$ alkyl group selected from Me, Et, Pr, i-Pr, n-Bu, i-Bu, t-Bu, pentyl, and hexyl;
   a substituted or unsubstituted linear or branched $C_1$-$C_6$ alkyl-aryl group selected from —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph;
   a substituted or unsubstituted linear or branched $C_1$-$C_6$ halogenated alkyl group selected from —CH$_2$F, —CH$_2$Cl, —CF$_3$, —CCl$_3$-CBr$_3$, —Cl$_3$, —CH$_2$CF$_3$, —CH$_2$CCl$_3$, —CH$_2$CBr$_3$, and —CH$_2$Cl$_3$);
   an —NH$_2$ group, or a substituted or unsubstituted linear or branched primary, secondary or tertiary $C_1$-$C_6$ amine group selected from —NMeH, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt;

a substituted or unsubstituted amino-aryl group selected from —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2, (3,4,5 or 6)F$_2$-Ph, —NH-2, (3,4,5 or 6)Cl2-Ph, —NH-2, (3,4,5 or 6)Br$_2$-Ph, —NH-2, (3,4,5 or 6)I$_2$-Ph, —NH-2, (3,4,5 or 6)Me$_2$-Ph, —NH-2, (3,4,5 or 6)Et$_2$-Ph, —NH-2, (3,4,5 or 6)Pr$_2$-Ph, and —NH-2, (3,4,5 or 6)Bu$_2$-Ph;

a substituted or unsubstituted cyclic amine or amido group selected from pyrrolidin-1-yl, pyrrolidin-2-yl, pyrrolidin-3-yl, piperidin-1-yl, piperidin-2-yl, piperidin-3-yl, piperidin-4-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, and 4-keto-piperidinyl;

a substituted or unsubstituted cyclic C3-C8 alkyl group selected from cyclopropyl, cyclobutyl, cyclopentyl, cyclohexyl, cycloheptyl and cyclooctyl;

an —OH or a substituted or unsubstituted linear or branched $C_1$-$C_6$ alcohol group selected from —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched $C_1$-$C_6$ carboxylic acid group selected from —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH;

a substituted or unsubstituted linear or branched carbonyl group selected from —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe, —(CO)-cyclopropyl, —(CO)-1,3-epoxypropan-2-yl, —(CO)NH$_2$, —(CO)NHMe, —(CO)NMe$_2$, —(CO)NHEt, —(CO)NEt$_2$, —(CO)-pyrollidine —N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;

a substituted or unsubstituted linear or branched $C_1$-$C_6$ carboxylic acid ester group selected from —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);

a substituted or unsubstituted linear or branched $C_1$-$C_6$ amide group selected from —CO—NH$_2$, —CO—NMeH, —CO—NMe, —CO—NEtH, —CO—NEtMe, —CO—NEt$_2$, —CO—NPrH, —CO—NPrMe, and —CO—NPrEt;

a substituted or unsubstituted linear or branched $C_1$-$C_7$ amino carbonyl group selected from —NH—CO-Me, —NH—CO-Et, —NH—CO-Pr, —NH—CO-Bu, —NH—CO-pentyl, —NH—CO-hexyl, —NH—CO-Ph, —NMe-CO-Me, —NMe-CO-Et, —NMe-CO-Pr, —NMe-CO-Bu, —NMe-CO-pentyl, —NMe-CO-hexyl, and —NMe-CO-Ph;

a substituted or unsubstituted linear or branched $C_1$-$C_7$ alkoxy or aryloxy group selected from —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —O-Ph, —O-CH$_2$-Ph, —O-CH$_2$-(2,3 or 4)-F-Ph, —O-CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe;

a substituted or unsubstituted linear or branched amino-alkoxy group selected from —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted sulphonyl group selected from —SO$_2$Me, —SO$_2$Et, —SO$_2$Pr, —SO$_2$iPr, —SO$_2$Ph, —SO$_2$-(2,3 or 4)-F-Ph, —SO$_2$—cyclopropyl, —SO$_2$CH$_2$CH$_2$OCH$_3$), —SO$_2$NH$_2$, —SO$_2$NHMe, —SO$_2$NMe$_2$, —SO$_2$NHEt, —SO$_2$NEt$_2$, —SO$_2$-pyrrolidine-N-yl, —SO$_2$-morpholine-N-yl, —SO$_2$NHCH$_2$OMe, and —SO$_2$NHCH$_2$CH$_2$OMe;

a substituted or unsubstituted aminosulphonyl group selected from —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, and —NHSO$_2$CH$_2$CH$_2$OCH$_3$;

a substituted or unsubstituted aromatic group selected from Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F$_2$-Ph-, 2, (3,4,5 or 6)-C12-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-C12-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$ -Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH)-Ph-, 4-(NH)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-; and a saturated or unsaturated, substituted or unsubstituted heterocyclic group selected from pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl, tetrazole-1-yl, tetrazole-2-yl, and tetrazole-5-yl;

each $R^{313}$ is independently selected from H, —OH, halogen and $C_1$-$C_6$ alkyl;

or alternatively, two $R^{313}$ groups attached to the same atom together form a carbonyl group (=O).

$X^9$, $X^{10}$, $X^{12}$ and $X^{15}$ are independently selected from C, N and O, and at least one of $X^9$, $X^{10}$, $X^{12}$ and $X^{15}$ is an N, in which the N is substituted by —R";

wherein R" is selected from H and any of the following groups:

a substituted or unsubstituted linear or branched $C_1$-$C_6$ alkyl group selected from Me, Et, Pr, i-Pr, n-Bu, i-Bu, t-Bu, pentyl, and hexyl);

a substituted or unsubstituted linear or branched $C_2$-$C_6$ alcohol group selected from —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$OH, and —CH$_2$CH$_2$CH$_2$CH$_2$CH$_2$OH;

a substituted or unsubstituted linear or branched $C_1$-$C_7$ alkoxy or aryloxy group linked through —O via at least two further C atoms selected from —CH$_2$CH$_2$OPh, —CH$_2$CH$_2$OMe, —CH$_2$CH$_2$OEt, —CH$_2$CH$_2$OPr, —CH$_2$CH$_2$OBu, —CH$_2$CH$_2$CH$_2$OPh, —CH$_2$CH$_2$CH$_2$OMe, —CH$_2$CH$_2$CH$_2$CH$_2$OMe, and —CH$_2$CH$_2$CH$_2$CH$_2$CH$_2$OMe;

a substituted or unsubstituted linear or branched $C_1$-$C_6$ halogenated alkyl group selected from —CH$_2$F, —CF$_3$, and —CH$_2$CF$_3$;

a substituted or unsubstituted cyclic amine or amido group selected from pyrrolidin-3-yl, piperidin-3-yl, piperidin-4-yl, 2-keto-pyrrolidinyl, 3-keto-pyrrolidinyl, 2-keto-piperidinyl, 3-keto-piperidinyl, and 4-keto-piperidinyl; which group is attached via a —CH$_2$— or a —CH$_2$CH$_2$— group;

a substituted or unsubstituted cyclic $C_3$-$C_8$ alkyl group selected from cyclopropyl, cyclobutyl, cyclopentyl, cyclohexyl, cycloheptyl and cyclooctyl;

a substituted or unsubstituted aromatic group selected from Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F$_2$-Ph-, 2, (3,4,5 or 6)-C12-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-C12-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph; and a saturated or unsaturated, substituted or unsubstituted, heterocyclic group selected from pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran- 6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl, and tetrazole-5-yl.

2. The compound of claim 1, or a pharmaceutically acceptable salt thereof, having the following formula:

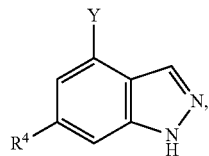

wherein Y is selected from the following formulae:

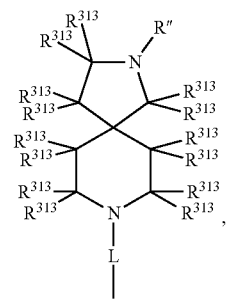

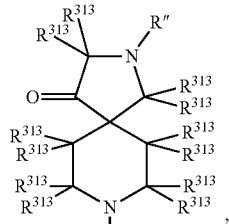

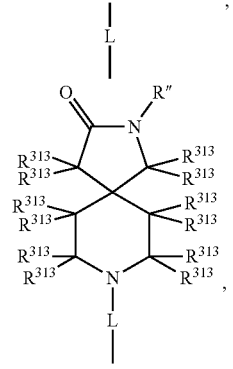

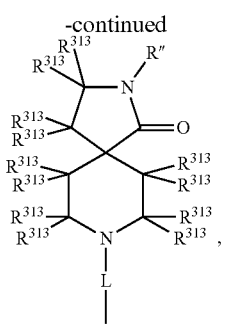

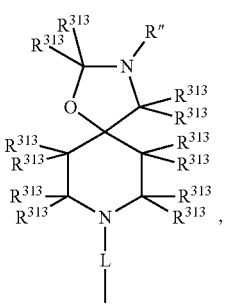

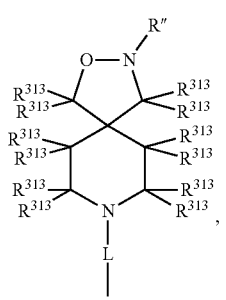

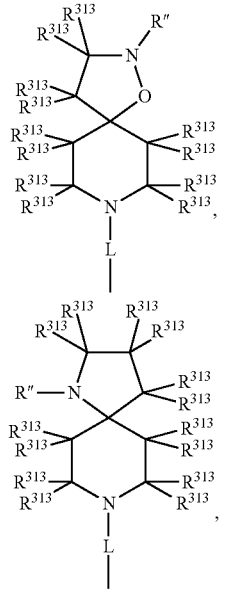

395
-continued
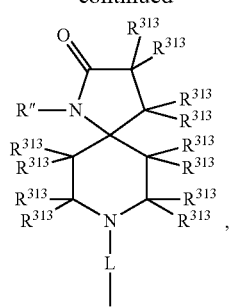
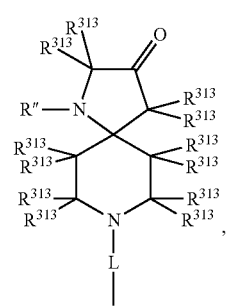
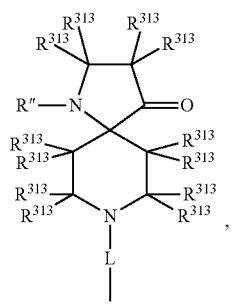
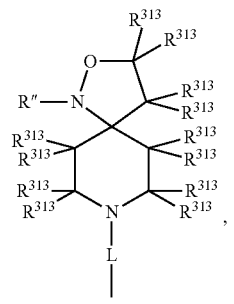
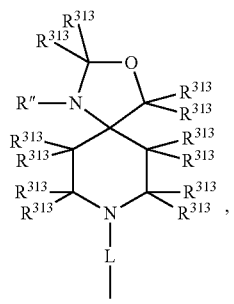
396
-continued
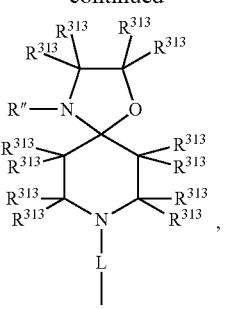
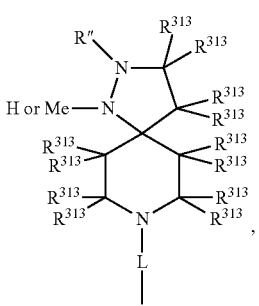
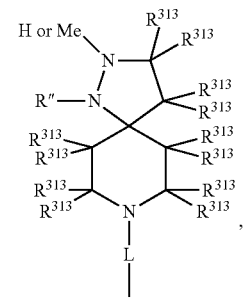
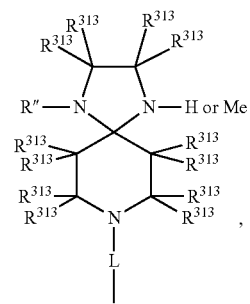
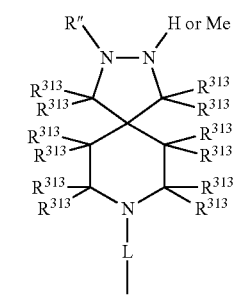

-continued

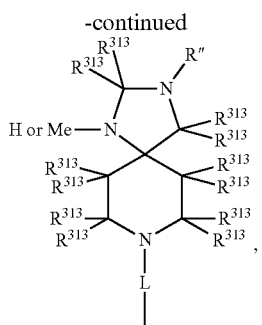

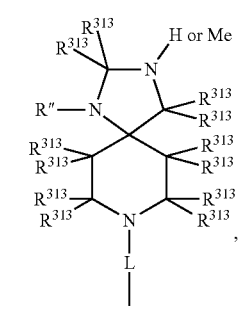

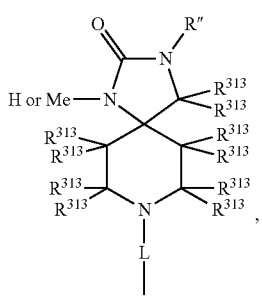

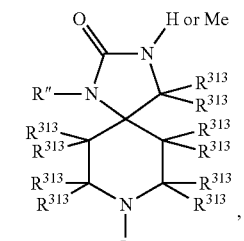

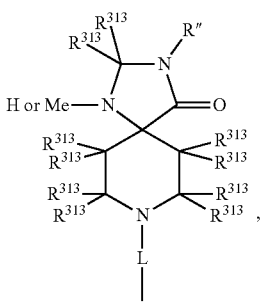

-continued

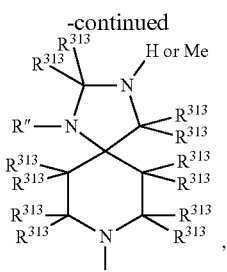

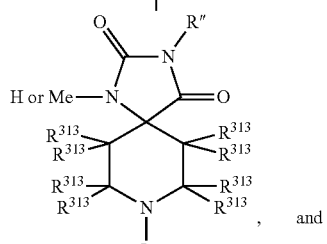, and

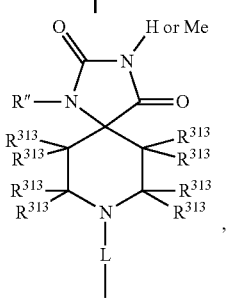

in which L is absent;
wherein R" is selected from H and any of the following groups:
a substituted or unsubstituted linear or branched $C_1$-$C_6$ alkyl group selected from Me, Et, Pr, i-Pr, n-Bu, i-Bu, t-Bu, pentyl, and hexyl;
a substituted or unsubstituted linear or branched $C_2$-$C_6$ alcohol group selected from —$CH_2CH_2OH$, —$CH_2CH_2CH_2OH$, —$CH(CH_3)CH_2OH$, —$C(CH_3)_2$ OH, —$CH_2CH_2CH_2CH_2OH$, —$CH(CH_3)CH_2CH_2OH$, —$CH(CH_3)CH(CH_3)OH$, —$CH(CH_2CH_3)CH_2OH$, —$C(CH_3)_2CH_2OH$, —$CH_2CH_2CH_2CH_2CH_2OH$, and —$CH_2CH_2CH_2CH_2CH_2CH_2OH$;
a substituted or unsubstituted linear or branched $C_1$-$C_7$ alkoxy or aryloxy group linked through —O via at least two further C atoms selected from —$CH_2CH_2OPh$, —$CH_2CH_2OMe$, —$CH_2CH_2OEt$, —$CH_2CH_2OPr$, —$CH_2CH_2OBu$, —$CH_2CH_2CH_2OPh$, —$CH_2CH_2CH_2OMe$, —$CH_2CH_2CH_2CH_2OMe$, and —$CH_2CH_2CH_2CH_2CH_2OMe$;
a substituted or unsubstituted linear or branched $C_1$-$C_6$ halogenated alkyl group selected from —$CH_2F$, —$CF_3$, and —$CH_2CF_3$;
a substituted or unsubstituted cyclic amine or amido group selected from pyrrolidin-3-yl, piperidin-3-yl, piperidin-4-yl, 2-keto-pyrrolidinyl, 3-keto-pyrrolidinyl, 2-keto-piperidinyl, 3-keto-piperidinyl, and 4-keto-piperidinyl; which group is attached via a —$CH_2$— or a —$CH_2CH_2$— group;

a substituted or unsubstituted cyclic C3-C8 alkyl group selected from cyclopropyl, cyclobutyl, cyclopentyl, cyclohexyl, cycloheptyl and cyclooctyl; which group is attached via a —CH$_2$— or a —CH$_2$CH$_2$— group;

a substituted or unsubstituted aromatic group selected from Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2, (3,4,5 or 6)-F$_2$-Ph-, 2, (3,4,5 or 6)-Cl2-Ph-, 2, (3,4,5 or 6)-Br$_2$-Ph-, 2, (3,4,5 or 6)-I$_2$-Ph-, 2, (3,4,5 or 6)-Me$_2$-Ph-, 2, (3,4,5 or 6)-Et$_2$-Ph-, 2, (3,4,5 or 6)-Pr$_2$-Ph-, 2, (3,4,5 or 6)-Bu$_2$-Ph-, 2, (3,4,5 or 6)-(CN)$_2$-Ph-, 2, (3,4,5 or 6)-(NO$_2$)$_2$-Ph-, 2, (3,4,5 or 6)-(NH$_2$)$_2$-Ph-, 2, (3,4,5 or 6)-(MeO)$_2$-Ph-, 2, (3,4,5 or 6)-(CF$_3$)$_2$-Ph-, 3, (4 or 5)-F$_2$-Ph-, 3, (4 or 5)-Cl2-Ph-, 3, (4 or 5)-Br$_2$-Ph-, 3, (4 or 5)-I$_2$-Ph-, 3, (4 or 5)-Me$_2$-Ph-, 3, (4 or 5)-Et$_2$-Ph-, 3, (4 or 5)-Pr$_2$-Ph-, 3, (4 or 5)-Bu$_2$-Ph-, 3, (4 or 5)-(CN)$_2$-Ph-, 3, (4 or 5)-(NO$_2$)$_2$-Ph-, 3, (4 or 5)-(NH$_2$)$_2$-Ph-, 3, (4 or 5)-(MeO)$_2$-Ph-, 3, (4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-; which group is attached via a —CH$_2$— or a —CH$_2$CH$_2$— group; and a saturated or unsaturated, substituted or unsubstituted, heterocyclic group selected from pyrrole-2-yl, pyrrole-3-yl, pyrazole-3-yl, pyrazole-4-yl, pyrazole-5-yl, imidazole-2-yl, imidazole-4-yl, imidazole-5-yl, 1,2,3-triazole-4-yl, 1,2,3-triazole-5-yl, 1,2,4-triazole-3-yl, 1,2,4-triazole-5-yl, pyridine-2-yl, pyridine-3-yl, pyridine-4-yl, pyridazine-3-yl, pyridazine-4-yl, pyrimidine-2-yl, pyrimidine-4-yl, pyrimidine-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl, and tetrazole-5-yl; which group is attached via a —CH$_2$— or a —CH$_2$CH$_2$— group.

3. A compound selected from one of the following, or a pharmaceutically acceptable salt thereof:

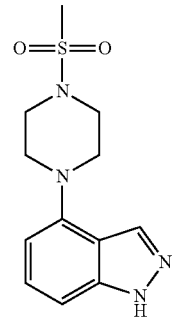

10

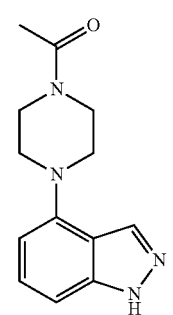

11

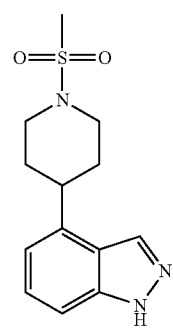

12

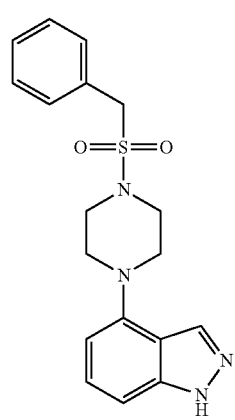

13

401
-continued
14
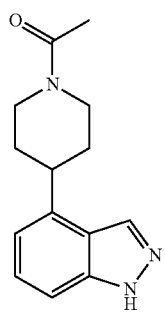
15
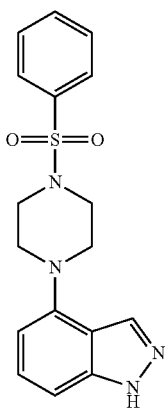
16
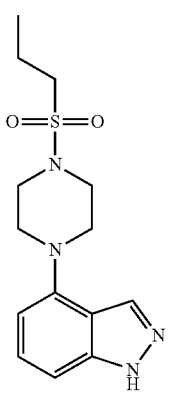
17
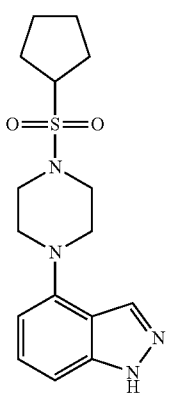
402
-continued
18
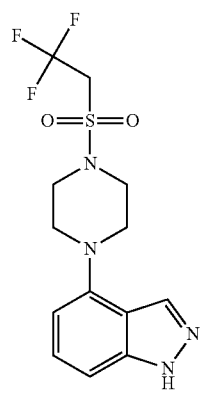
19
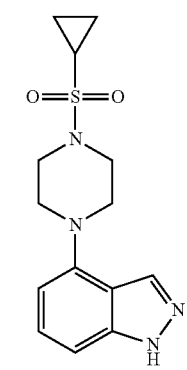
20
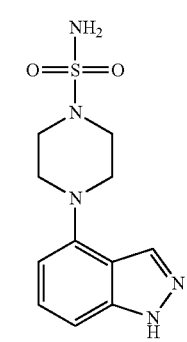
21
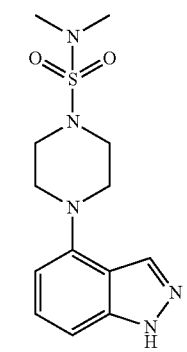

| 403 -continued | 404 -continued |
|---|---|
| 22 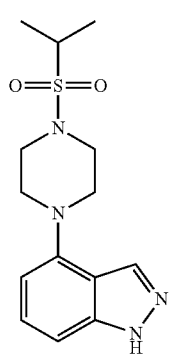 | 25 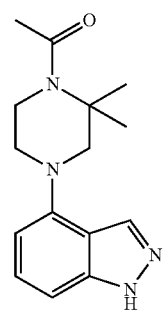 |
| 23 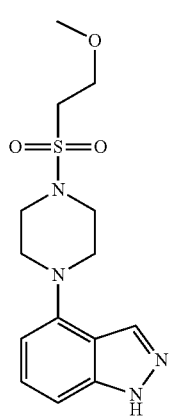 | 26 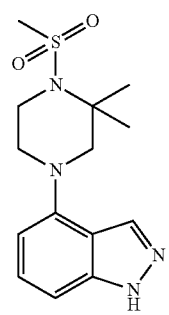 |
| | 27 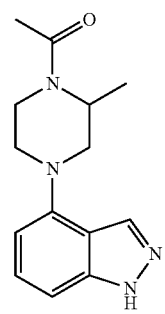 |
| 24 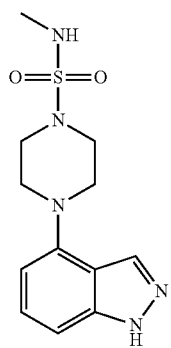 | 28 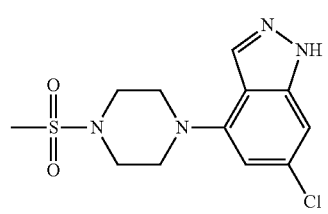 |

-continued
29
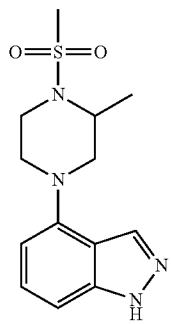
30
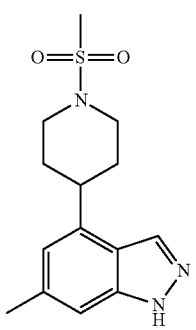
31
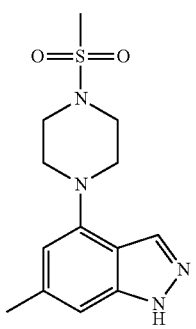
32
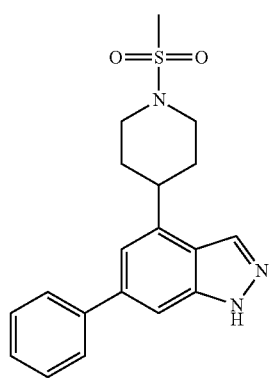
-continued
33
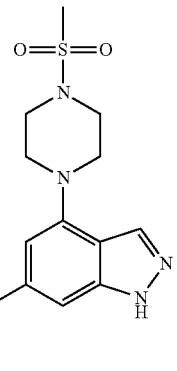
34
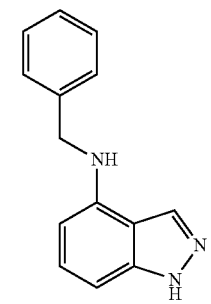
39
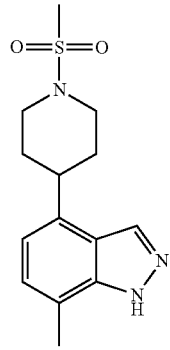
40
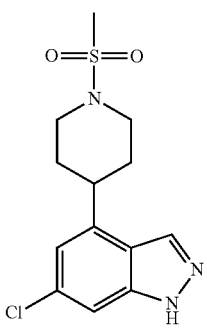

| 41 | 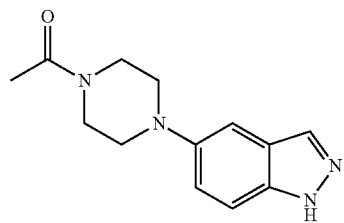 | 47 | 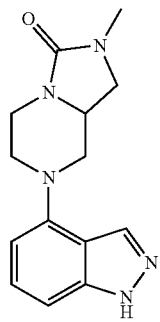 |
| 42 | 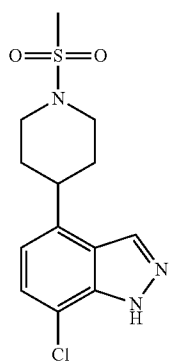 | | |
| 44 | 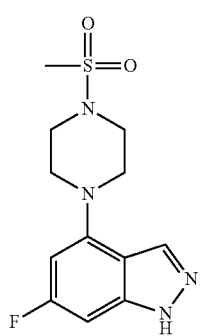 | 48 | 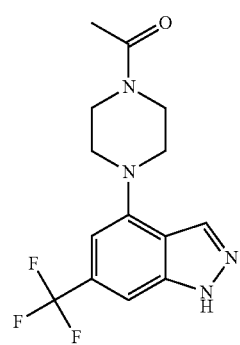 |
| 45 | 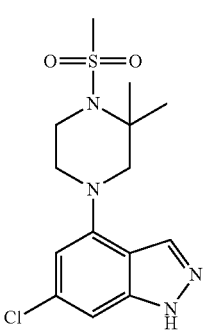 | 49 | 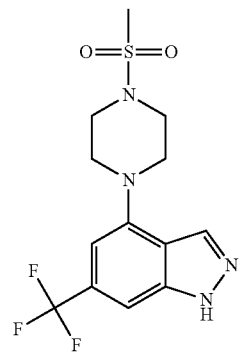 |
| 46 | 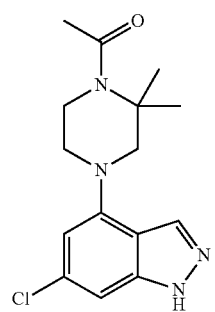 | 51 | 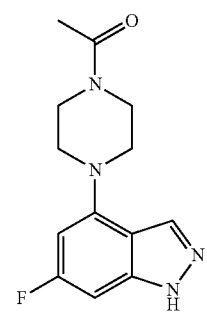 |

409
-continued
54
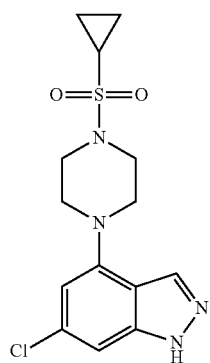
55
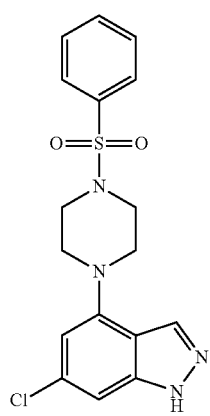
56
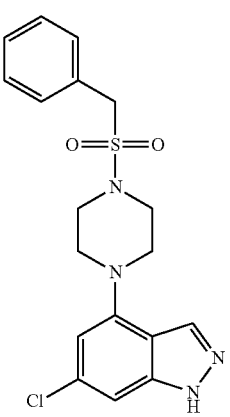
410
-continued
57
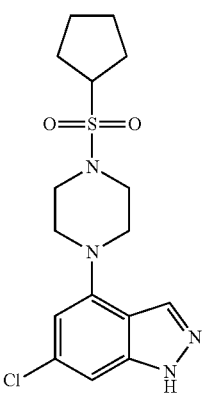
58
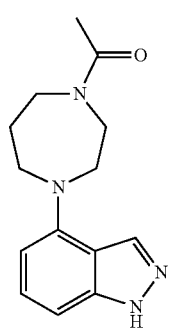
59
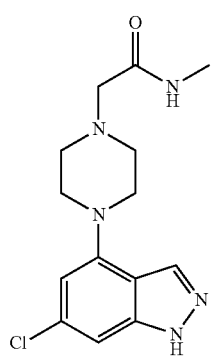
60
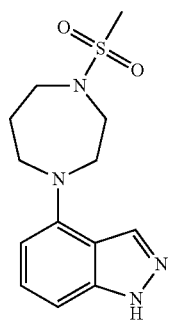

411
-continued
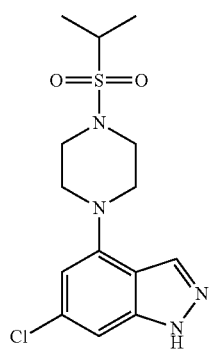
61
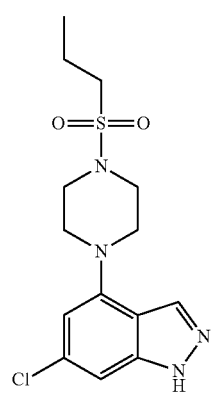
63
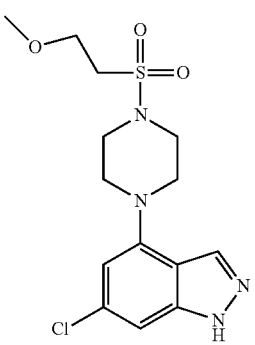
64
412
-continued
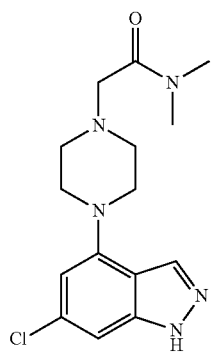
65
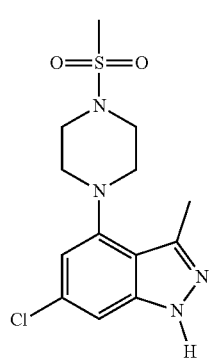
66
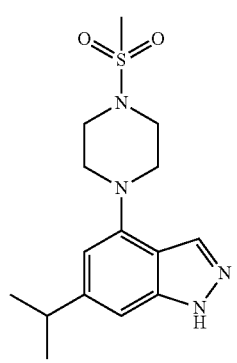
67
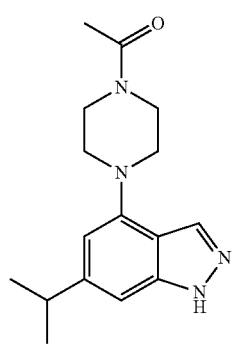
68

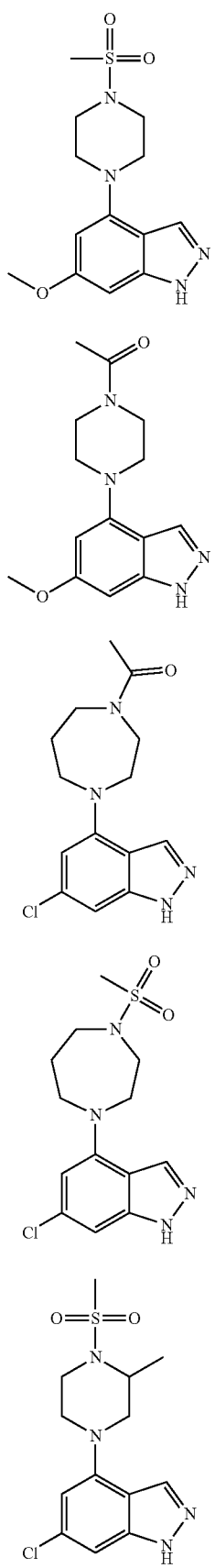
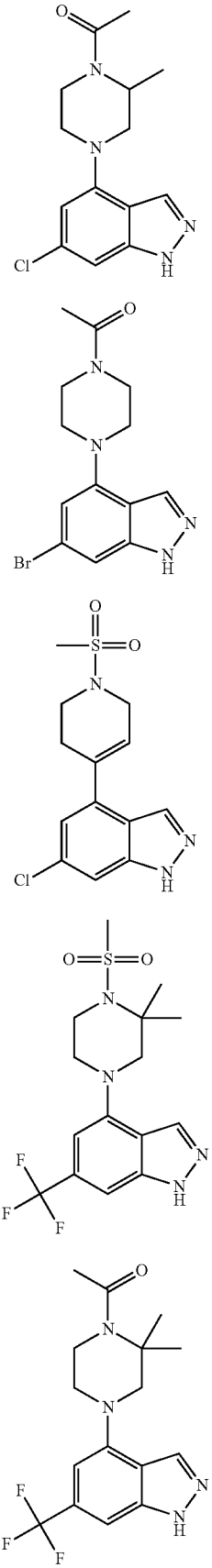

| 80 | 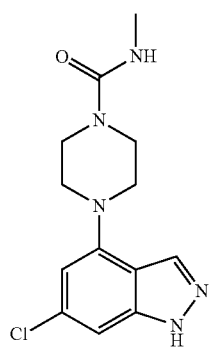 | 84 | 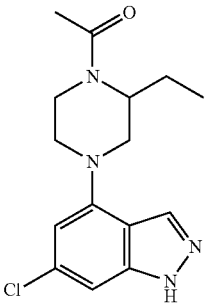 |
| 81 | 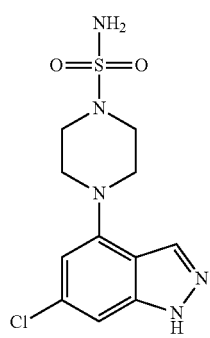 | 86 | 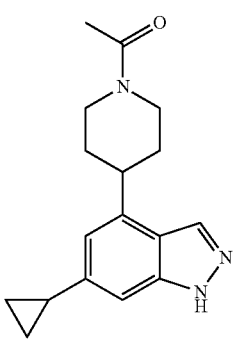 |
| | | 87 | 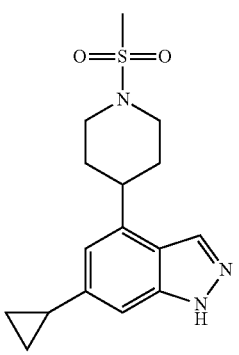 |
| 82 | 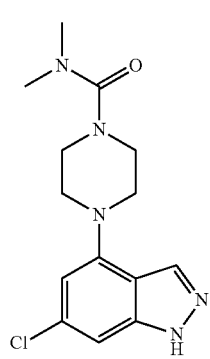 | 88 | 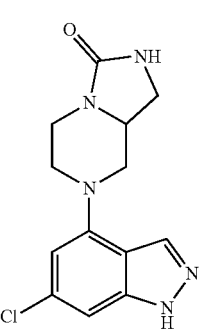 |
| 83 | 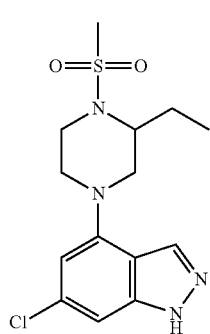 | 89 | |

417
-continued
90
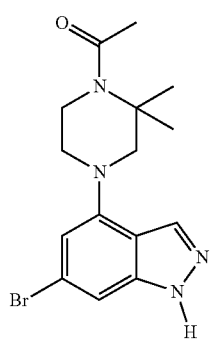
91
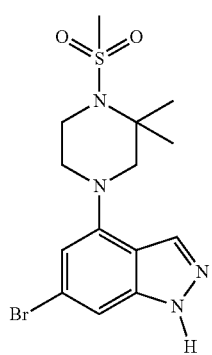
92
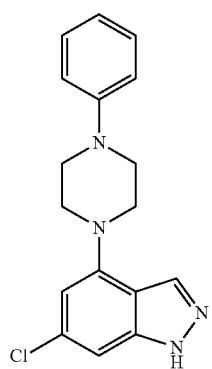
93
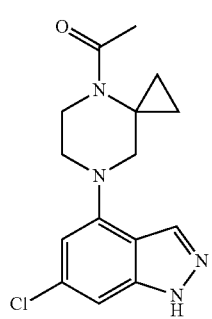
418
-continued
94
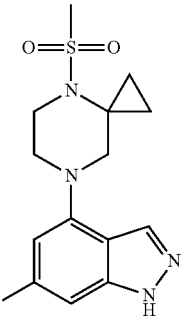
95
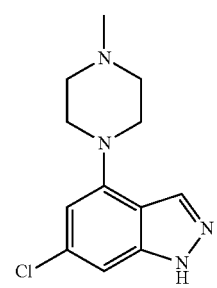
96
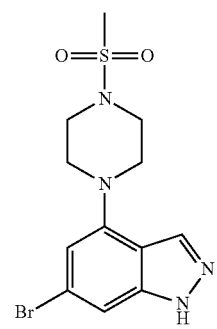
97
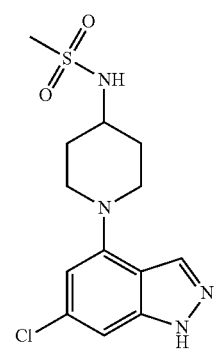
98
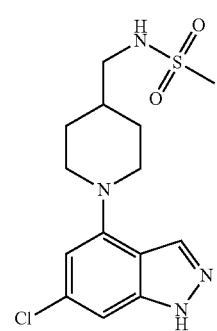

| | |
|---|---|
| 99 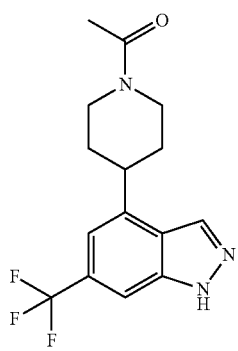 | 103 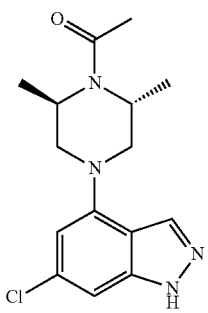 |
| 100 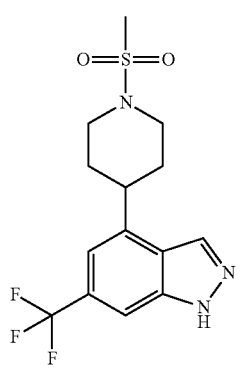 | 104 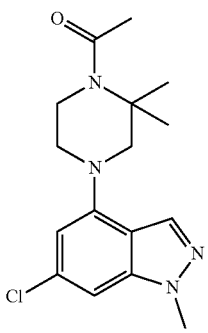 |
| 101 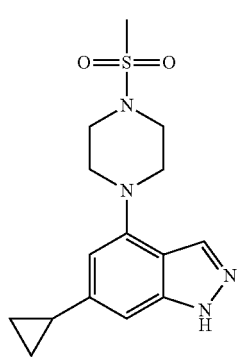 | 105 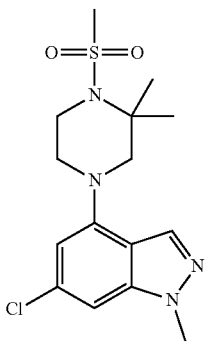 |
| 102 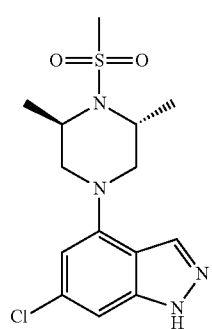 | 107 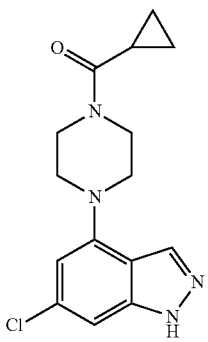 |

| 108 | 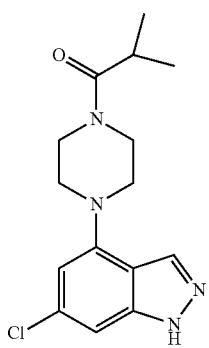 | 113 | 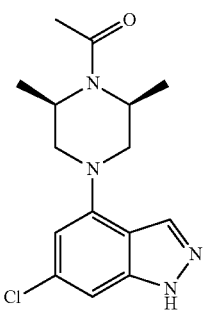 |
| 109 | 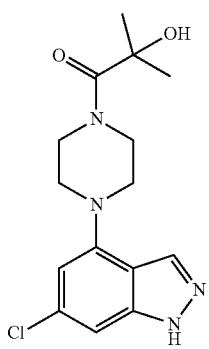 | 114 | 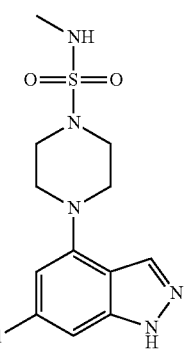 |
| 110 | 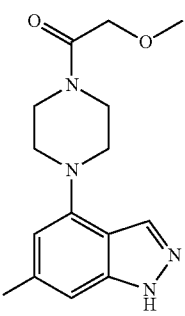 | 115 | 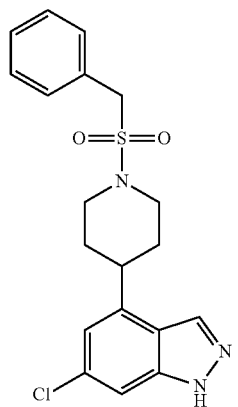 |
| 111 | | 116 | 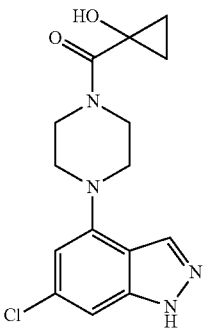 |
| 112 | | | |

| | |
|---|---|
| 117 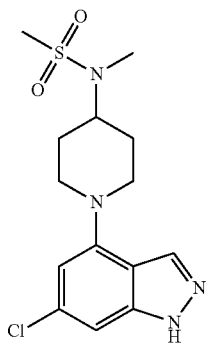 | 121 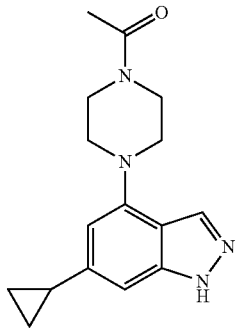 |
| 118 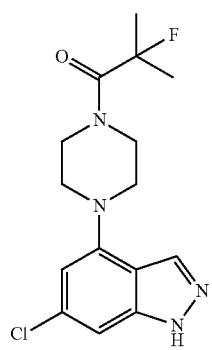 | 122 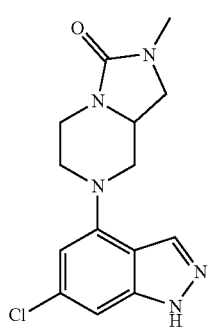 |
| 119 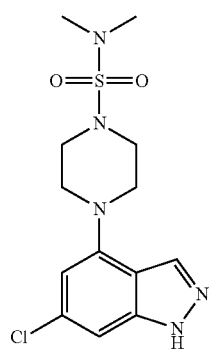 | 123 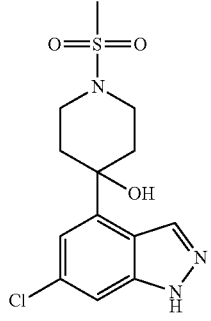 |
| 120 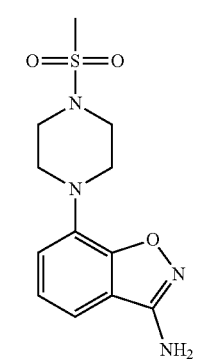 | 124 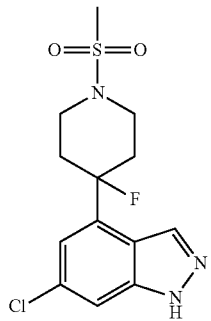 |
| | 125 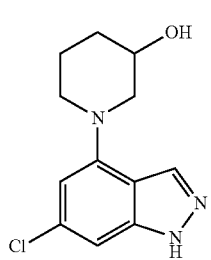 |

| 126 | 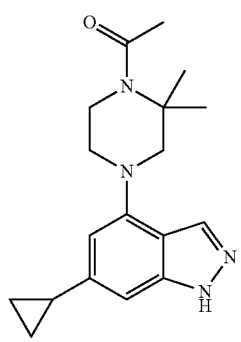 | 130 | 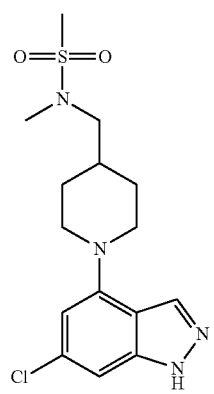 |
| 127 | 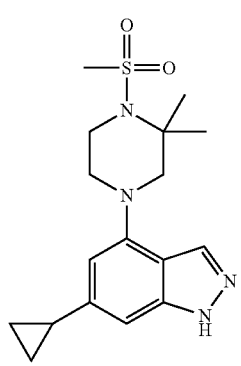 | 131 | 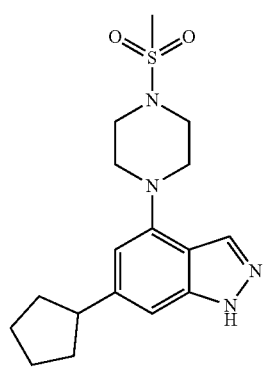 |
| 128 | 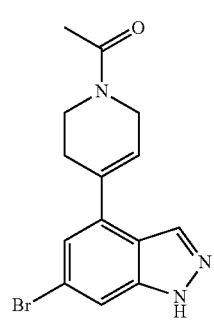 | 132 | 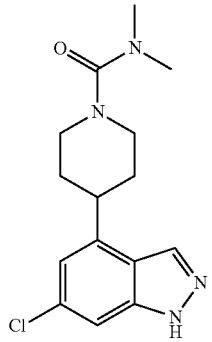 |
| 129 | 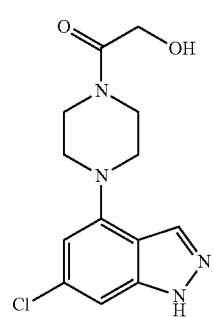 | 133 | 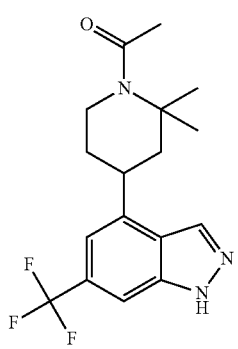 |

134 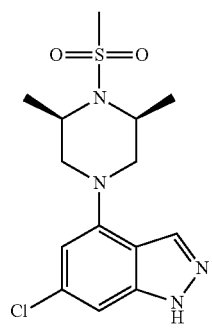
135 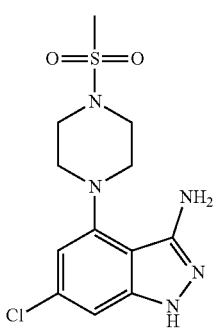
136 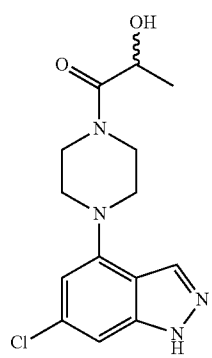
137 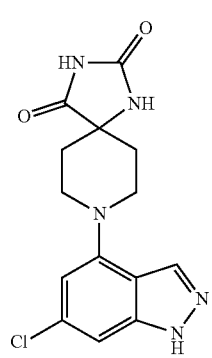
138 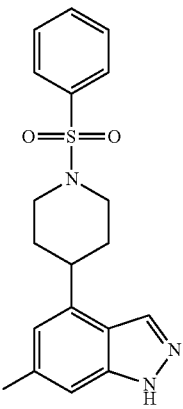
139 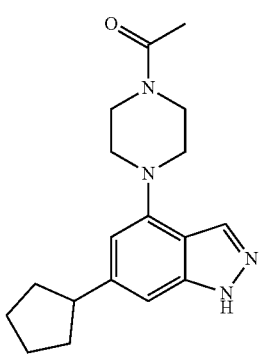
140 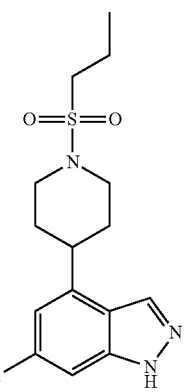
141 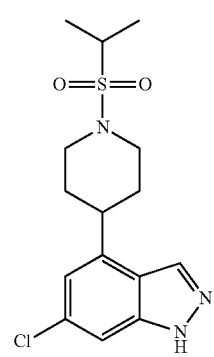

143 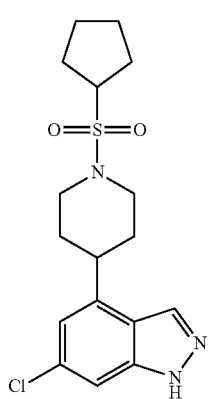
144 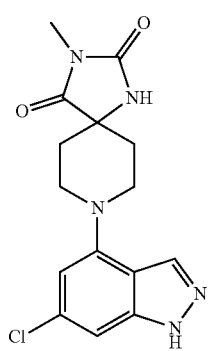
145 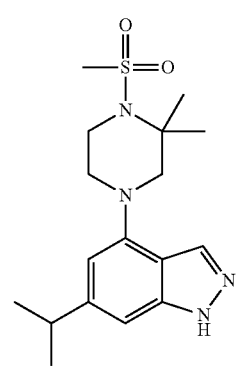
146 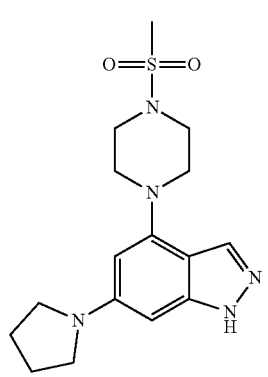
147 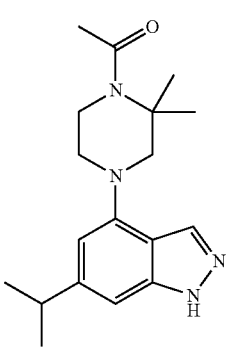
148 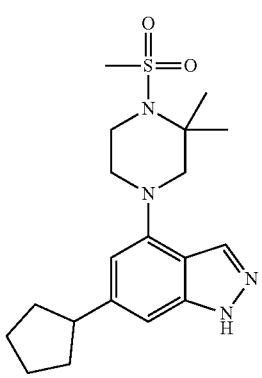
149 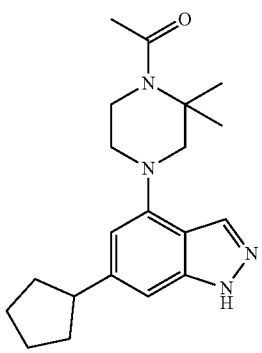
150 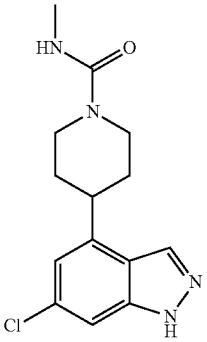

| 431 -continued | | 432 -continued | |
|---|---|---|---|
| 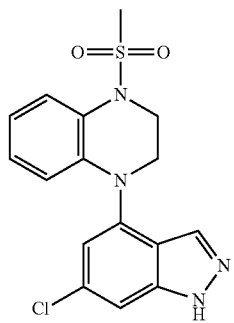 | 151 | 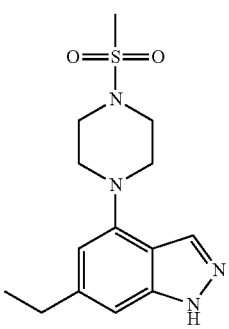 | 158 |
| 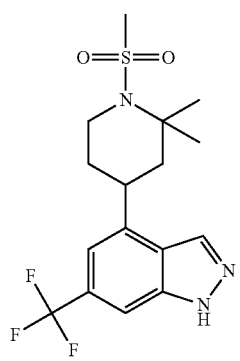 | 154 | 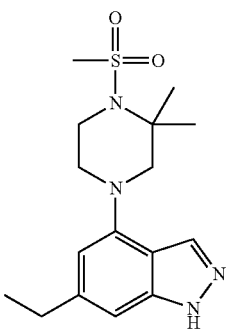 | 161 |
| 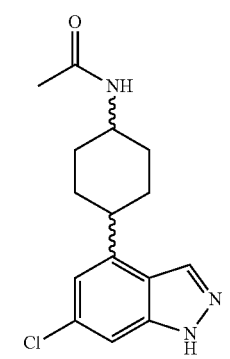 | 155 | 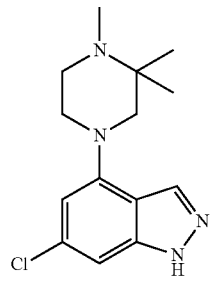 | 164 |
| 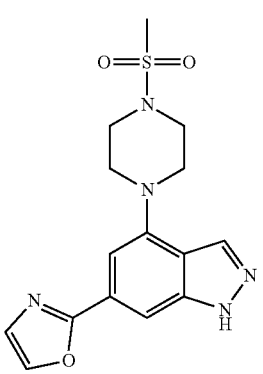 | 157 | 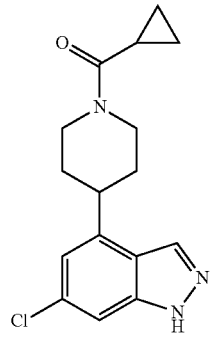 | 165 |
| | | 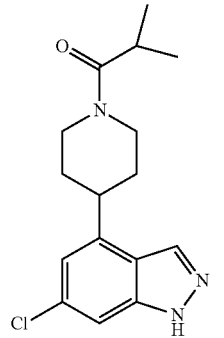 | 166 |

433
-continued
167
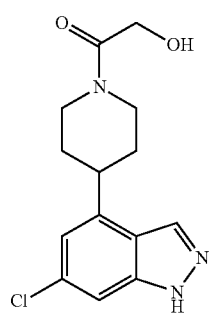
168
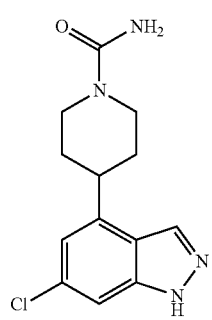
169
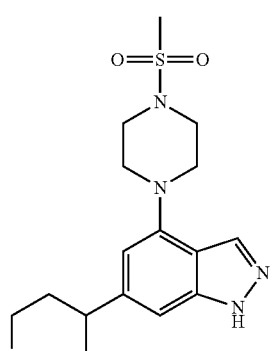
170
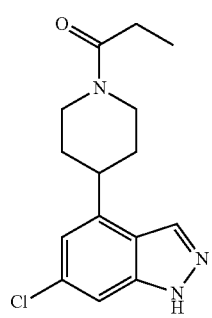
434
-continued
171
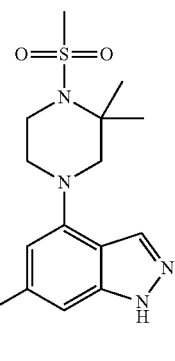
172
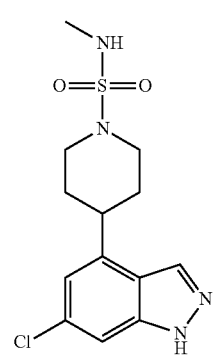
173
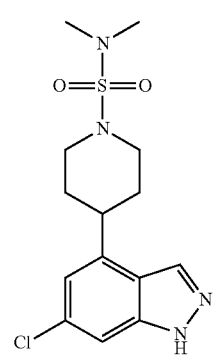
174
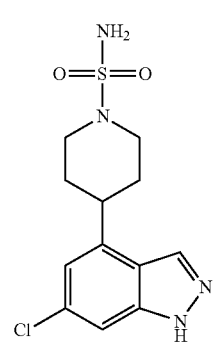

| 435 -continued | | 436 -continued | |
|---|---|---|---|
| 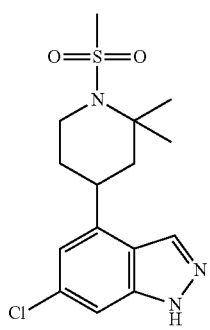 | 175 | 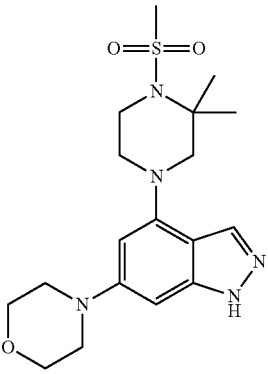 | 179 |
| 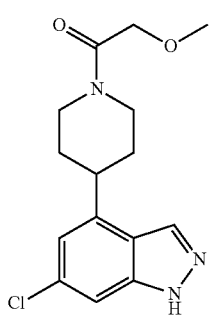 | 176 | 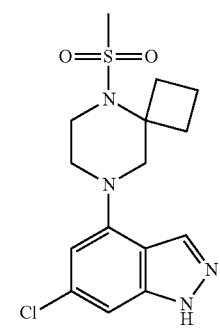 | 181 |
| 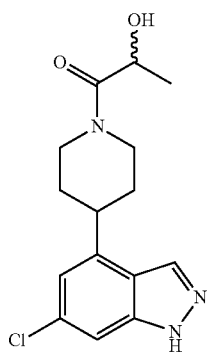 | 177 | 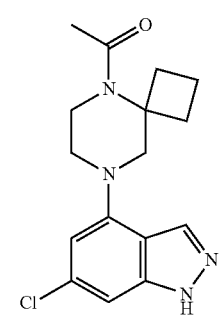 | 182 |
| 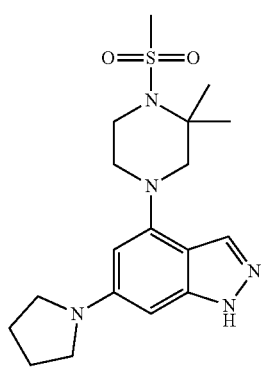 | 178 | 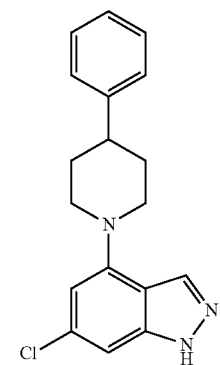 | 183 |

| 437 -continued | | 438 -continued | |
|---|---|---|---|
| 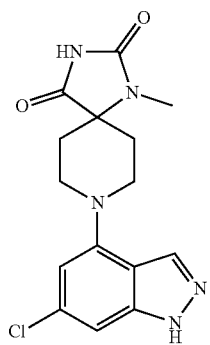 | 184 | 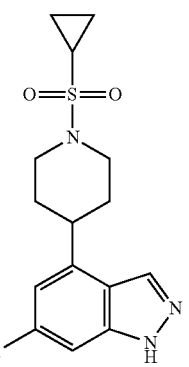 | 188 |
| 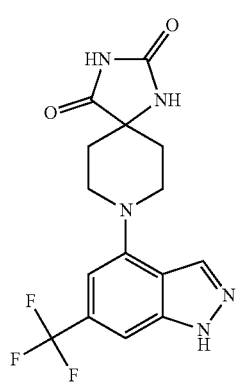 | 185 | 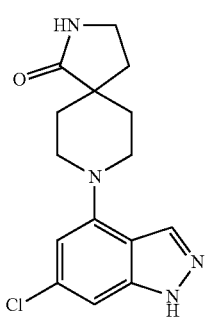 | 189 |
| 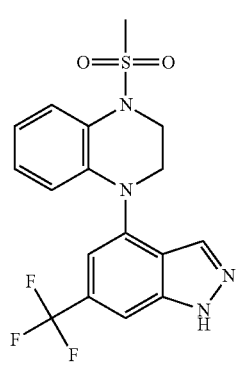 | 186 | 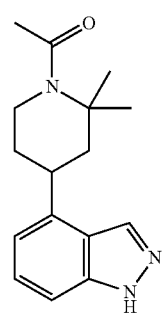 | 190 |
| 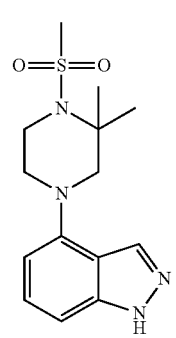 | 187 | 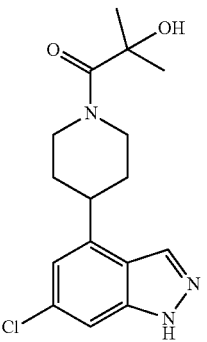 | 191 |

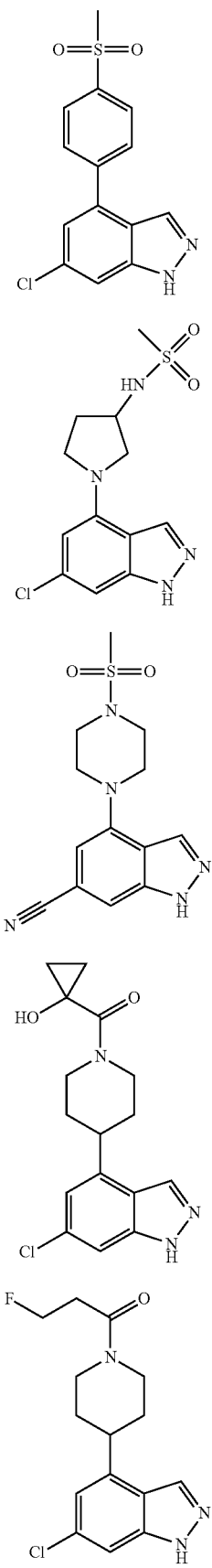
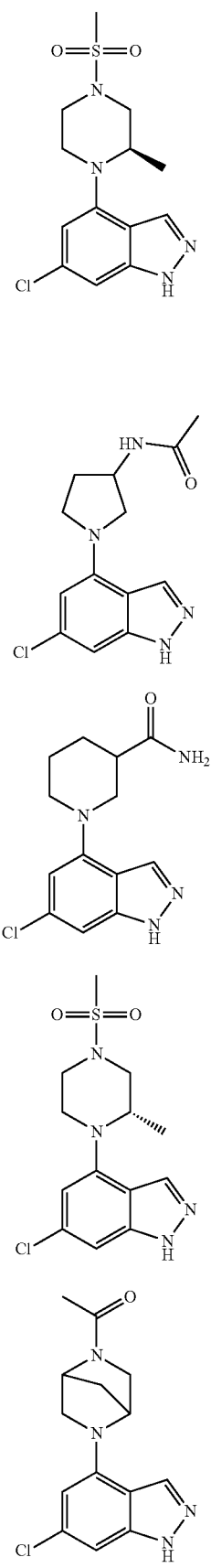

| | |
|---|---|
| 202 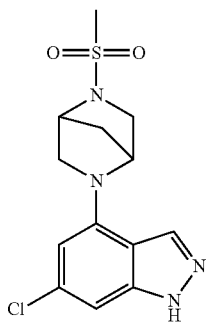 | 206 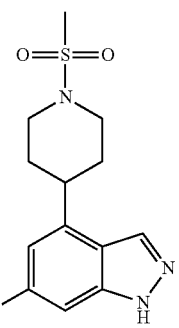 |
| 203 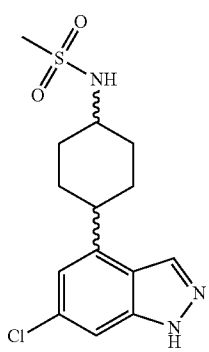 | 207 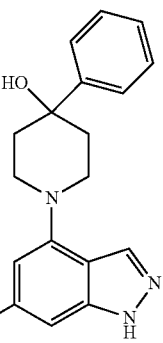 |
| 204 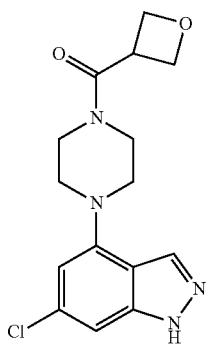 | 208 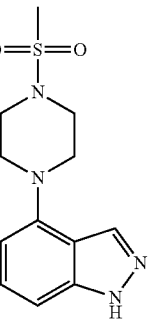 |
| | 209 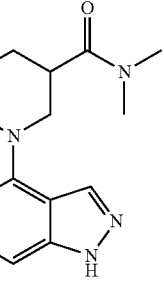 |
| 205 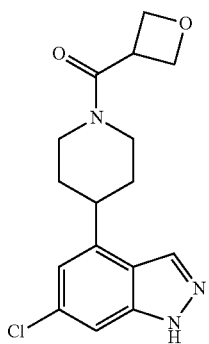 | 210 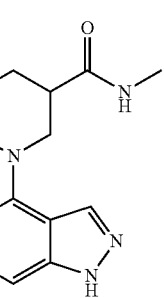 |

| 211 | 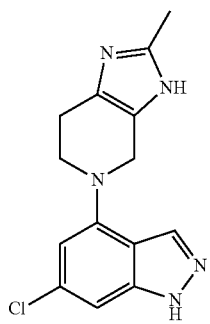 | 215 | 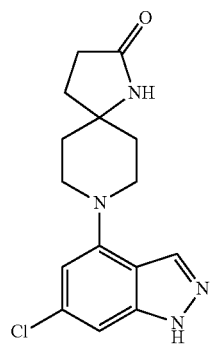 |
| 212 | 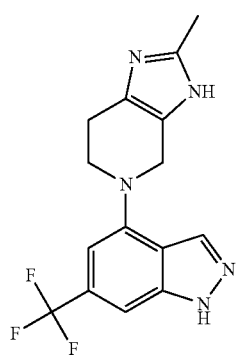 | 216 | 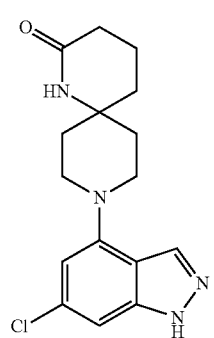 |
| 213 | 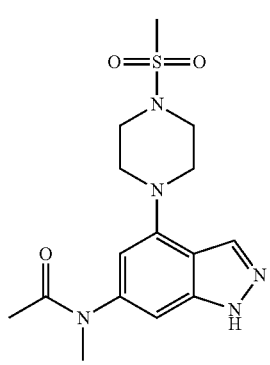 | 217 | 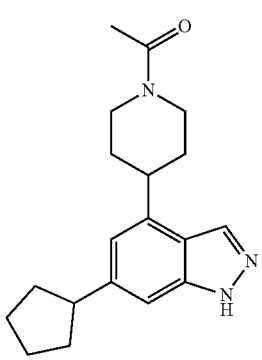 |
| 214 | 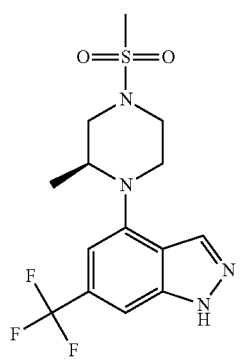 | 218 | 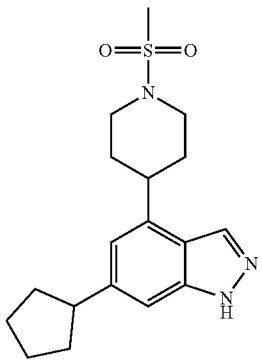 |

| 219 | 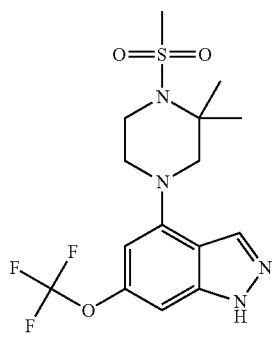 | 223 | 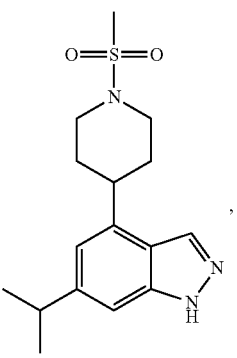 |
| 220 | 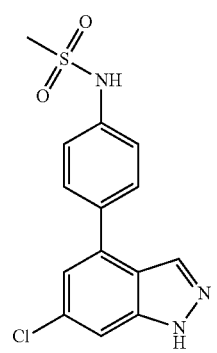 | 224 | 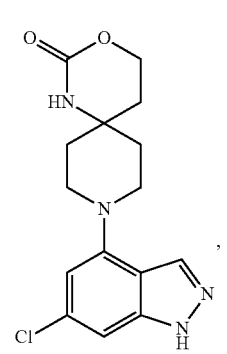 |
| 221 | 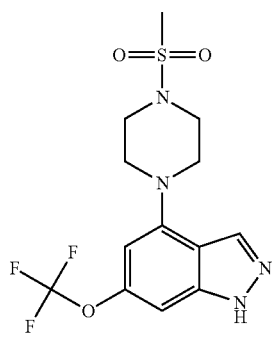 | 225 | 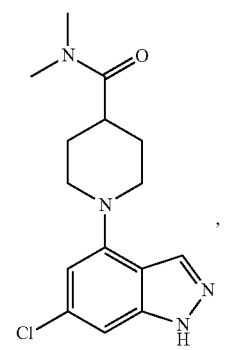 |
| 222 | 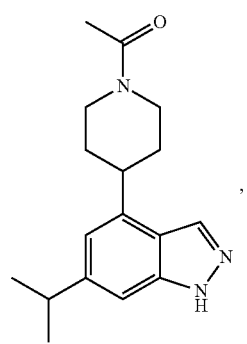 | 226 | 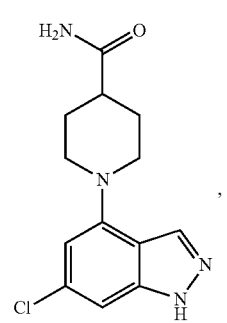 |

447
-continued
227 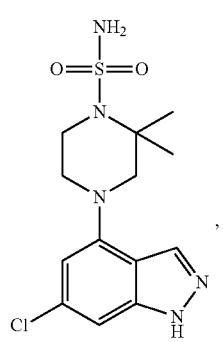
228 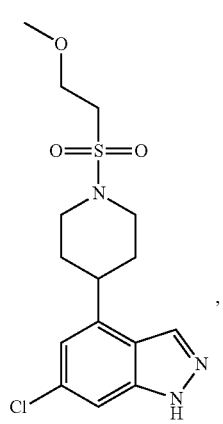
234 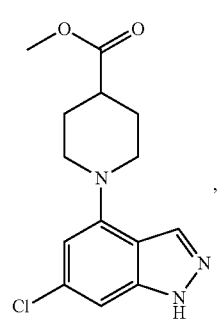
235 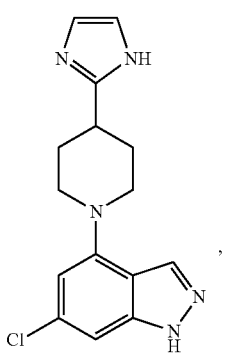
448
-continued
244 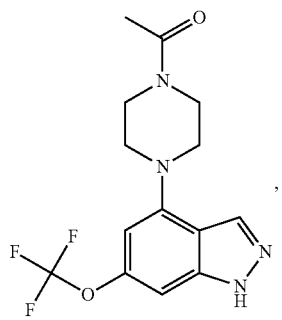
245 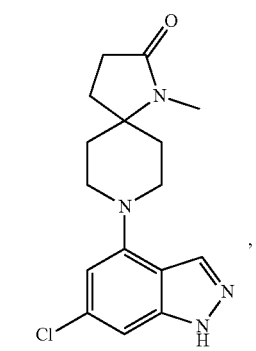
247 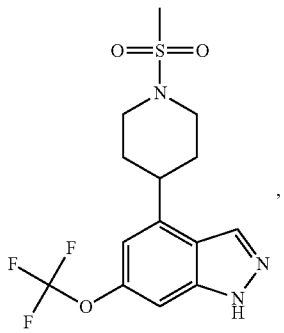
249 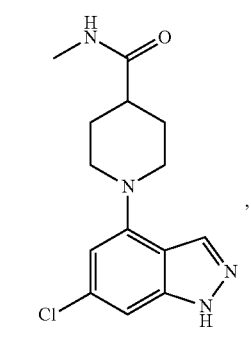

| | |
|---|---|
| 250 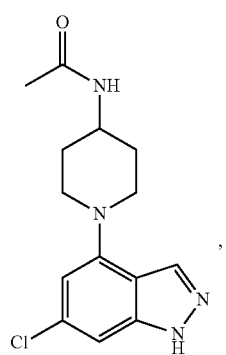 | 275 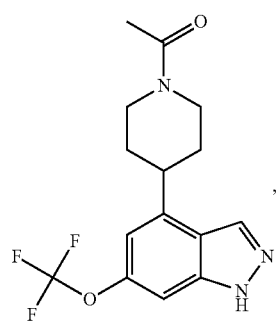 |
| 251 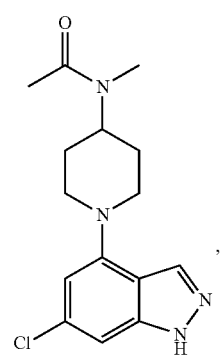 | 280 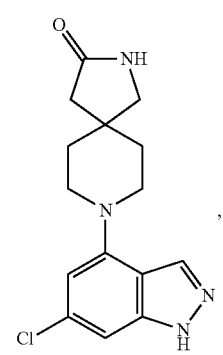 |
| 267 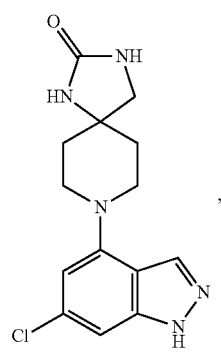 | 282 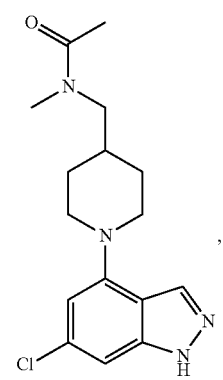 |
| 270 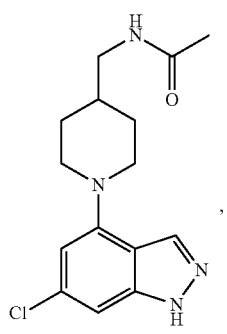 | 283 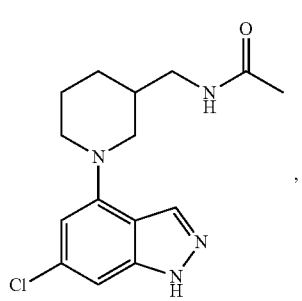 |

| 451 | | 452 | |
|---|---|---|---|
| 290 | 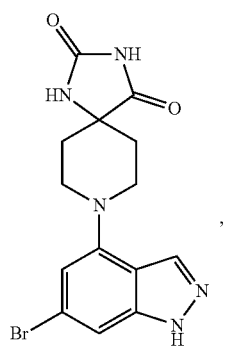 | 310 | 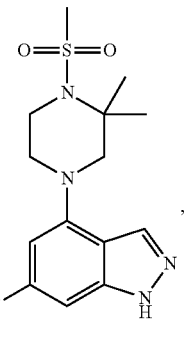 |
| 291 | 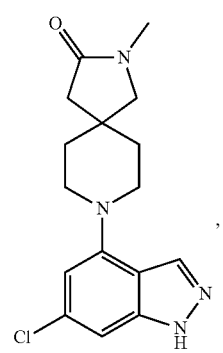 | 311 | 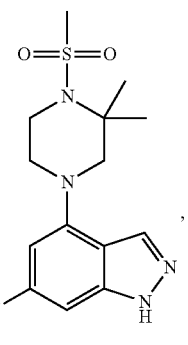 |
| 308 | 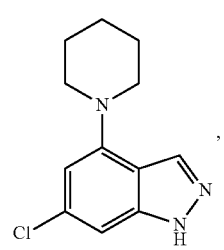 | 312 | 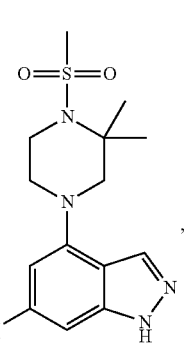 |
| 309 | 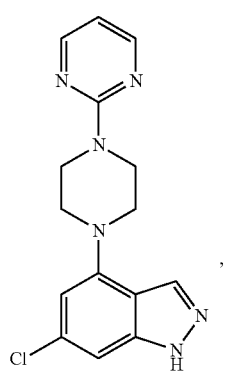 | 313 | 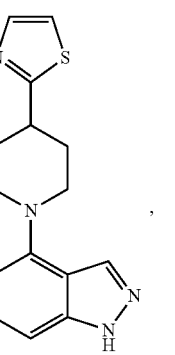 |

453
-continued
315
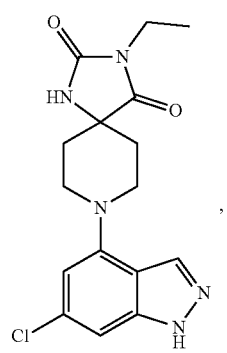,
316
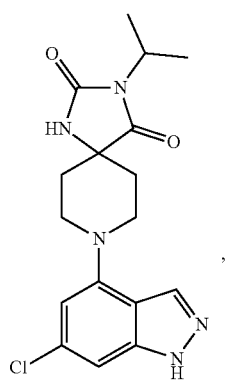,
323
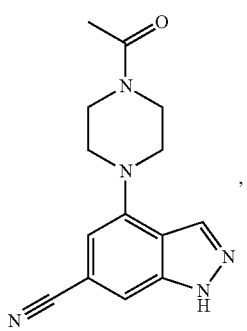,
324
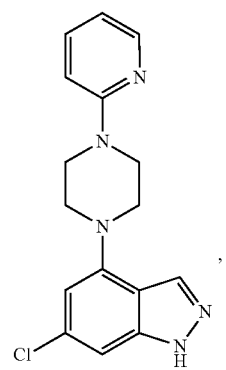,
454
-continued
325
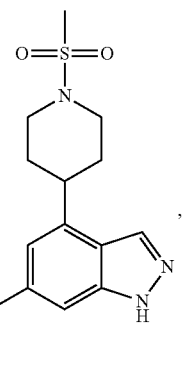,
326
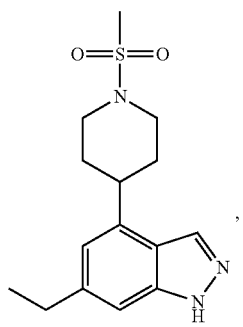,
329
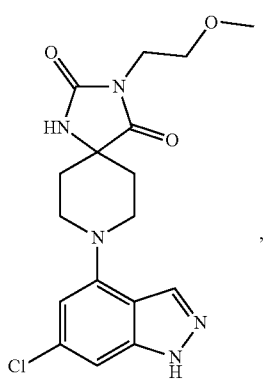,
330
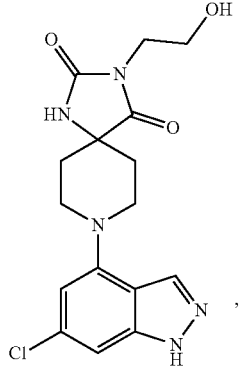,

| 455 -continued | | 456 -continued | |
|---|---|---|---|
| 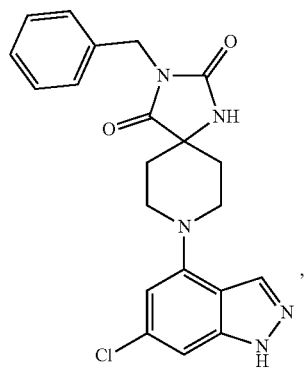 | 331 | 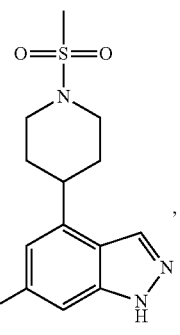 | 337 |
| 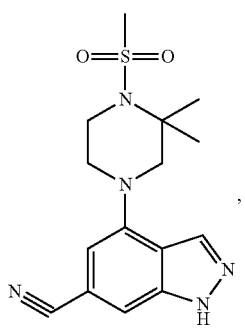 | 334 | 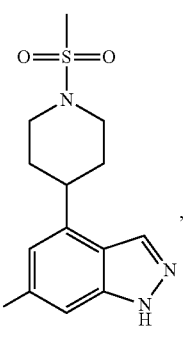 | 338 |
| 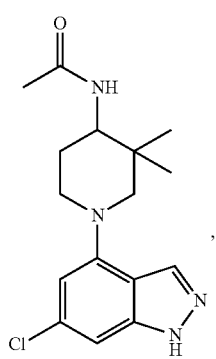 | 335 | 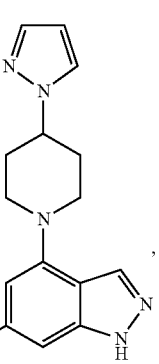 | 339 |
| 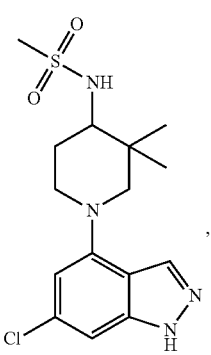 | 336 | 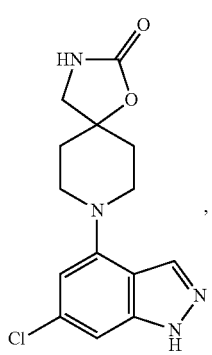 | 344 |

349
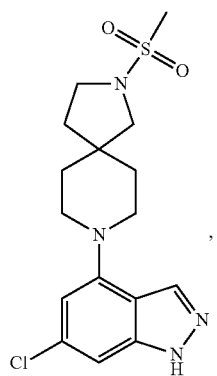
350
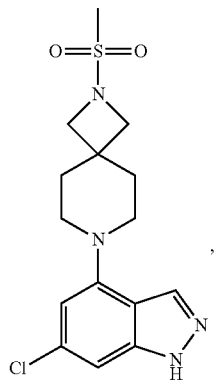
351
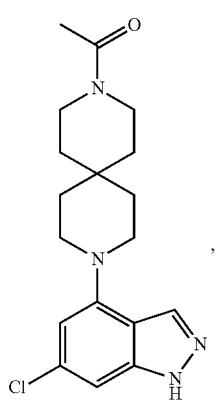
354
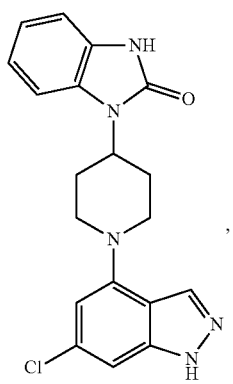
355
359
361
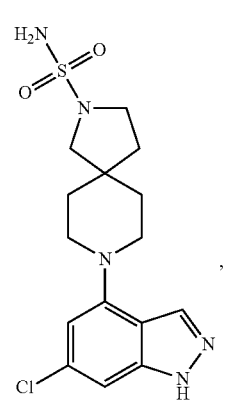

362 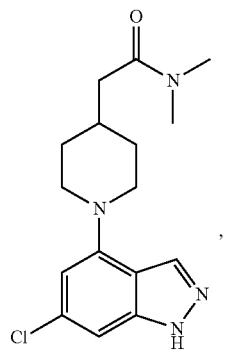
363 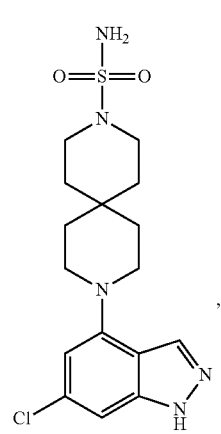
364 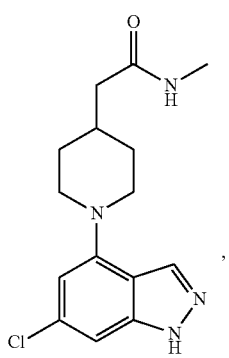
365 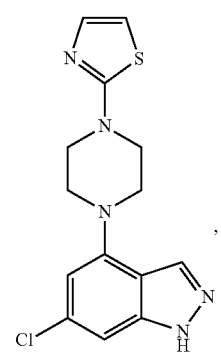
367 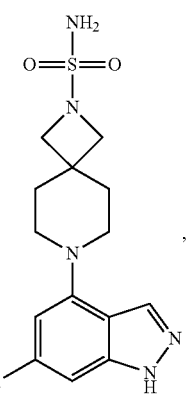
370 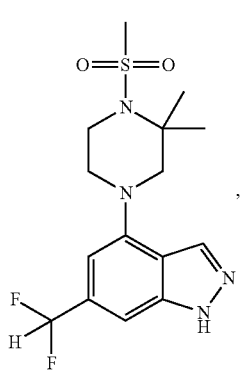
372 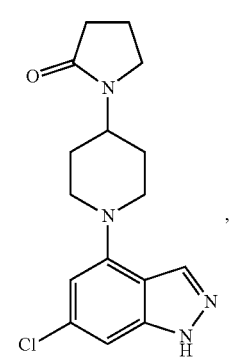
374 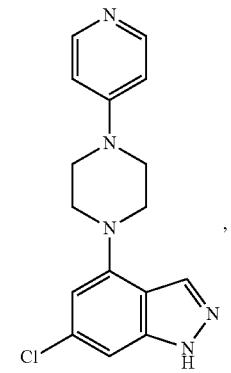

| | |
|---|---|
| 375 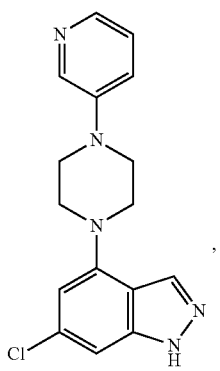 | 382 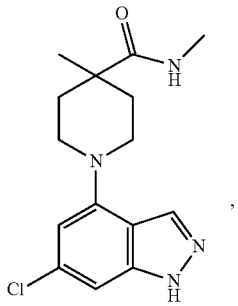 |
| 377 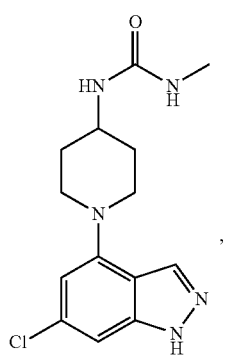 | 383 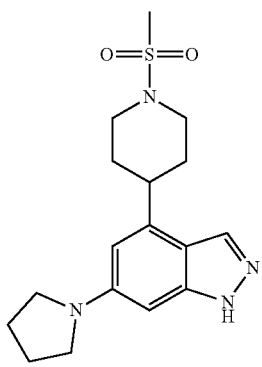 |
| 379 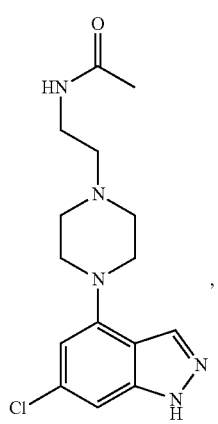 | 387 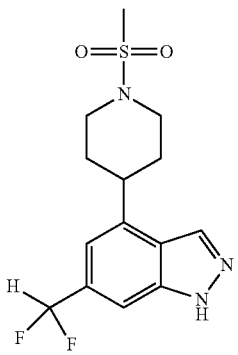 |
| 380 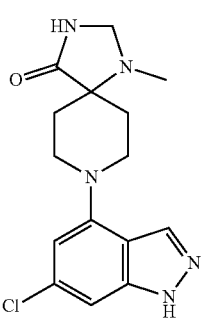 | 388 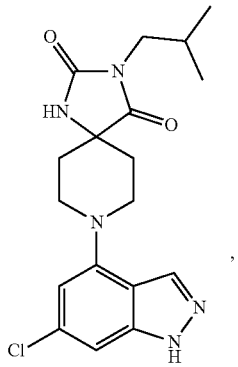 |

389
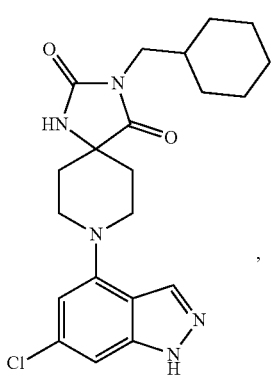
390
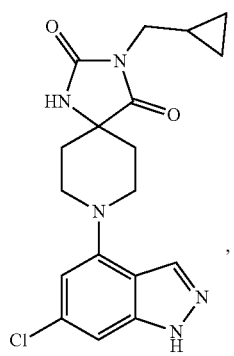
391
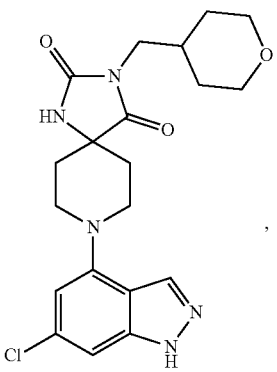
392
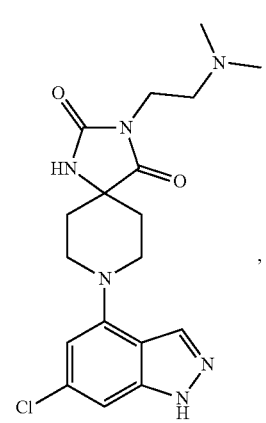
397
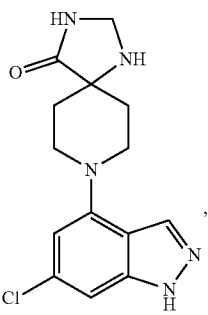
398
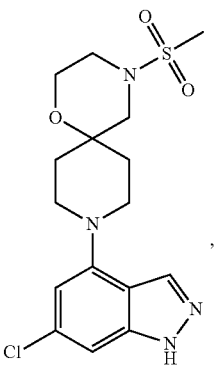
400
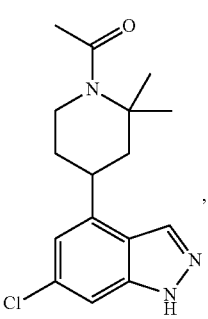
401
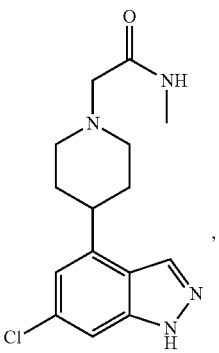

403
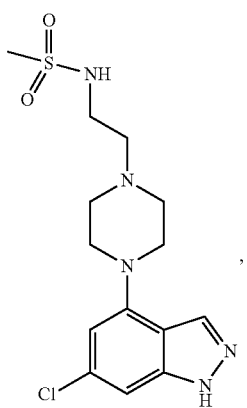
405
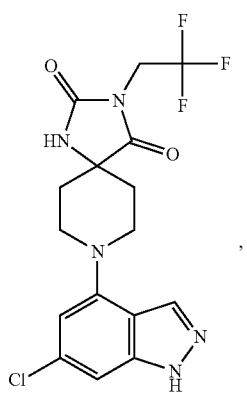
406
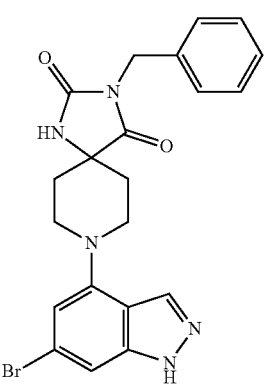
407
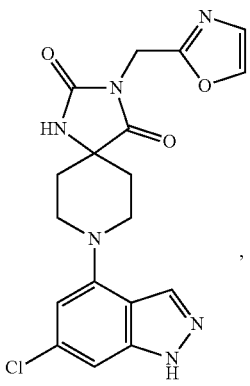
408
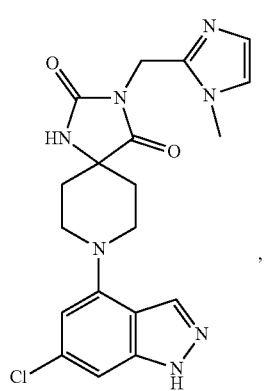
409
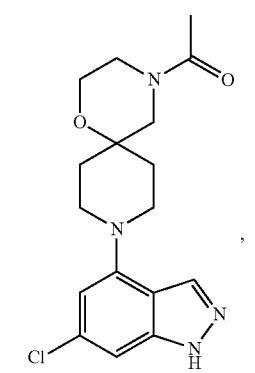
410
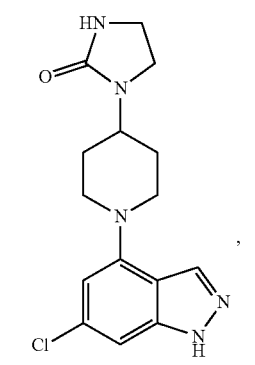
411
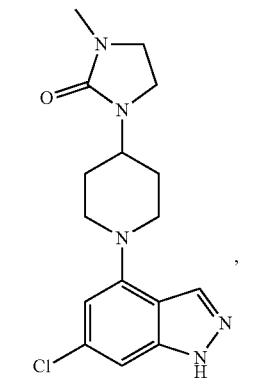

| | |
|---|---|
| 412 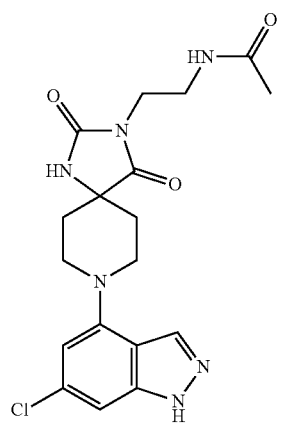 | 418 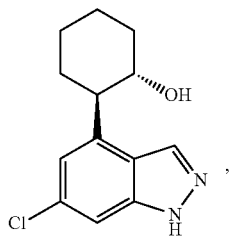 |
| 413 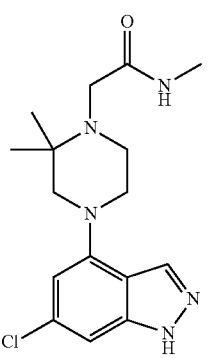 | 419 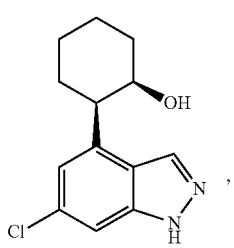 |
| 414 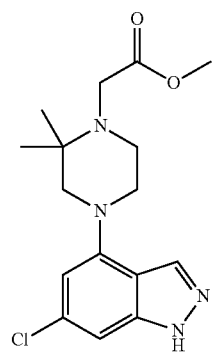 | 420 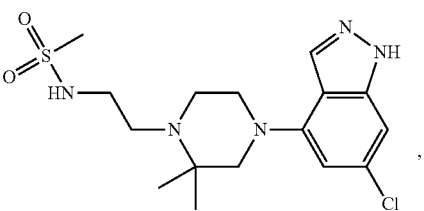 |
| | 421 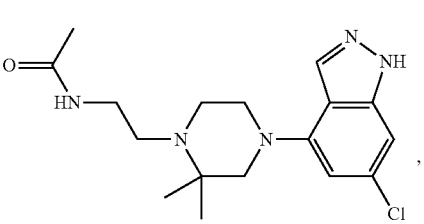 |
| 416 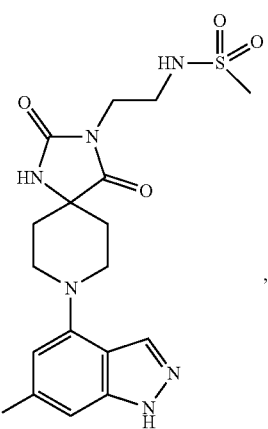 | 422 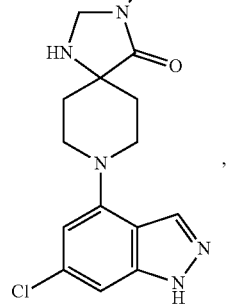 |

469
-continued
423
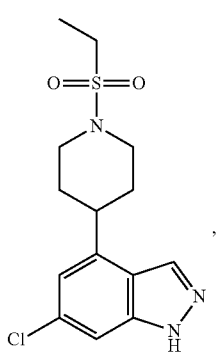
424
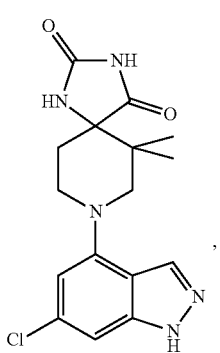
427
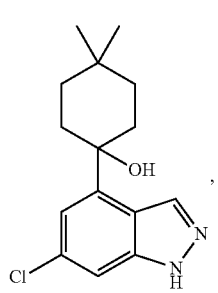
428
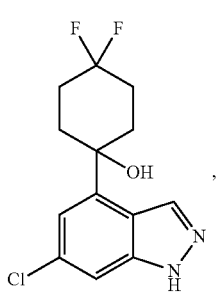
429
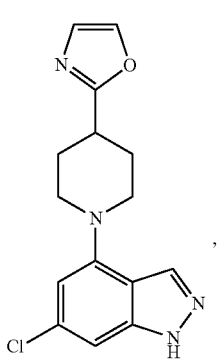
470
-continued
430
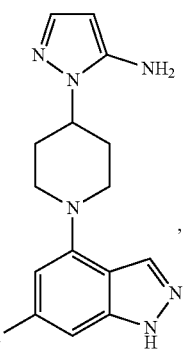
436
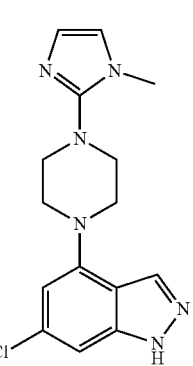
437
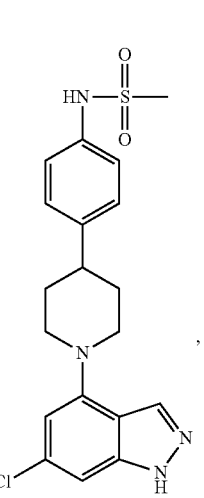
440
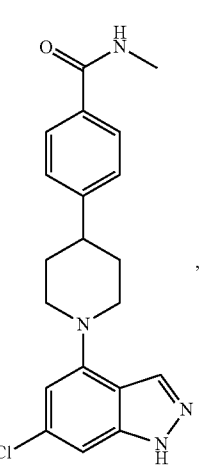

| 471 -continued | | 472 -continued | |
|---|---|---|---|
| 441 | 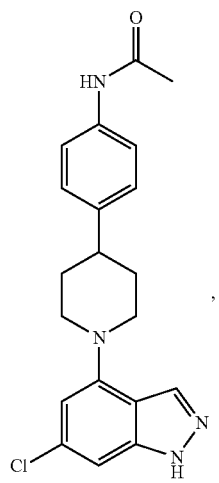 | 445 | 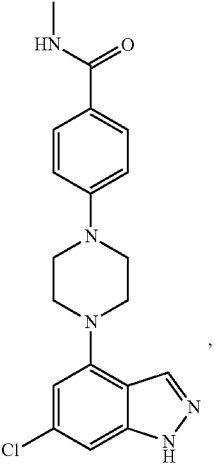 |
| 442 | 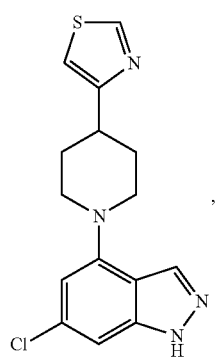 | 449 | 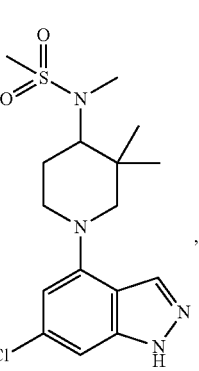 |
| 443 | 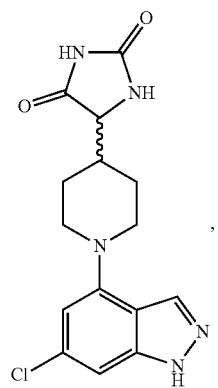 | 450 | 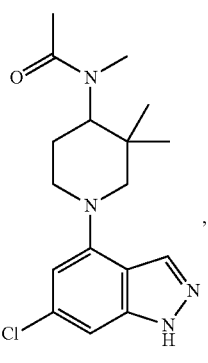 |
| 444 | 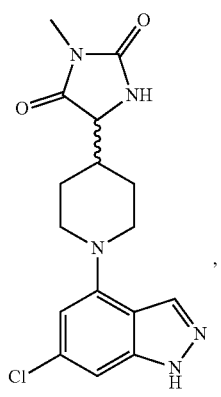 | 451 | 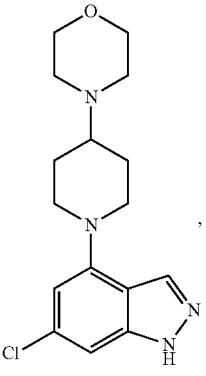 |

473
-continued
453
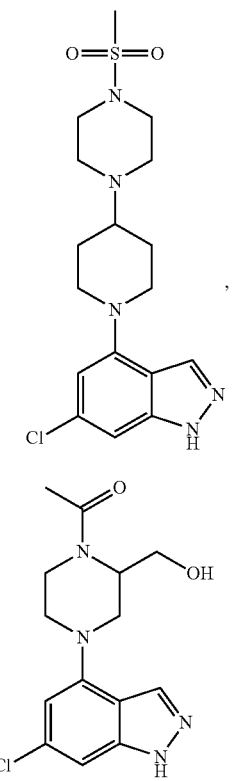
454
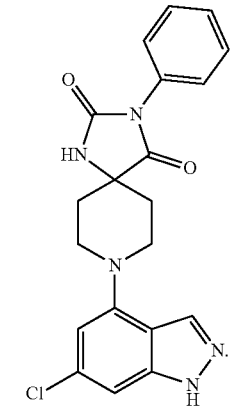
and
456
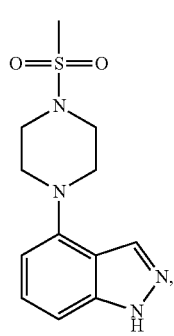
4. A compound selected from the following formulae, or a pharmaceutically acceptable salt thereof:
10
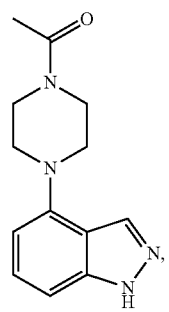
474
-continued
11
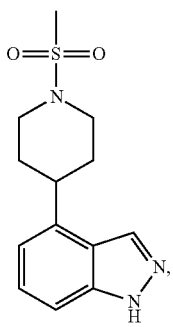
12
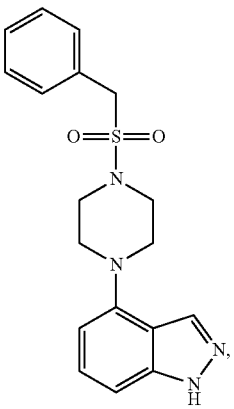
13
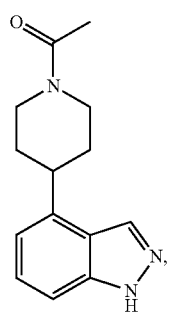
14

15
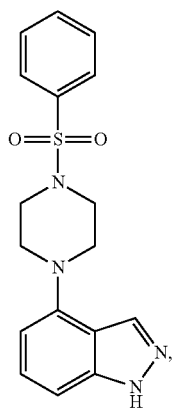
16
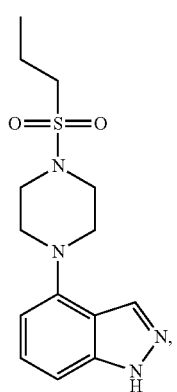
17
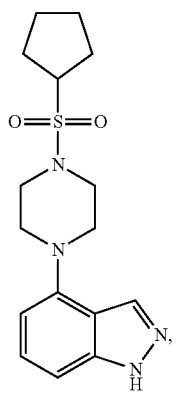
18
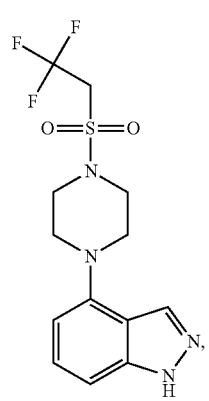
19
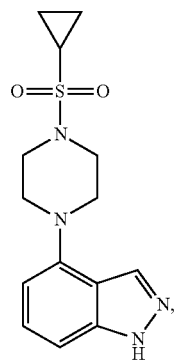
20
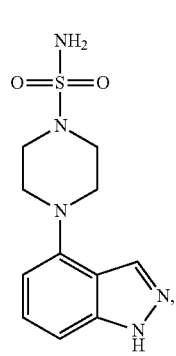
21
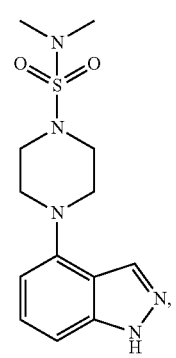
22
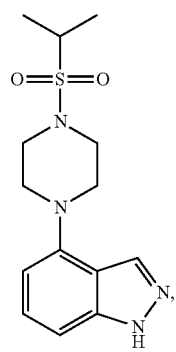

477
-continued
23
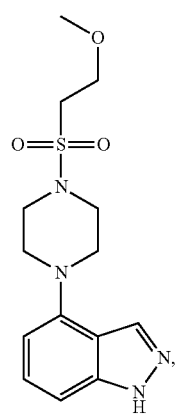
24
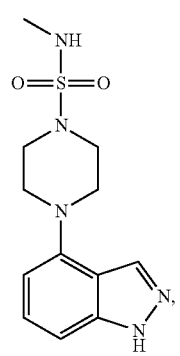
25
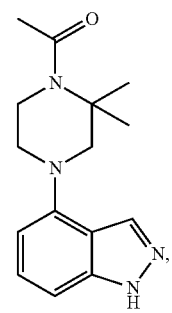
26
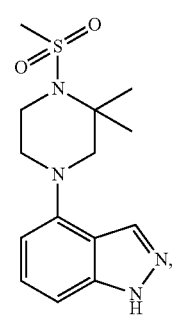
478
-continued
27
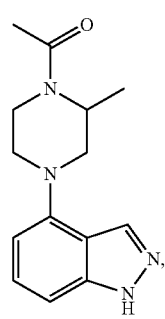
28
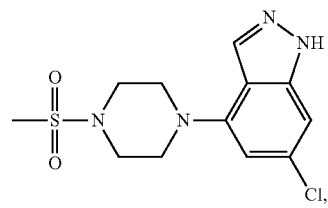
29
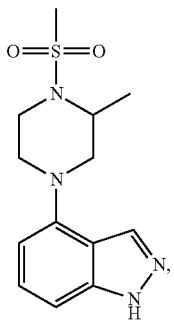
30
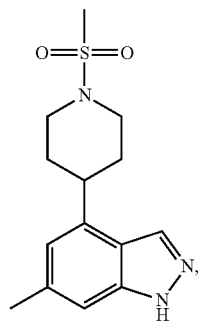
31
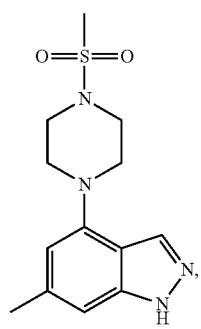

32
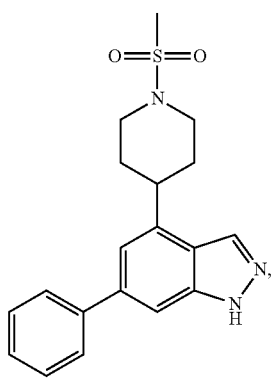
33
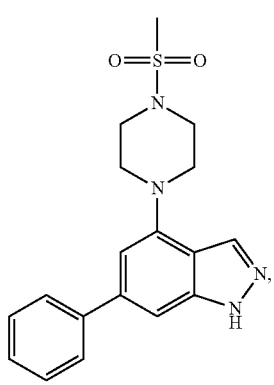
39
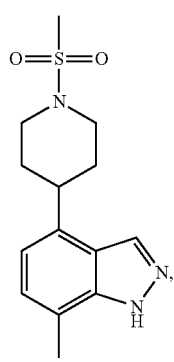
40
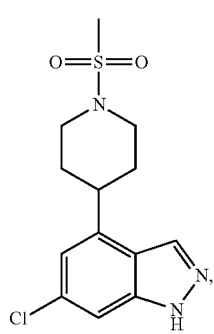
44
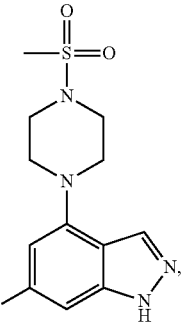
45
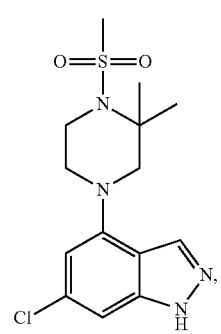
46
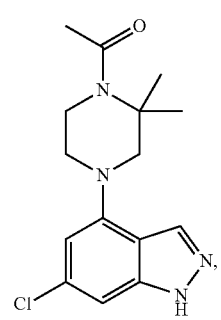
48
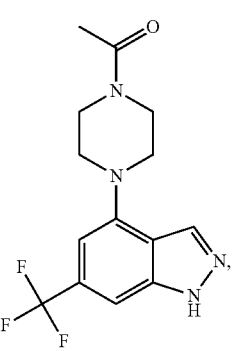

-continued
49
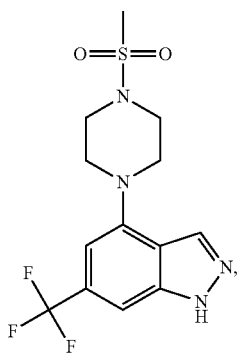
51
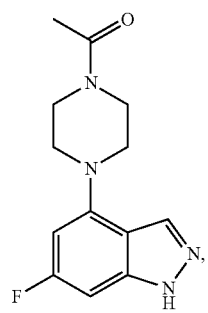
54
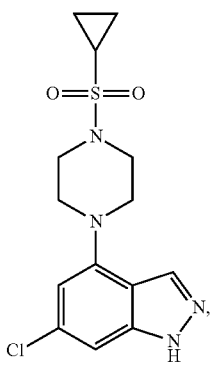
55
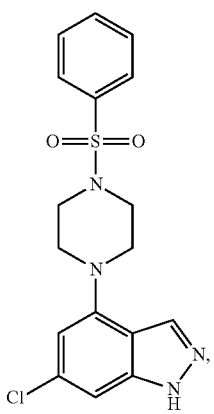
-continued
56
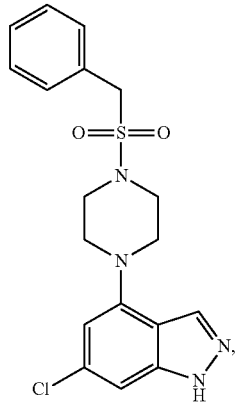
57
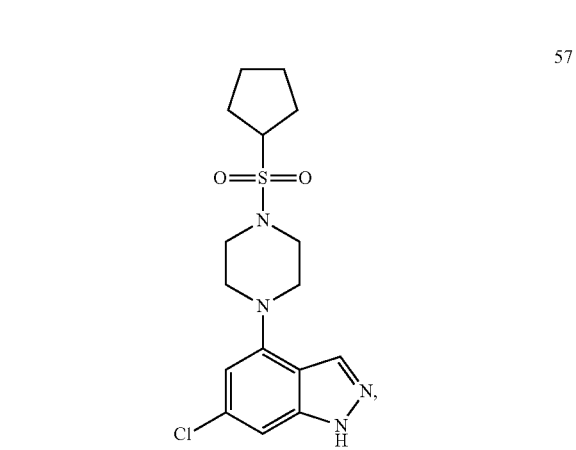
59
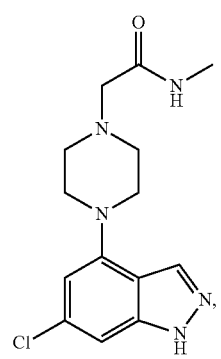
61
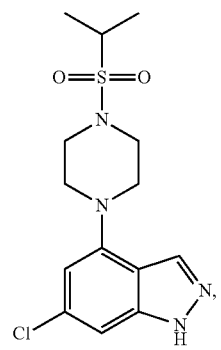

| 63 | 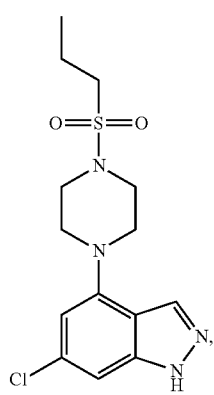 | 67 | 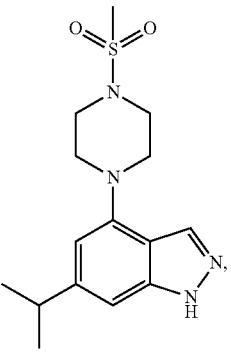 |
| 64 | | 68 | 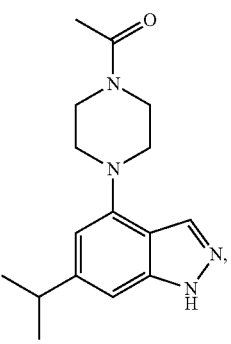 |
| 65 | 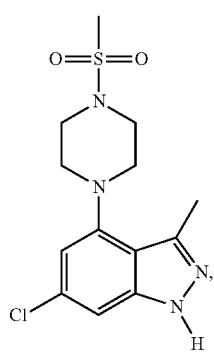 | 69 | 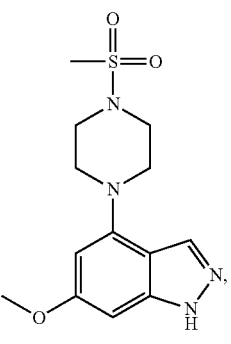 |
| 66 | | 70 | 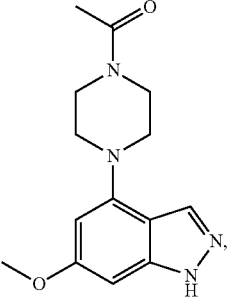 |

| 485 -continued | | 486 -continued | |
|---|---|---|---|
| 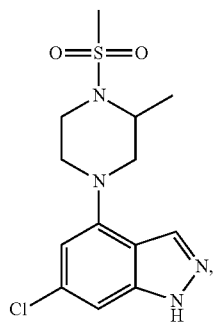 | 73 | 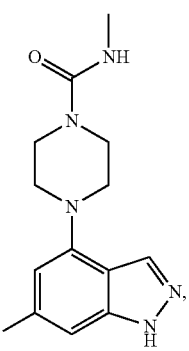 | 80 |
| 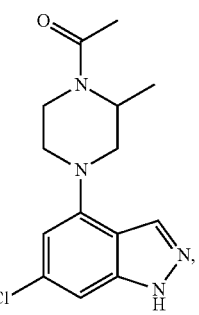 | 74 | 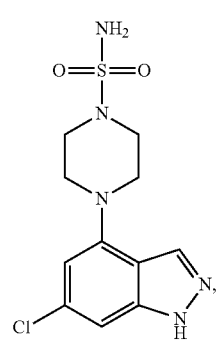 | 81 |
| 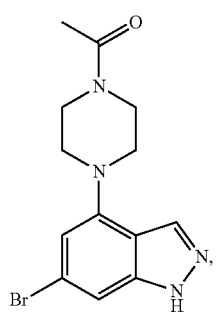 | 76 | 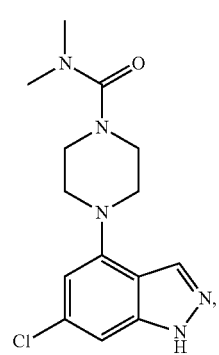 | 82 |
| 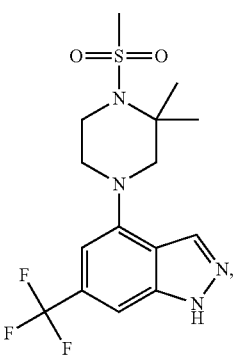 | 78 | 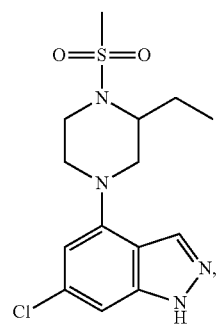 | 83 |
| 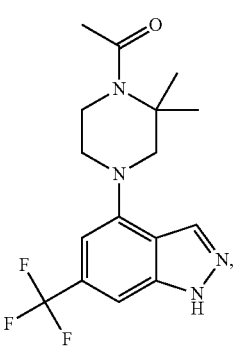 | 79 | | |

| 487 | 488 |
|---|---|
| 84 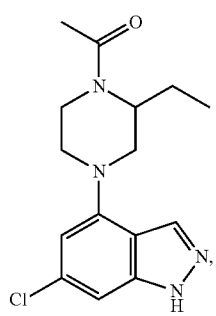 | 91 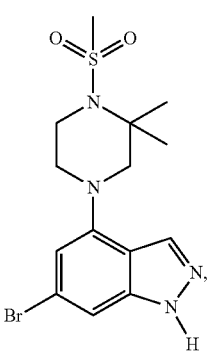 |
| 86 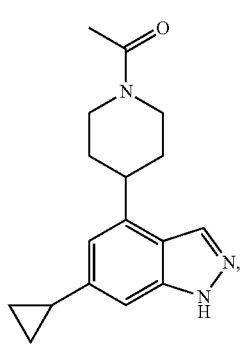 | 92 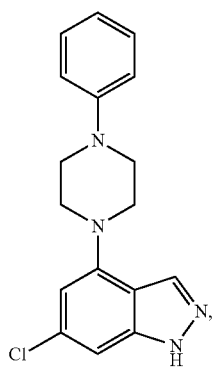 |
| 87 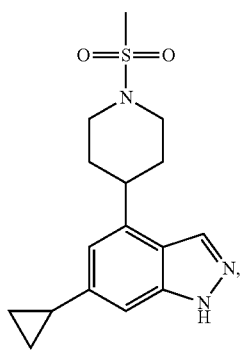 | 95 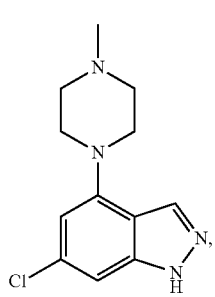 |
| 90 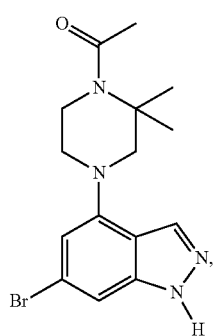 | 96 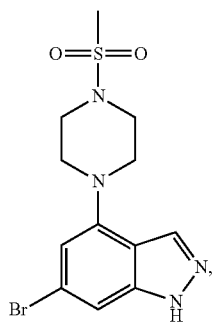 |

| 97 | 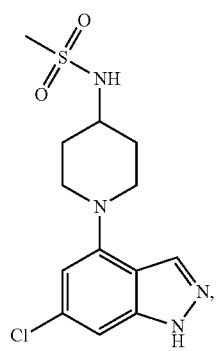 | 101 | 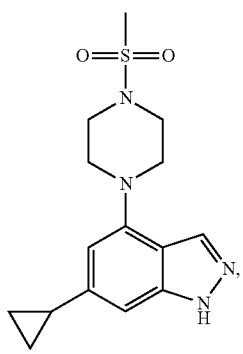 |
| 98 | 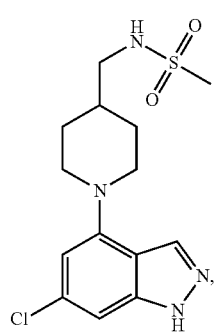 | 102 | 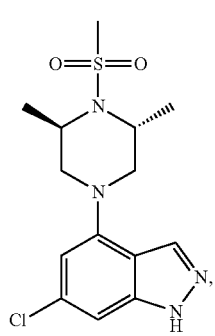 |
| 99 | 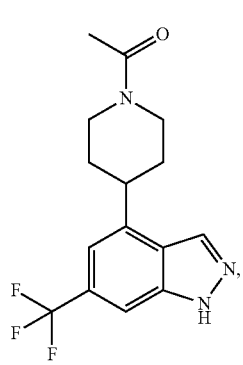 | 103 | 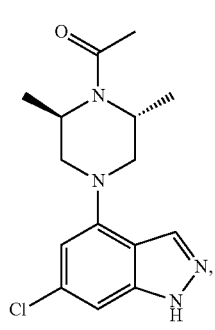 |
| 100 | 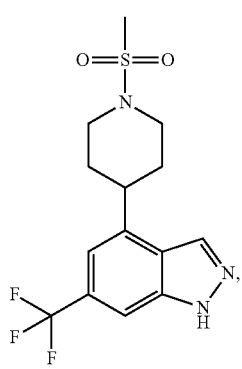 | 107 | 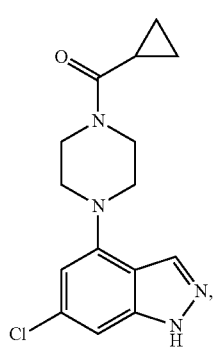 |

| 108 | 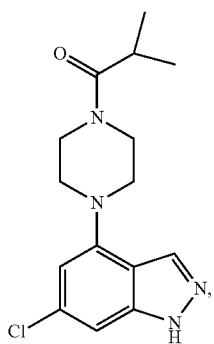 | 113 | 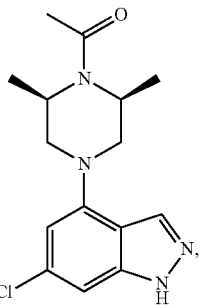 |
| --- | --- | --- | --- |
| 109 | 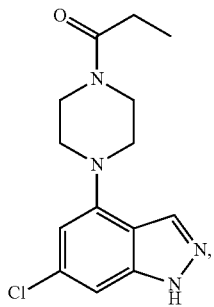 | 114 | 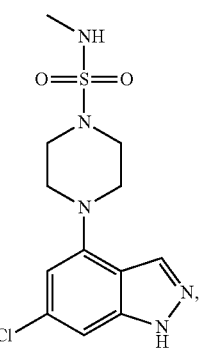 |
| 110 | 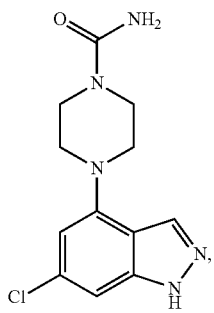 | 115 | 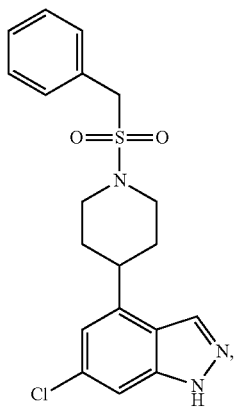 |
| 111 | 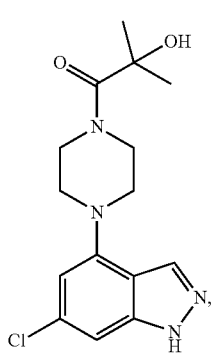 | 116 | 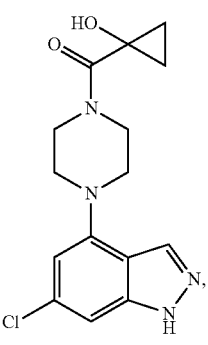 |
| 112 | 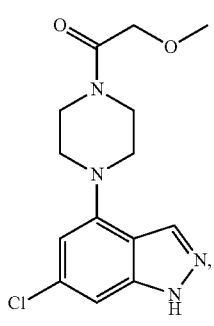 | | |

493
-continued
117
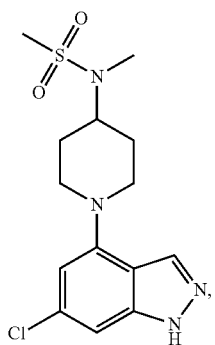
118
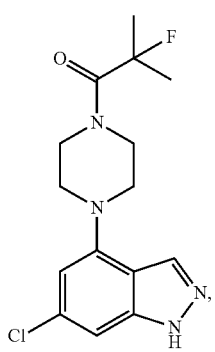
119
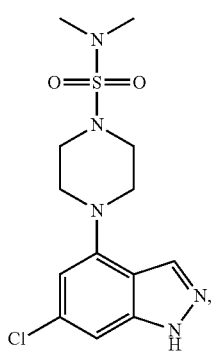
121
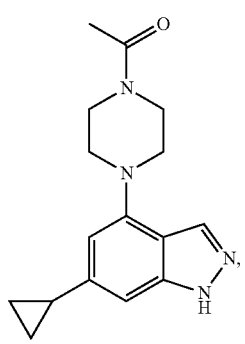
494
-continued
123
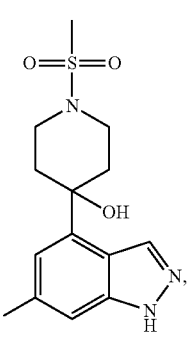
124
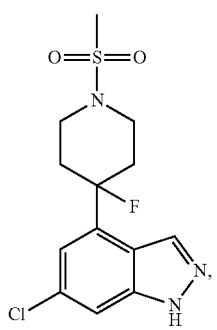
125
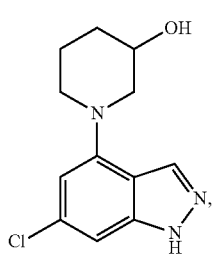
126
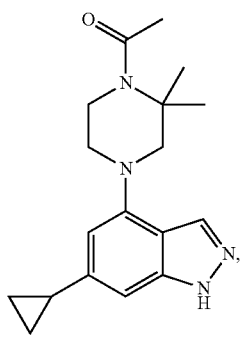
127
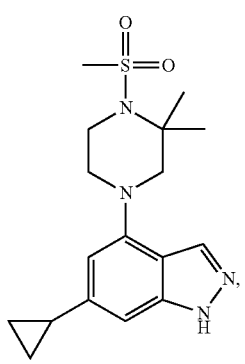

| | |
|---|---|
| 129 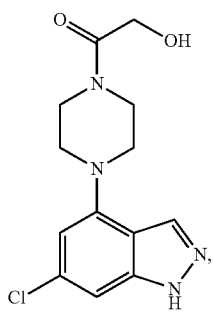 | 133 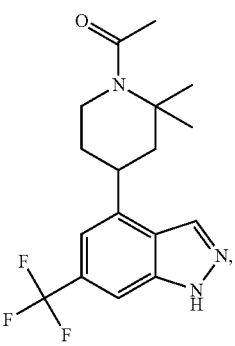 |
| 130 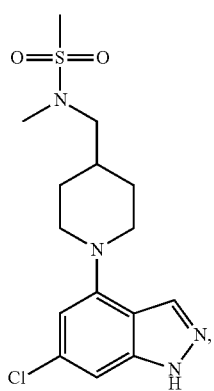 | 134 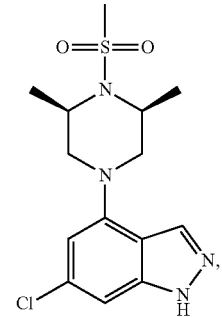 |
| 131 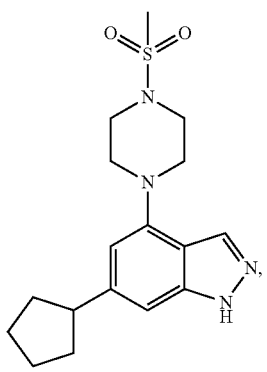 | 135 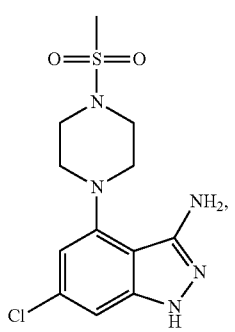 |
| 132 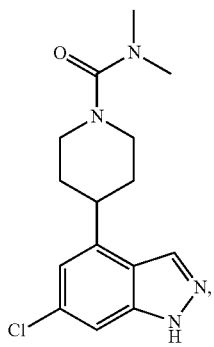 | 136 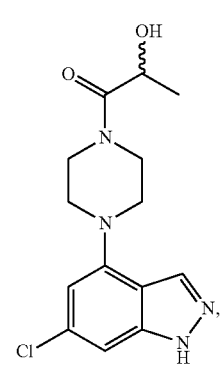 |

| 137 | 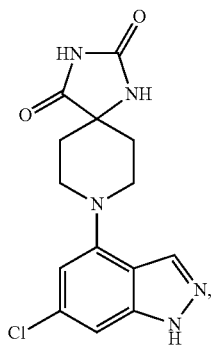 | 141 | 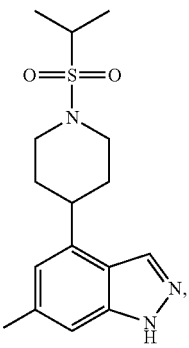 |
| 138 | 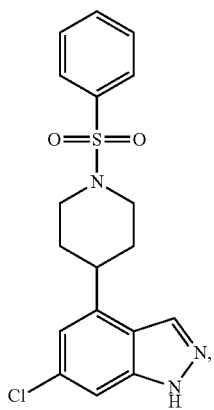 | 143 | 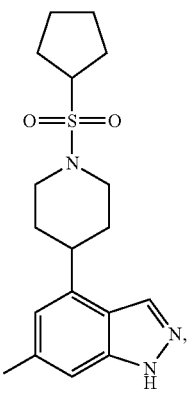 |
| 139 | 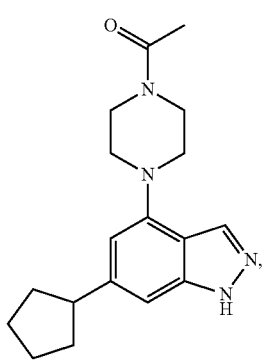 | 145 | 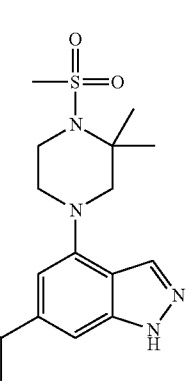 |
| 140 | 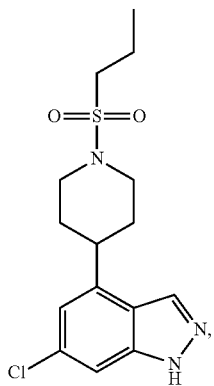 | 146 | 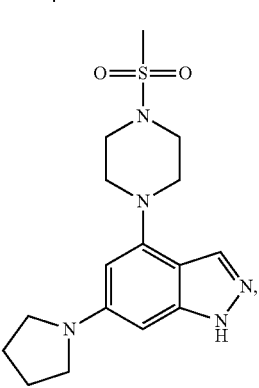 |

| | |
|---|---|
| 147 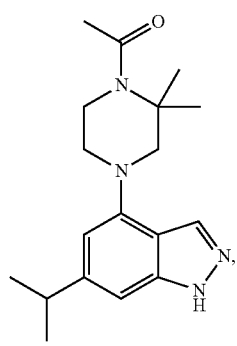 | 154 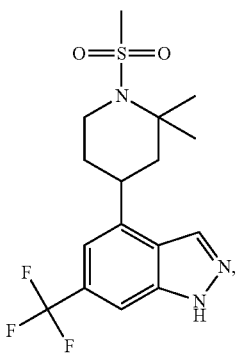 |
| 148 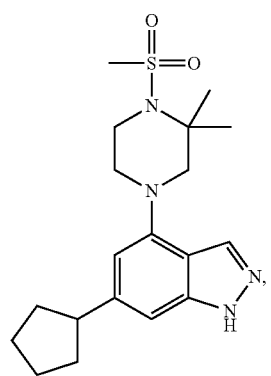 | 155 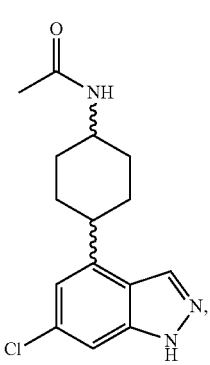 |
| 149 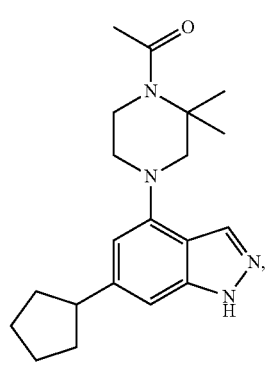 | 157 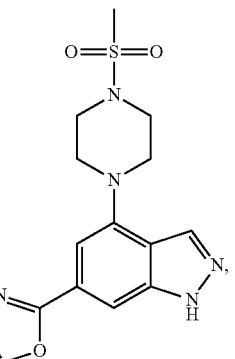 |
| 150 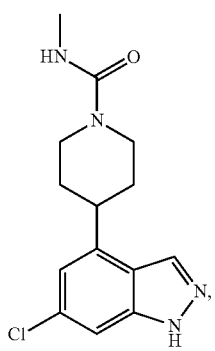 | 158 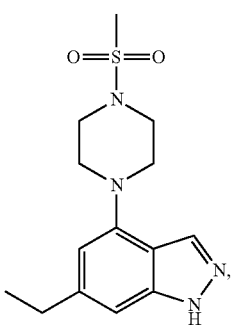 |

501
-continued
161
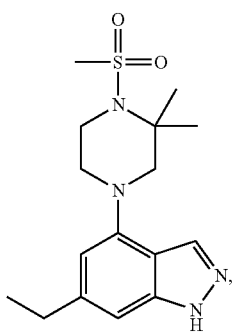
164
165
166
167
502
-continued
168
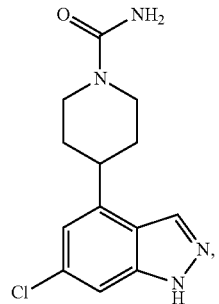
169
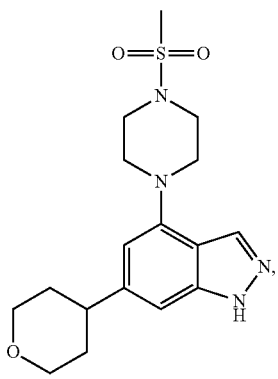
170
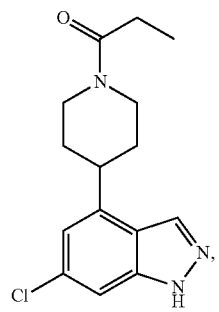
171
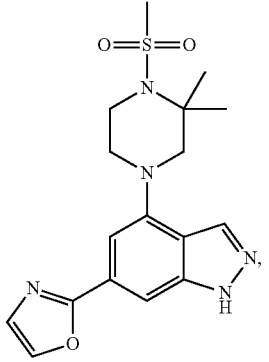

| 503 -continued | | 504 -continued | |
|---|---|---|---|
| 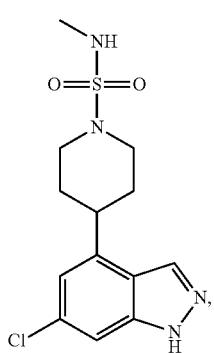 | 172 | 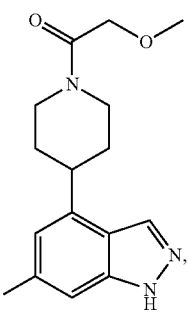 | 176 |
| 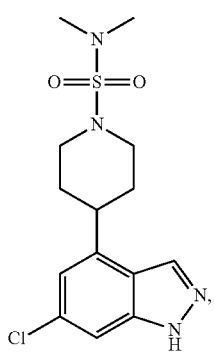 | 173 | 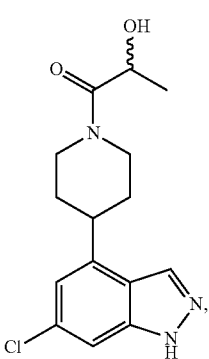 | 177 |
| 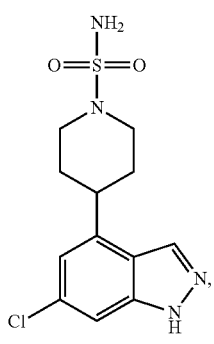 | 174 | 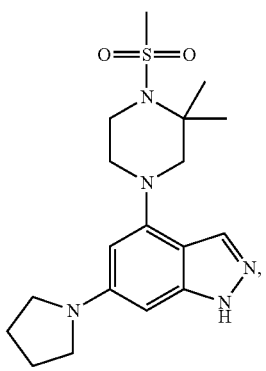 | 178 |
| 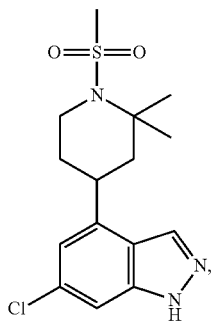 | 175 | 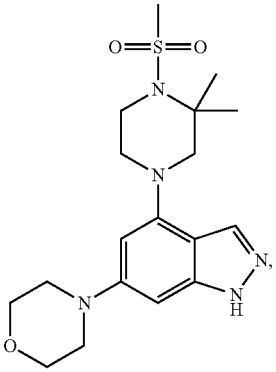 | 179 |

183 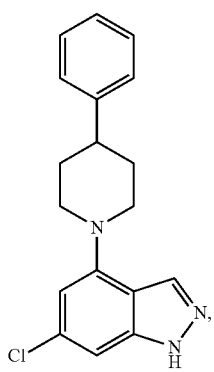
188 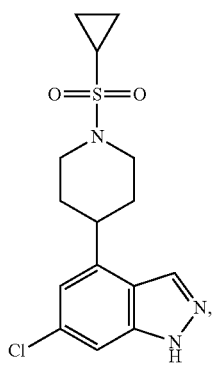
184 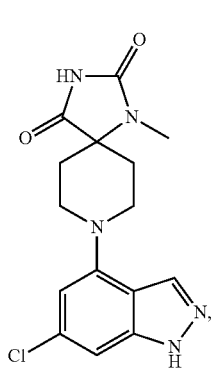
189 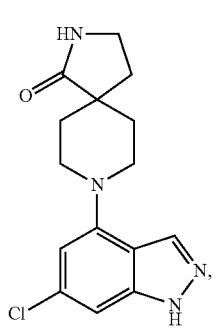
185 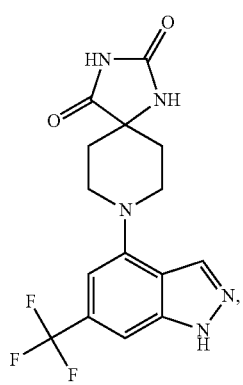
190 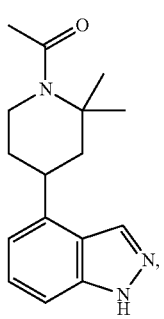
187 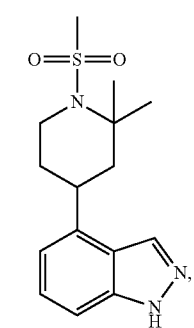
191 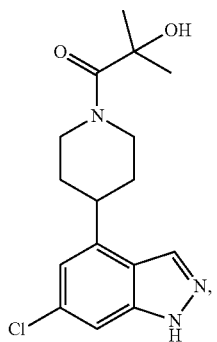

| | |
|---|---|
| 194 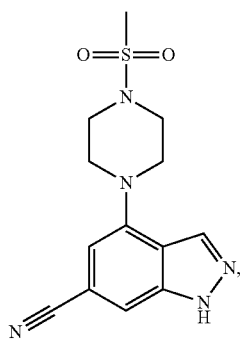 | 203 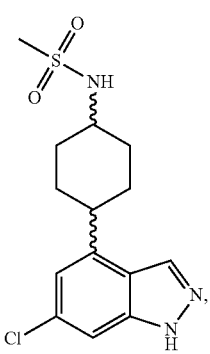 |
| 195 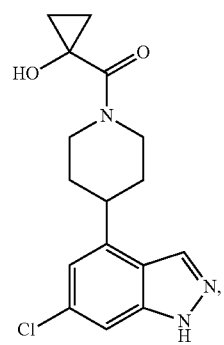 | 204 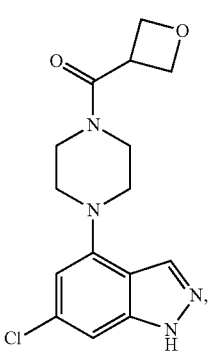 |
| 196 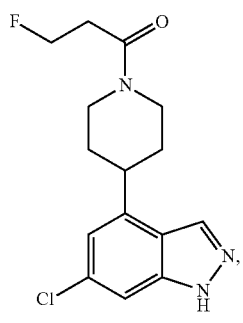 | 205 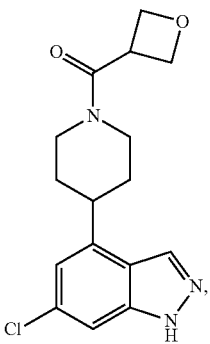 |
| 197 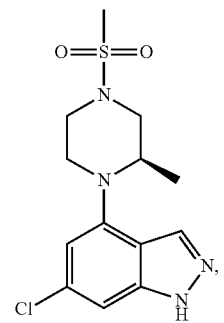 | 206 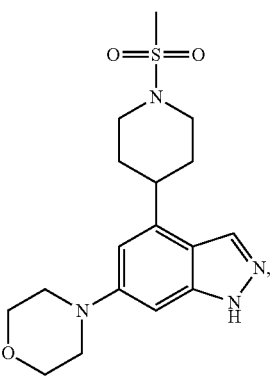 |
| 200 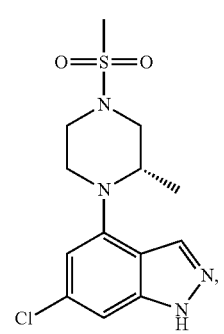 | |

| | |
|---|---|
| 207 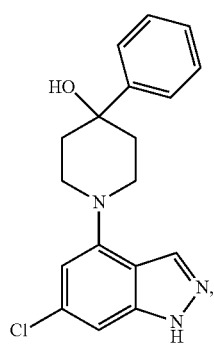 | 217 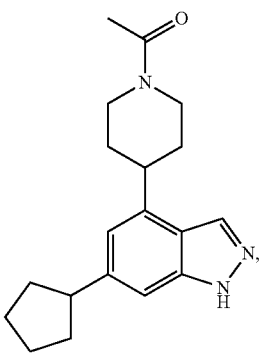 |
| 208 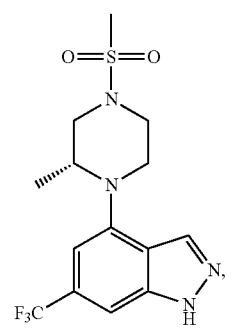 | 218 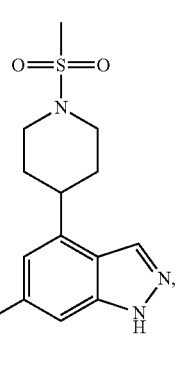 |
| 213 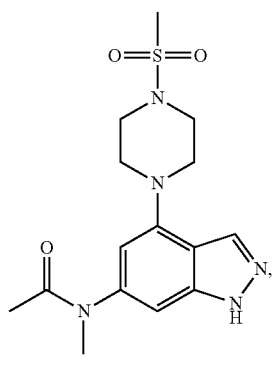 | 219 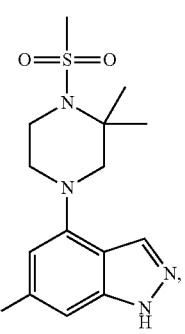 |
| 214 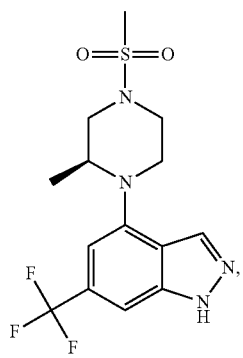 | 221 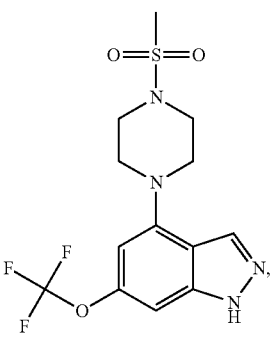 |

| | |
|---|---|
| 222 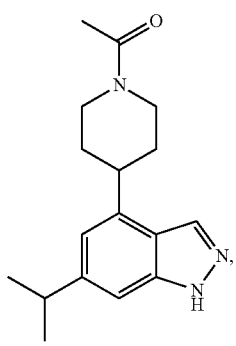 | 227 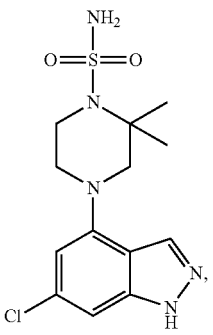 |
| 223 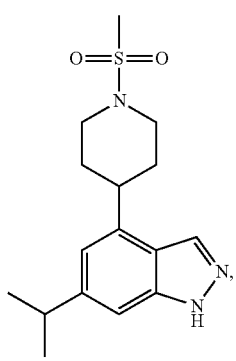 | 228 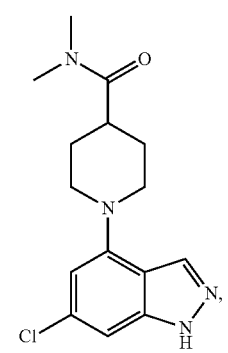 |
| 225 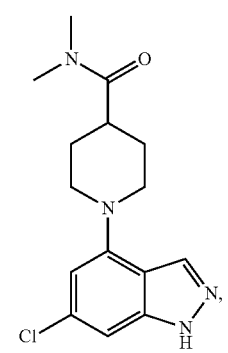 | 234 |
| 226 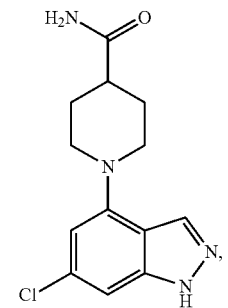 | 235 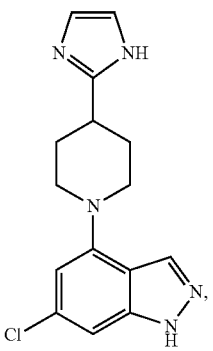 |

| | |
|---|---|
| 244 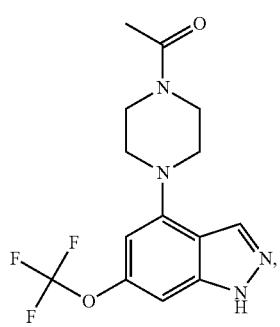 | 251 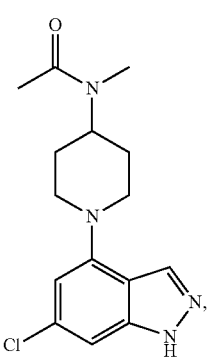 |
| 247 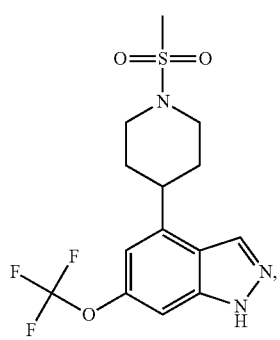 | 270 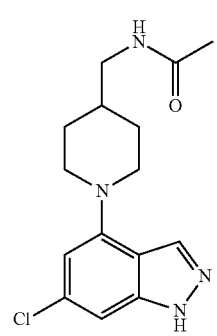 |
| 249 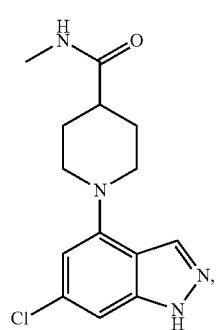 | 275 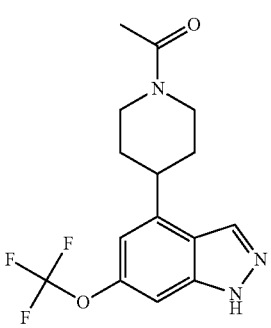 |
| 250 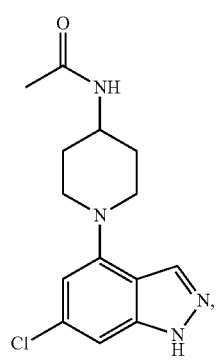 | 282 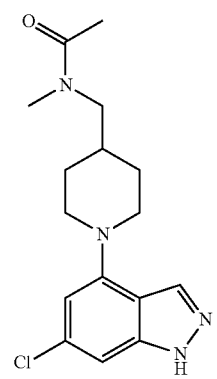 |

515
-continued
283 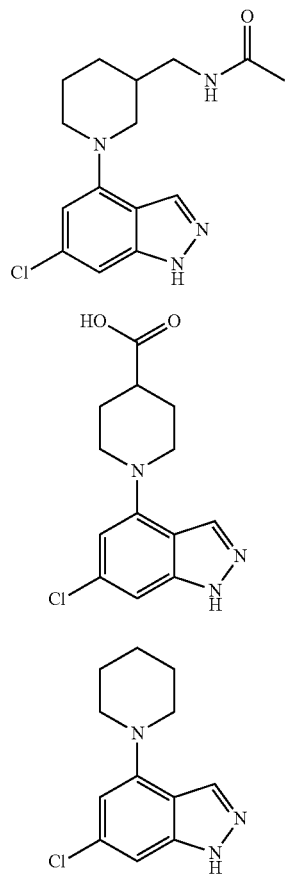
301
308 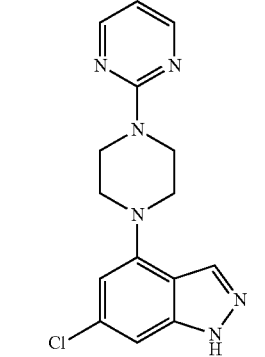
309 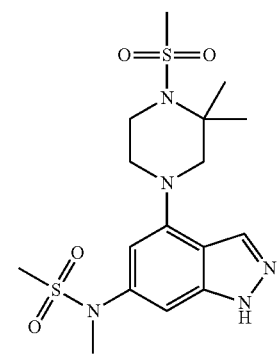
310
516
-continued
311 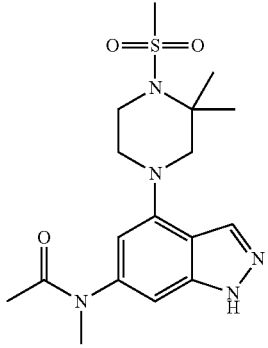
312 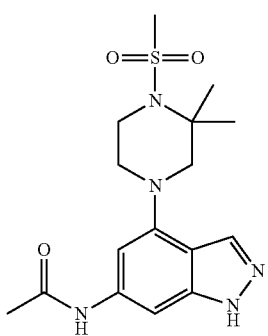
313 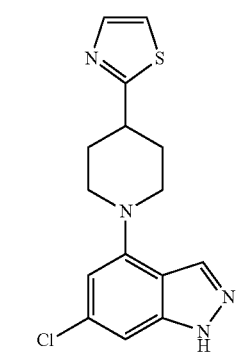
323 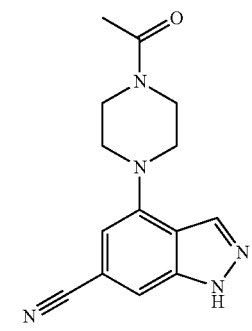

| | |
|---|---|
| 324 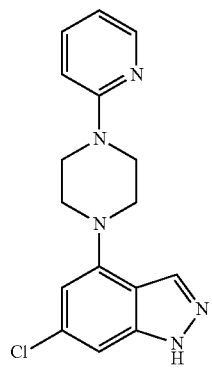 | 335 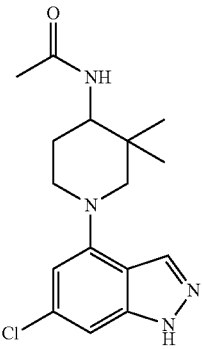 |
| 325 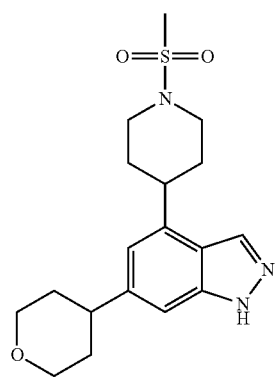 | 336 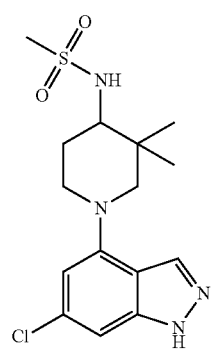 |
| 326 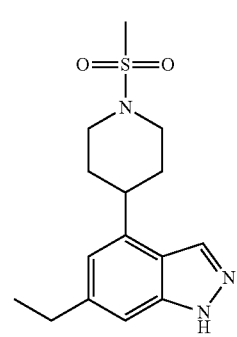 | 337 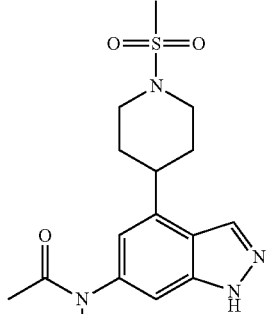 |
| 334 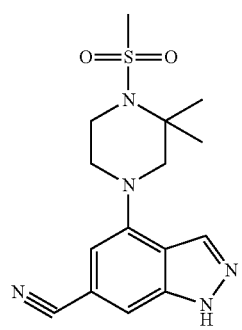 | 338 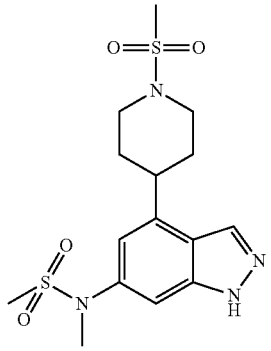 |

| 339 | 367 |
| --- | --- |
| 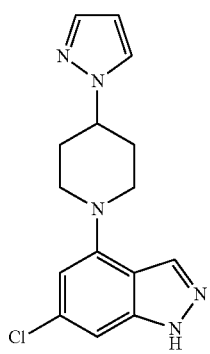 | 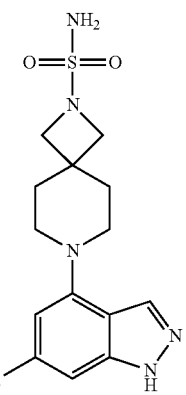 |
| 362 | 370 |
| 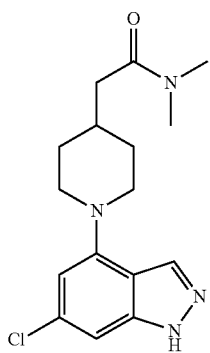 | 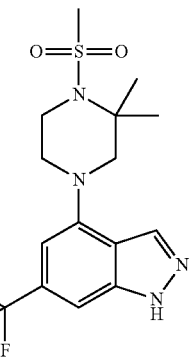 |
| 364 | 372 |
| 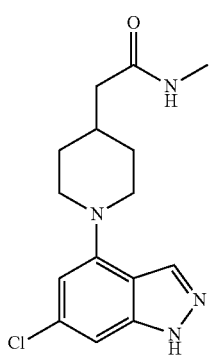 | 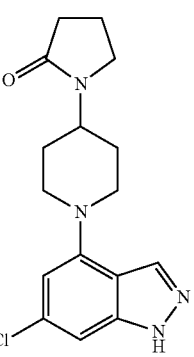 |
| 365 | 374 |
| 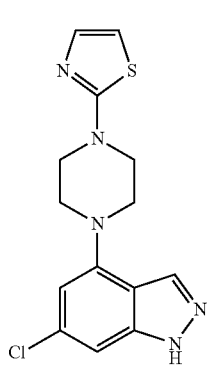 | 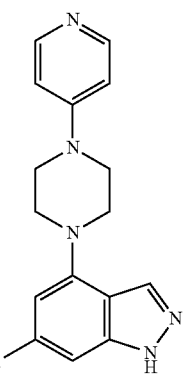 |

521
-continued
375
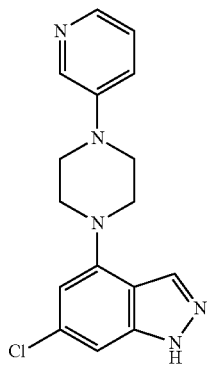
377
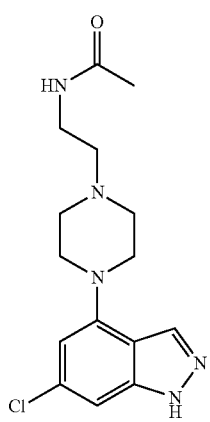
379
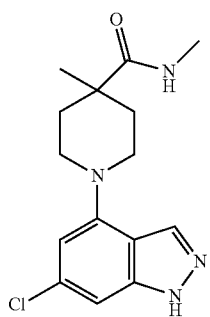
382
522
-continued
383
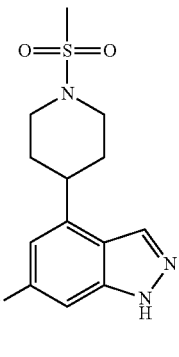
387
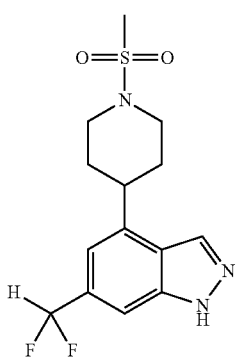
400
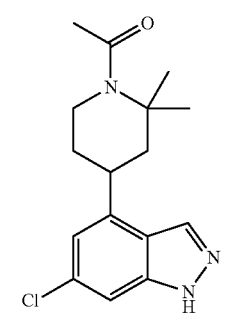

523
-continued
| | |
|---|---|
| 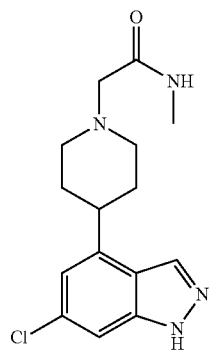 | 401 |
| 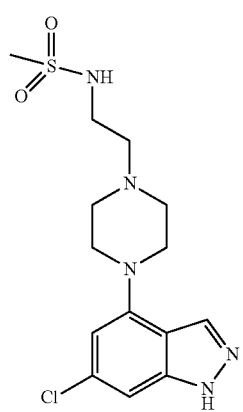 | 403 |
| 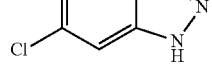 | 410 |
524
-continued
| | |
|---|---|
| 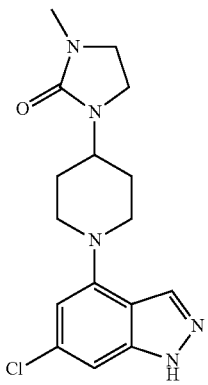 | 411 |
| 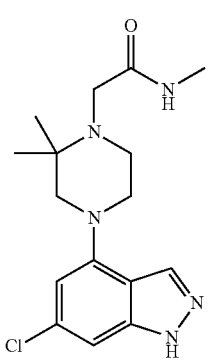 | 413 |
| 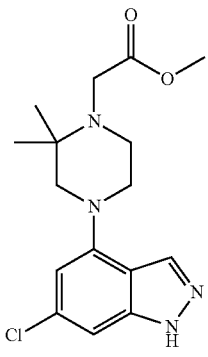 | 414 |
| 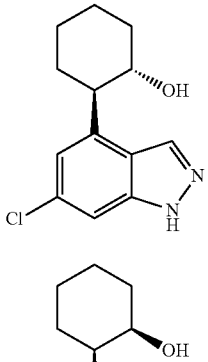 | 418 |
| 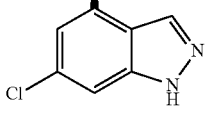 | 419 |

525
-continued
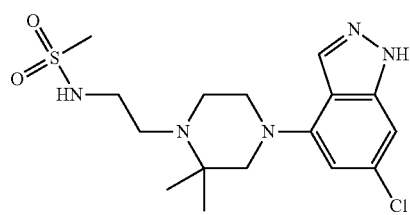
420
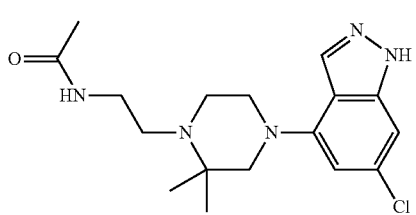
421
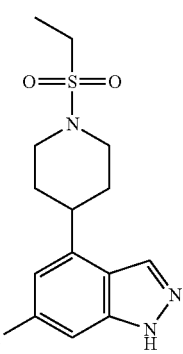
423
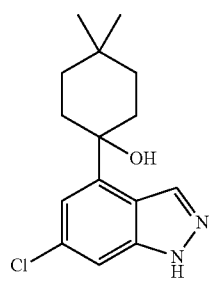
427
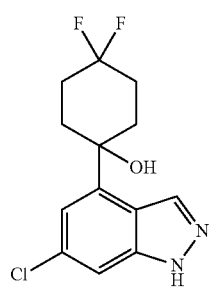
428
526
-continued
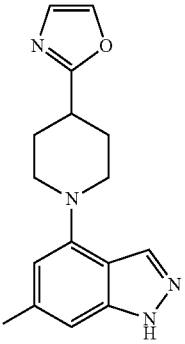
429
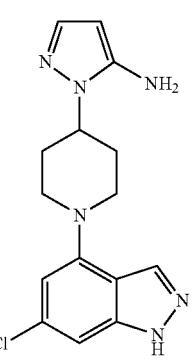
430
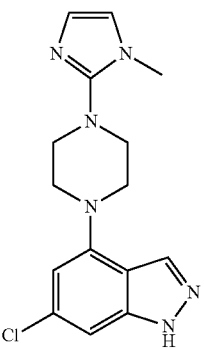
436
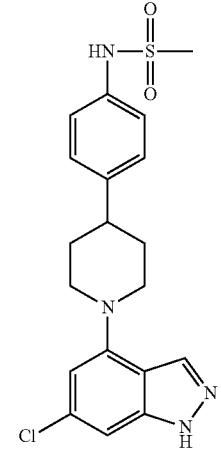
437

| 440 | 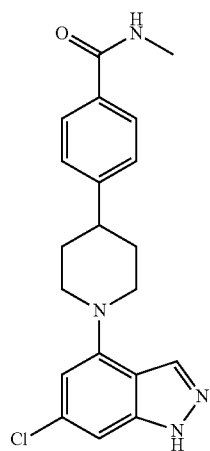 | 443 | 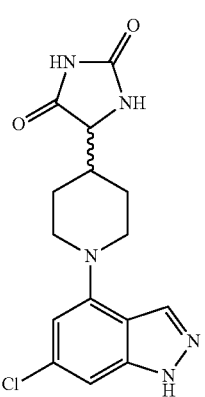 |
| --- | --- | --- | --- |
| 441 | 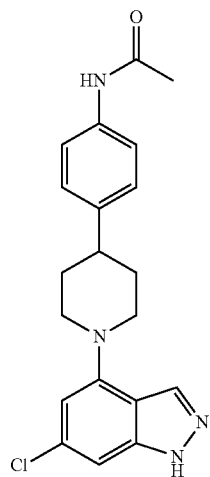 | 444 | 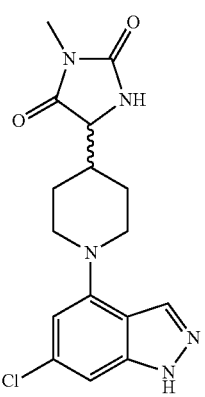 |
| | | 445 | 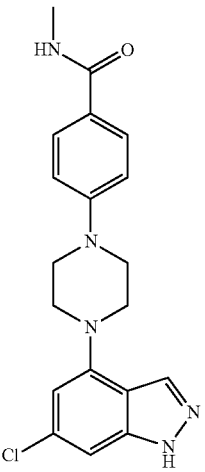 |
| 442 | 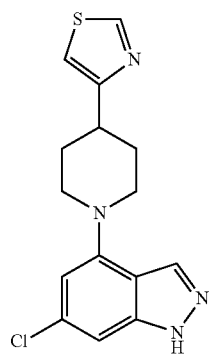 | 449 | 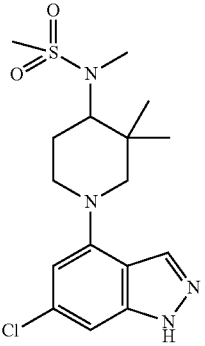 |

529
-continued

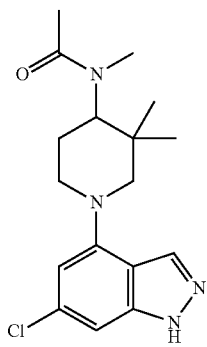
450

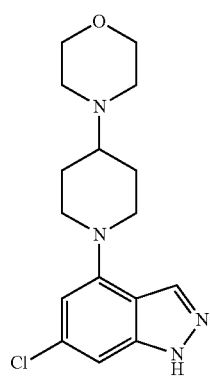
451

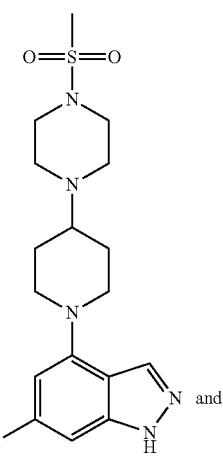
453

530
-continued

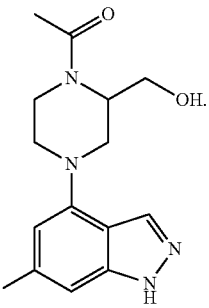
454

5. A pharmaceutical composition comprising a compound as defined in claim 1, or a pharmaceutically acceptable salt thereof, and a pharmaceutically acceptable additive and/or excipient, and/or wherein the compound is in the form of a pharmaceutically acceptable salt of the compound.

6. The pharmaceutical composition according to claim 5 for treating a cancer, further comprising a further agent for treating cancer; wherein the further agent is selected from an anti-microtubule agent, a platinum coordination complexe, an alkylating agent, an antibiotic agent, a topoisomerase II inhibitor, an antimetabolite, a topoisomerase I inhibitor, a hormone or hormone analogue, a signal transduction pathway inhibitor, a non-receptor tyrosine kinase angiogenesis inhibitor, an anti-tumor vaccine, an oncolytic virus, an immune stimulatory antibody, a novel adjuvant, a peptide, a cytokine, a chimeric antigen receptor T cell therapy (CAR-T), a small molecule immune modulator, a tumor microenvironment modulator, an anti-angiogenic agent, a proapoptotic agent and a cell cycle signalling inhibitor.

7. A pharmaceutical kit for treating a cancer, which pharmaceutical kit comprises:
  (a) a compound as defined in claim 1, or a pharmaceutically acceptable salt thereof; and
  (b) a further agent for treating cancer; wherein the further agent for treating cancer is selected from an anti-microtubule agent, a platinum coordination complexe, an alkylating agent, an antibiotic agent, a topoisomerase II inhibitor, an antimetabolite, a topoisomerase I inhibitor, a hormone or hormone analogue, a signal transduction pathway inhibitor, a non-receptor tyrosine kinase angiogenesis inhibitor, an anti-tumor vaccine, an oncolytic virus, an immune stimulatory antibody, a novel adjuvant, a peptide, a cytokine, a chimeric antigen receptor T cell therapy (CAR-T), a small molecule immune modulator, a tumor microenvironment modulator, an anti-angiogenic agent, a proapoptotic agent and a cell cycle signaling inhibitor;
  wherein the compound and the further agent are suitable for administration simultaneously, sequentially or separately.

8. The compound of claim 2, or a pharmaceutically acceptable salt thereof, having the following formula:

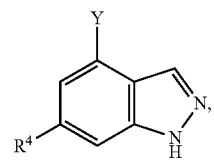

wherein R⁴ is selected from hydrogen, halogen, and $C_1$-$C_6$ alkyl; and
Y is one of the following formula:

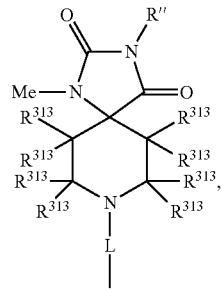

wherein L is absent;
$R^{11}$ is selected from H and $C_1$-$C_6$ alkyl.

9. A compound having the following formula, or a pharmaceuticallly acceptable salt thereof:

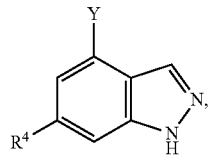

wherein R⁴ is selected from halogen and $C_1$-$C_6$ alkyl; and
Y is of the following formula:

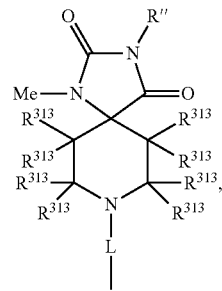

wherein L is absent;
each $R^{313}$ is independently selected from H, halogen, and $C_1$-$C_6$ alkyl; and
$R^{11}$ is selected from H and $C_1$-$C_6$ alkyl.

10. The compound of claim 9, or a pharamaceutically acceptable salt thereof, wherein:
R⁴ is halogen selected from -f, -Cl, and -Br;
each $R^{313}$ is independently selected from H, Me, Et, Pr and i-Pr; and;
$R^{11}$ is selected from H and Me.

* * * * *